(12) United States Patent
Seefeld et al.

(10) Patent No.: US 8,410,158 B2
(45) Date of Patent: Apr. 2, 2013

(54) INHIBITORS OF AKT ACTIVITY

(75) Inventors: Mark A. Seefeld, Collegeville, PA (US);
Meagan B. Rouse, Collegeville, PA (US); Dirk A. Heerding, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 499 days.

(21) Appl. No.: 12/526,111

(22) PCT Filed: Feb. 7, 2008

(86) PCT No.: PCT/US2008/053269
§ 371 (c)(1),
(2), (4) Date: Aug. 6, 2009

(87) PCT Pub. No.: WO2008/098104
PCT Pub. Date: Aug. 14, 2008

(65) Prior Publication Data
US 2010/0267759 A1    Oct. 21, 2010

Related U.S. Application Data

(60) Provisional application No. 60/888,586, filed on Feb. 7, 2007.

(51) Int. Cl.
*A01N 43/56* (2006.01)
*A61K 31/415* (2006.01)

(52) U.S. Cl. .................. 514/406; 548/364.1; 548/365.7; 548/373.1

(58) Field of Classification Search .................. 514/406; 548/364.1, 365.7, 373.1
See application file for complete search history.

(56) References Cited

U.S. PATENT DOCUMENTS

| 4,987,132 | A  | 1/1991  | Mase et al.       |
|-----------|----|---------|-------------------|
| 4,999,359 | A  | 3/1991  | Vecchietti et al. |
| 5,201,934 | A  | 4/1993  | Muenster et al.   |
| 5,258,357 | A  | 11/1993 | Muenster et al.   |
| 5,595,872 | A  | 1/1997  | Wetterau, II et al.|
| 5,631,269 | A  | 5/1997  | Broughton et al.  |
| 5,668,148 | A  | 9/1997  | Payne et al.      |
| 5,786,373 | A  | 7/1998  | Hartman et al.    |
| 5,807,854 | A  | 9/1998  | Bartroli et al.   |
| 5,846,990 | A  | 12/1998 | Murugesan et al.  |
| 5,942,544 | A  | 8/1999  | Maduskuie, Jr. et al.|
| 5,958,950 | A  | 9/1999  | Padia et al.      |
| 5,972,980 | A  | 10/1999 | Cornicelli et al. |
| 5,998,336 | A  | 12/1999 | Holcomb           |
| 6,001,866 | A  | 12/1999 | Cornicelli et al. |
| 6,130,333 | A  | 10/2000 | Huang et al.      |
| 6,162,819 | A  | 12/2000 | Schindler et al.  |
| 6,174,887 | B1 | 1/2001  | Haruta et al.     |
| 6,192,967 | B1 | 2/2001  | Huang             |
| 6,211,367 | B1 | 4/2001  | Cavalla et al.    |
| 6,359,134 | B1 | 3/2002  | Tawada et al.     |
| 6,420,561 | B1 | 7/2002  | Haruta et al.     |
| 6,469,171 | B1 | 10/2002 | Banwell et al.    |
| 6,545,055 | B1 | 4/2003  | Zhu et al.        |
| 6,624,309 | B1 | 9/2003  | Lloyd et al.      |
| 6,638,980 | B1 | 10/2003 | Su et al.         |
| 6,649,638 | B1 | 11/2003 | Brown et al.      |
| 6,750,239 | B2 | 6/2004  | Hale et al.       |
| 6,770,666 | B2 | 8/2004  | Hashimoto et al.  |
| 6,875,789 | B2 | 4/2005  | Tang et al.       |
| 6,897,208 | B2 | 5/2005  | Edwards et al.    |
| 6,914,069 | B2 | 7/2005  | Shroff et al.     |
| RE39,088  | E  | 5/2006  | Haruta et al.     |
| 7,041,687 | B2 | 5/2006  | Binch et al.      |
| 7,112,600 | B1 | 9/2006  | Hashimoto et al.  |
| 7,125,883 | B1 | 10/2006 | Zechel et al.     |
| 7,166,619 | B2 | 1/2007  | Li et al.         |
| 7,223,788 | B2 | 5/2007  | Schwink et al.    |
| 7,285,554 | B2 | 10/2007 | Kubota et al.     |
| 7,314,885 | B2 | 1/2008  | Aronov et al.     |
| 7,335,779 | B2 | 2/2008  | Ammendola et al.  |
| 7,521,473 | B2 | 4/2009  | Lee et al.        |
| 2002/0002183 | A1 | 1/2002 | Zhu et al.       |
| 2002/0103202 | A1 | 8/2002 | Pinto et al.     |
| 2002/0132844 | A1 | 9/2002 | Shroff et al.    |
| 2003/0069290 | A1 | 4/2003 | Wishka et al.    |
| 2003/0105143 | A1 | 6/2003 | Ammendola et al. |
| 2003/0139452 | A1 | 7/2003 | Tang et al.      |
| 2003/0144276 | A1 | 7/2003 | Kikuchi et al.   |
| 2003/0144337 | A1 | 7/2003 | Hale et al.      |
| 2003/0158238 | A1 | 8/2003 | Hale et al.      |
| 2003/0195240 | A1 | 10/2003| Kalindjian et al.|
| 2003/0220365 | A1 | 11/2003| Stewart et al.   |
| 2003/0232849 | A1 | 12/2003| Noe et al.       |
| 2004/0014774 | A1 | 1/2004 | Myers et al.     |
| 2004/0014971 | A1 | 1/2004 | Meerpoel et al.  |
| 2004/0034037 | A1 | 2/2004 | Harbeson et al.  |
| 2004/0063671 | A1 | 4/2004 | Arrhenius et al. |

(Continued)

FOREIGN PATENT DOCUMENTS

| CA | 2361636 A1 | 8/2000 |
| CN | 1733708    | 2/2006 |

(Continued)

OTHER PUBLICATIONS

Adams, et al., *Science*, 281:1322-1326 (1998).
Alessi, et al., *EMBO J.*, 15:6541-6551 (1996).
Backman, S., et al., *Current Opinion in Neurobiology*, 12(5):516 (2002).
Bartroli, et al., J. Med. Chem., 1998, vol. 41, No. 11, pp. 1855-1868.
Bellacosa, et al., *Int. J. Cancer*, 64:280-285 (1995).
J.C. Byrd, S. Stilgenbauer and I.W. Flinn, "Chronic lymphocytic leukemia." *Hematology / the Education Program of the American Society of Hematology*. American Society of Hematology. Education Program, 163-83 (2004).
Cheng, et al., *Proc. Natl. Acad. Sci. U.S.A.*, 89:9267-9271 (1992).
Cheng, et al., *Proc. Natl. Acad. Sci. U.S.A.*, 93:3636-3641 (1996).

(Continued)

*Primary Examiner* — Samira Jean-Louis
(74) *Attorney, Agent, or Firm* — Wayne J. Dustman; Edward R. Gimmi

(57) ABSTRACT

Invented are novel heterocyclic carboxamide compounds, the use of such compounds as inhibitors of protein kinase B activity and in the treatment of cancer and arthritis.

64 Claims, No Drawings

U.S. PATENT DOCUMENTS

| | | | |
|---|---|---|---|
| 2004/0063686 A1 | 4/2004 | Johnson et al. |
| 2004/0072362 A1 | 4/2004 | Dalvitt et al. |
| 2004/0077707 A1 | 4/2004 | Desai et al. |
| 2004/0116399 A1 | 6/2004 | Zhu et al. |
| 2004/0116425 A1 | 6/2004 | Li et al. |
| 2004/0132726 A1 | 7/2004 | Arora et al. |
| 2004/0152739 A1 | 8/2004 | Hanau et al. |
| 2004/0198799 A1 | 10/2004 | Brondyk et al. |
| 2005/0026985 A1 | 2/2005 | Shroff et al. |
| 2005/0032848 A1 | 2/2005 | Aquino et al. |
| 2005/0107436 A1 | 5/2005 | Xie et al. |
| 2005/0130954 A1 | 6/2005 | Mitchell et al. |
| 2005/0148605 A1 | 7/2005 | Grotzfeld et al. |
| 2005/0153978 A1 | 7/2005 | Alberti et al. |
| 2005/0154202 A1 | 7/2005 | Hagmann et al. |
| 2005/0182075 A1 | 8/2005 | Yuan |
| 2005/0197328 A1 | 9/2005 | Bailey et al. |
| 2005/0256121 A1* | 11/2005 | Jefferson et al. ............ 514/241 |
| 2006/0019967 A1 | 1/2006 | Wu et al. |
| 2006/0025416 A1 | 2/2006 | Phadke et al. |
| 2006/0052384 A1 | 3/2006 | Bouillot et al. |
| 2006/0058351 A1 | 3/2006 | Diaz et al. |
| 2006/0111355 A1 | 5/2006 | Garrick et al. |
| 2006/0122234 A1 | 6/2006 | Archer et al. |
| 2006/0128690 A1 | 6/2006 | Ishihara et al. |
| 2006/0135773 A1 | 6/2006 | Semple et al. |
| 2006/0148862 A1 | 7/2006 | Clary et al. |
| 2006/0148876 A1 | 7/2006 | Deuschle et al. |
| 2006/0247260 A1 | 11/2006 | Murata et al. |
| 2006/0252807 A1 | 11/2006 | Severance et al. |
| 2006/0288588 A1 | 12/2006 | Morabito |
| 2006/0293320 A1 | 12/2006 | Schmitz et al. |
| 2007/0004771 A1 | 1/2007 | Lee et al. |
| 2007/0021713 A1 | 1/2007 | Kumar et al. |
| 2007/0060570 A1 | 3/2007 | Eberle et al. |
| 2007/0123561 A1 | 5/2007 | Lee et al. |
| 2007/0149549 A1 | 6/2007 | Li et al. |
| 2007/0149561 A1 | 6/2007 | Dhanak et al. |
| 2007/0173521 A1 | 7/2007 | Xue et al. |
| 2007/0203154 A1 | 8/2007 | Zhou et al. |
| 2007/0265271 A1 | 11/2007 | Peters et al. |
| 2008/0009506 A1 | 1/2008 | Kusama et al. |
| 2008/0090882 A1 | 4/2008 | Dorsch et al. |
| 2008/0119456 A1 | 5/2008 | Ulven et al. |
| 2008/0188528 A1 | 8/2008 | Biediger et al. |
| 2009/0136979 A1 | 5/2009 | Jones et al. |
| 2009/0181983 A1 | 7/2009 | Corte |
| 2009/0186905 A1 | 7/2009 | Leahy et al. |

FOREIGN PATENT DOCUMENTS

| | | |
|---|---|---|
| DE | 3927483 A1 | 8/1989 |
| DE | 19904396 | 4/1999 |
| DE | 102004051277 | 10/2004 |
| DE | 102004054666 | 5/2006 |
| EP | 0335381 | 3/1989 |
| EP | 0712397 | 4/1999 |
| EP | 1498109 A1 | 7/2004 |
| EP | 1802583 A1 | 10/2004 |
| ES | 2005163 | 3/1989 |
| JP | 2000/256358 | 9/2000 |
| JP | 2001/247569 | 9/2001 |
| JP | 2005336172 | 12/2005 |
| JP | 2006232707 | 9/2006 |
| JP | 2007277230 | 10/2007 |
| WO | WO9315047 | 8/1993 |
| WO | WO 94/29300 | 12/1994 |
| WO | WO9736585 | 10/1997 |
| WO | WO9736875 | 10/1997 |
| WO | WO9736881 | 10/1997 |
| WO | WO9736886 | 10/1997 |
| WO | WO9736890 | 10/1997 |
| WO | WO9736896 | 10/1997 |
| WO | WO9736897 | 10/1997 |
| WO | WO9736898 | 10/1997 |
| WO | WO9736901 | 10/1997 |
| WO | WO0035919 | 6/2000 |
| WO | WO0138309 | 3/2001 |
| WO | WO0156557 | 8/2001 |
| WO | WO0156993 | 8/2001 |
| WO | WO0157022 | 8/2001 |
| WO | WO 02/07823 A2 | 1/2002 |
| WO | WO 03035619 | 5/2003 |
| WO | 2004/0024340 | 7/2004 |
| WO | 2005/0006711 | 3/2005 |
| WO | WO 2005/019182 | 3/2005 |
| WO | WO2005019200 | 3/2005 |
| WO | WO2007052843 | 6/2005 |
| WO | WO 2005/077345 | 8/2005 |
| WO | WO2005074642 | 8/2005 |
| WO | WO2005077373 | 8/2005 |
| WO | WO2005095386 | 10/2005 |
| WO | 2006/0014807 | 4/2006 |
| WO | WO2006084176 | 8/2006 |
| WO | WO2006110762 | 10/2006 |
| WO | 2006/0043513 | 11/2006 |
| WO | 2006/0043518 | 11/2006 |
| WO | 2006/0043617 | 11/2006 |
| WO | 2006/0062453 | 12/2006 |
| WO | WO 2006/136837 | 12/2006 |
| WO | WO2006129199 | 12/2006 |
| WO | WO2006136829 | 12/2006 |
| WO | WO2007002559 | 1/2007 |
| WO | WO2007002563 | 1/2007 |
| WO | WO2007/076423 A2 | 7/2007 |
| WO | WO 2007/087906 | 8/2007 |
| WO | WO2008080056 | 7/2008 |
| WO | WO 2008/098104 | 8/2008 |
| WO | WO2008/098105 A1 | 8/2008 |
| WO | WO2008098105 | 8/2008 |
| WO | WO2008121685 | 10/2008 |
| WO | WO2008121786 | 10/2008 |

OTHER PUBLICATIONS

Dalvit, et al., *J. Am. Chem. Soc.*, 2003, vol. 125, No. 25, pp. 7696-7703.
Downward, *Curr. Opin. Cell. Biol.*, 10:262-267 (1998).
Downward, *Science*, 279:673-674 (1998).
Dudek, et al., *Science*, 275:661-665 (1997).
Einzig et. al., *Proc. Am. Soc. Clin. Oncol.*, 20:46 (2001).
Forastire et. al., *Sem. Oncol.*, 20:56 (1990).
Franke, et al., *Cell*, 81:727-736 (1995).
Franke, et al., *Cell*, 88:435-437 (1997).
Hemmings, *Science*, 275:628-630 (1997).
Hemmings, *Science*, 277:534 (1997).
Holmes et al., *J. Nat. Cancer Inst.*, 83:1797 (1991).
Kauffmann-Zeh, et al., *Nature*, 385:544-548 (1997).
Kearns, C.M. et. al., *Seminars in Oncology*, 3(6) p. 16-23 (1995).
Kingston et al., *Studies in Organic Chemistry*, 26: 219-235 (1986).
Komander et al., *Biochem. J.*, 375(2):255-262 (2003).
Kulik, et al., *Mol. Cell. Biol.*, 17:1595-1606 (1997).
Kumar, *J. Biol. Chem.*, 256: 10435-10441 (1981).
Li, et al., Guldberg, et al., *Cancer Research*, 57:3660-3663 (1997).
Liaw, et al., *Nature Genetics*, 16:64-67 (1997).
Lin, et al., *Bioorganic and Medicinal Chemistry Letters*, 16(16): 4163-4168; 4163; 4166-4167 (2006).
Liu, et al., *Current Opinion Pharmacology*, 3:317-22 (2003).
Lu, et al., *J. Med. Chem.*, 2006, vol. 49, No. 17, pp. 5154-5161.
Maehama, T., et al., *Annual Review of Biochemistry*, 70:247 (2001).
Markman et al., *Yale Journal of Biology and Medicine*, 64:583-590 (1991).
McGuire et al., *Ann. Intern., Med.*, 111:273 (1989).
Meier, et al., *J Biol. Chem.*, 272:30491-30497 (1997).
Nakatani, et al., *J. Biol. Chem.*, 274:21528-21532 (1999).
Parsons, R.; Simpson, L., *Methods in Molecular Biology*, 222:147 (2003).
Risinger, et al., *Cancer Research*, 57:4736-4738 (1997).
Salvino, et al. *J. Comb. Chem.*, 2000, vol. 2, pp. 691-697.
Staal, *Proc. Natl.. Acad. Sci. U.S.A.*, 84:5034-7 (1987).
Schiff et al., *Nature*, 277:665-667 (1979).
Schiff et al., *Proc. Natl. Acad. Sci. USA*, 77:1561-1565 (1980).
Seefeld, et al., *Bioorganic & Medicinal Chem. Ltrs.*, 19:2244-2248 (2009).

Stal, et al., *Breast Cancer Research*, 5:R37-R44 (2003).
Stambolic, et al., *Cell*, 95:29-39 (1998).
Sun, et al., *Proc. Natl. Acad. Sci. U.S.A.*, 96:6199-6204 (1999).
Sun, et al., *Am. J. Pathol.*, 159:431-7 (2001).
Mitsunobu, *Synthesis*, 1-28 (1981).
Thornberry, et al., *Science*, 281:1312-1316 (1998).
Wani et al., *J. Am. Chem. Soc.*, 93:2325 (1971).
Williams, et al., *Curr. Biol.*, 10:439-448 (2000).
Woo et. al., *Nature*, 368:750 (1994).
Yonetoku, et al. Bioorganic & Med. Chem, 2006, vol. 14, No. 15, pp. 5370-5383.
Written Opinion of the International Searching Authority in Related Case PCT/US08/53269; Opinion dated Jul. 7, 2008.
Altomare, et al., *Oncogene*, 24(40):6080-6089 (2005).
Clinical Trials.gov, *Repeat Dose Safety Study for Compond to Treat Hematologic Cancer*, Study 1 of 1 for search of: GSK2110183, First Received on Mar. 20, 2009 (pp. 1-5).
Clinical Trials.gov, *A Study of MK2206 in Locally Advanced or Metastatic Solid Tumors (2206-007)*, Study 2 of 35 for search of:MK2206, First Received on Feb. 17, 2010 (pp. 1-4).
Clinical Trials.gov, *MK-2206 in the Treatment of Recurrent Platinum-Resistant Ovarian, Fallopian Tube, or Peritoneal Cancer*, Study 7 of 35 for search of:MK2206, First Received on Jan. 24, 2011 (pp. 1-4).
Clinical Trials.gov, *MK2206 in Treating Patients With Advanced Gastric or Gastroesophageal Junction Cancer*, Study 11 of 35 for search of:MK2206, First Received on Dec. 14, 2010 (pp. 1-5).
Clinical Trials.gov, *MK2206 in Treating Patients with Stage I, Stage II, or Stage III Breast Cancer*, Study 12 of 35 for search of:MK2206, First Received on Mar. 18, 2011 (pp. 1-5).
Clinical Trials.gov, *Study of MK-2206 in Patients With Metastatic Neuroendocrine Tumors*(NET), Study 14 of 35 for search of:MK2206, First Received on Jul. 21, 2010 (pp. 1-5).
Clinical Trials.gov, *Bicalutamide With or Without MK2206 in Treating Patients with Previously Treated Prostate Cancer*, Study 15 of 35 for search of:MK2206, First Received on Dec. 1, 2010 (pp. 1-6).
Clinical Trials.gov, *MK-2206 for Recurrent Malignant Glioma*, Study 16 of 35 for search of:MK2206, First Received on Nov. 24, 2010 (pp. 1-6).
Clinical Trials.gov, *Akt Inhibitor MK-2206 in Patients W/Advanced Breast Cancer Who Have Tumors With a PIK3CA Mutation and/or PTEN Loss*, Study 17 of 35, search of:MK2206, First Rec'd on Jan. 13, 2011 (pp. 1-5).
Clinical Trials.gov, *AKT Kinase Inhibitor MK-2206 With Relapsed Refractory Acute Myelogenous Leukemia*, Study 18 of 35 for search of:MK2206, First Received on Dec. 1, 2010 (pp. 1-4).
Clinical Trials.gov, *Clinical and Translational Study of MK-2206 In Patients With Metastatic KRAS-Wild-Type, PIK3CA-Mutated, Colorectal Cancer*, Study 19 of 35, search of :MK2206, First Rec'd on Aug. 20, 2010 (pp. 1-5).
Clinical Trials.gov, *Study of MK-2206 in Patients With Relapsed Lymphoma*, Study 21 of 35 for search of:MK2206, First Received on Dec. 10, 2010 (pp. 1-4).
Clinical Trials.gov, *MK2206 in Treating Younger Patients With Recurrent or Refractory Solid Tumors or Leukemia*, Study 23 of 35 for search of:MK2206, First Received on Oct. 29, 2010 (pp. 1-8).
Clinical Trials.gov, *MK2206 in Treating Patients With Recurrent or Metastatic Head and Neck Cancer*, Study 25 of 35 for search of:MK2206, First Received on May 6, 2011 (pp. 1-5).
Clinical Trials.gov, *MK2206 in Treating Patients with Recurrent or Advanced Endometrial Cancer*, Study 28 of 35 for search of:MK2206, First Received on Mar. 1, 2011 (pp. 1-6).
Clinical Trials.gov, *MK2206 or Everolimus in Treating Patients With Refractory Kidney Cancer*, Study 30 of 35 for search of:MK2206, First Received on Nov. 10, 2010 (pp. 1-6).
Clinical Trials.gov, *MK2206 in Treating Patients With Advanced Liver Cancer That Did Not Respond to Previous Therapy*, Study 33 of 35 for search of:MK2206, First Received on Nov. 10, 2010 (pp. 1-7).
Clinical Trials.gov, *Molecular Profiling and Targeted Therapy for Advanced Non-Small Cell Lung Cancer, Small Cell Lung Cancer and Thymic Malignancies*, Study 35 of 35 for search of:MK2206, First Received on Feb. 26, 2011 (pp. 1-10).
*Phase I, Open-Label, first-Time-In-Human Study of Oral AKT Inhibitor GSK2141795*, ClinicalTrials.gov, Jun. 12, 2009.
*Open Label Study to Investigate Pharmacokinetics& Pharmacodynamics of Repeat Escalating Doses of Oral AKT Inhibitor GSK2141795 in Subjects with Ovarian Cancer*, ClinicalTrials.gov, Oct. 21, 2010.
Gills, et al., *Current Oncology Reports*, 11:102-110 (2009).
Hernando, et al., *Nature Medicine*, 13(6):748-753 (2007).
Hideshima, et al., *Blood*, 107:4053-4062 (2006).
Ringel, et al., *Cancer Research*, 61(16):6105-6111 (2001).
Steelman, et al., *Expert Opinion on Therapeutic Targets*, 12(9):1139-1165 (2008).

* cited by examiner ical domains. Akt/PKBs are
INHIBITORS OF AKT ACTIVITY

This application is a 371 of International Application No. PCT/US2008/053269, filed 7 Feb. 2008, which claims the benefit of U.S. Provisional Application No. 60/888,586, filed 7 Feb. 2007.

FIELD OF THE INVENTION

This invention relates to novel heterocyclic carboxamide compounds, the use of such compounds as inhibitors of protein kinase B (hereinafter PKB/Akt, PKB or Akt) activity and in the treatment of cancer and arthritis.

BACKGROUND OF THE INVENTION

The present invention relates to heterocyclic carboxamide containing compounds that are inhibitors of the activity of one or more of the isoforms of the serine/threonine kinase, Akt (also known as protein kinase B), suitably the compounds of the invention are inhibitors of the activity of all three isoforms of the serine/threonine kinase, Akt. The present invention also relates to pharmaceutical compositions comprising such compounds and methods of using the instant compounds in the treatment of cancer and arthritis (Liu et al. *Current Opin. Pharmacology* 3:317-22 (2003)).

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-$x_L$, inhibits apoptotic cell death induced by various stimuli. On the other hand, expression of pro-apoptotic genes, such as Bax or Bad, leads to programmed cell death (Adams et al. *Science*, 281:1322-1326 (1998)). The execution of programmed cell death is mediated by caspase-1 related proteinases, including caspase-3, caspase-7, caspase-8 and caspase-9 etc (Thornberry et al. *Science*, 281:1312-1316 (1998)).

The phosphatidylinositol 3'-OH kinase (PI3K)/Akt/PKB pathway appears important for regulating cell survival/cell death (Kulik et al. *Mol. Cell. Biol.* 17:1595-1606 (1997); Franke et al, *Cell*, 88:435-437 (1997); Kauffmann-Zeh et al. *Nature* 385:544-548 (1997) Hemmings *Science*, 275:628-630 (1997); Dudek et al., *Science*, 275:661-665 (1997)). Survival factors, such as platelet derived growth factor (PDGF), nerve growth factor (NGF) and insulin-like growth factor-1 (IGF-1), promote cell survival under various conditions by inducing the activity of PI3K (Kulik et al. 1997, Hemmings 1997). Activated PI3K leads to the production of phosphatidylinositol (3,4,5)-triphosphate (PtdIns (3,4,5)-P3), which in turn binds to, and promotes the activation of, the serine/threonine kinase Akt, which contains a pleckstrin homology (PH)-domain (Franke et al *Cell*, 81:727-736 (1995); Hemmings *Science*, 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt/PKB mutants abolish survival-promoting activities of these growth factors or cytokines. It has been previously disclosed that inhibitors of PI3K (LY294002 or wortmanin) blocked the activation of Akt/PKB by upstream kinases. In addition, introduction of constitutively active PI3K or Akt/PKB mutants promotes cell survival under conditions in which cells normally undergo apoptotic cell death (Kulik et al. 1997, Dudek et al. 1997).

Analysis of Akt levels in human tumors showed that Akt2 is overexpressed in a significant number of ovarian (J. Q. Cheung et al. *Proc. Natl. Acad. Sci. U.S.A.* 89:9267-9271 (1992)) and pancreatic cancers (J. Q. Cheung et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999). It was demonstrated that Akt-2 was over-expressed in 12% of ovarian carcinomas and that amplification of Akt was especially frequent in 50% of undifferentiated tumors, suggestion that Akt may also be associated with tumor aggressiveness (Bellacosa, et al., *Int. J. Cancer*, 64, pp. 280-285, 1995). Increased Akt1 kinase activity has been reported in breast, ovarian and prostate cancers (Sun et al., *Am. J. Pathol.* 159: 431-7 (2001)).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis.

Three members of the Akt/PKB subfamily of second-messenger regulated serine/threonine protein kinases have been identified and termed Akt1/PKBα, Akt2/PKBβ, and Akt3/PKBγ respectively. The isoforms are homologous, particularly in regions encoding the catalytic domains. Akt/PKBs are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt/PKB. The current model of Akt/PKB activation proposes recruitment of the enzyme to the membrane by 3'-phosphorylated phosphoinositides, where phosphorylation of the regulatory sites of Akt/PKB by the upstream kinases occurs (B. A. Hemmings, *Science* 275:628-630 (1997); B. A. Hemmings, *Science* 276:534 (1997); J. Downward, *Science* 279:673-674 (1998)).

Phosphorylation of Akt1/PKBα occurs on two regulatory sites, $Thr^{308}$ in the catalytic domain activation loop and on $Ser^{473}$ near the carboxy terminus (D. R. Alessi et al. *EMBO J.* 15:6541-6551 (1996) and R. Meier et al. *J. Biol. Chem.* 272: 30491-30497 (1997)). Equivalent regulatory phosphorylation sites occur in Akt2/PKBβ and Akt3/PKBγ. The upstream kinase, which phosphorylates Akt/PKB at the activation loop site has been cloned and termed 3'-phosphoinositide dependent protein kinase 1 (PDK1). PDK1 phosphorylates not only Akt/PKB, but also p70 ribosomal S6 kinase, p90RSK, serum and glucocorticoid-regulated kinase (SGK), and protein kinase C. The upstream kinase phosphorylating the regulatory site of Akt/PKB near the carboxy terminus has not been identified yet, but recent reports imply a role for the integrin-linked kinase (ILK-1), a serine/threonine protein kinase, or autophosphorylation.

Inhibition of Akt activation and activity can be achieved by inhibiting PI3K with inhibitors such as LY294002 and wortmanin. However, PI3K inhibition has the potential to indiscriminately affect not just all three Akt isozymes but also other PH domain-containing signaling molecules that are dependent on PdtIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. The compound UCN-01 is a reported inhibitor of PDK1. *Biochem. J.* 375(2):255 (2003). Again, inhibition of PDK1 would result in inhibition of multiple protein kinases whose activities depend on PDK1, such as atypical PKC isoforms, SGK, and S6 kinases (Williams et al. *Curr. Biol.* 10:439-448 (2000).

Small molecule inhibitors of Akt are useful in the treatment of tumors, especially those with activated Akt (e.g. PTEN null tumors and tumors with ras mutations). PTEN is a critical negative regulator of Akt and its function is lost in many cancers, including breast and prostate carcinomas, glioblastomas, and several cancer syndromes including Bannayan-Zonana syndrome (Maehama, T. et al. *Annual Review of Biochemistry,* 70: 247 (2001)), Cowden disease (Parsons, R.; Simpson, L. *Methods in Molecular Biology* (Totowa, N.J., United States), 222 (*Tumor Suppressor Genes*, Volume 1): 147 (2003)), and Lhermitte-Duclos disease (Backman, S. et al. *Current Opinion in Neurobiology,* 12(5): 516 (2002)). Akt3 is up-regulated in estrogen receptor-deficient breast cancers and androgen-independent prostate cancer cell lines and Akt2 is over-expressed in pancreatic and ovarian carcinomas. Akt1 is amplified in gastric cancers (Staal, *Proc. Natl. Acad. Sci. USA* 84: 5034-7 (1987) and upregulated in breast cancers (Stal et al. *Breast Cancer Res.* 5: R37-R44 (2003)). Therefore a small molecule Akt inhibitor is expected to be useful for the treatment of these types of cancer as well as other types of cancer. Akt inhibitors are also useful in combination with further chemotherapeutic and anticancer agents.

It is an object of the instant invention to provide novel compounds that are inhibitors of Akt/PKB.

It is also an object of the present invention to provide pharmaceutical compositions that comprise a pharmaceutical carrier and compounds useful in the methods of the invention.

It is also an object of the present invention to provide a method for treating cancer that comprises administering such inhibitors of Akt/PKB activity.

It is also an object of the present invention to provide a method for treating arthritis that comprises administering such inhibitors of Akt/PKB activity.

SUMMARY OF THE INVENTION

This invention relates to novel compounds of Formula (I):

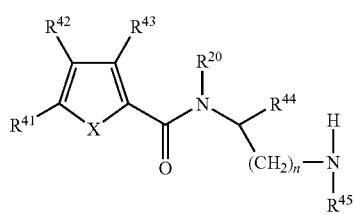

(I)

wherein:

$R^{41}$ and $R^{42}$ are independently selected from: hydrogen,

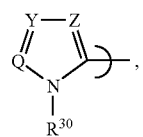

halogen, $C_{1-4}$alkyl, substituted $C_{1-4}$alkyl, $C_{1-4}$alkyloxy, substituted $C_{1-4}$alkyloxy, furan, substituted furan, thiophene and substituted thiophene, where Q and Y are independently selected from: nitrogen and —$C(R^{70})$—, and Z is selected from: nitrogen and —$C(R^{48})$—, provided that at least one and at most 2 of Q, Y and Z are nitrogen, and $R^{30}$ is selected from: $C_{1-4}$alkyl and $C_{1-4}$alkyl substituted with form one to three fluorine atoms, where $R^{70}$ is selected from: hydrogen, and halogen, and $R^{48}$ is selected from: hydrogen, $C_{1-4}$alkyl, substituted $C_{1-4}$alkyl, aryl, substituted aryl, heteroaryl, substituted heteroaryl, cylcoalkyl, substituted cycloalkyl, heterocycloalkyl, substituted heterocycloalkyl, and halogen;

$R^{43}$ is selected from: hydrogen, halogen, $C_{1-4}$alkyl, substituted $C_{1-4}$alkyl, $C_{1-4}$alkyloxy, substituted $C_{1-4}$alkyloxy, furan and thiophene;

$R^{44}$ is absent or selected from: —$(CR^{60}R^{61})_m$AR wherein the AR is unsubstituted, —$(CR^{60}R^{61})_m$AR wherein the AR is substituted and $C_{1-6}$alkyl, where m is 0 to 3 and AR is a cyclic or polycyclic aromatic or saturated or unsaturated non-aromatic ring containing from 3 to 16 carbon atoms and optionally containing from one to three heteroatoms, provided that when the ring is aromatic and the number of carbon atoms is 3 the ring contains at least two heteroatoms and when the ring is aromatic and the number of carbon atoms is 4 the ring contains at least one heteroatom, and $R^{60}$ and $R^{61}$ are independently selected from: hydrogen and $C_{1-4}$alkyl, provided that when m is 3 no more than 4 of $R^{60}$ and $R^{61}$ when added together are $C_{1-4}$alkyl, $R^{45}$ is selected from hydrogen and $C_{1-4}$alkyl;

$R^{20}$ is selected from hydrogen, $C_{1-4}$alkyl and hydroxy;

X is selected from O, S and $NR^{49}$, where $R^{49}$ is selected from hydrogen and $C_{1-4}$alkyl; and n is 0 to 2 and this moiety is optionally, if applicable, substituted by hydroxy$C_{1-4}$alkyl;

provided that one and only one of $R^{41}$ and $R^{42}$ is

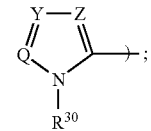

and/or pharmaceutically acceptable salts thereof.

This invention relates to a method of treating cancer, which comprises administering to a subject in need thereof an effective amount of an Akt/PKB inhibiting compound of Formula (I).

This invention relates to a method of treating arthritis, which comprises administering to a subject in need thereof an effective amount of an Akt/PKB inhibiting compound of Formula (I).

The present invention also relates to the discovery that the compounds of Formula (I) are active as inhibitors of Akt/PKB.

In a further aspect of the invention there is provided novel processes and novel intermediates useful in preparing the presently invented Akt/PKB inhibiting compounds.

Included in the present invention are pharmaceutical compositions that comprise a pharmaceutical carrier and compounds useful in the methods of the invention.

Also included in the present invention are methods of co-administering the presently invented Akt/PKB inhibiting compounds with further active ingredients.

DETAILED DESCRIPTION OF THE INVENTION

This invention relates to compounds of Formula (I) as described above.

The presently invented compounds of Formula (I) inhibit Akt/PKB activity. In particular, the compounds disclosed herein inhibit each of the three Akt/PKB isoforms.

Included among the presently invented compounds of Formula (I) are those in which:

$R^{41}$ and $R^{42}$ are independently selected from: hydrogen,

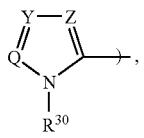

halogen, $C_{1-4}$alkyl, substituted $C_{1-4}$alkyl, $C_{1-4}$alkyloxy, substituted $C_{1-4}$alkyloxy, furan, substituted furan, thiophene and substituted thiophene,
  where Q is nitrogen, Y is selected from: nitrogen and —C($R^{70}$)—, and Z is selected from: nitrogen and —C($R^{48}$)—, provided that at most one of Y and Z are nitrogen, and
  $R^{30}$ is selected from: $C_{1-4}$alkyl and $C_{1-4}$alkyl substituted with form one to three fluorine atoms,
  where $R^{70}$ is selected from: hydrogen, and halogen, and
  $R^{48}$ is selected from: hydrogen, $C_{1-4}$alkyl, substituted $C_{1-4}$alkyl, aryl, substituted aryl, heteroaryl, substituted heteroaryl, cylcoalkyl, substituted cycloalkyl, heterocycloalkyl, substituted heterocycloalkyl, and halogen;
  $R^{43}$ is selected from: hydrogen, halogen, $C_{1-4}$alkyl, substituted $C_{1-4}$alkyl, $C_{1-4}$alkyloxy, substituted $C_{1-4}$alkyloxy, furan and thiophene;
  $R^{44}$ is absent or selected from: —$(CR^{60}R^{61})_m$AR wherein the AR is unsubstituted, —$(CR^{60}R^{61})_m$AR wherein the AR is substituted and $C_{1-6}$alkyl,
    where m is 0 to 3 and AR is a cyclic or polycyclic aromatic or saturated or unsaturated non-aromatic ring containing from 3 to 16 carbon atoms and optionally containing from one to three heteroatoms, provided that when the ring is aromatic and the number of carbon atoms is 3 the ring contains at least two heteroatoms and when the ring is aromatic and the number of carbon atoms is 4 the ring contains at least one heteroatom, and
    $R^{60}$ and $R^{61}$ are independently selected from: hydrogen and $C_{1-4}$alkyl, provided that when m is 3 no more than 4 of $R^{60}$ and $R^{61}$ when added together are $C_{1-4}$alkyl,
  $R^{45}$ is selected from hydrogen and $C_{1-4}$alkyl;
  $R^{20}$ is selected from hydrogen, $C_{1-4}$alkyl and hydroxy;
  X is selected from O, S and $NR^{49}$,
    where $R^{49}$ is selected from hydrogen and $C_{1-4}$alkyl; and
  n is 0 to 2 and this moiety is optionally, if applicable, substituted by hydroxy$C_{1-4}$alkyl;
  provided that one and only one of $R^{41}$ and $R^{42}$ is

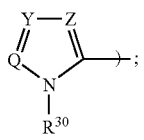

and/or pharmaceutically acceptable salts thereof.

Included among the presently invented compounds of Formula (I) are those in which:

$R^{41}$ and $R^{42}$ are independently selected from: hydrogen,

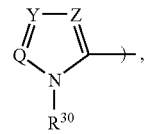

halogen, $C_{1-4}$alkyl, trifluoromethyl, methoxy, furan and thiophene,
  where Q is nitrogen, Y is selected from: nitrogen and —C($R^{70}$)—, and Z is selected from: nitrogen and —C($R^{48}$)—, provided that at most one of Y and Z are nitrogen, and
  $R^{30}$ is $C_{1-4}$alkyl,
  where $R^{70}$ is selected from: hydrogen, and halogen, and
  $R^{48}$ is selected from: hydrogen, $C_{1-4}$alkyl, trifluoromethyl, aryl, heteroaryl, cylcoalkyl, heterocycloalkyl, and halogen;
  $R^{43}$ is selected from: hydrogen, halogen, $C_{1-4}$alkyl and methoxy;
  $R^{44}$ is absent or selected from: —$(CR^{60}R^{61})_m$AAR wherein the AAR is unsubstituted, —$(CR^{60}R^{61})_m$AAR wherein the AAR is substituted and $C_{1-6}$alkyl,
    where m is 0 to 3 and AAR is selected from phenyl, indole, naphthalene, pyridine and cyclohexyl, and
    $R^{60}$ and $R^{61}$ are independently selected from: hydrogen and methyl, provided that when m is 3 no more than 4 of $R^{60}$ and $R^{61}$ when added together are methyl,
  $R^{45}$ is selected from hydrogen and $C_{1-4}$alkyl;
  $R^{20}$ is selected from hydrogen, methyl and hydroxy;
  X is selected from O, S and $NR^{49}$,
    where $R^{49}$ is selected from hydrogen and methyl; and
  n is 1 to 2 and this moiety is optionally substituted by hydroxylmethyl;
  provided that one and only one of $R^{41}$ and $R^{42}$ is

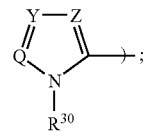

and/or pharmaceutically acceptable salts thereof.

Included among the presently invented compounds of Formula (I) are those in which:

$R^{41}$ and $R^{42}$ are independently selected from: hydrogen,

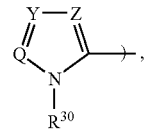

halogen, $C_{1-4}$alkyl, trifluoromethyl, methoxy and furan,
  where Q is nitrogen, Y is selected from: nitrogen and —C($R^{70}$)—, and Z is selected from: nitrogen and —C($R^{48}$)—, provided that at most one of Y and Z are nitrogen, and
  $R^{30}$ is $C_{1-4}$alkyl,
  where $R^{70}$ is selected from: hydrogen, and halogen, and
  $R^{48}$ is selected from: hydrogen, $C_{1-4}$alkyl, trifluoromethyl, phenyl, cyclopropyl, and halogen;
  $R^{43}$ is selected from: hydrogen, halogen, $C_{1-4}$alkyl and methoxy;

$R^{44}$ is absent or selected from: —$(CR^{60}R^{61})_m$AAR
wherein the AAR is unsubstituted, —$(CR^{60}R^{61})_m$AAR
wherein the AAR is substituted and $C_{1-6}$alkyl,
where m is 0 to 3 and AAR is selected from phenyl, indole, naphthalene, pyridine and cyclohexyl, and
$R^{60}$ and $R^{61}$ are independently selected from: hydrogen and methyl, provided that when m is 3 no more than 4 of $R^{60}$ and $R^{61}$ when added together are methyl,
$R^{45}$ is selected from hydrogen and $C_{1-4}$alkyl;
$R^{20}$ is selected from hydrogen, methyl and hydroxy;
X is selected from O, S and $NR^{49}$,
where $R^{49}$ is selected from hydrogen and methyl; and
n is 1 to 2 and this moiety is optionally substituted by hydroxylmethyl;
provided that one and only one of $R^{41}$ and $R^{42}$ is

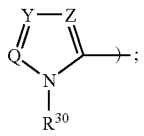

and/or pharmaceutically acceptable salts thereof.

Included among the presently invented compounds of Formula (I) are those in which:
$R^{41}$ is selected from: chlorine, ethyl, methyl and methoxy;
$R^{42}$ is

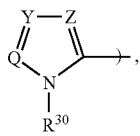

where Q is nitrogen, Y is —CH— and Z is —$C(R^{48})$—, and $R^{30}$ is selected from methyl and ethyl,
where $R^{48}$ is selected from: hydrogen, methyl, chlorine and bromine;
$R^{43}$ is hydrogen;
$R^{44}$ is —$CH_2$-phenyl wherein the phenyl is substituted by one or two substituents selected from fluorine and trifluoromethyl;
$R^{45}$ is hydrogen;
$R^{20}$ is hydrogen;
X is selected from O and S; and
n is 1;
and/or pharmaceutically acceptable salts thereof.

Included in the presently invented compounds of Formula (I) are compounds of Formula (AA):

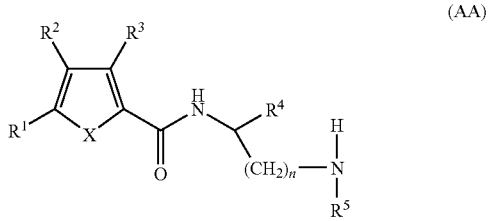

(AA)

wherein:
$R^1$ and $R^2$ are independently selected from: hydrogen,

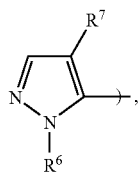

halogen, $C_{1-4}$alkyl, furan and thiophene,
where $R^6$ is $C_{1-4}$alkyl and $R^7$ is selected from hydrogen, $C_{1-4}$alkyl and halogen;
$R^3$ is selected from: hydrogen, halogen, $C_{1-4}$alkyl, furan and thiophene;
$R^4$ is selected from —$(CH_2)_m$aryl and —$(CH_2)_m$aryl wherein the aryl is substituted,
where m is 0 to 2;
$R^5$ is selected from hydrogen and $C_{1-4}$alkyl;
X is selected from O and S; and
n is 0 to 2;
provided that one and only one of $R^1$ and $R^2$ is

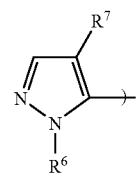

and further provided that at least one of $R^1$, $R^2$ and $R^3$ is hydrogen;
and/or pharmaceutically acceptable salts thereof.

Included in the presently invented compounds of Formula (I) are compounds of Formula (BB):

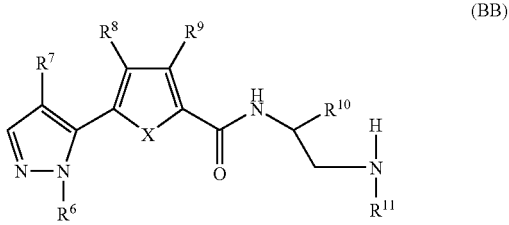

(BB)

wherein:
$R^8$ and $R^9$ are independently selected from: hydrogen, halogen, $C_{1-4}$alkyl, furan and thiophene;
$R^6$ is $C_{1-4}$alkyl;
$R^7$ is selected from hydrogen, $C_{1-4}$alkyl and halogen;
$R^{10}$ is selected from: —$(CH_2)_m C_5$-$C_{12}$aryl and —$(CH_2)_m C_5$-$C_{12}$aryl wherein the aryl is substituted,
where m is 0 to 2;
$R^{11}$ is selected from hydrogen and $C_{1-4}$alkyl;
X is selected from O and S; and
provided that at least one of $R^8$ and $R^9$ is hydrogen;
and/or pharmaceutically acceptable salts thereof.

Included in the presently invented compounds of Formula (I) are compounds of Formula (CC):

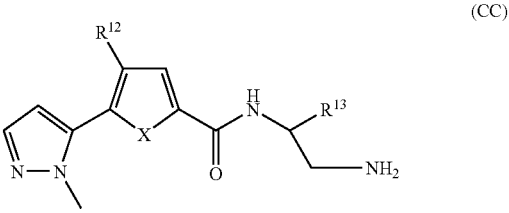

(CC)

wherein:
$R^{12}$ is selected from: hydrogen, halogen, $C_{1-4}$alkyl, furan and thiophene;

R$^{13}$ is selected from: —(CH$_2$)$_m$phenyl and —(CH$_2$)$_m$phenyl wherein the phenyl is substituted,
where m is 0 to 2;
X is selected from O and S; and
and/or pharmaceutically acceptable salts thereof.

Included among the compounds useful in the present invention are:

N-[2-amino-1-(phenylmethyl)ethyl]-4-bromo-5-(1-methyl-1H-pyrazol-5-yl)-2-furancarboxamide;
N-(2-amino-1-phenylethyl)-5-(1-methyl-1H-pyrazol-5-yl)-2-thiophenecarboxamide;
N-[2-amino-1-(phenylmethyl)ethyl]-5-(1-methyl-1H-pyrazol-5-yl)-2-thiophenecarboxamide;
N-[2-amino-1-(phenylmethyl)ethyl]-4-(1-methyl-1H-pyrazol-5-yl)-2-thiophenecarboxamide;
N-(2-amino-1-phenylethyl)-4-(1-methyl-1H-pyrazol-5-yl)-2-thiophenecarboxamide;
N-(2-amino-1-{[2-(trifluoromethyl)phenyl]methyl}ethyl)-5-(1-methyl-1H-pyrazol-5-yl)-2-thiophenecarboxamide;
N-[2-amino-1-(phenylmethyl)ethyl]-4-bromo-5-(1-methyl-1H-pyrazol-5-yl)-2-thiophenecarboxamide;
N-(2-amino-1-phenylethyl)-4-bromo-5-(1-methyl-1H-pyrazol-5-yl)-2-thiophenecarboxamide;
N-((1S)-2-amino-1-{[2-(trifluoromethyl)phenyl]methyl}ethyl)-5-(1-methyl-1H-pyrazol-5-yl)-2-furancarboxamide;
N-((1S)-2-amino-1-{[3-(trifluoromethyl)phenyl]methyl}ethyl)-5-(1-methyl-1H-pyrazol-5-yl)-2-thiophenecarboxamide;
N-((1S)-2-amino-1-{[2-(trifluoromethyl)phenyl]methyl}ethyl)-4-bromo-5-(1-methyl-1H-pyrazol-5-yl)-2-thiophenecarboxamide;
N-((1S)-2-amino-1-{[3-(trifluoromethyl)phenyl]methyl}ethyl)-4-bromo-5-(1-methyl-1H-pyrazol-5-yl)-2-thiophenecarboxamide;
N-((1S)-2-amino-1-{[3-(trifluoromethyl)phenyl]methyl}ethyl)-5-(1-methyl-1H-pyrazol-5-yl)-2-furancarboxamide;
N-((1S)-2-amino-1-{[3-(trifluoromethyl)phenyl]methyl}ethyl)-4-bromo-5-(1-methyl-1H-pyrazol-5-yl)-2-furancarboxamide;
N-((1S)-2-amino-1-{[2-(trifluoromethyl)phenyl]methyl}ethyl)-4-bromo-5-(1-methyl-1H-pyrazol-5-yl)-2-furancarboxamide;
N-[2-amino-1-(phenylmethyl)ethyl]-4-methyl-5-(1-methyl-1H-pyrazol-5-yl)-2-thiophenecarboxamide;
N-[2-amino-1-(phenylmethyl)ethyl]-4-(3-furanyl)-5-(1-methyl-1H-pyrazol-5-yl)-2-thiophenecarboxamide;
N-[(1S)-2-amino-1-(phenylmethyl)ethyl]-5-chloro-4-(1-methyl-1H-pyrazol-5-yl)-2-thiophenecarboxamide;
N-[2-amino-1-(phenylmethyl)ethyl]-4-bromo-3-(methyloxy)-5-(1-methyl-1H-pyrazol-5-yl)-2-thiophenecarboxamide;
N-[3-amino-1-(phenylmethyl)propyl]-4-bromo-5-(1-methyl-1H-pyrazol-5-yl)-2-thiophenecarboxamide;
4-bromo-N-[2-(methylamino)-1-phenylethyl]-5-(1-methyl-1H-pyrazol-5-yl)-2-thiophenecarboxamide;
N-[2-amino-1-(phenylmethyl)ethyl]-5-methyl-4-(1-methyl-1H-pyrazol-5-yl)-2-thiophenecarboxamide;
N-[2-amino-1-(phenylmethyl)ethyl]-5-chloro-4-(1-methyl-1H-pyrazol-5-yl)-2-thiophenecarboxamide;
N-[2-amino-1-(phenylmethyl)ethyl]-4-(4-chloro-1-methyl-1H-pyrazol-5-yl)-2-thiophenecarboxamide;
N-((1S)-2-amino-1-{[2-(trifluoromethyl)phenyl]methyl}ethyl)-5-chloro-4-(1-methyl-1H-pyrazol-5-yl)-2-thiophenecarboxamide;
N-((1S)-2-amino-1-{[2-(trifluoromethyl)phenyl]methyl}ethyl)-4-(4-chloro-1-methyl-1H-pyrazol-5-yl)-2-thiophenecarboxamide;
N-[2-amino-1-(phenylmethyl)ethyl]-4-(4-bromo-1-methyl-1H-pyrazol-5-yl)-5-methyl-2-thiophenecarboxamide;
N-((1S)-2-amino-1-{[2-(trifluoromethyl)phenyl]methyl}ethyl)-4-(4-bromo-1-methyl-1H-pyrazol-5-yl)-5-methyl-2-thiophenecarboxamide;
N-((1S)-2-amino-1-{[2-(trifluoromethyl)phenyl]methyl}ethyl)-4-(4-chloro-1-methyl-1H-pyrazol-5-yl)-5-methyl-2-thiophenecarboxamide;
N-[2-amino-1-(phenylmethyl)ethyl]-4-(4-chloro-1-methyl-1H-pyrazol-5-yl)-5-methyl-2-thiophenecarboxamide;
N-((1S)-2-amino-1-{[2-(trifluoromethyl)phenyl]methyl}ethyl)-5-chloro-4-(4-chloro-1-methyl-1H-pyrazol-5-yl)-2-thiophenecarboxamide;
N-((1S)-2-amino-1-{[2-(trifluoromethyl)phenyl]methyl}ethyl)-4-(4-bromo-1-methyl-1H-pyrazol-5-yl)-5-chloro-2-thiophenecarboxamide;
N-[2-amino-1-(phenylmethyl)ethyl]-4-(1-methyl-4-phenyl-1H-pyrazol-5-yl)-2-thiophenecarboxamide;
N-((1S)-2-amino-1-{[2-(trifluoromethyl)phenyl]methyl}ethyl)-4-(1-methyl-4-phenyl-1H-pyrazol-5-yl)-2-thiophenecarboxamide;
N-((1S)-2-amino-1-{[2-(trifluoromethyl)phenyl]methyl}ethyl)-5-(4-chloro-1-methyl-1H-pyrazol-5-yl)-4-methyl-2-thiophenecarboxamide;
N-((1S)-2-amino-1-{[2-(trifluoromethyl)phenyl]methyl}ethyl)-5-(4-bromo-1-methyl-1H-pyrazol-5-yl)-4-methyl-2-thiophenecarboxamide;
N-((1S)-2-amino-1-{[2-(trifluoromethyl)phenyl]methyl}ethyl)-4-(4-fluoro-1-methyl-1H-pyrazol-5-yl)-2-thiophenecarboxamide;
N-((1S)-2-amino-1-{[2-(trifluoromethyl)phenyl]methyl}ethyl)-4-(4-fluoro-1-methyl-1H-pyrazol-5-yl)-5-methyl-2-thiophenecarboxamide;
N-[1-(aminomethyl)-3-phenylpropyl]-4-bromo-5-(1-methyl-1H-pyrazol-5-yl)-2-thiophenecarboxamide;
N-[1-(aminomethyl)-3-phenylpropyl]-5-(1-methyl-1H-pyrazol-5-yl)-2-thiophenecarboxamide;
4-bromo-N-[3-(methylamino)-1-phenylpropyl]-5-(1-methyl-1H-pyrazol-5-yl)-2-thiophenecarboxamide;
N-[3-(methylamino)-1-phenylpropyl]-5-(1-methyl-1H-pyrazol-5-yl)-2-thiophenecarboxamide;
4-bromo-N-[2-(methylamino)-1-(phenylmethyl)ethyl]-5-(1-methyl-1H-pyrazol-5-yl)-2-thiophenecarboxamide
N-((1S)-2-amino-1-{[4-(trifluoromethyl)phenyl]methyl}ethyl)-4-bromo-5-(1-methyl-1H-pyrazol-5-yl)-2-thiophenecarboxamide;
N-[1-(aminomethyl)-2-methyl-2-phenylpropyl]-4-bromo-5-(1-methyl-1H-pyrazol-5-yl)-2-thiophenecarboxamide;
N-{(1S)-2-amino-1-[(2,4-dichlorophenyl)methyl]ethyl}-4-bromo-5-(1-methyl-1H-pyrazol-5-yl)-2-thiophenecarboxamide;
N-[2-amino-1-(phenylmethyl)ethyl]-4-bromo-5-(4-chloro-1-methyl-1H-pyrazol-5-yl)-2-thiophenecarboxamide;
N-[2-amino-1-(phenylmethyl)ethyl]-4-bromo-1-methyl-5-(1-methyl-1H-pyrazol-5-yl)-1H-pyrrole-2-carboxamide;
N-[2-amino-1-(phenylmethyl)ethyl]-1-methyl-5-(1-methyl-1H-pyrazol-5-yl)-1H-pyrrole-2-carboxamide;
N-[2-amino-1-(phenylmethyl)ethyl]-1-methyl-4-(1-methyl-1H-pyrazol-5-yl)-1H-pyrrole-2-carboxamide;
N-((1S)-2-amino-1-{[2-(trifluoromethyl)phenyl]methyl}ethyl)-4-(1-methyl-1H-pyrazol-5-yl)-2-thiophenecarboxamide;
N-[2-(methylamino)-1-(phenylmethyl)ethyl]-4-(1-methyl-1H-pyrazol-5-yl)-2-thiophenecarboxamide;

N-[2-amino-1-(phenylmethyl)ethyl]-N-methyl-4-(1-methyl-1H-pyrazol-5-yl)-2-thiophenecarboxamide;
N-[1-(aminomethyl)-2-methyl-2-phenylpropyl]-4-(1-methyl-1H-pyrazol-5-yl)-2-thiophenecarboxamide;
N-{(1S)-2-amino-1-[(2,4-dichlorophenyl)methyl]ethyl}-4-(1-methyl-1H-pyrazol-5-yl)-2-thiophenecarboxamide;
N-((1S)-2-amino-1-{[2-(trifluoromethyl)phenyl]methyl}ethyl)-5-methyl-4-(1-methyl-1H-pyrazol-5-yl)-2-thiophenecarboxamide;
N-{(1S)-2-amino-1-[(3-fluorophenyl)methyl]ethyl}-4-(1-methyl-1H-pyrazol-5-yl)-2-thiophenecarboxamide;
N-{(1S)-2-amino-1-[(4-fluorophenyl)methyl]ethyl}-4-(1-methyl-1H-pyrazol-5-yl)-2-thiophenecarboxamide;
N-((1S)-2-amino-1-{[3-(trifluoromethyl)phenyl]methyl}ethyl)-4-(1-methyl-1H-pyrazol-5-yl)-2-thiophenecarboxamide;
N-((1S)-2-amino-1-{[4-(trifluoromethyl)phenyl]methyl}ethyl)-4-(1-methyl-1H-pyrazol-5-yl)-2-thiophenecarboxamide;
N-[2-amino-1-(phenylmethyl)ethyl]-5-(1-methyl-1H-1,2,4-triazol-5-yl)-2-thiophenecarboxamide;
N-[2-amino-1-(phenylmethyl)ethyl]-5-(1-methyl-1H-imidazol-5-yl)-2-thiophenecarboxamide;
N-((1S)-2-amino-1-{[2-(trifluoromethyl)phenyl]methyl}ethyl)-3,4-dibromo-5-(1-methyl-1H-pyrazol-5-yl)-2-thiophenecarboxamide;
N-((1S)-2-amino-1-{[2-(trifluoromethyl)phenyl]methyl}ethyl)-4-bromo-5-(1-methyl-1H-pyrazol-5-yl)-2-thiophenecarboxamide;
N-{(1S)-2-amino-1-[(2-chlorophenyl)methyl]ethyl}-4-bromo-5-(1-methyl-1H-pyrazol-5-yl)-2-thiophenecarboxamide;
N-{(1S)-2-amino-1-[(2-fluorophenyl)methyl]ethyl}-4-bromo-5-(1-methyl-1H-pyrazol-5-yl)-2-thiophenecarboxamide;
N-[(1S)-2-amino-1-(1H-indol-3-ylmethyl)ethyl]-4-bromo-5-(1-methyl-1H-pyrazol-5-yl)-2-thiophenecarboxamide;
N-{(1S)-2-amino-1-[(2-chlorophenyl)methyl]ethyl}-4-(1-methyl-1H-pyrazol-5-yl)-2-thiophenecarboxamide;
N-{(1S)-2-amino-1-[(2-fluorophenyl)methyl]ethyl}-4-(1-methyl-1H-pyrazol-5-yl)-2-thiophenecarboxamide;
N-[2-amino-1-(1-naphthalenyl)ethyl]-4-bromo-5-(1-methyl-1H-pyrazol-5-yl)-2-thiophenecarboxamide;
N-[2-amino-1-(1-naphthalenyl)ethyl]-4-(1-methyl-1H-pyrazol-5-yl)-2-thiophenecarboxamide;
N-{2-amino-1-[2-(trifluoromethyl)phenyl]ethyl}-4-(1-methyl-1H-pyrazol-5-yl)-2-thiophenecarboxamide;
N-{2-amino-1-[2-(trifluoromethyl)phenyl]ethyl}-4-bromo-5-(1-methyl-1H-pyrazol-5-yl)-2-thiophenecarboxamide;
N-[2-amino-1-(phenylmethyl)ethyl]-4-(4-bromo-1-methyl-1H-pyrazol-5-yl)-2-thiophenecarboxamide;
N-((1S)-2-amino-1-{[2-(trifluoromethyl)phenyl]methyl}ethyl)-4-(4-bromo-1-methyl-1H-pyrazol-5-yl)-2-thiophenecarboxamide;
N-{(1S)-2-amino-1-[(3,5-difluorophenyl)methyl]ethyl}-4-(1-methyl-1H-pyrazol-5-yl)-2-thiophenecarboxamide;
N-{(1S)-2-amino-1-[(3-chlorophenyl)methyl]ethyl}-4-(1-methyl-1H-pyrazol-5-yl)-2-thiophenecarboxamide;
N-{(1S)-2-amino-1-[(4-chlorophenyl)methyl]ethyl}-4-(1-methyl-1H-pyrazol-5-yl)-2-thiophenecarboxamide;
N-((1S)-2-amino-1-{[2-(trifluoromethyl)phenyl]methyl}ethyl)-4-bromo-5-(1-methyl-1H-pyrazol-5-yl)-2-furancarboxamide;
N-(3-amino-1-phenylpropyl)-4-bromo-5-(1-methyl-1H-pyrazol-5-yl)-2-thiophenecarboxamide;
N-[2-amino-1-(phenylmethyl)ethyl]-5-(1-ethyl-1H-pyrazol-5-yl)-2-thiophenecarboxamide;
N-[2-amino-1-(phenylmethyl)ethyl]-3,4-dibromo-5-(1-methyl-1H-pyrazol-5-yl)-2-thiophenecarboxamide;
N-[2-amino-1-(phenylmethyl)ethyl]-5-(1,4-dimethyl-1H-pyrazol-5-yl)-2-thiophenecarboxamide;
N-[2-amino-1-(phenylmethyl)ethyl]-4-bromo-5-(1,4-dimethyl-1H-pyrazol-5-yl)-2-thiophenecarboxamide;
N-[2-amino-1-(phenylmethyl)ethyl]-4-(1,4-dimethyl-1H-pyrazol-5-yl)-2-thiophenecarboxamide;
N-[2-amino-1-(phenylmethyl)ethyl]-N-hydroxy-4-(1-methyl-1H-pyrazol-5-yl)-2-thiophenecarboxamide;
N-((1S)-2-amino-1-{[2-(trifluoromethyl)phenyl]methyl}ethyl)-4-(1,4-dimethyl-1H-pyrazol-5-yl)-2-thiophenecarboxamide;
N-((1S)-2-amino-1-{[2-(trifluoromethyl)phenyl]methyl}ethyl)-4-(1-ethyl-1H-pyrazol-5-yl)-2-thiophenecarboxamide;
N-[2-amino-1-(phenylmethyl)ethyl]-5-chloro-4-(1-ethyl-1H-pyrazol-5-yl)-2-thiophenecarboxamide;
N-((1S)-2-amino-1-{[2-(trifluoromethyl)phenyl]methyl}ethyl)-5-chloro-4-(1-ethyl-1H-pyrazol-5-yl)-2-thiophenecarboxamide;
N-((1S)-2-amino-1-{[2-(trifluoromethyl)phenyl]methyl}ethyl)-5-chloro-4-(1,4-dimethyl-1H-pyrazol-5-yl)-2-thiophenecarboxamide;
N-((1S)-2-amino-1-{[2-(trifluoromethyl)phenyl]methyl}ethyl)-4-(4-chloro-1-ethyl-1H-pyrazol-5-yl)-2-thiophenecarboxamide;
N-((1S)-2-amino-1-{[2-(trifluoromethyl)phenyl]methyl}ethyl)-4-(4-bromo-1-ethyl-1H-pyrazol-5-yl)-2-thiophenecarboxamide;
N-[2-amino-1-(phenylmethyl)ethyl]-3-(methyloxy)-4-(1-methyl-1H-pyrazol-5-yl)-2-thiophenecarboxamide;
N-{(1S)-2-amino-1-[(3-fluorophenyl)methyl]ethyl}-5-chloro-4-(1-methyl-1H-pyrazol-5-yl)-2-thiophenecarboxamide;
N-{(1S)-2-amino-1-[(3-fluorophenyl)methyl]ethyl}-5-chloro-4-(4-chloro-1-methyl-1H-pyrazol-5-yl)-2-thiophenecarboxamide;
N-((1S)-2-amino-1-{[2-(trifluoromethyl)phenyl]methyl}ethyl)-5-chloro-4-(4-fluoro-1-methyl-1H-pyrazol-5-yl)-2-thiophenecarboxamide;
N-((1S)-2-amino-1-{[2-(trifluoromethyl)phenyl]methyl}ethyl)-5-ethyl-4-(1-methyl-1H-pyrazol-5-yl)-2-thiophenecarboxamide;
N-((1S)-2-amino-1-{[2-(trifluoromethyl)phenyl]methyl}ethyl)-4-(1,4-dimethyl-1H-pyrazol-5-yl)-5-methyl-2-thiophenecarboxamide;
N-((1S)-2-amino-1-{[2-(trifluoromethyl)phenyl]methyl}ethyl)-4-(4-chloro-1-methyl-1H-pyrazol-5-yl)-5-ethyl-2-thiophenecarboxamide;
N-((1S)-2-amino-1-{[2-(trifluoromethyl)phenyl]methyl}ethyl)-4-(4-bromo-1-methyl-1H-pyrazol-5-yl)-5-ethyl-2-thiophenecarboxamide;
N-[(1S)-2-amino-1-(cyclohexylmethyl)ethyl]-4-(4-chloro-1-methyl-1H-pyrazol-5-yl)-5-methyl-2-thiophenecarboxamide;
N-[(1S)-2-amino-1-(cyclohexylmethyl)ethyl]-5-methyl-4-(1-methyl-1H-pyrazol-5-yl)-2-thiophenecarboxamide;
N-[(1S)-2-amino-1-(cyclohexylmethyl)ethyl]-5-chloro-4-(1-methyl-1H-pyrazol-5-yl)-2-thiophenecarboxamide;
N-[(1S)-2-amino-1-(cyclohexylmethyl)ethyl]-4-(4-bromo-1-methyl-1H-pyrazol-5-yl)-5-methyl-2-thiophenecarboxamide;
N-[(1S)-2-amino-1-(cyclohexylmethyl)ethyl]-5-chloro-4-(4-chloro-1-methyl-1H-pyrazol-5-yl)-2-thiophenecarboxamide;

N-[(1S)-2-amino-1-(cyclohexylmethyl)ethyl]-4-(4-bromo-1-methyl-1H-pyrazol-5-yl)-5-chloro-2-thiophenecarboxamide;

N-((1S)-2-amino-1-{[2-(trifluoromethyl)phenyl]methyl}ethyl)-4-(1-methyl-1H-pyrazol-5-yl)-2-furancarboxamide;

N-((1S)-2-amino-1-{[2-(trifluoromethyl)phenyl]methyl}ethyl)-4-(4-ethyl-1-methyl-1H-pyrazol-5-yl)-5-methyl-2-thiophenecarboxamide;

N-((1S)-2-amino-1-{[2-(trifluoromethyl)phenyl]methyl}ethyl)-4-(1,4-dimethyl-1H-pyrazol-5-yl)-5-ethyl-2-thiophenecarboxamide;

N-((1S)-2-amino-1-{[2-(trifluoromethyl)phenyl]methyl}ethyl)-5-methyl-4-[1-methyl-4-(1-methylethyl)-1H-pyrazol-5-yl]-2-thiophenecarboxamide;

N-((1S)-2-amino-1-{[2-(trifluoromethyl)phenyl]methyl}ethyl)-4-(4-chloro-1-methyl-1H-pyrazol-5-yl)-5-propyl-2-thiophenecarboxamide;

N-((1S)-2-amino-1-{[2-(trifluoromethyl)phenyl]methyl}ethyl)-4-(4-bromo-1-methyl-1H-pyrazol-5-yl)-5-propyl-2-thiophenecarboxamide;

N-((1S)-2-amino-1-{[2-(trifluoromethyl)phenyl]methyl}ethyl)-4-(1,4-dimethyl-1H-pyrazol-5-yl)-5-propyl-2-thiophenecarboxamide;

N-((1S)-2-amino-1-{[2-(trifluoromethyl)phenyl]methyl}ethyl)-5-methyl-4-(1-methyl-4-propyl-1H-pyrazol-5-yl)-2-thiophenecarboxamide;

N-((1S)-2-amino-1-{[2-(trifluoromethyl)phenyl]methyl}ethyl)-5-methyl-4-(1-methyl-1H-pyrazol-5-yl)-2-furancarboxamide;

N-((1S)-2-amino-1-{[2-(trifluoromethyl)phenyl]methyl}ethyl)-4-(4-bromo-1-methyl-1H-pyrazol-5-yl)-5-methyl-2-furancarboxamide;

N-((1S)-2-amino-1-{[2-(trifluoromethyl)phenyl]methyl}ethyl)-4-(4-chloro-1-methyl-1H-pyrazol-5-yl)-5-methyl-2-furancarboxamide;

N-((1S)-2-amino-1-{[2-(trifluoromethyl)phenyl]methyl}ethyl)-4-(1,4-dimethyl-1H-pyrazol-5-yl)-5-methyl-2-furancarboxamide;

N-{(1S)-2-amino-1-[(3-fluorophenyl)methyl]ethyl}-4-(4-chloro-1-methyl-1H-pyrazol-5-yl)-5-ethyl-2-thiophenecarboxamide;

N-{(1S)-2-amino-1-[(3-fluorophenyl)methyl]ethyl}-4-(1,4-dimethyl-1H-pyrazol-5-yl)-5-ethyl-2-thiophenecarboxamide;

N-((1S)-2-amino-1-{[3-(trifluoromethyl)phenyl]methyl}ethyl)-4-(1,4-dimethyl-1H-pyrazol-5-yl)-5-ethyl-2-thiophenecarboxamide;

N-((1S)-2-amino-1-{[2-(trifluoromethyl)phenyl]methyl}ethyl)-5-ethyl-4-(4-ethyl-1-methyl-1H-pyrazol-5-yl)-2-thiophenecarboxamide;

N-((1S)-2-amino-1-{[2-(trifluoromethyl)phenyl]methyl}ethyl)-5-ethyl-4-(1-methyl-4-propyl-1H-pyrazol-5-yl)-2-thiophenecarboxamide;

N-((1S)-2-amino-1-{[2-(trifluoromethyl)phenyl]methyl}ethyl)-4-(3-chloro-4-ethyl-1-methyl-1H-pyrazol-5-yl)-2-thiophenecarboxamide;

N-((1S)-2-amino-1-{[2-(trifluoromethyl)phenyl]methyl}ethyl)-4-(3-chloro-1-methyl-4-propyl-1H-pyrazol-5-yl)-2-thiophenecarboxamide;

N-((1S)-2-amino-1-{[2-(trifluoromethyl)phenyl]methyl}ethyl)-5-chloro-4-(1-methyl-1H-pyrazol-5-yl)-2-furancarboxamide;

N-((1S)-2-amino-1-{[2-(trifluoromethyl)phenyl]methyl}ethyl)-5-chloro-4-(4-chloro-1-methyl-1H-pyrazol-5-yl)-2-furancarboxamide;

N-((1S)-2-amino-1-{[2-(trifluoromethyl)phenyl]methyl}ethyl)-4-(3-chloro-4-ethyl-1-methyl-1H-pyrazol-5-yl)-2-furancarboxamide;

N-((1S)-2-amino-1-{[2-(trifluoromethyl)phenyl]methyl}ethyl)-4-(3-chloro-1,4-dimethyl-1H-pyrazol-5-yl)-2-furancarboxamide;

N-((1S)-2-amino-1-{[2-(trifluoromethyl)phenyl]methyl}ethyl)-4-(4-chloro-1-methyl-1H-pyrazol-5-yl)-5-ethyl-2-furancarboxamide;

N-{(1S)-2-amino-1-[(4-fluorophenyl)methyl]ethyl}-4-(4-chloro-1-methyl-1H-pyrazol-5-yl)-5-ethyl-2-furancarboxamide;

N-{(1S)-2-amino-1-[(3-fluorophenyl)methyl]ethyl}-4-(4-chloro-1-methyl-1H-pyrazol-5-yl)-5-ethyl-2-furancarboxamide;

N-{(1S)-2-amino-1-[(3-fluorophenyl)methyl]ethyl}-5-chloro-4-(1-methyl-1H-pyrazol-5-yl)-2-furancarboxamide;

N-{(1S)-2-amino-1-[(4-fluorophenyl)methyl]ethyl}-5-chloro-4-(1-methyl-1H-pyrazol-5-yl)-2-furancarboxamide;

N-((1S)-2-amino-1-{[3-(trifluoromethyl)phenyl]methyl}ethyl)-5-chloro-4-(1-methyl-1H-pyrazol-5-yl)-2-furancarboxamide;

N-{(1S)-2-amino-1-[(3-fluorophenyl)methyl]ethyl}-5-chloro-4-(4-chloro-1-methyl-1H-pyrazol-5-yl)-2-furancarboxamide;

N-((1S)-2-amino-1-{[3-(trifluoromethyl)phenyl]methyl}ethyl)-5-chloro-4-(4-chloro-1-methyl-1H-pyrazol-5-yl)-2-furancarboxamide;

N-{(1S)-2-amino-1-[(4-fluorophenyl)methyl]ethyl}-5-chloro-4-(4-chloro-1-methyl-1H-pyrazol-5-yl)-2-furancarboxamide;

N-{(1S)-2-amino-1-[(3-fluorophenyl)methyl]ethyl}-5-chloro-4-(1,4-dimethyl-1H-pyrazol-5-yl)-2-furancarboxamide;

N-{(1S)-2-amino-1-[(4-fluorophenyl)methyl]ethyl}-5-chloro-4-(1,4-dimethyl-1H-pyrazol-5-yl)-2-furancarboxamide;

N-((1S)-2-amino-1-{[3-(trifluoromethyl)phenyl]methyl}ethyl)-5-chloro-4-(1,4-dimethyl-1H-pyrazol-5-yl)-2-furancarboxamide;

N-((1S)-2-amino-1-{[2-(trifluoromethyl)phenyl]methyl}ethyl)-5-chloro-4-(1,4-dimethyl-1H-pyrazol-5-yl)-2-furancarboxamide;

N-((1S)-2-amino-1-{[2-(trifluoromethyl)phenyl]methyl}ethyl)-4-bromo-5-(4-chloro-1-methyl-1H-pyrazol-5-yl)-2-thiophenecarboxamide;

N-((1S)-2-amino-1-{[2-(trifluoromethyl)phenyl]methyl}ethyl)-4-bromo-5-(4-bromo-1-methyl-1H-pyrazol-5-yl)-2-thiophenecarboxamide;

N-{(1S)-2-amino-1-[(3,4-difluorophenyl)methyl]ethyl}-4-(1-methyl-1H-pyrazol-5-yl)-2-thiophenecarboxamide;

N-{(1S)-2-amino-1-[(3,4-dichlorophenyl)methyl]ethyl}-4-(1-methyl-1H-pyrazol-5-yl)-2-thiophenecarboxamide;

N-{(1S)-2-amino-1-[(2,6-difluorophenyl)methyl]ethyl}-4-(1-methyl-1H-pyrazol-5-yl)-2-thiophenecarboxamide;

N-{(1S)-2-amino-1-[(2,5-difluorophenyl)methyl]ethyl}-4-(1-methyl-1H-pyrazol-5-yl)-2-thiophenecarboxamide;

N-{(1S)-2-amino-1-[(2,4-difluorophenyl)methyl]ethyl}-4-(1-methyl-1H-pyrazol-5-yl)-2-thiophenecarboxamide;

N-((1S)-2-amino-1-{[3-(trifluoromethyl)phenyl]methyl}ethyl)-5-methyl-4-(1-methyl-1H-pyrazol-5-yl)-2-thiophenecarboxamide;

N-{(1S)-2-amino-1-[(4-fluorophenyl)methyl]ethyl}-5-chloro-4-(1-methyl-1H-pyrazol-5-yl)-2-thiophenecarboxamide;

N-((1S)-2-amino-1-{[3-(trifluoromethyl)phenyl]methyl}ethyl)-5-chloro-4-(1-methyl-1H-pyrazol-5-yl)-2-thiophenecarboxamide;
N-{(1S)-2-amino-1-[(4-fluorophenyl)methyl]ethyl}-5-methyl-4-(1-methyl-1H-pyrazol-5-yl)-2-thiophenecarboxamide;
N-{(1S)-2-amino-1-[(3-fluorophenyl)methyl]ethyl}-5-methyl-4-(1-methyl-1H-pyrazol-5-yl)-2-thiophenecarboxamide;
N-((1S)-2-amino-1-{[2-(trifluoromethyl)phenyl]methyl}ethyl)-4-(4-cyclopropyl-1-methyl-1H-pyrazol-5-yl)-2-thiophenecarboxamide;
N-((1S)-2-amino-1-{[2-(trifluoromethyl)phenyl]methyl}ethyl)-4-(4-ethyl-1-methyl-1H-pyrazol-5-yl)-2-thiophenecarboxamide;
N-((1S)-2-amino-1-{[3-(trifluoromethyl)phenyl]methyl}ethyl)-4-(4-chloro-1-methyl-1H-pyrazol-5-yl)-5-methyl-2-thiophenecarboxamide;
N-{(1S)-2-amino-1-[(4-fluorophenyl)methyl]ethyl}-4-(4-bromo-1-methyl-1H-pyrazol-5-yl)-5-methyl-2-thiophenecarboxamide;
N-{(1S)-2-amino-1-[(4-fluorophenyl)methyl]ethyl}-4-(4-chloro-1-methyl-1H-pyrazol-5-yl)-5-methyl-2-thiophenecarboxamide;
N-{(1S)-2-amino-1-[(3-fluorophenyl)methyl]ethyl}-4-(4-chloro-1-methyl-1H-pyrazol-5-yl)-5-methyl-2-thiophenecarboxamide;
N-{(1S)-2-amino-1-[(3-fluorophenyl)methyl]ethyl}-4-(4-bromo-1-methyl-1H-pyrazol-5-yl)-5-methyl-2-thiophenecarboxamide;
N-((1S)-2-amino-1-{[3-(trifluoromethyl)phenyl]methyl}ethyl)-4-(4-bromo-1-methyl-1H-pyrazol-5-yl)-5-methyl-2-thiophenecarboxamide;
N-((1S)-2-amino-1-{[3-(trifluoromethyl)phenyl]methyl}ethyl)-4-(1,4-dimethyl-1H-pyrazol-5-yl)-5-methyl-2-thiophenecarboxamide;
N-{(1S)-2-amino-1-[(3-fluorophenyl)methyl]ethyl}-4-(1,4-dimethyl-1H-pyrazol-5-yl)-5-methyl-2-thiophenecarboxamide;
N-{(1S)-2-amino-1-[(4-fluorophenyl)methyl]ethyl}-4-(1,4-dimethyl-1H-pyrazol-5-yl)-5-methyl-2-thiophenecarboxamide;
N-{(1S)-2-amino-1-[(3-fluorophenyl)methyl]ethyl}-4-(4-bromo-1-methyl-1H-pyrazol-5-yl)-5-chloro-2-thiophenecarboxamide;
N-((1S)-2-amino-1-{[3-(trifluoromethyl)phenyl]methyl}ethyl)-5-chloro-4-(4-chloro-1-methyl-1H-pyrazol-5-yl)-2-thiophenecarboxamide;
N-((1S)-2-amino-1-{[3-(trifluoromethyl)phenyl]methyl}ethyl)-4-(4-bromo-1-methyl-1H-pyrazol-5-yl)-5-chloro-2-thiophenecarboxamide;
N-{(1S)-2-amino-1-[(4-fluorophenyl)methyl]ethyl}-4-(4-bromo-1-methyl-1H-pyrazol-5-yl)-5-chloro-2-thiophenecarboxamide;
N-{(1S)-2-amino-1-[(4-fluorophenyl)methyl]ethyl}-5-chloro-4-(4-chloro-1-methyl-1H-pyrazol-5-yl)-2-thiophenecarboxamide;
N-{(1S)-2-amino-1-[(2,5-difluorophenyl)methyl]ethyl}-4-(4-chloro-1-methyl-1H-pyrazol-5-yl)-5-methyl-2-thiophenecarboxamide;
N-{(1S)-2-amino-1-[(2,5-difluorophenyl)methyl]ethyl}-5-methyl-4-(1-methyl-1H-pyrazol-5-yl)-2-thiophenecarboxamide;
N-{(1S)-2-amino-1-[(2,5-difluorophenyl)methyl]ethyl}-4-(1,4-dimethyl-1H-pyrazol-5-yl)-5-methyl-2-thiophenecarboxamide;
N-{(1S)-2-amino-1-[(2,5-difluorophenyl)methyl]ethyl}-5-chloro-4-(4-chloro-1-methyl-1H-pyrazol-5-yl)-2-thiophenecarboxamide;
N-{(1S)-2-amino-1-[(4-fluorophenyl)methyl]ethyl}-4-(3-chloro-1,4-dimethyl-1H-pyrazol-5-yl)-2-thiophenecarboxamide;
N-{(1S)-2-amino-1-[(3-fluorophenyl)methyl]ethyl}-4-(3-chloro-1,4-dimethyl-1H-pyrazol-5-yl)-2-thiophenecarboxamide;
N-[(1S)-2-amino-1-(cyclohexyl methyl)ethyl]-4-(3-chloro-1,4-dimethyl-1H-pyrazol-5-yl)-2-thiophenecarboxamide;
N-((1S)-2-amino-1-{[3-(trifluoromethyl)phenyl]methyl}ethyl)-4-(3-chloro-1,4-dimethyl-1H-pyrazol-5-yl)-2-thiophenecarboxamide;
N-{(1S)-2-amino-1-[(2,5-difluorophenyl)methyl]ethyl}-5-chloro-4-(1-methyl-1H-pyrazol-5-yl)-2-thiophenecarboxamide;
N-{(1S)-2-amino-1-[(3-fluorophenyl)methyl]ethyl}-4-(4-ethyl-1-methyl-1H-pyrazol-5-yl)-5-methyl-2-thiophenecarboxamide;
N-{(1S)-2-amino-1-[(4-fluorophenyl)methyl]ethyl}-4-(4-ethyl-1-methyl-1H-pyrazol-5-yl)-5-methyl-2-thiophenecarboxamide;
N-((1S)-2-amino-1-{[3-(trifluoromethyl)phenyl]methyl}ethyl)-4-(4-ethyl-1-methyl-1H-pyrazol-5-yl)-5-methyl-2-thiophenecarboxamide;
N-{(1S)-2-amino-1-[(3-fluorophenyl)methyl]ethyl}-4-(4-chloro-1-methyl-1H-pyrazol-5-yl)-5-methyl-2-furancarboxamide;
N-((1S)-2-amino-1-{[2-(trifluoromethyl)phenyl]methyl}ethyl)-5-(methyloxy)-4-(1-methyl-1H-pyrazol-5-yl)-2-thiophenecarboxamide;
N-{(1S)-2-amino-1-[(4-fluorophenyl)methyl]ethyl}-4-(4-chloro-1-methyl-1H-pyrazol-5-yl)-5-methyl-2-furancarboxamide;
N-((1S)-2-amino-1-{[3-(trifluoromethyl)phenyl]methyl}ethyl)-4-(4-chloro-1-methyl-1H-pyrazol-5-yl)-5-methyl-2-furancarboxamide;
N-((1S)-2-amino-1-{[2-(trifluoromethyl)phenyl]methyl}ethyl)-4-(4-chloro-1-methyl-1H-pyrazol-5-yl)-5-(methyloxy)-2-thiophenecarboxamide;
N-{(1S)-2-amino-1-[(2,5-difluorophenyl)methyl]ethyl}-5-chloro-4-(1,4-dimethyl-1H-pyrazol-5-yl)-2-thiophenecarboxamide;
N-{(1S)-2-amino-1-[(3-fluorophenyl)methyl]ethyl}-4-(4-chloro-1-methyl-1H-pyrazol-5-yl)-5-(methyloxy)-2-thiophenecarboxamide;
N-{(1S)-2-amino-1-[(4-fluorophenyl)methyl]ethyl}-4-(4-chloro-1-methyl-1H-pyrazol-5-yl)-5-(methyloxy)-2-thiophenecarboxamide;
N-((1S)-2-amino-1-{[3-(trifluoromethyl)phenyl]methyl}ethyl)-4-(4-chloro-1-methyl-1H-pyrazol-5-yl)-5-(methyloxy)-2-thiophenecarboxamide;
N-((1S)-2-amino-1-{[2-(trifluoromethyl)phenyl]methyl}ethyl)-4-chloro-5-(4-chloro-1-methyl-1H-pyrazol-5-yl)-2-thiophenecarboxamide;
N-((1S)-2-amino-1-{[2-(trifluoromethyl)phenyl]methyl}ethyl)-4-chloro-5-(4-bromo-1-methyl-1H-pyrazol-5-yl)-2-thiophenecarboxamide;
N-[(1S)-2-amino-1-(3-pyridinylmethyl)ethyl]-4-(1-methyl-1H-pyrazol-5-yl)-2-thiophenecarboxamide;
N-[(1R)-2-amino-1-phenylethyl]-4-(1-methyl-1H-pyrazol-5-yl)-2-thiophenecarboxamide;
N-[(1S)-2-amino-1-phenylethyl]-4-(1-methyl-1H-pyrazol-5-yl)-2-thiophenecarboxamide;
N-[(1S)-2-amino-1-phenylethyl]-5-methyl-4-(1-methyl-1H-pyrazol-5-yl)-2-thiophenecarboxamide;

N-[(1S)-2-amino-1-phenylethyl]-4-(4-chloro-1-methyl-1H-pyrazol-5-yl)-5-methyl-2-thiophenecarboxamide;
N-[(1S)-2-amino-1-phenylethyl]-4-(4-bromo-1-methyl-1H-pyrazol-5-yl)-5-methyl-2-thiophenecarboxamide;
N-[(1S)-2-amino-1-phenylethyl]-5-chloro-4-(1-methyl-1H-pyrazol-5-yl)-2-thiophenecarboxamide;
N-[2-amino-1-(4-fluorophenyl)ethyl]-5-chloro-4-(1-methyl-1H-pyrazol-5-yl)-2-thiophenecarboxamide;
N-[2-amino-1-(4-chlorophenyl)ethyl]-5-chloro-4-(1-methyl-1H-pyrazol-5-yl)-2-thiophenecarboxamide;
N-[2-amino-1-(3-chlorophenyl)ethyl]-5-chloro-4-(1-methyl-1H-pyrazol-5-yl)-2-thiophenecarboxamide;
N-[2-amino-1-(2-chlorophenyl)ethyl]-5-chloro-4-(1-methyl-1H-pyrazol-5-yl)-2-thiophenecarboxamide;
N-[2-amino-1-(4-fluorophenyl)ethyl]-5-chloro-4-(4-chloro-1-methyl-1H-pyrazol-5-yl)-2-thiophenecarboxamide;
N-[(1S)-2-amino-1-phenylethyl]-5-chloro-4-(4-chloro-1-methyl-1H-pyrazol-5-yl)-2-thiophenecarboxamide;
N-[(1S)-2-amino-1-phenylethyl]-4-(4-bromo-1-methyl-1H-pyrazol-5-yl)-5-chloro-2-thiophenecarboxamide;
N-[2-amino-1-(2-chlorophenyl)ethyl]-5-chloro-4-(4-chloro-1-methyl-1H-pyrazol-5-yl)-2-thiophenecarboxamide;
N-[2-amino-1-(3-chlorophenyl)ethyl]-5-chloro-4-(4-chloro-1-methyl-1H-pyrazol-5-yl)-2-thiophenecarboxamide;
N-(2-aminoethyl)-5-chloro-4-(4-chloro-1-methyl-1H-pyrazol-5-yl)-2-thiophenecarboxamide;
N-[2-amino-1-(4-chlorophenyl)ethyl]-5-chloro-4-(4-chloro-1-methyl-1H-pyrazol-5-yl)-2-thiophenecarboxamide;
N-[(1S)-2-amino-1-(cyclohexylmethyl)ethyl]-4-(1,4-dimethyl-1H-pyrazol-5-yl)-5-methyl-2-thiophenecarboxamide;
N-[(1S)-2-amino-1-phenylethyl]-4-(1,4-dimethyl-1H-pyrazol-5-yl)-5-methyl-2-thiophenecarboxamide;
N-[(1S)-2-amino-1-methylethyl]-5-chloro-4-(4-chloro-1-methyl-1H-pyrazol-5-yl)-2-thiophenecarboxamide;
N-{(1S)-2-amino-1-[3-(trifluoromethyl)phenyl]ethyl}-4-(4-chloro-1-methyl-1H-pyrazol-5-yl)-5-ethyl-2-thiophenecarboxamide;
N-[(1S)-1-(aminomethyl)-3-methylbutyl]-5-chloro-4-(4-chloro-1-methyl-1H-pyrazol-5-yl)-2-thiophenecarboxamide;
N-{(1S)-2-amino-1-[(4-fluorophenyl)methyl]ethyl}-4-(1,4-dimethyl-1H-pyrazol-5-yl)-5-ethyl-2-thiophenecarboxamide;
N-{(1S)-2-amino-1-[(3,4-difluorophenyl)methyl]ethyl}-5-methyl-4-(1-methyl-1H-pyrazol-5-yl)-2-thiophenecarboxamide;
N-{(1S)-2-amino-1-[(3,4-difluorophenyl)methyl]ethyl}-4-(4-chloro-1-methyl-1H-pyrazol-5-yl)-5-methyl-2-thiophenecarboxamide;
N-{(1S)-2-amino-1-[(3,4-difluorophenyl)methyl]ethyl}-5-chloro-4-(1-methyl-1H-pyrazol-5-yl)-2-thiophenecarboxamide;
N-{(1S)-2-amino-1-[(3,4-difluorophenyl)methyl]ethyl}-5-chloro-4-(4-chloro-1-methyl-1H-pyrazol-5-yl)-2-thiophenecarboxamide;
N-{(1S)-2-amino-1-[(3,4-difluorophenyl)methyl]ethyl}-4-(1,4-dimethyl-1H-pyrazol-5-yl)-5-methyl-2-thiophenecarboxamide;
N-{(1S)-2-amino-1-[(3,4-difluorophenyl)methyl]ethyl}-5-chloro-4-(4-chloro-1-methyl-1H-pyrazol-5-yl)-2-furancarboxamide;
N-{(1S)-2-amino-1-[(3,4-difluorophenyl)methyl]ethyl}-5-chloro-4-(1-methyl-1H-pyrazol-5-yl)-2-furancarboxamide;
N-{(1S)-2-amino-1-[(3,4-difluorophenyl)methyl]ethyl}-5-methyl-4-(1-methyl-1H-pyrazol-5-yl)-2-furancarboxamide;
N-{(1S)-2-amino-1-[(3,4-difluorophenyl)methyl]ethyl}-4-(4-chloro-1-methyl-1H-pyrazol-5-yl)-5-methyl-2-furancarboxamide;
N-{(1S)-2-amino-1-[(3,4-difluorophenyl)methyl]ethyl}-5-chloro-4-(1,4-dimethyl-1H-pyrazol-5-yl)-2-furancarboxamide;
N-{(1S)-2-amino-1-[(3,4-difluorophenyl)methyl]ethyl}-4-(1,4-dimethyl-1H-pyrazol-5-yl)-5-methyl-2-furancarboxamide;
N-{(1S)-2-amino-1-[(3-fluorophenyl)methyl]ethyl}-4-(4-chloro-1-ethyl-1H-pyrazol-5-yl)-2-thiophenecarboxamide;
N-((1S)-2-amino-1-{[3-(trifluoromethyl)phenyl]methyl}ethyl)-4-(4-chloro-1-ethyl-1H-pyrazol-5-yl)-2-thiophenecarboxamide;
N-{(1S)-2-amino-1-[(4-fluorophenyl)methyl]ethyl}-4-(4-chloro-1-ethyl-1H-pyrazol-5-yl)-2-thiophenecarboxamide;
N-{(1S)-2-amino-1-[(3,4-difluorophenyl)methyl]ethyl}-4-(4-chloro-1-ethyl-1H-pyrazol-5-yl)-2-thiophenecarboxamide;
N-{(1S)-2-amino-1-[(3-fluorophenyl)methyl]ethyl}-4-(4-bromo-1-ethyl-1H-pyrazol-5-yl)-2-thiophenecarboxamide;
N-((1S)-2-amino-1-{[2-(trifluoromethyl)phenyl]methyl}ethyl)-5-chloro-4-(4-chloro-1-ethyl-1H-pyrazol-5-yl)-2-thiophenecarboxamide;
N-{(1S)-2-amino-1-[(3-fluorophenyl)methyl]ethyl}-5-chloro-4-(4-chloro-1-ethyl-1H-pyrazol-5-yl)-2-thiophenecarboxamide;
N-{(1S)-2-amino-1-[(4-fluorophenyl)methyl]ethyl}-5-chloro-4-(4-chloro-1-ethyl-1H-pyrazol-5-yl)-2-thiophenecarboxamide;
N-((1S)-2-amino-1-{[3-(trifluoromethyl)phenyl]methyl}ethyl)-5-chloro-4-(4-chloro-1-ethyl-1H-pyrazol-5-yl)-2-thiophenecarboxamide;
N-((1S)-2-amino-1-{[2-(trifluoromethyl)phenyl]methyl}ethyl)-4-(1-methyl-1H-pyrazol-5-yl)-5-(trifluoromethyl)-2-thiophenecarboxamide;
N-((1S)-2-amino-1-{[2-(trifluoromethyl)phenyl]methyl}ethyl)-4-(1-ethyl-4-methyl-1H-pyrazol-5-yl)-2-thiophenecarboxamide;
(N-{(1S)-2-amino-1-[(3-fluorophenyl)methyl]ethyl}-4-(1-ethyl-4-methyl-1H-pyrazol-5-yl)-2-thiophenecarboxamide;
N-((1S)-2-amino-1-{[3-(trifluoromethyl)phenyl]methyl}ethyl)-4-(1-ethyl-4-methyl-1H-pyrazol-5-yl)-2-thiophenecarboxamide;
N-{(1S)-2-amino-1-[(4-fluorophenyl)methyl]ethyl}-4-(1-ethyl-4-methyl-1H-pyrazol-5-yl)-2-thiophenecarboxamide;
N-{(1S)-2-amino-1-[(3,4-difluorophenyl)methyl]ethyl}-4-(1-ethyl-4-methyl-1H-pyrazol-5-yl)-2-thiophenecarboxamide;
N-((1S)-2-amino-1-{[2-(trifluoromethyl)phenyl]methyl}ethyl)-5-chloro-4-(1-ethyl-4-methyl-1H-pyrazol-5-yl)-2-thiophenecarboxamide;
N-{(1S)-2-amino-1-[(3-fluorophenyl)methyl]ethyl}-5-chloro-4-(1-ethyl-4-methyl-1H-pyrazol-5-yl)-2-thiophenecarboxamide;
N-{(1S)-2-amino-1-[(3,4-difluorophenyl)methyl]ethyl}-5-chloro-4-(1-ethyl-4-methyl-1H-pyrazol-5-yl)-2-thiophenecarboxamide;

N-((1S)-2-amino-1-{[2-(trifluoromethyl)phenyl]methyl}ethyl)-4-(1,4-diethyl-1H-pyrazol-5-yl)-2-thiophenecarboxamide;

N-{(1S)-2-amino-1-[(3-fluorophenyl)methyl]ethyl}-5-chloro-4-(1,4-dimethyl-1H-pyrazol-5-yl)-2-thiophenecarboxamide;

N-((1S)-2-amino-1-{[3-(trifluoromethyl)phenyl]methyl}ethyl)-5-chloro-4-(1,4-dimethyl-1H-pyrazol-5-yl)-2-thiophenecarboxamide;

N-{(1S)-2-amino-1-[(4-fluorophenyl)methyl]ethyl}-5-chloro-4-(1,4-dimethyl-1H-pyrazol-5-yl)-2-thiophenecarboxamide;

N-{(1S)-2-amino-1-[(3-fluorophenyl)methyl]ethyl}-4-(1-ethyl-4-methyl-1H-pyrazol-5-yl)-2-furancarboxamide;

N-{(1S)-2-amino-1-[(3-fluorophenyl)methyl]ethyl}-4-(4-chloro-1-ethyl-1H-pyrazol-5-yl)-2-furancarboxamide;

N-[2-amino-1-(phenylmethyl)ethyl]-3-methyl-4-(1-methyl-1H-pyrazol-5-yl)-2-thiophenecarboxamide;

N-((1S)-2-amino-1-{[2-(trifluoromethyl)phenyl]methyl}ethyl)-4-[1-methyl-4-(trifluoromethyl)-1H-pyrazol-5-yl]-2-thiophenecarboxamide;

N-((1S)-2-amino-1-{[2-(trifluoromethyl)phenyl]methyl}ethyl)-4-(1-propyl-1H-pyrazol-5-yl)-2-thiophenecarboxamide;

N-((1S)-2-amino-1-{[2-(trifluoromethyl)phenyl]methyl}ethyl)-4-(4-chloro-1-propyl-1H-pyrazol-5-yl)-2-thiophenecarboxamide;

N-{(1S)-2-amino-1-[(3,4-difluorophenyl)methyl]ethyl}-5-chloro-4-(4-chloro-1-ethyl-1H-pyrazol-5-yl)-2-thiophenecarboxamide;

N-{(1S)-2-amino-1-[(3,4-difluorophenyl)methyl]ethyl}-5-chloro-4-(4-chloro-1-ethyl-1H-pyrazol-5-yl)-2-furancarboxamide;

N-[(1S)-2-amino-1-(phenylmethyl)ethyl]-4-(1-methyl-1H-1,2,3-triazol-5-yl)-2-thiophenecarboxamide;

N-[(1S)-2-amino-1-(phenylmethyl)ethyl]-5-chloro-4-(4-chloro-1-methyl-1H-1,2,3-triazol-5-yl)-2-thiophenecarboxamide;

N-{(1S)-2-amino-1-[(4-fluorophenyl)methyl]ethyl}-4-(1-methyl-1H-1,2,3-triazol-5-yl)-2-thiophenecarboxamide;

N-{(1S)-2-amino-1-[(3,4-difluorophenyl)methyl]ethyl}-4-(1-methyl-1H-1,2,3-triazol-5-yl)-2-thiophenecarboxamide;

N-{(1S)-2-amino-1-[(4-fluorophenyl)methyl]ethyl}-5-chloro-4-(4-chloro-1-methyl-1H-1,2,3-triazol-5-yl)-2-thiophenecarboxamide;

N-{(1S)-2-amino-1-[(3-fluorophenyl)methyl]ethyl}-4-(1-methyl-1H-1,2,3-triazol-5-yl)-2-thiophenecarboxamide;

N-{(1S)-2-amino-1-[(3,5-difluorophenyl)methyl]ethyl}-4-(1-methyl-1H-1,2,3-triazol-5-yl)-2-thiophenecarboxamide;

N-((1S)-2-amino-1-{[3-(trifluoromethyl)phenyl]methyl}ethyl)-4-(1-methyl-1H-1,2,3-triazol-5-yl)-2-thiophenecarboxamide;

N-{(1S)-2-amino-1-[(3-fluorophenyl)methyl]ethyl}-5-chloro-4-(4-chloro-1-methyl-1H-1,2,3-triazol-5-yl)-2-thiophenecarboxamide;

N-((1S)-2-amino-1-{[2-(trifluoromethyl)phenyl]methyl}ethyl)-5-chloro-4-(1-methyl-1H-1,2,3-triazol-5-yl)-2-thiophenecarboxamide;

N-[(1S)-2-amino-1-(phenylmethyl)ethyl]-5-methyl-4-(1-methyl-1H-1,2,3-triazol-5-yl)-2-thiophenecarboxamide;

N-((1S)-2-amino-1-{[2-(trifluoromethyl)phenyl]methyl}ethyl)-5-chloro-4-(4-chloro-1-methyl-1H-1,2,3-triazol-5-yl)-2-thiophenecarboxamide;

N-[(1S)-2-amino-1-(phenylmethyl)ethyl]-4-(4-chloro-1-methyl-1H-1,2,3-triazol-5-yl)-5-methyl-2-thiophenecarboxamide;

N-{(1S)-2-amino-1-[(3,5-difluorophenyl)methyl]ethyl}-4-(4-chloro-1-methyl-1H-1,2,3-triazol-5-yl)-2-thiophenecarboxamide;

N-{(1S)-2-amino-1-[(3,4-difluorophenyl)methyl]ethyl}-4-(4-chloro-1-methyl-1H-1,2,3-triazol-5-yl)-2-thiophenecarboxamide;

N-((1S)-2-amino-1-{[2-(trifluoromethyl)phenyl]methyl}ethyl)-4-(4-chloro-1-methyl-1H-1,2,3-triazol-5-yl)-2-thiophenecarboxamide;

N-{(1S)-2-amino-1-[(4-chlorophenyl)methyl]ethyl}-4-(4-chloro-1-methyl-1H-1,2,3-triazol-5-yl)-2-thiophenecarboxamide;

N-{(1S)-2-amino-1-[(2,4-dichlorophenyl)methyl]ethyl}-4-(4-chloro-1-methyl-1H-1,2,3-triazol-5-yl)-2-thiophenecarboxamide;

N-[(1S)-2-amino-1-(cyclohexylmethyl)ethyl]-4-(1-methyl-1H-1,2,3-triazol-5-yl)-2-thiophenecarboxamide;

N-[(1S)-2-amino-1-(cyclohexylmethyl)ethyl]-5-chloro-4-(4-chloro-1-methyl-1H-1,2,3-triazol-5-yl)-2-thiophenecarboxamide;

N-[(1S)-2-amino-1-(cyclohexylmethyl)ethyl]-5-chloro-4-(1-methyl-1H-1,2,3-triazol-5-yl)-2-thiophenecarboxamide;

N-[(1S)-2-amino-1-(cyclohexylmethyl)ethyl]-4-(4-chloro-1-methyl-1H-1,2,3-triazol-5-yl)-2-thiophenecarboxamide;

N-[(1S)-2-amino-1-(cyclohexylmethyl)ethyl]-4-(4-bromo-1-methyl-1H-1,2,3-triazol-5-yl)-5-chloro-2-thiophenecarboxamide;

N-[(1S)-2-amino-1-(phenylmethyl)ethyl]-5-(1-methyl-1H-1,2,3-triazol-5-yl)-2-thiophenecarboxamide;

N-[(1S)-2-amino-1-(phenylmethyl)ethyl]-5-(4-chloro-1-methyl-1H-1,2,3-triazol-5-yl)-2-thiophenecarboxamide;

N-((1S)-2-amino-1-{[2-(trifluoromethyl)phenyl]methyl}ethyl)-5-methyl-4-(1-methyl-1H-1,2,3-triazol-5-yl)-2-furancarboxamide;

N-((1S)-2-amino-1-{[2-(trifluoromethyl)phenyl]methyl}ethyl)-4-(1-methyl-1H-1,2,3-triazol-5-yl)-2-furancarboxamide;

N-((1S)-2-amino-1-{[2-(trifluoromethyl)phenyl]methyl}ethyl)-5-chloro-4-(4-chloro-1-methyl-1H-1,2,3-triazol-5-yl)-2-furancarboxamide;

N-{(1S)-2-amino-1-[(3-fluorophenyl)methyl]ethyl}-5-methyl-4-(1-methyl-1H-1,2,3-triazol-5-yl)-2-furancarboxamide;

N-{(1S)-2-amino-1-[(3,5-difluorophenyl)methyl]ethyl}-5-methyl-4-(1-methyl-1H-1,2,3-triazol-5-yl)-2-furancarboxamide;

N-{(1S)-2-amino-1-[(3,4-difluorophenyl)methyl]ethyl}-5-chloro-4-(4-chloro-1-methyl-1H-1,2,3-triazol-5-yl)-2-thiophenecarboxamide;

N-[(1S)-2-amino-1-(phenylmethyl)ethyl]-4-(1-methyl-1H-1,2,4-triazol-5-yl)-2-thiophenecarboxamide;

N-[(1S)-2-amino-1-(phenylmethyl)ethyl]-5-chloro-4-(1-methyl-1H-1,2,4-triazol-5-yl)-2-thiophenecarboxamide;

N-((1S)-2-amino-1-{[2-(trifluoromethyl)phenyl]methyl}ethyl)-4-(1-methyl-1H-1,2,4-triazol-5-yl)-2-thiophenecarboxamide;

N-{(1S)-2-amino-1-[(4-fluorophenyl)methyl]ethyl}-4-(1-methyl-1H-1,2,4-triazol-5-yl)-2-thiophenecarboxamide;

N-{(1S)-2-amino-1-[(4-fluorophenyl)methyl]ethyl}-5-chloro-4-(1-methyl-1H-1,2,4-triazol-5-yl)-2-thiophenecarboxamide;

N-[(1S)-2-amino-1-(cyclohexylmethyl)ethyl]-4-(1-methyl-1H-1,2,4-triazol-5-yl)-2-thiophenecarboxamide;

N-[(1S)-2-amino-1-(cyclohexylmethyl)ethyl]-5-chloro-4-(1-methyl-1H-1,2,4-triazol-5-yl)-2-thiophenecarboxamide;

N-((1S)-2-amino-1-{[2-(trifluoromethyl)phenyl]methyl}ethyl)-5-chloro-4-(1-methyl-1H-1,2,4-triazol-5-yl)-2-thiophenecarboxamide;

N-{(1S)-2-amino-1-[(3-fluorophenyl)methyl]ethyl}-4-(1-methyl-1H-1,2,4-triazol-5-yl)-2-thiophenecarboxamide;

N-{(1S)-2-amino-1-[(3-fluorophenyl)methyl]ethyl}-5-chloro-4-(1-methyl-1H-1,2,4-triazol-5-yl)-2-thiophenecarboxamide;

N-((1S)-2-amino-1-{[3-(trifluoromethyl)phenyl]methyl}ethyl)-4-(1-methyl-1H-1,2,4-triazol-5-yl)-2-thiophenecarboxamide;

N-((1S)-2-amino-1-{[3-(trifluoromethyl)phenyl]methyl}ethyl)-5-chloro-4-(1-methyl-1H-1,2,4-triazol-5-yl)-2-thiophenecarboxamide;

N-{(1S)-2-amino-1-[(3,5-difluorophenyl)methyl]ethyl}-4-(1-methyl-1H-1,2,4-triazol-5-yl)-2-thiophenecarboxamide;

N-{(1S)-2-amino-1-[(3,5-difluorophenyl)methyl]ethyl}-5-chloro-4-(1-methyl-1H-1,2,4-triazol-5-yl)-2-thiophenecarboxamide;

N-((1S)-2-amino-1-{[2-(trifluoromethyl)phenyl]methyl}ethyl)-5-methyl-4-(1-methyl-1H-1,2,4-triazol-5-yl)-2-thiophenecarboxamide;

N-{(1S)-2-amino-1-[(2-fluorophenyl)methyl]ethyl}-4-(1-methyl-1H-1,2,4-triazol-5-yl)-2-thiophenecarboxamide;

N-((1S)-2-amino-1-{[2-(trifluoromethyl)phenyl]methyl}ethyl)-5-methyl-4-(1-methyl-1H-1,2,3-triazol-5-yl)-2-thiophenecarboxamide;

N-((1S)-2-amino-1-{[2-(trifluoromethyl)phenyl]methyl}ethyl)-4-(4-chloro-1-methyl-1H-1,2,3-triazol-5-yl)-5-methyl-2-thiophenecarboxamide;

N-{(1S)-2-amino-1-[(2-fluorophenyl)methyl]ethyl}-5-chloro-4-(1-methyl-1H-1,2,4-triazol-5-yl)-2-thiophenecarboxamide;

N-((1S)-2-amino-1-{[2-(trifluoromethyl)phenyl]methyl}ethyl)-4-(1-methyl-1H-1,2,4-triazol-5-yl)-2-furancarboxamide;

N-{(1S)-2-amino-1-[(2,4-dichlorophenyl)methyl]ethyl}-4-(1-methyl-1H-1,2,3-triazol-5-yl)-2-thiophenecarboxamide;

N-{(1S)-2-amino-1-[(2,4-dichlorophenyl)methyl]ethyl}-4-(1-methyl-1H-1,2,4-triazol-5-yl)-2-thiophenecarboxamide;

N-{(1S)-2-amino-1-[(2,4-dichlorophenyl)methyl]ethyl}-5-chloro-4-(1-methyl-1H-1,2,4-triazol-5-yl)-2-thiophenecarboxamide;

N-{(1S)-2-amino-1-[(2,4-dichlorophenyl)methyl]ethyl}-5-chloro-4-(4-chloro-1-methyl-1H-1,2,3-triazol-5-yl)-2-thiophenecarboxamide;

N-{(1S)-2-amino-1-[(4-chlorophenyl)methyl]ethyl}-4-(1-methyl-1H-1,2,4-triazol-5-yl)-2-thiophenecarboxamide;

N-{(1S)-2-amino-1-[(4-chlorophenyl)methyl]ethyl}-5-chloro-4-(1-methyl-1H-1,2,4-triazol-5-yl)-2-thiophenecarboxamide;

N-{(1S)-2-amino-1-[(3,5-difluorophenyl)methyl]ethyl}-5-chloro-4-(4-chloro-1-methyl-1H-1,2,3-triazol-5-yl)-2-thiophenecarboxamide;

N-{(1S)-2-amino-1-[(4-chlorophenyl)methyl]ethyl}-5-chloro-4-(4-chloro-1-methyl-1H-1,2,3-triazol-5-yl)-2-thiophenecarboxamide;

N-{(1S)-2-amino-1-[(3-fluorophenyl)methyl]ethyl}-5-chloro-4-(1,4-dimethyl-1H-1,2,3-triazol-5-yl)-2-thiophenecarboxamide;

N-{(1S)-2-amino-1-[(3-fluorophenyl)methyl]ethyl}-4-(1,4-dimethyl-1H-1,2,3-triazol-5-yl)-2-thiophenecarboxamide;

N-{(1S)-2-amino-1-[(3,5-difluorophenyl)methyl]ethyl}-4-(1,4-dimethyl-1H-1,2,3-triazol-5-yl)-2-thiophenecarboxamide;

N-{(1S)-2-amino-1-[(3,5-difluorophenyl)methyl]ethyl}-5-chloro-4-(1,4-dimethyl-1H-1,2,3-triazol-5-yl)-2-thiophenecarboxamide;

N-{(1S)-2-amino-1-[(3,4-difluorophenyl)methyl]ethyl}-5-chloro-4-(1,4-dimethyl-1H-1,2,3-triazol-5-yl)-2-thiophenecarboxamide;

N-{(1S)-2-amino-1-[(3,4-difluorophenyl)methyl]ethyl}-5-chloro-4-(1-methyl-1H-1,2,4-triazol-5-yl)-2-thiophenecarboxamide;

N-{(1S)-2-amino-1-[(3,4-difluorophenyl)methyl]ethyl}-4-(1-methyl-1H-1,2,4-triazol-5-yl)-2-thiophenecarboxamide;

N-[(1S,2S)-2-amino-3-hydroxy-1-phenylpropyl]-5-chloro-4-(4-chloro-1-methyl-1H-pyrazol-5-yl)-2-thiophenecarboxamide;

N-{(1S)-2-amino-1-[(3-fluorophenyl)methyl]ethyl}-5-chloro-4-(4-chloro-1-methyl-1H-1,2,3-triazol-5-yl)-2-furancarboxamide; and N-{(1S)-2-amino-1-[(3,4-difluorophenyl)methyl]ethyl}-4-(4-chloro-1-ethyl-1H-pyrazol-5-yl)-5-methyl-2-furancarboxamide;

and/or pharmaceutically acceptable salts thereof.

Compounds of Formula (I) are included in the pharmaceutical compositions of the invention and used in the methods of the invention.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of the compounds of Formula (I).

Certain compounds described herein may form a solvate which is understood to be a complex of variable stoichiometry formed by a solute (in this invention, a compound of Formula I a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

By the term "aryl", and derivatives thereof, used alone or as part of a larger moiety as in "—$(CH_2)_m$aryl" as used herein, unless otherwise defined, is meant monocyclic, bicyclic, and tricyclic ring systems having a total of five to fourteen ring members, wherein at least one ring system is aromatic and wherein each ring in the system contains 3 to 7 members, such as phenyl, naphthalene, tetrahydronaphthalene and biphenyl. Suitably, by the term "aryl" is meant a monocyclic aromatic ring system having a total of five to 7 ring members.

By the term "heteroaryl", and derivatives thereof, used alone or as part of a larger moiety as in "—$(CH_2)_m$heteroaryl" as used herein, unless otherwise defined, is meant a cyclic aromatic ring containing from 3 to 7 carbon atoms and containing from one to 3 heteroatoms, provided that when the number of carbon atoms is 3 the aromatic ring contains at least two heteroatoms. Exemplary "heteroaryl" groups include pyridine and indole.

By the term "cycloalkyl", and derivatives thereof, used alone or as part of a larger moiety as in "—$(CH_2)_m$cycloalkyl" as used herein, unless otherwise defined, is meant a non-aromatic cyclic hydrocarbon ring having from three to seven carbon atoms. Exemplary "cycloalkyl" groups include cyclopropyl, cyclobutyl, cyclopentyl, and cyclohexyl.

By the term "heterocycloalkyl", and derivatives thereof, used alone or as part of a larger moiety as in "—$(CH_2)_m$heterocycloalkyl" as used herein, unless otherwise defined, is meant a non-aromatic cyclic hydrocarbon ring having from three to six carbon atoms and containing 1 or 2 heteroatoms. Exemplary "cycloalkyl" groups include piperazine and pyrrolidine.

By the term "$C_5$-$C_{12}$aryl", used alone or as part of a larger moiety as in "—$(CH_2)_mC_5$-$C_{12}$aryl", as used herein, is meant an aromatic group selected from: phenyl, naphthalene, tehrahydronaphthanlene and biphenyl.

The term "substituted" as used herein, unless otherwise defined, is meant that the subject chemical moiety has from one to five substituents, suitably from one to three substituents, selected from the group consisting of: —$CO_2R^{20}$, $C_1$-$C_4$alkyl, hydroxy$C_1$-$C_4$alkyl, $C_1$-$C_4$alkyloxy, amino, $C_1$-$C_4$alkylamino, amino$C_1$-$C_4$alkyl, di$C_1$-$C_4$alkylamino, hydroxy, nitro, tetrazole, cyano, oxo, halogen and trifluoromethyl, where $R^{20}$ is selected form hydrogen, $C_1$-$C_4$alkyl, and trifluoromethyl.

Suitably, the term "substituted" as used herein is meant that the subject chemical moiety has from one to three substituents, selected from the group consisting of: $C_1$-$C_4$alkyl, hydroxy$C_1$-$C_4$alkyl, $C_1$-$C_4$alkyloxy, amino, $C_1$-$C_4$alkylamino, amino$C_1$-$C_4$alkyl, hydroxy, tetrazole, halogen and trifluoromethyl.

Suitably, the term "substituted" as used herein is meant that the subject chemical moiety has from one to three substituents, selected from the group consisting of: halogen and trifluoromethyl.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein, including alkyl chains defined by the term "—$(CH_2)_n$", "—$(CH_2)_m$" and the like, is meant a linear or branched, saturated or unsaturated hydrocarbon chain, and unless otherwise defined, the carbon chain will contain from 1 to 12 carbon atoms. Examples of alkyl as used herein include: —$CH_3$, —$CH_2$—$CH_3$, —$CH_2$—$CH_2$-$CH_3$, —$CH(CH_3)_2$, —$CH_2$—$CH_2$-$C(CH_3)_3$, —C≡C—$C(CH_3)_3$, —$C(CH_3)_3$, —$(CH_2)_3$—$CH_3$, —$CH_2$—$CH(CH_3)_2$, —CH($CH_3$)—$CH_2$—$CH_3$, —CH=$CH_2$, and —C≡C—$CH_3$.

By the term "treating" and derivatives thereof as used herein, is meant prophylactic and therapeutic therapy. Prophylactic therapy is appropriate, for example, when a subject is considered at high risk for developing cancer, or when a subject has been exposed to a carcinogen.

As used herein, the term "effective amount" and derivatives thereof means that amount of a drug or pharmaceutical agent that will elicit the biological or medical response of a tissue, system, animal or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

The pharmaceutically acceptable salts of the compounds of the invention are readily prepared by those of skill in the art.

The novel compounds of Formulas (I), (AA), (BB) and (CC) are generally prepared as shown in Schemes 1 to 3 below, or by analogous methods, provided the X and 'R' substituents in Formulas (I), (AA), (BB) and (CC) respectively do not include any such substituents that render inoperative the processes of any of Schemes 1 to 3. All of the starting materials are commercially available or are readily made from commercially available starting materials by those of skill in the art.

General Schemes

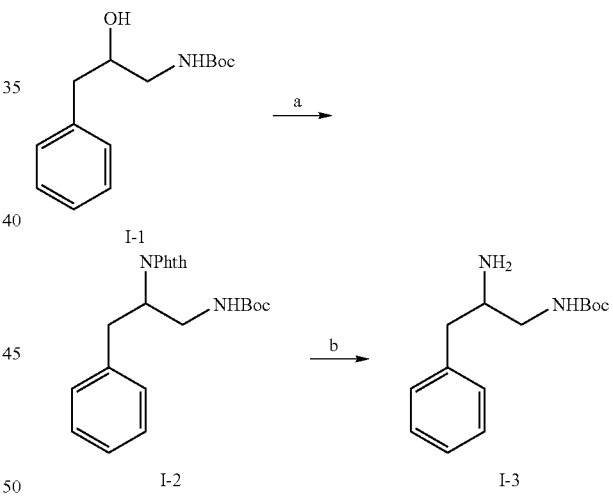

Reagents: (a) Phthalimide, PPh$_3$, DEAD, THF, RT; (b) NH$_2$NH$_2$, MeOH, 50° C.

Amino alcohol (I-1) was reacted under Mitsunobu conditions to provide the differentially protected diamine (I-2). Mitsunobu reactions are well know to those skilled in the art of organic synthesis. Methods and reaction conditions for such transformations are discussed in *Synthesis* 1981, 1-28. Selective deprotection of the phthalimide group of (I-2) using a nucleophilic amine such as hydrazine or methyl amine in a polar solvent such as methanol, afforded amine (I-3). Many different protecting groups are available to one skilled in the art and can be used here as long as they do not interfere with the processes listed herein. Methods for the protection of amines are described in standard reference volumes, such as Greene "Protective Groups in Organic Synthesis" (published by Wiley-Interscience).

Scheme 2

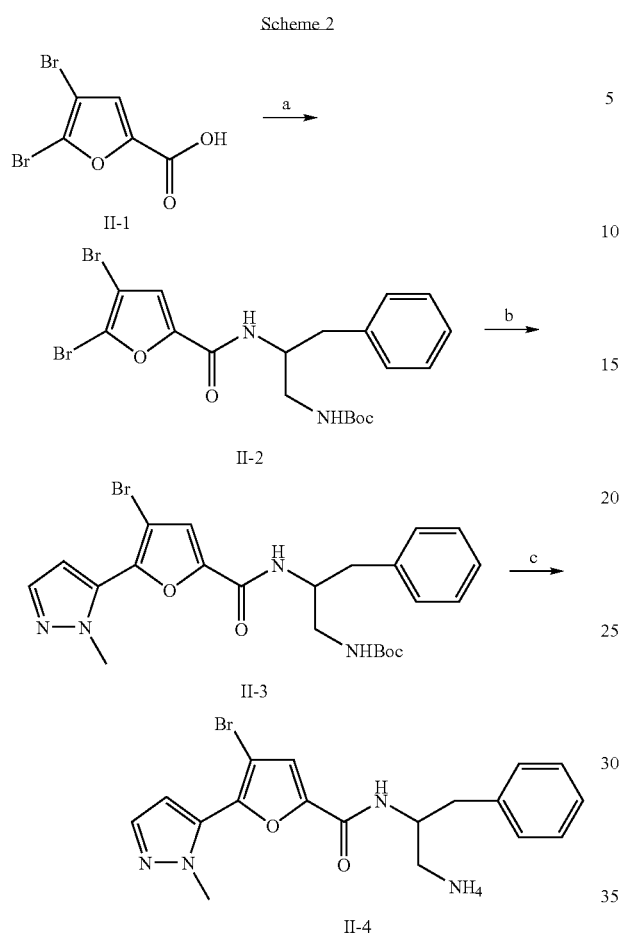

Reagents: (a) PyBrop, (i-Pr)$_2$NEt, 1,1-dimethylethyl (2-amino-3-phenylpropyl)carbamate, DCM, RT; (b) 5-(5,5-dimethyl-1,3,2-dioxaborinan-2-yl)-1-methyl-1H-pyrazole, K$_2$CO$_3$, Pd(PPh$_3$)$_4$, dioxane/H$_2$O; (c) TFA/DCM, RT.

Carboxylic acid (II-1) was reacted with 1,1-dimethylethyl (2-amino-3-phenylpropyl)carbamate to form amide (II-2). A variety of amide coupling reagents such as EDC, PyBrop, etc. are commercially available. Amide coupling reactions are generally run in solvents such as DCM or DMF, utilizing an organic base like Et$_3$N or (i-Pr)$_2$NEt. Dibromide (II-2) was regioselectively coupled with 1,1-dimethylethyl (2-{[(4,5-dibromo-2-furanyl)carbonyl]amino}-3-phenylpropyl)carbamate using a Suzuki coupling procedure. Suzuki-like couplings are typically run using a palladium(0) catalyst such as Pd(PPh$_3$)$_4$ with an inorganic base, for example K$_2$CO$_3$, Na$_2$CO$_3$ or K$_3$PO$_4$, in an aqueous mixture containing ethereal solvents such as DME, dioxane, or THF. Methods for palladium-mediated couplings are described in standard reference volumes, such as Schlosser "Organometallics in Synthesis" (published by Wiley and sons). Acidic treatment of II-3 with HCl or TFA to remove the Boc protecting group produced amine (II-4). Many different protecting groups are available to one skilled in the art and can be used here as long as they do not interfere with the processes listed herein. Methods for the protection of amines are described in standard reference volumes, such as Greene "Protective Groups in Organic Synthesis" (published by Wiley-Interscience).

Scheme 3

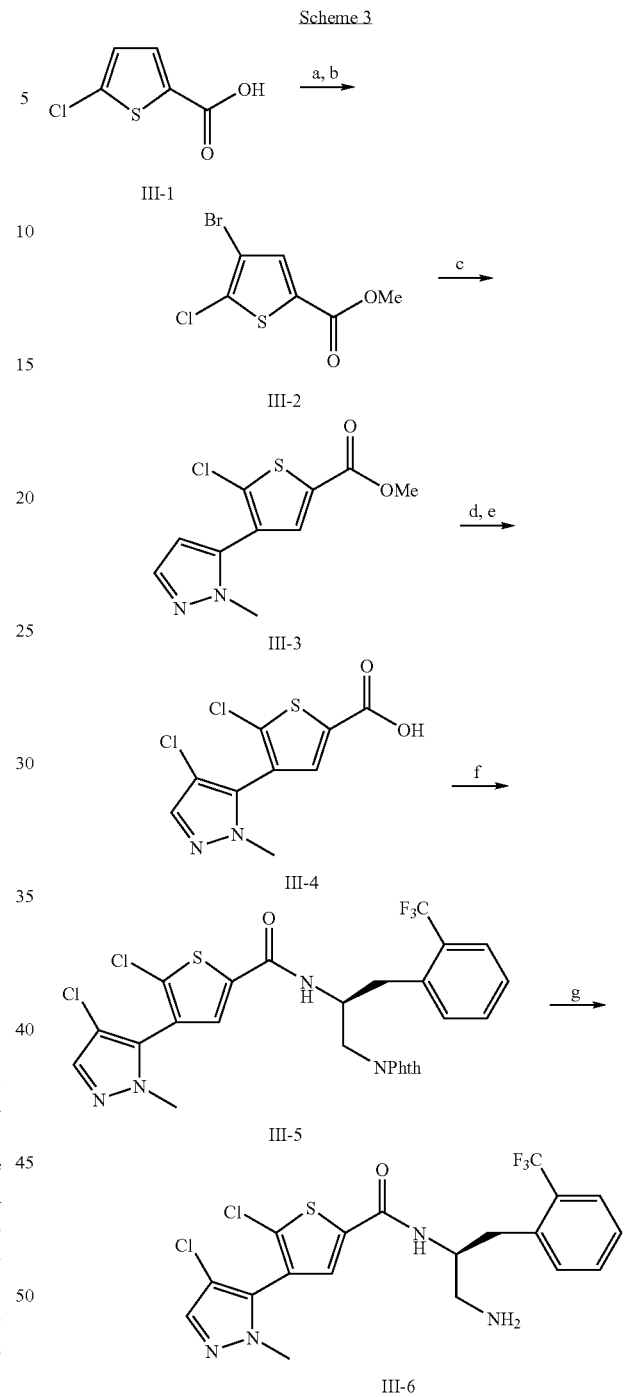

Reagents: (a) MeOH, H$_2$SO$_4$, 60° C.; (b) AlCl$_3$, Br$_2$, CHCl$_3$; (c) 5-(5,5-dimethyl-1,3,2-dioxaborinan-2-yl)-1-methyl-1H-pyrazole, K$_2$CO$_3$, Pd$_2$(t-Bu)$_3$, dioxane/H$_2$O, 70° C.; (d) NCS, THF, 70° C.; (e) 6M NaOH, THF/MeOH, 50° C.; (f) PyBrop, (i-Pr)$_2$NEt, 2-{(2S)-2-amino-3-[2-(trifluoromethyl)phenyl]propyl}-1H-isoindole-1,3(2H)-dione, DCM, RT; (g) NH$_2$NH$_2$, THF/MeOH, RT.

Carboxylic acid (III-1) was esterified under standard Fisher esterification conditions and then selectively halogenated with the aid of a Lewis acid to give (III-2). The dihalogenated ester was selectively coupled with 5-(5,5-dimethyl-1,3,2-dioxaborinane-2-yl)-1-methyl-1H-pyrazole using Suzuki coupling chemistry to give (III-3). Suzuki-like couplings are typically run using a palladium(0) catalyst such as Pd(PPh$_3$)$_4$ with an inorganic base, for example K$_2$CO$_3$, Na₂CO₃ or K₃PO₄, in an aqueous mixture containing ethereal solvents such as DME, dioxane, or THF. Methods for palladium-mediated couplings are described in standard reference volumes, such as Schlosser "Organometallics in Synthesis" (published by Wiley and sons). Ester (III-3) was chlorinated using NCS and in situ saponified using aqueous NaOH. The resulting carboxylic acid (III-4) was coupled with 2-{(2S)-2-amino-3-[2-(trifluoromethyl)phenyl]propyl}-1H-isoindole-1,3(2H)-dione to form amide (III-5). A variety of amide coupling reagents such as EDC, PyBrop, etc. are commercially available. Amide coupling reactions are generally run in solvents such as DCM or DMF, utilizing an organic base like Et₃N or (i-Pr)₂NEt. Amide (III-5) was deprotected using hydrazine to give amine (III-6). Many different protecting groups are available to one skilled in the art and can be used here as long as they do not interfere with the processes listed herein. Methods for the protection of amines are described in standard reference volumes, such as Greene "Protective Groups in Organic Synthesis" (published by Wiley-Interscience).

By the term "co-administering" and derivatives thereof as used herein is meant either simultaneous administration or any manner of separate sequential administration of an AKT inhibiting compound, as described herein, and a further active ingredient or ingredients, known to be useful in the treatment of cancer, including chemotherapy and radiation treatment, or to be useful in the treatment of arthritis. The term further active ingredient or ingredients, as used herein, includes any compound or therapeutic agent known to or that demonstrates advantageous properties when administered to a patient in need of treatment for cancer or arthritis. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclines, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (anti-neoplastic agent) for use in combination or co-administered with the presently invented AKT inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G₂/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325.1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-di-acetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleuko-blastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leukopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leukopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leukopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leukopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leukopenia, thrombocytopenia, and anemia, is the most common dose limiting side effect of gemcitabine administration.

Methotrexate, N-[4-[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leukopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

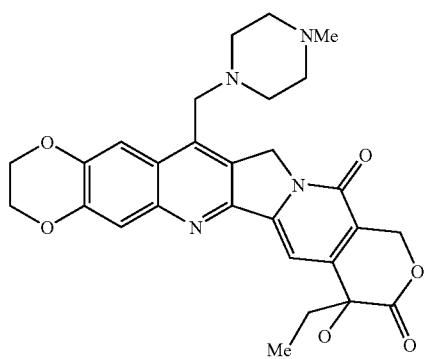

A known by the chemical name "7-(4-methylpiperazino-methylene)-10,11-ethylenedioxy-20(R,S)-camptothecin (racemic mixture) or "7-(4-methyl piperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphatidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and antisense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60.1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphatidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast Cancer Res., 2000, 2(3), 176-183); and 2CB VEGFR2 specific antibody (see Brekken, R. A. et al, Selective Inhibition of VEGFR2Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of Formula (I) and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Because the pharmaceutically active compounds of the present invention are active as AKT inhibitors they exhibit therapeutic utility in treating cancer and arthritis.

Suitably, the present invention relates to a method for treating or lessening the severity of a cancer selected from: brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, GIST (gastrointestinal stromal tumor) and testicular cancer.

Suitably, the present invention relates to a method for treating or lessening the severity of a cancer selected from: brain (gliomas), glioblastomas, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from ovarian, breast, pancreatic and prostate.

Isolation and Purification of His-Tagged AKT1 (aa 136-480)

Insect cells expressing His-tagged AKT1 (aa 136-480) were lysed in 25 mM HEPES, 100 mM NaCl, 20 mM imidazole; pH 7.5 using a polytron (5 mLs lysis buffer/g cells). Cell debris was removed by centrifuging at 28,000×g for 30 minutes. The supernatant was filtered through a 4.5-micron filter then loaded onto a nickel-chelating column pre-equilibrated with lysis buffer. The column was washed with 5 column volumes (CV) of lysis buffer then with 5 CV of 20% buffer B, where buffer B is 25 mM HEPES, 100 mM NaCl, 300 mM imidazole; pH 7.5. His-tagged AKT1 (aa 136-480) was eluted with a 20-100% linear gradient of buffer B over 10 CV. His-tagged AKT1 (136-480) eluting fractions were pooled and diluted 3-fold with buffer C, where buffer C is 25 mM HEPES, pH 7.5. The sample was then chromatographed over a Q-Sepharose HP column pre-equilibrated with buffer C. The column was washed with 5 CV of buffer C then step eluted with 5 CV 10% D, 5 CV 20% D, 5 CV 30% D, 5 CV 50% D and 5 CV of 100% D; where buffer D is 25 mM HEPES, 1000 mM NaCl; pH 7.5. His-tagged AKT1 (aa 136-480) containing fractions were pooled and concentrated in a 10-kDa molecular weight cutoff concentrator. His-tagged AKT1 (aa 136-480) was chromatographed over a Superdex 75 gel filtration column pre-equilibrated with 25 mM HEPES, 200 mM NaCl, 1 mM DTT; pH 7.5. His-tagged AKT1 (aa 136-480) fractions were examined using SDS-PAGE and mass spec. The protein was pooled, concentrated and frozen at −80 C.

His-tagged AKT2 (aa 138-481) and His-tagged AKT3 (aa 135-479) were isolated and purified in a similar fashion.

His-Tagged AKT Enzyme Assay

Compounds of the present invention were tested for AKT 1, 2, and 3 protein serine kinase inhibitory activity in substrate phosphorylation assays. This assay examines the ability of small molecule organic compounds to inhibit the serine phosphorylation of a peptide substrate. The substrate phosphorylation assays use the catalytic domains of AKT 1, 2, or 3. AKT 1, 2 and 3 are also commercially available from Upstate USA, Inc. The method measures the ability of the isolated enzyme to catalyze the transfer of the gamma-phosphate from ATP onto the serine residue of a biotinylated synthetic peptide SEQ. ID NO: 1 (Biotin-ahx-ARKRERAYSFGHHA-amide). Substrate phosphorylation was detected by the following procedure:

Assays were performed in 384well U-bottom white plates. 10 nM activated AKT enzyme was incubated for 40 minutes at room temperature in an assay volume of 20 ul containing 50 mM MOPS, pH 7.5, 20 mM $MgCl_2$, 4 uM ATP, 8 uM peptide, 0.04 uCi [g-$^{33}$P] ATP/well, 1 mM CHAPS, 2 mM DTT, and 1 ul of test compound in 100% DMSO. The reaction was stopped by the addition of 50 ul SPA bead mix (Dulbecco's PBS without $Mg^{2+}$ and $Ca^{2+}$, 0.1% Triton X-100, 5 mM EDTA, 50 uM ATP, 2.5 mg/ml Streptavidin-coated SPA beads.) The plate was sealed, the beads were allowed to settle overnight, and then the plate was counted in a Packard Topcount Microplate Scintillation Counter (Packard Instrument Co., Meriden, Conn.).

The data for dose responses were plotted as % Control calculated with the data reduction formula $100*(U1-C2)/(C1-C2)$ versus concentration of compound where U is the unknown value, C1 is the average control value obtained for DMSO, and C2 is the average control value obtained for 0.1M EDTA. Data are fitted to the curve described by: $y=((Vmax*x)/(K+x))$ where Vmax is the upper asymptote and K is the IC50.

Cloning of Full-Length Human (FL) AKT1:

Full-length human AKT1 gene was amplified by PCR from a plasmid containing myristylated-AKT1-ER (gift from Robert T. Abraham, Duke University under MTA, described in Klippel et al. in Molecular and Cellular Biology 1998 Volume 18 p. 5699) using the 5' primer: SEQ. ID NO: 2, 5' TATAT-AGGATCCATGAGCGACGTGGC 3' and the 3' primer: SEQ. ID NO: 3, AAATTTCTCGAGTCAGGCCGTGCT-GCTGG 3'. The 5' primer included a BamHI site and the 3'primer included an XhoI site for cloning purposes. The resultant PCR product was subcloned in pcDNA3 as a BamHI/XhoI fragment. A mutation in the sequence (IGC) coding for a Cysteine$^{25}$ was converted to the wild-type AKT1 sequence (CGC) coding for an Arginine$^{25}$ by site-directed mutagenesis using the QuikChange® Site Directed Mutagenesis Kit (Stratagene). The AKT1 mutagenic primer: SEQ. ID NO: 4,5' ACCTGGCGGCCACGCTACTTCCTCC and selection primer: SEQ. ID NO: 5,5' CTCGAGCATGCAAC-TAGAGGGCC (designed to destroy an XbaI site in the multiple cloning site of pcDNA3) were used according to manufacturer's suggestions. For expression/purification purposes, AKT1 was isolated as a BamHI/XhoI fragment and cloned into the BamHI/XhoI sites of pFastbacHTb (Invitrogen).

Expression of FL Human AKT1:

Expression was done using the BAC-to-BAC Baculovirus Expression System from Invitrogen (catalog #10359-016). Briefly 1) the cDNA was transferred from the FastBac vector into bacmid DNA, 2) the bacmid DNA was isolated and used to transfect Sf9 insect cells, 3) the virus was produced in Sf9 cells, 4) T. ni cells were infected with this virus and sent for purification.

Purification of FL Human AKT1:

For the purification of full-length AKT1, 130 g sf9 cells (batch #41646W02) were resuspended in lysis buffer (buffer A, 1 L, pH 7.5) containing 25 mM HEPES, 100 mM NaCl, and 20 mM imidazole. The cell lysis was carried out by Avestin (2 passes at 15K-20K psi). Cell debris was removed by centrifuging at 16K rpm for 1 hour and the supernatant was batch bound to 10 ml Nickel Sepharose HP beads at 4 C for over night. The beads were then transferred to column and the bound material was eluted with buffer B (25 mM HEPES, 100 mM NaCl, 300 mM imidazole, pH 7.5). AKT eluting fractions were pooled and diluted 3 fold using buffer C (25 mM HEPES, 5 mM DTT; pH 7.5). The sample was filtered and chromatographed over a 10 mL Q-HP column pre-equilibrated with buffer C at 2 mL/min.

The Q-HP column was washed with 3 column volume (CV) of buffer C, then step eluted with 5 CV 10% D, 5 CV 20% D, 5 CV 30% D, 5 CV 50% D and 5 CV of 100% D; where buffer D is 25 mM HEPES, 1000 mM NaCl, 5 mM DTT; pH 7.5. 5 mL fractions collected. AKT containing fractions were pooled and concentrated to 5 ml. The protein was next loaded to a 120 ml Superdex 75 sizing column that was pre-equilibrated with 25 mM HEPES, 200 mM NaCl, 5 mM DTT; pH 7.5. 2.5 mL fractions were collected.

AKT 1 eluting fractions were pooled, aliquoted (1 ml) and stored at −80 C. Mass spec and SDS-PAGE analysis were used to confirm purity and identity of the purified full-length AKT1.

Full length AKT2 and full length AKT3 were cloned, expressed and purified in a similar fashion.

AKT Enzyme Assay

Compounds of the present invention are tested for AKT 1, 2, and 3 protein serine kinase inhibitory activity in substrate phosphorylation assays. This assay examines the ability of small molecule organic compounds to inhibit the serine phosphorylation of a peptide substrate. The substrate phosphorylation assays use the catalytic domains of AKT 1, 2, or 3. AKT 1, 2 and 3 are also commercially available from Upstate USA, Inc. The method measures the ability of the isolated enzyme to catalyze the transfer of the gamma-phosphate from ATP onto the serine residue of a biotinylated synthetic peptide SEQ. ID NO: 1 (Biotin-ahx-ARKRERAYSFGHHA-amide). Substrate phosphorylation is detected by the following procedure:

Assays are performed in 384well U-bottom white plates. 10 nM activated AKT enzyme is incubated for 40 minutes at room temperature in an assay volume of 20 ul containing 50 mM MOPS, pH 7.5, 20 mM $MgCl_2$, 4 uM ATP, 8 uM peptide, 0.04 uCi [g-$^{33}$P] ATP/well, 1 mM CHAPS, 2 mM DTT, and 1 ul of test compound in 100% DMSO. The reaction is stopped by the addition of 50 ul SPA bead mix (Dulbecco's PBS without $Mg^{2+}$ and $Ca^{2+}$, 0.1% Triton X-100, 5 mM EDTA, 50 uM ATP, 2.5 mg/ml Streptavidin-coated SPA beads.) The plate is sealed, the beads are allowed to settle overnight, and then the plate is counted in a Packard Topcount Microplate Scintillation Counter (Packard Instrument Co., Meriden, Conn.).

The data for dose responses are plotted as % Control calculated with the data reduction formula 100*(U1−C2)/(C1−C2) versus concentration of compound where U is the unknown value, C1 is the average control value obtained for DMSO, and C2 is the average control value obtained for 0.1M EDTA. Data are fitted to the curve described by: y=((Vmax*x)/(K+x)) where Vmax is the upper asymptote and K is the IC50.

Compounds of the invention are tested for activity against AKT1, AKT2, and AKT3 in one or more of the above assays.

The majority of the compounds of the Examples were tested generally according to the above AKT enzyme assays and in at least one experimental run exhibited a pIC50 value: ≧5.9 against full length AKT1; ≧5.0 against full length AKT2; and ≧5.0 against full length AKT3.

The compounds of Examples 31, 32, 91, 95, 120, 128, 140, 161, 167, 169, 170, 190, 222, 225, 237, 249, 258 and 259 were tested generally according to the above AKT enzyme assays and in at least one experimental run exhibited a pIC50 value: ≧8.6 against full length AKT1; and ≧7.5 against full length AKT2. The majority of the compounds of Examples 31, 32, 91, 95, 120, 128, 140, 161, 167, 169, 170, 190, 222, 225, 237, 249, 258 and 259 were tested generally according to the above AKT enzyme assays and in at least one experimental run exhibited a pIC50 value; ≧7.6 against full length AKT3.

The compound of Example 96 was tested generally according to the above AKT enzyme assays and in at least one experimental run exhibited a pIC50 value: equal to 9.0 against full length AKT1; equal to 8.0 against full length AKT2; and equal to 8.8 against full length AKT3.

The compound of Example 137 was tested generally according to the above AKT enzyme assays and in at least one experimental run exhibited a pIC50 value: equal to 9.0 against full length AKT1; equal to 7.8 against full length AKT2; and equal to 8.4 against full length AKT3.

The compound of Example 224 was tested generally according to the above AKT enzyme assays and in at least one experimental run exhibited a pIC50 value: equal to 8.7 against full length AKT1; and equal to 7.8 against full length AKT2.

The compound of Example 161 was tested generally according to the above AKT enzyme assays and in at least one experimental run exhibited a pIC50 value: equal to 8.8 against full length AKT1; equal to 7.5 against full length AKT2; and equal to 7.6 against full length AKT3.

The compound of Example 222 was tested generally according to the above AKT enzyme assays and in at least one experimental run exhibited a pIC50 value: equal to 8.8 against full length AKT1; and equal to 7.9 against full length AKT2; and equal to 8.5 against full length AKT3.

In the above data, pIC50 is defined as −log(IC50) where the IC50 value is expressed in molar units.

The pharmaceutically active compounds within the scope of this invention are useful as AKT inhibitors in mammals, particularly humans, in need thereof.

The present invention therefore provides a method of treating cancer, arthritis and other conditions requiring AKT inhibition, which comprises administering an effective compound of Formula (I) and/or a pharmaceutically acceptable salt, hydrate, solvate or pro-drug thereof. The compounds of Formula (I) also provide for a method of treating the above indicated disease states because of their demonstrated ability to act as Akt inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of an Akt inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages, is preferred. Parenteral administration, at high dosages, however, also can be used when safe and convenient for the patient.

Optimal dosages to be administered may be readily determined by those skilled in the art, and will vary with the particular Akt inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing Akt inhibitory activity in mammals, including humans, comprises administering to a subject in need of such activity an effective Akt inhibiting amount of a pharmaceutically active compound of the present invention.

The invention also provides for the use of a compound of Formula (I) in the manufacture of a medicament for use as an Akt inhibitor.

The invention also provides for the use of a compound of Formula (I) in the manufacture of a medicament for use in therapy.

The invention also provides for the use of a compound of Formula (I) in the manufacture of a medicament for use in treating cancer.

The invention also provides for the use of a compound of Formula (I) in the manufacture of a medicament for use in treating arthritis.

The invention also provides for a pharmaceutical composition for use as an Akt inhibitor which comprises a compound of Formula (I) and a pharmaceutically acceptable carrier.

The invention also provides for a pharmaceutical composition for use in the treatment of cancer which comprises a compound of Formula (I) and a pharmaceutically acceptable carrier.

The invention also provides for a pharmaceutical composition for use in treating arthritis which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat cancer or arthritis, or compounds known to have utility when used in combination with an Akt inhibitor.

Without further elaboration, it is believed that one skilled in the art can, using the preceding description, utilize the present invention to its fullest extent. The following Examples are, therefore, to be construed as merely illustrative and not a limitation of the scope of the present invention in any way.

Experimental Details

The compounds of Examples 1 to 328 are readily made according to Schemes 1 to 3 or by analogous methods.

Preparation 1

Preparation of 1,1-dimethylethyl (2-amino-2-phenylethyl)carbamate

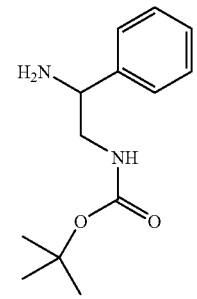 [SMILES: CC(C)(C)OC(=O)NCC(N)c1ccccc1]

a) 1,1-dimethylethyl (2-hydroxy-2-phenylethyl)carbamate

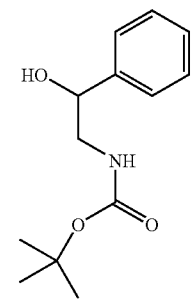 [SMILES: CC(C)(C)OC(=O)NCC(O)c1ccccc1]

To a solution of 2-amino-1-phenylethanol (5 g, 36.4 mmol) in THF (182 mL) at 25° C. was added Boc$_2$O (8.7 g, 40.1 mmol) in one portion. After 0.5 h, the solution was concentrated and the residue used directly without further purification: LC-MS (ES) m/z=238 (M+H)$^+$.

b) 1,1-dimethylethyl[2-(1,3-dioxo-1,3-dihydro-2H-isoindol-2-yl)-2-phenylethyl]carbamate

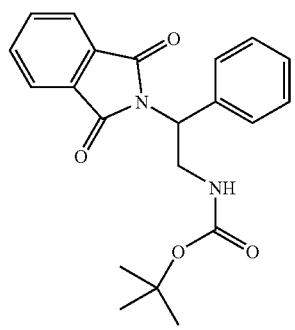 [SMILES: CC(C)(C)OC(=O)NCC(c1ccccc1)N1C(=O)c2ccccc2C1=O]

To a solution of 1,1-dimethylethyl (2-hydroxy-2-phenylethyl)carbamate (2 g, 8.44 mmol), phthalimide (1 g, 7.03 mmol) and triphenylphosphine (2.76 g, 10.5 mmol) in THF (35 mL) at 25° C. was added DEAD (1.7 mL, 10.5 mmol) dropwise. After 0.5 h, the solution was concentrated and c) 1,1-dimethylethyl (2-amino-2-phenylethyl)carbamate

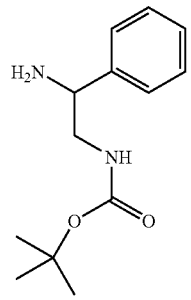 [SMILES: CC(C)(C)OC(=O)NCC(N)c1ccccc1]

A solution of 1,1-dimethylethyl[2-(1,3-dioxo-1,3-dihydro-2H-isoindol-2-yl)-2-phenylethyl]carbamate (2 g, 5.46 mmol) and either MeNH$_2$ (40 wt % in H$_2$O, 10 eq.) or NH$_2$NH$_2$ (10 eq.) in MeOH (0.5M, 10 mL) was heated to 60° C. in a sealed tube. After 12 h, the solution was concentrated and purified via column chromatography (silica-dry load, 2% MeOH in DCM (1% NH$_4$OH)) affording the title compound (1.1 g, 85%) as a white solid: LC-MS (ES) m/z=237 (M+H)$^+$.

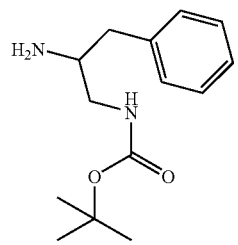 [SMILES: CC(C)(C)OC(=O)NCC(N)Cc1ccccc1]

Preparation of 1,1-dimethylethyl (2-amino-3-phenylpropyl)carbamate a) 1-amino-3-phenyl-2-propanol

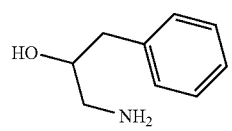

A solution of 2-(phenylmethyl)oxirane (7.5 g, 56.3 mmol) in NH$_4$OH (100 mL) was stirred at 25° C. in a sealed tube. After 12 h, the solution was concentrated and used directly: LCMS (ES) m/e 152 (M+H)$^+$.

b) 1,1-dimethyl ethyl (2-hydroxy-3-phenylpropyl)carbamate

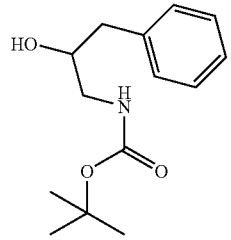 [SMILES: CC(C)(C)OC(=O)NCC(O)Cc1ccccc1]

To a solution of 1-amino-3-phenyl-2-propanol (7.6 g, 50 mmole) in THF (50 mL) at RT was added (Boc)$_2$O (12.0 g, 55 mmole). After stirring at RT for 2 h, the reaction solution was concentrated under vacuum and the residue purified on silica gel (5% MeOH in DCM (0.5% NH$_4$OH)) affording the title compound (13.1 g, 91%) as a clear yellow oil: LCMS (ES) m/z 252 (M+H)$^+$.

c) 1,1-dimethylethyl[2-(1,3-dioxo-1,3-dihydro-2H-isoindol-2-yl)-3-phenylpropyl]carbamate

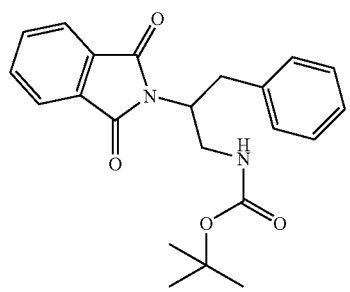 [SMILES: CC(C)(C)OC(=O)NCC(Cc1ccccc1)N1C(=O)c2ccccc2C1=O]

To a solution of 1,1-dimethylethyl (2-hydroxy-3-phenylpropyl)carbamate (10.0 g, 39.8 mmol), PPh$_3$ (12.5 g, 47.8 mmol) and phthalimide (6.44 g, 43.8 mmol) in THF (125 mL) at RT was added DEAD (9.4 mL, 59.7 mmol) over 5 min. After 1 h at RT, the reaction solution was concentrated and purified on silica (hexanes/EtOAc, 2:1) to give the title compound as a white solid (12.6 g, 83%): LCMS (ES) m/z 381 (M+H)$^+$.

d) 1,1-dimethylethyl (2-amino-3-phenylpropyl)carbamate

NH$_2$NH$_2$ (12.5 mL, 394 mmol) was added to a THF/MeOH (50 mL/50 mL) solution of 1,1-dimethylethyl (2-amino-4-phenylbutyl)carbamate (7.5 g, 19.7 mmol) and stirred at 50° C. in a sealed system. After 12 hours, the solids were filtered, washing with methanol. The filtrate was concentrated and purified by column chromatography using 5% MeOH in CHCl$_3$ containing 0.5% NH$_4$OH to give the title compound (3.75 g, 76%) as a white solid: LC-MS (ES) m/z=251 (M+H)$^+$.

--- purified via column chromatography (silica, 15% EtOAc in hexanes) affording the title compound (2 g, 80%) as a white foam: LC-MS (ES) m/z=367 (M+H)$^+$.

Preparation 3

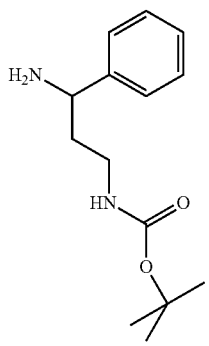

Preparation of 1,1-dimethylethyl (3-amino-3-phenylpropyl)carbamate a) 3-amino-1-phenyl-1-propanol

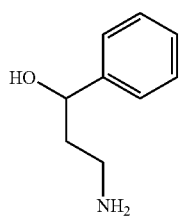 [SMILES: NCCC(O)c1ccccc1]

Benzoylacetonitrile (2 g, 13.8 mmol) in THF (35 mL) was added dropwise via addition funnel to a 0° C. solution of LAH (1.6 g, 41.3 mmol) in THF (35 mL). The resulting solution warmed to 25° C. and then was heated to 60° C. for an additional 2 h. After cooling to 0° C., a saturated solution of sodium potassium tartrate was added dropwise and the solution was extracted several times with DCM. The combined organic fractions were dried ($Na_2SO_4$), concentrated and purified via column chromatography (silica, 5-8% MeOH in DCM (1% $NH_4OH$)) affording the amino alcohol (1.4 g, 67%) as a clear oil: LCMS (ES) m/z 152 (M+H)$^+$.

b) 1,1-dimethyl ethyl (3-hydroxy-3-phenylpropyl)carbamate

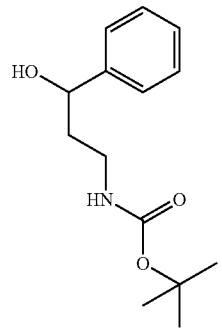 [SMILES: CC(C)(C)OC(=O)NCCC(O)c1ccccc1]

3-amino-1-phenyl-1-propanol (1.4 g, 9.27 mmol) was dissolved in THF (50 mL) and $Boc_2O$ (2.4 g, 11.1 mmol) was added in one portion. After 30 min., the solution was concentrated and the residue purified through via silica (0.5-1% MeOH in DCM (1% $NH_4OH$)) affording the title compound (1.6 g, 69%) as a pale white solid: LCMS (ES) m/z 152 (M+H)$^+$.

c) 1,1-dimethylethyl[3-(1,3-dioxo-1,3-dihydro-2H-isoindol-2-yl)-3-phenylpropyl]carbamate

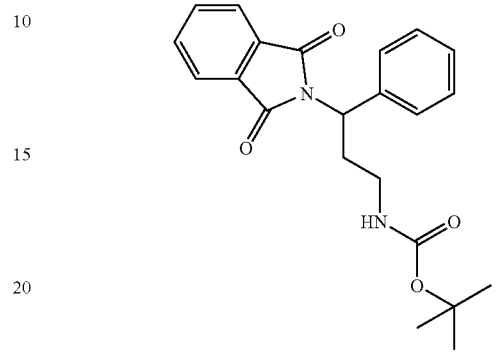

To a solution of 1,1-dimethylethyl (3-hydroxy-3-phenylpropyl)carbamate (3 g, 11.95 mmol), $PPh_3$ (4 g, 15.5 mmol) and phthalimide (1.8 g, 11.95 mmol) in THF (60 mL) at RT was added DEAD (2.4 mL, 15.5 mmol) over 5 min. After 1 h at RT, the reaction solution was concentrated and purified on silica (hexanes/EtOAc, 4:1) to give the title compound as a white solid (2.2 g, 48%): LCMS (ES) m/z 381 (M+H)$^+$.

c) 1,1-dimethylethyl (3-amino-3-phenylpropyl)carbamate $NH_2NH_2$ (1.8 mL, 57.7 mmol) was added to a THF/MeOH (1:1, 30 mL) solution of 1,1-dimethylethyl[3-(1,3-dioxo-1,3-dihydro-2H-isoindol-2-yl)-3-phenylpropyl]carbamate (2.2 g, 5.79 mmol) and stirred at 50° C. in a sealed system. After 12 hours, the solids were filtered, washing with methanol. The filtrate was concentrated and purified by column chromatography using 5% MeOH in $CHCl_3$ containing 1% $NH_4OH$ to give the title compound (1.1 g, 76%) as a white solid: LC-MS (ES) m/z=251 (M+H)$^+$.

Preparation 4

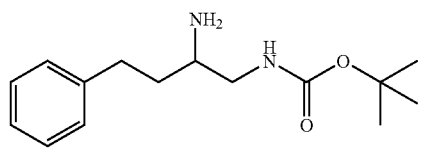

Preparation of 1,1-dimethylethyl (2-amino-4-phenylbutyl)carbamate a) 2-(2-phenylethyl)oxirane

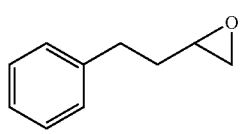 [SMILES: c1ccc(CCC2CO2)cc1]

3-chlorobenzenecarboperoxoic acid (12.1 g, 54.0 mmol) is added in one portion to a solution of 3-buten-1-ylbenzene (7.15 g, 54.1 mmol) in $CH_2Cl_2$ at 0° C. followed by warming to 25° C. overnight. Saturated $NaHCO_3$ was added and the mixture separated and the resulting clear oil (8.0 g, quant.) was carried forward without further purification: LC-MS (ES) m/z=149 $(M+H)^+$.

b) 1-amino-4-phenyl-2-butanol

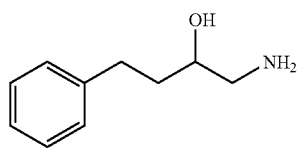 [SMILES: NCC(O)CCc1ccccc1]

2-(2-phenylethyl)oxirane (8.0 g, 54 mmol) was placed in a sealed tube with 7N $NH_3$-MeOH (130 mL) and stirred 2 hours at 70° C. followed by concentration to a clear oil (and was used without further purification in the following step.

c) 1,1-dimethylethyl (2-hydroxy-4-phenylbutyl)carbamate

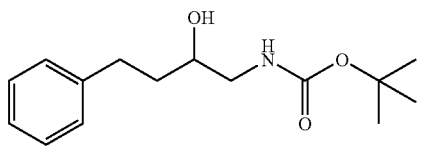 [SMILES: CC(C)(C)OC(=O)NCC(O)CCc1ccccc1]

1-amino-4-phenyl-2-butanol (7.4 g, 50.0 mmol) was dissolved in THF (50 mL) and $Boc_2O$ (13 g, 59.6 mmol) was added in one portion. After 30 min., the solution was concentrated and the residue purified through a silica plug (5% MeOH in DCM (0.5% $NH_4OH$)) affording the title compound (13.1 g, 91%) as a clear yellow oil: LCMS (ES) m/z 266 $(M+H)^+$.

d) 1,1-dimethylethyl[2-(1,3-dioxo-1,3-dihydro-2H-isoindol-2-yl)-4-phenylbutyl]carbamate

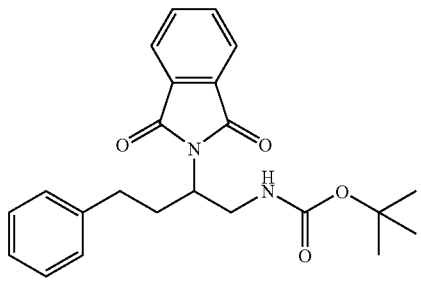 [SMILES: CC(C)(C)OC(=O)NCC(CCc1ccccc1)N1C(=O)c2ccccc2C1=O]

To a solution of 1,1-dimethylethyl (2-hydroxy-4-phenylbutyl)carbamate (3.0 g, 11.4 mmol), $PPh_3$ (3.6 g, 13.7 mmol) and phthalimide (1.84 g, 12.5 mmol) in THF (60 mL) at RT was added DEAD (1.8 mL, 11.4 mmol) over 5 min. After 0.5 h at RT, the reaction solution was concentrated and purified on silica (hexanes/EtOAC, 2:1) to give the title compound as a white solid (3.1 g, 69%): LCMS (ES) m/z 395 $(M+H)^+$.

e) 1,1-dimethylethyl (2-amino-4-phenylbutyl)carbamate $NH_2NH_2$ (2.5 mL, 79.6 mmol) was added to a THF/MeOH (40 mL/40 mL) solution of 1,1-dimethylethyl (2-amino-4-phenylbutyl)carbamate (3.1 g, 7.83 mmol) and stirred overnight. After 12 hours, the solution was concentrated and purified by column chromatography using 5% MeOH in $CHCl_3$ containing 0.5% $NH_4OH$ to give the title compound (1.4 g, 66%) as a white solid: LC-MS (ES) m/z=265 $(M+H)^+$.

Preparation 5

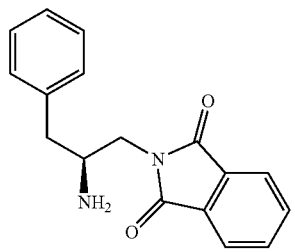

Preparation of 2-[(2S)-2-amino-3-phenylpropyl]-1H-isoindole-1,3(2H)-dione a) 1,1-dimethylethyl[(1S)-2-(1,3-dioxo-1,3-dihydro-2H-isoindol-2-yl)-1-(phenylmethyl)ethyl]carbamate

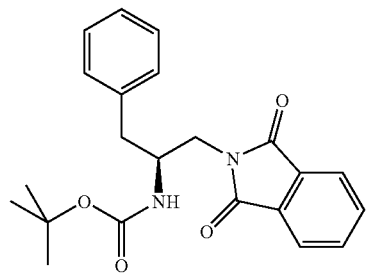 [SMILES: CC(C)(C)OC(=O)N[C@@H](Cc1ccccc1)CN1C(=O)c2ccccc2C1=O]

To a solution of (S)-(−)-2-(tert-butoxycarbonylamino)-3-phenyl-1-propanol (3.0 g, 11.9 mmole), $PPh_3$ (3.74 g, 14.4 mmole) and phthalimide (1.93 g, 13.1 mmole) in THF (75 mL) at RT was added DEAD (2.8 mL, 17.8 mmole) over 5 min. After 1.5 h at RT, the reaction solution was concentrated and purified on silica (hexanes/EtOAC, 2:1) to give the title compound as a white solid (4.3 g, 95%): LCMS (ES) m/z 381 $(M+H)^+$.

b) 2-[(2S)-2-amino-3-phenylpropyl]-1H-isoindole-1,3(2H)-dione

To a solution of 1,1-dimethylethyl[(1S)-2-(1,3-dioxo-1,3-dihydro-2H-isoindol-2-yl)-1-(phenylmethyl)ethyl]carbamate (4.3 g, 11.3 mmole) in MeOH (100 mL) at RT was added 4M HCl in dioxane (50 mL). After stirring for 3 h at RT, the reaction solution was concentrated to a white solid (quant.): LCMS (ES) m/z 281 $(M+H)^+$.

Preparation 6

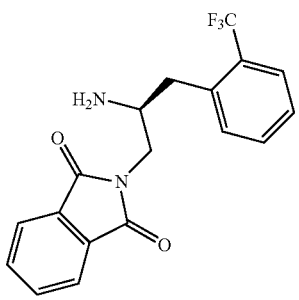

Preparation of 2-{(2S)-2-amino-3-[2-(trifluoromethyl)phenyl]propyl}-1H-isoindole-1,3(2H)-dione a) 1,1-dimethylethyl ((1S)-2-hydroxy-1-{[2-(trifluoromethyl)phenyl]methyl}ethyl)carbamate

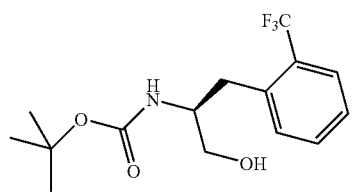 [SMILES: CC(C)(C)OC(=O)N[C@H](CO)Cc1ccccc1C(F)(F)F]

To a solution of N-{[(1,1-dimethylethyl)oxy]carbonyl}-2-(trifluoromethyl)-L-phenylalanine (5 g, 15 mmol) in THF (75 mL) at 0° C. stirred was added $BH_3$-THF (45 mL, 45 mmol-1M in THF). After 12 h, the reaction was quenched with AcOH:MeOH (1:5, 24 mL) and partitioned between saturated aqueous $NaHCO_3$ and DCM. The aqueous phase was then extracted several times with DCM. The combined organic fractions were dried over $Na_2SO_4$ and used directly (4.2 g, 88%): LCMS (ES) m/e 320 (M+H)$^+$.

b) 1,1-dimethylethyl ((1S)-2-(1,3-dioxo-1,3-dihydro-2H-isoindol-2-yl)-1-{[2-(trifluoromethyl)phenyl]methyl}ethyl)carbamate

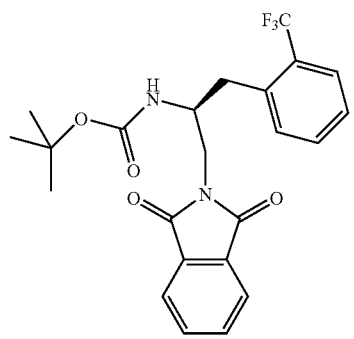 [SMILES: CC(C)(C)OC(=O)N[C@@H](Cc1ccccc1C(F)(F)F)CN1C(=O)c2ccccc2C1=O]

To a solution of 1,1-dimethylethyl ((1S)-2-hydroxy-1-{[2-(trifluoromethyl)phenyl]methyl}ethyl)carbamate (4.2 g, 13.2 mmol), triphenylphosphine (4.5 g, 17.1 mmol) and phthalimide (1.9 g, 13.2 mmol) in THF (66 mL) at 25° C. was added diethyl azodicarboxylate (2.7 mL, 17.1 mmol). After stirring at RT for 1 h, the reaction solution was concentrated under vacuum and the residue purified on silica gel (1% MeOH in DCM) affording the title compound (3.2 g, 54%) as a white solid: LCMS (ES) m/z 449 (M+H)$^+$.

c) 2-{(2S)-2-amino-3-[2-(trifluoromethyl)phenyl]propyl}-1H-isoindole-1,3(2H)-dione To a solution of 1,1-dimethylethyl ((1S)-2-(1,3-dioxo-1,3-dihydro-2H-isoindol-2-yl)-1-{[2-(trifluoromethyl)phenyl]methyl}ethyl)carbamate (3.2 g, 7.1 mmol) in MeOH (35 mL) at RT was added 4M HCl in dioxane (18 mL). After 12 h, the solution was concentrated affording the title compound (2.7 g, quant.) as the HCl salt: LCMS (ES) m/z 349 (M+H)$^+$.

Preparation 7

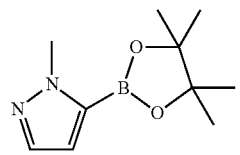

Preparation of 5-(5,5-dimethyl-1,3,2-dioxaborinane-2-yl)-1-methyl-1H-pyrazole

To a solution of 1-methylpyrazole (4.1 g, 50 mmole) in THF (100 mL) at 0° C. was added n-BuLi (2.2M in THF, 55 mmole). The reaction solution was stirred for 1 hour at RT and then cooled to −78° C. [J. Heterocyclic Chem. 41, 931 (2004)]. To the reaction solution was added 2-isopropoxy-4,4,5,5-tetramethyl-1,3,2-dioxaborolane (12.3 mL, 60 mmole). After 15 min at −78° C., the reaction was allowed to warm to 0° C. over 1 hour. The reaction was diluted with saturated $NH_4Cl$ solution and extracted with DCM. The organic fractions were washed with $H_2O$ (2×100 mL), dried over $Na_2SO_4$ and concentrated under vacuum to afford a tan solid (8.0 g, 77%) which was used without further purification. LCMS (ES) m/z 127 (M+H)$^+$ for [RB(OH)$_2$]; $^1$H NMR (CDCl$_3$, 400 MHz) δ 7.57 (s, 1H), 6.75 (s, 1H), 4.16 (s, 3H), and 1.41 (s, 12H).

Preparation 8

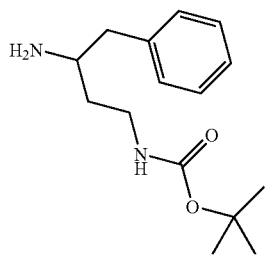

Preparation of 1,1-dimethylethyl (3-amino-4-phenylbutyl)carbamate a) 3-oxo-4-phenylbutanenitrile

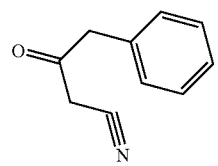 [SMILES: N#CCC(=O)Cc1ccccc1]

To a solution of cyanoacetic acid (2 g, 23.5 mmol) in THF (100 mL) at −78° C. was added nBuLi (10 mL, 25.9 mmol, 2.5M in hexanes). After 30 min, phenylacetyl chloride (1.6 mL, 11.8 mmol) was added dropwise. Following an additional 30 min, the solution was partitioned between 1N HCl- Et₂O and the aqueous phase was washed several times with Et₂O. The combined organic fractions were dried over Na₂SO₄, concentrated and purified via column chromatography (silica, 30% EtOAc in hexanes) yielding the title compound (770 mg, 40%) as a tan oil: LCMS (ES) m/z 160 (M+H)⁺.

b) 1,1-dimethylethyl (3-amino-4-phenylbutyl)carbamate

A solution of 3-oxo-4-phenylbutanenitrile (1.1 g, 6.92 mmol) in THF (10 mL) was added to a 0° C. solution of lithium aluminum hydride (787 mg, 20.8 mmol) in THF (25 mL). After 12 h, the solution was quenched with H₂O (943 uL), 6N NaOH (716 uL) and H₂O (3.5 mL). The resulting precipitate was filtered and the pad was washed several times with DCM. The filtrate was concentrated then redissolved in THF (30 mL) and Boc₂O (1.5 g, 6.92 mmol) was added in one portion. After 30 min, the solution was concentrated and purified via column chromatography (silica, 3% MeOH in DCM (1% NH₄OH)) yielding the title compound (1 g, 55%-2steps) as an orange solid: LCMS (ES) m/z 265 (M+H)⁺.

c) 1,1-dimethylethyl[3-(1,3-dioxo-1,3-dihydro-2H-isoindol-2-yl)-4-phenylbutyl]carbamate

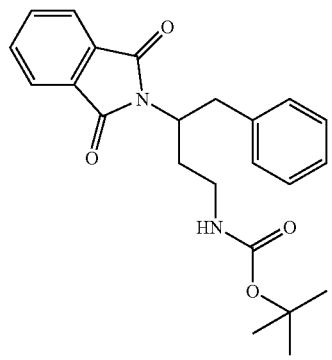 [SMILES: CC(C)(C)OC(=O)NCCC(Cc1ccccc1)N1C(=O)c2ccccc2C1=O]

To a solution of 1,1-dimethylethyl (3-amino-4-phenylbutyl)carbamate (1 g, 3.77 mmol), PPh₃ (1.3 g, 4.91 mmol) and phthalimide (555 mg, 3.77 mmol) in THF (18 mL) at RT was added DEAD (772 uL, 4.91 mmol) over 5 min. After 1 h at RT, the reaction solution was concentrated and purified on silica (hexanes/EtOAc, 5:1) to give the title compound as a white solid (725 mg, 49%): LCMS (ES) m/z 395 (M+H)⁺.

d) 1,1-dimethylethyl (3-amino-4-phenylbutyl)carbamate

NH₂NH₂ (577 uL, 18.4 mmol) was added to a THF/MeOH (1:1, 10 mL) solution of 1,1-dimethylethyl[3-(1,3-dioxo-1,3-dihydro-2H-isoindol-2-yl)-4-phenylbutyl]carbamate (725 mg, 1.84 mmol) and stirred at 50° C. in a sealed system. After 12 hours, the solids were filtered, washing with methanol. The filtrate was concentrated and purified by column chromatography using 5% MeOH in CHCl₃ containing 1% NH₄OH to give the title compound (483 mg, quant.) as a white solid: LC-MS (ES) m/z=264 (M+H)⁺.

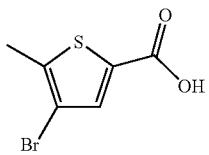

Preparation 9

Preparation of 4-bromo-5-methyl-2-thiophenecarboxylic Acid

A solution of bromine (725 uL, 14.1 mmol) in AcOH (2.8 mL) was added dropwise to 5-methyl-2-thiophenecarboxylic acid (2 g, 14.1 mmol) and FeCl₃ (456 mg, 2.81 mmol) in AcOH (28 mL) at 25° C. After 5 h, the solution was poured onto ice and the precipitate was filtered and washed with water affording the title compound (3 g, quant.) as a yellow powder: LCMS (ES) m/z 222 (M+H)⁺.

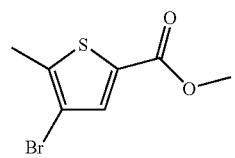

Preparation 10

Preparation of methyl 4-bromo-5-methyl-2-thiophenecarboxylate

A solution of 4-bromo-5-methyl-2-thiophenecarboxylic acid (3 g, 13.6 mmol) in MeOH (67 mL) and H₂SO₄ (3 mL) was stirred at 50° C. After 12 h, the solution was added to ice-H₂O and the pH was adjusted to ~11. The aqueous phase was extracted several times with DCM and the combined organic fractions were dried over Na₂SO₄, concentrated and used directly yielding the title compound (3 g, 94%) as an orange solid: LCMS (ES) m/z 236 (M+H)⁺.

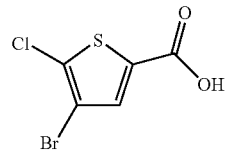

Preparation 11

Preparation of 4-bromo-5-chloro-2-thiophenecarboxylic Acid

A solution of bromine (634 uL, 12.3 mmol) in AcOH (2.5 mL) was added dropwise to 5-chloro-2-thiophenecarboxylic acid (2 g, 12.3 mmol) and FeCl₃ (399 mg, 2.50 mmol) in AcOH (25 mL) at 25° C. The reaction mixture was warmed to reflux where additional bromine (634 uL, 12.3 mmol) and FeCl₃ (399 mg, 2.50 mmol) were added. After 7 d, the solution was poured onto ice and the precipitate was filtered and washed with water affording the title compound (3 g, quant.) as a yellow powder: LCMS (ES) m/z 242 (M+H)⁺.

Preparation 12

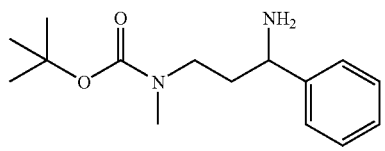

Preparation of 1,1-dimethylethyl (3-amino-3-phenylpropyl)methylcarbamate a) 1,1-dimethylethyl (3-hydroxy-3-phenylpropyl)methylcarbamate

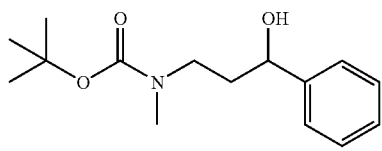 [SMILES: CN(CCC(O)c1ccccc1)C(=O)OC(C)(C)C]

3-(methylamino)-1-phenyl-1-propanol (4.12 g, 24.9 mmol) was dissolved in THF (30 mL) and Boc$_2$O (1M/THF, 30 mL, 30 mmol) was added in one portion. After 30 min., the solution was concentrated and the residue purified through a silica plug (5% MeOH in DCM (0.5% NH$_4$OH)) affording the title compound (6.4 g, 97%) as a clear yellow oil: LCMS (ES) m/z 265 (M+H)$^+$.

b) 1,1-dimethylethyl[3-(1,3-dioxo-1,3-dihydro-2H-isoindol-2-yl)-3-phenylpropyl]methylcarbamate

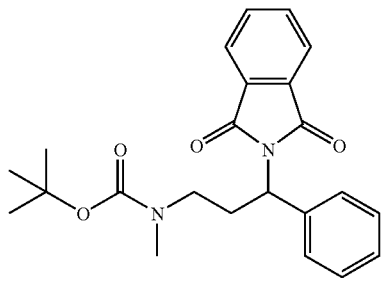 [SMILES: CN(CCC(c1ccccc1)N1C(=O)c2ccccc2C1=O)C(=O)OC(C)(C)C]

To a solution of 1,1-dimethylethyl (3-hydroxy-3-phenylpropyl)methylcarbamate (2.8 g, 10.4 mmol), PPh$_3$ (3.3 g, 12.7 mmol) and phthalimide (1.86 g, 12.6 mmol) in THF (50 mL) at RT was added DEAD (1.98 mL, 12.6 mmol) over 5 min. After 0.5 h at RT, MeOH (10 mL) was added and the reaction solution was absorbed onto silica and purified via chromatography (hexanes/EtOAC, 2:1) to give the title compound as a white solid (2.7 g, 65%): LCMS (ES) m/z 395 (M+H)$^+$.

c) 1,1-dimethylethyl (3-amino-3-phenylpropyl)methylcarbamate

NH$_2$NH$_2$ (1.7 mL, 54.2 mmol) was added to a THF/MeOH (50 mL/10 mL) solution of 1,1-dimethylethyl[3-(1,3-dioxo-1,3-dihydro-2H-isoindol-2-yl)-3-phenylpropyl]methylcarbamate (2.7 g, 6.8 mmol) and stirred overnight. After 12 hours, the solution was absorbed onto silica and purified by column chromatography using 5% MeOH in CHCl$_3$ containing 0.5% NH$_4$OH to give the title compound (1.4 mg, 77%) as a white solid: LC-MS (ES) m/z=265 (M+H)$^+$.

Preparation 13

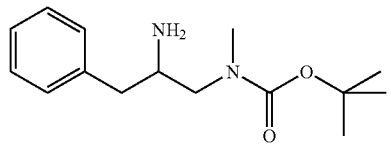

Preparation of 1,1-dimethylethyl (2-amino-3-phenylpropyl)methylcarbamate a) 1,1-dimethylethyl (2-hydroxy-3-phenylpropyl)methylcarbamate

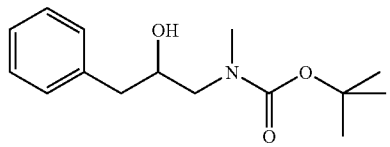 [SMILES: CN(CC(O)Cc1ccccc1)C(=O)OC(C)(C)C]

To a solution of 1-(methylamino)-3-phenyl-2-propanol (13 g, 78 mmol) [prepared according to Galons, H. et al Eur. J. Med. Chem. Chim. Ther. 1979 14, 165-170.] in THF (390 mL) at RT was added (Boc)$_2$O (21.6 g, 99 mmol). After stirring at RT for 2 h, the reaction solution was absorbed onto silica and purified via chromatography (35% EtOAc/Hex) affording the title compound (11.6 g, 56%) as a clear yellow oil: LCMS (ES) m/z 266 (M+H)$^+$.

b) 1,1-dimethylethyl[2-(1,3-dioxo-1,3-dihydro-2H-isoindol-2-yl)-3-phenylpropyl]methylcarbamate

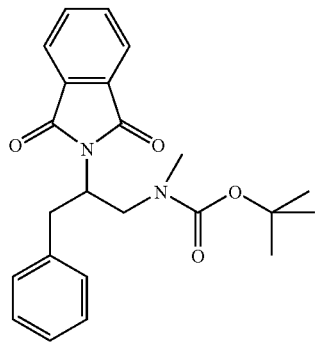 [SMILES: CN(CC(Cc1ccccc1)N1C(=O)c2ccccc2C1=O)C(=O)OC(C)(C)C]

To a solution of 1,1-dimethylethyl (2-hydroxy-3-phenylpropyl)methylcarbamate (11.6 g, 43.72 mmol), PPh$_3$ (14.3 g, 54.5 mmol) and phthalimide (8.7 g, 59.1 mmol) in THF (220 mL) at RT was added DEAD (8.5 mL, 54 mmol) over 15 min. After 0.5 h at RT, MeOH (10 mL) was added and the reaction solution was absorbed onto silica and purified via chromatography (hexanes/EtOAC, 2:1) to give the title compound as a white solid (9.97 g, 57%): LCMS (ES) m/z 395 (M+H)$^+$.

c) 1,1-dimethylethyl (2-amino-3-phenylpropyl)methylcarbamate

NH$_2$NH$_2$ (7 mL, 0.2 mol) was added to a THF/MeOH (100 mL/25 mL) solution of 1,1-dimethylethyl[2-(1,3-dioxo-1,3- dihydro-2H-isoindol-2-yl)-3-phenylpropyl]methylcarbamate (2.7 g, 6.8 mmol) and stirred overnight. After 12 hours, the solution was absorbed onto silica and purified by column chromatography using 5% MeOH in CHCl₃ containing 0.5% NH₄OH to give the title compound (5.8 mg, 88%) as a white solid: LC-MS (ES) m/z=265 (M+H)⁺.

Preparation 14

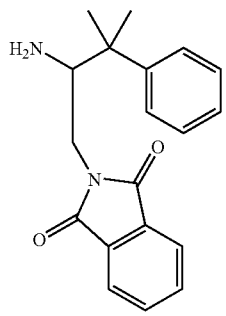

Preparation of 2-(2-amino-3-methyl-3-phenylbutyl)-1H-isoindole-1,3(2H)-dione a) methyl 2-azido-3-methyl-3-phenylbutanoate

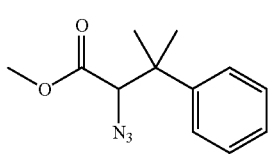 [SMILES: COC(=O)C(N=[N+]=[N-])C(C)(C)c1ccccc1]

To a solution of KHMDS (36 mL, 17.9 mmol) in THF (70 mL) at −78° C. was added methyl 3-methyl-3-phenylbutanoate (3 g, 15.6 mmol) in THF (15 mL) dropwise. After 1 h, trisylazide (5 g, 18.7 mmol) in THF (15 mL) was added dropwise over 10 min. After an additional 5 min, acetic acid (4.1 mL) was added and the reaction mixture warmed to 25° C. over 1 h. The solution was then partitioned between H₂O-DCM and the aqueous phase was washed several times with DCM. The combined organic fractions were dried over Na₂SO₄, concentrated and purified via column chromatography (silica, 20% EtOAc in hexanes) yielding the title compound (2.6 g, 71%) contaminated with 33% methyl 3-methyl-3-phenylbutanoate to be purified out in the following steps: LCMS (ES) m/e 234 (M+H)⁺.

b) methyl beta,beta-dimethylphenylalaninate

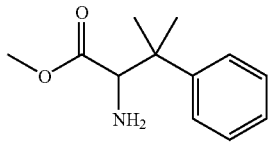

A solution of methyl 2-azido-3-methyl-3-phenylbutanoate (2.6 g, 11.2 mmol) and PPh₃ (4.4 g, 16.7 mmol) in H₂O (400 uL) and THF (100 mL) was stirred at 25° C. over 2 d then at 50° C. for 12 h. The solution was concentrated and purified via column chromatography (silica, 5% MeOH in DCM (1% NH₄OH)) yielding the title compound (1.4 g, quant.): LCMS (ES) m/e 208 (M+H)⁺.

c) 2-amino-3-methyl-3-phenyl-1-butanol

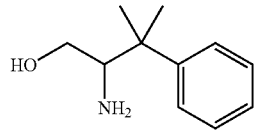

To a solution of methyl beta,beta-dimethylphenylalaninate (1.4 g, 6.76 mmol) in THF (20 mL) at 0° C. was added dropwise a solution of lithium aluminum hydride (384 mg, 10.1 mmol) in THF (10 mL). After warming to 25° C. over 12 h, the solution was quenched by sequential addition of H₂O (659 uL), 6N NaOH (500 uL) and H₂O (2.4 mL). The resulting precipitate was filtered and the pad washed thoroughly with DCM. The filtrate was concentrated and purified via column chromatography (silica, 2-5% MeOH in DCM (1% NH₄OH)) yielding the title compound (770 mg, 64%): LCMS (ES) m/e 179 (M+H)⁺.

d) 1,1-dimethylethyl[1-(hydroxymethyl)-2-methyl-2-phenylpropyl]carbamate

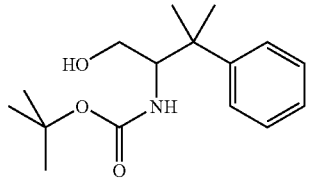 [SMILES: CC(C)(C)OC(=O)NC(CO)C(C)(C)c1ccccc1]

Boc₂O (1 g, 4.76 mmol) was added in one portion to 2-amino-3-methyl-3-phenyl-1-butanol (770 mg, 4.33 mmol) in THF (20 mL) at 25° C. After 30 min, the solution was concentrated yielding the title compound (1.2 g, quant.) as a white solid which was used without further purification: LCMS (ES) m/e 279 (M+H)⁺.

e) 1,1-dimethylethyl {1-[(1,3-dioxo-1,3-dihydro-2H-isoindol-2-yl)methyl]-2-methyl-2-phenylpropyl}carbamate

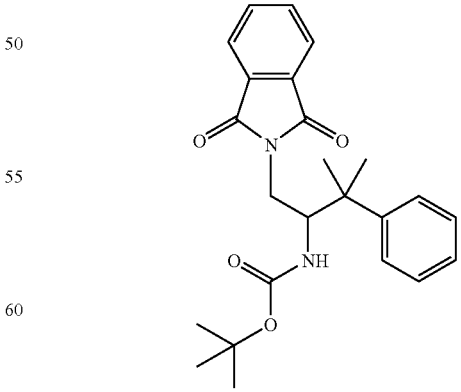

To a solution of 1,1-dimethylethyl[1-(hydroxymethyl)-2-methyl-2-phenylpropyl]carbamate (775 mg, 2.8 mmol), triphenylphosphine (915 mg, 3.5 mmol) and phthalimide (499 mg, 3.4 mmol) in THF (15 mL) at 25° C. was added diethyl azodicarboxylate (0.54 mL, 3.4 mmol). After stirring at RT for 1 h, MeOH was added (5 mL) and the solution was adsorbed onto silica and purified via column chromatography (1% MeOH in DCM) affording the title compound (723 mg, 64%) as a white solid: LCMS (ES) m/z 409 (M+H)+.

f) 2-(2-amino-3-methyl-3-phenylbutyl)-1H-isoindole-1,3(2H)-dione

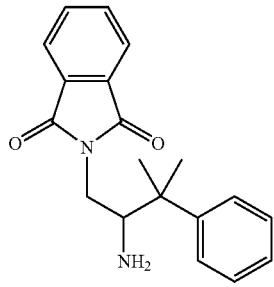 [SMILES: CC(C)(c1ccccc1)C(N)CN1C(=O)c2ccccc2C1=O]

To a solution of 1,1-dimethylethyl {1-[(1,3-dioxo-1,3-dihydro-2H-isoindol-2-yl)methyl]-2-methyl-2-phenylpropyl}carbamate (723 mg, 1.77 mmol) in CHCl₃:MeOH (10:1, 55 mL) at RT was added 4M HCl in dioxane (10 mL). After stirring for 3 h at RT, the reaction solution was concentrated to a white solid (quant.): LCMS (ES) m/z 309 (M+H)+.

Preparation 15

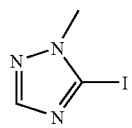

Preparation of 5-iodo-1-methyl-1H-1,2,4-triazole 1-methyl-1H-1,2,4-triazole (2.05 g, 24.7 mmol) was added slowly over 15 minutes to an Et₂O solution of nBuLi at −70° C. The mixture was stirred for 60 minutes at −70° C. and allowed to warm to −30° C. A solution of 12 (6.5 g, 25.6 mmol) in THF (27 mL) was added slowly over 15 minutes and the mixture was allowed to warm to room temperature and stir for 60 minutes. The mixture was partitioned with saturated Na₂S₂O₃, the phases were separated and the organic solvent removed. The crude iodide was used without further purification: LCMS (ES) m/z 210 (M+H)+.

Preparation 16

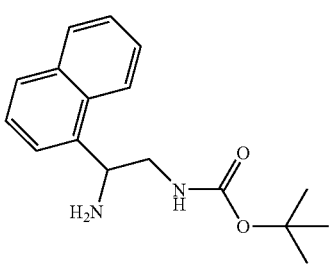

Preparation of 1,1-dimethylethyl[2-amino-2-(1-naphthalenyl)ethyl]carbamate a) hydroxy(1-naphthalenyl)acetonitrile

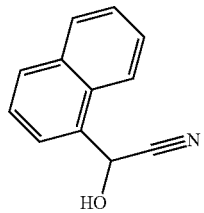 [SMILES: N#CC(O)c1cccc2ccccc12]

To a solution of potassium cyanide in ether (100 mL) at 0° C. was added dropwise a mixture of 1-naphthalenecarbaldehyde (1.56 g, 10 mmol) and acetic acid (1.41 g, 23.5 mmol) in ether (10 mL). The resulting mixture was warmed to 25° C. for 20 h, where the precipitate was filtered and the filtrate was concentrated affording the title compound as a clear oil (1.67 g, 9.14 mmol, 91%): LCMS (ES) m/z 184 (M+H)+.

b) 2-amino-1-(1-naphthalenyl)ethanol

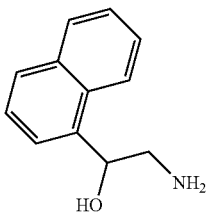 [SMILES: NCC(O)c1cccc2ccccc12]

To a solution of hydroxy(1-naphthalenyl)acetonitrile (1.67 g, 9.14 mol) in THF (90 mL) at 0° C. was added dropwise a solution of LAH-THF (1M, 11 mL, 11 mmol). After 2 hrs, the solution was quenched by sequential addition of H₂O (0.42 mL), 6N NaOH (6M, 0.32 mL) and H₂O (1.6 mL). The resulting precipitate was filtered and the filtrate was concentrated and used directly yielding the title compound (0.897 g, 4.8 mmol, 53%) as a clear oil: LCMS (ES) m/z 188 (M+H)+.

c). 1,1-dimethylethyl[2-hydroxy-2-(1-naphthalenyl)ethyl]carbamate

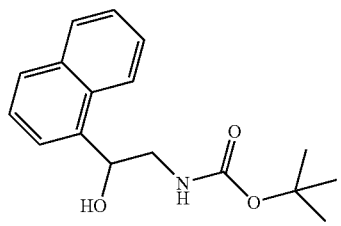 [SMILES: CC(C)(C)OC(=O)NCC(O)c1cccc2ccccc12]

To a solution of 2-amino-1-(1-naphthalenyl)ethanol (1.38 g, 4.8 mmol) in dichloromethane (50 mL) was added Boc anhydride (1.155 g, 5.3 mmole). After stirring at RT for 12 h, the reaction solution was concentrated and partitioned between NaHCO₃ sat./DCM. The aqueous phase was washed several times with DCM. The combined organic fractions were dried over Na₂SO₄, concentrated and used directly yielding the title compound as a white solid (1.378 g, 4.8 mmol, quant): LCMS (ES) m/z 288 (M+H)+.

d) 1,1-dimethylethyl[2-(1,3-dioxo-1,3-dihydro-2H-isoindol-2-yl)-2-(1-naphthalenyl)ethyl]carbamate

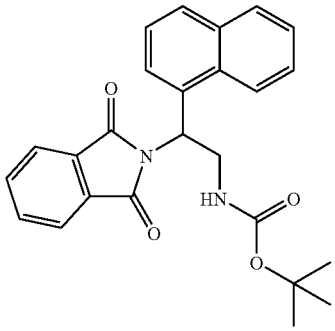 [SMILES: CC(C)(C)OC(=O)NCC(c1cccc2ccccc12)N1C(=O)c2ccccc2C1=O]

To a solution of 1,1-dimethylethyl[2-hydroxy-2-(1-naphthalenyl)ethyl]carbamate (1.38 g, 4.8 mmol), triphenylphosphine (1.52 g, 5.76 mmol) and phthalimide (0.74 g, 5.04 mmol) in THF (50 mL) at 25° C. was added diethyl azodicarboxylate (0.87 mL, 5.52 mmol). After stirring at RT for 1 h, the reaction solution was concentrated under vacuum and the residue purified on silica gel (20% EtOAc in hexanes) affording the title compound (1.29 g, 3.1 mmol, 65%) as a white solid: LCMS (ES) m/z 387 (M+H)+.

e) 1,1-dimethylethyl[2-amino-2-(1-naphthalenyl)ethyl]carbamate

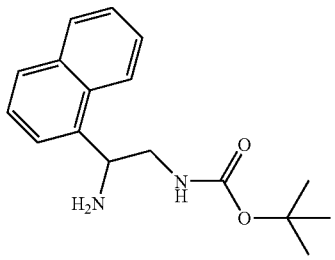 [SMILES: CC(C)(C)OC(=O)NCC(N)c1cccc2ccccc12]

To a solution of 1,1-dimethylethyl[2-(1,3-dioxo-1,3-dihydro-2H-isoindol-2-yl)-2-(1-naphthalenyl)ethyl]carbamate (1.29 g, 3.1 mmol) in MeOH (30 mL) was added anhydrous hydrazine (0.5 mL, 15.5 mmol) at 25° C. After 12 h, the solution was partitioned between DCM/H$_2$O. The aqueous phase was washed several times with DCM and the combined organic fractions were dried over Na$_2$SO$_4$, concentrated and used directly yielding the title compound as a white solid (491 mg, 1.72 mmole, 55%): LCMS (ES) m/z 287 (M+H)+.

Preparation 17

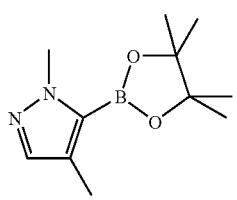

Preparation of 1,4-dimethyl-5-(4,4,5,5-tetramethyl-1,3,2-dioxaborolan-2-yl)-1H-pyrazole To a suspension of NaH (60% in mineral oil, 3.5 g, 146 mmol, washed with 200 mL of hexane) in THF (200 mL) was added 4-methyl-1H-pyrazole (10 g, 122 mmol) at 0° C. dropwise. After stirring at RT for 1 h, to above suspension was added MeI (7.3 mL, 117 mmol) dropwise at 0° C. The reaction mixture was stirred overnight. The NaI by-product was removed by filtration and the filtrate solution was used directly in the next step.

At 0° C., to above THF solution of 1,4-dimethylpyrazole was added n-BuLi (2.5M in hexane, 58.5 mL, 146 mmole). The reaction solution was stirred for 2 hour at RT and then cooled to −78° C. [J. Heterocyclic Chem. 41, 931 (2004)]. To the reaction solution was added 2-isopropoxy-4,4,5,5-tetramethyl-1,3,2-dioxaborolane (27.2 g, 146 mmole). After 15 min at −78° C., the reaction was allowed to warm to 0° C. and stir for 3 h. The reaction was diluted with saturated NH$_4$Cl solution and extracted with DCM. The organics were dried over Na$_2$SO$_4$ and concentrated under vacuum to afford the title compound as a brown solid (21 g, 78%) which was used directly without further purification: LC-MS: 141 (M-C$_6$H$_{12}$)+, 223 (M+H)+. $^1$H NMR (CDCl$_3$): δ 7.28 (s, 1H), 4.03 (s, 3H), 2.22 (s, 3H), and 1.32 (s, 12H).

Preparation 18

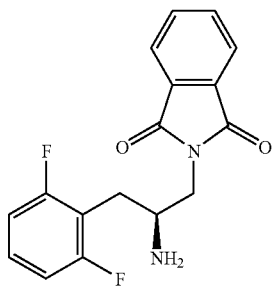

Preparation of 2-[(2S)-2-amino-3-(2,6-difluorophenyl)propyl]-1H-isoindole-1,3(2H)-dione a) N-{[(1,1-dimethylethyl)oxy]carbonyl}-2,6-difluoro-L-phenylalanine

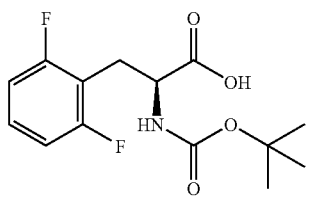 [SMILES: CC(C)(C)OC(=O)N[C@@H](Cc1c(F)cccc1F)C(=O)O]

1,4-Dioxane (55 mL) and water (12 mL) was added to 2,6-difluoro-L-phenylalanine (3.00 g, 12.62 mmol) in a 200 mL round-bottomed flask. The mixture was cooled to 0° C. followed by the slow addition of NaOH (12.62 mL, 31.6 mmol) and then Boc$_2$O (3.42 g, 15.20 mmol). The mixture was allowed to warm to room temperature and monitored for completion by LC-MS. Upon completion, the mixture was cooled to 0° C. and made neutral by the slow addition of 2.5M HCl (12 mL). The solvents removed under reduced pressure. The resulting solid was sonicated with 20% MeOH/CHCl$_3$ (150 mL), filtered and the organic solvent removed to give the product (4.3 g, 14.4 mmol, quant.) as a white solid which was used in the next step without further purification: LC-MS (ES) m/z=302 (M+H)+.

b) 1,1-dimethylethyl[(1S)-2-(2,6-difluorophenyl)-1-(hydroxymethyl)ethyl]carbamate

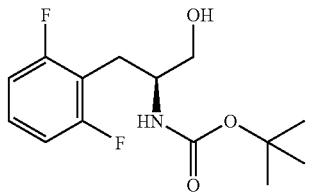 [SMILES: CC(C)(C)OC(=O)N[C@H](CO)Cc1c(F)cccc1F]

BH$_3$.THF (64.7 ml, 64.7 mmol) was added slowly to a tetrahydrofuran (THF) (60 mL) solution of N-{[(1,1-dimethylethyl)oxy]carbonyl}-2,6-difluoro-L-phenylalanine (4.33 g, 14.37 mmol) at 0° C. in a 200 mL round-bottomed flask. The mixture was stirred for 2 hours and then placed in the freezer overnight. Excess reagent was quenched by the slow addition of AcOH in MeOH at 0° C. and the mixture warmed to room temperature for 2 hours. The THF volume was reduced by ½ and the product partitioned between CHCl$_3$ and aqueous NaHCO$_{3(sat)}$. The combined organic fractions were dried over Na$_2$SO$_4$ and used directly without further purification (3.4 g, 78%): LC-MS (ES) m/z=288 (M+H)$^+$.

c) 1,1-dimethylethyl {(1S)-2-(2,6-difluorophenyl)-1-[(1,3-dioxo-1,3-dihydro-2H-isoindol-2-yl)methyl]ethyl}carbamate

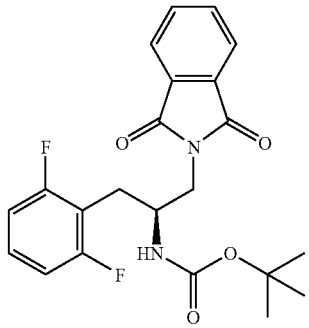 [SMILES: CC(C)(C)OC(=O)N[C@@H](Cc1c(F)cccc1F)CN1C(=O)c2ccccc2C1=O]

To a 200 mL round-bottomed flask was added 1,1-dimethylethyl[(1S)-2-(2,6-difluorophenyl)-1-(hydroxymethyl)ethyl]carbamate (3.38 g, 11.76 mmol), phthalimide (2.02 g, 13.73 mmol), and PS-TPP (Polymer bound TriphenylPhosphine (2.15 mmol/g, 4.92 g, 14.76 mmol) in Tetrahydrofuran (THF) (58.8 ml). DEAD (2.23 ml, 14.09 mmol) was added and the mixture stirred at ambient temperature for approximately 30 minutes at which point MeOH was added. The mixture was filtered through Celite adsorbed onto silica and purified via column chromatography affording the title compound (2.7 g, 55%): LC-MS (ES) m/z=317 (M+H)$^+$.

d) 2-[(2S)-2-amino-3-(2,6-difluorophenyl)propyl]-1H-isoindole-1,3(2H)-dione

In a 200 mL round-bottomed flask was added 1,1-dimethylethyl {(1S)-2-(2,6-difluorophenyl)-1-[(1,3-dioxo-1,3-dihydro-2H-isoindol-2-yl)methyl]ethyl}carbamate (2.72 g, 6.40 mmol) in Chloroform (75 ml) and Methanol (10 ml). HCl/1,4-Dioxane (40.0 ml, 160 mmol) was added and the mixture stirred overnight. The solvents were removed affording the title compound (2.4 g, quant.) as the HCl salt: LC-MS (ES) m/z=317 (M+H)$^+$.

Preparation 19

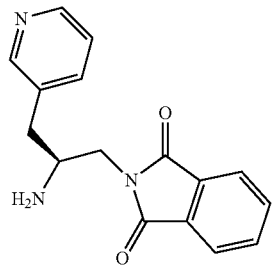

Preparation of 2-[(2S)-2-amino-3-(3-pyridinyl)propyl]-1H-isoindole-1,3(2H)-dione a) 1,1-dimethylethyl[(1S)-2-hydroxy-1-(3-pyridinylmethyl)ethyl]carbamate

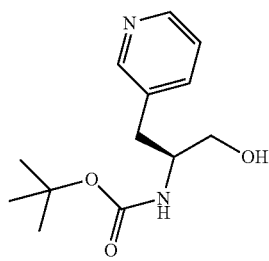 [SMILES: CC(C)(C)OC(=O)N[C@H](CO)Cc1cccnc1]

To a solution of Boc-L-3-pyridylaniline (1.064 g, 4 mmol) in THF (5 mL) at 0° C. was added BH$_3$-THF (20 mL, 20 mmol-1M in THF) dropwise. After 2 h, the reaction was quenched with AcOH:MeOH (1:5, 14.3 mL) at 0° C., followed by Et$_3$N (1.67 mL, 12 mmol) and 12 (2.03 g, 8 mmol). The resulting mixture was warmed to ambient temperature and stirred for 20 h, turning from brown to colorless. The solution was concentrated and partitioned between DCM and water. The aqueous phase was then extracted several times with DCM. The combined organic fractions were dried over Na$_2$SO$_4$ and concentrated to afford the desired product as a colorless oil which was used without further purification (957.6 mg, 95%): LC-MS (ES) m/z=253 (M+H)$^+$.

b) 1,1-dimethylethyl[(1S)-2-(1,3-dioxo-1,3-dihydro-2H-isoindol-2-yl)-1-(3-pyridinylmethyl)ethyl]carbamate

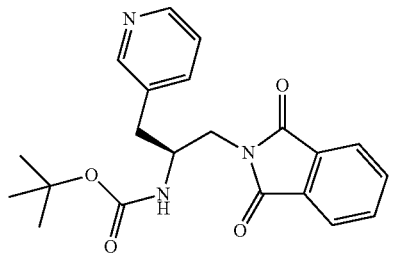 [SMILES: CC(C)(C)OC(=O)N[C@@H](Cc1cccnc1)CN1C(=O)c2ccccc2C1=O]

To a solution of 1,1-dimethylethyl[(1S)-2-hydroxy-1-(3-pyridinylmethyl)ethyl]carbamate (958 mg, 3.8 mmol), triphenylphosphine (1.21 g, 4.6 mmol) and phthalimide (617 mg, 4.2 mmol) in THF (40 mL) at 25° C. was added diethyl azodicarboxylate (0.72 mL, 4.6 mmol). After stirring at RT for 1 h, the reaction solution was concentrated under vacuum and the residue purified on silica gel (0-50% ethyl acetate/hexane) affording the title compound (797 mg, 55%) as a white solid: LCMS (ES) m/z 382 (M+H)+.

c) 2-[(2S)-2-amino-3-(3-pyridinyl)propyl]-1H-isoindole-1,3(2H)-dione

To a solution of 1,1-dimethylethyl[(1S)-2-(1,3-dioxo-1,3-dihydro-2H-isoindol-2-yl)-1-(3-pyridinylmethyl)ethyl]carbamate (796.7 mg, 2.1 mmol) in DCM (10 mL) at RT was added 1M HCl in dioxane (10 mL). After 20 h, the solution was concentrated affording the title compound (404 mg, 68%) as the HCl salt: LCMS (ES) m/z 282 (M+H)+.

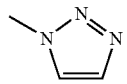

Preparation 20

Preparation of 1-methyl-1H-1,2,3-triazole

To a solution of 1,2,3-triazole (10 g, 145 mmol) in 150 ml of THF were added potassium carbonate (40 g, 290 mmol) and MeI (13.58 ml, 217 mmol). The resulting reaction mixture was stirred at rt for 3 hr. The reaction mixture was filtered and the filtrate was concentrated to afford the title compound (9.2 g, 78%). 1H NMR (400 MHz, CDCl₃) δ ppm 7.71 (s, 1H), 7.55 (s, 1H), 4.14 (s, 3H).

Preparation 21

Preparation of 1,4-dimethyl-5-(tributylstannanyl)-1H-1,2,3-triazole

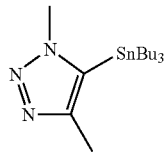

a) 1,4-dimethyl-1H-1,2,3-triazole

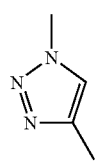

A solution of methylamine (25.4 ml, 50.8 mmol, 2M in MeOH) was added dropwise to a suspension of N'-(2,2-dichloro-1-methylethylidene)-4-methylbenzenesulfonohydrazide (ref: Sakai, K. et al, Bull. Chem. Soc. Jpn., 1986, 59, 179-183) (3 g, 10.16 mmol) in methanol (10 ml) at 0° C. The solid went into solution. The resulting dark brown mixture was stirred at 0° C. for 2 h, evaporated, and the solid was filtered and rinsed with EtOAc. The combined filtrates were concentrated and purified on a 25M biotage column, which was eluted with 50-75% of EA/hexane to give 0.57 g of brown liquid. LC-MS (ES) m/z=98 (M+H)+, ¹H NMR (CDCl₃, 400 MHz) δ 7.27 (s, 1H), 4.06 (s, 3H), 2.35 (s, 3H).

b) 1,4-dimethyl-5-(tributylstannanyl)-1H-1,2,3-triazole

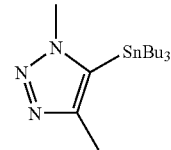

A solution of 1,4-dimethyl-1,2,3-triazole (0.56 g, 5.77 mmol) in THF (5 mL) was added dropwise to a solution of BuLi (2.77 ml, 6.92 mmol, 2.5 M in hexane) in 30 mL of THF at −78° C. under N₂. The resulting cloudy mixture was stirred at −70° C. for 1 h.

Then tributyltinchloride (1.711 ml, 6.34 mmol) was added. The reaction mixture became clear and was stirred at this temperature for 30 min, and gradually warmed to rt. To the reaction mixture was added 10 ml of NH₄Cl and 10 ml of water. The reaction mixture was extracted with ether. The combined organic layers were washed with brine, dried over Na₂SO₄, and concentrated. The residue was purified on FCC (20% EA/Hexane) to give 1.7 g of a clear liquid (73%). LC-MS (ES) m/z=388 (M+H)+, ¹H NMR (CDCl₃, 400 MHz) δ 4.05 (s, 3H), 2.38 (s, 3H), 1.5-0.9 (m, 27H)

Preparation 22

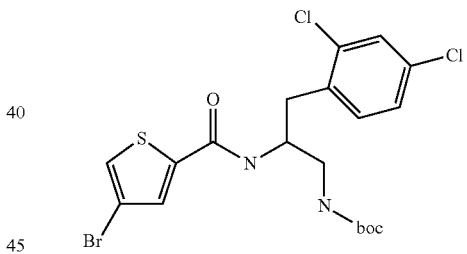

Preparation of 1,1-dimethylethyl[(2S)-2-{[(4-bromo-2-thienyl)carbonyl]amino}-3-(2,4-dichlorophenyl)propyl]carbamate A solution of 4-bromo-2-thiophenecarboxylic acid (1.29 g, 6.22 mmol), 2-[(2S)-2-amino-3-(2,4-dichlorophenyl)propyl]-1H-isoindole-1,3(2H)-dione (2.0 g, 5.19 mmol), PyBrop (3.62 g, 7.78 mmol) and Hunig's Base (3.62 ml, 20.74 mmol) in DCM (50 ml) was stirred at RT for 30 min. The reaction mixture was washed with H₂O, 1N HCl, NaHCO₃ (sat. aq.) and brine. The solvent was removed and the residue was dissolved in MeOH, hydrazine monohydrate (1.3 g, 26 mmol) was added. The reaction was stirred at rt overnight. The white solid formed, and was filtered and rinsed with DCM. To the filtrates were added (Boc)₂O (1.7 g, 7.78 mmol) and NaHCO₃ (sat. aq., 3 ml). The reaction mixture was stirred at RT for 2 hours and was washed with NaHCO₃ (sat. aq.) and brine. The solvent was removed and the residue was purified by biotage (50% H/E) to give the product (2.0 g, 76%). LC-MS (ES) m/z=531.0 (M+Na)+.

Example 1

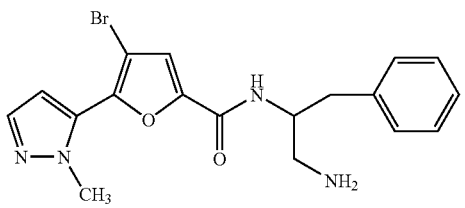 [SMILES: Cn1nccc1-c1oc(C(=O)NC(CN)Cc2ccccc2)cc1Br]

Preparation of N-[2-amino-1-(phenylmethyl)ethyl]-4-bromo-5-(1-methyl-1H-pyrazol-5-yl)-2-furancarboxamide a) 1,1-dimethylethyl (2-{[(4,5-dibromo-2-furanyl)carbonyl]amino}-3-phenylpropyl)carbamate

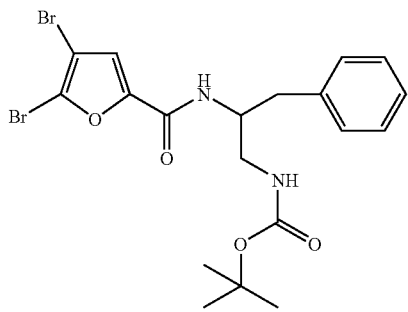 [SMILES: CC(C)(C)OC(=O)NCC(Cc1ccccc1)NC(=O)c1cc(Br)c(Br)o1]

To a solution of 4,5-dibromo-2-furancarboxylic acid (2.81 g, 10.4 mmol), PyBrOP (5.6 g, 12.0 mmol) and diisopropylethyl amine (4.2 mL, 24.0 mmol) in DCM (70 mL) at 25° C. was added 1,1-dimethylethyl (2-amino-3-phenylpropyl)carbamate (2.0 g, 8.0 mmol). After 16 h, the solution was partitioned between H$_2$O and washed with DCM. The combined organic fractions were dried (Na$_2$SO$_4$), concentrated and purified via column chromatography (silica, hexanes/EtOAc, 2:1) affording the title compound (4.3 g, 82%) as a white solid: LC-MS (ES) m/z=503 (M+H)$^+$.

b) 1,1-dimethylethyl[2-({[4-bromo-5-(1-methyl-1H-pyrazol-5-yl)-2-furanyl]carbonyl}amino)-3-phenylpropyl]carbamate

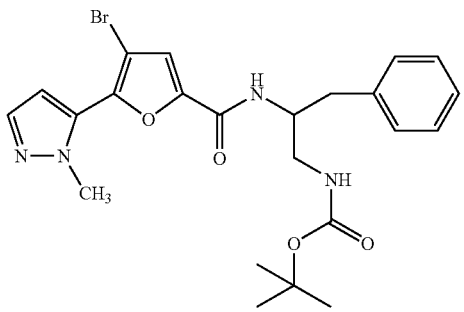 [SMILES: Cn1nccc1-c1oc(C(=O)NC(CNC(=O)OC(C)(C)C)Cc2ccccc2)cc1Br]

To a solution of 1,1-dimethylethyl (2-{[(4,5-dibromo-2-furanyl)carbonyl]amino}-3-phenylpropyl)carbamate (0.30 g, 0.60 mmol) in dioxane/H$_2$O (5:1, 8.6 mL) was added K$_2$CO$_3$ (0.25 g, 1.8 mmol), tetrakistriphenylphosphine Pd(0) (70 mg, 0.06 mmol), and 5-(5,5-dimethyl-1,3,2-dioxaborinane-2-yl)-1-methyl-1H-pyrazole (0.12 g, 0.60 mmol). The reaction mixture was heated to 80° C. in a sealed tube for 12 h. The reaction solution was poured onto H$_2$O (100 mL) and extracted with DCM. The organics were dried (Na$_2$SO$_4$), concentrated under vacuum, and purified on silica gel (hexanes/EtOAc, 1:1) to give the title compound (0.20 g, 66%) as a white solid: LC-MS (ES) m/z=504.

c) N-[2-amino-1-(phenylmethyl)ethyl]-4-bromo-5-(1-methyl-1H-pyrazol-5-yl)-2-furancarboxamide 1,1-Dimethylethyl[2-({[4-bromo-5-(1-methyl-1H-pyrazol-5-yl)-2-furanyl]carbonyl}amino)-3-phenylpropyl]carbamate (0.20 g, 0.40 mmol) was dissolved in DCM (10 mL) and treated with TFA (5 mL). After 2 h, the solution was concentrated, and purified on reverse-phase HPLC (C18 column: H$_2$O/CH$_3$CN, 95-5%) affording the TFA salt of the title compound (0.16 g, 91%) as a white powder: LC-MS (ES) m/z=405 (M+H)$^+$, $^1$H NMR (d$_4$-MeOH, 400 MHz) δ 7.59 (s, 1H), 7.33 (m, 3H), 7.30 (m, 2H), 6.85 (s, 1H), 4.57 (m, 1H), 4.03 (s, 3H), 3.25 (m, 1H), 3.14 (m, 1H), and 2.98 (m, 2H).

Example 2

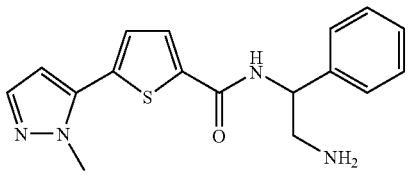 [SMILES: Cn1nccc1-c1ccc(C(=O)NC(CN)c2ccccc2)s1]

Preparation of N-(2-amino-1-phenylethyl)-5-(1-methyl-1H-pyrazol-5-yl)-2-thiophenecarboxamide a) 1,1-dimethylethyl (2-{[(5-bromo-2-thienyl)carbonyl]amino}-2-phenylethyl)carbamate

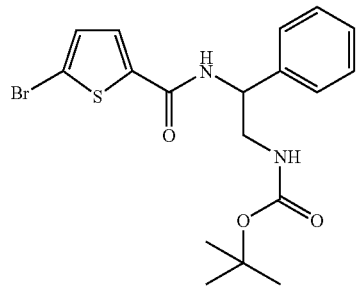 [SMILES: CC(C)(C)OC(=O)NCC(NC(=O)c1ccc(Br)s1)c1ccccc1]

To a solution of 5-bromo-2-thiophenecarboxylic acid (3.2 g, 15.2 mmol), PyBrOP (8.5 g, 18.2 mmol) and diisopropylethyl amine (10.6 mL, 60.9 mmol) in DCM (76 mL) at 25° C. was added 1,1-dimethylethyl (2-amino-2-phenylethyl)carbamate (3.6 g, 3.14 mmol)[prepared in Preparation 1]. After 16 h, the solution was partitioned between H$_2$O and washed with DCM. The combined organic fraction were dried (Na$_2$SO$_4$), concentrated and purified via column chromatography (silica, 1% MeOH in DCM) affording the title compound (4 g, 62%) as a white solid: LC-MS (ES) m/z=426 (M+H)$^+$.

b) 1,1-dimethylethyl[2-phenyl-2-({[5-(4,4,5,5-tetramethyl-1,3,2-dioxaborolan-2-yl)-2-thienyl]carbonyl}amino)ethyl]carbamate

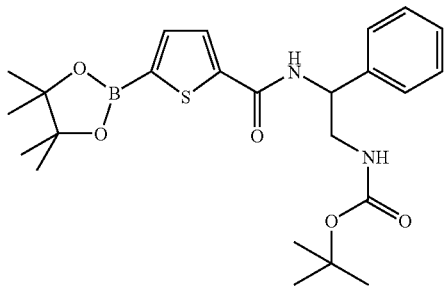 [SMILES: CC(C)(C)OC(=O)NCC(NC(=O)c1ccc(B2OC(C)(C)C(C)(C)O2)s1)c1ccccc1]

To a solution of 1,1-dimethylethyl (2-{[(5-bromo-2-thienyl)carbonyl]amino}-2-phenylethyl)carbamate (1 g, 2.35 mmol) in DMF (9 mL) were added KOAc (693 mg, 7.05 mmol), bis(pinacolato)diboron (1.2 g, 4.71 mmol) and Pd(dppf)Cl$_2$ (169 mg, 0.212 mmol). The reaction contents were heated to 80° C. in a sealed tube for 18 hours and were then partitioned between 6N NaOH and DCM. The pH of the aqueous fraction was adjusted to ~3 with 3M HCl and washed several times with DCM. The combined organic fractions were dried over Na$_2$SO$_4$, concentrated to a solid under vacuum and used directly in the next reaction: LC-MS (ES) m/z=473 (M+H)$^+$ boronic ester, 391 (M+H)$^+$ boronic acid.

c) 1,1-dimethylethyl[2-({[5-(1-methyl-1H-pyrazol-5-yl)-2-thienyl]carbonyl}amino)-2-phenylethyl]carbamate

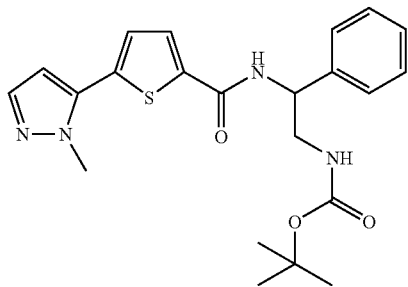 [SMILES: Cn1nccc1-c1ccc(C(=O)NC(CNC(=O)OC(C)(C)C)c2ccccc2)s1]

To a solution of 1,1-dimethylethyl[2-phenyl-2-({[5-(4,4,5,5-tetramethyl-1,3,2-dioxaborolan-2-yl)-2-thienyl]carbonyl}amino)ethyl]carbamate (200 mg, 0.42 mmol) in dioxane/H$_2$O (5:1, 8.6 mL) was added K$_2$CO$_3$ (234 mg, 1.69 mmol), tetrakistriphenylphosphine Pd(0) (24 mg, 0.02 mmol), and 5-iodo-1-methyl-1H-pyrazole (97 mg, 0.47 mmol) [prepared according to Effenberger, F.; et al *J. Org. Chem.* 1984, 49, 24, 4687]. The reaction mixture was heated to 80° C. in a sealed tube for 12 h. The reaction solution was poured onto H$_2$O (100 mL) and extracted with DCM. The organics were dried (Na$_2$SO$_4$), concentrated under vacuum, and purified on silica gel (1% MeOH in DCM) to give the title compound (56 mg, 31%) as a yellow solid: LC-MS (ES) m/z=427.

d) N-(2-amino-1-phenylethyl)-5-(1-methyl-1H-pyrazol-5-yl)-2-thiophenecarboxamide 1,1-dimethylethyl[2-({[5-(1-methyl-1H-pyrazol-5-yl)-2-thienyl]carbonyl}amino)-2-phenylethyl]carbamate (56 mg, 0.131 mmol) was dissolved in MeOH (2 mL) and treated with excess 4M HCl in dioxane (656 µL, 2.62 mmol). After 4 h, the solution was concentrated affording the title compound (46 mg, quant.) as a yellow solid: LC-MS (ES) m/z 327 (M+H)$^+$, $^1$H NMR (d6-DMSO, 400 MHz) δ 9.46 (d, J=8.2 Hz, 1H), 8.27 (bs, 1H), 8.20 (d, J=4.0 Hz, 1H), 7.48-7.75 (m, 3H), 7.37-7.40 (m, 2H), 7.31-7.33 (m, 1H), 6.58 (d, J=1.9 Hz, 1H), 5.21-5.30 (m, 1H), 3.97 (s, 3H), 3.36-3.41 (m, 1H), 3.19-3.25 (m, 1H).

Example 3

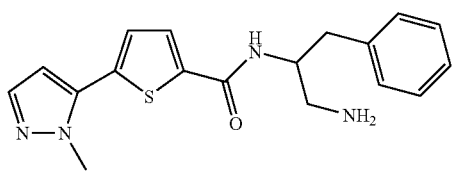 [SMILES: Cn1nccc1-c1ccc(C(=O)NC(CN)Cc2ccccc2)s1]

Preparation of N-[2-amino-1-(phenylmethyl)ethyl]-5-(1-methyl-1H-pyrazol-5-yl)-2-thiophenecarboxamide The title compound was prepared as an tan solid according to Example 2, except substituting 1,1-dimethylethyl (2-amino-3-phenylpropyl)carbamate (1.65 g, 7.97 mmol) [prepared in Preparation 2] for 1,1-dimethylethyl (2-amino-2-phenylethyl)carbamate: LC-MS (ES) m/z 341 (M+H)$^+$, $^1$H NMR (d$_6$-DMSO, 400 MHz) δ 8.74 (d, J=8.5 Hz, 1H), 8.05 (bs, 1H), 7.89 (d, J=3.9 Hz, 1H), 7.47 (d, J=1.9 Hz, 1H), 7.43 (d, J=3.9 Hz, 1H), 7.26-7.29 (m, 3H), 7.20-7.22 (m, 1H), 6.56 (d, J=2.0 Hz, 1H), 4.31-4.42 (m, 1H), 2.98-3.01 (m, 2H), 2.91-2.93 (m, 2H).

Example 4

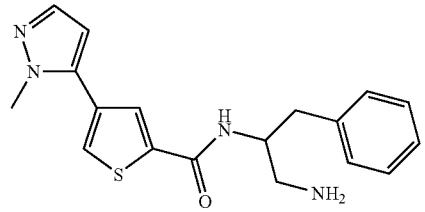 [SMILES: Cn1nccc1-c1csc(C(=O)NC(CN)Cc2ccccc2)c1]

Preparation of N-[2-amino-1-(phenylmethyl)ethyl]-4-(1-methyl-1H-pyrazol-5-yl)-2-thiophenecarboxamide The title compound was prepared as a yellow solid according to Example 2, except substituting 4-bromo-2-thiophenecarboxylic acid (1 g, 4.83 mmol) for 5-bromo-2-thiophenecarboxylic acid and 1,1-dimethylethyl (2-amino-3-phenylpropyl)carbamate (1.2 g, 4.83 mmol)[prepared in Preparation 2] for 1,1-dimethylethyl (2-amino-2-phenylethyl)carbamate: LC-MS (ES) m/z 441 (M+H)$^+$, $^1$H NMR (d6-DMSO, 400 MHz) δ 8.98 (bs, 1H), 8.29 (s, 1H), 8.17 (bs, 2H), 7.98 (s, 1H), 7.46 (s, 1H), 7.27-7.29 (m, 3H), 7.19 (s, 1H), 6.46 (s, 1H), 4.35-4.37 (m, 1H), 3.51 (s, 3H), 2.75-3.12 (m, 4H).

Example 5

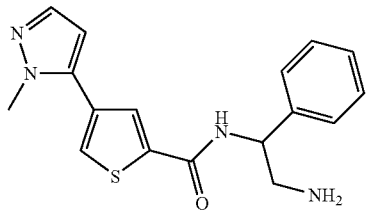 [SMILES: Cn1nccc1-c1csc(C(=O)NC(CN)c2ccccc2)c1]

Preparation of N-(2-amino-1-phenylethyl)-4-(1-methyl-1H-pyrazol-5-yl)-2-thiophenecarboxamide The title compound was prepared as a yellow solid according to Example 2, except substituting 4-bromo-2-thiophenecarboxylic acid (650 mg, 3.14 mmol) for 5-bromo-2-thiophenecarboxylic acid: LC-MS (ES) m/z 427 (M+H)$^+$, $^1$H NMR (d6-DMSO, 400 MHz) δ 9.65 (d, J=7.3 Hz, 1H), 8.58 (s, 1H), 8.31 (br s, 2H), 7.99 (s, 1H), 7.42-7.51 (m, 2H), 7.72-7.80 (m, 2H), 7.20-7.31 (m, 1H), 6.51 (s, 1H), 3.52 (s, 1H), 5.25-5.35 (m, 1H), 3.51 (s, 3H), 3.32-3.48 (m, 1H), 3.15-3.21 (m, 1H).

Example 6

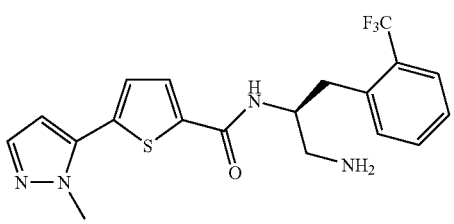 [SMILES: Cn1nccc1-c1ccc(C(=O)N[C@H](CN)Cc2ccccc2C(F)(F)F)s1]

Preparation of N-(2-amino-1-{[2-(trifluoromethyl)phenyl]methyl}ethyl)-5-(1-methyl-1H-pyrazol-5-yl)-2-thiophenecarboxamide a) 5-(1-methyl-1H-pyrazol-5-yl)-2-thiophenecarboxylic Acid

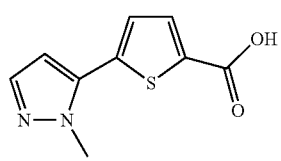

To a solution of 5-bromo-2-thiophenecarboxylic acid (100 mg, 0.48 mmol) in dioxane/H$_2$O (5:1, 6 mL) was added K$_2$CO$_3$ (267 mg, 1.93 mmol), tetrakistriphenylphosphine Pd(0) (28 mg, 24 umol) and 5-(5,5-dimethyl-1,3,2-dioxaborinane-2-yl)-1-methyl-1H-pyrazole (94 mg, 0.48 mmol). The reaction mixture was heated to 80° C. in a sealed tube for 12 h and was then partitioned between 6N NaOH and DCM. The pH of the aqueous phase was adjusted to ~3 with 3M HCl and washed several times with DCM. The combined organic fractions were dried (Na$_2$SO$_4$), concentrated under vacuum and used directly without further purification (~100 mg, quant.): LC-MS (ES) m/z=209 (M+H)$^+$.

b) N-((1S)-2-(1,3-dioxo-1,3-dihydro-2H-isoindol-2-yl)-1-{[2-(trifluoromethyl)phenyl]methyl}ethyl)-5-(1-methyl-1H-pyrazol-5-yl)-2-thiophenecarboxamide

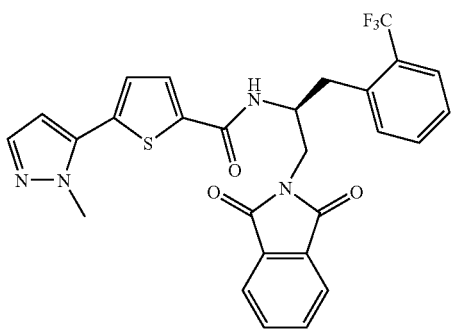 [SMILES: Cn1nccc1-c1ccc(C(=O)N[C@@H](Cc2ccccc2C(F)(F)F)CN2C(=O)c3ccccc3C2=O)s1]

To a solution of 5-(1-methyl-1H-pyrazol-5-yl)-2-thiophenecarboxylic acid (100 mg, 0.48 mmol), PyBrOP (270 mg, 0.58 mmol) and diisopropylethyl amine (420 μL, 2.4 mmol) in DCM (5 mL) at 25° C. was added 2-{(2S)-2-amino-3-[2-(trifluoromethyl)phenyl]propyl}-1H-isoindole-1,3 (2H)-dione-HCl (168 mg, 0.48 mmol)[from Preparation 6]. After 16 h, the solution was partitioned between H$_2$O and washed with DCM. The combined organic fractions were dried (Na$_2$SO$_4$), concentrated and purified via column chromatography (silica) affording the title compound (74 mg, 28%) as a white solid: LC-MS (ES) m/z=539 (M+H)$^+$.

c) N-(2-amino-1-{[2-(trifluoromethyl)phenyl]methyl}ethyl)-5-(1-methyl-1H-pyrazol-5-yl)-2-thiophenecarboxamide To a solution of N-((1S)-2-(1,3-dioxo-1,3-dihydro-2H-isoindol-2-yl)-1-{[2-(trifluoromethyl)phenyl]methyl}ethyl)-5-(1-methyl-1H-pyrazol-5-yl)-2-thiophenecarboxamide (74 mg, 0.14 mmol) in MeOH/THF (2 mL, 1:1) at RT was added hydrazine (86 μL, 2.75 mmol). After stirring for 18 h at RT, the reaction solution was concentrated under vacuum and purified via column chromatography (silica, 3% MeOH in DCM (1% NH$_4$OH)) yielding the title compound.

The neutral compound from above was dissolved in MeOH (2 mL), treated with excess 4M HCl in dioxane (500 μL) and concentrated affording the HCl salt of the title compound: LC-MS (ES) m/z=409 (M+H)$^+$, $^1$H NMR (d6-DMSO, 400 MHz) δ 8.97 (d, J=9.0 Hz, 1H), 8.17 (bs, 1H), 8.00 (d, 3.8 Hz, 1H), 7.68 (d, J=7.8 Hz, 1H), 7.55-7.61 (m, 2H), 7.42-7.47 (m 2H), 6.56 (d, J=2.0 Hz, 1H), 4.47-4.51 (m, 1H), 4.18 (s, 3H), 3.09-3.11 (m, 4H).

Example 7

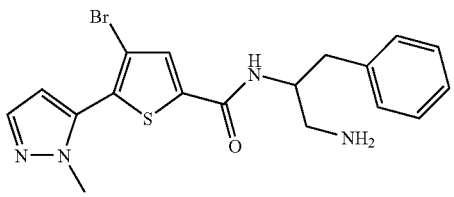 [SMILES: Cn1nccc1-c1sc(C(=O)NC(CN)Cc2ccccc2)cc1Br]

Preparation of N-[2-amino-1-(phenylmethyl)ethyl]-4-bromo-5-(1-methyl-1H-pyrazol-5-yl)-2-thiophenecarboxamide The title compound was prepared as a yellow solid according to Example 1, except substituting 4,5-dibromo thiophenecarboxylic acid (376 mg, 1.32 mmol) for 4,5-dibromo furancarboxylic acid: LC-MS (ES) m/z=419 (M+H)$^+$, $^1$H NMR (d6-DMSO, 400 MHz) δ 8.92 (d, J=8.6 Hz, 1H), 8.03-8.06 (m, 2H), 7.56 (d, J=1.9 Hz, 1H), 7.26-7.32 (m, 3H), 7.21-7.23 (m, 1H), 6.55 (d, J=1.9 Hz, 1H), 4.32-4.42 (m, 1H), 3.77 (s, 3H), 3.00-3.01 (m, 2H), 2.89-2.91 (m, 2H).

Example 8

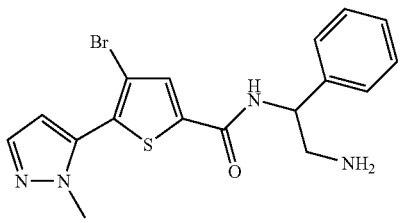 [SMILES: Cn1nccc1-c1sc(C(=O)NC(CN)c2ccccc2)cc1Br]

Preparation of N-(2-amino-1-phenylethyl)-4-bromo-5-(1-methyl-1H-pyrazol-5-yl)-2-thiophenecarboxamide The title compound was prepared as a yellow solid according to Example 1, except substituting 4,5-dibromo thiophenecarboxylic acid (2.2 g, 7.69 mmol) for 4,5-dibromo furancarboxylic acid and 1,1-dimethylethyl (2-amino-2-phenylethyl)carbamate (1.1 g, 4.66 mmol) for 1,1-dimethylethyl (2-amino-2-phenylpropyl)carbamate: LC-MS (ES) m/z=406 (M+H)$^+$, $^1$H NMR (d6-DMSO, 400 MHz) δ 9.47 (d, J=7.9 Hz, 1H), 8.26 (s, 1H), 8.17 (bs, 1H), 7.58 (d, J=1.6 Hz, 1H), 7.38-7.46 (m, 3H), 7.30-7.34 (m, 1H), 6.56 (d, J=1.6 Hz, 1H), 5.28-5.37 (m, 1H), 3.81 (s, 3H), 3.35-3.41 (m, 1H), 3.21-3.28 (m, 1H).

Example 9

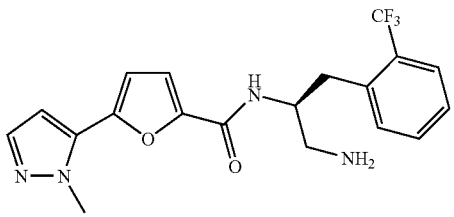 [SMILES: Cn1nccc1-c1ccc(C(=O)N[C@H](CN)Cc2ccccc2C(F)(F)F)o1]

Preparation of N-((1S)-2-amino-1-{[2-(trifluoromethyl)phenyl]methyl}ethyl)-5-(1-methyl-1H-pyrazol-5-yl)-2-furancarboxamide The title compound was prepared as a white solid according to the procedure of Example 6, except substituting 5-bromo-2-furancarboxylic acid (58 mg, 0.3 mmol) for 5-bromo-2-thiophenecarboxylic acid: LC-MS (ES) m/z=393 (M+H)$^+$, $^1$H NMR (CD$_3$OD, 400 MHz) δ 7.62 (br s, 1H), 7.57 (m, 1H), 7.51 (m, 3H), 7.22 (m, 1H), 6.91 (m, 1H), 6.76 (m, 1H), 4.6 (m, 1H), 4.07 (m, 3H) and 3.15 (m, 4H).

Example 10

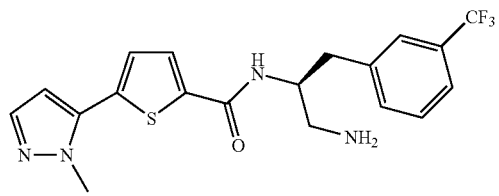 [SMILES: Cn1nccc1-c1ccc(C(=O)N[C@H](CN)Cc2cccc(C(F)(F)F)c2)s1]

Preparation of N-((1S)-2-amino-1-{[3-(trifluoromethyl)phenyl]methyl}ethyl)-5-(1-methyl-1H-pyrazol-5-yl)-2-thiophenecarboxamide The title compound was prepared as a yellow solid according to the procedure of Example 6, except substituting 2-{(2S)-2-amino-3-[3-(trifluoromethyl)phenyl]propyl}-1H-isoindole-1,3(2H)-dione-HCl (306 mg, 0.80 mmol) for 2-{(2S)-2-amino-3-[2-(trifluoromethyl)phenyl]propyl}-1H-isoindole-1,3(2H)-dione-HCl: LC-MS (ES) m/z=409 (M+H)$^+$, $^1$H NMR (400 MHz, MeOD) δ ppm 2.81-2.88 (m, 1H) 2.93 (td, J=9.03, 4.93 Hz, 2H) 3.09 (dd, J=13.89, 5.31 Hz, 1H) 4.00 (s, 3H) 4.28-4.35 (m, 1H) 6.53 (d, J=2.02 Hz, 1H) 7.32 (d, J=4.04 Hz, 1H) 7.45-7.52 (m, 3H) 7.54-7.58 (m, 1H) 7.60 (s, 1H) 7.70 (d, J=4.04 Hz, 1H).

Example 11

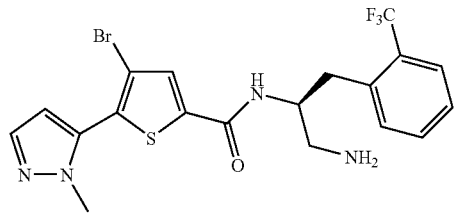 [SMILES: Cn1nccc1-c1sc(C(=O)N[C@H](CN)Cc2ccccc2C(F)(F)F)cc1Br]

Preparation of N-((1S)-2-amino-1-{[2-(trifluoromethyl)phenyl]methyl}ethyl)-4-bromo-5-(1-methyl-1H-pyrazol-5-yl)-2-thiophenecarboxamide The title compound was prepared as a white solid according to the procedure of Example 6, except substituting 4,5-dibromo-2-thiophenecarboxylic acid (237 mg, 0.83 mmol) for 5-bromo-2-thiophenecarboxylic acid: LC-MS (ES) m/z=488 (M+H)$^+$, $^1$H NMR (400 MHz, DMSO-d$_6$) δ ppm 2.97-3.10 (m, 4H) 3.78 (s, 3H) 4.42-4.54 (m, 1H) 6.56 (d, J=2.02 Hz, 1H) 7.45 (t, J=7.58 Hz, 1H) 7.50-7.54 (m, 1H) 7.56-7.63 (m, 2H) 7.71 (d, J=7.58 Hz, 1H) 7.92 (s, 1H) 8.76 (d, J=9.09 Hz, 1H)

Example 12

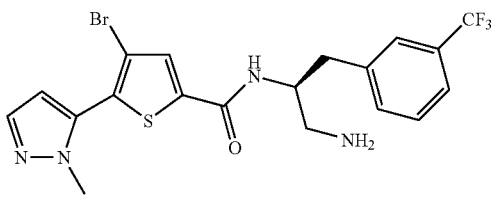

Preparation of N-((1S)-2-amino-1-{[3-(trifluoromethyl)phenyl]methyl}ethyl)-4-bromo-5-(1-methyl-1H-pyrazol-5-yl)-2-thiophenecarboxamide The title compound was prepared as a white solid according to the procedure of Example 6, except substituting 4,5-dibromo-2-thiophenecarboxylic acid (237 mg, 0.83 mmol) for 5-bromo-2-thiophenecarboxylic acid and substituting 2-{(2S)-2-amino-3-[3-(trifluoromethyl)phenyl]propyl}-1H-isoindole-1,3(2H)-dione-HCl (206 mg, 0.535 mmol) for 2-{(2S)-2-amino-3-[2-(trifluoromethyl)phenyl]propyl}-1H-isoindole-1,3(2H)-dione-HCl: LC-MS (ES) m/z=488 (M+H)$^+$, $^1$H NMR (CD$_3$OD, 400 MHz) δ ppm 2.97-3.07 (m, 1H) 3.10-3.21 (m, 2H) 3.27 (d, J=3.54 Hz, 1H) 3.82 (s, 3H) 4.50-4.59 (m, 1H) 6.51 (d, J=2.02 Hz, 1H) 7.50-7.60 (m, 4H) 7.62 (s, 1H) 7.71 (s, 1H).

Example 13

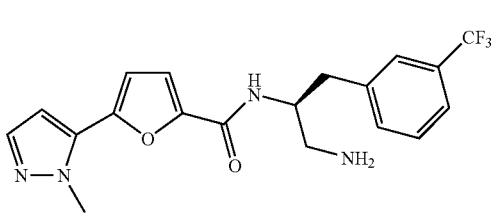

Preparation of N-((1S)-2-amino-1-{[3-(trifluoromethyl)phenyl]methyl}ethyl)-5-(1-methyl-1H-pyrazol-5-yl)-2-furancarboxamide The title compound was prepared as a white solid according to the procedure of Example 6, except substituting 5-bromo-2-furancarboxylic acid (44 mg, 0.23 mmol) for 5-bromo-2-thiophenecarboxylic acid and substituting 2-{(2S)-2-amino-3-[3-(trifluoromethyl)phenyl]propyl}-1H-isoindole-1,3(2H)-dione-HCl (87 mg, 0.25 mmol) for 2-{(2S)-2-amino-3-[2-(trifluoromethyl)phenyl]propyl}-1H-isoindole-1,3(2H)-dione-HCl: LC-MS (ES) m/z=393 (M+H)$^+$, $^1$H NMR (CD$_3$OD, 400 MHz) δ 7.63 (br s, 1H), 7.57 (m, 1H), 7.51 (m, 3H), 7.22 (m, 1H), 6.91 (m, 1H), 6.77 (m, 1H), 4.6 (m, 1H), 4.07 (m, 3H) and 3.14 (m, 4H).

Example 14

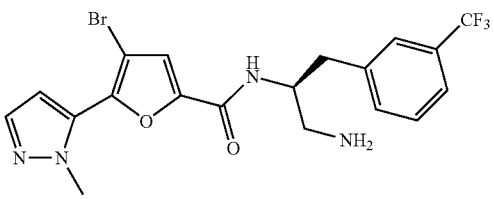 [SMILES: Cn1nccc1-c1sc(C(=O)N[C@H](CN)Cc2cccc(C(F)(F)F)c2)cc1Br]

Preparation of N-((1S)-2-amino-1-{[3-(trifluoromethyl)phenyl]methyl}ethyl)-4-bromo-5-(1-methyl-1H-pyrazol-5-yl)-2-furancarboxamide The title compound was prepared as a white solid according to the procedure of Example 6, except substituting 4,5-dibromo-2-furancarboxylic acid (82 mg, 0.3 mmol) for 5-bromo-2-thiophenecarboxylic acid and substituting 2-{(2S)-2-amino-3-[3-(trifluoromethyl)phenyl]propyl}-1H-isoindole-1,3(2H)-dione-HCl (115 mg, 0.3 mmol) for 2-{(2S)-2-amino-3-[2-(trifluoromethyl)phenyl]propyl}-1H-isoindole-1,3(2H)-dione-HCl: LC-MS (ES) m/z=472 (M+H)$^+$, $^1$H NMR (CD$_3$OD, 400 MHz) δ 7.61 (m, 2H), 7.53 (m, 3H), 7.30 (m, 1H), 6.84 (m, 1H), 4.59 (m, 1H), 4.03 (s, 3H), 3.28 (m, 1H), 3.17 (m, 2H) and 3.01 (m, 1H)

Example 15

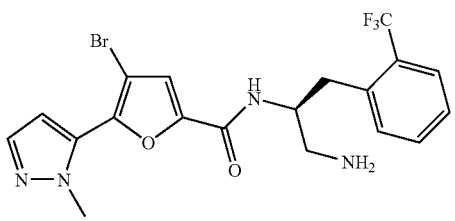

Preparation of N-((1S)-2-amino-1-{[2-(trifluoromethyl)phenyl]methyl}ethyl)-4-bromo-5-(1-methyl-1H-pyrazol-5-yl)-2-furancarboxamide The title compound was prepared as a white solid according to the procedure of Example 6, except substituting 4,5-dibromo-2-furancarboxylic acid (82 mg, 0.3 mmol) for 5-bromo-2-thiophenecarboxylic acid: LC-MS (ES) m/z=472 (M+H)$^+$, $^1$H NMR (CD$_3$OD, 400 MHz) δ 7.71 (m, 1H), 7.60 (m, 1H), 7.53 (m, 2H), 7.44 (m, 1H), 7.33 (m, 1H), 6.88 (m, 1H), 4.7 (m, 1H), 4.06 (s, 3H), 3.25 (m, 3H) and 3.09 (m, 1H).

Example 16

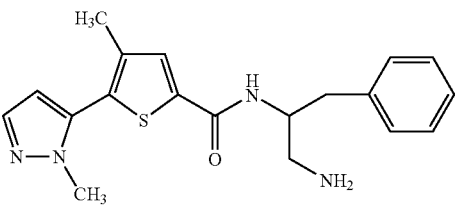 [SMILES: Cc1cc(C(=O)NC(CN)Cc2ccccc2)sc1-c1ccnn1C]

Preparation of N-[2-amino-1-(phenylmethyl)ethyl]-4-methyl-5-(1-methyl-1H-pyrazol-5-yl)-2-thiophenecarboxamide a) 1,1-dimethylethyl[2-({[4-methyl-5-(1-methyl-1H-pyrazol-5-yl)-2-thienyl]carbonyl}amino)-3-phenylpropyl]carbamate

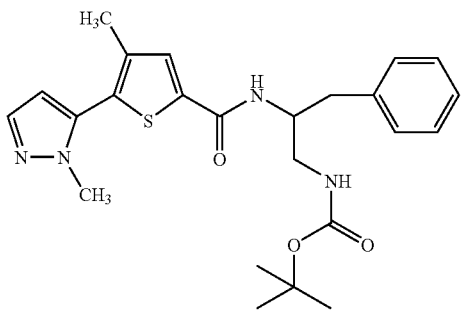 [SMILES: Cc1cc(C(=O)NC(CNC(=O)OC(C)(C)C)Cc2ccccc2)sc1-c1ccnn1C]

To a solution of 1,1-dimethylethyl[2-({[4-bromo-5-(1-methyl-1H-pyrazol-5-yl)-2-thienyl]carbonyl}amino)-3-phenylpropyl]carbamate (0.35 g, 0.67 mmol) [from Example 7] in dioxane/H$_2$O (5:1, 25:5 mL) was added K$_2$CO$_3$ (0.28 mg, 2.0 mmol), tetrakistriphenylphosphine Pd(0) (77 mg, 0.06 mmol), and trimethylboroxine (0.17 mL, 1.2 mmol). The reaction mixture was heated to 80° C. in a sealed tube for 12 h. The reaction solution was concentrated under vacuum and purified on silica gel (hexanes/EtOAc, 1:1) to give the title compound (0.10 g, 33%) as a white solid: LC-MS (ES) m/z=455 (M+H)$^+$.

b) N-[2-amino-1-(phenylmethyl)ethyl]-4-methyl-5-(1-methyl-1H-pyrazol-5-yl)-2-thiophenecarboxamide 1,1-dimethylethyl[2-({[4-methyl-5-(1-methyl-1H-pyrazol-5-yl)-2-thienyl]carbonyl}amino)-3-phenylpropyl]carbamate (0.10 g, 0.22 mmol) was dissolved in MeOH (10 mL) and THF (5 mL) and treated with 4 M HCl in dioxane (5 mL). After 4 h, the solution was concentrated affording the HCl salt of the title compound (68 mg, 91%) as a white powder: LC-MS (ES) m/z=355 (M+H)$^+$, $^1$H NMR (d$_4$-MeOH, 400 MHz) δ 7.79 (s, 1H), 7.68 (s, 1H), 7.31 (m, 4H), 7.25 (m, 1H), 6.56 (s, 1H), 4.54 (m, 1H), 3.87 (s, 3H), 3.69 (s, 2H), 3.34 (m, 2H), 3.03 (d, J=7.6 Hz, 2H) and 2.21 (s, 3H).

Example 17

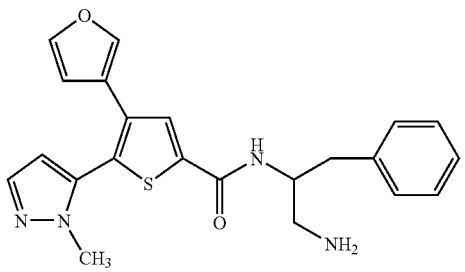 [SMILES: Cn1nccc1-c1sc(C(=O)NC(CN)Cc2ccccc2)cc1-c1ccoc1]

Preparation of N-[2-amino-1-(phenylmethyl)ethyl]-4-(3-furanyl)-5-(1-methyl-1H-pyrazol-5-yl)-2-thiophenecarboxamide The title compound was prepared as a white solid according to the procedure of Example 16, except substituting 3-furan boronic acid (0.13 g, 1.2 mmole) for trimethylboroxine: LC-MS (ES) m/z=472 (M+H)$^+$, $^1$H NMR (CD$_3$OD, 400 MHz) δ 8.13 (s, 1H), 7.81 (s, 1H), 7.53 (m, 2H), 7.34 (m, 4H), 7.26 (m, 1H), 6.61 (s, 1H), 6.20 (s, 1H), 4.57 (m, 1H), 3.68 (s, 2H), 3.63 (s, 3H), 3.24 (m, 2H) and 3.07 (m, 2H)

Example 18

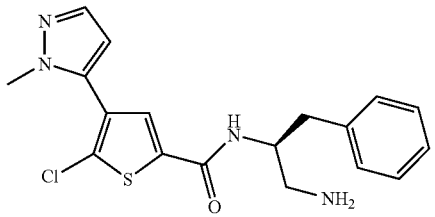 [SMILES: Cn1nccc1-c1cc(C(=O)N[C@H](CN)Cc2ccccc2)sc1Cl]

Preparation of N-[(1S)-2-amino-1-(phenylmethyl)ethyl]-5-chloro-4-(1-methyl-1H-pyrazol-5-yl)-2-thiophenecarboxamide a) methyl 5-chloro-2-thiophenecarboxylate

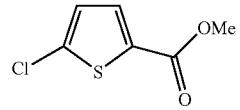

To a solution of 5-chloro-2-thiophenecarboxylic acid (2.0 g, 12.3 mmol) in dry MeOH (75 mL) was added H$_2$SO$_4$ (1 mL). The reaction mixture was heated to 50° C. for 20 h and was then concentrated under vacuum. The residue was dissolved in DCM and washed several times with saturated NaHCO$_3$ solution. The organic fraction was dried (Na$_2$SO$_4$), concentrated under vacuum and used directly without further purification 21.3 g, quant.): LC-MS (ES) m/z=177 (M+H)$^+$.

b) methyl 5-chloro-4-iodo-2-thiophenecarboxylate

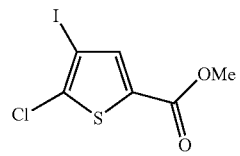 [SMILES: COC(=O)c1cc(I)c(Cl)s1]

To a solution of 5-chloro-2-thiophenecarboxylic acid (5.0 g, 28.0 mmol) in acetic acid (150 mL) was added ZnCl$_2$ (38 g, 280 mmoles) and benzyltrimethylammonium dichloroiodate (20.5 g, 58.8 mmole) [*Bull. Chem. Soc. Jpn.* 64, 2566-2568 (1991)]. The reaction mixture was heated to 70° C. for 48 h and was then concentrated under vacuum. The residue was extracted with hexanes (2×200 mL) and the hexane solution washed with saturated NaHCO$_3$ solution. The organic fractions were dried (Na$_2$SO$_4$), concentrated under vacuum and purified on silica gel (hexanes/EtOAc, 4:1) to give the title compound (3.8 g, 45%) as a light yellow solid: LC-MS (ES) m/z=302 (M+H)$^+$.

c) methyl 5-chloro-4-(1-methyl-1H-pyrazol-5-yl)-2-thiophenecarboxylate

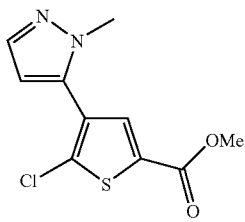 [SMILES: COC(=O)c1cc(-c2ccnn2C)c(Cl)s1]

To a solution of methyl 5-chloro-4-iodo-2-thiophenecarboxylate (1.75 g, 5.8 mmol) in dioxane/H$_2$O (50:5 mL) was added K$_2$CO$_3$ (3.4 g, 24.9 mmol), tetrakistriphenylphosphine Pd(0) (0.96 g, 0.83 mmol), and 5-(5,5-dimethyl-1,3,2-dioxaborinane-2-yl)-1-methyl-1H-pyrazole (3.4 g, 16.5 mmol). The reaction mixture was heated to 80° C. in a sealed tube for 15 h. The reaction solution was concentrated under vacuum and purified on silica gel (hexanes/EtOAc, 4:1) to give the title compound (0.35 g, 24%) as a yellow oil: LC-MS (ES) m/z=257 (M+H)$^+$.

d) 5-chloro-4-(1-methyl-1H-pyrazol-5-yl)-2-thiophenecarboxylic Acid

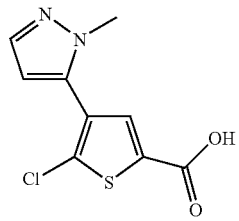

To a solution of methyl 5-chloro-4-(1-methyl-1H-pyrazol-5-yl)-2-thiophenecarboxylate (0.30 g, 1.17 mmole) in THF (10 mL) and MeOH (10 mL) was added 6N NaOH (5 mL). The reaction solution was heated to 50° C. for 2 hrs. The reaction solution was concentrated under vacuum, made acidic (pH ~2) with 3N HCl, and extracted with DCM. The organic solution was dried (Na$_2$SO$_4$) and concentrated to a solid (0.22 g) which was used without further purification. LC-MS (ES) m/z=243 (M+H)$^+$.

e) 5-chloro-N-[(1S)-2-(1,3-dioxo-1,3-dihydro-2H-isoindol-2-yl)-1-(phenylmethyl)ethyl]-4-(1-methyl-1H-pyrazol-5-yl)-2-thiophenecarboxamide

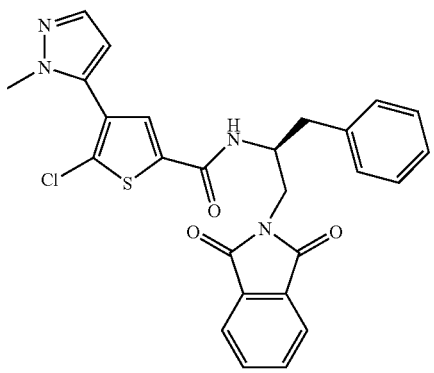 [SMILES: Cn1nccc1-c1cc(C(=O)N[C@@H](Cc2ccccc2)CN2C(=O)c3ccccc3C2=O)sc1Cl]

To a solution of 5-chloro-4-(1-methyl-1H-pyrazol-5-yl)-2-thiophenecarboxylic acid (0.21 g, 0.87 mmol), PyBrOP (610 mg, 1.3 mmol) and diisopropylethyl amine (0.76 mL, 4.35 mmol) in DCM (20 mL) at 25° C. was added 2-[(2S)-2-amino-3-phenylpropyl]-1H-isoindole-1,3(2H)-dione HCl (380 mg, 0.96 mmol)[prepared according to Preparation 5]. After 16 h, the solution was partitioned between H$_2$O and washed with DCM. The combined organic fractions were dried (Na$_2$SO$_4$), concentrated and purified via column chromatography (silica) affording the title compound (200 mg, 46%) as a white solid: LC-MS (ES) m/z=505 (M+H)$^+$.

f) N-[(1S)-2-amino-1-(phenylmethyl)ethyl]-5-chloro-4-(1-methyl-1H-pyrazol-5-yl)-2-thiophenecarboxamide To a solution of 5-chloro-N-[(1S)-2-(1,3-dioxo-1,3-dihydro-2H-isoindol-2-yl)-1-(phenylmethyl)ethyl]-4-(1-methyl-1H-pyrazol-5-yl)-2-thiophenecarboxamide (200 mg, 0.40 mmol) in MeOH/THF (10 mL, 1:1) at RT was added hydrazine hydrate (0.20 mL, 4.0 mmol). After stirring for 24 h at RT, the reaction solution was concentrated under vacuum and purified via column chromatography (silica, 3% MeOH in DCM (1% NH$_4$OH)) yielding the title compound as a light yellow solid.

The neutral compound from above was dissolved in DCM (2 mL), treated with excess 4M HCl in dioxane (1 mL) and concentrated affording the HCl salt (102 mg) of the title compound: LC-MS (ES) m/z=375 (M+H)$^+$, 7.78 (s, 1H), 7.63 (s, 1H), 7.31 (m, 4H), 7.26 (m, 1H), 6.55 (s, 1H), 4.54 (m, 1H), 3.91 (s, 3H), 3.24 (m, 2H) and 3.03 (m, 2H).

Example 19

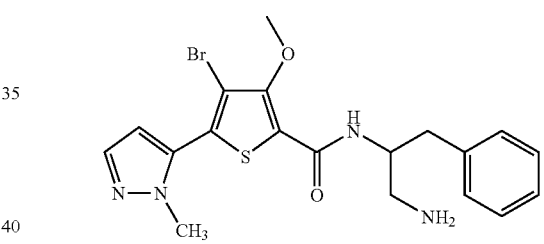

Preparation of N-[2-amino-1-(phenylmethyl)ethyl]-4-bromo-3-(methyloxy)-5-(1-methyl-1H-pyrazol-5-yl)-2-thiophenecarboxamide a) methyl 4-bromo-3-hydroxy-5-(1-methyl-1H-pyrazol-5-yl)-2-thiophenecarboxylate

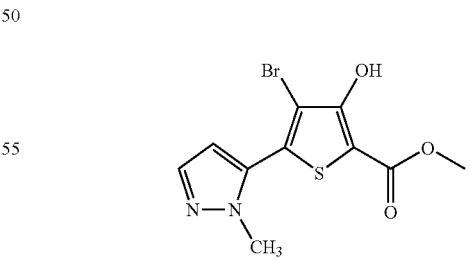

Methyl 4,5-dibromo-3-hydroxy-2-thiophenecarboxylate (500 mg, 1.59 mmol), 5-(5,5-dimethyl-1,3,2-dioxaborinane-2-yl)-1-methyl-1H-pyrazole (339 mg, 1.75 mmol), Pd(PPh$_3$)$_4$ (92 mg, 79.4 µmol) and K$_2$CO$_3$ (876 mg, 6.35 mmol) in dioxane (6.6 mL) and H$_2$O (1.3 mL) were combined in a sealed tube. After 12 h at 80° C., the reaction contents were partitioned between H$_2$O/DCM. The aqueous phase was washed several times with DCM and the combined organic fractions were dried over $Na_2SO_4$, concentrated and purified via column chromatography (silica, 0.5% MeOH in DCM) affording the title compound (75 mg, 15%) as a brown residue: LCMS (ES) m/z=318 (M+H)$^+$.

b) methyl 4-bromo-3-(methyloxy)-5-(1-methyl-1H-pyrazol-5-yl)-2-thiophenecarboxylate

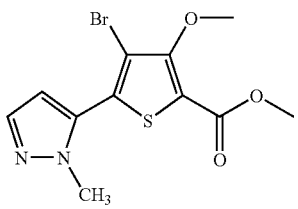 [SMILES: COC(=O)c1sc(-c2ccnn2C)c(Br)c1OC]

To a solution of methyl 4-bromo-3-hydroxy-5-(1-methyl-1H-pyrazol-5-yl)-2-thiophenecarboxylate (175 mg, 0.554 mmol), MeOH (26 μL, 0.609 mmol), PPh$_3$ (189 mg, 0.720 mmol) in THF (6 mL) at 25° C. was added DEAD (113 μL, 0.720 mmol) in one portion. After 30 min, the reaction was concentrated and purified via column chromatography (silica, 20% EtOAc in hexanes) affording the title compound (135 mg, 74%) as a white solid: LC-MS (ES) m/z=332 (M+H)$^+$.

c) 1,1-dimethylethyl[2-({[4-bromo-3-(methyloxy)-5-(1-methyl-1H-pyrazol-5-yl)-2-thienyl]carbonyl}amino)-3-phenylpropyl]carbamate

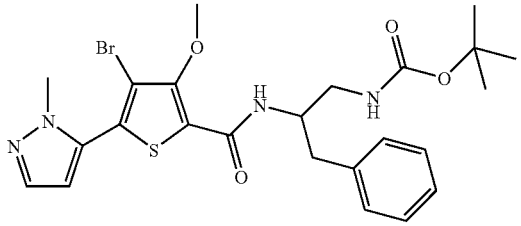 [SMILES: COc1c(C(=O)NC(CNC(=O)OC(C)(C)C)Cc2ccccc2)sc(-c2ccnn2C)c1Br]

i) A solution of methyl 4-bromo-3-(methyloxy)-5-(1-methyl-1H-pyrazol-5-yl)-2-thiophenecarboxylate (135 mg, 0.410 mmol) in 6N NaOH (4 mL) and THF (4 mL) was stirred in a sealed tube at 80° C. After 2 h, the solution was acidified to pH 3 using 1N HCl then extracted several times with DCM. The combined organic fractions were dried over $Na_2SO_4$, concentrated and used directly: LCMS (ES) m/z=318 (M+H)$^+$.

ii) To a solution of the crude acid, 1,1-dimethylethyl (2-amino-3-phenylpropyl)carbamate (88 mg, 0.351 mmol) [from Preparation 2], diisopropylethyl amine (305 μL, 1.76 mmol) in DCM (3.5 mL) was added PyBrop (196 mg, 0.422 mmol) in one portion. After 12 h, additional diisopropylethyl amine (305 μL, 1.76 mmol) and PyBrop (196 mg, 0.422 mmol) were added. After 2 h, the reaction contents were partitioned between $H_2O$/DCM. The aqueous phase was washed several times with DCM and the combined organic fractions were dried over $Na_2SO_4$, concentrated and used directly: LCMS (ES) m/z=550 (M+H)$^+$.

d) N-[2-amino-1-(phenylmethyl)ethyl]-4-bromo-3-(methyloxy)-5-(1-methyl-1H-pyrazol-5-yl)-2-thiophenecarboxamide A solution of 1,1-dimethylethyl[2-({[4-bromo-3-(methyloxy)-5-(1-methyl-1H-pyrazol-5-yl)-2-thienyl]carbonyl}amino)-3-phenylpropyl]carbamate (crude from part e) in TFA-DCM (3 mL, 1:2) was stirred at 25° C. After 30 min, the solution was concentrated and the residue neutralized through a silica plug (3% MeOH in DCM (1% $NH_4OH$)) affording the free base of the title compound.

The free base, as a solution in MeOH, was then treated with excess 4M HCl in dioxane affording the title compound as the HCl salt: LC-MS (ES) m/z 450 (M+H)$^+$, $^1$H NMR (400 MHz, DMSO-d$_6$) δ ppm 8.07 (br. s., 3H) 7.85 (d, J=8.84 Hz, 1H) 7.58 (d, J=2.02 Hz, 1H) 7.32 (d, J=7.07 Hz, 2H) 7.26-7.29 (m, 2H) 7.20-7.24 (m, 1H) 6.54 (d, J=2.02 Hz, 1H) 4.50-4.55 (m, 1H) 3.79 (d, J=6.82 Hz, 3H) 3.74 (d, J=6.57 Hz, 1H) 3.17 (s, 1H) 2.98-3.10 (m, 4H).

Example 20

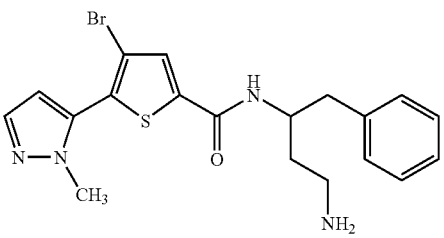 [SMILES: Cn1nccc1-c1sc(C(=O)NC(CCN)Cc2ccccc2)cc1Br]

Preparation of N-[3-amino-1-(phenylmethyl)propyl]-4-bromo-5-(1-methyl-1H-pyrazol-5-yl)-2-thiophenecarboxamide a) 4-bromo-5-(1-methyl-1H-pyrazol-5-yl)-2-thiophenecarboxylic Acid

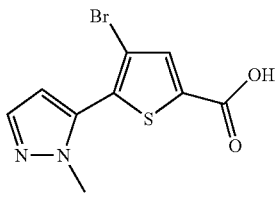

To a solution of 4,5-dibromo-2-thiophenecarboxylic acid (1 g, 3.5 mmol) in dioxane/$H_2O$ (5:1, 18 mL) was added $K_2CO_3$ (1.9 g, 13.98 mmol), tetrakistriphenylphosphine Pd(0) (201 mg, 0.175 mmol) and 5-(5,5-dimethyl-1,3,2-dioxaborinane-2-yl)-1-methyl-1H-pyrazole (678 mg, 3.5 mmol). The reaction mixture was heated to 80° C. in a sealed tube for 12 h and was then partitioned between 6N NaOH and DCM. The pH of the aqueous phase was adjusted to ~3 with 3M HCl and washed several times with DCM. The combined organic fractions were dried ($Na_2SO_4$), concentrated under vacuum and used directly without further purification (~1 g, quant.): LC-MS (ES) m/z=288 (M+H)$^+$.

b) 1,1-dimethylethyl[3-({[4-bromo-5-(1-methyl-1H-pyrazol-5-yl)-2-thienyl]carbonyl}amino)-4-phenylbutyl]carbamate

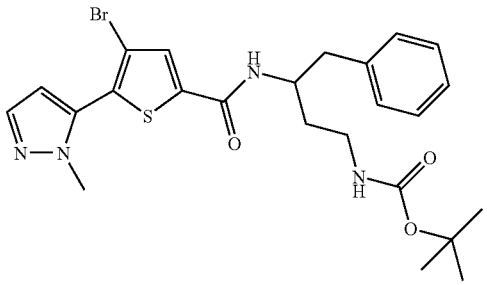 [SMILES: Cn1nccc1-c1sc(C(=O)NC(CCNC(=O)OC(C)(C)C)Cc2ccccc2)cc1Br]

To a solution of 4-bromo-5-(1-methyl-1H-pyrazol-5-yl)-2-thiophenecarboxylic acid (250 mg, 0.874 mmol), PyBrOP (489 mg, 8.74 mmol) and diisopropylethyl amine (762 µL, 4.37 mmol) in DCM (8 mL) at 25° C. was added 1,1-dimethylethyl (3-amino-4-phenylbutyl)carbamate (230 mg, 0.874 mmol)[prepared according to Preparation 8]. After 16 h, the solution was partitioned between H$_2$O and washed with DCM. The combined organic fractions were dried (Na$_2$SO$_4$), concentrated and purified via column chromatography (silica) affording the title compound (130 mg, 29%) as a white solid: LC-MS (ES) m/z=533 (M+H)$^+$.

c) N-[3-amino-1-(phenylmethyl)propyl]-4-bromo-5-(1-methyl-1H-pyrazol-5-yl)-2-thiophenecarboxamide A solution of 1,1-dimethylethyl[3-({[4-bromo-5-(1-methyl-1H-pyrazol-5-yl)-2-thienyl]carbonyl}amino)-4-phenylbutyl]carbamate (130 mg, 0.24 mmol) in TFA-DCM (3 mL, 1:2) was stirred at 25° C. After 30 min, the solution was concentrated and the residue neutralized through a silica plug (3% MeOH in DCM (1% NH$_4$OH)) affording the free base of the title compound.

The free base, as a solution in MeOH, was then treated with excess 4M HCl in dioxane affording the title compound (40 mg, 40%) as the HCl salt: LC-MS (ES) m/z 433 (M+H)$^+$, $^1$H NMR (400 MHz, DMSO-d$_6$) δ ppm 8.68 (d, J=8.59 Hz, 1H) 7.97 (s, 1H) 7.77 (br s, 3H) 7.57 (d, J=2.02 Hz, 1H) 7.28 (d, J=2.27 Hz, 3H) 7.25-7.32 (m, 2H) 6.55 (d, J=2.02 Hz, 1H) 4.17-4.24 (m, 1H) 3.78 (s, 3H) 2.77-2.89 (m, 4H) 1.85-1.92 (m, 1H) 1.81 (td, J=9.54, 4.93 Hz, 1H).

Example 21

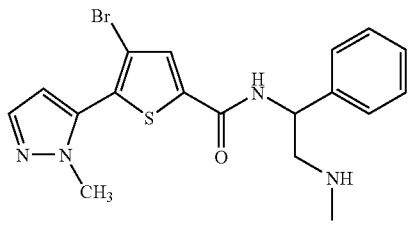 [SMILES: CNCC(NC(=O)c1cc(Br)c(-c2ccnn2C)s1)c1ccccc1]

Preparation of 4-bromo-N-[2-(methylamino)-1-phenylethyl]-5-(1-methyl-1H-pyrazol-5-yl)-2-thiophenecarboxamide The title compound was prepared as an off-white solid according to the procedure of Example 1, except substituting 1,1-dimethylethyl (2-amino-2-phenylethyl)methylcarbamate (1 g, 4.02 mmol) [Prepared according to the procedure of Preparation 1] for 1,1-dimethylethyl (2-amino-2-phenylethyl)carbamate and substituting 4,5-dibromo-2-thiophenecarboxylic acid (1.89 g, 6.6 mmol) for 4,5-dibromo-2-furancarboxylic acid: LCMS (ES) m/z 420 (M+H)$^+$, $^1$H NMR (400 MHz, DMSO-d$_6$) δ ppm 9.64 (d, J=8.34 Hz, 1H) 8.91 (br. s., 1H) 8.33 (s, 1H) 7.58 (d, J=2.02 Hz, 1H) 7.42-7.50 (m, 2H) 7.38-7.42 (m, 2H) 7.34 (d, J=7.07 Hz, 1H) 6.56 (d, J=2.02 Hz, 1H) 5.37-5.44 (m, 1H) 3.79 (s, 3H) 3.47-3.54 (m, 1H) 3.33 (td, J=8.46, 3.79 Hz, 1H) 2.63 (t, J=5.31 Hz, 3H).

Example 22

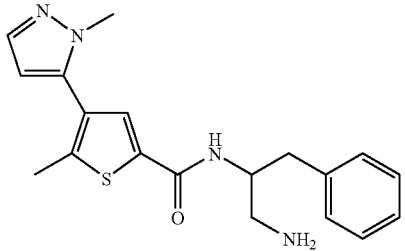 [SMILES: Cc1sc(C(=O)NC(CN)Cc2ccccc2)cc1-c1ccnn1C]

Preparation of N-[2-amino-1-(phenylmethyl)ethyl]-5-methyl-4-(1-methyl-1H-pyrazol-5-yl)-2-thiophenecarboxamide The title compound was prepared as a yellow solid according to the procedure of Example 1, except substituting 4-bromo-5-methyl-2-thiophenecarboxylic acid (81 mg, 0.368 mmol)[from Preparation 10] for 4,5-dibromo-2-furancarboxylic acid: LC-MS (ES) m/z 355 (M+H)$^+$, $^1$H NMR (400 MHz, DMSO-d$_6$) δ ppm 8.84 (d, J=8.34 Hz, 1H) 8.15 (br. s., 3H) 8.00 (s, 1H) 7.52 (d, J=1.77 Hz, 1H) 7.24-7.31 (m, 4H) 7.17-7.23 (m, 1H) 6.36 (d, J=1.77 Hz, 1H) 4.35 (d, J=3.03 Hz, 1H) 3.78 (s, 3H) 3.03 (dd, J=6.82, 2.53 Hz, 1H) 2.93-2.99 (m, 2H) 2.90 (d, J=6.06 Hz, 1H) 2.38 (s, 3H).

Example 23

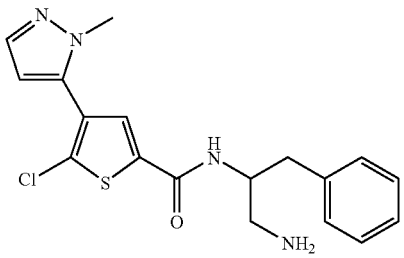 [SMILES: Cn1nccc1-c1cc(C(=O)NC(CN)Cc2ccccc2)sc1Cl]

Preparation of N-[2-amino-1-(phenylmethyl)ethyl]-5-chloro-4-(1-methyl-1H-pyrazol-5-yl)-2-thiophenecarboxamide The title compound was prepared as a white solid according to the procedure of Example 1, except substituting 4-bromo-5-chloro-2-thiophenecarboxylic acid (250 mg, 1.04 mmol)[from Preparation 11] for 4,5-dibromo-2-furancarboxylic acid: LC-MS (ES) m/z 375 (M+H)$^+$, $^1$H NMR (400 MHz, DMSO-d$_6$) δ ppm 9.09 (d, J=8.59 Hz, 1H) 8.14 (s, 3H) 8.10 (br. s., 1H) 7.55 (d, J=1.77 Hz, 1H) 7.25-7.32 (m, 4H) 7.21 (dd, J=6.19, 2.40 Hz, 1H) 6.48 (d, J=2.02 Hz, 1H) 4.35 (d, J=8.59 Hz, 1H) 3.84 (s, 3H) 2.99 (d, J=10.86 Hz, 1H) 2.89-2.96 (m, 3H).

Example 24

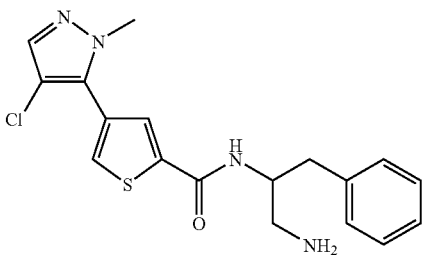 [SMILES: Cn1ncc(Cl)c1-c1csc(C(=O)NC(CN)Cc2ccccc2)c1]

Preparation of N-[2-amino-1-(phenylmethyl)ethyl]-4-(4-chloro-1-methyl-1H-pyrazol-5-yl)-2-thiophenecarboxamide a) 4-(1-methyl-1H-pyrazol-5-yl)-2-thiophenecarboxylic Acid

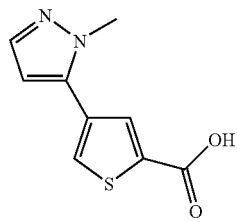

To a solution of 4-bromo-2-thiophenecarboxylic acid (1 g, 4.83 mmol) in dioxane/H$_2$O (5:1, 16 mL) was added K$_2$CO$_3$ (2.7 g, 19 mmol), tetrakistriphenylphosphine Pd(0) (279 mg, 0.241 mmol) and 5-(5,5-dimethyl-1,3,2-dioxaborinane-2-yl)-1-methyl-1H-pyrazole (1.2 g, 6.27 mmol). The reaction mixture was heated to 80° C. in a sealed tube for 2 h and additional tetrakistriphenylphosphine Pd(0) (279 mg, 0.241 mmol) and 5-(5,5-dimethyl-1,3,2-dioxaborinane-2-yl)-1-methyl-1H-pyrazole (1.2 g, 6.27 mmol) were added. After 12 h, the reaction was partitioned between 6N NaOH and DCM. The pH of the aqueous phase was adjusted to ~3 with 3M HCl and washed several times with DCM. The combined organic fractions were dried (Na$_2$SO$_4$), concentrated under vacuum and used directly without further purification (~1 g, quant.): LCMS (ES) m/z=209 (M+H)$^+$.

b) 4-(4-chloro-1-methyl-1H-pyrazol-5-yl)-2-thiophenecarboxylic Acid

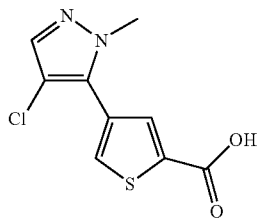

A solution of 4-(1-methyl-1H-pyrazol-5-yl)-2-thiophenecarboxylic acid (600 mg, 2.88 mmol) and N-chlorosuccinimide (384 mg, 2.88 mmol) in THF (14 mL) was stirred in a sealed tube at 70° C. After 1 h, the solution was partitioned between H$_2$O-DCM, the aqueous phase was adjusted to pH 3 and the aqueous phase was washed several times with DCM. The combined organic fractions were dried (Na$_2$SO$_4$), con- centrated under vacuum and used directly without further purification (698 mg, quant.): LCMS (ES) m/z=243 (M+H)$^+$.

c) 1,1-dimethylethyl[2-({[4-(4-chloro-1-methyl-1H-pyrazol-5-yl)-2-thienyl]carbonyl}amino)-3-phenyl-propyl]carbamate

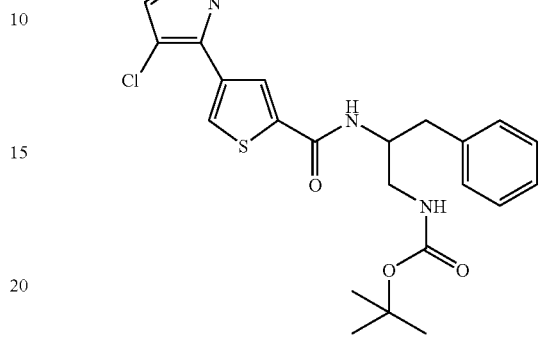

To a solution of 4-(4-chloro-1-methyl-1H-pyrazol-5-yl)-2-thiophenecarboxylic acid (350 mg, 1.45 mmol), 1,1-dimethylethyl (2-amino-3-phenylpropyl)carbamate (362 mg, 1.45 mmol)[from Preparation 2] and diisopropylethyl amine (1.3 mL, 7.23 mmol) in DCM (7 mL) was added PyBrop (809 mg, 1.74 mmol) in one portion. After 1 h, the reaction contents were partitioned between H$_2$O/DCM. The aqueous phase was washed several times with DCM and the combined organic fractions were dried over Na$_2$SO$_4$, concentrated and used directly: LCMS (ES) m/z=476 (M+H)$^+$.

d) N-[2-amino-1-(phenylmethyl)ethyl]-4-(4-chloro-1-methyl-1H-pyrazol-5-yl)-2-thiophenecarboxamide A solution of 1,1-dimethylethyl[2-({[4-(4-chloro-1-methyl-1H-pyrazol-5-yl)-2-thienyl]carbonyl}amino)-3-phenyl-propyl]carbamate (crude from part c) in TFA-DCM (3 mL, 1:2) was stirred at 25° C. After 30 min, the solution was concentrated and the residue neutralized through a silica plug (4% MeOH in DCM (1% NH$_4$OH)) affording the free base of the title compound.

The free base, as a solution in MeOH, was then treated with excess 4M HCl in dioxane affording the title compound (90 mg, 17%-2steps) as the HCl salt: LCMS (ES) m/z 476 (M+H)$^+$, $^1$H NMR (400 MHz, DMSO-d$_6$) δ ppm 8.75 (d, J=8.08 Hz, 1H) 8.10 (d, J=1.52 Hz, 2H) 8.08 (s, 3H) 7.68 (s, 1H) 7.26-7.32 (m, 4H) 7.22 (dd, J=6.06, 2.53 Hz, 1H) 4.39 (br. s., 1H) 3.87 (s, 3H) 2.91 (d, J=7.33 Hz, 4H).

Example 25

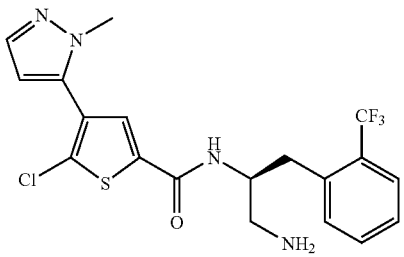 [SMILES: Cn1nccc1-c1cc(C(=O)N[C@H](CN)Cc2ccccc2C(F)(F)F)sc1Cl]

Preparation of N-((1S)-2-amino-1-{[2-(trifluoromethyl)phenyl]methyl}ethyl)-5-chloro-4-(1-methyl-1H-pyrazol-5-yl)-2-thiophenecarboxamide a) 4-bromo-5-chloro-N-((1S)-2-(1,3-dioxo-1,3-dihydro-2H-isoindol-2-yl)-1-{[2-(trifluoromethyl)phenyl]methyl}ethyl)-2-thiophenecarboxamide

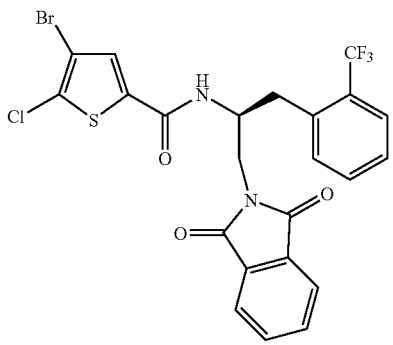 [SMILES: O=C(N[C@@H](Cc1ccccc1C(F)(F)F)CN1C(=O)c2ccccc2C1=O)c1cc(Br)c(Cl)s1]

To a solution of 4-bromo-5-chloro-2-thiophenecarboxylic acid (1.3 g, 5.42 mmol), PyBrOP (3 g, 6.5 mmol) and diisopropylethyl amine (4.7 mL, 27.1 mmol) in DCM (54 mL) at 25° C. was added 2-{(2S)-2-amino-3-[2-(trifluoromethyl)phenyl]propyl}-1H-isoindole-1,3(2H)-dione (2.0 g, 5.42 mmol) [prepared in Preparation 6]. After 1 h, the solution was partitioned between H$_2$O and washed with DCM. The combined organic fractions were dried (Na$_2$SO$_4$), concentrated and used directly: LCMS (ES) m/z=572 (M+H)$^+$.

b) 1,1-dimethylethyl {(2S)-2-{[(4-bromo-5-chloro-2-thienyl)carbonyl]amino}-3-[2-(trifluoromethyl)phenyl]propyl}carbamate

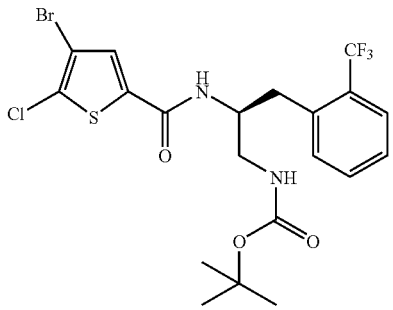 [SMILES: CC(C)(C)OC(=O)NC[C@H](Cc1ccccc1C(F)(F)F)NC(=O)c1cc(Br)c(Cl)s1]

To a solution of 4-bromo-5-chloro-N-((1S)-2-(1,3-dioxo-1,3-dihydro-2H-isoindol-2-yl)-1-{[2-(trifluoromethyl)phenyl]methyl}ethyl)-2-thiophenecarboxamide (crude from part a) in THF-MeOH (1:1, 20 mL) was added hydrazine (1.59 mL, 54.2 mmol). After 12 h, the solution was filtered and the filtrate concentrated, dry loaded onto silica and purified via column chromatography (2% MeOH in DCM (1% NH$_4$OH)) affording the free base which was dissolved in THF (25 mL) and treated with Boc$_2$O (1.2 g, 5.31 mmol). After 30 min the solution was concentrated affording a white powder of the title compound (800 mg, 27%-3 steps): LCMS (ES) m/z=542 (M+H)$^+$.

c) 1,1-dimethylethyl {(2S)-2-({[5-chloro-4-(1-methyl-1H-pyrazol-5-yl)-2-thienyl]carbonyl}amino)-3-[2-(trifluoromethyl)phenyl]propyl}carbamate

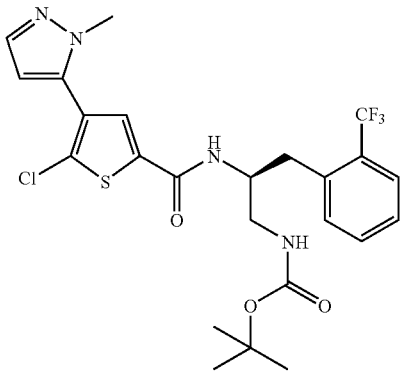 [SMILES: Cn1nccc1-c1cc(C(=O)N[C@H](CNC(=O)OC(C)(C)C)Cc2ccccc2C(F)(F)F)sc1Cl]

To a solution of 1,1-dimethylethyl {(2S)-2-{[(4-bromo-5-chloro-2-thienyl)carbonyl]amino}-3-[2-(trifluoromethyl)phenyl]propyl}carbamate (750 mg, 1.38 mmol) in dioxane/H$_2$O (5:1, 6 mL) was added K$_2$CO$_3$ (762 mg, 5.52 mmol), tetrakistriphenylphosphine Pd(0) (80 mg, 69 umol), and 5-(5,5-dimethyl-1,3,2-dioxaborinane-2-yl)-1-methyl-1H-pyrazole (373 mg, 1.8 mmol). The reaction mixture was heated to 80° C. in a sealed tube for 2 h where additional tetrakistriphenylphosphine Pd(0) (80 mg, 69 umol) and 5-(5,5-dimethyl-1,3,2-dioxaborinane-2-yl)-1-methyl-1H-pyrazole (373 mg, 1.8 mmol) were added. After 12 h, the solution was poured onto H$_2$O (100 mL) and extracted with DCM. The organics were dried (Na$_2$SO$_4$), concentrated under vacuum, and purified on silica gel (hexanes/EtOAc, 1:1) to give the title compound (194 mg, 26%) as a white solid: LC-MS (ES) m/z=544.

c) N-((1S)-2-amino-1-{[2-(trifluoromethyl)phenyl]methyl}ethyl)-5-chloro-4-(1-methyl-1H-pyrazol-5-yl)-2-thiophenecarboxamide 1,1-dimethylethyl {(2S)-2-({[5-chloro-4-(1-methyl-1H-pyrazol-5-yl)-2-thienyl]carbonyl}amino)-3-[2-(trifluoromethyl)phenyl]propyl}carbamate (194 mg, 0.357 mmol) was dissolved in TFA-DCM (3 mL, 1:2) and stirred at 25° C. After 30 min, the solution was concentrated with a toluene azeotrope and the residue neutralized through a silica plug (2-5% MeOH in DCM (1% NH$_4$OH)) affording the free base of the title compound.

The free base, as a solution in MeOH, was then treated with excess 4M HCl in dioxane affording the title compound (134 mg, 85%) as the HCl salt: LCMS (ES) m/z 444 (M+H)$^+$, $^1$H NMR (400 MHz, DMSO-d$_6$) δ ppm 9.10 (d, J=9.09 Hz, 1H) 8.11 (s, 1H) 8.10 (bs, 3H) 7.70 (d, J=8.08 Hz, 1H) 7.57 (d, J=2.02 Hz, 2H) 7.43 (s, 1H) 6.49 (d, J=2.02 Hz, 1H) 4.47 (br. s., 1H) 3.85 (s, 3H) 3.06 (d, J=8.34 Hz, 4H).

Example 26

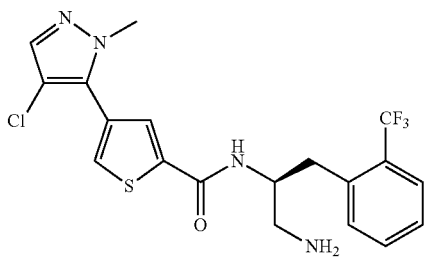 [SMILES: Cn1ncc(Cl)c1-c1csc(C(=O)N[C@H](CN)Cc2ccccc2C(F)(F)F)c1]

Preparation of N-((1S)-2-amino-1-{[2-(trifluoromethyl)phenyl]methyl}ethyl)-4-(4-chloro-1-methyl-1H-pyrazol-5-yl)-2-thiophenecarboxamide a) 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

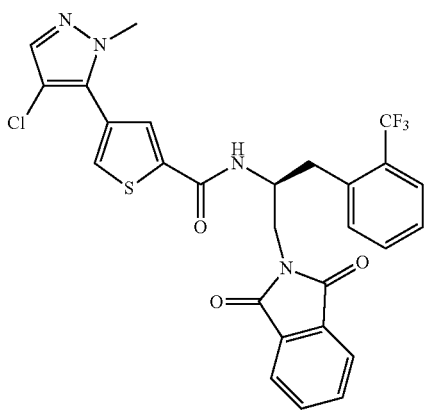 [SMILES: Cn1ncc(Cl)c1-c1csc(C(=O)N[C@@H](Cc2ccccc2C(F)(F)F)CN2C(=O)c3ccccc3C2=O)c1]

The title compound was prepared as white solid according to the procedure of Example 24, except substituting 2-{(2S)-2-amino-3-[2-(trifluoromethyl)phenyl]propyl}-1H-isoindole-1,3(2H)-dione (288 mg, 0.826 mmol)[from Preparation 6] for 1,1-dimethylethyl (2-amino-3-phenylpropyl)carbamate: LCMS (ES) m/z 444 (M+H)⁺.

b) N-((1S)-2-amino-1-{[2-(trifluoromethyl)phenyl]methyl}ethyl)-4-(4-chloro-1-methyl-1H-pyrazol-5-yl)-2-thiophenecarboxamide To a solution of 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (150 mg, 0.262 mmol) in THF-MeOH (1:1, 2 mL) was added hydrazine (123 uL, 2.62 mmol). After 12 h, the solution was filtered and the filtrate was concentrated, dry loaded onto silica and purified via column chromatography (2% MeOH in DCM (1% NH₄OH)) affording the free base of the title compound.

The free base, as a solution in MeOH, was then treated with excess 4M HCl in dioxane affording the title compound (30 mg, 26%) as the HCl salt: LCMS (ES) m/z 444 (M+H)⁺, $^1$H NMR (400 MHz, DMSO-d₆) δ ppm 8.69 (s, 1H) 8.11 (d, J=1.26 Hz, 1H) 8.03 (d, J=1.26 Hz, 1H) 7.93 (bs, 3H) 7.69 (s, 2H) 7.53-7.59 (m, 2H) 7.44 (d, J=4.80 Hz, 1H) 4.49 (br. s., 1H) 3.87 (s, 3H) 2.99-3.12 (m, 4H).

Example 27

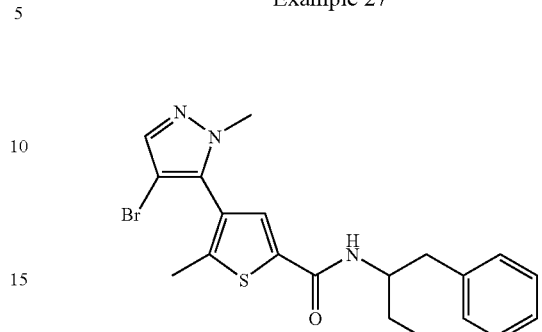

Preparation of N-[2-amino-1-(phenylmethyl)ethyl]-4-(4-bromo-1-methyl-1H-pyrazol-5-yl)-5-methyl-2-thiophenecarboxamide The title compound was prepared as a white solid according to the procedure of Example 24, except substituting 4-bromo-5-methyl-2-thiophenecarboxylic acid (1 g, 4.52 mmol)[from Preparation 9] for 4-(1-methyl-1H-pyrazol-5-yl)-2-thiophenecarboxylic acid and substituting NBS (325 mg, 2.43 mmol) for NCS: LCMS (ES) m/z 434 (M+H)⁺, $^1$H NMR (400 MHz, DMSO-d₆) δ ppm 8.65 (br. s., 1H) 8.01 (br. s., 3H) 7.80 (s, 1H) 7.70 (s, 1H) 7.25-7.32 (m, 4H) 7.21 (td, J=6.19, 2.78 Hz, 1H) 4.31-4.35 (m, 1H) 3.71 (s, 3H) 2.86-2.92 (m, 4H) 2.33 (s, 3H).

Example 28

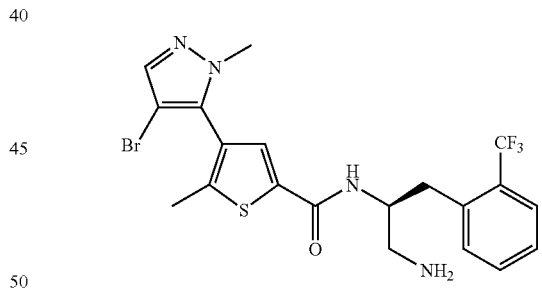

Preparation of N-((1S)-2-amino-1-{[2-(trifluoromethyl)phenyl]methyl}ethyl)-4-(4-bromo-1-methyl-1H-pyrazol-5-yl)-5-methyl-2-thiophenecarboxamide The title compound was prepared as a white solid according to the procedure of Example 26, except substituting 4-bromo-5-methyl-2-thiophenecarboxylic acid (1 g, 4.52 mmol)[from Preparation 9] for 4-(1-methyl-1H-pyrazol-5-yl)-2-thiophenecarboxylic acid and substituting NBS (325 mg, 2.43 mmol) for NCS: LCMS (ES) m/z 502 (M+H)⁺, $^1$H NMR (400 MHz, DMSO-d₆) δ ppm 8.81 (br. s., 1H) 8.05 (br. s., 3H) 7.83-7.90 (m, 1H) 7.67-7.74 (m, 2H) 7.53-7.60 (m, 2H) 7.39-7.47 (m, 1H) 4.48 (d, J=5.05 Hz, 1H) 3.68-3.76 (m, 3H) 3.01-3.08 (m, 4H) 2.33 (s, 3H).

Example 29

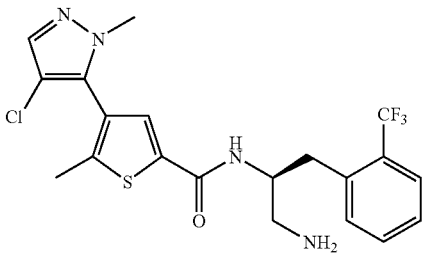 [SMILES: Cc1sc(C(=O)N[C@H](CN)Cc2ccccc2C(F)(F)F)cc1-c1c(Cl)cnn1C]

Preparation of N-((1S)-2-amino-1-{[2-(trifluoromethyl)phenyl]methyl}ethyl)-4-(4-chloro-1-methyl-1H-pyrazol-5-yl)-5-methyl-2-thiophenecarboxamide The title compound was prepared as a white solid according to the procedure of Example 26, except substituting 4-bromo-5-methyl-2-thiophenecarboxylic acid (1 g, 4.52 mmol)[from Preparation 9] for 4-(1-methyl-1H-pyrazol-5-yl)-2-thiophenecarboxylic acid: LCMS (ES) m/z 457 (M+H)$^+$, $^1$H NMR (400 MHz, DMSO-d$_6$) δ ppm 8.76 (br. s., 1H) 8.03 (br. s., 3H) 7.86 (s, 1H) 7.70 (s, 2H) 7.53-7.60 (m, 2H) 7.39-7.47 (m, 1H) 4.46 (d, J=9.35 Hz, 1H) 3.72 (s, 3H) 3.03-3.10 (m, 4H) 2.34 (s, 3H).

Example 30

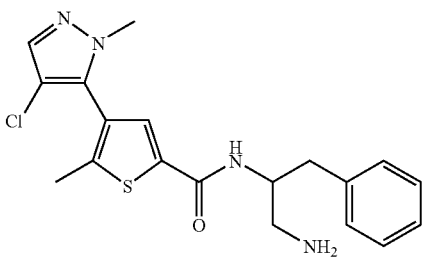 [SMILES: Cc1sc(C(=O)NC(CN)Cc2ccccc2)cc1-c1c(Cl)cnn1C]

Preparation of N-[2-amino-1-(phenylmethyl)ethyl]-4-(4-chloro-1-methyl-1H-pyrazol-5-yl)-5-methyl-2-thiophenecarboxamide The title compound was prepared as a white solid according to the procedure of Example 24, except substituting 4-bromo-5-methyl-2-thiophenecarboxylic acid (1 g, 4.52 mmol)[from Preparation 9] for 4-(1-methyl-1H-pyrazol-5-yl)-2-thiophenecarboxylic acid: LCMS (ES) m/z 389 (M+H)$^+$, $^1$H NMR (400 MHz, DMSO-d$_6$) δ ppm 8.67 (br. s., 1H) 8.01 (br. s., 3H) 7.82 (s, 1H) 7.70 (s, 1H) 7.25-7.32 (m, 4H) 7.19-7.23 (m, 1H) 4.31-4.38 (m, 1H) 3.71 (s, 3H) 2.97 (br. s., 2H) 2.89 (t, J=6.19 Hz, 2H) 2.34 (s, 3H).

Example 31

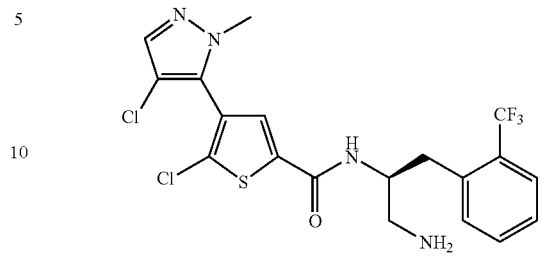

Preparation of N-((1S)-2-amino-1-{[2-(trifluoromethyl)phenyl]methyl}ethyl)-5-chloro-4-(4-chloro-1-methyl-1H-pyrazol-5-yl)-2-thiophenecarboxamide a) 1,1-dimethylethyl {(2S)-2-({[5-chloro-4-(4-chloro-1-methyl-1H-pyrazol-5-yl)-2-thienyl]carbonyl}amino)-3-[2-(trifluoromethyl)phenyl]propyl}carbamate

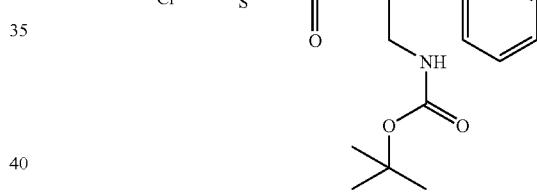

A solution of 1,1-dimethylethyl {(2S)-2-({[5-chloro-4-(1-methyl-1H-pyrazol-5-yl)-2-thienyl]carbonyl}amino)-3-[2-(trifluoromethyl)phenyl]propyl}carbamate (110 mg, 0.202 mmol)[prepared in Example 25] and N-chlorosuccinimide (35 mg, 0.263 mmol) in THF (2 mL) was stirred in a sealed tube at 70° C. After 1 h, the solution was partitioned between H$_2$O-DCM and the aqueous phase was washed several times with DCM. The combined organic fractions were dried (Na$_2$SO$_4$), concentrated under vacuum and used directly without further purification: LCMS (ES) m/z=578 (M+H)$^+$.

b) N-((1S)-2-amino-1-{[2-(trifluoromethyl)phenyl]methyl}ethyl)-5-chloro-4-(4-chloro-1-methyl-1H-pyrazol-5-yl)-2-thiophenecarboxamide 1,1-dimethylethyl {(2S)-2-({[5-chloro-4-(4-chloro-1-methyl-1H-pyrazol-5-yl)-2-thienyl]carbonyl}amino)-3-[2-(trifluoromethyl)phenyl]propyl}carbamate (crude from part a) was dissolved in TFA-DCM (3 mL, 1:2) and stirred at 25° C. After 30 min, the solution was concentrated and the residue neutralized through a silica plug (5% MeOH in DCM (1% NH$_4$OH)) affording the free base of the title compound.

The free base, as a solution in MeOH, was then treated with excess 4M HCl in dioxane affording the title compound (43 mg, 44%-2 steps) as the HCl salt: LCMS (ES) m/z 478 (M+H)$^+$, $^1$H NMR (400 MHz, DMSO-d$_6$) δ ppm 9.10 (d, J=8.84 Hz, 1H) 8.06 (s, 4H) 7.75 (s, 1H) 7.70 (d, J=7.83 Hz, 1H) 7.54-7.61 (m, 2H) 7.43 (t, J=7.45 Hz, 1H) 4.47 (t, J=8.84 Hz, 1H) 3.78 (s, 3H) 2.98-3.12 (m, 4H).

Example 32

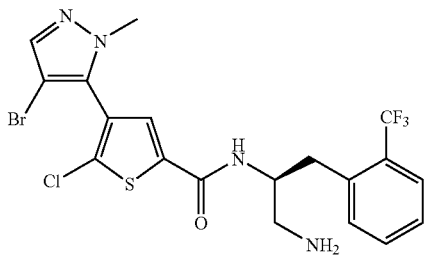

Preparation of N-((1S)-2-amino-1-{[2-(trifluoromethyl)phenyl]methyl}ethyl)-4-(4-bromo-1-methyl-1H-pyrazol-5-yl)-5-chloro-2-thiophenecarboxamide a) 1,1-dimethylethyl {(2S)-2-({[4-(4-bromo-1-methyl-1H-pyrazol-5-yl)-5-chloro-2-thienyl]carbonyl}amino)-3-[2-(trifluoromethyl)phenyl]propyl}carbamate

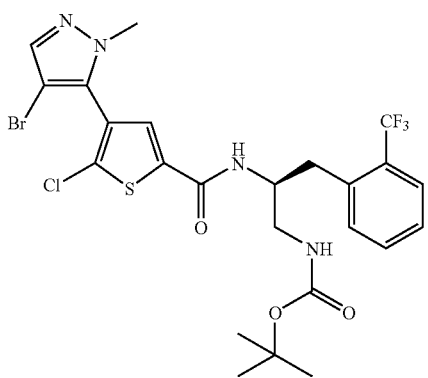 [SMILES: Cn1ncc(Cl)c1-c1cc(C(=O)N[C@H](CNC(=O)OC(C)(C)C)Cc2ccccc2C(F)(F)F)sc1Cl]

A solution of 1,1-dimethylethyl {(2S)-2-({[5-chloro-4-(1-methyl-1H-pyrazol-5-yl)-2-thienyl]carbonyl}amino)-3-[2-(trifluoromethyl)phenyl]propyl}carbamate (121 mg, 0.22 mmol)[prepared in Example 25] and N-bromosuccinimide (52 mg, 0.290 mmol) in THF (2 mL) was stirred in a sealed tube at 70° C. After 1 h, the solution was partitioned between H₂O-DCM and the aqueous phase was washed several times with DCM. The combined organic fractions were dried (Na₂SO₄), concentrated under vacuum and used directly without further purification: LCMS (ES) m/z=622 (M+H)⁺.

b) N-((1S)-2-amino-1-{[2-(trifluoromethyl)phenyl]methyl}ethyl)-5-chloro-4-(4-chloro-1-methyl-1H-pyrazol-5-yl)-2-thiophenecarboxamide 1,1-dimethylethyl {(2S)-2-({[4-(4-bromo-1-methyl-1H-pyrazol-5-yl)-5-chloro-2-thienyl]carbonyl}amino)-3-[2-(trifluoromethyl)phenyl]propyl}carbamate (crude from part a) was dissolved in TFA-DCM (3 mL, 1:2) and stirred at 25° C. After 30 min, the solution was concentrated and the residue neutralized through a silica plug (5% MeOH in DCM (1% NH₄OH)) affording the free base of the title compound.

The free base, as a solution in MeOH, was then treated with excess 4M HCl in dioxane affording the title compound (42 mg, 44%-2 steps) as the HCl salt: LCMS (ES) m/z 522 (M+H)⁺, ¹H NMR (400 MHz, DMSO-d₆) δ ppm 9.13 (d, J=9.09 Hz, 1H) 8.17 (br. s., 1H) 8.05 (s, 3H) 7.75 (s, 1H) 7.69 (d, J=7.83 Hz, 1H) 7.54-7.61 (m, 2H) 7.43 (t, J=7.58 Hz, 1H) 4.46 (d, J=9.60 Hz, 1H) 3.78 (s, 3H) 2.99-3.13 (m, 4H).

Example 33

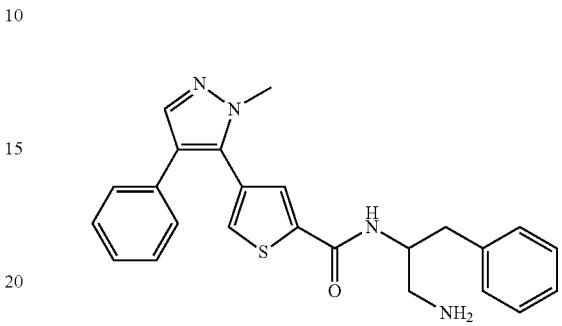

Preparation of N-[2-amino-1-(phenylmethyl)ethyl]-4-(1-methyl-4-phenyl-1H-pyrazol-5-yl)-2-thiophenecarboxamide a) 4-(4-bromo-1-methyl-1H-pyrazol-5-yl)-2-thiophenecarboxylic Acid

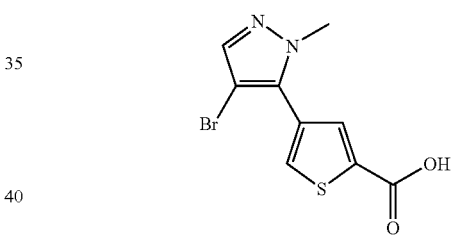

The title compound was prepare as an orange oil according to Example 24, except substituting N-bromosuccinimide (1 g, 5.77 mmol) for N-chlorosuccinimide: LCMS (ES) m/z 288 (M+H)⁺.

b) 4-(1-methyl-4-phenyl-1H-pyrazol-5-yl)-2-thiophenecarboxylic Acid

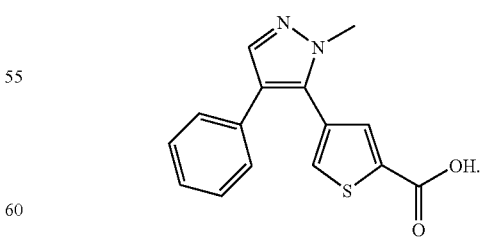

To a solution of 4-(4-bromo-1-methyl-1H-pyrazol-5-yl)-2-thiophenecarboxylic acid (688 mg, 2.41 mmol) in dioxane/H₂O (5:1, 12 mL) was added K₂CO₃ (1.3 g, 9.6 mmol), tetrakistriphenylphosphine Pd(0) (139 mg, 0.120 mmol), and 5-(5,5-dimethyl-1,3,2-dioxaborinane-2-yl)-1-methyl-1H- pyrazole (293 mg, 2.41 mmol). The reaction mixture was heated to 80° C. in a sealed tube for 2 h where additional tetrakistriphenylphosphine Pd(0) (139 mg, 0.120 mmol) and 5-(5,5-dimethyl-1,3,2-dioxaborinane-2-yl)-1-methyl-1H-pyrazole (293 mg, 2.41 mmol) were added. After 12 h, the solution was poured onto H$_2$O and the pH was adjusted to ~4 with aqueous HCl. The aqueous phase was extracted several times with DCM and the combined organic fractions were dried (Na$_2$SO$_4$) and concentrated affording the title compound white was used directly without further purification: LC-MS (ES) m/z=284 (M+H)$^+$.

c) 1,1-dimethylethyl[2-({[4-(1-methyl-4-phenyl-1H-pyrazol-5-yl)-2-thienyl]carbonyl}amino)-3-phenyl-propyl]carbamate

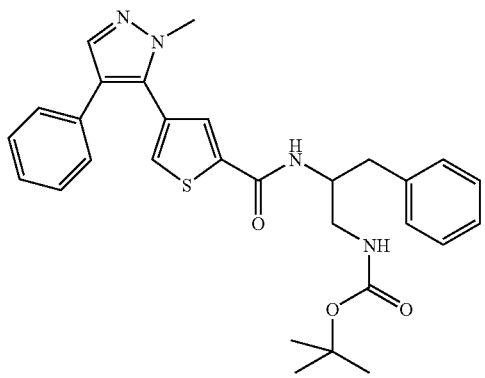 [SMILES: Cn1ncc(-c2ccccc2)c1-c1csc(C(=O)NC(CNC(=O)OC(C)(C)C)Cc2ccccc2)c1]

To a solution of 4-(1-methyl-4-phenyl-1H-pyrazol-5-yl)-2-thiophenecarboxylic acid (341 mg, 1.2 mmol), 1,1-dimethylethyl (2-amino-3-phenylpropyl)carbamate (300 mg, 1.2 mmol)[from Preparation 2], diisopropylethyl amine (1 mL, 6.01 mmol) in DCM (6 mL) was added PyBrop (673 mg, 1.44 mmol) in one portion. After 1 h, the reaction contents were partitioned between H$_2$O/DCM. The aqueous phase was washed several times with DCM and the combined organic fractions were dried over Na$_2$SO$_4$, concentrated and used directly: LCMS (ES) m/z=517 (M+H)$^+$.

d) N-[2-amino-1-(phenylmethyl)ethyl]-4-(1-methyl-4-phenyl-1H-pyrazol-5-yl)-2-thiophenecarboxamide A solution of 1,1-dimethylethyl[2-({[4-(1-methyl-4-phenyl-1H-pyrazol-5-yl)-2-thienyl]carbonyl}amino)-3-phenyl-propyl]carbamate (crude from part c) in TFA-DCM (3 mL, 1:2) was stirred at 25° C. After 30 min, the solution was concentrated and the residue neutralized through a silica plug (4% MeOH in DCM (1% NH$_4$OH)) affording the free base of the title compound.

The free base, as a solution in MeOH, was then treated with excess 4M HCl in dioxane affording the title compound (105 mg, 21%-3steps) as the HCl salt: LCMS (ES) m/z 417 (M+H)$^+$, $^1$H NMR (400 MHz, DMSO-d$_6$) δ ppm 8.82 (d, J=8.34 Hz, 1H) 8.14 (br. s., 3H) 7.96 (s, 1H) 7.90 (d, J=1.26 Hz, 1H) 7.82 (s, 1H) 7.29 (s, 1H) 7.25 (t, J=8.46 Hz, 9H) 4.34 (dd, J=7.45, 5.68 Hz, 1H) 3.75 (s, 3H) 2.94-3.00 (m, 2H) 2.89 (dd, J=6.82, 5.31 Hz, 2H).

Example 34

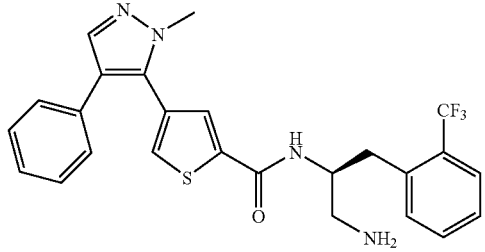 [SMILES: Cn1ncc(-c2ccccc2)c1-c1csc(C(=O)N[C@H](CN)Cc2ccccc2C(F)(F)F)c1]

Preparation of N-((1S)-2-amino-1-{[2-(trifluoromethyl)phenyl]methyl}ethyl)-4-(1-methyl-4-phenyl-1H-pyrazol-5-yl)-2-thiophenecarboxamide a) N-((1S)-2-(1,3-dioxo-1,3-dihydro-2H-isoindol-2-yl)-1-{[2-(trifluoromethyl)phenyl]methyl}ethyl)-4-(1-methyl-4-phenyl-1H-pyrazol-5-yl)-2-thiophenecarboxamide

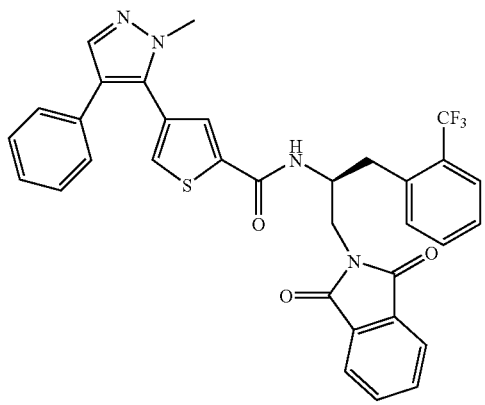 [SMILES: Cn1ncc(-c2ccccc2)c1-c1csc(C(=O)N[C@@H](Cc2ccccc2C(F)(F)F)CN2C(=O)c3ccccc3C2=O)c1]

The title compound was prepared as a white solid according to the procedure of Example 33, except substituting 2-{(2S)-2-amino-3-[2-(trifluoromethyl)phenyl]propyl}-1H-isoindole-1,3(2H)-dione (420 mg, 1.2 mmol) [from Preparation 6] for 1,1-dimethylethyl (2-amino-3-phenylpropyl)carbamate: LCMS (ES) m/z 615 (M+H)$^+$.

b) N-((1S)-2-amino-1-{[2-(trifluoromethyl)phenyl]methyl}ethyl)-4-(1-methyl-4-phenyl-1H-pyrazol-5-yl)-2-thiophenecarboxamide To a solution of N-((1S)-2-(1,3-dioxo-1,3-dihydro-2H-isoindol-2-yl)-1-{[2-(trifluoromethyl)phenyl]methyl}ethyl)-4-(1-methyl-4-phenyl-1H-pyrazol-5-yl)-2-thiophenecarboxamide (crude from part a) in THF-MeOH (1:1, 10 mL) was added hydrazine (384 uL, 12 mmol). After 12 h, the solution was filtered and the filtrate was concentrated, dry loaded onto silica and purified via column chromatography (2% MeOH in DCM (1% NH$_4$OH)) affording the free base of the title compound.

The free base, as a solution in MeOH, was then treated with excess 4M HCl in dioxane affording the title compound (40 mg, 7%) as the HCl salt: LCMS (ES) m/z 485 (M+H)$^+$, $^1$H NMR (400 MHz, DMSO-d$_6$) δ ppm 8.78 (d, J=9.09 Hz, 1H) 8.05 (br. s., 3H) 7.91 (dd, J=9.09, 1.26 Hz, 2H) 7.83 (s, 1H)

7.69 (d, J=7.33 Hz, 1H) 7.50-7.53 (m, 1H) 7.43 (d, J=7.58 Hz, 1H) 7.47 (t, J=6.82 Hz, 1H) 7.23-7.30 (m, 4H) 7.22 (s, 1H) 4.47 (br. s., 1H) 3.75 (s, 3H) 3.01 (d, J=8.08 Hz, 4H).

Example 35

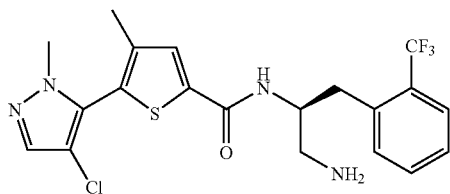 [SMILES: Cc1cc(C(=O)N[C@H](CN)Cc2ccccc2C(F)(F)F)sc1-c1c(Cl)cnn1C]

Preparation of N-((1S)-2-amino-1-{[2-(trifluoromethyl)phenyl]methyl}ethyl)-5-(4-chloro-1-methyl-1H-pyrazol-5-yl)-4-methyl-2-thiophenecarboxamide a) methyl 4-methyl-5-(1-methyl-1H-pyrazol-5-yl)-2-thiophenecarboxylate

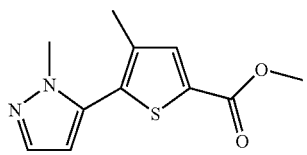 [SMILES: COC(=O)c1cc(C)c(-c2ccnn2C)s1]

To a solution of methyl 5-bromo-4-methyl-2-thiophenecarboxylate (1 g, 4.25 mmol) in dioxane/H₂O (5:1, 20 mL) was added K₂CO₃ (2.3 g, 17 mmol), bis(tri-t-butylphosphine)palladium(0) (108 mg, 0.213 mmol) and 5-(5,5-dimethyl-1,3,2-dioxaborinane-2-yl)-1-methyl-1H-pyrazole (1.2 g, 5.52 mmol). The reaction mixture was heated to 80° C. in a sealed tube for 2 h and additional tetrakistriphenylphosphine Pd(0) (279 mg, 0.241 mmol) and 5-(5,5-dimethyl-1,3,2-dioxaborinane-2-yl)-1-methyl-1H-pyrazole (1.2 g, 6.27 mmol) were added. After 12 h, the reaction was partitioned between H₂O-DCM and the aqueous phase was washed several times with DCM. The combined organic fractions were dried over Na₂SO₄, concentrated and used directly without further purification: LCMS (ES) m/z=237 (M+H)⁺.

b) 4-methyl-5-(1-methyl-1H-pyrazol-5-yl)-2-thiophenecarboxylic Acid

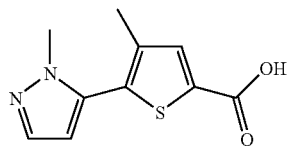

A solution of methyl 4-methyl-5-(1-methyl-1H-pyrazol-5-yl)-2-thiophenecarboxylate (crude from part a) in THF (4 mL) and 6N NaOH (4 mL) was heated to 70° C. After 1 h, the solution was poured onto H₂O and the pH was adjusted to ~4 with aqueous HCl. The aqueous phase was extracted several times with DCM and the combined organic fractions were dried (Na₂SO₄) and concentrated affording the title compound as a white solid which was used directly without further purification: LCMS (ES) m/z=223 (M+H)⁺.

c) N-((1S)-2-amino-1-{[2-(trifluoromethyl)phenyl]methyl}ethyl)-5-(4-chloro-1-methyl-1H-pyrazol-5-yl)-4-methyl-2-thiophenecarboxamide The title compound was prepared as a white solid according to the procedure of Example 27, except substituting 4-methyl-5-(1-methyl-1H-pyrazol-5-yl)-2-thiophenecarboxylic acid (424 mg, 1.92 mmol) for 4-(1-methyl-1H-pyrazol-5-yl)-2-thiophenecarboxylic acid: LCMS (ES) m/z 457 (M+H)⁺, ¹H NMR (400 MHz, DMSO-d₆) δ ppm 8.84 (d, J=8.84 Hz, 1H) 8.05 (br. s., 3H) 7.84 (s, 1H) 7.74 (s, 1H) 7.71 (d, J=8.08 Hz, 1H) 7.56-7.63 (m, 2H) 7.44 (t, J=7.20 Hz, 1H) 4.47-4.54 (m, 1H) 3.70 (s, 3H) 2.93-3.12 (m, 4H) 2.10 (s, 3H).

Example 36

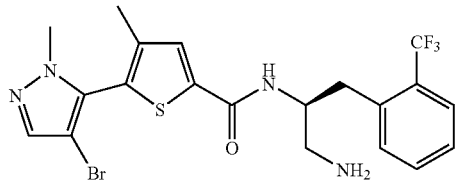 [SMILES: Cc1cc(C(=O)N[C@H](CN)Cc2ccccc2C(F)(F)F)sc1-c1c(Br)cnn1C]

Preparation of N-((1S)-2-amino-1-{[2-(trifluoromethyl)phenyl]methyl}ethyl)-5-(4-bromo-1-methyl-1H-pyrazol-5-yl)-4-methyl-2-thiophenecarboxamide a) methyl 4-methyl-5-(1-methyl-1H-pyrazol-5-yl)-2-thiophenecarboxylate

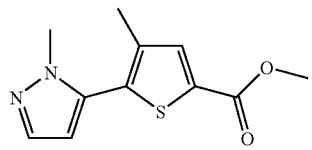 [SMILES: COC(=O)c1cc(C)c(-c2ccnn2C)s1]

To a solution of methyl 5-bromo-4-methyl-2-thiophenecarboxylate (1 g, 4.25 mmol) in dioxane/H₂O (5:1, 20 mL) was added K₂CO₃ (2.3 g, 17 mmol), bis(tri-t-butylphosphine)palladium(0) (108 mg, 0.213 mmol) and 5-(5,5-dimethyl-1,3,2-dioxaborinane-2-yl)-1-methyl-1H-pyrazole (1.2 g, 5.52 mmol). The reaction mixture was heated to 80° C. in a sealed tube for 2 h and additional tetrakistriphenylphosphine Pd(0) (279 mg, 0.24 mmol) and 5-(5,5-dimethyl-1,3,2-dioxaborinane-2-yl)-1-methyl-1H-pyrazole (1.2 g, 6.27 mmol) were added. After 12 h, the reaction was partitioned between H₂O-DCM and the aqueous phase was washed several times with DCM. The combined organic fractions were dried over Na₂SO₄, concentrated and used directly without further purification: LCMS (ES) m/z=237 (M+H)⁺.

b) 4-methyl-5-(1-methyl-1H-pyrazol-5-yl)-2-thiophenecarboxylic Acid

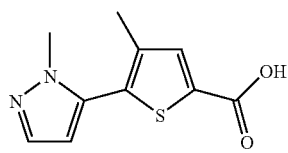

A solution of methyl 4-methyl-5-(1-methyl-1H-pyrazol-5-yl)-2-thiophenecarboxylate (crude from part a) in THF (4 mL) and 6N NaOH (4 mL) was heated to 70° C. After 1 h, the solution was poured onto H₂O and the pH was adjusted to ~4 with aqueous HCl. The aqueous phase was extracted several times with DCM and the combined organic fractions were dried (Na₂SO₄) and concentrated affording the title compound white was used directly without further purification: LCMS (ES) m/z=223 (M+H)⁺.

c) N-((1S)-2-amino-1-{[2-(trifluoromethyl)phenyl]methyl}ethyl)-5-(4-bromo-1-methyl-1H-pyrazol-5-yl)-4-methyl-2-thiophenecarboxamide The title compound was prepared as a white solid according to the procedure of Example 26, except substituting 4-methyl-5-(1-methyl-1H-pyrazol-5-yl)-2-thiophenecarboxylic acid (424 mg, 1.92 mmol) for 4-(1-methyl-1H-pyrazol-5-yl)-2-thiophenecarboxylic acid and substituting N-bromosuccinimide (376 mg, 2.11 mmol) for N-chlorosuccinimide: LCMS (ES) m/z 502 (M+H)⁺, ¹H NMR (400 MHz, DMSO-d₆) δ ppm 8.84 (d, J=9.09 Hz, 1H) 8.05 (br. s., 3H) 7.83 (s, 1H) 7.67-7.74 (m, 2H) 7.60 (q, J=7.83 Hz, 2H) 7.40-7.47 (m, 1H) 4.50 (d, J=4.04 Hz, 1H) 3.71 (s, 3H) 2.98-3.12 (m, 4H) 2.09 (s, 3H).

Example 37

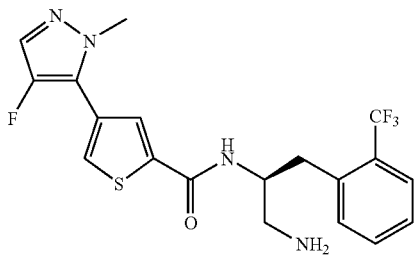 [SMILES: Cn1ncc(F)c1-c1csc(C(=O)N[C@H](CN)Cc2ccccc2C(F)(F)F)c1]

Preparation of N-((1S)-2-amino-1-{[2-(trifluoromethyl)phenyl]methyl}ethyl)-4-(4-fluoro-1-methyl-1H-pyrazol-5-yl)-2-thiophenecarboxamide a) methyl 4-bromo-2-thiophenecarboxylate

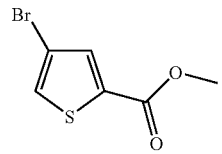

To a solution of 4-bromo-2-thiophenecarboxylic acid (4 g, 19 mmol) in MeOH (100 mL) was added H₂SO₄ (5 mL) dropwise at 25° C. The solution was stirred for 12 h at 50° C. and was poured into ice-H₂O and the pH was adjusted to ~11 with aqueous NaOH. The aqueous phase was extracted several times with DCM and the combined organic fractions were dried over Na₂SO₄, concentrated and used directly (4.27 g, quant.): LCMS (ES) m/z 222 (M+H)⁺.

b) methyl 4-(1-methyl-1H-pyrazol-5-yl)-2-thiophenecarboxylate

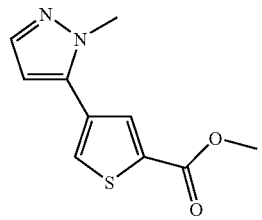

To a solution of methyl 4-bromo-2-thiophenecarboxylate (1 g, 4.52 mmol) in dioxane/H₂O (5:1, 16 mL) was added K₂CO₃ (2.7 g, 19 mmol), bis(tri-t-butylphosphine)palladium (0) (116 mg, 0.226 mmol) and 5-(5,5-dimethyl-1,3,2-dioxaborinane-2-yl)-1-methyl-1H-pyrazole (1.2 g, 5.88 mmol). The reaction mixture was heated to 80° C. in a sealed tube. After 1 h, the reaction was partitioned between H₂O-DCM and the aqueous phase was extracted several times with DCM. The combined organic fractions were dried over Na₂SO₄, concentrated and used directly: LCMS (ES) m/z 223 (M+H)⁺.

c) methyl 4-(4-fluoro-1-methyl-1H-pyrazol-5-yl)-2-thiophenecarboxylate

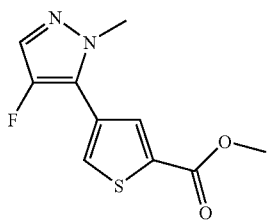 [SMILES: COC(=O)c1cc(-c2c(F)cnn2C)cs1]

A solution of methyl 4-(1-methyl-1H-pyrazol-5-yl)-2-thiophenecarboxylate (330 mg, 1.49 mmol) and Selectfluor® (793 mg, 2.23 mmol) in THF (7 mL) and H₂O (500 uL) was stirred in a sealed tube at 70° C. After 1 h, additional selectfluor (793 mg, 2.23 mmol) was added and the solution stirred an additional 12 h. The reaction mixture was then partitioned between H₂O-DCM, the aqueous phase was washed several times with DCM. The combined organic fractions were dried (Na₂SO₄), concentrated and purified via column chromatography (silica, 20% EtOAc in hexanes) affording the title compound (126 mg, 33%) as a white solid: LCMS (ES) m/z=241 (M+H)⁺.

d) 4-(4-fluoro-1-methyl-1H-pyrazol-5-yl)-2-thiophenecarboxylic Acid

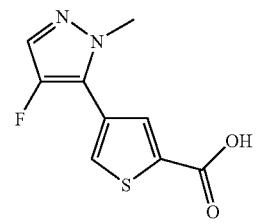

A solution of methyl 4-(4-fluoro-1-methyl-1H-pyrazol-5-yl)-2-thiophenecarboxylate (126 mg, 0.53 mmol) in THF (1 mL) and 6N NaOH (1 mL) was heated to 70° C. After 1 h, the solution was poured onto H₂O and the pH was adjusted to ~4 with aqueous HCl. The aqueous phase was extracted several times with DCM and the combined organic fractions were dried (Na₂SO₄) and concentrated affording the title compound white was used directly without further purification: LCMS (ES) m/z=227 (M+H)⁺.

e) N-((1S)-2-(1,3-dioxo-1,3-dihydro-2H-isoindol-2-yl)-1-{[2-(trifluoromethyl)phenyl]methyl}ethyl)-4-(4-fluoro-1-methyl-1H-pyrazol-5-yl)-2-thiophenecarboxamide

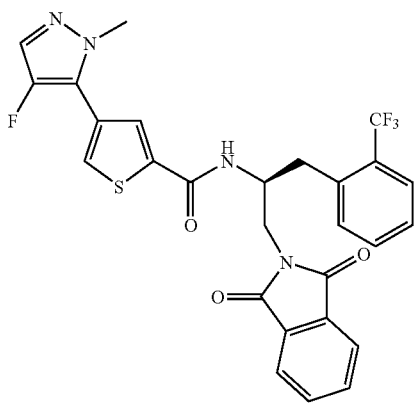 [SMILES: Cn1ncc(F)c1-c1csc(C(=O)N[C@@H](Cc2ccccc2C(F)(F)F)CN2C(=O)c3ccccc3C2=O)c1]

To a solution of 4-(4-fluoro-1-methyl-1H-pyrazol-5-yl)-2-thiophenecarboxylic acid (84 mg, 0.372 mmol), 2-{(2S)-2-amino-3-[2-(trifluoromethyl)phenyl]propyl}-1H-isoindole-1,3(2H)-dione (130 mg, 0.372 mmol)[from Preparation 6], diisopropylethyl amine (323 uL, 1.86 mmol) in DCM (4 mL) was added PyBrop (208 mg, 0.446 mmol) in one portion. After 1 h, the reaction contents were partitioned between H₂O/DCM. The aqueous phase was washed several times with DCM and the combined organic fractions were dried over Na₂SO₄, concentrated and purified via column chromatography (silica, 0.5% MeOH-DCM) affording the title compound (135 mg, 65%) as a white solid: LCMS (ES) m/z=557 (M+H)⁺.

f) N-((1S)-2-amino-1-{[2-(trifluoromethyl)phenyl]methyl}ethyl)-4-(4-fluoro-1-methyl-1H-pyrazol-5-yl)-2-thiophenecarboxamide To a solution of N-((1S)-2-(1,3-dioxo-1,3-dihydro-2H-isoindol-2-yl)-1-{[2-(trifluoromethyl)phenyl]methyl}ethyl)-4-(4-fluoro-1-methyl-1H-pyrazol-5-yl)-2-thiophenecarboxamide (135 mg, 0.242 mmol) in THF-MeOH (1:1, 2 mL) was added hydrazine (75 uL, 2.42 mmol). After 12 h, the solution was filtered and the filtrate was concentrated, dry loaded onto silica and purified via column chromatography (3% MeOH in DCM (1% NH₄OH)). The title compound was further purified via Gilson reverse phase chromatography using 5-95% mobile phase gradient affording the TFA-salt of the title compound which was neutralized through a silica plug ((5% MeOH in DCM (1% NH₄OH)) then transferred to the HCl salt using excess 4M HCl in dioxane (40 mg, 26%): LCMS (ES) m/z 427 (M+H)⁺, ¹H NMR (400 MHz, DMSO-d₆) d ppm 8.88 (d, J=8.84 Hz, 1H) 8.13 (s, 1H) 8.06 (bs, 3H) 7.70 (d, J=7.83 Hz, 1H) 7.55-7.62 (m, 3H) 7.54 (br. s., 1H) 7.41 (d, J=2.53 Hz, 1H) 4.49 (d, J=5.05 Hz, 1H) 3.92 (s, 3H) 2.99-3.11 (m, 4H).

Example 38

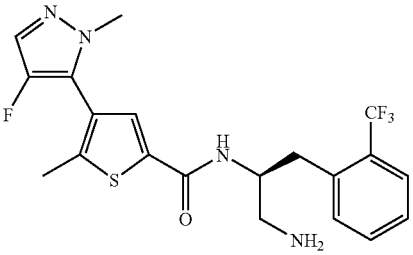 [SMILES: Cc1sc(C(=O)N[C@H](CN)Cc2ccccc2C(F)(F)F)cc1-c1c(F)cnn1C]

Preparation of N-((1S)-2-amino-1-{[2-(trifluoromethyl)phenyl]methyl}ethyl)-4-(4-fluoro-1-methyl-1H-pyrazol-5-yl)-5-methyl-2-thiophenecarboxamide The title compound was prepared as a yellow solid according to the procedure of Example 37, except substituting methyl 4-bromo-5-methyl-2-thiophenecarboxylate (1 g, 4.26 mmol)[from Preparation 11] for methyl 4-bromo-2-thiophenecarboxylate: LCMS (ES) m/z 441 (M+H)⁺, ¹H NMR (400 MHz, DMSO-d6) δ ppm 8.78 (d, J=9.60 Hz, 1H) 8.03 (br s, 3H) 7.91 (s, 1H) 7.69 (d, J=7.83 Hz, 1H) 7.62 (d, J=4.55 Hz, 1H) 7.52-7.59 (m, 2H) 7.39-7.46 (m, 1H) 4.47 (br. s., 1H) 3.74 (s, 3H) 3.06 (br. s., 4H) 2.36 (s, 3H).

Example 39

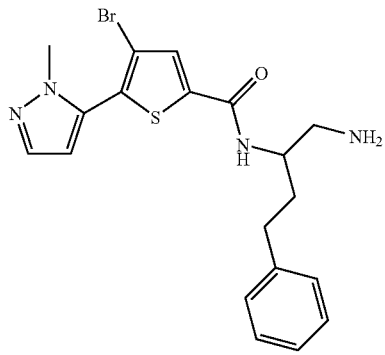 [SMILES: Cn1nccc1-c1sc(C(=O)NC(CN)CCc2ccccc2)cc1Br]

Preparation of N-[1-(aminomethyl)-3-phenylpropyl]-4-bromo-5-(1-methyl-1H-pyrazol-5-yl)-2-thiophenecarboxamide The title compound was prepared as a yellow solid according to the procedure of Example 20, except substituting 1,1-dimethylethyl (2-amino-4-phenylbutyl)carbamate (0.44 g, 1.7 mmol) [from Preparation 4] for 1,1-dimethylethyl (3-amino-4-phenylbutyl)carbamate: LC-MS (ES) m/z=435 (M+H)⁺, ¹H NMR (400 MHz, MeOD) δ ppm 1.92-2.22 (m, 2H) 2.71-2.82 (m, 2H) 3.02-3.11 (m, 1H) 3.12-3.24 (m, 1H) 3.88 (s, 3H) 4.30 (s, 1H) 6.59 (d, J=1.77 Hz, 1H) 7.17 (t, J=7.07 Hz, 1H) 7.22-7.29 (m, 4H) 7.67 (d, J=1.77 Hz, 1H) 7.85 (s, 1H).

Example 40

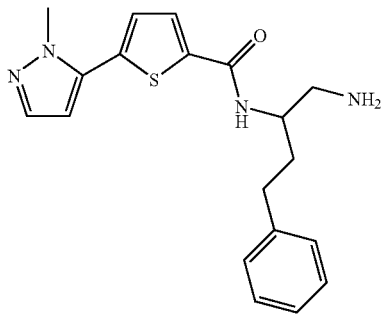 [SMILES: Cn1nccc1-c1ccc(C(=O)NC(CN)CCc2ccccc2)s1]

Preparation of N-[1-(aminomethyl)-3-phenylpropyl]-5-(1-methyl-1H-pyrazol-5-yl)-2-thiophenecarboxamide The title compound was prepared as a yellow solid according to the procedure of Example 20, except substituting 5-(1-methyl-1H-pyrazol-5-yl)-2-thiophenecarboxylic acid (223 mg, 1.07 mmol) for 4-bromo-5-(1-methyl-1H-pyrazol-5-yl)-2-thiophenecarboxylic acid and substituting 1,1-dimethylethyl (2-amino-4-phenylbutyl)carbamate (0.51 g, 1.9 mmol) [from Preparation 4] for 1,1-dimethylethyl (3-amino-4-phenylbutyl)carbamate: LC-MS (ES) m/z 355 (M+H)$^+$, $^1$H NMR (400 MHz, MeOD) δ ppm 1.87-1.99 (m, 2H) 2.69-2.91 (m, 4H) 4.00-4.07 (m, 3H) 4.08-4.16 (m, 1H) 6.56 (d, J=2.02 Hz, 1H) 7.15 (t, J=6.95 Hz, 1H) 7.20-7.28 (m, 4H) 7.35 (d, J=3.79 Hz, 1H) 7.51 (d, J=1.77 Hz, 1H) 7.79 (d, J=3.79 Hz, 1H).

Example 41

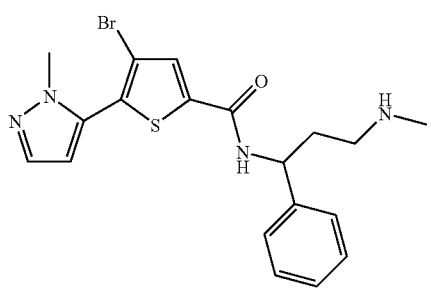 [SMILES: CNCCC(NC(=O)c1cc(Br)c(-c2ccnn2C)s1)c1ccccc1]

Preparation of 4-bromo-N-[3-(methylamino)-1-phenylpropyl]-5-(1-methyl-1H-pyrazol-5-yl)-2-thiophenecarboxamide The title compound was prepared as a yellow solid according to the procedure of Example 20, except substituting 1,1-dimethylethyl (3-amino-3-phenylpropyl)methylcarbamate (289 mg, 1.09 mmol) [from Preparation 12] for 1,1-dimethylethyl (3-amino-4-phenylbutyl)carbamate: LC-MS (ES) m/z 435 (M+H)$^+$, $^1$H NMR (400 MHz, MeOD) δ ppm 2.12-2.23 (m, 2H) 2.45-2.52 (m, 3H) 2.64-2.74 (m, 1H) 2.76 (dd, J=8.72, 5.94 Hz, 1H) 3.77-3.88 (m, 3H) 5.10-5.20 (m, 1H) 6.52 (d, J=2.02 Hz, 1H) 7.30 (d, J=6.82 Hz, 1H) 7.35-7.45 (m, 4H) 7.57 (d, J=1.77 Hz, 1H) 7.89 (s, 1H).

Example 42

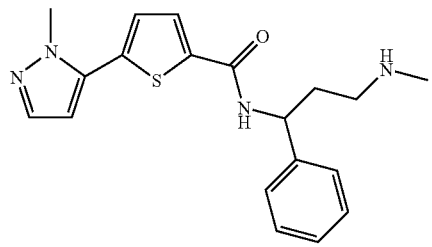 [SMILES: CNCCC(NC(=O)c1ccc(-c2ccnn2C)s1)c1ccccc1]

Preparation of N-[3-(methylamino)-1-phenylpropyl]-5-(1-methyl-1H-pyrazol-5-yl)-2-thiophenecarboxamide The title compound was prepared as a yellow solid according to the procedure of Example 20, except substituting 1,1-dimethylethyl (3-amino-3-phenylpropyl)methylcarbamate (430 mg, 1.63 mmol) [from Preparation 12] for 1,1-dimethylethyl (2-amino-4-phenylbutyl)carbamate and substituting 5-(1-methyl-1H-pyrazol-5-yl)-2-thiophenecarboxylic acid (224 mg, 1.08 mmol) for 4-bromo-5-(1-methyl-1H-pyrazol-5-yl)-2-thiophenecarboxylic acid: LC-MS (ES) m/z 355 (M+H)$^+$, $^1$H NMR (400 MHz, MeOD) δ ppm 2.18-2.28 (m, 2H) 2.55 (s, 3H) 2.77-2.85 (m, 1H) 2.87 (dd, J=8.84, 5.81 Hz, 1H) 4.01 (s, 3H) 5.19 (dd, J=8.59, 6.57 Hz, 1H) 6.55 (d, J=2.02 Hz, 1H) 7.31 (d, J=7.07 Hz, 1H) 7.34-7.41 (m, 3H) 7.44-7.47 (m, 2H) 7.50 (d, J=2.02 Hz, 1H) 7.85 (d, J=4.04 Hz, 1H).

Example 43

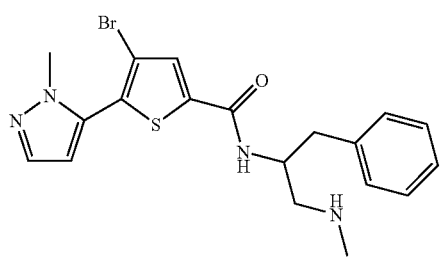 [SMILES: CNCC(Cc1ccccc1)NC(=O)c1cc(Br)c(-c2ccnn2C)s1]

Preparation of 4-bromo-N-[2-(methylamino)-1-(phenylmethyl)ethyl]-5-(1-methyl-1H-pyrazol-5-yl)-2-thiophenecarboxamide The title compound was prepared as a yellow solid according to the procedure of Example 20, except substituting 1,1-dimethylethyl (2-amino-3-phenylpropyl)methylcarbamate (0.26 g, 1.09 mmol) [from Preparation 12] for 1,1-dimethylethyl (3-amino-4-phenylbutyl)carbamate: LC-MS (ES) m/z 435 (M+H)$^+$, $^1$H NMR (400 MHz, MeOD) δ ppm 2.60 (s, 3H) 2.90-3.01 (m, 2H) 3.06 (d, J=6.57 Hz, 2H) 3.83 (s, 3H)

4.48-4.58 (m, 1H) 6.52 (d, J=1.77 Hz, 1H) 7.17-7.27 (m, 1H) 7.27-7.33 (m, 4H) 7.57 (d, J=2.02 Hz, 1H) 7.77 (s, 1H).

Example 44

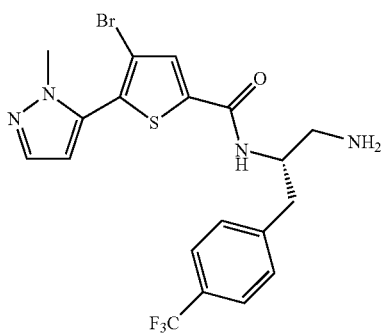 [SMILES: Cn1nccc1-c1sc(C(=O)N[C@H](CN)Cc2ccc(C(F)(F)F)cc2)cc1Br]

Preparation of N-((1S)-2-amino-1-{[4-(trifluoromethyl)phenyl]methyl}ethyl)-4-bromo-5-(1-methyl-1H-pyrazol-5-yl)-2-thiophenecarboxamide The title compound was prepared as a yellow solid according to Example 6, except substituting 2-{(2S)-2-amino-3-[4-(trifluoromethyl)phenyl]propyl}-1H-isoindole-1,3(2H)-dione (0.22 g, 0.62 mmol) [prepared according to the procedure of Preparation 6] for 2-{(2S)-2-amino-3-[2-(trifluoromethyl)phenyl]propyl}-1H-isoindole-1,3(2H)-dione-HCl. The reaction mixture was absorbed onto silica and purified via column chromatography to yield the title compound, which was further purified by Gilson reverse phase chromatography 5-95% H$_2$O (1% TFA)/MeCN (1% TFA) to afford the TFA salt: LC-MS (ES) m/z 489 (M+H)$^+$, $^1$H NMR (400 MHz, MeOD) δ ppm 3.04-3.30 (m, 4H) 3.81-3.85 (m, 3H) 4.59 (dd, J=6.32, 3.28 Hz, 1H) 6.52 (d, J=2.02 Hz, 1H) 7.50 (d, J=8.08 Hz, 2H) 7.58 (d, J=2.02 Hz, 1H) 7.64 (d, J=8.08 Hz, 2H) 7.73 (s, 1H).

Example 45

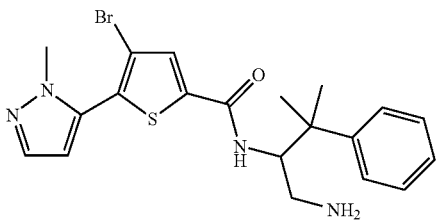

Preparation of N-[1-(aminomethyl)-2-methyl-2-phenylpropyl]-4-bromo-5-(1-methyl-1H-pyrazol-5-yl)-2-thiophenecarboxamide The title compound was prepared as a white solid according to the procedure of Example 6, except substituting 4-bromo-5-(1-methyl-1H-pyrazol-5-yl)-2-thiophenecarboxylic acid (194 mg, 0.68 mmol) for 5-(1-methyl-1H-pyrazol-5-yl)-2-thiophenecarboxylic acid and substituting 2-(2-amino-3-methyl-3-phenylbutyl)-1H-isoindole-1,3(2H)-dione (0.20 g, 0.58 mmol) [prepared according to preparation 16] for 2-{(2S)-2-amino-3-[2-(trifluoromethyl)phenyl]propyl}-1H-isoindole-1,3(2H)-dione-HCl. The reaction mixture was absorbed onto silica and purified via column chromatography (silica, 3% MeOH in DCM (1% NH$_4$OH)) yielding the title compound, which was further purified by Gilson reverse phase chromatography 5-95% H$_2$O (1% TFA)/MeCN (1% TFA) to afford the TFA salt: LC-MS (ES) m/z 448 (M+H)$^+$, $^1$H NMR (400 MHz, MeOD) δ ppm 1.40 (s, 3H) 1.47 (s, 3H) 2.85-2.92 (m, 1H) 3.01 (d, J=11.37 Hz, 1H) 3.83-3.86 (m, 3H) 4.74 (dd, J=11.37, 2.27 Hz, 1H) 6.54 (d, J=2.02 Hz, 1H) 7.28 (t, J=7.33 Hz, 1H) 7.41 (t, J=7.71 Hz, 3H) 7.52 (d, J=7.58 Hz, 2H) 7.59 (d, J=2.02 Hz, 1H) 7.89 (s, 1H).

Example 46

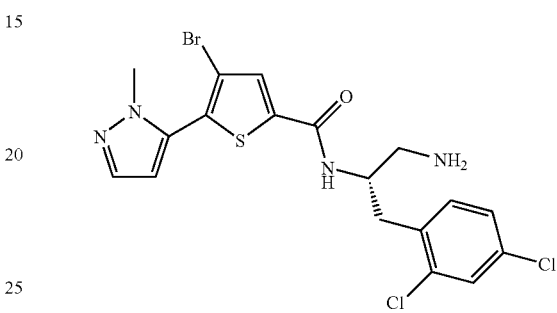

Preparation of N-{(1S)-2-amino-1-[(2,4-dichlorophenyl)methyl]ethyl}-4-bromo-5-(1-methyl-1H-pyrazol-5-yl)-2-thiophenecarboxamide The title compound was prepared as a white solid according to the procedure of Example 6, except substituting 4-bromo-5-(1-methyl-1H-pyrazol-5-yl)-2-thiophenecarboxylic acid (135 mg, 0.47 mmol) for 5-(1-methyl-1H-pyrazol-5-yl)-2-thiophenecarboxylic acid and substituting 2-[(2S)-2-amino-3-(2,4-dichlorophenyl)propyl]-1H-isoindole-1,3(2H)-dione (153 mg, 0.44 mmol) [prepared according to the procedure of Preparation 6] for N-{[(1,1-dimethylethyl)oxy]carbonyl}-2-(trifluoromethyl)-L-phenylalanine. The reaction mixture was absorbed onto silica and purified via column chromatography (silica, 3% MeOH in DCM (1% NH$_4$OH)) yielding the title compound, which was further purified by Gilson reverse phase chromatography 5-95% H$_2$O (1% TFA)/MeCN (1% TFA) to afford the TFA salt: LC-MS (ES) m/z 491 (M+H)$^+$, $^1$H NMR (400 MHz, MeOD) δ ppm 3.03 (dd, J=13.89, 9.35 Hz, 1H) 3.14-3.21 (m, 1H) 3.21-3.29 (m, 2H) 3.84 (s, 3H) 4.62-4.70 (m, 1H) 6.53 (d, J=2.02 Hz, 1H) 7.28-7.32 (m, 1H) 7.33-7.37 (m, 1H) 7.51 (d, J=2.02 Hz, 1H) 7.58 (d, J=2.02 Hz, 1H) 7.73-7.76 (m, 1H).

Example 47

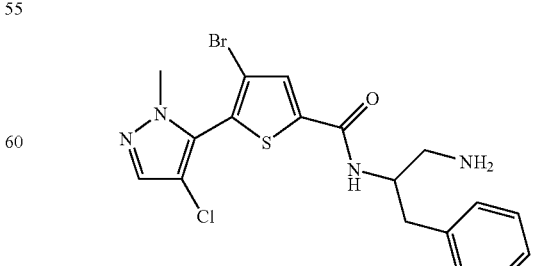

Preparation of N-[2-amino-1-(phenylmethyl)ethyl]-4-bromo-5-(4-chloro-1-methyl-1H-pyrazol-5-yl)-2-thiophenecarboxamide The title compound was prepared as a pale yellow solid according to the procedure of Example 30, except substituting 4,5-dibromo-2-thiophenecarboxylic acid (2.84 g, 9.9 mmol) for 4-bromo-2-thiophenecarboxylic acid: LC-MS (ES) m/z 457 (M+H)$^+$, $^1$H NMR (400 MHz, MeOD) δ ppm 2.95-3.07 (m, 4H) 3.75 (s, 3H) 4.44 (dd, J=6.44, 4.93 Hz, 1H) 7.18-7.24 (m, 1H) 7.27-7.32 (m, 4H) 7.59 (s, 1H) 7.86 (s, 1H).

Example 48

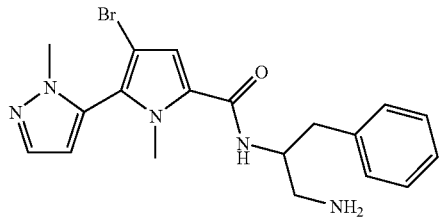 [SMILES: Cn1nccc1-c1c(Br)cc(C(=O)NC(CN)Cc2ccccc2)n1C]

Preparation of N-[2-amino-1-(phenylmethyl)ethyl]-4-bromo-1-methyl-5-(1-methyl-1H-pyrazol-5-yl)-1H-pyrrole-2-carboxamide a) 4,5-dibromo-1-methyl-1H-pyrrole-2-carboxylic Acid

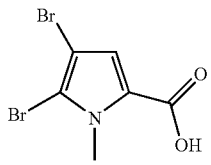

NBS (6.3 g, 35.4 mmol) was added in portions over 15 minutes to a stirred solution of 1-methyl-1H-pyrrole-2-carboxylic acid (2.1 g, 16.78 mmol) in DMF (30 mL) at 0° C. Upon complete addition the mixture was slowly brought to 70° C. After 1 h, the solution was partitioned between H$_2$O—CHCl$_3$, the aqueous phase was adjusted to pH 3 and the aqueous phase was washed several times with CHCl$_3$. The combined organic fractions were dried (Na$_2$SO$_4$) and concentrated under vacuum to yield a 3:4 mixture of 5-bromo-1-methyl-1H-pyrrole-2-carboxylic acid and 4,5-dibromo-1-methyl-1H-pyrrole-2-carboxylic acid (3.4 g) which was used directly without further purification: LCMS (ES) m/z=206/286 (M+H)$^+$.

b) 1,1-dimethylethyl (2-{[(4,5-dibromo-1-methyl-1H-pyrrol-2-yl)carbonyl]amino}-3-phenylpropyl)carbamate

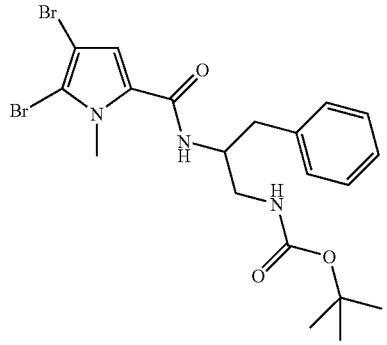 [SMILES: Cn1c(C(=O)NC(CNC(=O)OC(C)(C)C)Cc2ccccc2)cc(Br)c1Br]

To a solution of 5-bromo-1-methyl-1H-pyrrole-2-carboxylic acid and 4,5-dibromo-1-methyl-1H-pyrrole-2-carboxylic acid (1.3 g), 1,1-dimethylethyl (2-amino-3-phenylpropyl)carbamate (1.2 g, 4.8 mmol) [from Preparation 2] and PyBrop (2.6 g, 5.6 mmol) in CHCl$_3$ (30 mL) was added diisopropylethyl amine (2.8 mL, 16.1 mmol). The reaction mixture was stirred overnight, adsorbed onto silica and purified via column chromatography [1:3 EtOAc/hexanes] to give a 1:1 mixture of 1,1-dimethylethyl (2-{[(5-bromo-1-methyl-1H-pyrrol-2-yl)carbonyl]amino}-3-phenylpropyl)carbamate and 1,1-dimethylethyl (2-{[(4,5-dibromo-1-methyl-1H-pyrrol-2-yl)carbonyl]amino}-3-phenylpropyl)carbamate (800 mg): LCMS (ES) m/z=438/518 (M+H)$^+$.

c) 1,1-dimethylethyl[2-({[4-bromo-1-methyl-5-(1-methyl-1H-pyrazol-5-yl)-1H-pyrrol-2-yl]carbonyl}amino)-3-phenylpropyl]carbamate

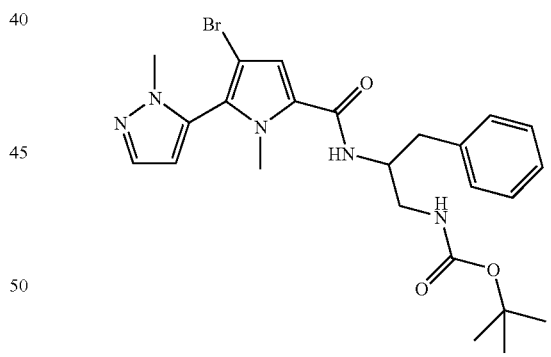

To a solution of a 1:1 mixture of 1,1-dimethylethyl (2-{[(5-bromo-1-methyl-1H-pyrrol-2-yl)carbonyl]amino}-3-phenylpropyl)carbamate and 1,1-dimethylethyl (2-{[(4,5-dibromo-1-methyl-1H-pyrrol-2-yl)carbonyl]amino}-3-phenylpropyl)carbamate (307 mg) in dioxane/H$_2$O (5:1, 5.6 mL) was added Cs$_2$CO$_3$ (800 mg, 2.5 mmol), tetrakistriphenylphosphine Pd(0) (44 mg, 0.04 mmol) and 1-methyl-5-(4,4,5,5-tetramethyl-1,3,2-dioxaborolan-2-yl)-1H-pyrazole (157 mg, 0.75 mmol). The reaction mixture was heated to 80° C. in a sealed tube for 2 h after which additional tetrakistriphenylphosphine Pd(0) (20 mg, 0.02 mmol) and 5-(5,5-dimethyl-1,3,2-dioxaborinane-2-yl)-1-methyl-1H-pyrazole (177 mg, 0.85 mmol) were added. After 12 h, the reaction mixture was adsorbed onto silica and purified via column chromatography to give two isomers: the title compound 1,1-dimethylethyl[2-({[4-bromo-1-methyl-5-(1-methyl-1H-pyrazol-5-yl)-1H-pyrrol-2-yl]carbonyl}amino)-3-phenylpropyl]carbamate (17 mg, 0.033 mmol) and 1,1-dimethylethyl[2-({[1-methyl-5-(1-methyl-1H-pyrazol-5-yl)-1H-pyrrol-2-yl]carbonyl}amino)-3-phenylpropyl]carbamate (20 mg, 0.05 mmol).

d) N-[2-amino-1-(phenylmethyl)ethyl]-4-bromo-1-methyl-5-(1-methyl-1H-pyrazol-5-yl)-1H-pyrrole-2-carboxamide 1,1-dimethylethyl[3-{[4-bromo-5-(1-methyl-1H-pyrazol-5-yl)-2-thienyl]amino}-3-oxo-2-(phenylmethyl)propyl]carbamate (0.045 g, 0.09 mmol) dissolved in CHCl$_3$ (4 mL) and MeOH (1 mL) was treated with 4 M HCl in dioxane (2 mL). After stirring for 18 h at RT, the reaction solution was adsorbed onto silica and purified via column chromatography (silica, 3% MeOH in DCM (1% NH$_4$OH)) yielding the title compound as a white solid.

The neutral compound from above was dissolved in MeOH (2 mL), treated with excess 2M HCl in Et$_2$O (150 µL) and concentrated affording the HCl salt of the title compound: LC-MS (ES) m/z 418 (M+H)$^+$, $^1$H NMR (400 MHz, MeOD) δ ppm 2.76-2.98 (m, 4H) 3.57 (d, J=2.78 Hz, 3H) 3.71 (d, J=1.26 Hz, 3H) 4.28 (ddd, J=8.27, 5.12, 2.78 Hz, 1H) 6.44 (dd, J=7.58, 2.02 Hz, 1H) 6.85 (s, 1H) 7.18-7.24 (m, 1H) 7.27-7.32 (m, 4H) 7.61 (d, J=2.02 Hz, 1H).

Example 49

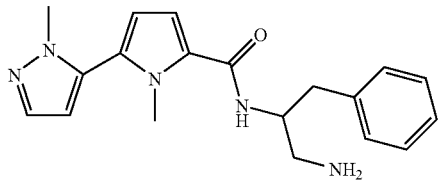

Preparation of N-[2-amino-1-(phenylmethyl)ethyl]-1-methyl-5-(1-methyl-1H-pyrazol-5-yl)-1H-pyrrole-2-carboxamide 1,1-dimethylethyl[2-({[1-methyl-5-(1-methyl-1H-pyrazol-5-yl)-1H-pyrrol-2-yl]carbonyl}amino)-3-phenylpropyl]carbamate (20 mg, 0.05 mmol) [prepared in Example 48] in CHCl$_3$ (4 mL) and MeOH (1 mL) was treated with 4 M HCl in dioxane (2 mL). After stirring for 18 h at RT, the reaction solution was adsorbed onto silica and purified via column chromatography (silica, 3% MeOH in DCM (1% NH$_4$OH)) yielding the title compound.

The above compound was dissolved in MeOH (2 mL), treated with excess 2M HCl in Et$_2$O (150 µL) and concentrated affording the HCl salt of the title compound: LC-MS (ES) m/z 338 (M+H)$^+$, $^1$H NMR (400 MHz, MeOD) δ ppm 2.74-2.81 (m, 1H) 2.83-2.90 (m, 2H) 2.92-2.98 (m, 1H) 3.63 (s, 3H) 3.76 (s, 3H) 4.29 (ddd, J=8.02, 5.12, 2.53 Hz, 1H) 6.27 (d, J=4.04 Hz, 1H) 6.39 (d, J=2.02 Hz, 1H) 6.80 (d, J=4.04 Hz, 1H) 7.20 (td, J=5.87, 2.65 Hz, 1H) 7.26-7.31 (m, 4H) 7.57 (d, J=2.02 Hz, 1H).

Example 50

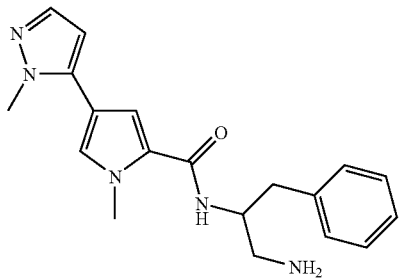 [SMILES: Cn1cc(-c2ccnn2C)cc1C(=O)NC(CN)Cc1ccccc1]

Preparation of N-[2-amino-1-(phenylmethyl)ethyl]-1-methyl-4-(1-methyl-1H-pyrazol-5-yl)-1H-pyrrole-2-carboxamide a) 1,1-dimethylethyl (2-{[(4-bromo-1-methyl-1H-pyrrol-2-yl)carbonyl]amino}-3-phenylpropyl)carbamate

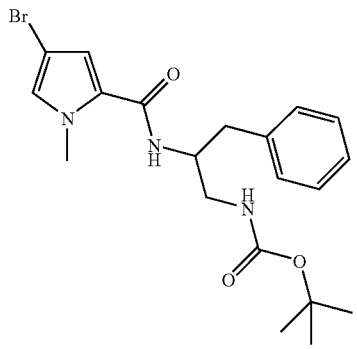 [SMILES: Cn1cc(Br)cc1C(=O)NC(CNC(=O)OC(C)(C)C)Cc1ccccc1]

To a 50 mL round-bottomed flask was added 4-bromo-1-methyl-1H-pyrrole-2-carboxylic acid (610 mg, 3.0 mmol), 1,1-dimethylethyl (2-amino-3-phenylpropyl)carbamate (748 mg, 2.99 mmol) [prepared according to the procedure of Preparation 2] and PyBrop (1.71 g, 3.67 mmol) in Chloroform (15 mL). DIEA (1.8 mL, 10.3 mmol) was added and the mixture stirred overnight at room temperature. The reaction mixture was adsorbed onto silica and purified via column chromatography (Hex/EtOAc) affording the title compound (335 mg, 26%): LC-MS (ES) m/z=438 (M+H)$^+$.

b) 1,1-dimethylethyl[2-({[1-methyl-4-(1-methyl-1H-pyrazol-5-yl)-1H-pyrrol-2-yl]carbonyl}amino)-3-phenylpropyl]carbamate

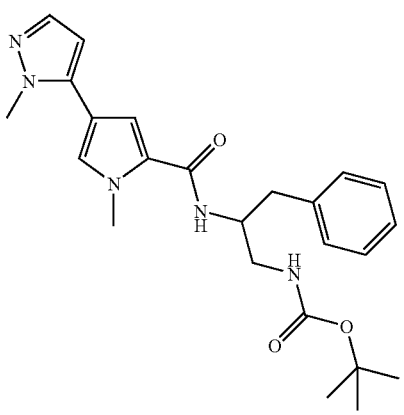 [SMILES: Cn1cc(-c2ccnn2C)cc1C(=O)NC(CNC(=O)OC(C)(C)C)Cc1ccccc1]

To a solution of 1,1-dimethylethyl (2-{[(4-bromo-1-methyl-1H-pyrrol-2-yl)carbonyl]amino}-3-phenylpropyl)carbamate (313 mg, 0.717 mmol) in dioxane/H$_2$O (4:1, 6.25 mL) was added Cs$_2$CO$_3$ (840 mg, 2.6 mmol), tetrakistriphenylphosphine Pd(0) (62 mg, 0.05 mmol) and 5-(5,5-dimethyl-1,3,2-dioxaborinane-2-yl)-1-methyl-1H-pyrazole (202 mg, 1.04 mmol). The reaction mixture was heated to 80° C. in a sealed tube for 12 h and was then partitioned between H$_2$O and CHCl$_3$. The combined organic fractions were dried (Na$_2$SO$_4$), concentrated under vacuum, adsorbed onto silica gel and purified via column chromatography (35% EtOAc/Hex) affording the title compound (285 mg, 91%): LC-MS (ES) m/z=438 (M+H)$^+$.

c) N-[2-amino-1-(phenylmethyl)ethyl]-1-methyl-4-(1-methyl-1H-pyrazol-5-yl)-1H-pyrrole-2-carboxamide HCl in Dioxane (4M, 2 mL) was added to a solution of 1,1-dimethylethyl[2-({[1-methyl-4-(1-methyl-1H-pyrazol-5-yl)-1H-pyrrol-2-yl]carbonyl}amino)-3-phenylpropyl]carbamate (285 mg, 0.65 mmol) in CHCl3/MeOH (10:1, 10 mL) affording the title compound as a white solid (71 mg, 0.21 mmol, 32%): LC-MS (ES) m/z 338 (M+H)$^+$, $^1$H NMR (400 MHz, MeOD) δ ppm 2.77-2.93 (m, 4H) 3.86 (s, 3H) 3.92 (s, 3H) 4.29 (ddd, J=8.15, 4.74, 2.02 Hz, 1H) 6.30 (d, J=2.02 Hz, 1H) 6.94 (d, J=1.77 Hz, 1H) 7.14 (d, J=1.77 Hz, 1H) 7.19 (td, J=5.56, 3.03 Hz, 1H) 7.25-7.30 (m, 4H) 7.41 (d, J=1.77 Hz, 1H).

Example 51

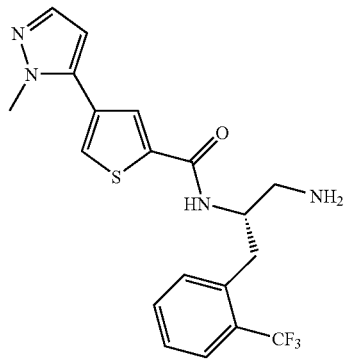 [SMILES: Cn1nccc1-c1csc(C(=O)N[C@H](CN)Cc2ccccc2C(F)(F)F)c1]

Preparation of N-((1S)-2-amino-1-{[2-(trifluoromethyl)phenyl]methyl}ethyl)-4-(1-methyl-1H-pyrazol-5-yl)-2-thiophenecarboxamide The title compound was prepared as a white solid according to the procedure of Example 6, except substituting 4-(1-methyl-1H-pyrazol-5-yl)-2-thiophenecarboxylic acid (232 mg, 1.11 mmol) for 5-(1-methyl-1H-pyrazol-5-yl)-2-thiophenecarboxylic acid. The reaction mixture was absorbed onto silica and purified via column chromatography (silica, 3% MeOH in DCM (1% NH$_4$OH)) yielding the title compound, which was further purified by Gilson reverse phase chromatography 5-95% H$_2$O (1% TFA)/MeCN (1% TFA) to afford the TFA salt: LC-MS (ES) m/z 409 (M+H)$^+$, $^1$H NMR (400 MHz, MeOD) δ ppm 3.09-3.30 (m, 4H) 3.97-4.00 (m, 3H) 4.62-4.72 (m, 1H) 6.48 (d, J=2.02 Hz, 1H) 7.43 (ddd, J=8.08, 4.42, 4.17 Hz, 1H) 7.51-7.56 (m, 3H) 7.72 (d, J=7.83 Hz, 1H) 7.89-7.93 (m, 2H).

Example 52

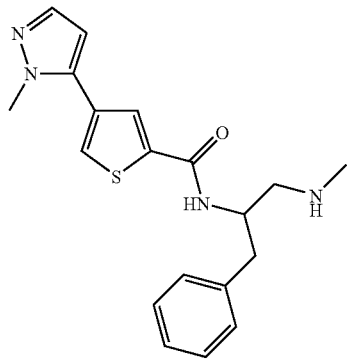

Preparation of N-[2-(methylamino)-1-(phenylmethyl)ethyl]-4-(1-methyl-1H-pyrazol-5-yl)-2-thiophenecarboxamide The title compound was prepared as a yellow solid according to the procedure of Example 20, except substituting 1,1-dimethylethyl (2-amino-3-phenylpropyl)methylcarbamate (0.32 g, 1.2 mmol) [from Preparation 13] for 1,1-dimethylethyl (3-amino-4-phenylbutyl)carbamate and substituting 4-(1-methyl-1H-pyrazol-5-yl)-2-thiophenecarboxylic acid (220 mg, 1.06 mmol) for 4-bromo-5-(1-methyl-1H-pyrazol-5-yl)-2-thiophenecarboxylic acid: LC-MS (ES) m/z 355 (M+H)$^+$, $^1$H NMR (400 MHz, MeOD) δ ppm 2.41 (s, 3H) 2.81 (td, J=11.81, 7.96 Hz, 2H) 2.87-2.97 (m, 2H) 3.96 (s, 3H) 4.43-4.52 (m, 1H) 6.45 (d, J=1.52 Hz, 1H) 7.16-7.23 (m, 1H) 7.25-7.30 (m, 4H) 7.50 (d, J=1.52 Hz, 1H) 7.85 (d, J=13.14 Hz, 2H).

Example 53

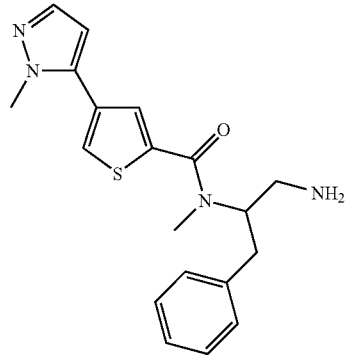 [SMILES: CN(C(=O)c1cc(-c2ccnn2C)cs1)C(CN)Cc1ccccc1]

Preparation of N-[2-amino-1-(phenylmethyl)ethyl]-N-methyl-4-(1-methyl-1H-pyrazol-5-yl)-2-thiophenecarboxamide The title compound was prepared as a white solid according to the procedure of Example 6, except substituting 2-[2-(methylamino)-3-phenylpropyl]-1H-isoindole-1,3(2H)-dione (200 mg, 0.7 mmol)[prepared according to the procedure of Preparation 6] for 2-{(2S)-2-amino-3-[2-(trifluoromethyl)phenyl]propyl}-1H-isoindole-1,3(2H)-dione-HCl and substituting 4-(1-methyl-1H-pyrazol-5-yl)-2-thiophenecarboxylic acid (150 mg, 0.72 mmol) for 4-bromo-5-(1-methyl-1H-pyrazol-5-yl)-2-thiophenecarboxylic acid. The reaction mixture was absorbed onto silica and purified via column chromatography (silica, 3% MeOH in DCM (1% NH$_4$OH))

yielding the title compound, which was further purified by Gilson reverse phase chromatography 5-95% H₂O (1% TFA)/MeCN (1% TFA) to afford the TFA salt: LC-MS (ES) m/z 355 (M+H)⁺, ¹H NMR (400 MHz, MeOD) δ ppm 2.86 (s, 3H) 2.97 (dd, J=14.02, 8.72 Hz, 2H) 3.12-3.23 (m, 2H) 3.70 (m, 1H) 3.97 (s, 3H) 6.47 (d, J=2.02 Hz, 1H) 7.30-7.35 (m, 1H) 7.37-7.43 (m, 5H) 7.51 (d, J=2.02 Hz, 1H) 7.88 (d, J=1.52 Hz, 1H) 7.94 (d, J=1.52 Hz, 1H).

Example 54

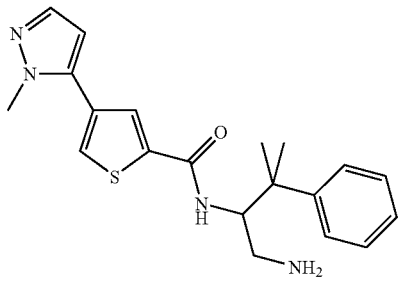 [SMILES: Cn1nccc1-c1csc(C(=O)NC(CN)C(C)(C)c2ccccc2)c1]

Preparation of N-[1-(aminomethyl)-2-methyl-2-phenylpropyl]-4-(1-methyl-1H-pyrazol-5-yl)-2-thiophenecarboxamide The title compound was prepared as a white solid according to the procedure of Example 6, except substituting 4-(1-methyl-1H-pyrazol-5-yl)-2-thiophenecarboxylic acid (129 mg, 0.62 mmol) for 5-(1-methyl-1H-pyrazol-5-yl)-2-thiophenecarboxylic acid and substituting 2-(2-amino-3-methyl-3-phenylbutyl)-1H-isoindole-1,3(2H)-dione (0.20 g, 0.58 mmol) [prepared according to the procedure of Preparation 14] for 2-{(2S)-2-amino-3-[2-(trifluoromethyl)phenyl]propyl}-1H-isoindole-1,3(2H)-dione-HCl: LC-MS (ES) m/z 369 (M+H)⁺, ¹H NMR (400 MHz, MeOD) δ ppm 1.36 (s, 3H) 1.41 (s, 3H) 2.61 (d, J=6.82 Hz, 2H) 3.99 (s, 3H) 4.49 (t, J=6.95 Hz, 1H) 6.49 (d, J=1.77 Hz, 1H) 7.23 (t, J=7.33 Hz, 1H) 7.36 (t, J=7.71 Hz, 2H) 7.47-7.52 (m, 3H) 7.89 (d, J=1.26 Hz, 1H) 8.00 (d, J=1.52 Hz, 1H)).

Example 55

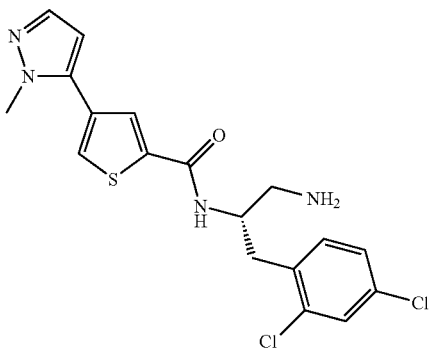 [SMILES: Cn1nccc1-c1csc(C(=O)N[C@H](CN)Cc2ccc(Cl)cc2Cl)c1]

Preparation of N-{(1S)-2-amino-1-[(2,4-dichlorophenyl)methyl]ethyl}-4-(1-methyl-1H-pyrazol-5-yl)-2-thiophenecarboxamide The title compound was prepared as a white solid according to the procedure of Example 6, except substituting 4-(1-methyl-1H-pyrazol-5-yl)-2-thiophenecarboxylic acid (99 mg, 0.48 mmol) for 5-(1-methyl-1H-pyrazol-5-yl)-2-thiophenecarboxylic acid and substituting 2-[(2S)-2-amino-3-(2,4-dichlorophenyl)propyl]-1H-isoindole-1,3(2H)-dione (155 mg, 0.44 mmol) [prepared according to procedure of Preparation 6] for N-{[(1,1-dimethylethyl)oxy]carbonyl}-2-(trifluoromethyl)-L-phenylalanine. The reaction mixture was absorbed onto silica and purified via column chromatography (silica, 3% MeOH in DCM (1% NH₄OH)) yielding the title compound, which was further purified by Gilson reverse phase chromatography 5-95% H₂O (1% TFA)/MeCN (1% TFA) to afford the TFA salt: LC-MS (ES) m/z 411 (M+H)⁺, ¹H NMR (400 MHz, MeOD) δ ppm 3.05-3.28 (m, 4H) 3.97 (s, 3H) 4.63-4.72 (m, 1H) 6.47 (d, J=2.02 Hz, 1H) 7.26-7.29 (m, 1H) 7.34-7.37 (m, 1H) 7.49 (d, J=2.27 Hz, 1H) 7.51 (d, J=2.02 Hz, 1H) 7.86 (d, J=1.52 Hz, 1H) 7.90 (d, J=1.52 Hz, 1H).

Example 56

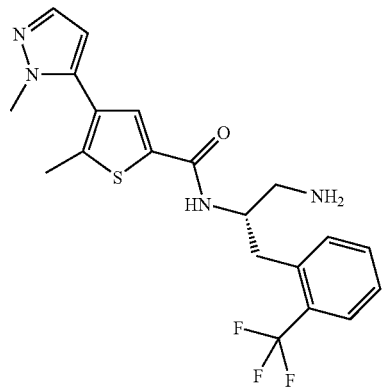 [SMILES: Cc1sc(C(=O)N[C@H](CN)Cc2ccccc2C(F)(F)F)cc1-c1ccnn1C]

Preparation of N-((1S)-2-amino-1-{[2-(trifluoromethyl)phenyl]methyl}ethyl)-5-methyl-4-(1-methyl-1H-pyrazol-5-yl)-2-thiophenecarboxamide a) N-((1S)-2-(1,3-dioxo-1,3-dihydro-2H-isoindol-2-yl)-1-{[2-(trifluoromethyl)phenyl]methyl}ethyl)-5-methyl-4-(1-methyl-1H-pyrazol-5-yl)-2-thiophenecarboxamide

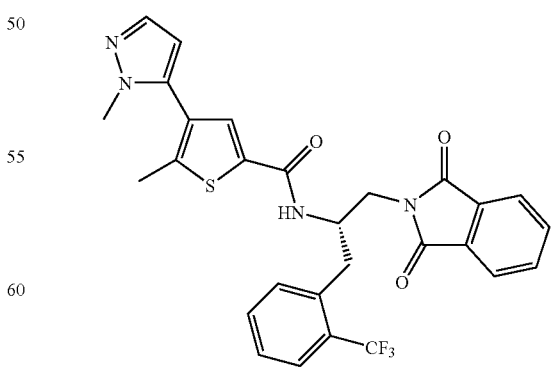

To a 50 mL round-bottomed flask was added 5-methyl-4-(1-methyl-1H-pyrazol-5-yl)-2-thiophenecarboxylic acid (206 mg, 0.93 mmol) [prepared according to the procedure of Preparation 9], 2-{(2S)-2-amino-3-[2-(trifluoromethyl)phenyl]propyl}-1H-isoindole-1,3(2H)-dione (209 mg, 0.60 mmol) [prepared according to the procedure of Preparation 6] and PyBrop (340 mg, 0.73 mmol) in Chloroform (15 mL). DIEA (0.81 mL, 4.65 mmol) was added and the mixture stirred overnight at room temperature. Upon completion, the reaction mixture was adsorbed onto silica and purified via column chromatography (25-75% EtOAc/Hex) affording the title compound (112 mg, 0.203 mmol, 22%): LC-MS (ES) m/z=553 (M+H)+ b) N-((1S)-2-amino-1-{[2-(trifluoromethyl)phenyl]methyl}ethyl)-5-methyl-4-(1-methyl-1H-pyrazol-5-yl)-2-thiophenecarboxamide To a 50 mL round-bottomed flask was added N-((1S)-2-(1,3-dioxo-1,3-dihydro-2H-isoindol-2-yl)-1-{[2-(trifluoromethyl)phenyl]methyl}ethyl)-5-methyl-4-(1-methyl-1H-pyrazol-5-yl)-2-thiophenecarboxamide (112 mg, 0.203 mmol) in Tetrahydrofuran (THF) (6 mL) and Methanol (1 mL). Hydrazine (40 µL, 1.3 mmol) was added and the mixture stirred overnight at room temperature. Upon completion, the mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (43 mg, 0.102 mmol, 50% yield): LC-MS (ES) m/z 423 (M+H)+, $^1$H NMR (400 MHz, DMSO-d₆) δ ppm 2.38 (s, 3H) 3.01 (m, 1H) 3.08 (d, J=6.57 Hz, 3H) 3.76-3.83 (m, 3H) 4.47 (m, 1H) 6.37 (d, J=2.02 Hz, 1H) 7.41 (t, J=7.58 Hz, 1H) 7.50-7.57 (m, 2H) 7.57-7.63 (m, 1H) 7.68 (d, J=7.58 Hz, 1H) 8.04 (d, J=9.09 Hz, 1H) 8.15 (s, 3H) 8.96 (s, 1H).

Example 57

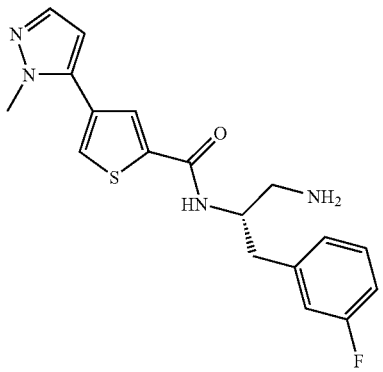 [SMILES: Cn1nccc1-c1csc(C(=O)N[C@H](CN)Cc2cccc(F)c2)c1]

Preparation of N-{(1S)-2-amino-1-[(3-fluorophenyl)methyl]ethyl}-4-(1-methyl-1H-pyrazol-5-yl)-2-thiophenecarboxamide The title compound was prepared as a white solid according to the procedure of Example 6, except substituting 4-(1-methyl-1H-pyrazol-5-yl)-2-thiophenecarboxylic acid (222 mg, 1.07 mmol) for 5-(1-methyl-1H-pyrazol-5-yl)-2-thiophenecarboxylic acid and substituting 2-[(2S)-2-amino-3-(3-fluorophenyl)propyl]-1H-isoindole-1,3(2H)-dione (357 mg, 1.2 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 359 (M+H)+, $^1$H NMR (400 MHz, DMSO-d₆) δ ppm 2.96-3.06 (m, 4H) 3.92-3.98 (m, 3H) 4.40 (dd, J=8.08, 5.56 Hz, 1H) 6.48 (d, J=1.77 Hz, 1H) 7.02 (td, J=8.46, 2.02 Hz, 1H) 7.14 (t, J=8.08 Hz, 2H) 7.26-7.35 (m, 1H) 7.47 (d, J=1.77 Hz, 1H) 7.99 (d, J=1.26 Hz, 1H) 8.16-8.27 (m, 3H) 8.34 (d, J=1.26 Hz, 1H) 9.08 (d, J=8.34 Hz, 1H).

Example 58

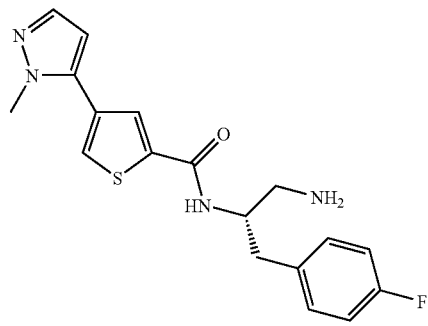 [SMILES: Cn1nccc1-c1csc(C(=O)N[C@H](CN)Cc2ccc(F)cc2)c1]

Preparation of N-{(1S)-2-amino-1-[(4-fluorophenyl)methyl]ethyl}-4-(1-methyl-1H-pyrazol-5-yl)-2-thiophenecarboxamide The title compound was prepared as a white solid according to the procedure of Example 6, except substituting 4-(1-methyl-1H-pyrazol-5-yl)-2-thiophenecarboxylic acid (138 mg, 0.66 mmol) for 5-(1-methyl-1H-pyrazol-5-yl)-2-thiophenecarboxylic acid and substituting 2-[(2S)-2-amino-3-(4-fluorophenyl)propyl]-1H-isoindole-1,3(2H)-dione (196 mg, 0.66 mmol) [prepared according to the procedure of Preparation 6] for 2-{(2S)-2-amino-3-[2-(trifluoromethyl)phenyl]propyl}1H-isoindole-1,3(2H)-dione-HCl. The reaction mixture was adsorbed onto silica and purified via column chromatography (silica, 3% MeOH in DCM (1% NH₄OH)) yielding the title compound, which was further purified by Gilson reverse phase chromatography 5-95% H₂O (1% TFA)/MeCN (1% TFA) to afford the TFA salt: LC-MS (ES) m/z 359 (M+H)+, $^1$H NMR (400 MHz, DMSO-d₆) δ ppm 2.80-3.03 (m, 4H) 3.89-3.97 (m, 3H) 4.30-4.40 (m, 1H) 6.45 (d, J=1.77 Hz, 1H) 7.12 (t, J=8.84 Hz, 2H) 7.29 (dd, J=8.34, 5.56 Hz, 2H) 7.48 (d, J=1.77 Hz, 1H) 7.92 (br. s, 3H) 7.96 (d, J=1.26 Hz, 1H) 8.02 (d, J=1.26 Hz, 1H) 8.58 (d, J=8.84 Hz, 1H).

Example 59

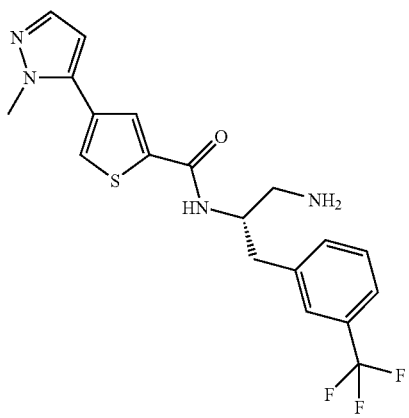 [SMILES: Cn1nccc1-c1csc(C(=O)N[C@H](CN)Cc2cccc(C(F)(F)F)c2)c1]

Preparation of N-((1S)-2-amino-1-{[3-(trifluoromethyl)phenyl]methyl}ethyl)-4-(1-methyl-1H-pyrazol-5-yl)-2-thiophenecarboxamide The title compound was prepared as a white solid according to the procedure of Example 6, except substituting 4-(1-methyl-1H-pyrazol-5-yl)-2-thiophenecarboxylic acid (189 mg, 0.91 mmol) for 5-(1-methyl-1H-pyrazol-5-yl)-2-thiophenecarboxylic acid and substituting 2-{(2S)-2-amino-3-[3-(trifluoromethyl)phenyl]propyl}-1H-isoindole-1,3(2H)-dione (297 mg, 0.85 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 409 (M+H)+, 1H NMR (400 MHz, DMSO-d6) δ ppm 3.06 (d, J=7.07 Hz, 4H) 3.91-3.98 (m, 3H) 4.35-4.45 (m, 1H) 6.46 (d, J=1.77 Hz, 1H) 7.47 (d, J=1.77 Hz, 1H) 7.49-7.57 (m, 2H) 7.58-7.63 (m, 1H) 7.69 (s, 1H) 7.98 (d, J=1.52 Hz, 1H) 8.23 (s, 3H) 8.32 (d, J=1.26 Hz, 1H) 9.11 (d, J=8.84 Hz, 1H).

Example 60

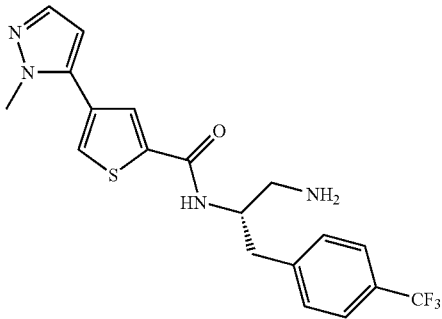 [SMILES: Cn1nccc1-c1csc(C(=O)N[C@H](CN)Cc2ccc(C(F)(F)F)cc2)c1]

Preparation of N-((1S)-2-amino-1-{[4-(trifluoromethyl)phenyl]methyl}ethyl)-4-(1-methyl-1H-pyrazol-5-yl)-2-thiophenecarboxamide The title compound was prepared as a white solid according to the procedure of Example 6, except substituting 4-(1-methyl-1H-pyrazol-5-yl)-2-thiophenecarboxylic acid (240 mg, 0.9 mmol) for 5-(1-methyl-1H-pyrazol-5-yl)-2-thiophenecarboxylic acid and substituting 2-{(2S)-2-amino-3-[4-(trifluoromethyl)phenyl]propyl}-1H-isoindole-1,3(2H)-dione (278 mg, 0.80 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 409 (M+H)+, 1H NMR (400 MHz, DMSO-d6) δ ppm 3.04 (m, 4H) 3.96 (s, 3H) 4.42 (s, 1H) 6.44-6.49 (m, 1H) 7.47 (d, J=1.77 Hz, 1H) 7.52 (d, J=7.83 Hz, 2H) 7.66 (d, J=8.08 Hz, 2H) 8.01 (s, 1H) 8.05-8.32 (br. m, 3H) 8.34 (m, 1H) 8.9-9.2 (br. s, 1H).

Example 61

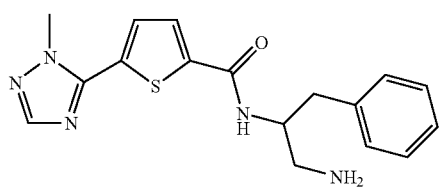 [SMILES: Cn1ncnc1-c1ccc(C(=O)NC(CN)Cc2ccccc2)s1]

Preparation of N-[2-amino-1-(phenylmethyl)ethyl]-5-(1-methyl-1H-1,2,4-triazol-5-yl)-2-thiophenecarboxamide a) 1,1-dimethylethyl[2-({[5-(1-methyl-1H-1,2,4-triazol-5-yl)-2-thienyl]carbonyl}amino)-3-phenylpropyl]carbamate

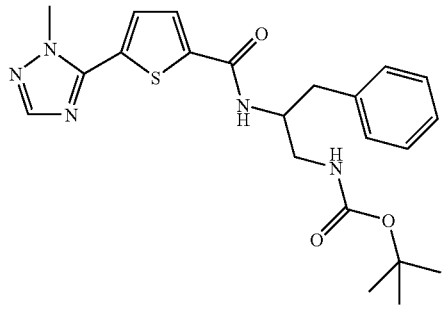 [SMILES: Cn1ncnc1-c1ccc(C(=O)NC(CNC(=O)OC(C)(C)C)Cc2ccccc2)s1]

To a solution of 1,1-dimethylethyl[3-phenyl-2-({[5-(4,4,5,5-tetramethyl-1,3,2-dioxaborolan-2-yl)-2-thienyl]carbonyl}amino)propyl]carbamate (154 mg, 0.32 mmol) [prepared according to the procedure of Example 3] in Dioxane/H2O (5:1, 3.1 mL) was added Cs2CO3 (415 mg, 1.27 mmol), tetrakistriphenylphosphine Pd(0) (29 mg, 0.03 mmol), and 5-iodo-1-methyl-1H-1,2,4-triazole (95 mg, 0.46 mmol) [prepared according to the procedure of Preparation 15]. The reaction mixture was heated to 85° C. in a sealed tube for 12 hours. The reaction was partitioned between H2O and CHCl3, the organic layer dried with Na2SO4, absorbed onto silica and purified via column chromatography (35-50% EtOAc/Hexanes) affording the title compound as a yellow solid (61 mg, 28%): LC-MS (ES) m/z=521.

b) N-[2-amino-1-(phenylmethyl)ethyl]-5-(1-methyl-1H-1,2,4-triazol-5-yl)-2-thiophenecarboxamide HCl in Dioxane (4M, 1 mL) was added to a solution of 1,1-dimethylethyl[2-({[5-(1-methyl-1H-1,2,4-triazol-5-yl)-2-thienyl]carbonyl}amino)-3-phenylpropyl]carbamate (61 mg, 0.12 mmol) in CHCl3/MeOH (10:1, 10 mL) and the mixture stirred overnight. Upon completion, the mixture was adsorbed onto silica gel and purified via chromatography (90:10:1 CHCl3/MeOH/NH4OH). The neutral compound was dissolved in MeOH (2 mL), treated with excess 2M HCl in Et2O and concentrated affording the HCl salt of the title compound as a white solid (30 mg, 0.09 mmol, 77%): LC-MS (ES) m/z 341 (M+H)+, 1H NMR (400 MHz, MeOD) δ ppm 2.79-2.91 (m, 3H) 2.94 (t, J=5.56 Hz, 1H) 4.10 (s, 3H) 4.25-4.34 (m, 1H) 7.18 (ddd, J=8.27, 5.75, 3.16 Hz, 1H) 7.24-7.29 (m, 4H) 7.63 (d, J=4.04 Hz, 1H) 7.75 (d, J=4.04 Hz, 1H) 7.95 (s, 1H).

Example 62

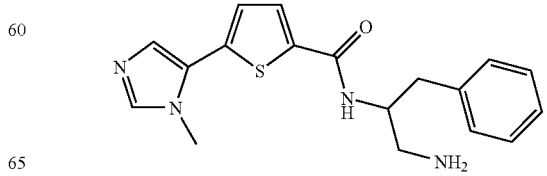

Preparation of N-[2-amino-1-(phenylmethyl)ethyl]-5-(1-methyl-1H-imidazol-5-yl)-2-thiophenecarboxamide a) 1,1-dimethylethyl[2-({[5-(1-methyl-1H-imidazol-5-yl)-2-thienyl]carbonyl}amino)-3-phenylpropyl]carbamate

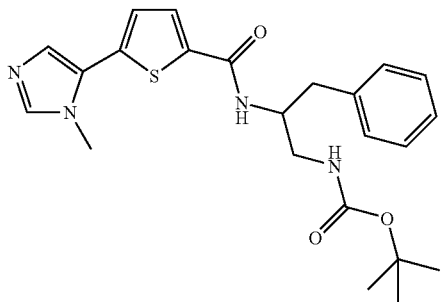 [SMILES: Cn1cncc1-c1ccc(C(=O)NC(CNC(=O)OC(C)(C)C)Cc2ccccc2)s1]

To a solution of 1,1-dimethylethyl[2-phenyl-2-({[5-(4,4,5,5-tetramethyl-1,3,2-dioxaborolan-2-yl)-2-thienyl]carbonyl}amino)ethyl]carbamate (72 mg, 0.15 mmol) [prepared according to the procedure of Example 3] in dioxane/H$_2$O (5:1, 1.4 mL) was added Cs$_2$CO$_3$ (200 mg, 0.61 mmol), tetrakistriphenylphosphine Pd(0) (8.5 mg, 0.01 mmol), and 5-bromo-1-methyl-1H-imidazole (64 mg, 0.40 mmol). The reaction mixture was heated to 85° C. in a sealed tube for 12 h. Upon completion, the reaction mixture was partitioned between H$_2$O (25 mL) and CHCl$_3$. The organics were dried (Na$_2$SO$_4$), concentrated under vacuum, adsorbed onto silica gel and purified via column chromatography (35-50% EtOAc/Hexanes) to give the title compound (19.6 mg, 31%) as a yellow solid: LC-MS (ES) m/z=441.

b) N-[2-amino-1-(phenylmethyl)ethyl]-5-(1-methyl-1H-imidazol-5-yl)-2-thiophenecarboxamide HCl in Dioxane (4M, 1 mL) was added to a solution of 1,1-dimethylethyl[2-({[5-(1-methyl-1H-imidazol-5-yl)-2-thienyl]carbonyl}amino)-3-phenylpropyl]carbamate (19.6 mg, 0.04 mmol) in CHCl$_3$/MeOH (10:1, 5 mL). Upon completion of the reaction, the mixture was adsorbed onto silica gel and purified via chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound as a white solid (19 mg, 0.05 mmol, quant.): LC-MS (ES) m/z 341 (M+H)$^+$, $^1$H NMR (400 MHz, MeOD) δ ppm 2.77-2.83 (m, 1H) 2.85-2.91 (m, 2H) 2.93-2.99 (m, 1H) 3.82 (s, 3H) 4.30 (ddd, J=8.08, 4.80, 1.77 Hz, 1H) 7.15-7.31 (m, 7H) 7.69 (d, J=4.04 Hz, 1H) 7.76 (s, 1H).

Example 63

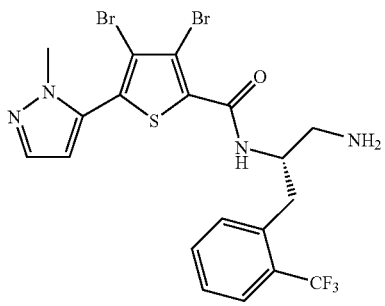 [SMILES: Cn1nccc1-c1sc(C(=O)N[C@H](CN)Cc2ccccc2C(F)(F)F)c(Br)c1Br]

Preparation of N-((1S)-2-amino-1-{[2-(trifluoromethyl)phenyl]methyl}ethyl)-3,4-dibromo-5-(1-methyl-1H-pyrazol-5-yl)-2-thiophenecarboxamide The title compound was prepared as a white solid according to the procedure of Example 6, except substituting 3,4-dibromo-5-(1-methyl-1H-pyrazol-5-yl)-2-thiophenecarboxylic acid (253 mg, 0.69 mmol) for 5-(1-methyl-1H-pyrazol-5-yl)-2-thiophenecarboxylic acid. The reaction mixture was adsorbed onto silica and purified via column chromatography (silica, 3% MeOH in DCM (1% NH$_4$OH)) yielding the title compound, which was further purified by Gilson reverse phase chromatography 5-95% H$_2$O (1% TFA)/MeCN (1% TFA) to afford the TFA salt: LC-MS (ES) m/z 569 (M+H)$^+$, $^1$H NMR (400 MHz, MeOD) δ ppm 3.14-3.30 (m, 4H) 3.82 (s, 3H) 4.73 (dd, J=9.47, 4.67 Hz, 1H) 6.54 (d, J=2.02 Hz, 1H) 7.44-7.50 (m, 1H) 7.56-7.62 (m, 3H) 7.74 (d, J=7.83 Hz, 1H).

Example 64

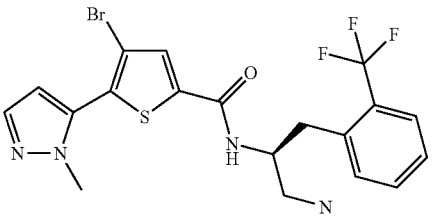 [SMILES: Cn1nccc1-c1sc(C(=O)N[C@H](CN)Cc2ccccc2C(F)(F)F)cc1Br]

Preparation of N-((1S)-2-amino-1-{[2-(trifluoromethyl)phenyl]methyl}ethyl)-4-bromo-5-(1-methyl-1H-pyrazol-5-yl)-2-thiophenecarboxamide The title compound was prepared as a yellow solid according to the procedure of Example 6, except substituting 4,5-dibromo-2-thiophenecarboxylic acid (143 mg, 0.50 mmol) for 5-bromo-2-thiophenecarboxylic acid: LC-MS (ES) m/z 488 (M+H)$^+$, $^1$H NMR (400 MHz, MeOD) δ ppm 3.15 (s, 2H) 3.23 (s, 2H) 3.84 (s, 3H) 4.65 (s, 1H) 6.52-6.57 (m, 1H) 7.46 (s, 1H) 7.52-7.61 (m, 3H) 7.72 (s, 1H) 7.81 (s, 1H).

Example 65

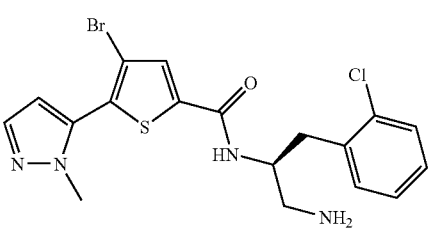 [SMILES: Cn1nccc1-c1sc(C(=O)N[C@H](CN)Cc2ccccc2F)cc1Br]

Preparation of N-{(1S)-2-amino-1-[(2-chlorophenyl)methyl]ethyl}-4-bromo-5-(1-methyl-1H-pyrazol-5-yl)-2-thiophenecarboxamide The title compound was prepared as a white solid according to the procedure of Example 6, except substituting 4,5-dibromo-2-thiophenecarboxylic acid (143 mg, 0.5 mmol) for 5-bromo-2-thiophenecarboxylic acid and substituting 2-[(2S)-2-amino-3-(2-chlorophenyl)propyl]-1H-isoindole- 1,3(2H)-dione-HCl (157 mg, 0.5 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 455 (M+H)+, 1H NMR (400 MHz, MeOD) δ ppm 3.11 (s, 1H) 3.22 (s, 1H) 3.27 (s, 2H) 3.85 (s, 3H) 4.70 (s, 1H) 6.57 (s, 1H) 7.26 (s, 2H) 7.41 (s, 2H) 7.66 (s, 1H) 7.88 (s, 1H).

Example 66

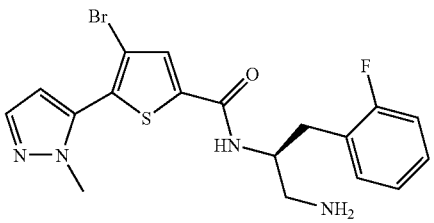

Preparation of N-{(1S)-2-amino-1-[(2-fluorophenyl)methyl]ethyl}-4-bromo-5-(1-methyl-1H-pyrazol-5-yl)-2-thiophenecarboxamide The title compound was prepared as a light yellow solid according to the procedure of Example 6, except substituting 4,5-dibromo-2-thiophenecarboxylic acid (143 mg, 0.5 mmol) for 5-bromo-2-thiophenecarboxylic acid and substituting 2-[(2S)-2-amino-3-(2-fluorophenyl)propyl]-1H-isoindole-1,3(2H)-dione-HCl (149 mg, 0.5 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 438 (M+H)+, 1H NMR (400 MHz, MeOD) δ ppm 3.00 (s, 1H) 3.09 (s, 1H) 3.15 (dd, J=3.41, 1.64 Hz, 2H) 3.83 (s, 4H) 4.58 (s, 1H) 6.52 (d, J=2.02 Hz, 1H) 7.08-7.17 (m, 3H) 7.27-7.37 (m, 3H) 7.59 (d, J=2.02 Hz, 1H) 7.74 (d, J=3.54 Hz, 1H).

Example 67

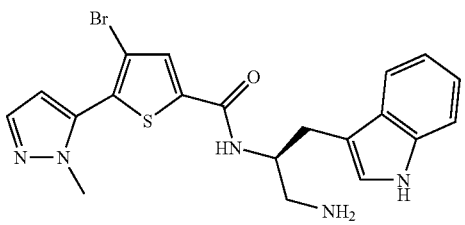 [SMILES: Cn1nccc1-c1sc(C(=O)N[C@H](CN)Cc2c[nH]c3ccccc23)cc1Br]

Preparation of N-[(1S)-2-amino-1-(1H-indol-3-ylmethyl)ethyl]-4-bromo-5-(1-methyl-1H-pyrazol-5-yl)-2-thiophenecarboxamide The title compound was prepared as a yellow solid according to the procedure of Example 6, except substituting 4,5-dibromo-2-thiophenecarboxylic acid (143 mg, 0.5 mmol) for 5-bromo-2-thiophenecarboxylic acid and substituting 2-[(2S)-2-amino-3-(1H-indol-3-yl)propyl]-1H-isoindole-1,3(2H)-dione-dione-HCl (160 mg, 0.5 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 459 (M+H)+, 1H NMR (400 MHz, MeOD) δ ppm 3.15 (dt, J=10.42, 6.79 Hz, 3H) 3.27 (dd, J=4.04, 2.27 Hz, 1H) 3.84 (s, 3H) 4.63 (d, J=6.82 Hz, 1H) 6.54 (d, J=2.02 Hz, 1H) 7.05 (t, J=7.45 Hz, 1H) 7.13 (t, J=7.07 Hz, 1H) 7.19 (s, 1H) 7.37 (d, J=8.08 Hz, 1H) 7.64-7.73 (m, 2H) 7.77 (s, 1H).

Example 68

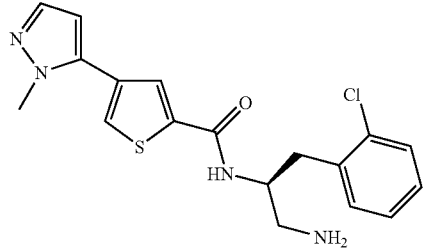 [SMILES: Cn1nccc1-c1csc(C(=O)N[C@H](CN)Cc2ccccc2F)c1]

Preparation of N-{(1S)-2-amino-1-[(2-chlorophenyl)methyl]ethyl}-4-(1-methyl-1H-pyrazol-5-yl)-2-thiophenecarboxamide The title compound was prepared as a yellow solid according to the procedure of Example 6 except substituting 4-bromo-2-thiophenecarboxylic acid (104 mg, 0.5 mmol) for 5-bromo-2-thiophenecarboxylic acid and substituting 2-[(2S)-2-amino-3-(2-chlorophenyl)propyl]-1H-isoindole-1,3(2H)-dione-HCl (157 mg, 0.5 mmol) [prepared according to Preparation 6] for 2-{(2S)-2-amino-3-[2-(trifluoromethyl)phenyl]propyl}-1H-isoindole-1,3(2H)-dione-HCl: LC-MS (ES) m/z 375 (M+H)+, 1H NMR (400 MHz, MeOD) δ ppm 3.11-3.20 (m, 1H) 3.22-3.31 (m, 3H) 4.23 (s, 3H) 4.75 (s, 1H) 6.96 (s, 1H) 7.18-7.26 (m, 2H) 7.38 (d, J=6.06 Hz, 1H) 7.46 (d, J=4.55 Hz, 1H) 8.22 (s, 2H) 8.32 (s, 1H).

Example 69

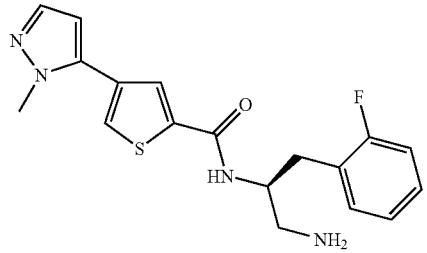

Preparation of N-{(1S)-2-amino-1-[(2-fluorophenyl)methyl]ethyl}-4-(1-methyl-1H-pyrazol-5-yl)-2-thiophenecarboxamide The title compound was prepared as a yellow solid according to the procedure of Example 6, except substituting 4-bromo-2-thiophenecarboxylic acid (104 mg, 0.5 mmol) for 5-bromo-2-thiophenecarboxylic acid and substituting 2-[(2S)-2-amino-3-(2-fluorophenyl)propyl]-1H-isoindole-1,3(2H)-dione-HCl (149 mg, 0.5 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 359 (M+H)+, 1H NMR (400 MHz, MeOD) δ ppm 3.06-3.17 (m, 2H) 3.25-3.31 (m, 2H) 4.18 (s, 3H) 4.59-4.67 (m, 1H) 6.88 (s, 1H) 7.05-7.12 (m, 2H) 7.23-7.30 (m, 1H) 7.36-7.42 (m, 1H) 8.12 (d, J=1.01 Hz, 1H) 8.17 (s, 1H) 8.21 (s, 1H).

Example 70

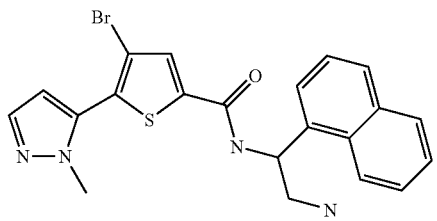 [SMILES: Cn1nccc1-c1sc(C(=O)NC(CN)c2cccc3ccccc23)cc1Br]

Preparation of N-[2-amino-1-(1-naphthalenyl)ethyl]-4-bromo-5-(1-methyl-1H-pyrazol-5-yl)-2-thiophenecarboxamide The title compound was prepared as a white solid according to the procedure of Example 20, except substituting 1,1-dimethylethyl[2-amino-2-(1-naphthalenyl)ethyl]carbamate (143 mg, 0.5 mmol) [from Preparation 16] for 1,1-dimethylethyl (3-amino-4-phenylbutyl)carbamate: LC-MS (ES) m/z 456 (M+H)+, $^1$H NMR (400 MHz, MeOD) δ ppm 3.60 (s, 1H) 3.72 (s, 1H) 3.84 (s, 3H) 6.33 (d, J=10.11 Hz, 1H) 6.55 (s, 1H) 7.55-7.61 (m, 3H) 7.64 (d, J=8.34 Hz, 1H) 7.74 (s, 1H) 7.92-7.99 (m, 2H) 8.09 (s, 1H) 8.26 (s, 1H).

Example 71

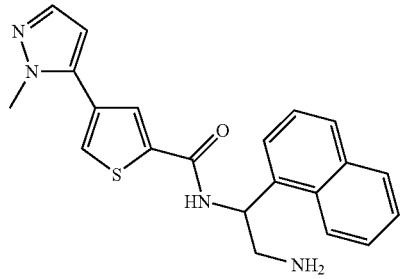 [SMILES: Cn1nccc1-c1csc(C(=O)NC(CN)c2cccc3ccccc23)c1]

Preparation of N-[2-amino-1-(1-naphthalenyl)ethyl]-4-(1-methyl-1H-pyrazol-5-yl)-2-thiophenecarboxamide The title compound was prepared as a white solid according to the procedure of Example 20, except substituting 4-bromo-2-thiophenecarboxylic acid (104 mg, 0.5 mmol) for 4,5-dibromo-2-thiophenecarboxylic acid and substituting 1,1-dimethylethyl[2-amino-2-(1-naphthalenyl)ethyl]carbamate (143 mg, 0.5 mmol) [from Preparation 16] for 1,1-dimethylethyl (3-amino-4-phenylbutyl)carbamate: LC-MS (ES) m/z 377 (M+H)+, $^1$H NMR (400 MHz, MeOD) δ ppm 3.62 (d, J=4.04 Hz, 1H) 3.67-3.78 (m, 1H) 4.08-4.10 (m, 3H) 6.35 (s, 1H) 6.73 (d, J=2.27 Hz, 1H) 7.55-7.60 (m, 2H) 7.62-7.67 (m, 1H) 7.76 (d, J=7.33 Hz, 1H) 7.88 (d, J=2.53 Hz, 1H) 7.93-7.99 (m, 2H) 8.10 (d, J=1.52 Hz, 1H) 8.23-8.27 (m, 2H).

Example 72

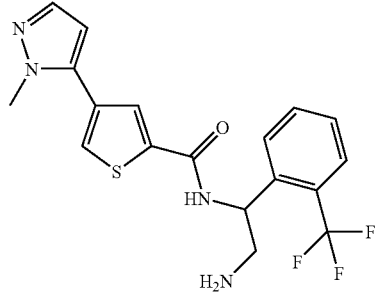 [SMILES: Cn1nccc1-c1csc(C(=O)NC(CN)c2ccccc2C(F)(F)F)c1]

Preparation of N-{2-amino-1-[2-(trifluoromethyl)phenyl]ethyl}-4-(1-methyl-1H-pyrazol-5-yl)-2-thiophenecarboxamide The title compound was prepared as a white solid according to the procedure of Example 20, except substituting 4-bromo-2-thiophenecarboxylic acid (104 mg, 0.5 mmol) for 4,5-dibromo-2-thiophenecarboxylic acid and substituting 1,1-dimethylethyl {2-amino-2-[2-(trifluoromethyl)phenyl]ethyl}carbamate (152 mg, 0.5 mmol) [prepared according to the procedure of Preparation 16] for 1,1-dimethylethyl (3-amino-4-phenylbutyl)carbamate: LC-MS (ES) m/z 395 (M+H)+, $^1$H NMR (400 MHz, MeOD) δ ppm 3.36-3.39 (m, 1H) 3.46-3.53 (m, 1H) 3.98 (s, 3H) 5.86-5.91 (m, 1H) 6.48 (s, 1H) 7.51 (d, J=2.02 Hz, 1H) 7.60 (s, 1H) 7.76 (s, 1H) 7.83 (d, J=8.08 Hz, 2H) 7.94 (s, 1H) 8.05 (s, 1H).

Example 73

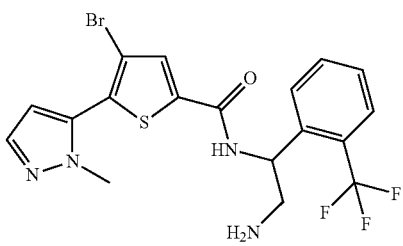 [SMILES: Cn1nccc1-c1sc(C(=O)NC(CN)c2ccccc2C(F)(F)F)cc1Br]

Preparation of N-{2-amino-1-[2-(trifluoromethyl)phenyl]ethyl}-4-bromo-5-(1-methyl-1H-pyrazol-5-yl)-2-thiophenecarboxamide The title compound was prepared as a white solid according to the procedure of Example 20, except substituting 1,1-dimethylethyl {2-amino-2-[2-(trifluoromethyl)phenyl]ethyl}carbamate (152 mg, 0.5 mmol) [prepared according to the procedure of Preparation 16] for 1,1-dimethylethyl (3-amino-4-phenylbutyl)carbamate: LC-MS (ES) m/z 474 (M+H)+, $^1$H NMR (400 MHz, MeOD) δ ppm 3.37 (s, 1H)

3.65 (s, 1H) 3.89-4.00 (m, 3H) 5.88 (s, 1H) 6.76 (d, J=2.27 Hz, 1H) 7.58 (s, 1H) 7.77 (d, J=9.60 Hz, 2H) 7.91-8.03 (m, 2H) 8.26 (d, J=2.27 Hz, 1H).

Example 74

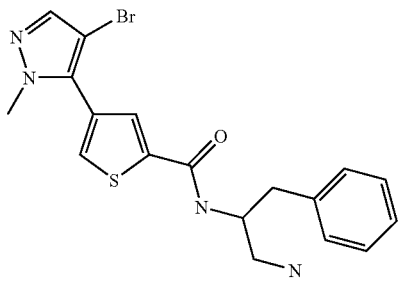 [SMILES: Cn1ncc(Br)c1-c1csc(C(=O)NC(CN)Cc2ccccc2)c1]

Preparation of N-[2-amino-1-(phenylmethyl)ethyl]-4-(4-bromo-1-methyl-1H-pyrazol-5-yl)-2-thiophenecarboxamide The title compound was prepared as a yellow solid according to the procedure of Example 24, except substituting NBS (194 mg, 1.09 mmol) for NCS: LC-MS (ES) m/z 418 (M+H)+, 1H NMR (400 MHz, MeOD) δ ppm 3.03 (d, J=7.33 Hz, 2H) 3.23 (s, 2H) 3.90 (s, 3H) 4.56 (d, J=1.77 Hz, 1H) 7.20-7.27 (m, 1H) 7.28-7.34 (m, 4H) 7.58 (s, 1H) 7.96 (s, 2H).

Example 75

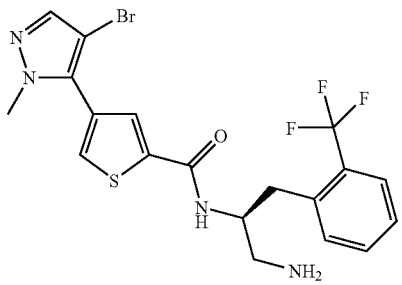 [SMILES: Cn1ncc(Br)c1-c1csc(C(=O)N[C@H](CN)Cc2ccccc2C(F)(F)F)c1]

Preparation of N-((1S)-2-amino-1-{[2-(trifluoromethyl)phenyl]methyl}ethyl)-4-(4-bromo-1-methyl-1H-pyrazol-5-yl)-2-thiophenecarboxamide The title compound was prepared as a yellow solid according to the procedure of Example 25, except substituting NBS (67 mg, 0.5 mmol) for NCS: LC-MS (ES) m/z 488 (M+H)+, 1H NMR (400 MHz, MeOD) δ ppm 3.10-3.19 (m, 1H) 3.20-3.28 (m, 3H) 3.91 (s, 3H) 4.66 (dd, J=8.59, 3.03 Hz, 1H) 7.39-7.47 (m, 1H) 7.51-7.58 (m, 2H) 7.59 (s, 1H) 7.72 (d, J=8.08 Hz, 1H) 7.98 (s, 2H).

Example 76

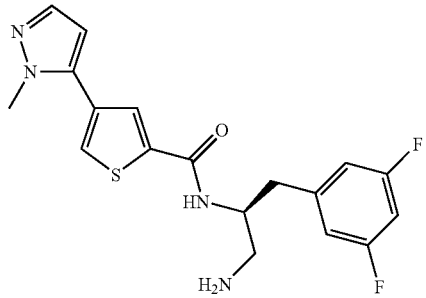 [SMILES: Cn1nccc1-c1csc(C(=O)N[C@H](CN)Cc2cc(F)cc(F)c2)c1]

Preparation of N-{(1S)-2-amino-1-[(3,5-difluorophenyl)methyl]ethyl}-4-(1-methyl-1H-pyrazol-5-yl)-2-thiophenecarboxamide The title compound was prepared as a light yellow solid according to the procedure of Example 6, except substituting 4-bromo-2-thiophenecarboxylic acid (104 mg, 0.5 mmol) for 5-bromo-2-thiophenecarboxylic acid and substituting 2-[(2S)-2-amino-3-(3,5-difluorophenyl)propyl]-1H-isoindole-1,3(2H)-dione-HCl (158 mg, 0.5 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 395 (M+H)+, 1H NMR (400 MHz, DMSO) δ ppm 2.94-3.06 (m, 4H) 3.95 (s, 3H) 4.40 (d, J=6.06 Hz, 1H) 6.46 (d, J=1.77 Hz, 1H) 7.00-7.10 (m, 3H) 7.47 (d, J=1.77 Hz, 1H) 7.99 (d, J=1.26 Hz, 1H) 8.10 (s, 2H) 8.21 (s, 1H) 8.92 (d, J=8.0 Hz, 1H).

Example 77

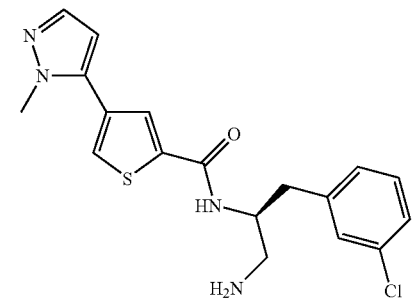 [SMILES: Cn1nccc1-c1csc(C(=O)N[C@H](CN)Cc2cccc(Cl)c2)c1]

Preparation of N-{(1S)-2-amino-1-[(3-chlorophenyl)methyl]ethyl}-4-(1-methyl-1H-pyrazol-5-yl)-2-thiophenecarboxamide The title compound was prepared as an off-white solid according to the procedure of Example 6, except substituting 4-bromo-2-thiophenecarboxylic acid (104 mg, 0.5 mmol) for 5-bromo-2-thiophenecarboxylic acid and substituting 2-[(2S)-2-amino-3-(3-chlorophenyl)propyl]-1H-isoindole-1,3(2H)-dione (157 mg, 0.5 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 395 (M+H)+, 1H NMR (400 MHz, DMSO) δ ppm 2.92-3.04 (m, 4H) 3.92-3.98 (m, 3H) 4.36 (d, J=5.56 Hz, 1H) 6.47 (s, 1H) 7.19-7.29 (m, 2H) 7.29-7.35 (m, 1H) 7.37-7.42 (m, 1H) 7.47 (s, 1H) 8.17 (s, 3H) 8.85-9.07 (m, 1H).

Example 78

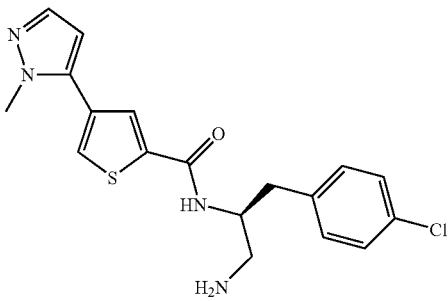 [SMILES: Cn1nccc1-c1csc(C(=O)N[C@H](CN)Cc2ccc(Cl)cc2)c1]

Preparation of N-{(1S)-2-amino-1-[(4-chlorophenyl)methyl]ethyl}-4-(1-methyl-1H-pyrazol-5-yl)-2-thiophenecarboxamide The title compound was prepared as an off-white solid according to the procedure of Example 6, except substituting 4-bromo-2-thiophenecarboxylic acid (104 mg, 0.5 mmol) for 5-bromo-2-thiophenecarboxylic acid and substituting 2-[(2S)-2-amino-3-(4-chlorophenyl)propyl]-1H-isoindole-1,3(2H)-dione (157 mg, 0.5 mmol) [prepared according to the procedure of Preparation 6] for 2-{(2S)-2-amino-3-[2-(trifluoromethyl)phenyl]propyl}-1H-isoindole-1,3(2H)-dione-HCl: LC-MS (ES) m/z 395 (M+H)$^+$, $^1$H NMR (400 MHz, DMSO) δ ppm 2.92-2.97 (m, 2H) 2.99-3.04 (m, 2H) 4.01 (s, 3H) 4.32-4.42 (m, 1H) 6.43-6.50 (m, 1H) 7.27-7.37 (m, 4H) 7.47 (d, J=1.77 Hz, 1H) 7.99 (d, J=1.26 Hz, 1H) 8.21 (s, 3H) 8.94-9.10 (m, 1H).

Example 79

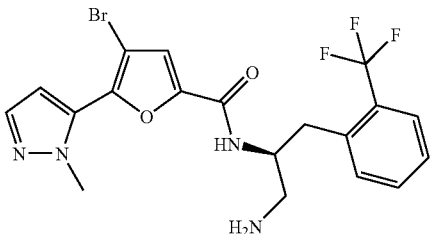

Preparation of N-((1S)-2-amino-1-{[2-(trifluoromethyl)phenyl]methyl}ethyl)-4-bromo-5-(1-methyl-1H-pyrazol-5-yl)-2-furancarboxamide The title compound was prepared as a white solid according to the procedure of Example 6, except substituting 4,5-dibromo-2-furancarboxylic acid (135 mg, 0.5 mmol) for 5-bromo-2-thiophenecarboxylic acid: LC-MS (ES) m/z 472 (M+H)$^+$, $^1$H NMR (400 MHz, DMSO) δ ppm 3.11 (d, J=9.85 Hz, 1H) 3.21-3.31 (m, 3H) 4.06 (s, 3H) 4.70 (s, 1H) 6.87 (d, J=2.02 Hz, 1H) 7.33 (s, 1H) 7.41-7.48 (m, 1H) 7.50-7.57 (m, 2H) 7.60 (d, J=2.02 Hz, 1H) 7.71 (d, J=7.83 Hz, 1H).

Example 80

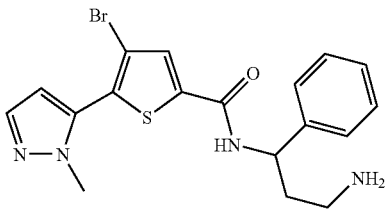 [SMILES: Cn1nccc1-c1sc(C(=O)NC(CCN)c2ccccc2)cc1Br]

Preparation of N-(3-amino-1-phenylpropyl)-4-bromo-5-(1-methyl-1H-pyrazol-5-yl)-2-thiophenecarboxamide The title compound was prepared as a white solid according to the procedure of Example 20, except substituting 1,1-dimethylethyl[3-(methylamino)-3-phenylpropyl]carbamate (125 mg, 0.5 mmoles) [from Preparation 3] for 1,1-dimethylethyl (3-amino-4-phenylbutyl)carbamate: LC-MS (ES) m/z 420 (M+H)$^+$, $^1$H NMR (400 MHz, DMSO) δ ppm 2.25-2.37 (m, 2H) 2.96 (d, J=8.08 Hz, 1H) 3.04-3.13 (m, 1H) 3.84 (s, 3H) 5.22 (t, J=7.58 Hz, 1H) 6.53 (d, J=1.52 Hz, 1H) 7.35 (d, J=6.57 Hz, 1H) 7.44 (dt, J=15.09, 7.48 Hz, 4H) 7.58.

Example 81

Preparation of N-[2-amino-1-(phenylmethyl)ethyl]-5-(1-ethyl-1H-pyrazol-5-yl)-2-thiophenecarboxamide

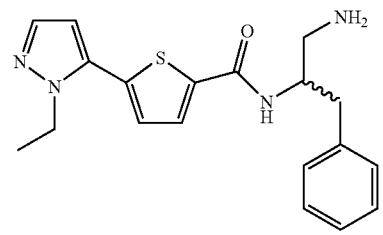 [SMILES: CCn1nccc1-c1ccc(C(=O)NC(CN)Cc2ccccc2)s1]

a) 1-ethyl-5-(4,4,5,5-tetramethyl-1,3,2-dioxaborolan-2-yl)-1H-pyrazole

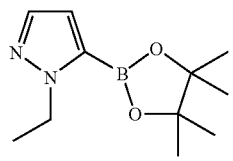 [SMILES: CCn1nccc1B1OC(C)(C)C(C)(C)O1]

To a suspension of NaH (60% in mineral oil, 2.2 g, 55 mmol) in THF (50 mL) was added pyrazole (3.4 g, 50 mmol) in THF (10 mL) at room temperature. After 30 min, to above suspension was added EtI (7.75 g, 50 mmol) dropwise. After the reaction was complete (20 h), the suspension was filtered, and the resulting solution was used directly with further purification.

At 0° C., to above solution of 4-methylpyrazole (~50 mmol) was added n-BuLi (2.5M in hexane, 22 mL, 55 mmol). The reaction solution was stirred for 1 hour at RT and then cooled to −78° C. [*J. Heterocyclic Chem.* 41, 931 (2004)]. To the reaction solution was added 2-isopropoxy-4,4,5,5-tetramethyl-1,3,2-dioxaborolane (10.2 g, 55 mmol). After 15 min at −78° C., the reaction was allowed to warm to 0° C. over 1 hour. The reaction was diluted with saturated NH$_4$Cl solution and extracted with DCM. The organics were dried over Na$_2$SO$_4$ and concentrated under vacuum to afford a tan solid (9.8 g, 89%) which was used without further purification. LCMS (ES) m/z 141 (M+H)$^+$ for [RB(OH)$_2$]; $^1$H NMR (CDCl$_3$, 400 MHz) δ ppm 7.52 (d, J=2 Hz, 1H), 6.36 (d, J=2 Hz, 1H), 4.48 (q, J=7.2 Hz, 2H), 1.44 (t, J=7.2 Hz, 3H), 1.36 (s, 12H)

b) 1,1-dimethylethyl[2-({[5-(1-ethyl-1H-pyrazol-5-yl)-2-thienyl]carbonyl}amino)-3-phenylpropyl]carbamate

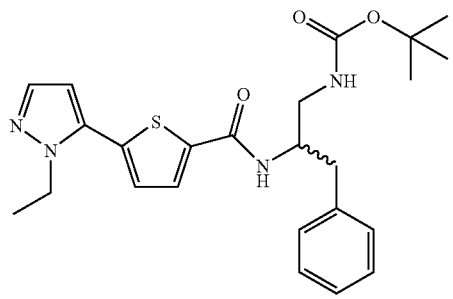 [SMILES: CCn1nccc1-c1ccc(C(=O)NC(CNC(=O)OC(C)(C)C)Cc2ccccc2)s1]

To a solution of 1,1-dimethylethyl (2-{[(5-bromo-2-thienyl)carbonyl]amino}-3-phenylpropyl)carbamate (100 mg, 0.23 mmol) in dioxane/H$_2$O (5:1, 6 mL) was added K$_2$CO$_3$ (100 mg, 0.72 mmol), tetrakistriphenylphosphine Pd(0) (30 mg, 26 μmol) and 1-ethyl-5-(4,4,5,5-tetramethyl-1,3,2-dioxaborolan-2-yl)-1H-pyrazole (64 mg, 0.29 mmol). The reaction mixture was heated to 70° C. in a sealed tube. After 12 h, the reaction mixture was concentrated under vacuum and purified on silica (hex/EtOAc, 40-60%) to afford the title compound (0.074 g, 71%) as a light yellow solid: LC-MS (ES) m/z 455 (M+H)$^+$.

c) N-[2-amino-1-(phenylmethyl)ethyl]-5-(1-ethyl-1H-pyrazol-5-yl)-2-thiophenecarboxamide

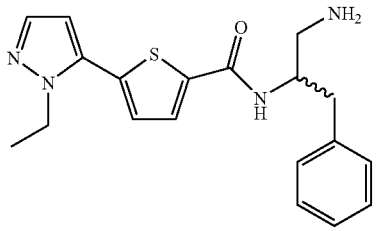 [SMILES: CCn1nccc1-c1ccc(C(=O)NC(CN)Cc2ccccc2)s1]

1,1-Dimethylethyl[2-({[5-(1-ethyl-1H-pyrazol-5-yl)-2-thienyl]carbonyl}amino)-3-phenylpropyl]carbamate (74 mg, 0.16 mmol) was dissolved in DCM (2 mL) and treated with TFA (1 mL). After 1 h, the solution was concentrated and neutralized through silica using 4% MeOH in DCM (1% NH$_4$OH). The title compound was further purified using reverse-phase HPLC (C18 column: H$_2$O/CH$_3$CN, 40-10%) affording the bis-TFA salt of the title compound (47 mg, 50%) as a white solid: LCMS (ES) m/z 355 (M+H)$^+$, $^1$H NMR (d$_4$-MeOD, 400 MHz) δ ppm 7.71 (d, J=3.8 Hz, 1H), 7.55 (d, J=2.0 Hz, 1H), 7.34-7.22 (m, 6H), 6.51 (d. J=1.8 Hz, 1H), 4.55 (m, 1H), 4.34 (q, J=7.1 Hz, 2H), 3.22 (dd, J=3.5, 13.1 Hz, 1H), 3.13 (dd, J=10.1, 13.1 Hz, 1H), 3.00 (m, 2H), and 1.42 (t, J=7.1 Hz, 3H).

Example 82

Preparation of N-[2-amino-1-(phenylmethyl)ethyl]-3,4-dibromo-5-(1-methyl-1H-pyrazol-5-yl)-2-thiophenecarboxamide

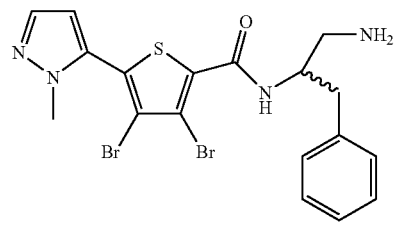 [SMILES: Cn1nccc1-c1sc(C(=O)NC(CN)Cc2ccccc2)c(Br)c1Br]

The title compound was prepared as a yellow solid according to the procedure of Example 1, except substituting 1,1-dimethylethyl (3-phenyl-2-{[(3,4,5-tribromo-2-thienyl)carbonyl]amino}propyl)carbamate (120 mg, 0.20 mmol) for 1,1-dimethylethyl[2-({[4-bromo-5-(1-methyl-1H-pyrazol-5-yl)-2-furanyl]carbonyl}amino)-3-phenylpropyl]carbamate: LC-MS (ES) m/z 499 (M+H)$^+$, $^1$H NMR (d$_4$-MeOD, 400 MHz) δ ppm 7.59 (d, J=2.0 Hz, 1H), 7.37-7.24 (m, 5H), 6.53 (d, J=2.0 Hz, 1H), 4.62 (m, 1H), 3.27 (d, J=13.1, 4.3 Hz, 1H), 3.21 (dd, J=13.1, 9.4 Hz, 1H), 3.09 (dd, J=14.2, 6.1 Hz, 1H), 3.02 (dd, J=13.9, 9.1 Hz, 1H), and 1.96 (s, 3H).

Example 83

N-[2-amino-1-(phenylmethyl)ethyl]-5-(1,4-dimethyl-1H-pyrazol-5-yl)-2-thiophenecarboxamide

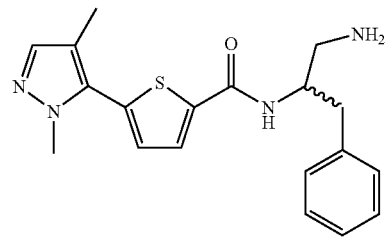 [SMILES: Cc1cnn(C)c1-c1ccc(C(=O)NC(CN)Cc2ccccc2)s1]

a) N-[2-amino-1-(phenylmethyl)ethyl]-5-(1,4-dimethyl-1H-pyrazol-5-yl)-2-thiophenecarboxamide The title compound was prepared as a yellow solid according to the procedure of Example 1, except substituting 1,4-dimethyl-5-(4,4,5,5-tetramethyl-1,3,2-dioxaborolan-2-yl)-1H-pyrazole (64.0 mg, 0.23 mmol) [from Preparation 17] for 1,1-dimethylethyl[2-({[4-bromo-5-(1-methyl-1H-pyrazol-5-yl)-2-furanyl]carbonyl}amino)-3-phenylpropyl]carbamate, and substituting 1,1-dimethyl ethyl (2-{[(5-bromo-2-thienyl)carbonyl]amino}-3-phenylpropyl)carbamate (110 mg, 0.25 mmol) for 1,1-dimethylethyl (2-{[(5-bromo-3-thienyl)carbonyl]amino}-2-phenylethyl)carbamate: LC-MS (ES) m/z 355 (M+H)⁺, ¹H NMR (d₄-MeOD, 400 MHz) δ ppm 7.75 (d, J=3.8 Hz, 1H), 7.40 (br s, 1H), 7.32-7.23 (m, 5H), 7.21 (d, J=3.8 Hz, 1H), 4.56 (m, 1H), 3.86 (s, 3H), 3.23 (dd, J=13.1, 3.8 Hz, 1H), 3.15 (dd, J=12.9, 10.1 Hz, 1H), 3.01 (m, 2H) and 2.10 (s, 3H).

Example 84

N-[2-amino-1-(phenylmethyl)ethyl]-4-bromo-5-(1,4-dimethyl-1H-pyrazol-5-yl)-2-thiophenecarboxamide

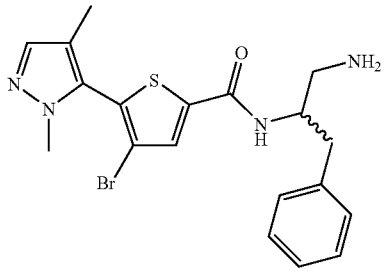 [SMILES: Cc1cnn(C)c1-c1sc(C(=O)NC(CN)Cc2ccccc2)cc1Br]

The title compound was prepared as a yellow solid according to the procedure of Example 1, except substituting 1,4-dimethyl-5-(4,4,5,5-tetramethyl-1,3,2-dioxaborolan-2-yl)-1H-pyrazole (77 mg, 0.23 mmol) [from Preparation 17] for 1-methyl-5-(4,4,5,5-tetramethyl-1,3,2-dioxaborolan-2-yl)-1H-pyrazole, and substituting 1,1-dimethylethyl (2-{[(4,5-dibromo-2-thienyl)carbonyl]amino}-3-phenylpropyl)carbamate (150 mg, 0.29 mmol) for 1,1-dimethylethyl[2-({[4-bromo-5-(1-methyl-1H-pyrazol-5-yl)-2-furanyl]carbonyl}amino)-3-phenylpropyl]carbamate: LC-MS (ES) m/z 434 (M+H)⁺, ¹H NMR (d₄-MeOD, 400 MHz) δ ppm 7.77 (s, 1H), 7.43 (s, 1H), 7.35-7.23 (m, 5H), 4.55 (m, 1H), 3.72 (s, 3H), 3.23 (dd, J=3.5 Hz, 1H), 3.13 (dd, J=10.6, 13.1 Hz, 1H), 3.02-2.95 (m, 2H), and 1.99 (s, 3H).

Example 85

N-[2-amino-1-(phenylmethyl)ethyl]-4-(1,4-dimethyl-1H-pyrazol-5-yl)-2-thiophenecarboxamide

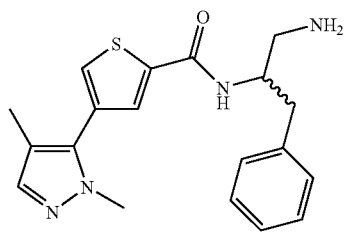 [SMILES: Cc1cnn(C)c1-c1csc(C(=O)NC(CN)Cc2ccccc2)c1]

The title compound was prepared as a yellow solid according to the procedure of Example 1, except substituting 1,4-dimethyl-5-(4,4,5,5-tetramethyl-1,3,2-dioxaborolan-2-yl)-1H-pyrazole (220 mg, 1.0 mmol) [from Preparation 17] for 1-methyl-5-(4,4,5,5-tetramethyl-1,3,2-dioxaborolan-2-yl)-1H-pyrazole, and substituting 1,1-dimethylethyl (2-{[(4-bromo-2-thienyl)carbonyl]amino}-3-phenylpropyl)carbamate (150 mg, 0.34 mmol) for 1,1-dimethylethyl[2-({[4-bromo-5-(1-methyl-1H-pyrazol-5-yl)-2-furanyl]carbonyl}amino)-3-phenylpropyl]carbamate: LC-MS (ES) m/z=355 (M+H)⁺, ¹H NMR (d₄-MeOD, 400 MHz) δ ppm 8.14-8.13 (m, 3H), 7.35-7.20 (m, 5H), 4.58 (m, 1H), 4.07 (s, 3H), 3.36-3.22 (m, 2H), 3.12-3.01 (m, 2H), and 2.21 (s, 3H).

Example 86

N-[2-amino-1-(phenylmethyl)ethyl]-N-hydroxy-4-(1-methyl-1H-pyrazol-5-yl)-2-thiophenecarboxamide

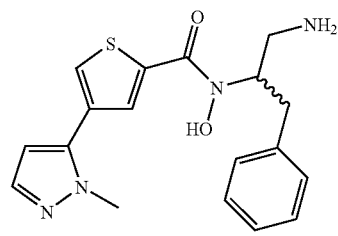 [SMILES: Cn1nccc1-c1csc(C(=O)N(O)C(CN)Cc2ccccc2)c1]

a) 1,1-dimethylethyl {2-[[(4-bromo-2-thienyl)carbonyl](hydroxy)amino]-3-phenylpropyl}carbamate

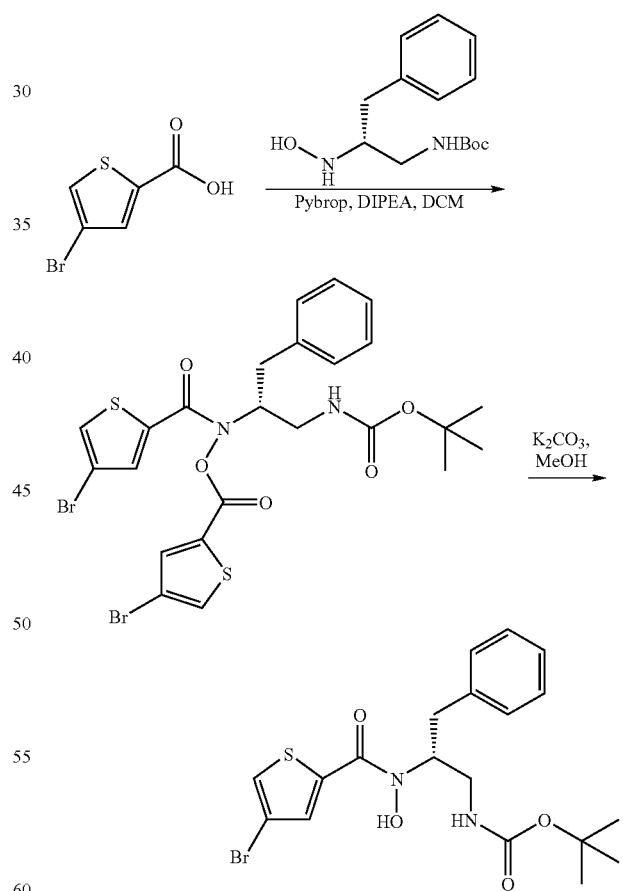

To a solution of 4-bromo-2-thiophenecarboxylic acid (1.0 g, 4.83 mmol) in DCM (10 mL) was added PyBrop (3.4 g, 7.24 mmol) and Hunig's base (2 mL, 12.6 mmol). After 15 min, 1,1-dimethylethyl[2-(hydroxyamino)-3-phenylpropyl]carbamate (641 mg, 2.41 mmol) was added to the reaction mixture in DCM (2 mL) and stirred for 2 h at RT. The reaction solution was concentrated to give crude 1,1-dimethylethyl[2-([(4-bromo-2-thienyl)carbonyl]{[(4-bromo-2-thienyl)carbonyl]oxy}amino)-3-phenylpropyl]carbamate. LC-MS (ES) m/z=645 (M+H)⁺.

To a solution of 1,1-dimethylethyl[2-([(4-bromo-2-thienyl)carbonyl]{[(4-bromo-2-thienyl)carbonyl]oxy}amino)-3-phenylpropyl]carbamate in MeOH (5 mL) was added $K_2CO_3$ (1.0 g, 7.3 mmol). The mixture was stirred at RT for 2 h. The mixture was concentrated under vacuum and purified on silica gel (EtOAc/Hexane, 30%) to give the title compound (410 mg, 37% for two steps) as an off white solid: LC-MS (ES) m/z=456 (M+H)⁺.

b) 1,1-dimethylethyl[2-(hydroxy{[4-(1-methyl-1H-pyrazol-5-yl)-2-thienyl]carbonyl}amino)-3-phenylpropyl]carbamate

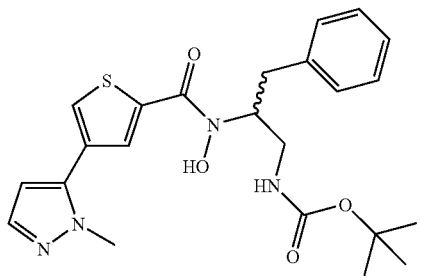 [SMILES: Cn1nccc1-c1csc(C(=O)N(O)C(CNC(=O)OC(C)(C)C)Cc2ccccc2)c1]

To a solution of 1,1-dimethylethyl {2-[[(4-bromo-2-thienyl)carbonyl](hydroxy)amino]-3-phenylpropyl}carbamate (100 mg, 0.22 mmol) in dioxane/$H_2O$ (5:1, 6 mL) was added $K_2CO_3$ (91 mg, 0.66 mmol), tetrakistriphenylphosphine Pd(0) (23 mg, 0.022 mmol) and 1-methyl-5-(4,4,5,5-tetramethyl-1,3,2-dioxaborolan-2-yl)-1H-pyrazole (68 mg, 0.33 mmol). The reaction mixture was heated to 75° C. in a sealed tube. After 2 h, the reaction mixture was concentrated under vacuum and purified on silica (EtOAc/Hex, 20-40%) to afford the title compound (87 mg, 87%): LC-MS (ES) m/z=456 (M+H)⁺.

c) N-[2-amino-1-(phenylmethyl)ethyl]-N-hydroxy-4-(1-methyl-1H-pyrazol-5-yl)-2-thiophenecarboxamide

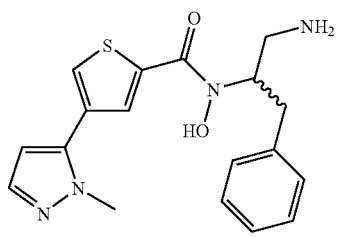 [SMILES: Cn1nccc1-c1csc(C(=O)N(O)C(CN)Cc2ccccc2)c1]

1,1-Dimethylethyl[2-(hydroxy{[4-(1-methyl-1H-pyrazol-5-yl)-2-thienyl]carbonyl}amino)-3-phenylpropyl]carbamate (84 mg, 0.19 mmol) was dissolved in DCM (2 mL) and treated with TFA (1 mL). The reaction was stirred over 1 h, and concentrated, and purified by reverse-phase HPLC (C18 column: $H_2O$/$CH_3CN$, 40-10%), and concentrated to afford the bis-TFA salt of the title compound (51.2 mg, 64.8%). LC-MS (ES) m/z 357 (M+H)⁺, ¹H NMR (d₄-MeOD, 400 MHz) δ ppm 8.03 (s, 1H), 7.94 (d, J=1.8 Hz, 1H), 7.52 (d, J=1.8 Hz, 1H), 6.46 (d, J=1.8 Hz, 1H), 7.34-7.18 (m, 5H), 5.16 (m, 1H), 3.95 (s, 3H), 3.38 (dd, J=13.1, 10.6 Hz, 1H), 3.17-3.11 (m, 2H), and 2.95 (dd, J=13.6, 6.6 Hz, 1H)

Example 87

N-((1S)-2-amino-1-{[2-(trifluoromethyl)phenyl]methyl}ethyl)-4-(1,4-dimethyl-1H-pyrazol-5-yl)-2-thiophenecarboxamide

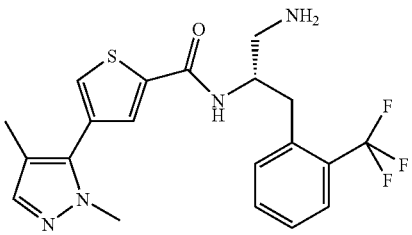 [SMILES: Cc1cnn(C)c1-c1csc(C(=O)N[C@H](CN)Cc2ccccc2C(F)(F)F)c1]

a) 4-bromo-N-((1S)-2-(1,3-dioxo-1,3-dihydro-2H-isoindol-2-yl)-1-{[2-(trifluoromethyl)phenyl]methyl}ethyl)-2-thiophenecarboxamide

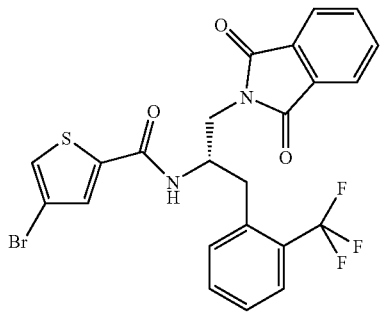 [SMILES: O=C(N[C@@H](Cc1ccccc1C(F)(F)F)CN1C(=O)c2ccccc2C1=O)c1cc(Br)cs1]

To a solution of 4-bromo-2-thiophenecarboxylic acid (80 mg, 0.39 mmol) in DCM (2 mL) at 25° C. was added bromo-tris-pyrrolidino phosphoniumhexafluorophosphate (PyBrOP) (218 mg, 0.47 mmol) in one portion, followed by addition of DIPEA (0.2 mL, 1.14 mmol). After stirring for 10 min, diamine 2-{(2S)-2-amino-3-[2-(trifluoromethyl)phenyl]propyl}-1H-isoindole-1,3(2H)-dione (165 mg, 0.43 mmol) was added to above solution. After 2 h, the solution was concentrated and purified via column chromatography (silica, 10% MeOH in $CH_3Cl$) affording the title compound (206 mg, 99%) as a white solid: LC-MS (ES) m/z 538 (M+H)⁺.

b) 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

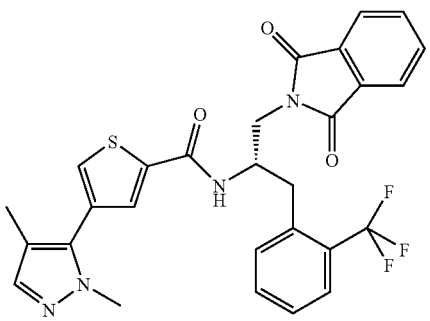 [SMILES: Cc1cnn(C)c1-c1csc(C(=O)N[C@@H](Cc2ccccc2C(F)(F)F)CN2C(=O)c3ccccc3C2=O)c1]

To a solution of 4-bromo-N-((1S)-2-(1,3-dioxo-1,3-dihydro-2H-isoindol-2-yl)-1-{[2-(trifluoromethyl)phenyl]methyl}ethyl)-2-thiophenecarboxamide (200 mg, 0.37 mmol) in dioxane/H₂O (5:1, 6 mL) was added K₂CO₃ (0.17 g, 1.23 mmol), tetrakistriphenylphosphine Pd(0) (42 mg, 0.036 mmol) and 1,4-dimethyl-5-(4,4,5,5-tetramethyl-1,3,2-dioxaborolan-2-yl)-1H-pyrazole (413 mg, 1.86 mmol) [from Preparation 17]. The reaction mixture was heated to 80° C. in a sealed tube for 2 h. The reaction solution was concentrated under vacuum, and purified on silica gel (10-50% EtOAc/Hex) to give the title compound (192 mg, 94%) as a white solid: LC-MS (ES) m/z 553 (M+H)⁺.

c) N-((1S)-2-amino-1-{[2-(trifluoromethyl)phenyl]methyl}ethyl)-4-(1,4-dimethyl-1H-pyrazol-5-yl)-2-thiophenecarboxamide

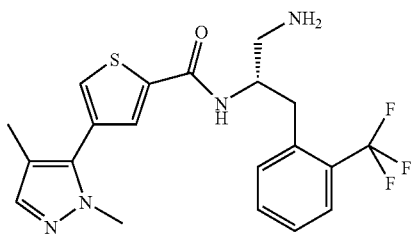 [SMILES: Cc1cnn(C)c1-c1csc(C(=O)N[C@H](CN)Cc2ccccc2C(F)(F)F)c1]

4-(1,4-Dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (110 mg, 0.198 mmol) was dissolved in MeOH (2 mL) and was treated with NH₂NH₂ (0.5 mL, 15.93 mmol). The reaction was stirred over 10 h, concentrated and the residue in DCM (2 mL) was treated with TFA (1.0 mL). After stirring for 2 h, the solvent was removed and the residue was purified by reverse-phase HPLC (C18 column: H₂O/CH₃CN, 40-10%), and concentrated to afford the bis-TFA salt of the title compound. The bis-TFA salt was neutralized through a silica plug (90:9:1 CHCl₃/MeOH/NH₄OH) affording the free base of the title compound. The free base, as a solution in MeOH, was then treated with excess 4M HCl in dioxane affording the title compound (62 mg, 34.6%) as the HCl salt: LC-MS (ES) m/z 423 (M+H)⁺, ¹H NMR (d4-MeOD, 400 MHz) δ ppm 8.27 (s, 1H), 8.22 (s, 1H), 8.18 (s, 1H), 7.70 (d, 7.8 Hz, 1H), 7.64 (d, J=7.6 Hz, 1H), 7.51 (dd, J=7.3, 7.3 Hz, 1H), 7.41 (dd, J=7.6, 7.3 Hz, 1H), 4.69 (m, 1H), 4.12 (s, 3H), 3.41-3.19 (m, 4H), and 2.24 (s, 3H).

Example 88

N-((1S)-2-amino-1-{[2-(trifluoromethyl)phenyl]methyl}ethyl)-4-(1-ethyl-1H-pyrazol-5-yl)-2-thiophenecarboxamide

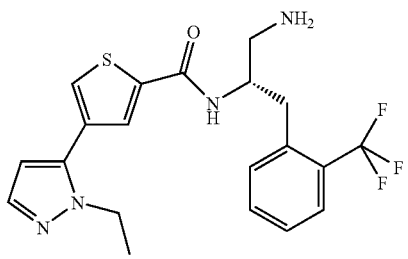 [SMILES: CCn1nccc1-c1csc(C(=O)N[C@H](CN)Cc2ccccc2C(F)(F)F)c1]

The title compound was prepared as a white solid according to the procedure of Example 87, except substituting 1-ethyl-5-(4,4,5,5-tetramethyl-1,3,2-dioxaborolan-2-yl)-1H-pyrazole (104 mg, 0.47 mmol) for 1,4-dimethyl-5-(4,4,5,5-tetramethyl-1,3,2-dioxaborolan-2-yl)-1H-pyrazole.
LC-MS (ES) m/z=423 (M+H)⁺, ¹H NMR (d₄-MeOD, 400 MHz) δ ppm 8.35-8.31 (m, 2H), 8.21 (br s, 1H), 7.70 (d, J=7.8 Hz, 1H), 7.64 (d, J=7.3 Hz, 1H), 7.51 (dd, J=7.3, 7.3 Hz, 1H), 7.42 (dd J=7.6, 7.3 Hz, 1H), 7.00 (m, 1H), 4.70-4.61 (m, 3H), 3.40-3.17 (m, 4H), and 1.57 (t, J=6.8 Hz, 3H).

Example 89

N-[2-amino-1-(phenylmethyl)ethyl]-5-chloro-4-(1-ethyl-1H-pyrazol-5-yl)-2-thiophenecarboxamide

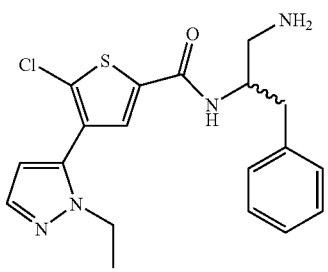 [SMILES: CCn1nccc1-c1cc(C(=O)NC(CN)Cc2ccccc2)sc1Cl]

a) 5-chloro-4-methyl-2-thiophenecarboxylic Acid

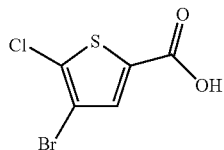

To a solution of 4-bromo-2-thiophenecarboxylic acid (2.07 g, 10 mmol) in DMF (5 mL) was added NCS (2.7 g, 15 mmol) in one portion. The reaction mixture was stirred at 50° C. for 10 h, and then cooled to room temperature. The desired product precipitated after water (5 mL) was added. The white solid was filtered and dried under high vacuum to give 1.9 g (79%). LC-MS (ES) m/z=242 (M+H)⁺, b) 1,1-dimethylethyl (2-{[(4-bromo-5-chloro-2-thienyl)carbonyl]amino}-3-phenylpropyl)carbamate

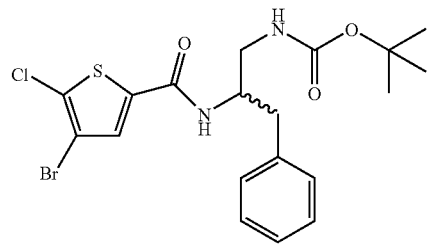 [SMILES: CC(C)(C)OC(=O)NCC(Cc1ccccc1)NC(=O)c1cc(Br)c(Cl)s1]

To a solution of 5-chloro-4-methyl-2-thiophenecarboxylic acid (242 mg, 1.0 mmol) and diisopropylethyl amine (2.5 mL, 14.60 mmol) in DCM (50 mL) at 25° C. was added PyBrOP (2.5 g, 5.30 mmol) in one portion. After 30 min, 1,1-dimethylethyl (2-amino-3-phenylpropyl)carbamate (250 mg, 1.0 mmol) was added at one portion. After 2 h, the solution was concentrated and purified via column chromatography (silica, 10-40% EtOAc in Hexane) affording the title compound (460 mg, 97%) as a white solid: LC-MS (ES) m/z=474 (M+H)⁺.

c) 1,1-dimethylethyl[2-({[5-chloro-4-(1-ethyl-1H-pyrazol-5-yl)-2-thienyl]carbonyl}amino)-3-phenyl-propyl]carbamate

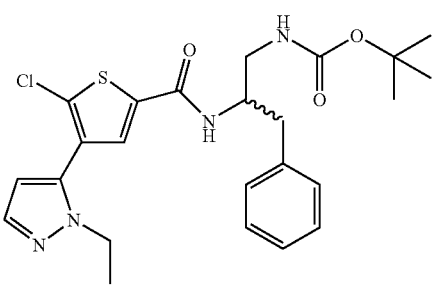 [SMILES: CCn1nccc1-c1cc(C(=O)NC(CNC(=O)OC(C)(C)C)Cc2ccccc2)sc1Cl]

To a solution of 1,1-dimethylethyl (2-{[(4-bromo-5-chloro-2-thienyl)carbonyl]amino}-3-phenylpropyl)carbamate (100 mg, 0.21 mmol) in THF (5 mL) was added Na$_2$CO$_3$ (2N, 0.3 mL, 0.6 mmol), Pd(dppf)Cl$_2$ (20 mg, 24 µmol) and 1-ethyl-5-(4,4,5,5-tetramethyl-1,3,2-dioxaborolan-2-yl)-1H-pyrazole (92 mg, 0.42 mmol). The reaction mixture was heated to 80° C. in a sealed tube under N$_2$. After 2 h, the reaction mixture was concentrated under vacuum and purified on silica (hex/EtOAc, 20-50%) to afford the title compound (74 mg, 72%) as a light yellow solid: LC-MS (ES) m/z 489 (M+H)⁺.

d) N-[2-amino-1-(phenylmethyl)ethyl]-5-chloro-4-(1-ethyl-1H-pyrazol-5-yl)-2-thiophenecarboxamide

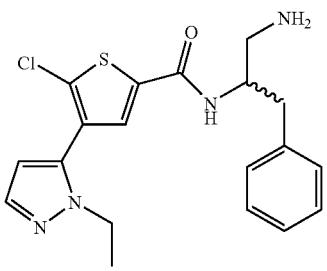 [SMILES: CCn1nccc1-c1cc(C(=O)NC(CN)Cc2ccccc2)sc1Cl]

1,1-dimethylethyl[2-({[5-chloro-4-(1-ethyl-1H-pyrazol-5-yl)-2-thienyl]carbonyl}amino)-3-phenylpropyl]carbamate (61 mg, 0.12 mmol) was dissolved in DCM (2 mL) and treated with TFA (1 mL). After 0.5 h, the solution was concentrated and neutralized through silica using 4% MeOH in DCM (1% NH$_4$OH). The title compound was further purified using reverse-phase HPLC (C18 column: H$_2$O/CH$_3$CN, 40-10%) affording the bis-TFA salt of the title compound (41 mg, 53%) as a white solid. LC-MS (ES) m/z=389 (M+H)⁺. ¹H NMR (d$_4$-MeOD, 400 MHz) δ ppm 7.61 (d, J=2.0 Hz, 1H), 7.59 (s, 1H), 7.33-7.21 (m, 5H), 6.41 (d, J=2.0 Hz, 1H), 4.52 (m, 1H), 4.10 (q, J=7.1 Hz, 2H), 3.22 (dd, J=12.9, 3.5 Hz, 1H), 3.12 (dd, J=12.6, 10.1 Hz, 1H), 2.98 (m, 2H), and 1.35 (t, J=7.1 Hz, 3H).

Example 90

N-((1S)-2-amino-1-{[2-(trifluoromethyl)phenyl]methyl}ethyl)-5-chloro-4-(1-ethyl-1H-pyrazol-5-yl)-2-thiophenecarboxamide

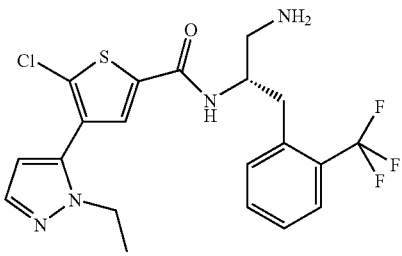 [SMILES: CCn1nccc1-c1cc(C(=O)N[C@H](CN)Cc2ccccc2C(F)(F)F)sc1Cl]

a) 5-chloro-N-((1S)-2-(1,3-dioxo-1,3-dihydro-2H-isoindol-2-yl)-1-{[2-(trifluoromethyl)phenyl]methyl}ethyl)-4-(1-ethyl-1H-pyrazol-5-yl)-2-thiophenecarboxamide

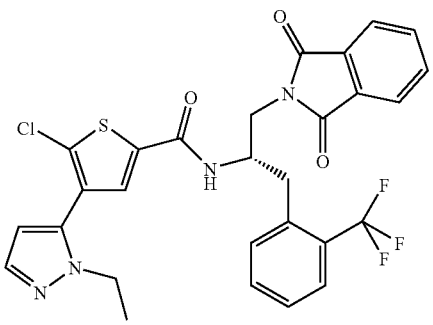 [SMILES: CCn1nccc1-c1cc(C(=O)N[C@@H](Cc2ccccc2C(F)(F)F)CN2C(=O)c3ccccc3C2=O)sc1Cl]

The title compound was prepared as an off-white solid according to the procedure of Example 89(c), except substituting 4-bromo-5-chloro-N-((1S)-2-(1,3-dioxo-1,3-dihydro-2H-isoindol-2-yl)-1-{[2-(trifluoromethyl)phenyl]methyl}ethyl)-2-thiophenecarboxamide (150 mg, 0.26 mmol) for 1,1-dimethylethyl (2-{[(4-bromo-5-chloro-2-thienyl)carbonyl]amino}-3-phenylpropyl)carbamate: LC-MS (ES) m/z 587 (M+H)⁺.

b) N-((1S)-2-amino-1-{[2-(trifluoromethyl)phenyl]methyl}ethyl)-5-chloro-4-(1-ethyl-1H-pyrazol-5-yl)-2-thiophenecarboxamide

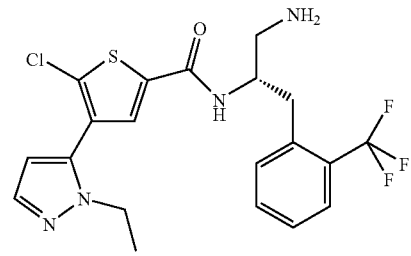 [SMILES: CCn1nccc1-c1cc(C(=O)N[C@H](CN)Cc2ccccc2C(F)(F)F)sc1Cl]

To a solution of 5-chloro-N-((1S)-2-(1,3-dioxo-1,3-dihydro-2H-isoindol-2-yl)-1-{[2-(trifluoromethyl)phenyl]methyl}ethyl)-4-(1-ethyl-1H-pyrazol-5-yl)-2-thiophenecarboxamide (110 mg, 0.19 mmol) in MeOH/THF (5 mL/0.5 mL) was added hydrazine (0.5 mL, 15.9 mmol). After stirring overnight at RT, the reaction mixture was concentrated, and purified by reverse-phase HPLC (C18 column: H₂O/CH₃CN, 40-10%) to afford the bis-TFA salt of the title compound. The bis-TFA salt was dissolved in water, and neutralized by ammonium hydroxide. The mixture was extracted with DCM (5 mL×3), dried over Na₂SO₄, and concentrated to give a free base of the title compound, which was dissolved in MeOH (2 mL), and treated with HCl (aq, 37%). After stirring overnight, the reaction solution was concentrated to give the title compound (26 mg, 26%) as a di-HCl salt: LC-MS (ES) m/z=457 (M+H)⁺. ¹H NMR (d₄-MeOD, 400 MHz) δ ppm 8.28 (d, J=2.5 Hz, 1H), 8.07 (s, 1H), 7.70 (d, J=7.6 Hz, 1H), 7.62 (d, J=7.6 Hz, 1H), 7.53 (dd, J=7.3, 7.6 Hz, 1H), 7.43 (dd, J=7.6, 7.6 Hz, 1H), 6.90 (d, J=2.5 Hz, 1H), 4.66 (m, 1H), 4.43 (q, J=7.3 Hz, 2H), 3.37-3.16 (m, 4H), and 1.50 (t, J=7.3 Hz, 3H).

Example 91

N-((1S)-2-amino-1-{[2-(trifluoromethyl)phenyl]methyl}ethyl)-5-chloro-4-(1,4-dimethyl-1H-pyrazol-5-yl)-2-thiophenecarboxamide

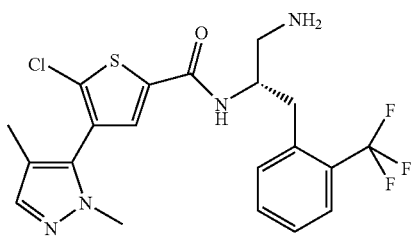 [SMILES: Cc1cnn(C)c1-c1cc(C(=O)N[C@H](CN)Cc2ccccc2C(F)(F)F)sc1Cl]

a) 5-chloro-4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

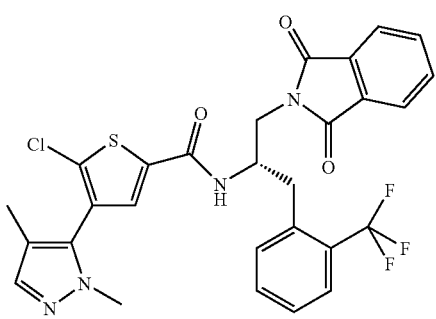 [SMILES: Cc1cnn(C)c1-c1cc(C(=O)N[C@@H](Cc2ccccc2C(F)(F)F)CN2C(=O)c3ccccc3C2=O)sc1Cl]

To a solution of 4-bromo-5-chloro-N-((1S)-2-(1,3-dioxo-1,3-dihydro-2H-isoindol-2-yl)-1-{[2-(trifluoromethyl)phenyl]methyl}ethyl)-2-thiophenecarboxamide (260 mg, 0.46 mmol) in THF (5 mL) was added Na₂CO₃ (2N, 0.7 mL, 1.4 mmol), Pd(dppf)Cl₂ (40 mg, 48 μmol) and 1,4-dimethyl-5-(4,4,5,5-tetramethyl-1,3,2-dioxaborolan-2-yl)-1H-pyrazole (303 mg, 1.38 mmol). The reaction mixture was heated to 75° C. in a sealed tube under N₂. After 8 h, the reaction mixture was concentrated under vacuum and purified on silica (10:1 CHCl₃/MeOH) to afford the title compound (196 mg, 73.4%): LC-MS (ES) m/z=587 (M+H)⁺.

b) N-((1S)-2-amino-1-{[2-(trifluoromethyl)phenyl]methyl}ethyl)-5-chloro-4-(1,4-dimethyl-1H-pyrazol-5-yl)-2-thiophenecarboxamide

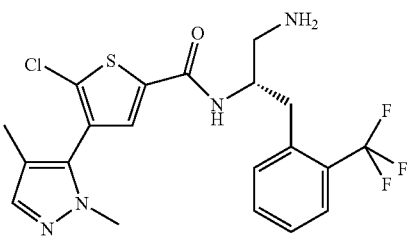 [SMILES: Cc1cnn(C)c1-c1cc(C(=O)N[C@H](CN)Cc2ccccc2C(F)(F)F)sc1Cl]

To a solution of 5-chloro-4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (196 mg, 0.34 mmol) in MeOH/THF (2 mL/0.5 mL) was added hydrazine (0.5 mL, 15.9 mmol). After stirring overnight at RT, the reaction mixture was concentrated, and purified on silica (50% MeOH in CHCl₃ (0.5% NH₄OH) to give a free base of the title compound, which was dissolved in MeOH (2 mL), and treated with HCl (aq, 37%). After stirring overnight, the reaction solution was concentrated to give the title compound (107 mg, 51%) as a di-HCl salt: LC-MS (ES) m/z=457 (M+H)⁺. ¹H NMR (d₄-MeOD, 400 MHz) δ ppm 7.96 (s, 1H), 7.90 (m, 1H), 7.70 (d, J=7.6 Hz, 1H), 7.60 (d, J=7.6 Hz, 1H), 7.53 (t, J=7.3 Hz, 1H), 7.43 (t, J=7.3 Hz, 1H), 4.66 (m, 1H), 3.91 (s, 3H), 3.33-3.14 (m, 4H), and 2.10 (s, 3H).

Example 92

N-((1S)-2-amino-1-{[2-(trifluoromethyl)phenyl]methyl}ethyl)-4-(4-chloro-1-ethyl-1H-pyrazol-5-yl)-2-thiophenecarboxamide

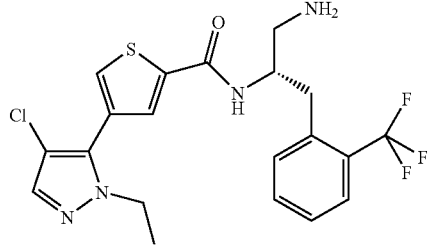 [SMILES: CCn1ncc(Cl)c1-c1csc(C(=O)N[C@H](CN)Cc2ccccc2C(F)(F)F)c1]

a) methyl 4-(4-chloro-1-ethyl-1H-pyrazol-5-yl)-2-thiophenecarboxylate

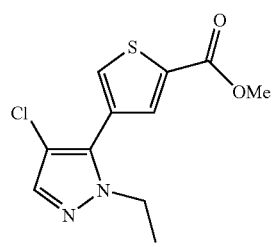 [SMILES: CCn1ncc(Cl)c1-c1csc(C(=O)OC)c1]

To a solution of methyl 4-bromo-2-thiophenecarboxylate (1.0 g, 4.52 mmol) in dioxane/H₂O (5:1, 6 mL) was added K₂CO₃ (1.86 g, 13.5 mmol), tetrakistriphenylphosphine Pd(0) (260 mg, 0.23 mmol) and 1-ethyl-5-(4,4,5,5-tetramethyl-1,3,2-dioxaborolan-2-yl)-1H-pyrazole (1.3 g, 5.85 mmol). The reaction mixture was heated to 70° C. in a sealed tube. After 2 h, the reaction mixture was concentrated under vacuum and purified on silica (hex/EtOAc, 20-40%) to afford methyl 4-(1-ethyl-1H-pyrazol-5-yl)-2-thiophenecarboxylate (0.7 g, 66%) as a light yellow solid: LC-MS (ES) m/z=237 (M+H)$^+$.

To a solution of the above compound (0.5 g, 2.11 mmol) in THF (10 mL) was added NCS (0.364 g, 2.74 mmol). The reaction mixture was heated to 70° C. under nitrogen. After 2 h, the reaction mixture was concentrated under vacuum and purified on silica (Hexanes/EtOAc, 10-20%) to afford the title compound (0.45 g, 78%) as a light yellow solid: LC-MS (ES) m/z 271 (M+H)$^+$.

(b) 4-(4-chloro-1-ethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

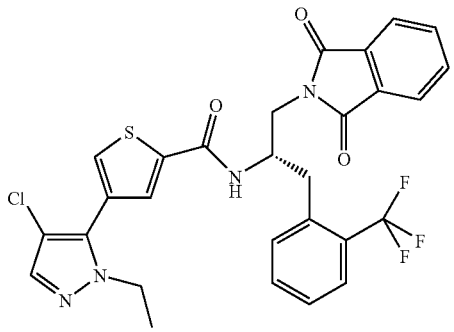 [SMILES: CCn1ncc(Cl)c1-c1csc(C(=O)N[C@@H](Cc2ccccc2C(F)(F)F)CN2C(=O)c3ccccc3C2=O)c1]

To a solution of methyl 4-(4-chloro-1-ethyl-1H-pyrazol-5-yl)-2-thiophenecarboxylate (0.3 g, 1.1 mmol) in THF/H$_2$O (5 mL/0.5 mL) was added KOH (0.2 g, 3.4 mmol). The reaction mixture was heated to 50° C. for 4 h and then concentrated and diluted with H$_2$O (2 mL). The pH was adjusted to 3 with aqueous HCl. The mixture was extracted with DCM (3×5 mL) and the collected organic fractions were concentrated under vacuum to give crude 4-(4-chloro-1-ethyl-1H-pyrazol-5-yl)-2-thiophenecarboxylic acid (260 mg) which was used directly without further purification. LC-MS (ES) m/z=256 (M+H)$^+$.

To a solution of 4-(4-chloro-1-ethyl-1H-pyrazol-5-yl)-2-thiophenecarboxylic acid (0.26 g, 1.0 mmol), 2-{(2S)-2-amino-3-[2-(trifluoromethyl)phenyl]propyl}-1H-isoindole-1,3(2H)-dione (0.35 g, 1.1 mmol) and DIPEA (0.5 mL, 2.86 mmol) in DCM (5 mL) at 25° C. was added PyBrOP (0.6 g, 1.2 mmol) in one portion. After 2 h, the solution was concentrated and purified via column chromatography (silica, 20-50% EtOAc/hexane) affording the title compound (0.54 g, 91%) as a white solid: LC-MS (ES) m/z=588 (M+H)$^+$.

c) N-((1S)-2-amino-1-{[2-(trifluoromethyl)phenyl]methyl}ethyl)-4-(4-chloro-1-ethyl-1H-pyrazol-5-yl)-2-thiophenecarboxamide

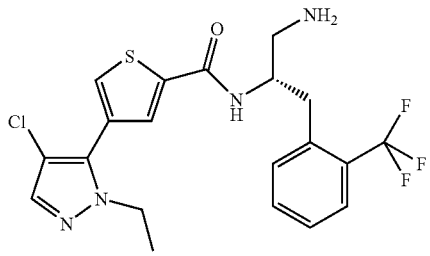 [SMILES: CCn1ncc(Cl)c1-c1csc(C(=O)N[C@H](CN)Cc2ccccc2C(F)(F)F)c1]

4-(4-chloro-1-ethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (350 mg, 0.60 mmol) was dissolved in MeOH (5 mL) and treated with NH$_2$NH$_2$ (0.5 mL, 15.93 mmol). The mixture was stirred at RT overnight, and concentrated. The residue was purified by column chromatography (silica, 2-5% MeOH in CHCl$_3$ (0.5% NH$_4$OH) affording the free base of the title compound, which was treated with HCl(aq) in MeOH to give title compound (0.16 g, 51%) as a off white solid: LC-MS (ES) m/z=457 (M+H)$^+$. $^1$H NMR (d$_4$-MeOD, 400 MHz) δ ppm 7.97-7.94 (m, 2H), 7.71 (d, J=7.8 Hz, 1H), 7.61 (s, 1H), 7.56-7.51 (m, 2H), 7.43 (dd, J=7.6, 7.6 Hz, 1H), 4.67 (m, 1H), 4.22 (q, J=7.1 Hz, 2H), 3.36-3.12 (m, 4H), and 1.38 (t, J=7.1 Hz, 3H).

Example 93

N-((1S)-2-amino-1-{[2-(trifluoromethyl)phenyl]methyl}ethyl)-4-(4-bromo-1-ethyl-1H-pyrazol-5-yl)-2-thiophenecarboxamide

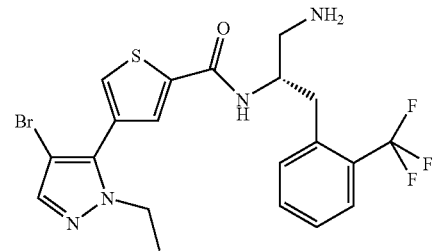 [SMILES: CCn1ncc(Br)c1-c1csc(C(=O)N[C@H](CN)Cc2ccccc2C(F)(F)F)c1]

a) methyl 4-(4-bromo-1-ethyl-1H-pyrazol-5-yl)-2-thiophenecarboxylate

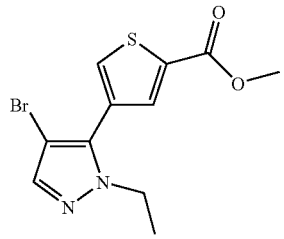 [SMILES: CCn1ncc(Br)c1-c1csc(C(=O)OC)c1]

To a solution of methyl 4-(1-ethyl-1H-pyrazol-5-yl)-2-thiophenecarboxylate (0.45 g, 1.9 mmol) [see example 92(a)] in THF (5 mL) was added NBS (0.33 g, 2.5 mmol). The reaction mixture was heated to 70° C. under nitrogen. After 2 h, the reaction mixture was concentrated under vacuum and purified on silica (EtOAc/hexanes, 10-30%) to afford the title compound (0.47 g, 78%). LC-MS (ES) m/z=316 (M+H)$^+$.

b) 4-(4-bromo-1-ethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

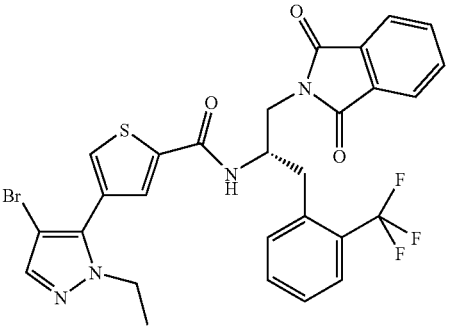

To a solution of methyl 4-(4-bromo-1-ethyl-1H-pyrazol-5-yl)-2-thiophenecarboxylate (0.2 g, 0.63 mmol) in THF/H₂O (5 mL/1 mL) was added KOH (0.15 g, 2.4 mmol). The reaction mixture was heated to 50° C. for 10 h and then concentrated and diluted with H₂O (2 mL). The pH was adjusted to 6 with aqueous HCl. The mixture was extracted with DCM (3×5 mL) and the collected organic fractions were concentrated under vacuum to give crude 4-(4-bromo-1-ethyl-1H-pyrazol-5-yl)-2-thiophenecarboxylic acid, which was used directly without further purification. LC-MS (ES) m/z=302 (M+H)⁺.

To a solution of 4-(4-bromo-1-ethyl-1H-pyrazol-5-yl)-2-thiophenecarboxylic acid 156 mg, 0.52 mmol), 2-{(2S)-2-amino-3-[2-(trifluoromethyl)phenyl]propyl}-1H-isoindole-1,3(2H)-dione (0.18 g, 0.52 mmol) and DIPEA (0.5 mL, 2.86 mmol) in DCM (5 mL) at 25° C. was added PyBrOP (0.29 g, 0.62 mmol) in one portion. After 2 h, the solution was concentrated and purified via column chromatography (silica, 20-60% EtOAc/hexane) affording the title compound (0.281 g, 86%). LC-MS (ES) m/z=632 (M+H)⁺.

c) N-((1S)-2-amino-1-{[2-(trifluoromethyl)phenyl]methyl}ethyl)-4-(4-bromo-1-ethyl-1H-pyrazol-5-yl)-2-thiophenecarboxamide

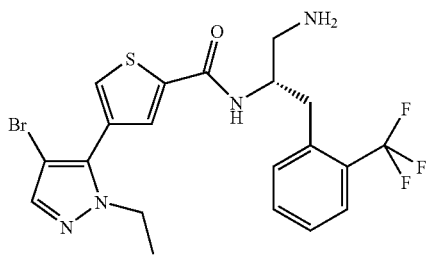

4-(4-bromo-1-ethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (250 mg, 0.39 mmol) was dissolved in MeOH (5 mL) and treated with NH₂NH₂ (0.5 mL, 15.93 mmol). The mixture was stirred at RT overnight, and concentrated. The residue was purified by column chromatography [silica, 2-10% MeOH in CHCl₃ (0.5% NH₄OH)] affording the free base of the title compound, which was treated with HCl(aq) in MeOH to give the title compound (144 mg, 51%) as an off white solid: LC-MS (ES) m/z 502 (M+H)⁺. ¹H NMR (d₄-MeOD, 400 MHz) δ ppm 7.93-7.87 (m, 2H), 7.72 (d, J=8.1 Hz, 1H), 7.62 (s, 1H), 7.57-7.51 (m, 2H), 7.43 (t, J=6.6 Hz, 1H), 4.67 (m, 1H), 4.25 (q, J=7.3 Hz, 2H), 3.37-3.11 (m, 4H), and 1.37 (t, J=7.1 Hz, 3H).

Example 94

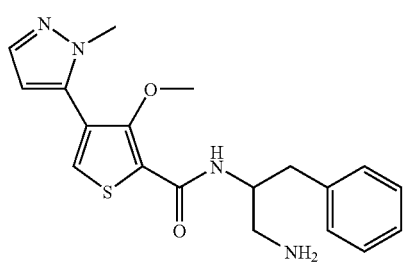

Preparation of N-[2-amino-1-(phenylmethyl)ethyl]-3-(methyloxy)-4-(1-methyl-1H-pyrazol-5-yl)-2-thiophenecarboxamide a) methyl 3-(methyloxy)-4-(1-methyl-1H-pyrazol-5-yl)-2-thiophenecarboxylate

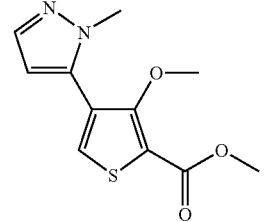 [SMILES: COC(=O)c1scc(-c2ccnn2C)c1OC]

Methyl 4-bromo-3-(methyloxy)-2-thiophenecarboxylate (250 mg, 0.10 mmol) [prepared according to Corral, C.; El-Ashmawy, M. B.; Lissavetzky, J.; Basilio, A.; Giraldez, A.; Eur. J. Med. Chem. Chim. Ther. 22; 1987; 251-254.], 5-(5,5-dimethyl-1,3,2-dioxaborinane-2-yl)-1-methyl-1H-pyrazole (250 mg, 1.20 mmol), Pd(PPh₃)₄ (58 mg, 49.8 μmol) and K₂CO₃ (550 mg, 3.98 mmol) in dioxane (5 mL) and H₂O (1 mL) were combined in a sealed tube. After 12 h at 80° C., the reaction contents were partitioned between H₂O/DCM. The aqueous phase was washed several times with DCM and the combined organic fractions were dried over Na₂SO₄, concentrated and purified via column chromatography (silica, 0.5% MeOH in DCM) affording the title compound (215 mg, 86%) as a brown residue: LCMS (ES) m/z=253 (M+H)⁺.

b) 1,1-dimethylethyl[2-({[3-(methyloxy)-4-(1-methyl-1H-pyrazol-5-yl)-2-thienyl]carbonyl}amino)-3-phenylpropyl]carbamate

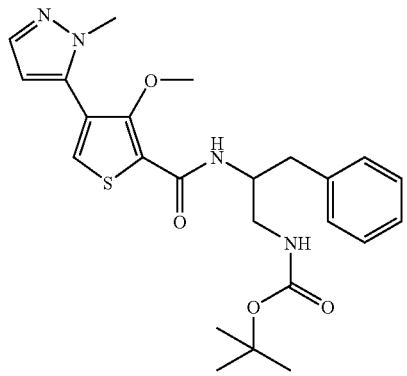 [SMILES: COc1c(-c2ccnn2C)csc1C(=O)NC(CNC(=O)OC(C)(C)C)Cc1ccccc1]

i) A solution of methyl 3-(methyloxy)-4-(1-methyl-1H-pyrazol-5-yl)-2-thiophenecarboxylate (215 mg, 0.853 mmol) in 6N NaOH (4 mL) and THF (4 mL) was stirred in a sealed tube at 70° C. After 2 h, the solution was acidified to pH 3 using 1N HCl then extracted several times with DCM. The combined organic fractions were dried over Na₂SO₄, concentrated and used directly: LCMS (ES) m/z=239 (M+H)⁺.

ii) To a solution of the crude acid, 1,1-dimethylethyl (2-amino-3-phenylpropyl)carbamate (210 mg, 0.844 mmol) [from Preparation 2] and diisopropylethyl amine (735 μL, 4.22 mmol) in DCM (8 mL) was added PyBrop (472 mg, 1.01 mmol) in one portion. After 1 h, the reaction contents were partitioned between H₂O/DCM. The aqueous phase was washed several times with DCM and the combined organic fractions were dried over Na$_2$SO$_4$, concentrated and used directly: LCMS (ES) m/z=471 (M+H)$^+$.

c) N-[2-amino-1-(phenylmethyl)ethyl]-3-(methyloxy)-4-(1-methyl-1H-pyrazol-5-yl)-2-thiophenecarboxamide A solution of 1,1-dimethylethyl[2-({[3-(methyloxy)-4-(1-methyl-1H-pyrazol-5-yl)-2-thienyl]carbonyl}amino)-3-phenylpropyl]carbamate (crude from part b) in TFA-DCM (3 mL, 1:2) was stirred at 25° C. After 30 min, the solution was concentrated with a toluene azeotrope and the residue neutralized through a silica plug (3% MeOH in DCM (1% NH$_4$OH)) affording the free base of the title compound.

The free base, as a solution in MeOH, was then treated with excess 4M HCl in dioxane affording the title compound (270 mg, 86%-2steps) as the HCl salt: LCMS (ES) m/z 371 (M+H)$^+$, $^1$H NMR (400 MHz, DMSO-d$_6$) δ ppm 8.06 (br. s., 3H) 7.91 (s, 1H) 7.72 (d, J=8.59 Hz, 1H) 7.52 (d, J=1.77 Hz, 1H) 7.25-7.31 (m, 4H) 7.18-7.23 (m, 1H) 6.39 (d, J=2.02 Hz, 1H) 4.52 (br. s., 1H) 3.78 (s, 3H) 3.41 (s, 3H) 2.97-3.05 (m, 4H).

Example 95

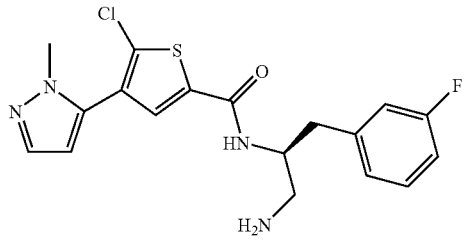 [SMILES: Cn1nccc1-c1cc(C(=O)N[C@H](CN)Cc2cccc(F)c2)sc1Cl]

Preparation of N-{(1S)-2-amino-1-[(3-fluorophenyl)methyl]ethyl}-5-chloro-4-(1-methyl-1H-pyrazol-5-yl)-2-thiophenecarboxamide a) methyl 5-chloro-2-thiophenecarboxylate

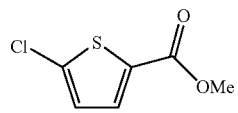

To a solution of 5-chloro-2-thiophenecarboxylic acid (20 g, 123 mmoles) in MeOH (200 mL) was added conc. H$_2$SO$_4$ (5 mL). After heating to 55° C. for 12 h, the reaction solution was concentrated and diluted with DCM (250 mL). The DCM solution was washed with aqueous NaHCO$_3$, then H$_2$O and dried over Na$_2$SO$_4$. Concentration under vacuum gave the title compound as a yellow oil (21.5 g, 99%): LCMS (ES) m/z 178 (M+H)$^+$.

b) methyl 4-bromo-5-chloro-2-thiophenecarboxylate

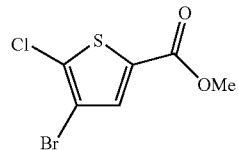 [SMILES: COC(=O)c1cc(Br)c(Cl)s1]

To a 1 L round bottom flask was added aluminum chloride (11.32 g, 85 mmol) and methyl 5-chloro-2-thiophenecarboxylate (10 g, 56.6 mmol) dissolved in CHCl$_3$ (250 mL). Br$_2$ (4.08 ml, 79 mmol) was added dropwise over 10 minutes. After stirring for 6 h at 25° C., the light orange reaction solution was washed with sat NaHCO$_3$. The organic layer was dried Na$_2$SO$_4$, filtered and concentrated. The residue was purified on silica gel [hexanes/EtOAc, 9:1] to give the product [12 g, 80%] as a white solid. LCMS (ES) m/z 256 (M+H)$^+$.

c) methyl 5-chloro-4-(1-methyl-1H-pyrazol-5-yl)-2-thiophenecarboxylate

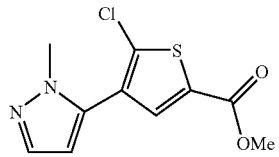 [SMILES: COC(=O)c1cc(-c2ccnn2C)c(Cl)s1]

To a 300 mL sealed flask was added 1-methyl-5-(4,4,5,5-tetramethyl-1,3,2-dioxaborolan-2-yl)-1H-pyrazole (8.14 g, 39.1 mmol), potassium carbonate (12.98 g, 94 mmol), methyl 4-bromo-5-chloro-2-thiophenecarboxylate (8 g, 31.3 mmol) and bis(tri-t-butylphosphine)palladium(0) (0.40 g, 0.78 mmol) in 1,4-dioxane (50 ml) and H$_2$O (6 ml). After stirring for 90 min at 75° C., the reaction solution was diluted with DCM (100 mL) and washed with H$_2$O. The organic layer was dried Na$_2$SO$_4$, filtered and concentrated. The reaction residue was purified on silica gel [hexanes/EtOAc, 2:1] to give the product [5.7 g, 70%] as a tan solid: LCMS (ES) m/z 258 (M+H)$^+$.

d) 5-chloro-4-(1-methyl-1H-pyrazol-5-yl)-2-thiophenecarboxylic Acid

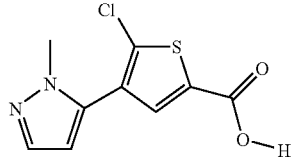

To a 250 mL round-bottomed flask was added methyl 5-chloro-4-(1-methyl-1H-pyrazol-5-yl)-2-thiophenecarboxylate (4.4 g, 17.14 mmol) and sodium hydroxide (28.6 ml, 171 mmol) in tetrahydrofuran (THF) (50 ml) and MeOH (50 mL). The reaction solution was stirred at RT for 12 h and then made acidic (pH ~2) with 2.5 M HCl and extracted with DCM. The organic layer was separated, dried (Na$_2$SO$_4$) and concentrated to an off-white solid (4.2 g, 94%) which was used directly without further purification: LCMS (ES) m/z 243 (M+H)+.

e) 5-chloro-N-{(1S)-2-(1,3-dioxo-1,3-dihydro-2H-isoindol-2-yl)-1-[(3-fluorophenyl)methyl]ethyl}-4-(1-methyl-1H-pyrazol-5-yl)-2-thiophenecarboxamide

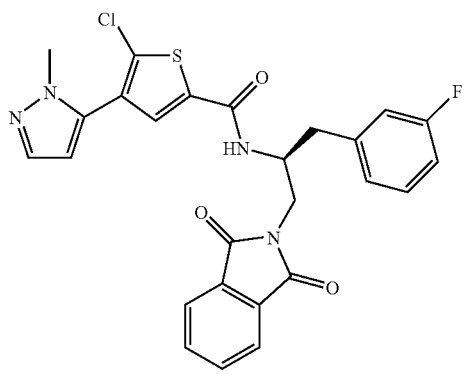 [SMILES: Cn1nccc1-c1cc(C(=O)N[C@@H](Cc2cccc(F)c2)CN2C(=O)c3ccccc3C2=O)sc1Cl]

To a 500 mL round-bottomed flask was added 5-chloro-4-(1-methyl-1H-pyrazol-5-yl)-2-thiophenecarboxylic acid (4.2 g, 17.31 mmol), 2-[(2S)-2-amino-3-(3-fluorophenyl)propyl]-1H-isoindole-1,3(2H)-dione (6.37 g, 19.04 mmol) [prepared according to the procedure of Preparation 6], N,N-diisopropyl ethylamine (4.53 ml, 26.0 mmol) and Pybrop (12.05 g, 26.0 mmol) in dichloromethane (DCM) (150 ml). After stirring at RT for 12 h, the reaction solution was washed with H₂O (2×100 mL) and the organic layer was dried Na₂SO₄, filtered and concentrated. The crude product was added to a silica gel column and was eluted with [EtOAc/hexanes, 1:1] to give the product [7.8 g, 86%] as a white solid: LCMS (ES) m/z 524 (M+H)+.

f) N-{(1S)-2-amino-1-[(3-fluorophenyl)methyl]ethyl}-5-chloro-4-(1-methyl-1H-pyrazol-5-yl)-2-thiophenecarboxamide To a 250 mL round-bottomed flask was added 5-chloro-N-{(1S)-2-(1,3-dioxo-1,3-dihydro-2H-isoindol-2-yl)-1-[(3-fluorophenyl)methyl]ethyl}-4-(1-methyl-1H-pyrazol-5-yl)-2-thiophenecarboxamide (7.8 g, 14.91 mmol) and hydrazine (14.50 ml, 298 mmol) in tetrahydrofuran (THF) (75 ml) and methanol (75 mL). After 24 h at RT, the precipitate was filtered, the filtrate was concentrated. The crude product was purified on a silica gel column [CHCl₃/MeOH/NH₄OH, 90:9:1] to give the title compound as a white solid.

The free base product was treated with 4M HCl in dioxane (15 mL). After 5 min, the solution was concentrated and dried under vacuum to afford the product (6.8 g, 95%) as an HCl salt: LCMS (ES) m/z 467 (M+H)+, ¹H NMR (400 MHz, CD3OD) δ ppm 7.97 (s, 2H), 7.31 (s, 1H), 7.14 (m, 2H), 6.98 (m, 1H), 6.75 (s, 1H), 4.54 (m, 1H), 3.98 (s, 3H), 3.24 (m, 2H), 3.04 (m, 2H).

Example 96

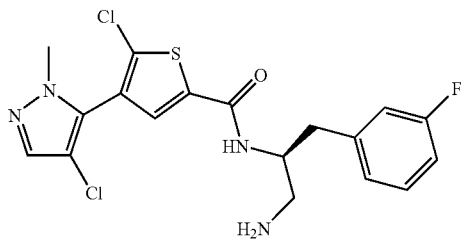 [SMILES: Cn1ncc(Cl)c1-c1cc(C(=O)N[C@H](CN)Cc2cccc(F)c2)sc1Cl]

Preparation of N-{(1S)-2-amino-1-[(3-fluorophenyl)methyl]ethyl}-5-chloro-4-(4-chloro-1-methyl-1H-pyrazol-5-yl)-2-thiophenecarboxamide a) 5-chloro-4-(4-chloro-1-methyl-1H-pyrazol-5-yl)-2-thiophenecarboxylic Acid

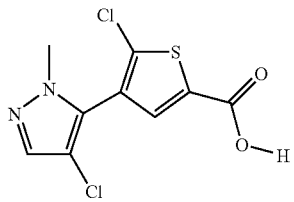 [SMILES: Cn1ncc(Cl)c1-c1cc(C(=O)O)sc1Cl]

To a 500 mL flask was added methyl 5-chloro-4-(1-methyl-1H-pyrazol-5-yl)-2-thiophenecarboxylate (5 g, 19.48 mmol) [from Example 95] and NCS (3.12 g, 23.37 mmol) in tetrahydrofuran (THF) (100 ml) (50 mL). After stirring for 4 h at 70° C., the yellow reaction solution was treated with 6M NaOH (32 mL, 195 mmole) and stirred an additional 2 hours. The reaction solution was diluted with H₂O (50 mL) and DCM (200 mL). The organic layer was separated and the aqueous layer made acidic with 6N HCl. The acidic aqueous solution was extracted with DCM (3×200 mL), dried over Na₂SO₄, and concentrated to give the crude product [2.6 g, 48%] as a tan solid: LCMS (ES) m/z 277 (M+H)+.

b) 5-chloro-4-(4-chloro-1-methyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide

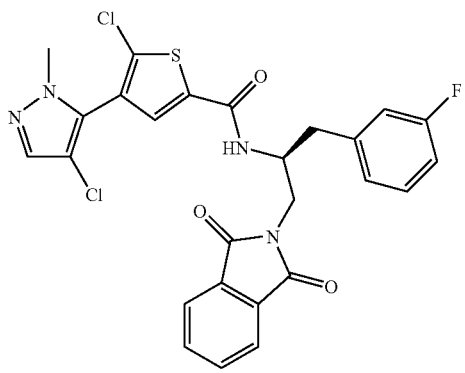 [SMILES: Cn1ncc(Cl)c1-c1cc(C(=O)N[C@@H](Cc2cccc(F)c2)CN2C(=O)c3ccccc3C2=O)sc1Cl]

To a 500 mL round-bottomed flask was added 5-chloro-4-(4-chloro-1-methyl-1H-pyrazol-5-yl)-2-thiophenecarboxylic acid (6 g, 21.65 mmol), 2-[(2S)-2-amino-3-(3-fluorophenyl)propyl]-1H-isoindole-1,3(2H)-dione (7.25 g, 21.65 mmol) [prepared according to the procedure of Preparation 6], N,N-diisopropyl ethylamine (5.67 ml, 32.5 mmol) and Pybrop (15.08 g, 32.5 mmol) in Dichloromethane (DCM) (150 ml). After stirring at RT for 12 h, the reaction solution was washed with $H_2O$ (2×100 mL) and the organic layer was dried $Na_2SO_4$, filtered and concentrated. The crude product was added to a silica gel column and was eluted with [EtOAc/hexanes, 1:1] to give the product [9.0 g, 74%] as a white solid: LCMS (ES) m/z 558 (M+H)$^+$.

c) N-{(1S)-2-amino-1-[(3-fluorophenyl)methyl]ethyl}-5-chloro-4-(4-chloro-1-methyl-1H-pyrazol-5-yl)-2-thiophenecarboxamide To a 250 mL round-bottomed flask was added 5-chloro-4-(4-chloro-1-methyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide (9 g, 16.15 mmol) and hydrazine (15.69 ml, 323 mmol) in tetrahydrofuran (THF) (75 ml) and methanol (75 mL). After 24 h at RT, the precipitate was filtered, the filtrate was concentrated, and the crude product was purified on a silica gel column [$CHCl_3$/MeOH/$NH_4OH$, 90:9:1] to give the title compound as a white solid.

The free base product was treated with 4M HCl in dioxane (15 mL). After 5 min, the product solution was concentrated and dried under vacuum to afford the product (6.5 g, 91%) as an HCl salt: LCMS (ES) m/z 428 (M+H)$^+$, $^1$H NMR (400 MHz, $CD_3OD$) δ ppm 7.75 (s, 1H), 7.60 (s, 1H), 7.32 (m, 1H) 7.14 (m, 2H), 6.98 (m, 1H), 4.54 (m, 1H), 3.78 (s, 3H), 3.24 (m, 2H), 3.02 (m, 2H).

Example 97

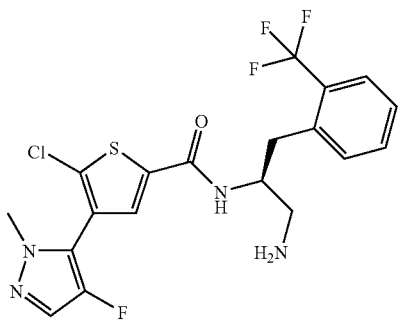

Preparation of N-((1S)-2-amino-1-{[2-(trifluoromethyl)phenyl]methyl}ethyl)-5-chloro-4-(4-fluoro-1-methyl-1H-pyrazol-5-yl)-2-thiophenecarboxamide a) methyl 5-chloro-4-(4-fluoro-1-methyl-1H-pyrazol-5-yl)-2-thiophenecarboxylate

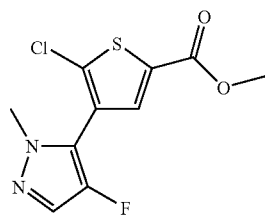

To a solution of methyl 5-chloro-4-(1-methyl-1H-pyrazol-5-yl)-2-thiophenecarboxylate (250 mg, 0.974 mmol)[prepared according to the procedure in Example 95] in acetonitrile (4.864 ml) and $H_2O$ (486 μl) was added selectfluor (449 mg, 1.27 mmol). The resulting solution was stirred at 70° C. in a sealed tube for 1 h after which additional selectfluor (449 mg, 1.266 mmol) was added in one portion. After stirring 12 h, the solution was partitioned between $H_2O$-DCM. The aqueous phase was washed several times with DCM-THF and the combined organic fractions were dried over $Na_2SO_4$, concentrated and purified via column chromatography (silica, 10% EtOAc in hexanes) affording methyl 5-chloro-4-(4-fluoro-1-methyl-1H-pyrazol-5-yl)-2-thiophenecarboxylate (65 mg, 0.237 mmol, 24.30% yield) as a yellow solid; LCMS (ES) m/z 274, 276 (M, M+H).

b) 5-chloro-4-(4-fluoro-1-methyl-1H-pyrazol-5-yl)-2-thiophenecarboxylic Acid

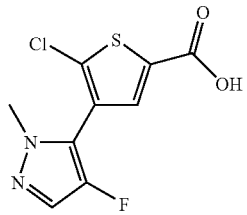

A solution of methyl 5-chloro-4-(4-fluoro-1-methyl-1H-pyrazol-5-yl)-2-thiophenecarboxylate (65 mg, 0.237 mmol) in 6N sodium hydroxide (0.39 ml, 2.37 mmol) and tetrahydrofuran (2 ml) was stirred at 70° C. in a sealed tube for 1 h. The resulting solution was cooled and then partitioned between $H_2O$-DCM. The aqueous phase was adjusted to pH ~4 and then washed several times with DCM. The combined organic fractions were dried over $Na_2SO_4$ and concentrated affording 5-chloro-4-(4-fluoro-1-methyl-1H-pyrazol-5-yl)-2-thiophenecarboxylic acid (54 mg, 0.17 mmol, 72% yield) as a yellow oil; LCMS (ES) m/e 261, 263 (M, M+2)$^+$.

c) 5-chloro-N-((1S)-2-(1,3-dioxo-1,3-dihydro-2H-isoindol-2-yl)-1-{[2-(trifluoromethyl)phenyl]methyl}ethyl)-4-(4-fluoro-1-methyl-1H-pyrazol-5-yl)-2-thiophenecarboxamide

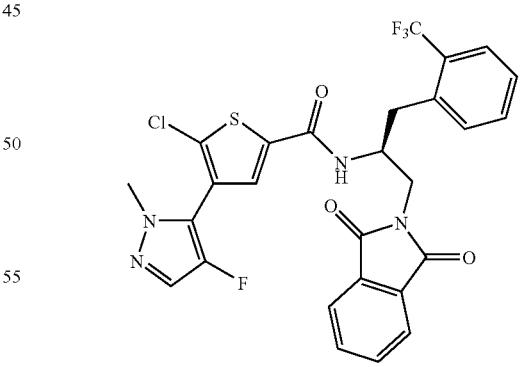

To a solution of 5-chloro-4-(4-fluoro-1-methyl-1H-pyrazol-5-yl)-2-thiophenecarboxylic acid (53 mg, 0.203 mmol), 2-{(2S)-2-amino-3-[2-(trifluoromethyl)phenyl]propyl}-1H-isoindole-1,3(2H)-dione (78 mg, 0.203 mmol)[prepared according to Preparation 6] and diisopropylethylamine (0.18 ml, 1.02 mmol) in DCM at 25° C. was added bromo-tris-pyrrolidino-phosphonium hexafluorophosphate (95 mg, 0.203 mmol) in one portion. The solution stirred at 25° C.

over 12 h and was then partitioned between H₂O-DCM. The aqueous phase was washed several times with DCM and the combined organic fractions were dried over Na₂SO₄, concentrated and purified via column chromatography (silica, 40% EtOAc in hexanes) yielding 5-chloro-N-((1S)-2-(1,3-dioxo-1,3-dihydro-2H-isoindol-2-yl)-1-{[2-(trifluoromethyl)phenyl]methyl}ethyl)-4-(4-fluoro-1-methyl-1H-pyrazol-5-yl)-2-thiophenecarboxamide (106 mg, 0.129 mmol, 63.5% yield) as a clear oil; LCMS (ES) m/e 591, 593 (M, M+H)⁺.

d) N-((1S)-2-amino-1-{[2-(trifluoromethyl)phenyl]methyl}ethyl)-5-chloro-4-(4-fluoro-1-methyl-1H-pyrazol-5-yl)-2-thiophenecarboxamide

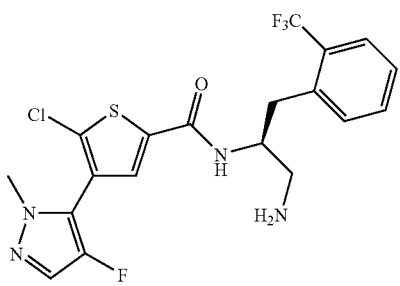 [SMILES: Cn1ncc(F)c1-c1cc(C(=O)N[C@H](CN)Cc2ccccc2C(F)(F)F)sc1Cl]

To a solution of 5-chloro-N-((1S)-2-(1,3-dioxo-1,3-dihydro-2H-isoindol-2-yl)-1-{[2-(trifluoromethyl)phenyl]methyl}ethyl)-4-(4-fluoro-1-methyl-1H-pyrazol-5-yl)-2-thiophenecarboxamide (106 mg, 0.179 mmol) in tetrahydrofuran (1.095 ml) and methanol (1.095 ml) at 25° C. was added hydrazine (0.056 ml, 1.79 mmol) dropwise. After 48 h, the solution was concentrated, dry loaded (silica, 5% MeOH in DCM (1% NH₄OH)) and purified initially by column chromatography. The residue was then further purified via gilson reverse phase chromatography using 2%-95% mobile phase affording the TFA salt of the title compound. This compound was neutralized through a plug of silica (5% MeOH in DCM (1% NH₄OH)) concentrated and transferred to the HCl salt adding excess 4M HCl in dioxane (500 ul) to the residue in MeOH (2 ml) affording the HCl salt of N-((1S)-2-amino-1-{[2-(trifluoromethyl)phenyl]methyl}ethyl)-5-chloro-4-(4-fluoro-1-methyl-1H-pyrazol-5-yl)-2-thiophenecarboxamide (17 mg, 0.029 mmol, 16.16% yield) as a white solid: LCMS (ES) m/z=461, 463 (M, M+2)⁺, ¹H NMR (400 MHz, DMSO-d6) δ ppm 9.11 (s, 1H) 8.11 (s, 1H) 7.71 (br. s., 3H) 7.66-7.70 (m, 2H) 7.54-7.61 (m, 2H) 7.41-7.44 (m, 1H) 4.47 (br. s., 1H) 3.79 (s, 3H) 3.07-3.16 (m, 4H).

Example 98

Preparation of N-((1S)-2-amino-1-{[2-(trifluoromethyl)phenyl]methyl}ethyl)-5-ethyl-4-(1-methyl-1H-pyrazol-5-yl)-2-thiophenecarboxamide a) methyl 4-bromo-5-ethyl-2-thiophenecarboxylate

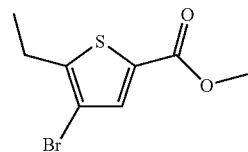

To a solution of 4-bromo-5-ethyl-2-thiophenecarboxylic acid (1 g, 4.25 mmol) in methanol (21.27 ml) was added sulfuric acid (0.23 mL, 4.25 mmol). The resulting solution was stirred at 50° C. for 48 h. H₂O (50 mL) was added and the reaction was cooled to 0° C. in an ice-bath. The pH was adjusted to ~12 and the aqueous phase was washed several times with DCM. The combined organic fractions were dried over Na₂SO₄, concentrated and used directly without further purification providing methyl 4-bromo-5-ethyl-2-thiophenecarboxylate (1.060 g, 4.25 mmol, 100% yield): LCMS (ES) m/e 248, 250 (M, M+2)⁺.

b) methyl 5-ethyl-4-(1-methyl-1H-pyrazol-5-yl)-2-thiophenecarboxylate

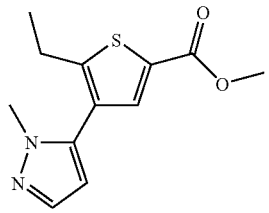

A solution of methyl 4-bromo-5-ethyl-2-thiophenecarboxylate (300 mg, 1.204 mmol), potassium carbonate (832 mg, 6.02 mmol), 1-methyl-5-(4,4,5,5-tetramethyl-1,3,2-dioxaborolan-2-yl)-1H-pyrazole (326 mg, 1.565 mmol)[prepared according to Preparation 7] and bis(tri-t-butylphosphine)palladium(0) (30.8 mg, 0.060 mmol) were combined in a sealed tube and stirred at 80° C. for 1 h. The reaction contents were then partitioned between H₂O-DCM and the aqueous phase was washed several times with DCM. The combined organic fractions were dried over Na₂SO₄ and concentrated affording methyl 5-ethyl-4-(1-methyl-1H-pyrazol-5-yl)-2-thiophenecarboxylate (301 mg, 1.204 mmol, 100% yield) as a brown oil: LCMS (ES) m/e 251 (M+H)⁺.

c) 5-ethyl-4-(1-methyl-1H-pyrazol-5-yl)-2-thiophenecarboxylic Acid

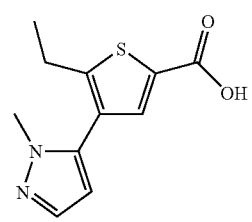 [SMILES: CCc1sc(C(=O)O)cc1-c1ccnn1C]

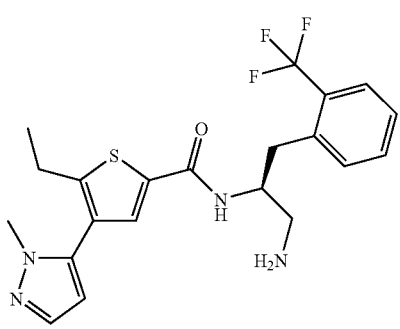

A solution of methyl 5-ethyl-4-(1-methyl-1H-pyrazol-5-yl)-2-thiophenecarboxylate (300 mg, 1.198 mmol) in 6N sodium hydroxide (2.397 ml, 1.198 mmol) and tetrahydrofuran (5.992 ml) was stirred at 70° C. in a sealed tube for 1 h. The resulting solution was cooled and then partitioned between H₂O-DCM. The aqueous phase was adjusted to pH ~4 and then washed several times with DCM. The combined organic fractions were dried over Na₂SO₄ and concentrated affording 5-ethyl-4-(1-methyl-1H-pyrazol-5-yl)-2-thiophenecarboxylic acid (283 mg, 1.2 mmol, 100% yield) as a yellow oil; LCMS (ES) m/z=236 (M+H)⁺.

d) N-((1S)-2-(1,3-dioxo-1,3-dihydro-2H-isoindol-2-yl)-1-{[2-(trifluoromethyl)phenyl]methyl}ethyl)-5-ethyl-4-(1-methyl-1H-pyrazol-5-yl)-2-thiophenecarboxamide

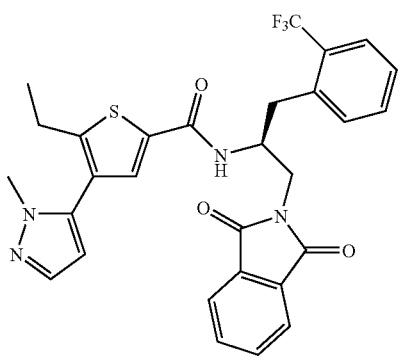 [SMILES: CCc1sc(C(=O)N[C@@H](Cc2ccccc2C(F)(F)F)CN2C(=O)c3ccccc3C2=O)cc1-c1ccnn1C]

To a solution of 5-ethyl-4-(1-methyl-1H-pyrazol-5-yl)-2-thiophenecarboxylic acid (283 mg, 1.2 mmol), 2-{(2S)-2-amino-3-[2-(trifluoromethyl)phenyl]propyl}-1H-isoindole-1,3(2H)-dione (461 mg, 1.2 mmol)[prepared according to Preparation 6] and diisopropylethylamine (1.043 ml, 5.99 mmol) in DCM at 25° C. was added bromo-tris-pyrrolidino-phosphonium hexafluorophosphate (615 mg, 1.317 mmol) in one portion. The solution was stirred at 25° C. over 12 h and was then partitioned between H₂O-DCM. The aqueous phase was washed several times with DCM and the combined organic fractions were dried over Na₂SO₄, concentrated and purified via column chromatography (silica, 50% EtOAc in hexanes) yielding N-((1S)-2-(1,3-dioxo-1,3-dihydro-2H-isoindol-2-yl)-1-{[2-(trifluoromethyl)phenyl]methyl}ethyl)-5-ethyl-4-(1-methyl-1H-pyrazol-5-yl)-2-thiophenecarboxamide (486 mg, 0.86 mmol, 71.6% yield) as a clear oil: LCMS (ES) m/e 567 (M+H)+.

e) N-((1S)-2-amino-1-{[2-(trifluoromethyl)phenyl]methyl}ethyl)-5-ethyl-4-(1-methyl-1H-pyrazol-5-yl)-2-thiophenecarboxamide

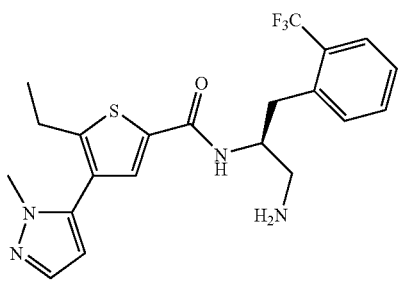 [SMILES: CCc1sc(C(=O)N[C@H](CN)Cc2ccccc2C(F)(F)F)cc1-c1ccnn1C]

To a solution of N-((1S)-2-(1,3-dioxo-1,3-dihydro-2H-isoindol-2-yl)-1-{[2-(trifluoromethyl)phenyl] methyl}ethyl)-5-ethyl-4-(1-methyl-1H-pyrazol-5-yl)-2-thiophenecarboxamide (486 mg, 0.86 mmol) in tetrahydrofuran (2.144 ml) and methanol (2.14 ml) at 25° C. was added hydrazine (0.269 ml, 8.58 mmol) dropwise. After 12 h, the solution was concentrated, dry loaded and purified via column chromatography (silica, 5% MeOH in DCM (1% NH₄OH)). The free base was then converted to the HCl salt by adding excess 4M HCl in dioxane (500 ul) to the residue in MeOH (2 ml) affording N-((1S)-2-amino-1-{[2-(trifluoromethyl)phenyl]methyl}ethyl)-5-ethyl-4-(1-methyl-1H-pyrazol-5-yl)-2-thiophenecarboxamide (250 mg, 0.491 mmol, 57.2% yield)-2 HCl as a white solid: LCMS (ES) m/z=437 (M+H)⁺, ¹H NMR (400 MHz, DMSO-d6) δ ppm 8.84 (d, J=8.84 Hz, 1H) 8.08 (br. s., 3H) 7.93 (s, 1H) 7.69 (d, J=7.83 Hz, 1H) 7.51-7.61 (m, 3H) 7.39-7.46 (m, 1H) 6.34 (d, J=2.02 Hz, 1H) 4.48 (br. s., 1H) 3.77 (s, 3H) 2.99-3.11 (m, 4H) 2.74 (q, J=7.49 Hz, 2H) 1.16 (t, J=7.45 Hz, 3H).

Example 99

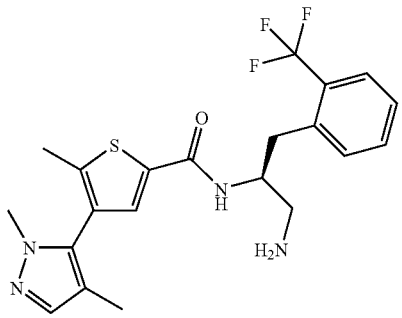

Preparation of N-((1S)-2-amino-1-{[2-(trifluoromethyl)phenyl]methyl}ethyl)-4-(1,4-dimethyl-1H-pyrazol-5-yl)-5-methyl-2-thiophenecarboxamide a) methyl 5-methyl-4-(1-methyl-1H-pyrazol-5-yl)-2-thiophenecarboxylate

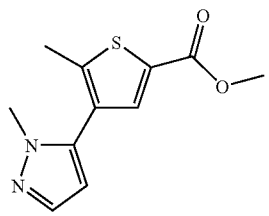

A solution of methyl 4-bromo-5-methyl-2-thiophenecarboxylate (2 g, 8.51 mmol)[prepared in Preparation 10], potassium carbonate (5.88 g, 42.5 mmol), 1-methyl-5-(4,4,5,5-tetramethyl-1,3,2-dioxaborolan-2-yl)-1H-pyrazole (2.124 g, 10.21 mmol)[prepared according to Preparation 7] and bis(tri-t-butylphosphine)palladium(0) (0.217 g, 0.425 mmol) in 1,4-Dioxane (35.4 ml) and H₂O (7.09 ml) was stirred at 80° C. in a sealed tube for 1 h. The reaction mixture was then partitioned between H₂O-DCM and the aqueous phase was washed several times with DCM. The combined organic fractions were dried over Na₂SO₄, concentrated and purified via column chromatography (silica, 25% EtOAc in hexanes) affording methyl 5-methyl-4-(1-methyl-1H-pyrazol-5-yl)-2-thiophenecarboxylate. This reaction was run in several b) methyl 4-(4-bromo-1-methyl-1H-pyrazol-5-yl)-5-methyl-2-thiophenecarboxylate

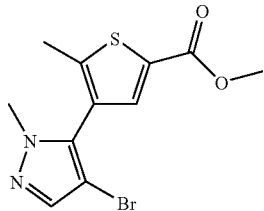

A solution of methyl 5-methyl-4-(1-methyl-1H-pyrazol-5-yl)-2-thiophenecarboxylate (580 mg, 2.45 mmol) and n-bromosuccinimide (437 mg, 2.45 mmol) in tetrahydrofuran (12.300 ml) was stirred in a sealed tube for 1 h at 70° C. The solution was then partitioned between H₂O-DCM and the aqueous phase was washed several times with DCM. The combined organic fractions were dried over Na₂SO₄, concentrated then purified via column chromatography (silica, 20% EtOAc in hexanes) yielding methyl 4-(4-bromo-1-methyl-1H-pyrazol-5-yl)-5-methyl-2-thiophenecarboxylate (600 mg, 1.90 mmol, 78% yield) as a yellow oil: LCMS (ES) m/e 314, 316 (M, M+H)⁺.

c) methyl 4-(1,4-dimethyl-1H-pyrazol-5-yl)-5-methyl-2-thiophenecarboxylate

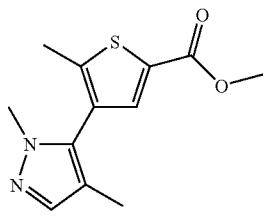

A solution of methyl 4-(4-bromo-1-methyl-1H-pyrazol-5-yl)-5-methyl-2-thiophenecarboxylate (420 mg, 1.33 mmol), potassium carbonate (921 mg, 6.66 mmol), PdCl₂(dppf) (98 mg, 0.13 mmol) and trimethylboroxine (0.371 ml, 2.67 mmol) in N,N-dimethylformamide (6.663 ml) was stirred at 110° C. in a sealed tube for 2 h. This reaction was run in two batches (100 mg and 420 mg) which were combined and partitioned between H₂O-DCM. The aqueous phase was washed several times with DCM and the combined organic fractions were dried over Na₂SO₄, concentrated and purified via column chromatography (10-50% EtOAc in hexanes) affording methyl 4-(1,4-dimethyl-1H-pyrazol-5-yl)-5-methyl-2-thiophenecarboxylate (240 mg, 58%) as a yellow oil: LCMS (ES) m/e 251 (M+H)⁺.

d) 4-(1,4-dimethyl-1H-pyrazol-5-yl)-5-methyl-2-thiophenecarboxylic Acid

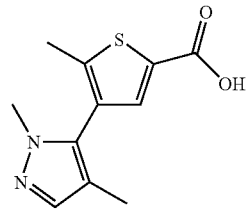

A solution of methyl 4-(1,4-dimethyl-1H-pyrazol-5-yl)-5-methyl-2-thiophenecarboxylate (240 mg, 0.96 mmol) in 6N sodium hydroxide (3.20 ml, 19.18 mmol) and tetrahydrofuran (4.79 ml) was stirred at 70° C. in a sealed tube for 1 h. The resulting solution was cooled and then partitioned between H₂O-DCM. The aqueous phase was adjusted to pH ~4 and then washed several times with DCM. The combined organic fractions were dried over Na₂SO₄ and concentrated affording 4-(1,4-dimethyl-1H-pyrazol-5-yl)-5-methyl-2-thiophenecarboxylic acid (217 mg, 0.92 mmol, 96% yield) as a yellow oil: LCMS (ES) m/e 236 (M+H)⁺.

e) 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-thiophenecarboxamide

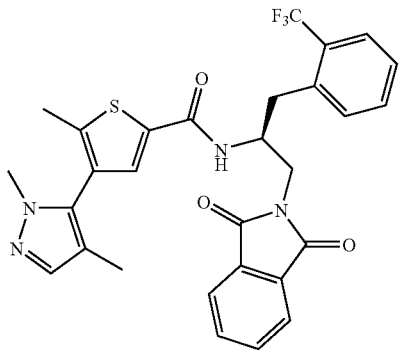 [SMILES: Cc1cnn(C)c1-c1cc(C(=O)N[C@@H](Cc2ccccc2C(F)(F)F)CN2C(=O)c3ccccc3C2=O)sc1C]

To a solution of methyl 4-methyl-5-(1-methyl-1H-pyrazol-5-yl)-2-thiophenecarboxylate (217 mg, 0.918 mmol), 2-{(2S)-2-amino-3-[2-(trifluoromethyl)phenyl]propyl}-1H-isoindole-1,3(2H)-dione (353 mg, 0.92 mmol)[prepared according to Preparation 6] and diisopropylethylamine (0.800 ml, 4.59 mmol) in DCM at 25° C. was added bromo-tris-pyrrolidino-phosphonium hexafluorophosphate (472 mg, 1.01 mmol) in one portion. The solution stirred at 25° C. for 12 h and was then partitioned between H₂O-DCM. The aqueous phase was washed several times with DCM and the combined organic fractions were dried over Na₂SO₄, concentrated and purified via column chromatography (silica, 30-70% EtOAc in hexanes) yielding 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-thiophenecarboxamide (373 mg, 0.66 mmol, 71.7% yield) as a yellow foam: LCMS (ES) m/e 567 (M+H)⁺.

f) N-((1S)-2-amino-1-{[2-(trifluoromethyl)phenyl]methyl}ethyl)-4-(1,4-dimethyl-1H-pyrazol-5-yl)-5-methyl-2-thiophenecarboxamide

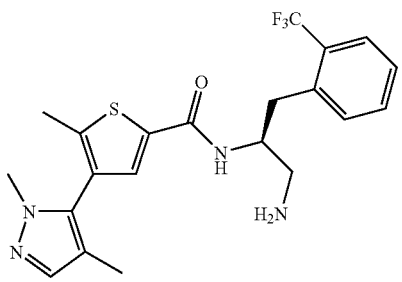 [SMILES: Cc1cnn(C)c1-c1cc(C(=O)N[C@H](CN)Cc2ccccc2C(F)(F)F)sc1C]

To a solution of 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-thiophenecarboxamide (373 mg, 0.66 mmol) in tetrahydrofuran (1.65 ml) and methanol (1.65 ml) at 25° C. was added hydrazine (0.21 ml, 6.58 mmol) dropwise. After 12 h, the solution was concentrated, dry loaded onto silica and purified by column chromatography (5% MeOH in DCM (1% NH₄OH)). The free base was transferred to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(1,4-dimethyl-1H-pyrazol-5-yl)-5-methyl-2-thiophenecarboxamide (253 mg, 0.497 mmol, 75% yield) as a yellow solid: LCMS (ES) m/z=437 (M+H)⁺, ¹H NMR (400 MHz, DMSO-d6) δ ppm 8.80 (d, J=8.59 Hz, 1H) 8.09 (br. s., 3H) 7.82 (s, 1H) 7.69 (d, J=7.83 Hz, 1H) 7.58 (t, J=8.08 Hz, 1H) 7.43 (t, J=7.33 Hz, 1H) 7.38 (s, 1H) 4.47 (br. s., 1H) 3.64 (s, 3H) 2.99-3.07 (m, 4H) 2.27 (s, 3H) 1.89 (s, 3H).

Example 100

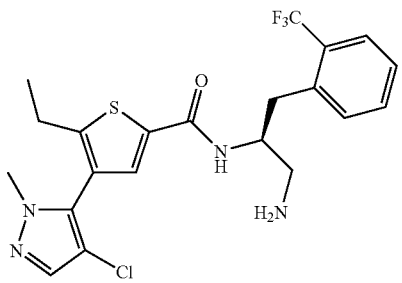 [SMILES: CCc1sc(C(=O)N[C@H](CN)Cc2ccccc2C(F)(F)F)cc1-c1c(Cl)cnn1C]

Preparation of N-((1S)-2-amino-1-{[2-(trifluoromethyl)phenyl]methyl}ethyl)-4-(4-chloro-1-methyl-1H-pyrazol-5-yl)-5-ethyl-2-thiophenecarboxamide a) 4-(4-chloro-1-methyl-1H-pyrazol-5-yl)-5-ethyl-2-thiophenecarboxylic Acid

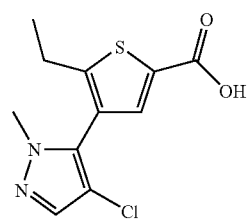

A solution of methyl 5-ethyl-4-(1-methyl-1H-pyrazol-5-yl)-2-thiophenecarboxylate (300 mg, 1.2 mmol) [Prepared in Example 98] and N-chlorosuccinimide (160 mg, 1.2 mmol) in tetrahydrofuran (6 ml) was stirred in a sealed tube for 1 h at 70° C. 6N sodium hydroxide (1 ml, 5.99 mmol) was added in one portion and the solution stirred an additional 1 h. The reaction mixture was then partitioned between H₂O-DCM and the pH of the aqueous phase was adjusted to 4 and washed several times with DCM. The combined organic fractions were dried over Na₂SO₄, concentrated then purified via column chromatography (silica, 20% EtOAC in hexanes) yielding 4-(4-chloro-1-methyl-1H-pyrazol-5-yl)-5-ethyl-2-thiophenecarboxylic acid (325 mg, 1.20 mmol, 100% yield) as a yellow oil: LCMS (ES) m/e 271, 273 (M, M+2)⁺.

b) 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-thiophenecarboxamide

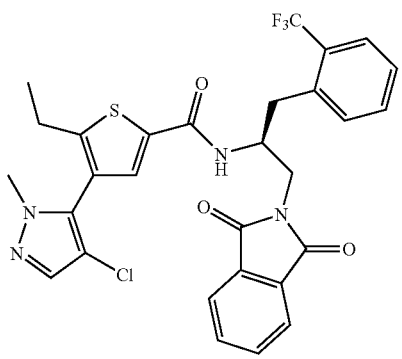 [SMILES: CCc1sc(C(=O)N[C@@H](Cc2ccccc2C(F)(F)F)CN2C(=O)c3ccccc3C2=O)cc1-c1c(Cl)cnn1C]

To a solution of 4-(4-chloro-1-methyl-1H-pyrazol-5-yl)-5-ethyl-2-thiophenecarboxylic acid (200 mg, 0.74 mmol), N,N-diisopropylethylamine (0.64 ml, 3.69 mmol) and 2-{(2S)-2-amino-3-[2-(trifluoromethyl)phenyl]propyl}-1H-isoindole-1,3(2H)-dione (284 mg, 0.74 mmol)[prepared according to Preparation 6] in DCM at 25° C. was added bromo-tris-pyrrolidino-phosphonium hexafluorophosphate (414 mg, 0.886 mmol) in one portion. The solution stirred at 25° C. for 1 h and was then partitioned between H₂O-DCM. The aqueous phase was washed several times with DCM and the combined organic fractions were dried over Na₂SO₄, concentrated and purified via column chromatography (silica, 50% EtOAc in hexanes) yielding 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-thiophenecarboxamide (316 mg, 0.526 mmol, 71% yield) as a white foam: LCMS (ES) m/e 601, 603 (M, M+2)⁺.

c) N-((1S)-2-amino-1-{[2-(trifluoromethyl)phenyl]methyl}ethyl)-4-(4-chloro-1-methyl-1H-pyrazol-5-yl)-5-ethyl-2-thiophenecarboxamide

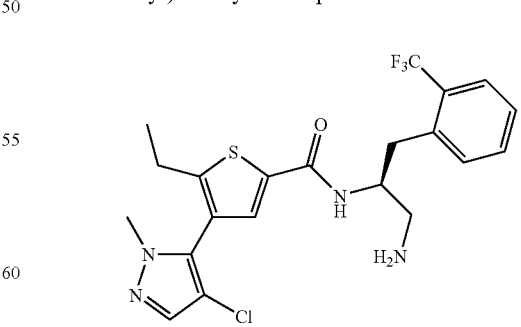

To a solution of 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-thiophenecarboxamide (316 mg, 0.53 mmol) in tetrahydrofuran (1.314 ml) and methanol (1.3 ml) at 25° C. was added hydrazine (0.16 ml, 5.26 mmol) dropwise. After 12 h, the solution was concentrated, purified via column chromatography (silica, 5% MeOH in DCM (1% NH$_4$OH)) and converted to the HCl salt by adding excess 2M HCl in Et$_2$O (2 ml) to the residue in MeOH (5 ml) affording the HCl salt of N-((1S)-2-amino-1-{[2-(trifluoromethyl)phenyl]methyl}ethyl)-4-(4-chloro-1-methyl-1H-pyrazol-5-yl)-5-ethyl-2-thiophenecarboxamide (163 mg, 0.30 mmol, 57% yield) as a white solid: LCMS (ES) m/z=471, 473 (M, M+2)$^+$, $^1$H NMR (400 MHz, DMSO-d6) δ ppm 8.82 (br. s., 1H) 8.04 (bs, 3H) 7.85 (s, 1H) 7.65-7.72 (m, 2H) 7.52-7.59 (m, 2H) 7.39-7.46 (m, 1H) 4.41-4.47 (m, 1H) 3.71 (s, 3H) 2.98-3.07 (m, 4H) 2.67 (q, J=7.58 Hz, 2H) 1.16 (t, J=7.58 Hz, 3H).

Example 101

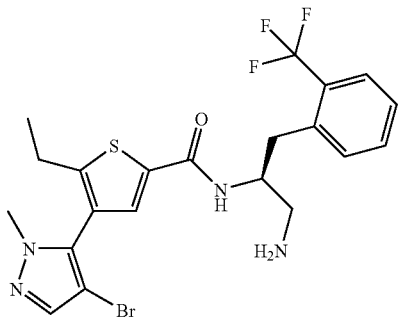

Preparation of N-((1S)-2-amino-1-{[2-(trifluoromethyl)phenyl]methyl}ethyl)-4-(4-bromo-1-methyl-1H-pyrazol-5-yl)-5-ethyl-2-thiophenecarboxamide a) 4-(4-bromo-1-methyl-1H-pyrazol-5-yl)-5-ethyl-2-thiophenecarboxylic Acid

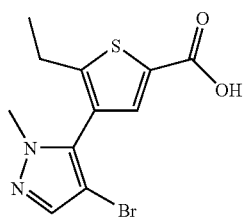

A solution of methyl 5-ethyl-4-(1-methyl-1H-pyrazol-5-yl)-2-thiophenecarboxylate (300 mg, 1.2 mmol) [Prepared in Example 98] and N-bromosuccinimide (213 mg, 1.2 mmol) in Tetrahydrofuran (5.99 ml) was stirred in a sealed tube for 1 h at 70° C. Aqueous sodium hydroxide (4.0 ml, 23.97 mmol) was added in one portion and the solution stirred an additional 1 h. The reaction mixture was then partitioned between H$_2$O-DCM and the pH of the aqueous phase was adjusted to ~4 and washed several times with DCM. The combined organic fractions were dried over Na$_2$SO$_4$, concentrated then purified via column chromatography (silica, 20% EtOAC in hexanes) yielding 4-(4-bromo-1-methyl-1H-pyrazol-5-yl)-5-ethyl-2-thiophenecarboxylic acid (378 mg, 1.2 mmol, 100% yield) as a yellow oil: LCMS (ES) m/e 314, 316 (M, M+2)$^+$.

b) 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-thiophenecarboxamide

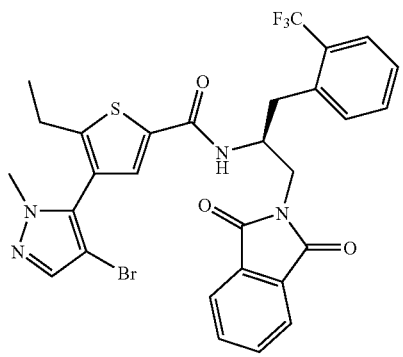

To a solution of 4-(4-bromo-1-methyl-1H-pyrazol-5-yl)-5-ethyl-2-thiophenecarboxylic acid (200 mg, 0.57 mmol), 2-{(2S)-2-amino-3-[2-(trifluoromethyl)phenyl]propyl}-1H-isoindole-1,3(2H)-dione (181 mg, 0.57 mmol) [Prepared according to Preparation 6] and N,N-diisopropylethylamine (0.50 ml, 2.87 mmol) in Dichloromethane (4.23 ml) at 25° C. was added bromo-tris-pyrrolidino-phosphonium hexafluorophosphate (295 mg, 0.632 mmol) in one portion. The solution stirred at 25° C. for 1 h and was then partitioned between H$_2$O-DCM. The aqueous phase was washed several times with DCM and the combined organic fractions were dried over Na$_2$SO$_4$, concentrated and purified via column chromatography (silica, 50% EtOAc in hexanes) yielding 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-thiophenecarboxamide (240 mg, 0.37 mmol, 64.8% yield) as a white foam: LCMS (ES) m/e 645, 647 (M, M+2)$^+$.

c) N-((1S)-2-amino-1-{[2-(trifluoromethyl)phenyl]methyl}ethyl)-4-(4-bromo-1-methyl-1H-pyrazol-5-yl)-5-ethyl-2-thiophenecarboxamide

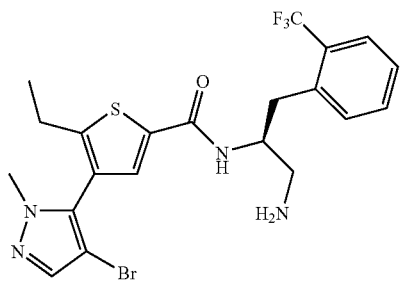 [SMILES: CCc1sc(C(=O)N[C@H](CN)Cc2ccccc2C(F)(F)F)cc1-c1c(Cl)cnn1C]

To a solution of 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-thiophenecarboxamide (240 mg, 0.37 mmol) in tetrahydrofuran (1.31 ml) and methanol (1.31 ml) at 25° C. was added hydrazine (0.12 ml, 3.72 mmol) dropwise. After 12 h, the solution was concentrated, purified via column chromatography (silica, 5% MeOH in DCM (1% NH$_4$OH)) and converted to the HCl salt by adding excess 4M HCl in dioxane (2 ml) to the residue in MeOH (5 ml) affording the HCl salt of N-((1S)-2-amino- 1-{[2-(trifluoromethyl)phenyl]methyl}ethyl)-4-(4-bromo-1-methyl-1H-pyrazol-5-yl)-5-ethyl-2-thiophenecarboxamide (167 mg, 0.28 mmol, 76% yield) as a white solid: LCMS (ES) m/z=515, 517 (M, M+2)+, ¹H NMR (400 MHz, DMSO-d6) δ ppm 8.77 (dd, J=15.66, 9.09 Hz, 1H) 8.02 (br. s., 3H) 7.80 (s, 1H) 7.66-7.72 (m, 2H) 7.54-7.61 (m, 2H) 7.41-7.48 (m, 1H) 4.42-4.47 (m, 1H) 3.71 (s, 3H) 2.98-3.06 (m, 4H) 2.66 (dd, J=7.45, 3.16 Hz, 2H) 1.15 (t, J=7.45 Hz, 3H).

Example 102

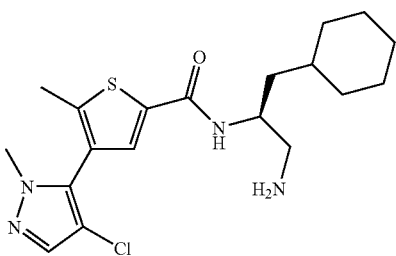 [SMILES: Cc1sc(C(=O)N[C@H](CN)CC2CCCCC2)cc1-c1c(Cl)cnn1C]

Preparation of N-[(1S)-2-amino-1-(cyclohexylmethyl)ethyl]-4-(4-chloro-1-methyl-1H-pyrazol-5-yl)-5-methyl-2-thiophenecarboxamide a) 4-(4-chloro-1-methyl-1H-pyrazol-5-yl)-5-methyl-2-thiophenecarboxylic Acid

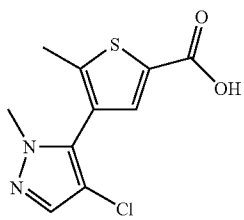

A solution of methyl 5-methyl-4-(1-methyl-1H-pyrazol-5-yl)-2-thiophenecarboxylate (2.75 g, 11.64 mmol) [Prepared in Example 99] and N-chlorosuccinimide (1.55 g, 11.64 mmol) in tetrahydrofuran (58 ml) was stirred in a sealed tube for 1 h at 70° C. Sodium hydroxide (9.70 ml, 58 mmol) was added in one portion and the solution stirred an additional 1 h. The reaction mixture was then partitioned between H₂O-DCM and the pH of the aqueous phase was adjusted to 4 and washed several times with DCM. The combined organic fractions were dried over Na₂SO₄, concentrated then purified via column chromatography (silica, 20% EtOAc in hexanes) yielding 4-(4-chloro-1-methyl-1H-pyrazol-5-yl)-5-methyl-2-thiophenecarboxylic acid (2.3 g, 8.96 mmol, 77% yield) as a yellow oil: LCMS (ES) m/e 257, 259 (M, M+2)+.

b) 4-(4-chloro-1-methyl-1H-pyrazol-5-yl)-N-{(1S)-2-cyclohexyl-1-[(1,3-dioxo-1,3-dihydro-2H-isoindol-2-yl)methyl]ethyl}-5-methyl-2-thiophenecarboxamide

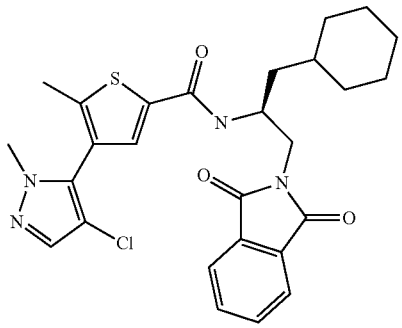 [SMILES: Cc1sc(C(=O)N[C@@H](CC2CCCCC2)CN2C(=O)c3ccccc3C2=O)cc1-c1c(Cl)cnn1C]

To a solution of 4-(4-chloro-1-methyl-1H-pyrazol-5-yl)-5-methyl-2-thiophenecarboxylic acid (159 mg, 0.62 mmol), N,N-diisopropylethylamine (0.54 ml, 3.10 mmol) and 2-[(2S)-2-amino-3-cyclohexylpropyl]-1H-isoindole-1,3 (2H)-dione (200 mg, 0.62 mmol) [Prepared according to the procedure of Preparation 6, except substituting 3-cyclohexyl-N-{[(1,1-dimethylethyl)oxy]carbonyl}-L-alanine (5 g, 18.4 mmol) for N-{[(1,1-dimethylethyl)oxy]carbonyl}-2-(trifluoromethyl)-L-phenylalanine] in DCM at 25° C. was added bromo-tris-pyrrolidino-phosphonium hexafluorophosphate (347 mg, 0.74 mmol) in one portion. The solution stirred at 25° C. for 1 h and was then partitioned between H₂O-DCM. The aqueous phase was washed several times with DCM and the combined organic fractions were dried over Na₂SO₄, concentrated and purified via column chromatography (silica, 45% EtOAc in hexanes) yielding 4-(4-chloro-1-methyl-1H-pyrazol-5-yl)-N-{(1S)-2-cyclohexyl-1-[(1,3-dioxo-1,3-dihydro-2H-isoindol-2-yl)methyl]ethyl}-5-methyl-2-thiophenecarboxamide (231 mg, 0.44 mmol, 71% yield) as a clear oil: LCMS (ES) m/e 525, 527 (M, M+2)+.

c) N-[(1S)-2-amino-1-(cyclohexylmethyl)ethyl]-4-(4-chloro-1-methyl-1H-pyrazol-5-yl)-5-methyl-2-thiophenecarboxamide

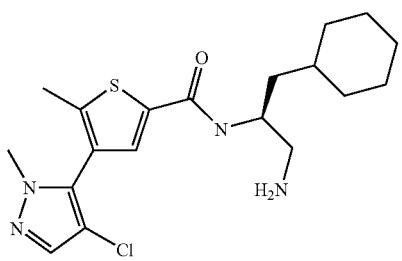 [SMILES: Cc1sc(C(=O)N[C@H](CN)CC2CCCCC2)cc1-c1c(Cl)cnn1C]

To a solution of 4-(4-chloro-1-methyl-1H-pyrazol-5-yl)-N-{(1S)-2-cyclohexyl-1-[(1,3-dioxo-1,3-dihydro-2H-isoindol-2-yl)methyl]ethyl}-5-methyl-2-thiophenecarboxamide (231 mg, 0.44 mmol) in tetrahydrofuran (2.20 ml) and methanol (2.20 ml) at 25° C. was added hydrazine (0.14 ml, 4.40 mmol) dropwise. After 12 h, the solution was concentrated, dry loaded onto silica and purified by column chromatography (5% MeOH in DCM (1% NH₄OH)). The free base was then transferred to the HCl salt adding excess 4M HCl in dioxane (1 ml) to the residue in MeOH (2 ml) affording the HCl salt of N-[(1S)-2-amino-1-(cyclohexyl methyl)ethyl]-4-(4-chloro-1-methyl-1H-pyrazol-5-yl)-5-methyl-2-thiophenecarboxamide (124 mg, 0.27 mmol, 60% yield) as a yellow solid: LCMS (ES) m/z=394, 396 (M, M+2)⁺, ¹H NMR (400 MHz, DMSO-d₆) δ ppm 8.51 (br. s., 1H) 7.97 (br. s., 3H) 7.86 (s, 1H) 7.70 (s, 1H) 4.24-4.26 (m, 1H) 3.71 (s, 3H) 2.90-2.99 (m, 2H) 2.36 (s, 3H) 1.75-1.79 (m, 1H) 1.61 1.64 (m, 4H) 1.48-1.51 (m, 1H) 1.31-1.36 (m, 2H) 1.10-1.14 (m, 2H) 0.91-0.94 (m, 2H).

Example 103

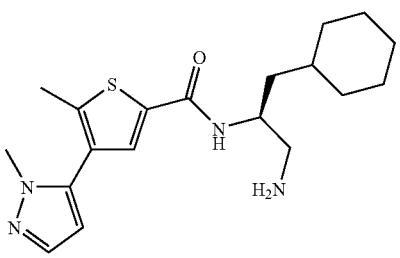 [SMILES: Cc1sc(C(=O)N[C@H](CN)CC2CCCCC2)cc1-c1ccnn1C]

Preparation of N-[(1S)-2-amino-1-(cyclohexylmethyl)ethyl]-5-methyl-4-(1-methyl-1H-pyrazol-5-yl)-2-thiophenecarboxamide a) 5-methyl-4-(1-methyl-1H-pyrazol-5-yl)-2-thiophenecarboxylic Acid

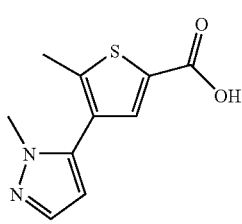

A solution of methyl 5-methyl-4-(1-methyl-1H-pyrazol-5-yl)-2-thiophenecarboxylate (250 mg, 1.06 mmol) [Prepared in Example 99] in 6N sodium hydroxide (1.76 ml, 10.6 mmol) and tetrahydrofuran (5.290 ml) was stirred at 70° C. in a sealed tube for 1 h. The resulting solution was cooled and partitioned between H₂O-DCM. The aqueous phase was adjusted to pH ~4 and then washed several times with DCM. The combined organic fractions were dried over Na₂SO₄ and concentrated affording 5-methyl-4-(1-methyl-1H-pyrazol-5-yl)-2-thiophenecarboxylic acid (151 mg, 0.68 mmol, 64% yield) as a white solid; LCMS (ES) m/z=223 (M+H)⁺.

b) N-{(1S)-2-cyclohexyl-1-[(1,3-dioxo-1,3-dihydro-2H-isoindol-2-yl)methyl]ethyl}-5-methyl-4-(1-methyl-1H-pyrazol-5-yl)-2-thiophenecarboxamide

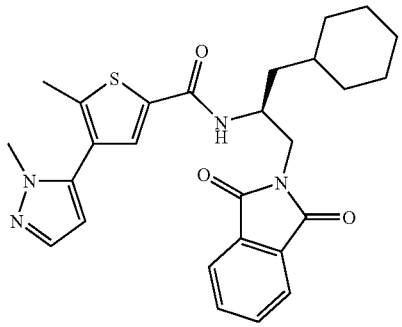

To a solution of 5-methyl-4-(1-methyl-1H-pyrazol-5-yl)-2-thiophenecarboxylic acid (138 mg, 0.62 mmol), N,N-diisopropylethylamine (0.541 ml, 3.10 mmol) and 2-[(2S)-2-amino-3-cyclohexylpropyl]-1H-isoindole-1,3(2H)-dione (200 mg, 0.62 mmol) [Prepared according to the procedure of Preparation 6, except substituting 3-cyclohexyl-N-{[(1,1-dimethylethyl)oxy]carbonyl}-L-alanine (5 g, 18.4 mmol) for N-{[(1,1-dimethylethyl)oxy]carbonyl}-2-(trifluoromethyl)-L-phenylalanine] in DCM at 25° C. was added bromo-tris-pyrrolidino-phosphonium hexafluorophosphate (347 mg, 0.74 mmol) in one portion. The solution stirred at 25° C. for 1 h and was then partitioned between H₂O-DCM. The aqueous phase was washed several times with DCM and the combined organic fractions were dried over Na₂SO₄, concentrated and purified via column chromatography (silica, 50% EtOAc in hexanes) yielding N-{(1S)-2-cyclohexyl-1-[(1,3-dioxo-1,3-dihydro-2H-isoindol-2-yl)methyl]ethyl}-5-methyl-4-(1-methyl-1H-pyrazol-5-yl)-2-thiophenecarboxamide (285 mg, 0.581 mmol, 94% yield) as a white foam: LCMS (ES) m/e 491, 493 (M, M+2)⁺.

c) N-[(1S)-2-amino-1-(cyclohexylmethyl)ethyl]-5-methyl-4-(1-methyl-1H-pyrazol-5-yl)-2-thiophenecarboxamide

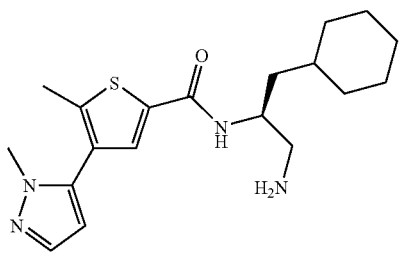 [SMILES: Cc1sc(C(=O)N[C@H](CN)CC2CCCCC2)cc1-c1ccnn1C]

To a solution of N-{(1S)-2-cyclohexyl-1-[(1,3-dioxo-1,3-dihydro-2H-isoindol-2-yl)methyl]ethyl}-5-methyl-4-(1-methyl-1H-pyrazol-5-yl)-2-thiophenecarboxamide (285 mg, 0.581 mmol) in tetrahydrofuran (2.905 ml) and methanol (2.91 ml) at 25° C. was added hydrazine (0.18 ml, 5.81 mmol) dropwise. After 12 h, the solution was concentrated, dry loaded onto silica and purified by column chromatography (5% MeOH in DCM (1% NH₄OH)). The free base was then transferred to the HCl salt by adding excess 4M HCl in dioxane (1 ml) to the residue in MeOH (2 ml) affording the HCl salt of N-[(1S)-2-amino-1-(cyclohexylmethyl)ethyl]-5- methyl-4-(1-methyl-1H-pyrazol-5-yl)-2-thiophenecarboxamide (173 mg, 0.40 mmol, 69% yield) as a yellow solid: LCMS (ES) m/z=360 (M+H)+, 1H NMR (400 MHz, DMSO-d6) δ ppm 8.55 (d, J=8.59 Hz, 1H) 8.01 (br. s., 3) 7.94 (s, 1H) 7.52 (d, J=2.02 Hz, 1H) 6.35 (d, J=1.77 Hz, 1H) 4.24-4.27 (m, 1H) 3.77 (s, 3H) 2.91-2.94 (m, 2H) 2.39 (s, 3H) 1.72-1.77 (m, 1H) 1.60-1.64 (m, 4H) 1.49-1.52 (m, 1H) 1.21-1.29 (m, 2H) 1.15-1.25 (m, 2H) 0.89-0.94 (m, 2H).

Example 104

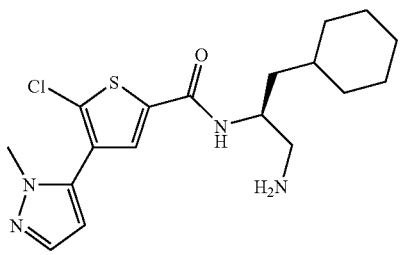 [SMILES: Cn1nccc1-c1cc(C(=O)N[C@H](CN)CC2CCCCC2)sc1Cl]

Preparation of N-[(1S)-2-amino-1-(cyclohexyl methyl)ethyl]-5-chloro-4-(1-methyl-1H-pyrazol-5-yl)-2-thiophenecarboxamide a) 5-chloro-N-{(1S)-2-cyclohexyl-1-[(1,3-dioxo-1,3-dihydro-2H-isoindol-2-yl)methyl]ethyl}-4-(1-methyl-1H-pyrazol-5-yl)-2-thiophenecarboxamide

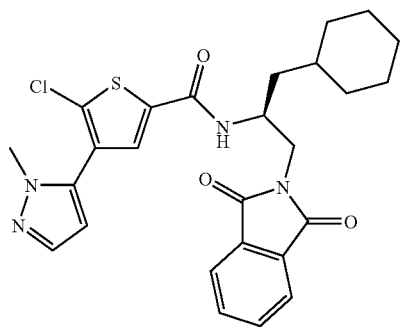 [SMILES: Cn1nccc1-c1cc(C(=O)N[C@@H](CC2CCCCC2)CN2C(=O)c3ccccc3C2=O)sc1Cl]

To a solution of 5-chloro-4-(1-methyl-1H-pyrazol-5-yl)-2-thiophenecarboxylic acid (150 mg, 0.62 mmol) [Prepared in Example 95], N,N-diisopropylethylamine (0.54 ml, 3.10 mmol) and 2-[(2S)-2-amino-3-cyclohexylpropyl]-1H-isoindole-1,3(2H)-dione (200 mg, 0.62 mmol) [Prepared according to the procedure of Preparation 6, except substituting 3-cyclohexyl-N-{[(1,1-dimethylethyl)oxy]carbonyl}-L-alanine (5 g, 18.4 mmol) for N-{[(1,1-dimethylethyl)oxy]carbonyl}-2-(trifluoromethyl)-L-phenylalanine] in DCM at 25° C. was added bromo-tris-pyrrolidino-phosphonium hexafluorophosphate (347 mg, 0.74 mmol) in one portion. The solution stirred at 25° C. for 1 h and was then partitioned between H2O-DCM. The aqueous phase was washed several times with DCM and the combined organic fractions were dried over Na2SO4, concentrated and purified via column chromatography (silica, 45% EtOAc in hexanes) yielding 5-chloro-N-{(1S)-2-cyclohexyl-1-[(1,3-dioxo-1,3-dihydro-2H-isoindol-2-yl)methyl]ethyl}-4-(1-methyl-1H-pyrazol-5-yl)-2-thiophenecarboxamide (168 mg, 0.33 mmol, 53% yield) as a clear oil: LCMS (ES) m/e 511, 513 (M, M+2)+.

b) N-[(1S)-2-amino-1-(cyclohexylmethyl)ethyl]-5-chloro-4-(1-methyl-1H-pyrazol-5-yl)-2-thiophenecarboxamide

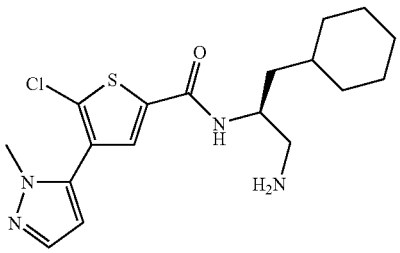 [SMILES: Cn1nccc1-c1cc(C(=O)N[C@H](CN)CC2CCCCC2)sc1Cl]

To a solution of 5-chloro-N-{(1S)-2-cyclohexyl-1-[(1,3-dioxo-1,3-dihydro-2H-isoindol-2-yl)methyl]ethyl}-4-(1-methyl-1H-pyrazol-5-yl)-2-thiophenecarboxamide (168 mg, 0.33 mmol) in tetrahydrofuran (1.644 ml) and methanol (1.644 ml) at 25° C. was added hydrazine (0.10 ml, 3.29 mmol) dropwise. After 12 h, the solution was concentrated, dry loaded onto silica and purified by column chromatography (silica, 5% MeOH in DCM (1% NH4OH)). The free base was then transferred to the HCl salt adding excess 4M HCl in dioxane (1 mL) to the residue in MeOH (2 ml) affording the HCl salt of N-[(1S)-2-amino-1-(cyclohexylmethyl)ethyl]-5-chloro-4-(1-methyl-1H-pyrazol-5-yl)-2-thiophenecarboxamide (79 mg, 0.17 mmol, 53% yield) as a yellow solid: LCMS (ES) m/z=380, 382 (M, M+2)+, 1H NMR (400 MHz, DMSO-d6) δ ppm 8.82 (d, J=8.59 Hz, 1H) 8.10 (s, 1H) 7.99 (br. s., 3H) 7.55 (d, J=1.77 Hz, 1H) 6.48 (d, J=2.02 Hz, 1H) 4.22-4.28 (m, 1H) 3.81 (s, 3H) 2.90-2.95 (m, 2H) 1.74-1.78 (m, 1H) 1.62-1.65 (m, 4H) 1.48-1.51 (m, 1H) 1.37-1.39 (m, 2H) 1.09-1.13 (m, 2H) 0.92-0.96 (m, 2H).

Example 105

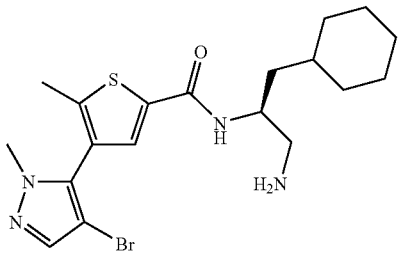

Preparation of N-[(1S)-2-amino-1-(cyclohexylmethyl)ethyl]-4-(4-bromo-1-methyl-1H-pyrazol-5-yl)-5-methyl-2-thiophenecarboxamide a) 4-(4-bromo-1-methyl-1H-pyrazol-5-yl)-5-methyl-2-thiophenecarboxylic Acid

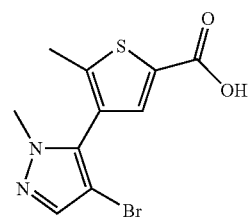 [SMILES: Cc1sc(C(=O)O)cc1-c1c(Br)cnn1C]

A solution of methyl 5-methyl-4-(1-methyl-1H-pyrazol-5-yl)-2-thiophenecarboxylate (250 mg, 1.058 mmol)[prepared in Example 99] and N-bromosuccinimide (188 mg, 1.06 mmol) in tetrahydrofuran (5.29 ml) was stirred in a sealed tube for 1 h at 70° C. Sodium hydroxide (3.53 ml, 21.16 mmol) was added in one portion and the solution stirred an additional 1 h. The reaction mixture was then partitioned between H₂O-DCM and the pH of the aqueous phase was adjusted to 4 and washed several times with DCM. The combined organic fractions were dried over Na₂SO₄ and concentrated yielding 4-(4-bromo-1-methyl-1H-pyrazol-5-yl)-5-methyl-2-thiophenecarboxylic acid (289 mg, 0.96 mmol, 91% yield) as a yellow oil: LCMS (ES) m/e 301, 303 (M, M+2)⁺.

b) 4-(4-bromo-1-methyl-1H-pyrazol-5-yl)-N-{(1S)-2-cyclohexyl-1-[(1,3-dioxo-1,3-dihydro-2H-isoindol-2-yl)methyl]ethyl}-5-methyl-2-thiophenecarboxamide

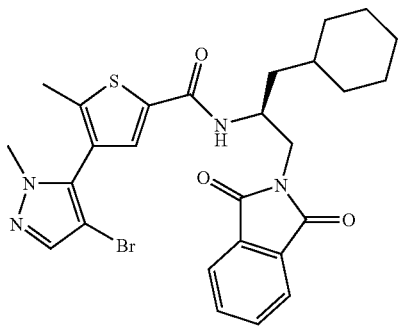

To a solution of 4-(4-bromo-1-methyl-1H-pyrazol-5-yl)-5-methyl-2-thiophenecarboxylic acid (187 mg, 0.62 mmol), N,N-diisopropylethylamine (0.54 ml, 3.10 mmol) and 2-[(2S)-2-amino-3-cyclohexylpropyl]-1H-isoindole-1,3(2H)-dione (200 mg, 0.62 mmol)) [Prepared according to the procedure of Preparation 6, except substituting 3-cyclohexyl-N-{[(1,1-dimethylethyl)oxy]carbonyl}-L-alanine (5 g, 18.4 mmol) for N-{[(1,1-dimethylethyl)oxy]carbonyl}-2-(trifluoromethyl)-L-phenylalanine] in DCM at 25° C. was added bromo-tris-pyrrolidino-phosphonium hexafluorophosphate (347 mg, 0.74 mmol) in one portion. The solution stirred at 25° C. for 1 h and was then partitioned between H₂O-DCM. The aqueous phase was washed several times with DCM and the combined organic fractions were dried over Na₂SO₄, concentrated and purified via column chromatography (silica, 50% EtOAc in hexanes) yielding 4-(4-bromo-1-methyl-1H-pyrazol-5-yl)-N-{(1S)-2-cyclohexyl-1-[(1,3-dioxo-1,3-dihydro-2H-isoindol-2-yl)methyl]ethyl}-5-methyl-2-thiophenecarboxamide (226 mg, 0.40 mmol, 64% yield) as a white foam: LCMS (ES) m/e 569, 571 (M, M+2)⁺.

c) N-[(1S)-2-amino-1-(cyclohexylmethyl)ethyl]-4-(4-bromo-1-methyl-1H-pyrazol-5-yl)-5-methyl-2-thiophenecarboxamide

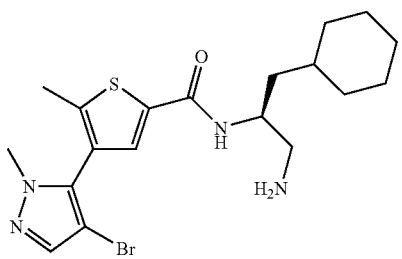

To a solution of 4-(4-bromo-1-methyl-1H-pyrazol-5-yl)-N-{(1S)-2-cyclohexyl-1-[(1,3-dioxo-1,3-dihydro-2H-isoindol-2-yl)methyl]ethyl}-5-methyl-2-thiophenecarboxamide (226 mg, 0.40 mmol) in tetrahydrofuran (1.98 ml) and methanol (1.98 ml) at 25° C. was added hydrazine (0.13 ml, 3.97 mmol) dropwise. After 12 h, the solution was concentrated, dry loaded onto silica and purified by column chromatography. The free base was then transferred to the HCl salt adding excess 4M HCl in dioxane (1 ml) to the residue in MeOH (2 ml) affording the HCl salt of N-[(1S)-2-amino-1-(cyclohexylmethyl)ethyl]-4-(4-bromo-1-methyl-1H-pyrazol-5-yl)-5-methyl-2-thiophenecarboxamide (153 mg, 0.30 mmol, 75% yield) as a yellow solid: LCMS (ES) m/z=439, 441 (M, M+2)⁺, ¹H NMR (400 MHz, DMSO-d₆) δ ppm 8.51 (br. s., 1H) 7.96 (br. s., 3H) 7.83 (br. s., 1H) 7.70 (s, 1H) 4.21-4.25 (m, 1H) 3.94 (s, 3H) 2.89-2.92 (m, 2H) 2.35 (s, 3H) 1.76-1.79 (m, 1H) 1.60-1.64 (m, 4H) 1.48-1.54 (m, 1H) 1.26-1.32 (m, 2H) 1.09-1.16 (m, 2H) 0.92-0.95 (m, 1H) 0.82-0.86 (m, 1H).

Example 106

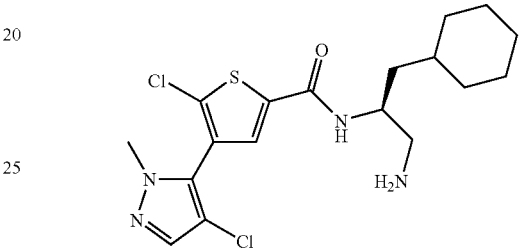

Preparation of N-[(1S)-2-amino-1-(cyclohexylmethyl)ethyl]-5-chloro-4-(4-chloro-1-methyl-1H-pyrazol-5-yl)-2-thiophenecarboxamide a) 5-chloro-4-(4-chloro-1-methyl-1H-pyrazol-5-yl)-N-{(1S)-2-cyclohexyl-1-[(1,3-dioxo-1,3-dihydro-2H-isoindol-2-yl)methyl]ethyl}-2-thiophenecarboxamide

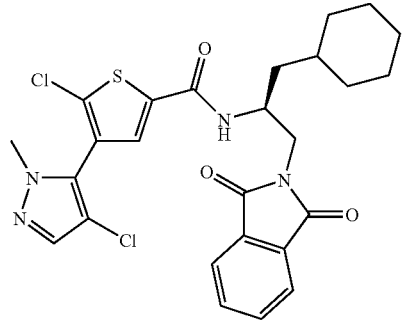 [SMILES: Cn1ncc(Cl)c1-c1cc(C(=O)N[C@@H](CC2CCCCC2)CN2C(=O)c3ccccc3C2=O)sc1Cl]

To a solution of 5-chloro-4-(4-chloro-1-methyl-1H-pyrazol-5-yl)-2-thiophenecarboxylic acid (216 mg, 0.78 mmol) [prepared according to Example 96], N,N-diisopropylethylamine (0.68 ml, 3.90 mmol) and 2-[(2S)-2-amino-3-cyclohexylpropyl]-1H-isoindole-1,3(2H)-dione (252 mg, 0.78 mmol) [Prepared according to the procedure of Preparation 6, except substituting 3-cyclohexyl-N-{[(1,1-dimethylethyl)oxy]carbonyl}-L-alanine (5 g, 18.4 mmol) for N-{[(1,1-dimethylethyl)oxy]carbonyl}-2-(trifluoromethyl)-L-phenylalanine] in DCM at 25° C. was added bromo-tris-pyrrolidino-phosphonium hexafluorophosphate (401 mg, 0.86 mmol) in one portion. The solution stirred at 25° C. for 12 h and was then partitioned between H₂O-DCM. The aqueous phase was washed several times with DCM and the combined organic fractions were dried over Na₂SO₄, concentrated and purified via column chromatography (silica, 40% EtOAc in hexanes) yielding 5-chloro-4-(4-chloro-1-methyl-1H-pyrazol-5-yl)-N-{(1S)-2-cyclohexyl-1-[(1,3-dioxo-1,3-dihydro-2H-isoindol-2-yl)methyl]ethyl}-2-thiophenecarboxamide (303 mg, 0.55 mmol, 71% yield) as a clear oil: LCMS (ES) m/e 545, 547 (M, M+2)⁺.

b) N-[(1S)-2-amino-1-(cyclohexylmethyl)ethyl]-5-chloro-4-(4-chloro-1-methyl-1H-pyrazol-5-yl)-2-thiophenecarboxamide

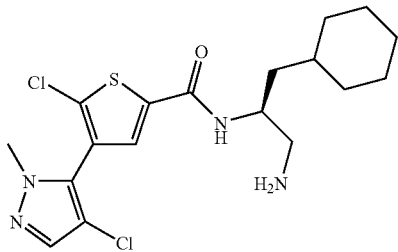

To a solution of 5-chloro-4-(4-chloro-1-methyl-1H-pyrazol-5-yl)-N-{(1S)-2-cyclohexyl-1-[(1,3-dioxo-1,3-dihydro-2H-isoindol-2-yl)methyl]ethyl}-2-thiophenecarboxamide (303 mg, 0.55 mmol) in tetrahydrofuran (2.78 ml) and methanol (2.78 ml) at 25° C. was added hydrazine (0.17 ml, 5.55 mmol) dropwise. After 12 h, the solution was concentrated, dry loaded onto silica and purified by column chromatography (5% MeOH in DCM (1% NH₄OH)). The free base was then converted to the HCl salt by adding excess 4M HCl in dioxane (1 ml) to the residue in MeOH (2 ml) affording the HCl salt of N-[(1S)-2-amino-1-(cyclohexyl methyl)ethyl]-5-chloro-4-(4-chloro-1-methyl-1H-pyrazol-5-yl)-2-thiophenecarboxamide (190 mg, 0.389 mmol, 70.0% yield) as a yellow solid: LCMS (ES) m/z=415, 417 (M, M+2)⁺, ¹H NMR (400 MHz, DMSO-d₆) δ ppm 8.84 (br. s., 1H) 8.06 (s, 4H) 7.74 (s, 1H) 4.25 (dd, J=8.84, 4.29 Hz, 1H) 3.77 (s, 3H) 2.87-2.93 (m, 2H) 1.71-1.79 (m, 1H) 1.64 (d, J=9.85 Hz, 3H) 1.54 (br. s., 1H) 1.48 (br. s., 1H) 1.37 (dd, J=13.26, 4.93 Hz, 1H) 1.14 (br. s., 1H) 1.17 (d, J=7.33 Hz, 2H) 0.93 (d, J=10.86 Hz, 1H) 0.82-0.89 (m, 1H).

Example 107

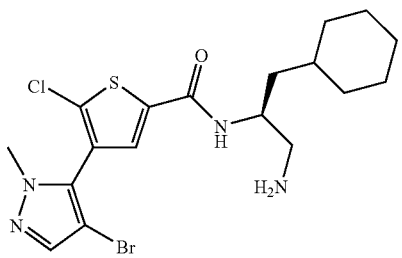 [SMILES: Cn1ncc(Br)c1-c1cc(C(=O)N[C@H](CN)CC2CCCCC2)sc1Cl]

Preparation of N-[(1S)-2-amino-1-(cyclohexylmethyl)ethyl]-4-(4-bromo-1-methyl-1H-pyrazol-5-yl)-5-chloro-2-thiophenecarboxamide a) 4-(4-bromo-1-methyl-1H-pyrazol-5-yl)-5-chloro-2-thiophenecarboxylic Acid

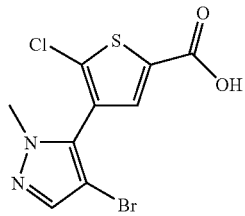

A solution of 5-chloro-4-(1-methyl-1H-pyrazol-5-yl)-2-thiophenecarboxylic acid (50 mg, 0.21 mmol)[prepared in Example 95] and NBS (36.7 mg, 0.21 mmol) in tetrahydrofuran (2.06 ml) was stirred in a sealed tube for 1 h at 70° C. The reaction mixture was then partitioned between H₂O-DCM and the aqueous phase was washed several times with DCM. The combined organic fractions were dried over Na₂SO₄ and concentrated yielding 4-(4-bromo-1-methyl-1H-pyrazol-5-yl)-5-chloro-2-thiophenecarboxylic acid (82 mg, 0.16 mmol, 79% yield) as a yellow oil: LCMS (ES) m/e 257, 259 (M, M+2)⁺.

b) 4-(4-bromo-1-methyl-1H-pyrazol-5-yl)-5-chloro-N-{(1S)-2-cyclohexyl-1-[(1,3-dioxo-1,3-dihydro-2H-isoindol-2-yl)methyl]ethyl}-2-thiophenecarboxamide

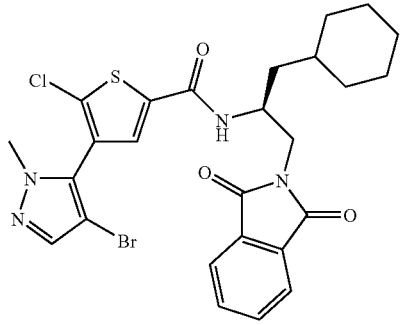

To a solution of 4-(4-bromo-1-methyl-1H-pyrazol-5-yl)-5-chloro-2-thiophenecarboxylic acid (81 mg, 0.252 mmol), n,n-diisopropylethylamine (0.22 ml, 1.26 mmol) and 2-[(2S)-2-amino-3-cyclohexylpropyl]-1H-isoindole-1,3(2H)-dione (81 mg, 0.25 mmol) in DCM at 25° C. was added bromo-tris-pyrrolidino-phosphonium hexafluorophosphate (141 mg, 0.302 mmol) in one portion. The solution stirred at 25° C. for 12 h and was then partitioned between H₂O-DCM. The aqueous phase was washed several times with DCM and the combined organic fractions were dried over Na₂SO₄, concentrated and purified via column chromatography (silica, 40% EtOAc in hexanes) yielding 4-(4-bromo-1-methyl-1H-pyrazol-5-yl)-5-chloro-N-{(1S)-2-cyclohexyl-1-[(1,3-dioxo-1,3-dihydro-2H-isoindol-2-yl)methyl]ethyl}-2-thiophenecarboxamide (47 mg, 0.080 mmol, 31.6% yield) as a clear oil: LCMS (ES) m/e 589, 591 (M, M+2)⁺.

c) N-[(1S)-2-amino-1-(cyclohexylmethyl)ethyl]-4-(4-bromo-1-methyl-1H-pyrazol-5-yl)-5-chloro-2-thiophenecarboxamide

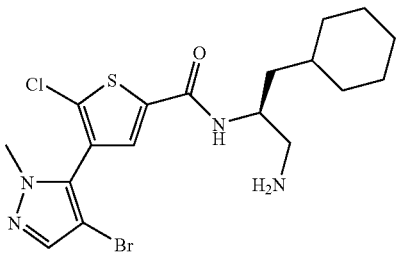 [SMILES: Cn1ncc(Br)c1-c1cc(C(=O)N[C@H](CN)CC2CCCCC2)sc1Cl]

To a solution of 4-(4-bromo-1-methyl-1H-pyrazol-5-yl)-5-chloro-N-{(1S)-2-cyclohexyl-1-[(1,3-dioxo-1,3-dihydro-2H-isoindol-2-yl)methyl]ethyl}-2-thiophenecarboxamide (48 mg, 0.08 mmol) in tetrahydrofuran (0.41 ml) and methanol (0.41 ml) at 25° C. was added hydrazine (0.03 ml, 0.81 mmol) dropwise. After 12 h, the solution was concentrated, dry loaded onto silica and purified by column chromatography (5% MeOH in DCM (1% NH$_4$OH)). The free base was then converted to the HCl salt by adding excess 4M HCl in dioxane (1 ml) to the residue in MeOH (2 ml) affording the HCl salt of N-[(1S)-2-amino-1-(cyclohexylmethyl)ethyl]-4-(4-bromo-1-methyl-1H-pyrazol-5-yl)-5-chloro-2-thiophenecarboxamide (11 mg, 0.02 mmol, 24% yield) as a yellow solid: LCMS (ES) m/z=459, 461 (M, M+2)$^+$, $^1$H NMR (400 MHz, DMSO-d$_6$) δ ppm 8.73 (br. s., 1H) 7.96 (br. s., 4H) 7.74 (s, 1H) 4.21-4.26 (m, 1H) 3.77 (s, 3H) 2.92-2.99 (m, 2H) 1.73-1.79 (m, 1H) 1.62-1.67 (m, 4H) 1.49-1.51 (m, 1H) 1.25 (br. s., 2H) 1.06-1.13 (m, 2H) 0.95 (d, J=6.82 Hz, 1H) 0.82-0.89 (m, 1H).

Example 108

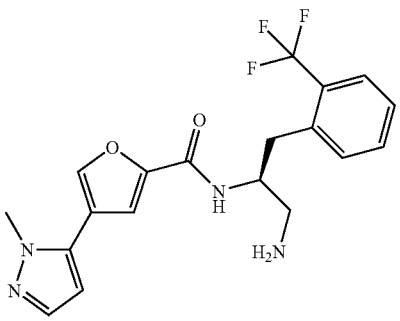 [SMILES: Cn1nccc1-c1coc(C(=O)N[C@H](CN)Cc2ccccc2C(F)(F)F)c1]

Preparation of N-((1S)-2-amino-1-{[2-(trifluoromethyl)phenyl]methyl}ethyl)-4-(1-methyl-1H-pyrazol-5-yl)-2-furancarboxamide a) methyl 4,5-dibromo-2-furancarboxylate

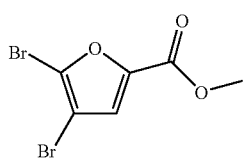

To a solution of 4,5-dibromo-2-furancarboxylic acid (5.7 g, 21.1 mmol) in methanol (106 ml) was added sulfuric acid (11.3 ml, 211 mmol). The resulting solution stirred at 50° C. over 4 days. The reaction mixture was partitioned between H$_2$O-DCM and the aqueous phase was washed several times with DCM. The combined organic fractions were dried over Na$_2$SO$_4$, concentrated and used directly without further purification providing methyl 4,5-dibromo-2-furancarboxylate (5.5 g, 19.4 mmol, 92% yield): LCMS (ES) m/e 283 (M+H)$^+$.

b) methyl 4-bromo-2-furancarboxylate

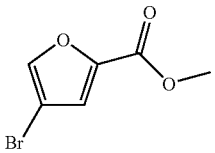

To a solution of methyl 4,5-dibromo-2-furancarboxylate (1 g, 3.52 mmol) in tetrahydrofuran (14.1 ml) at −40° C. was added isopropylmagnesium chloride (1.85 ml, 3.70 mmol). After 2 h, H$_2$O (3.52 ml) was added and the solution warmed to 25° C. The reaction mixture was then partitioned between H$_2$O-DCM and the aqueous phase was washed several times with DCM. The combined organic fractions were dried over Na$_2$SO$_4$, concentrated and purified by column chromatography (3% EtOAc in hexanes) affording methyl 4-bromo-2-furancarboxylate (470 mg, 2.04 mmol, 58% yield) as a white solid: LCMS (ES) m/e 204, 206 (M, M+2)$^+$.

c) methyl 4-(1-methyl-1H-pyrazol-5-yl)-2-furancarboxylate

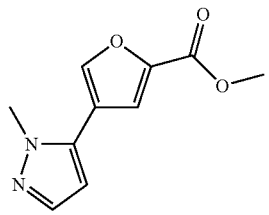

A solution of methyl 4-bromo-2-furancarboxylate (470 mg, 2.29 mmol), potassium carbonate (1.58 g, 11.46 mmol), 1-methyl-5-(4,4,5,5-tetramethyl-1,3,2-dioxaborolan-2-yl)-1H-pyrazole (525 mg, 2.52 mmol)[prepared according to Preparation 7] and bis(tri-t-butylphosphine)palladium(0) (58.6 mg, 0.115 mmol) in 1,4-Dioxane (9.5 ml) and water (1.9 ml) was stirred at 80° C. in a sealed tube for 1 h. The solution was partitioned between H$_2$O-DCM and the aqueous phase was washed several times with DCM. The combined organic fractions were dried over Na$_2$SO$_4$, concentrated and purified via column chromatography (30% EtOAc in hexanes) affording methyl 4-(1-methyl-1H-pyrazol-5-yl)-2-furancarboxylate (124 mg, 0.60 mmol, 26% yield) as a white powder: LCMS (ES) m/e 206 (M+H)$^+$.

d) 4-(1-methyl-1H-pyrazol-5-yl)-2-furancarboxylic Acid

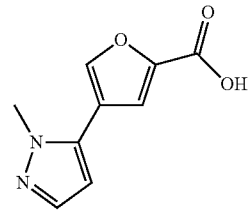

A solution of methyl 4-(1-methyl-1H-pyrazol-5-yl)-2-furancarboxylate (124 mg, 0.60 mmol) in 6N sodium hydroxide (2.0 ml, 12.0 mmol) and tetrahydrofuran (3.0 ml) was stirred at 70° C. in a sealed tube for 2 h. The resulting solution was cooled and then partitioned between H₂O-DCM. The aqueous phase was adjusted to pH ~4 and then washed several times with DCM. The combined organic fractions were dried over Na₂SO₄ and concentrated affording 4-(1-methyl-1H-pyrazol-5-yl)-2-furancarboxylic acid (54 mg, 0.28 mmol, 47% yield) as a white solid: LCMS (ES) m/e 192 (M+H)⁺.

e) N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)-2-furancarboxamide

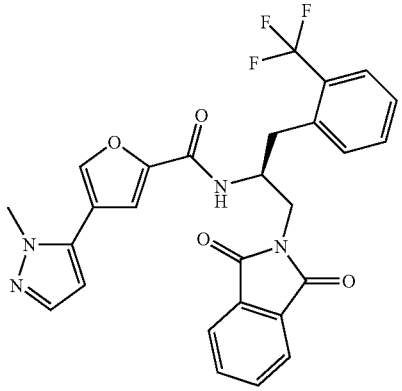 [SMILES: Cn1nccc1-c1coc(C(=O)N[C@@H](Cc2ccccc2C(F)(F)F)CN2C(=O)c3ccccc3C2=O)c1]

To a solution of 4-(1-methyl-1H-pyrazol-5-yl)-2-furancarboxylic acid (54 mg, 0.28 mmol), 2-{(2S)-2-amino-3-[2-(trifluoromethyl)phenyl]propyl}-1H-isoindole-1,3(2H)-dione (108 mg, 0.28 mmol)[prepared in Preparation 6] and N,N-diisopropylethylamine (0.24 ml, 1.40 mmol) in DCM at 25° C. was added bromo-tris-pyrrolidino-phosphonium hexafluorophosphate (158 mg, 0.34 mmol) in one portion. The solution stirred at 25° C. for 1 h and was then partitioned between H₂O-DCM. The aqueous phase was washed several times with DCM and the combined organic fractions were dried over Na₂SO₄, concentrated and purified via column chromatography (silica, 50% EtOAc in hexanes) yielding N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)-2-furancarboxamide (100 mg, 0.14 mmol, 50% yield) as a white solid: LCMS (ES) m/e 523 (M+H)⁺.

f) N-((1S)-2-amino-1-{[2-(trifluoromethyl)phenyl]methyl}ethyl)-4-(1-methyl-1H-pyrazol-5-yl)-2-furancarboxamide

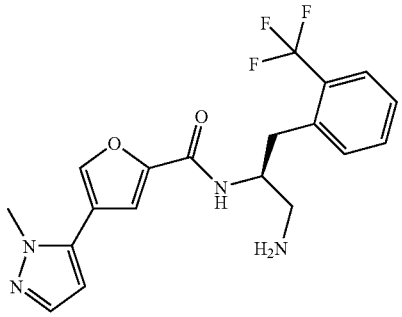 [SMILES: Cn1nccc1-c1coc(C(=O)N[C@H](CN)Cc2ccccc2C(F)(F)F)c1]

To a solution of N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)-2-furancarboxamide (100 mg, 0.19 mmol) in tetrahydrofuran (1 ml) and methanol (1 ml) at 25° C. was added hydrazine (0.06 ml, 1.91 mmol) dropwise. After 12 h, the solution was concentrated, dry loaded onto silica and purified by column chromatography (5% MeOH in DCM (1% NH₄OH)). The free base was transferred to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(1-methyl-1H-pyrazol-5-yl)-2-furancarboxamide (56 mg, 0.12 mmol, 62% yield) as a yellow solid: LCMS (ES) m/z=393 (M+H)⁺, ¹H NMR (400 MHz, DMSO-d₆) δ ppm 8.70 (d, J=9.09 Hz, 1H) 8.28 (s, 1H) 8.07 (br. s., 3H) 7.69 (d, J=8.08 Hz, 1H) 7.56 (d, J=8.08 Hz, 2H) 7.50 (s, 1H) 7.45 (d, J=1.77 Hz, 2H) 6.51 (d, J=1.77 Hz, 1H) 4.50-4.57 (m, 1H) 3.93 (s, 3H) 3.02-3.16 (m, 4H).

Example 109

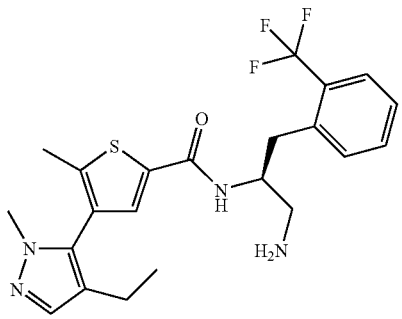 [SMILES: CCc1cnn(C)c1-c1cc(C(=O)N[C@H](CN)Cc2ccccc2C(F)(F)F)sc1C]

Preparation of N-((1S)-2-amino-1-{[2-(trifluoromethyl)phenyl]methyl}ethyl)-4-(4-ethyl-1-methyl-1H-pyrazol-5-yl)-5-methyl-2-thiophenecarboxamide a) methyl 4-(4-ethenyl-1-methyl-1H-pyrazol-5-yl)-5-methyl-2-thiophenecarboxylate

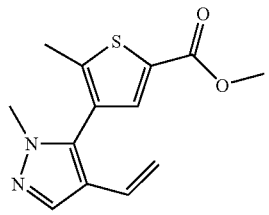

A solution of methyl 4-(4-bromo-1-methyl-1H-pyrazol-5-yl)-5-methyl-2-thiophenecarboxylate (200 mg, 0.64 mmol) [prepared in Example 99], potassium carbonate (438 mg, 3.17 mmol), bis(tri-t-butylphosphine)palladium(0) (324 mg, 0.64 mmol) and 2,4,6-trivinylcycloboroxane-pyridine complex (77 mg, 0.32 mmol) in 1,4-dioxane (5.3 ml) and H₂O (1 ml) was stirred at 80° C. in a sealed tube for 12 h. The reaction contents were partitioned between H₂O-DCM and the aqueous phase was washed several times with DCM. The combined organic fractions were dried over Na₂SO₄, concentrated and purified via column chromatography (10-50% EtOAc in hexanes) affording methyl 4-(4-ethenyl-1-methyl-1H-pyrazol-5-yl)-5-methyl-2-thiophenecarboxylate (135 mg, 0.515 mmol, 81% yield) as a yellow oil: LCMS (ES) m/z=250 (M+H)⁺.

b) methyl 4-(4-ethyl-1-methyl-1H-pyrazol-5-yl)-5-methyl-2-thiophenecarboxylate

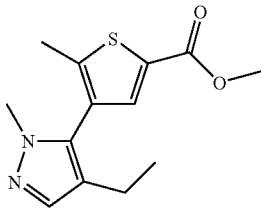

To a solution of methyl 4-(4-ethenyl-1-methyl-1H-pyrazol-5-yl)-5-methyl-2-thiophenecarboxylate (135 mg, 0.52 mmol) in methanol (2.6 ml) was added Pd—C (21.9 mg, 0.21 mmol). The reaction mixture was hydrogenated at 1 atm (balloon) for 1 h. The solution was then purged with $N_2$, filtered through Celite and concentrated affording methyl 4-(4-ethyl-1-methyl-1H-pyrazol-5-yl)-5-methyl-2-thiophenecarboxylate (145 mg, 0.51 mmol, 99% yield) as a yellow oil which was used without further purification: LCMS (ES) m/e 265 (M+H)+.

c) 4-(4-ethyl-1-methyl-1H-pyrazol-5-yl)-5-methyl-2-thiophenecarboxylic Acid

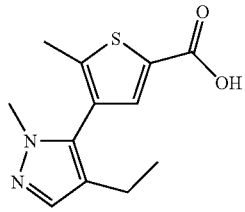 [SMILES: CCc1cnn(C)c1-c1cc(C(=O)O)sc1C]

A solution of methyl 4-(4-ethyl-1-methyl-1H-pyrazol-5-yl)-5-methyl-2-thiophenecarboxylate (145 mg, 0.55 mmol) in 6N sodium hydroxide (1.8 ml, 10.97 mmol) and tetrahydrofuran (4.8 ml) was stirred at 60° C. in a sealed tube for 12 h. The resulting solution was cooled and then partitioned between $H_2O$-DCM. The aqueous phase was adjusted to pH ~4 and then washed several times with DCM. The combined organic fractions were dried over $Na_2SO_4$ and concentrated affording 4-(4-ethyl-1-methyl-1H-pyrazol-5-yl)-5-methyl-2-thiophenecarboxylic acid (137 mg, 0.55 mmol, 100% yield) as a yellow oil: LCMS (ES) m/e 250 (M+H)+.

d) N-((1S)-2-(1,3-dioxo-1,3-dihydro-2H-isoindol-2-yl)-1-{[2-(trifluoromethyl)phenyl]methyl}ethyl)-4-(4-ethyl-1-methyl-1H-pyrazol-5-yl)-5-methyl-2-thiophenecarboxamide

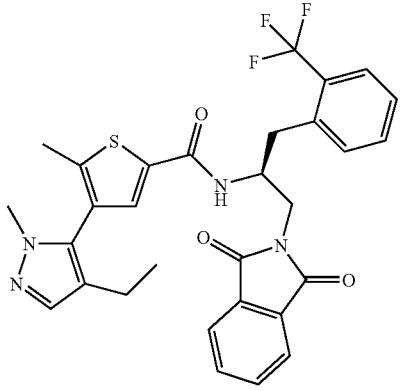 [SMILES: CCc1cnn(C)c1-c1cc(C(=O)N[C@@H](Cc2ccccc2C(F)(F)F)CN2C(=O)c3ccccc3C2=O)sc1C]

To a solution of 4-(4-ethyl-1-methyl-1H-pyrazol-5-yl)-5-methyl-2-thiophenecarboxylic acid (137 mg, 0.55 mmol), 2-{(2S)-2-amino-3-[2-(trifluoromethyl)phenyl]propyl}-1H-isoindole-1,3(2H)-dione (211 mg, 0.55 mmol)[prepared in Preparation 6] and diisopropylethylamine (0.48 ml, 2.74 mmol) in Dichloromethane (5.47 ml) at 25° C. was added bromo-tris-pyrrolidino-phosphonium hexafluorophosphate (281 mg, 0.60 mmol) in one portion. The solution stirred at 25° C. for 1 h and was then partitioned between $H_2O$-DCM. The aqueous phase was washed several times with DCM and the combined organic fractions were dried over $Na_2SO_4$, concentrated and purified via column chromatography (silica, 40-70% EtOAc in hexanes) yielding N-((1S)-2-(1,3-dioxo-1,3-dihydro-2H-isoindol-2-yl)-1-{[2-(trifluoromethyl)phenyl]methyl}ethyl)-4-(4-ethyl-1-methyl-1H-pyrazol-5-yl)-5-methyl-2-thiophenecarboxamide (262 mg, 0.45 mmol, 82% yield) as a clear oil: LCMS (ES) m/e 581 (M+H)+.

e) N-((1S)-2-amino-1-{[2-(trifluoromethyl)phenyl]methyl}ethyl)-4-(4-ethyl-1-methyl-1H-pyrazol-5-yl)-5-methyl-2-thiophenecarboxamide

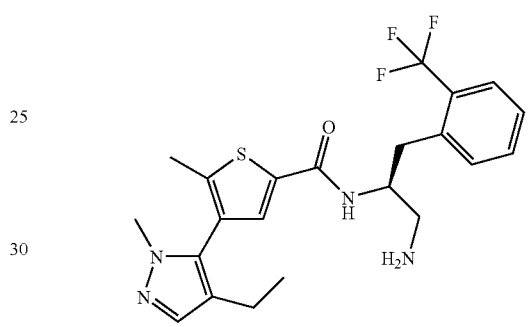

To a solution of N-((1S)-2-(1,3-dioxo-1,3-dihydro-2H-isoindol-2-yl)-1-{[2-(trifluoromethyl)phenyl]methyl}ethyl)-4-(4-ethyl-1-methyl-1H-pyrazol-5-yl)-5-methyl-2-thiophenecarboxamide (262 mg, 0.45 mmol) in tetrahydrofuran (2.256 ml) and methanol (2.256 ml) at 25° C. was added hydrazine (0.14 ml, 4.51 mmol) dropwise. After 12 h, the solution was concentrated, dry loaded onto silica and purified by column chromatography (5% MeOH in DCM (1% $NH_4OH$)). The free base was converted to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(4-ethyl-1-methyl-1H-pyrazol-5-yl)-5-methyl-2-thiophenecarboxamide (170 mg, 0.32 mmol, 72% yield) as a yellow solid: LCMS (ES) m/z=451 (M+H)+, $^1$H NMR (400 MHz, DMSO-$d_6$) δ ppm 8.72 (br. s., 1H) 8.05 (br. s., 2H) 7.76 (s, 1H) 7.69 (d, J=7.83 Hz, 1H) 7.49-7.52 (m, 2H) 7.40-7.45 (m, 2H) 4.42-4.47 (m, 1H) 3.61 (br. s., 3H) 3.01-3.07 (m, 4H) 2.52-2.59 (m, 2H) 2.26 (s, 3H) 1.02-1.09 (m, 3H).

Example 110

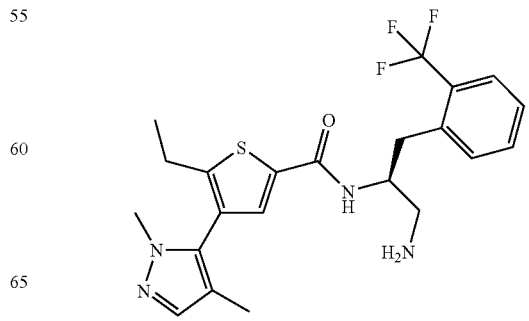

Preparation of N-((1S)-2-amino-1-{[2-(trifluoromethyl)phenyl]methyl}ethyl)-4-(1,4-dimethyl-1H-pyrazol-5-yl)-5-ethyl-2-thiophenecarboxamide a) methyl 4-(4-bromo-1-methyl-1H-pyrazol-5-yl)-5-ethyl-2-thiophenecarboxylate

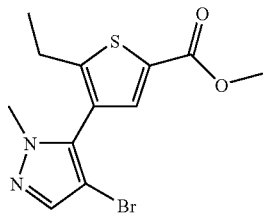

A solution of methyl 5-ethyl-4-(1-methyl-1H-pyrazol-5-yl)-2-thiophenecarboxylate (980 mg, 3.92 mmol)[prepared in Example 98] and N-bromosuccinimide (697 mg, 3.92 mmol) in tetrahydrofuran (19.6 ml) was stirred in a sealed tube for 1 h at 70° C. The reaction mixture was then partitioned between $H_2O$-DCM and the aqueous phase was washed several times with DCM. The combined organic fractions were dried over $Na_2SO_4$, concentrated then purified via column chromatography (silica, 10-40% EtOAC in hexanes) yielding methyl 4-(4-bromo-1-methyl-1H-pyrazol-5-yl)-5-ethyl-2-thiophenecarboxylate (1.1 g, 3.34 mmol, 85% yield) as a yellow oil: LCMS (ES) m/e 329, 331 (M, M+2)$^+$.

b) methyl 4-(1,4-dimethyl-1H-pyrazol-5-yl)-5-ethyl-2-thiophenecarboxylate

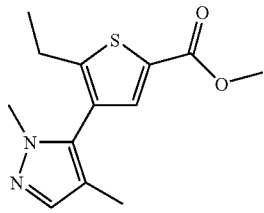

A solution of methyl 4-(4-bromo-1-methyl-1H-pyrazol-5-yl)-5-ethyl-2-thiophenecarboxylate (300 mg, 0.911 mmol), potassium carbonate (630 mg, 4.56 mmol), $PdCl_2$(dppf) (66.7 mg, 0.091 mmol) and trimethylboroxin (0.25 ml, 1.82 mmol) in N,N-dimethylformamide (9.1 ml) was stirred at 110° C. in a sealed tube for 2 h. The reaction mixture was partitioned between $H_2O$-DCM and the aqueous phase was washed several times with DCM. The combined organic fractions were dried over $Na_2SO_4$, concentrated and purified via column chromatography (10-50% EtOAc in hexanes) affording methyl 4-(1,4-dimethyl-1H-pyrazol-5-yl)-5-ethyl-2-thiophenecarboxylate (143 mg, 0.51 mmol, 56% yield) as a yellow oil: LCMS (ES) m/z=265 (M+H)$^+$.

c) 4-(1,4-dimethyl-1H-pyrazol-5-yl)-5-ethyl-2-thiophenecarboxylic Acid

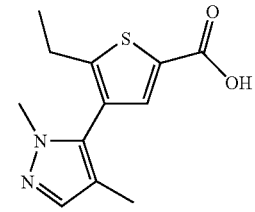 [SMILES: CCc1sc(C(=O)O)cc1-c1c(C)cnn1C]

A solution of methyl 4-(1,4-dimethyl-1H-pyrazol-5-yl)-5-ethyl-2-thiophenecarboxylate (143 mg, 0.54 mmol) in 6N sodium hydroxide (0.90 ml, 5.41 mmol) and tetrahydrofuran (5.4 ml) was stirred at 70° C. in a sealed tube for 1 h. The resulting solution was cooled and then partitioned between $H_2O$-DCM. The aqueous phase was adjusted to pH ~4 and then washed several times with DCM. The combined organic fractions were dried over $Na_2SO_4$ and concentrated affording 4-(1,4-dimethyl-1H-pyrazol-5-yl)-5-ethyl-2-thiophenecarboxylic acid (136 mg, 0.54 mmol, 100% yield) as a yellow oil: LCMS (ES) m/e 251 (M+H)$^+$.

d) 4-(1,4-dimethyl-1H-pyrazol-5-yl)-N-((1S)-2-(1,3-dioxo-1,3-dihydro-2H-isoindol-2-yl)-1-[2-(trifluoromethyl)phenyl]methylethyl)-5-ethyl-2-thiophenecarboxamide

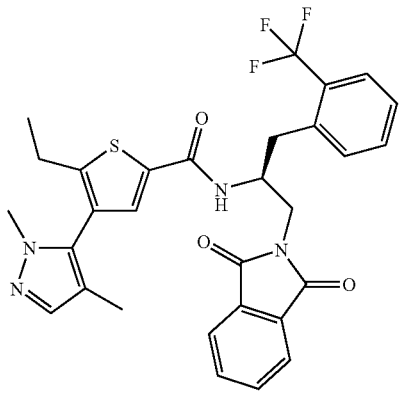 [SMILES: CCc1sc(C(=O)N[C@@H](Cc2ccccc2C(F)(F)F)CN2C(=O)c3ccccc3C2=O)cc1-c1c(C)cnn1C]

To a solution of 4-(1,4-dimethyl-1H-pyrazol-5-yl)-5-ethyl-2-thiophenecarboxylic acid (130 mg, 0.52 mmol), 2-{(2S)-2-amino-3-[2-(trifluoromethyl)phenyl]propyl}-1H-isoindole-1,3(2H)-dione (200 mg, 0.52 mmol)[prepared according to Preparation 6] and diisopropylethylamine (0.45 ml, 2.60 mmol) in DCM at 25° C. was added bromo-tris-pyrrolidino-phosphonium hexafluorophosphate (267 mg, 0.57 mmol) in one portion. The solution stirred at 25° C. for 12 h and was then dry loaded onto silica and purified via column chromatography (silica, 30-70% EtOAc in hexanes) yielding 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-thiophenecarboxamide (278 mg, 0.43 mmol, 82% yield) as a yellow oil: LCMS (ES) m/e 581 (M+H)$^+$.

e) N-((1S)-2-amino-1-{[2-(trifluoromethyl)phenyl]methyl}ethyl)-4-(1,4-dimethyl-1H-pyrazol-5-yl)-5-ethyl-2-thiophenecarboxamide

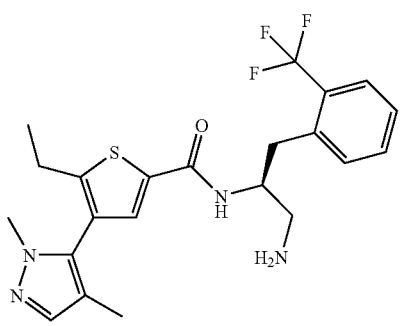 [SMILES: CCc1sc(C(=O)N[C@H](CN)Cc2ccccc2C(F)(F)F)cc1-c1c(C)cnn1C]

To a solution of 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-thiophenecarboxamide (278 mg, 0.48 mmol) in tetrahydrofuran (2.4 ml) and methanol (2.4 ml) at 25° C. was added hydrazine (0.15 ml, 4.79 mmol) dropwise. After 12 h, the solution was concentrated, dry loaded onto silica and purified by column chromatography (3-15% MeOH in DCM (1% NH$_4$OH)). The free base was converted to the HCl salt by addition of excess 2M HCl in Et$_2$O (1 ml) to the residue in MeOH (2 ml) affording the HCl salt of N-((1S)-2-amino-1-{[2-(trifluoromethyl)phenyl]methyl}ethyl)-4-(1,4-dimethyl-1H-pyrazol-5-yl)-5-ethyl-2-thiophenecarboxamide (196 mg, 0.36 mmol, 76% yield) as a yellow solid: LCMS (ES) m/z=451 (M+H)$^+$, $^1$H NMR (400 MHz, DMSO-d$_6$) δ ppm 8.86-8.93 (m, 1H) 8.15 (br. s., 3H) 7.83 (s, 1H) 7.69 (d, J=7.58 Hz, 1H) 7.55 (br. s., 1H) 7.52 (t, J=7.45 Hz, 1H) 7.42 (t, J=7.45 Hz, 1H) 7.38 (s, 1H) 4.22-4.27 (m, 1H) 3.62 (s, 3H) 2.97-3.09 (m, 4H) 2.60 (q, J=7.49 Hz, 2H) 1.88 (s, 3H) 1.13 (t, J=7.58 Hz, 3H).

Example 111

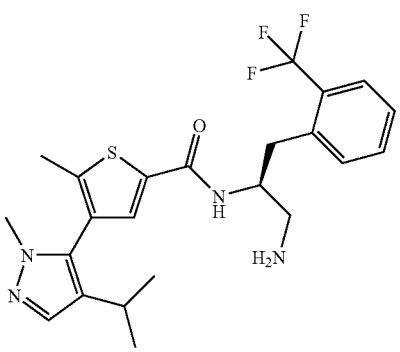 [SMILES: Cc1sc(C(=O)N[C@H](CN)Cc2ccccc2C(F)(F)F)cc1-c1c(C(C)C)cnn1C]

Preparation of N-((1S)-2-amino-1-{[2-(trifluoromethyl)phenyl]methyl}ethyl)-5-methyl-4-[1-methyl-4-(1-methylethyl)-1H-pyrazol-5-yl]-2-thiophenecarboxamide a) methyl 5-methyl-4-[1-methyl-4-(1-methylethenyl)-1H-pyrazol-5-yl]-2-thiophenecarboxylate

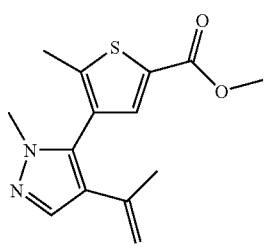

A solution of methyl 4-(4-bromo-1-methyl-1H-pyrazol-5-yl)-5-methyl-2-thiophenecarboxylate (300 mg, 0.95 mmol), potassium carbonate (658 mg, 4.76 mmol), bis(tri-t-butylphosphine)palladium(0) (24.32 mg, 0.05 mmol) and 4,4,5,5-tetramethyl-2-(1-methylethenyl)-1,3,2-dioxaborolane (0.18 ml, 0.95 mmol) in 1,4-dioxane (5.3 ml) and H$_2$O (1.0 ml) was stirred at 80° C. in a sealed tube for 12 h. The reaction contents were partitioned between H$_2$O-DCM and the aqueous phase was washed several times with DCM. The combined organic fractions were dried over Na$_2$SO$_4$, concentrated and purified via column chromatography (10-50% EtOAc in hexanes) affording methyl 5-methyl-4-[1-methyl-4-(1-methylethenyl)-1H-pyrazol-5-yl]-2-thiophenecarboxylate (171 mg, 0.58 mmol, 61% yield) as a yellow oil: LCMS (ES) m/z=276 (M+H)$^+$.

b) methyl 5-methyl-4-[1-methyl-4-(1-methylethyl)-1H-pyrazol-5-yl]-2-thiophenecarboxylate

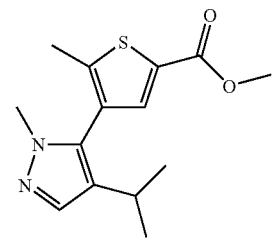

To a solution of methyl 5-methyl-4-[1-methyl-4-(1-methylethenyl)-1H-pyrazol-5-yl]-2-thiophenecarboxylate (171 mg, 0.62 mmol) in methanol (3 ml) was added PdOH$_2$ (34.8 mg, 0.25 mmol). The reaction mixture was hydrogenated at 1 atm (balloon) for 1 h. The solution was then purged with N$_2$, filtered through Celite and concentrated affording methyl 5-methyl-4-[1-methyl-4-(1-methylethyl)-1H-pyrazol-5-yl]-2-thiophenecarboxylate (173 mg, 0.62 mmol, 100% yield) as a clear oil which was used without further purification: LCMS (ES) m/e 279 (M+H)$^+$.

c) 5-methyl-4-[1-methyl-4-(1-methylethyl)-1H-pyrazol-5-yl]-2-thiophenecarboxylic Acid

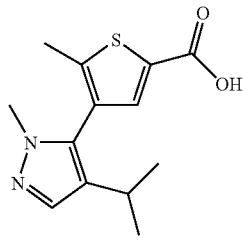 [SMILES: Cc1sc(C(=O)O)cc1-c1c(C(C)C)cnn1C]

A solution of methyl 5-methyl-4-[1-methyl-4-(1-methylethyl)-1H-pyrazol-5-yl]-2-thiophenecarboxylate (173 mg, 0.62 mmol) in 6N sodium hydroxide (1 ml, 6.21 mmol) and tetrahydrofuran (5.4 ml) was stirred at 70° C. in a sealed tube for 1 h. The resulting solution was cooled and then partitioned between H$_2$O-DCM. The aqueous phase was adjusted to pH ~4 and then washed several times with DCM. The combined organic fractions were dried over Na$_2$SO$_4$ and concentrated affording 5-methyl-4-[1-methyl-4-(1-methylethyl)-1H-pyrazol-5-yl]-2-thiophenecarboxylic acid (148 mg, 0.49 mmol, 79% yield) as a white foam: LCMS (ES) m/e 265 (M+H)$^+$.

d) N-((1S)-2-(1,3-dioxo-1,3-dihydro-2H-isoindol-2-yl)-1-{[2-(trifluoromethyl)phenyl]methyl}ethyl)-5-methyl-4-[1-methyl-4-(1-methylethyl)-1H-pyrazol-5-yl]-2-thiophenecarboxamide

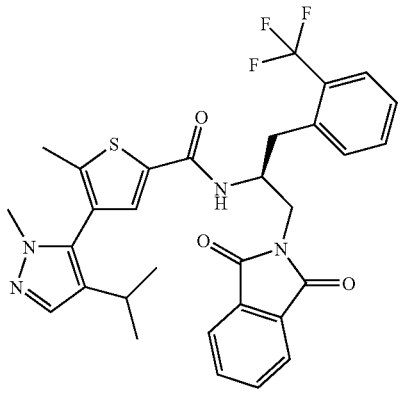 [SMILES: Cc1sc(C(=O)N[C@@H](Cc2ccccc2C(F)(F)F)CN2C(=O)c3ccccc3C2=O)cc1-c1c(C(C)C)cnn1C]

To a solution of 5-methyl-4-[1-methyl-4-(1-methylethyl)-1H-pyrazol-5-yl]-2-thiophenecarboxylic acid (137 mg, 0.52 mmol), 2-{(2S)-2-amino-3-[2-(trifluoromethyl)phenyl]propyl}-1H-isoindole-1,3(2H)-dione (200 mg, 0.52 mmol) [Prepared in Preparation 6] and diisopropylethylamine (0.45 ml, 2.60 mmol) in DCM at 25° C. was added bromo-tris-pyrrolidino-phosphonium hexafluorophosphate (267 mg, 0.572 mmol) in one portion. The solution stirred at 25° C. for 12 h and was then dry loaded onto silica and purified via column chromatography (silica, 30-70% EtOAc in hexanes) yielding N-((1S)-2-(1,3-dioxo-1,3-dihydro-2H-isoindol-2-yl)-1-{[2-(trifluoromethyl)phenyl]methyl}ethyl)-5-methyl-4-[1-methyl-4-(1-methylethyl)-1H-pyrazol-5-yl]-2-thiophenecarboxamide (211 mg, 0.334 mmol, 64.2% yield) as a yellow oil: LCMS (ES) m/e 595 (M+H)$^+$.

e) N-((1S)-2-amino-1-{[2-(trifluoromethyl)phenyl]methyl}ethyl)-5-methyl-4-[1-methyl-4-(1-methylethyl)-1H-pyrazol-5-yl]-2-thiophenecarboxamide

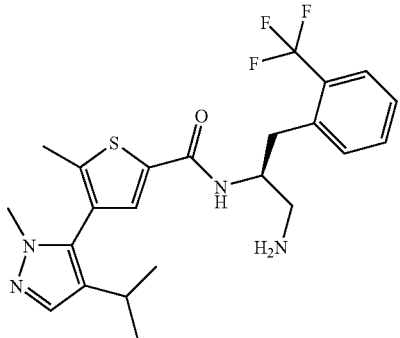 [SMILES: Cc1sc(C(=O)N[C@H](CN)Cc2ccccc2C(F)(F)F)cc1-c1c(C(C)C)cnn1C]

To a solution of N-((1S)-2-(1,3-dioxo-1,3-dihydro-2H-isoindol-2-yl)-1-{[2-(trifluoromethyl)phenyl]methyl}ethyl)-5-methyl-4-[1-methyl-4-(1-methylethyl)-1H-pyrazol-5-yl]-2-thiophenecarboxamide (211 mg, 0.36 mmol) in tetrahydrofuran (2.4 ml) and methanol (2.4 ml) at 25° C. was added hydrazine (0.11 ml, 3.55 mmol) dropwise. After 12 h, the solution was concentrated, dry loaded onto silica and purified by column chromatography (5% MeOH in DCM (1% NH$_4$OH)). The free base was converted to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-5-methyl-4-[1-methyl-4-(1-methylethyl)-1H-pyrazol-5-yl]-2-thiophenecarboxamide (108 mg, 0.20 mmol, 57% yield) as a yellow solid: LCMS (ES) m/z=465 (M+H)$^+$, $^1$H NMR (400 MHz, DMSO-d$_6$) δ ppm 8.71 (d, J=8.59 Hz, 1H) 8.07 (br. s., 3H) 7.74 (s, 1H) 7.65-7.68 (m, 1H) 7.55-7.60 (m, 1H) 7.46-7.49 (m, 1H) 7.39-7.46 (m, 2H) 4.47 (br. s., 1H) 3.57 (s, 3H) 2.99-3.05 (m, 4H) 2.49-2.52 (m, 1H) 2.25 (s, 3H) 1.07-1.14 (m, 6H).

Example 112

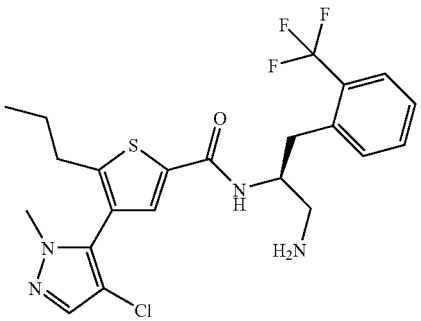 [SMILES: CCCc1sc(C(=O)N[C@H](CN)Cc2ccccc2C(F)(F)F)cc1-c1c(Cl)cnn1C]

Preparation of N-((1S)-2-amino-1-{[2-(trifluoromethyl)phenyl]methyl}ethyl)-4-(4-chloro-1-methyl-1H-pyrazol-5-yl)-5-propyl-2-thiophenecarboxamide a) methyl 4-bromo-5-propyl-2-thiophenecarboxylate

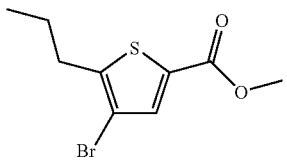

To a solution of 4-bromo-5-propyl-2-thiophenecarboxylic acid (5.0 g, 20.07 mmol) in methanol (100 ml) was added sulfuric acid (5.35 ml, 100 mmol). The resulting solution stirred at 50° C. for 36 h. H$_2$O (50 mL) was added the aqueous phase was washed several times with DCM. The combined organic fractions were washed with saturated NaHCO$_3$, dried over Na$_2$SO$_4$, concentrated and used directly without further purification providing methyl 4-bromo-5-propyl-2-thiophenecarboxylate (5.1 g, 18.61 mmol, 93% yield) as a yellow oil: LCMS (ES) m/e 262, 264 (M, M+2)$^+$.

b) methyl 4-(1-methyl-1H-pyrazol-5-yl)-5-propyl-2-thiophenecarboxylate

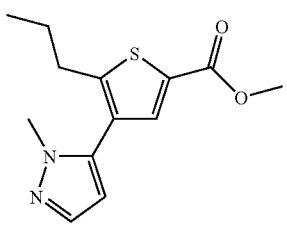 [SMILES: CCCc1sc(C(=O)OC)cc1-c1ccnn1C]

A solution of methyl 4-bromo-5-propyl-2-thiophenecarboxylate (1.0 g, 3.80 mmol), potassium carbonate (2.63 g, 19.00 mmol), 1-methyl-5-(4,4,5,5-tetramethyl-1,3,2-dioxaborolan-2-yl)-1H-pyrazole (0.949 g, 4.56 mmol)[prepared according to Preparation 7] and bis(tri-t-butylphosphine)palladium(0) (0.097 g, 0.19 mmol) were combined in a sealed tube and stirred at 80° C. for 1 h. The reaction contents were then partitioned between $H_2O$-DCM and the aqueous phase was washed several times with DCM. The combined organic fractions were dried over $Na_2SO_4$ and concentrated and purified by column chromatography (10-50% EtOAc in hexanes) affording methyl 4-(1-methyl-1H-pyrazol-5-yl)-5-propyl-2-thiophenecarboxylate (1.07 g, 3.76 mmol, 99% yield) as a yellow oil: LCMS (ES) m/e 265 (M+H)$^+$.

c) 4-(4-chloro-1-methyl-1H-pyrazol-5-yl)-5-propyl-2-thiophenecarboxylic Acid

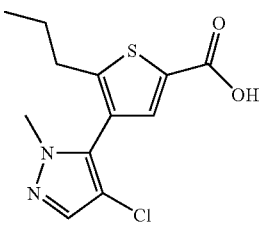 [SMILES: CCCc1sc(C(=O)O)cc1-c1c(Cl)cnn1C]

A solution of methyl 4-(1-methyl-1H-pyrazol-5-yl)-5-propyl-2-thiophenecarboxylate (356 mg, 1.35 mmol) and N-chlorosuccinimide (180 mg, 1.35 mmol) in tetrahydrofuran (6.7 ml) was stirred in a sealed tube for 1 h at 70° C. 6N sodium hydroxide (2.2 ml, 13.47 mmol) was added in one portion and the solution stirred an additional 12 h. The reaction mixture was then partitioned between $H_2O$-DCM and the pH of the aqueous phase was adjusted to ~4 and washed several times with DCM. The combined organic fractions were dried over $Na_2SO_4$, concentrated and used directly without further purification yielding 4-(4-chloro-1-methyl-1H-pyrazol-5-yl)-5-propyl-2-thiophenecarboxylic acid (357 mg, 1.25 mmol, 93% yield) as a yellow oil: LCMS (ES) m/e 271, 273 (M, M+2)$^+$.

d) 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-propyl-2-thiophenecarboxamide

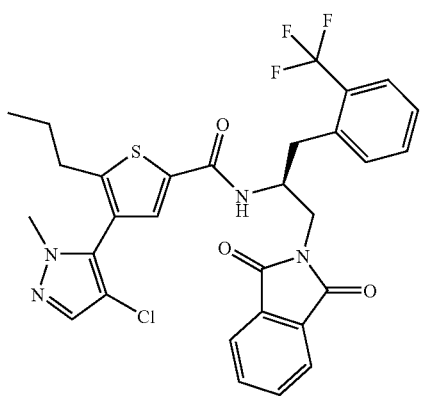 [SMILES: CCCc1sc(C(=O)N[C@@H](Cc2ccccc2C(F)(F)F)CN2C(=O)c3ccccc3C2=O)cc1-c1c(Cl)cnn1C]

To a solution of 4-(4-chloro-1-methyl-1H-pyrazol-5-yl)-5-propyl-2-thiophenecarboxylic acid (148 mg, 0.52 mmol), 2-{(2S)-2-amino-3-[2-(trifluoromethyl)phenyl]propyl}-1H-isoindole-1,3(2H)-dione (200 mg, 0.52 mmol) [Prepared according to Preparation 6] and diisopropylethylamine (0.45 ml, 2.60 mmol) in DCM at 25° C. was added bromo-tris-pyrrolidino-phosphonium hexafluorophosphate (267 mg, 0.57 mmol) in one portion. The solution stirred at 25° C. for 12 h and was then dry loaded onto silica and purified via column chromatography (silica, 30-70% EtOAc in hexanes) yielding 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-propyl-2-thiophenecarboxamide (245 mg, 0.39 mmol, 75% yield) as a yellow oil: LCMS (ES) m/e 615, 617 (M, M+2)$^+$.

e) N-((1S)-2-amino-1-{[2-(trifluoromethyl)phenyl]methyl}ethyl)-4-(4-chloro-1-methyl-1H-pyrazol-5-yl)-5-propyl-2-thiophenecarboxamide

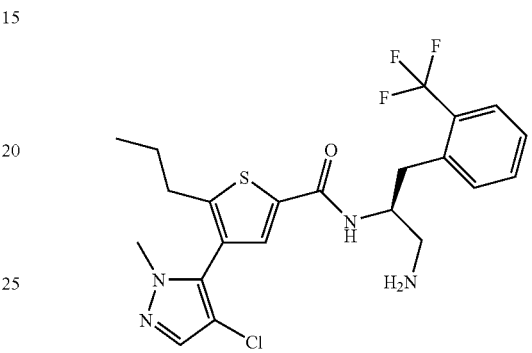

To a solution of 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-propyl-2-thiophenecarboxamide (245 mg, 0.40 mmol) in tetrahydrofuran (2.4 ml) and methanol (2.4 ml) at 25° C. was added hydrazine (0.12 ml, 3.98 mmol) dropwise. After 12 h, the solution was concentrated, dry loaded onto silica and purified by column chromatography (5% MeOH in DCM (1% $NH_4OH$)). The free base was transferred to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(4-chloro-1-methyl-1H-pyrazol-5-yl)-5-propyl-2-thiophenecarboxamide (178 mg, 0.32 mmol, 80% yield) as a yellow solid: LCMS (ES) m/z=485, 487 (M, M+2)$^+$, $^1$H NMR (400 MHz, DMSO-$d_6$) δ ppm 8.96 (br. s., 1H) 8.13 (br. s., 3H) 7.93 (s, 1H) 7.66-7.73 (m, 2H) 7.62 (br. s., 1H) 7.55 (t, J=7.45 Hz, 1H) 7.42 (t, J=7.45 Hz, 1H) 4.48 (br. s., 1H) 3.71 (s, 3H) 2.99-3.08 (m, 4H) 2.63 (t, J=7.20 Hz, 2H) 1.53-1.57 (m, 2H) 0.83 (t, J=7.33 Hz, 3H).

Example 113

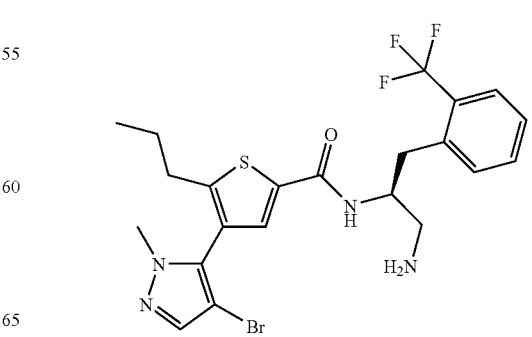

Preparation of N-((1S)-2-amino-1-{[2-(trifluoromethyl)phenyl]methyl}ethyl)-4-(4-bromo-1-methyl-1H-pyrazol-5-yl)-5-propyl-2-thiophenecarboxamide a) 4-(4-bromo-1-methyl-1H-pyrazol-5-yl)-5-propyl-2-thiophenecarboxylic Acid

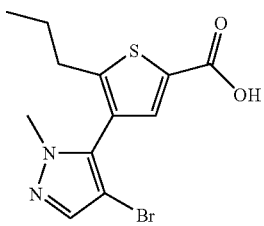

A solution of methyl 4-(1-methyl-1H-pyrazol-5-yl)-5-propyl-2-thiophenecarboxylate (714 mg, 2.70 mmol)[prepared in Example 112] and N-bromosuccinimide (481 mg, 2.70 mmol) in tetrahydrofuran (12 ml) was stirred in a sealed tube for 1 h at 70° C. The reaction mixture was divided and half of the solution was treated with 6N sodium hydroxide (2.251 ml, 13.51 mmol). The reaction mixture stirred at 70° C. in a sealed tube for 12 h and was partitioned between $H_2O$-DCM. The pH of the aqueous phase was adjusted to ~4 and washed several times with DCM. The combined organic fractions were dried over $Na_2SO_4$, concentrated and used directly affording 4-(4-bromo-1-methyl-1H-pyrazol-5-yl)-5-propyl-2-thiophenecarboxylic acid (445 mg, 1.35 mmol, 50% yield): LCMS (ES) m/e 329, 331 (M, M+2)$^+$.

b) 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-propyl-2-thiophenecarboxamide

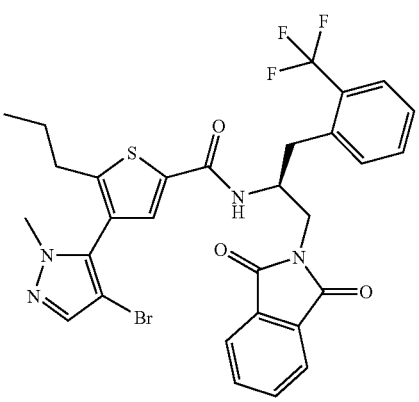 [SMILES: CCCc1sc(C(=O)N[C@@H](Cc2ccccc2C(F)(F)F)CN2C(=O)c3ccccc3C2=O)cc1-c1c(Br)cnn1C]

To a solution of 4-(4-bromo-1-methyl-1H-pyrazol-5-yl)-5-propyl-2-thiophenecarboxylic acid (171 mg, 0.52 mmol), 2-{(2S)-2-amino-3-[2-(trifluoromethyl)phenyl]propyl}-1H-isoindole-1,3(2H)-dione (200 mg, 0.52 mmol)[prepared according to Preparation 6] and diisopropylethylamine (0.45 ml, 2.60 mmol) in DCM at 25° C. was added bromo-tris-pyrrolidino-phosphonium hexafluorophosphate (267 mg, 0.57 mmol) in one portion. The solution stirred at 25° C. for 12 h and was then dry loaded onto silica and purified via column chromatography (silica, 30-70% EtOAc in hexanes) yielding 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-propyl-2-thiophenecarboxamide (251 mg, 0.37 mmol, 72% yield) as a yellow oil: LCMS (ES) m/e 659,661 (M, M+2)$^+$.

c) N-((1S)-2-amino-1-{[2-(trifluoromethyl)phenyl]methyl}ethyl)-4-(4-bromo-1-methyl-1H-pyrazol-5-yl)-5-propyl-2-thiophenecarboxamide

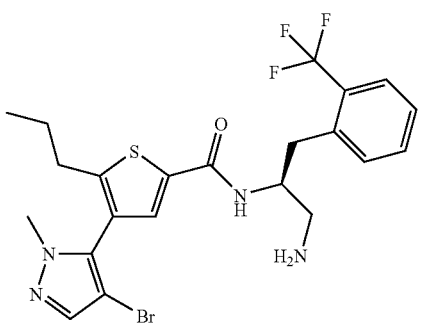 [SMILES: CCCc1sc(C(=O)N[C@H](CN)Cc2ccccc2C(F)(F)F)cc1-c1c(Br)cnn1C]

To a solution of 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-propyl-2-thiophenecarboxamide (251 mg, 0.38 mmol) in tetrahydrofuran (2.4 ml) and methanol (2.4 ml) at 25° C. was added hydrazine (0.12 ml, 3.81 mmol) dropwise. After 12 h, the solution was concentrated, dry loaded onto silica and purified by column chromatography (5% MeOH in DCM (1% $NH_4OH$)). The free base was transferred to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(4-bromo-1-methyl-1H-pyrazol-5-yl)-5-propyl-2-thiophenecarboxamide (178 mg, 0.30 mmol, 78% yield) as a yellow solid: LCMS (ES) m/z=529, 531 (M, M+2)$^+$, $^1$H NMR (400 MHz, DMSO-$d_6$) δ ppm 8.94 (d, J=8.84 Hz, 1H) 8.10 (br. s., 3H) 7.87 (d, J=1.77 Hz, 1H) 7.65-7.72 (m, 2H) 7.58 (dd, J=14.78, 7.71 Hz, 2H) 7.43 (t, J=7.45 Hz, 1H) 4.48 (br. s., 1H) 3.71 (s, 3H) 2.99-3.08 (m, 4H) 2.58-2.66 (m, 2H) 1.53 (ddd, J=13.89, 6.82, 6.57 Hz, 2H) 0.83 (dd, J=7.33, 2.02 Hz, 3H).

Example 114

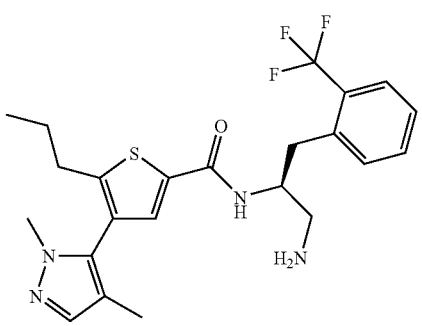 [SMILES: CCCc1sc(C(=O)N[C@H](CN)Cc2ccccc2C(F)(F)F)cc1-c1c(C)cnn1C]

Preparation of N-((1S)-2-amino-1-{[2-(trifluoromethyl)phenyl]methyl}ethyl)-4-(1,4-dimethyl-1H-pyrazol-5-yl)-5-propyl-2-thiophenecarboxamide a) methyl 4-(4-bromo-1-methyl-1H-pyrazol-5-yl)-5-propyl-2-thiophenecarboxylate

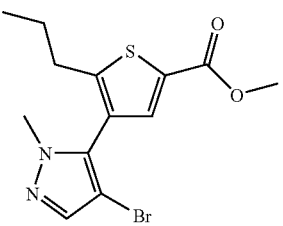 [SMILES: CCCc1sc(C(=O)OC)cc1-c1c(Br)cnn1C]

A solution of methyl 4-(1-methyl-1H-pyrazol-5-yl)-5-propyl-2-thiophenecarboxylate (714 mg, 2.70 mmol) and N-bromosuccinimide (481 mg, 2.70 mmol) in tetrahydrofuran (12 ml) was stirred in a sealed tube for 1 h at 70° C. The reaction mixture was divided and half was partitioned between H₂O-DCM. The aqueous phase was washed several times with DCM and the combined organic fractions were dried over Na₂SO₄, concentrated and used directly yielding methyl 4-(4-bromo-1-methyl-1H-pyrazol-5-yl)-5-propyl-2-thiophenecarboxylate (464 mg, 1.35 mmol, 50% yield) as an orange oil: LCMS (ES) m/e 343, 345 (M, M+2)⁺.

b) methyl 4-(1,4-dimethyl-1H-pyrazol-5-yl)-5-propylthiophene-2-carboxylate

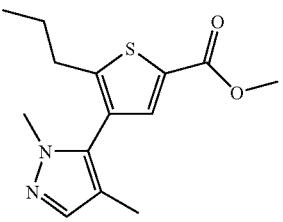 [SMILES: CCCc1sc(C(=O)OC)cc1-c1c(C)cnn1C]

A solution of methyl 4-(4-bromo-1-methyl-1H-pyrazol-5-yl)-5-propyl-2-thiophenecarboxylate (242 mg, 0.71 mmol) PdCl₂(dppf) (52 mg, 0.07 mmol), potassium carbonate (487 mg, 3.53 mmol) and trimethylboroxine (0.20 ml, 1.41 mmol) in N,N-Dimethylformamide (3.5 ml) was stirred at 110° C. in a sealed tube for 2 h. The reaction mixture was partitioned between H₂O-DCM and the aqueous phase was washed several times with DCM. The combined organic fractions were dried over Na₂SO₄, concentrated and purified via column chromatography (10-50% EtOAc in hexanes) affording methyl 4-(1,4-dimethyl-1H-pyrazol-5-yl)-5-propyl-2-thiophenecarboxylate (184 mg, 0.60 mmol, 84% yield) as a yellow oil: LCMS (ES) m/z=279 (M+H)⁺.

c) 4-(1,4-dimethyl-1H-pyrazol-5-yl)-5-propylthiophene-2-carboxylic Acid

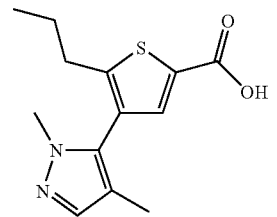 [SMILES: CCCc1sc(C(=O)O)cc1-c1c(C)cnn1C]

A solution of methyl 4-(1,4-dimethyl-1H-pyrazol-5-yl)-5-propyl-2-thiophenecarboxylate (0.184 g, 0.66 mmol) in 6N sodium hydroxide (2.2 ml, 13.22 mmol) and tetrahydrofuran (6.6 ml) was stirred at 70° C. in a sealed tube for 1 h. The resulting solution was cooled and then partitioned between H₂O-DCM. The aqueous phase was adjusted to pH ~4 and then washed several times with DCM. The combined organic fractions were dried over Na₂SO₄ and concentrated affording 4-(1,4-dimethyl-1H-pyrazol-5-yl)-5-propyl-2-thiophenecarboxylic acid (180 mg, 0.66 mmol, 100% yield) as a yellow oil: LCMS (ES) m/e 265 (M+H)⁺.

d) 4-(1,4-dimethyl-1H-pyrazol-5-yl)-N-{(1S)-2-(1,3-dioxo-1,3-dihydro-2H-isoindol-2-yl)-1-[2-(trifluoromethyl)benzyl]ethyl}-5-propylthiophene-2-carboxamide

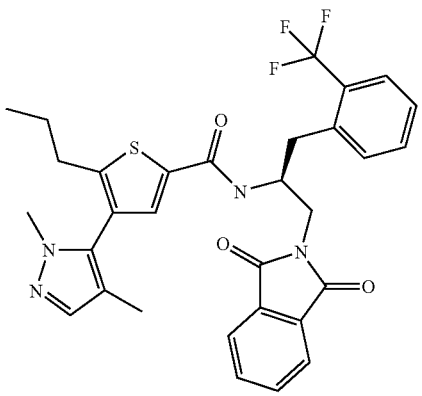 [SMILES: CCCc1sc(C(=O)N[C@@H](Cc2ccccc2C(F)(F)F)CN2C(=O)c3ccccc3C2=O)cc1-c1c(C)cnn1C]

To a solution of 4-(1,4-dimethyl-1H-pyrazol-5-yl)-5-propyl-2-thiophenecarboxylic acid (180 mg, 0.68 mmol), 2-{(2S)-2-amino-3-[2-(trifluoromethyl)phenyl]propyl}-1H-isoindole-1,3(2H)-dione (262 mg, 0.68 mmol)[prepared in Preparation 6] and diisopropylethylamine (0.59 ml, 3.40 mmol) in DCM at 25° C. was added bromo-tris-pyrrolidino-phosphonium hexafluorophosphate (350 mg, 0.75 mmol) in one portion. The solution stirred at 25° C. for 2 h and was then dry loaded onto silica and purified via column chromatography (silica, 30-70% EtOAc in hexanes) yielding 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-propyl-2-thiophenecarboxamide (243 mg, 0.41 mmol, 60% yield) as a yellow oil: LCMS (ES) m/e 595 (M+H)⁺.

e) N-{(1S)-2-amino-1-[2-(trifluoromethyl)benzyl]ethyl}-4-(1,4-dimethyl-1H-pyrazol-5-yl)-5-propylthiophene-2-carboxamide

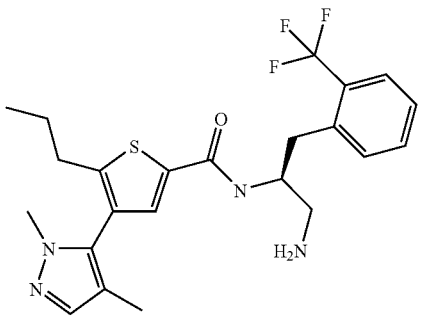 [SMILES: CCCc1sc(C(=O)N[C@H](CN)Cc2ccccc2C(F)(F)F)cc1-c1c(C)cnn1C]

To a solution of 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-propyl-2-thiophenecarboxamide (243 mg, 0.41 mmol) in tetrahydrofuran (2 ml) and methanol (2 ml) at 25° C. was added hydrazine (0.13 ml, 4.09 mmol) dropwise. After 12 h, the solution was concentrated, dry loaded onto silica and purified by column chromatography (5% MeOH in DCM (1% NH₄OH)). The free base was converted to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(1,4-dimethyl-1H-pyrazol-5-yl)-5-propyl-2-thiophenecarboxamide (172 mg, 0.30 mmol, 74% yield) as a yellow solid: LCMS (ES) m/z=465 (M+H)⁺, ¹H NMR (400 MHz, DMSO-d₆) δ ppm 8.80 (br. s., 1H) 8.08 (br. s., 3H) 7.78 (s, 1H) 7.69 (d, J=7.58 Hz, 1H) 7.50-7.55 (m, 2H) 7.43 (t, J=7.71 Hz, 1H) 7.37 (s, 1H) 4.49 (d, J=10.36 Hz, 1H) 3.61 (s, 3H) 2.99-3.06 (m, 4H) 2.54-2.59 (m, 2H) 1.87 (s, 3H) 1.48-1.55 (m, 2H) 0.81 (t, J=7.33 Hz, 3H).

Example 115

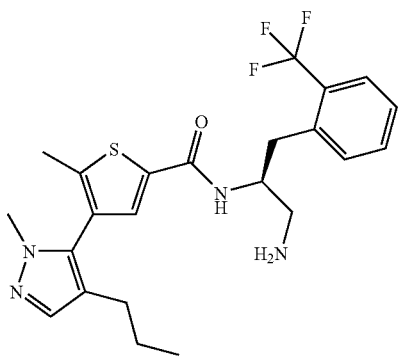 [SMILES: CCCc1cnn(C)c1-c1cc(C(=O)N[C@H](CN)Cc2ccccc2C(F)(F)F)sc1C]

Preparation of N-{(1S)-2-amino-1-[2-(trifluoromethyl)benzyl]ethyl}-5-methyl-4-(1-methyl-4-propyl-1H-pyrazol-5-yl)thiophene-2-carboxamide a) methyl 5-methyl-4-{1-methyl-4-[(1E)-prop-1-en-1-yl]-1H-pyrazol-5-yl}thiophene-2-carboxylate

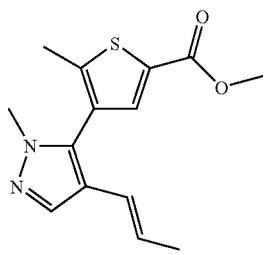

A solution of methyl 4-(4-bromo-1-methyl-1H-pyrazol-5-yl)-5-methyl-2-thiophenecarboxylate (320 mg, 1.015 mmol) [prepared in Example 99], potassium carbonate (702 mg, 5.08 mmol), bis(tri-t-butylphosphine)palladium(0) (25.9 mg, 0.05 mmol) and (1Z)-1-propen-1-ylboronic acid (87 mg, 1.01 mmol) in 1,4-dioxane (5.3 ml) and water (1.3 ml) was stirred at 80° C. in a sealed tube for 12 h. The reaction contents were partitioned between H₂O-DCM and the aqueous phase was washed several times with DCM. The combined organic fractions were dried over Na₂SO₄, concentrated and purified via column chromatography (10-50% EtOAc in hexanes) affording methyl 5-methyl-4-{1-methyl-4-[(1Z)-1-propen-1-yl]-1H-pyrazol-5-yl}-2-thiophenecarboxylate (243 mg, 0.88 mmol, 87% yield) as a yellow oil: LCMS (ES) m/z=277 (M+H)⁺.

b) methyl 5-methyl-4-(1-methyl-4-propyl-1H-pyrazol-5-yl)-2-thiophenecarboxylate

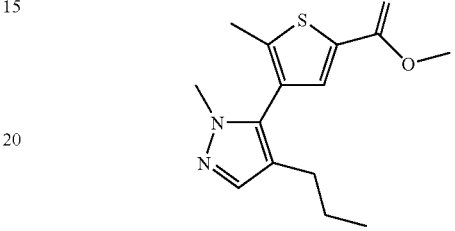

To a solution of methyl 5-methyl-4-{1-methyl-4-[(1Z)-1-propen-1-yl]-1H-pyrazol-5-yl}-2-thiophenecarboxylate (243 mg, 0.88 mmol) in methanol (6.8 ml) was added Pd(OH)₂ (49 mg, 0.35 mmol). The reaction mixture was hydrogenated at 1 atm (balloon) for 1 h. The solution was then purged with N₂, filtered through Celite and concentrated affording methyl 5-methyl-4-(1-methyl-4-propyl-1H-pyrazol-5-yl)-2-thiophenecarboxylate (217 mg, 0.69 mmol, 78% yield) as a clear oil which was used without further purification: LCMS (ES) m/e 279 (M+H)⁺.

c) 5-methyl-4-(1-methyl-4-propyl-1H-pyrazol-5-yl)-2-thiophenecarboxylic Acid

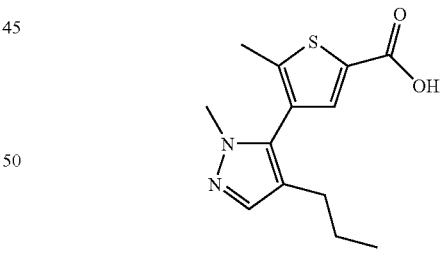

A solution of methyl 5-methyl-4-(1-methyl-4-propyl-1H-pyrazol-5-yl)-2-thiophenecarboxylate (217 mg, 0.78 mmol) in 6N sodium hydroxide (2.60 ml, 15.59 mmol) and tetrahydrofuran (5.4 ml) was stirred at 70° C. in a sealed tube for 1 h. The resulting solution was cooled and then partitioned between H₂O-DCM. The aqueous phase was adjusted to pH ~4 and then washed several times with DCM. The combined organic fractions were dried over Na₂SO₄ and concentrated affording 5-methyl-4-(1-methyl-4-propyl-1H-pyrazol-5-yl)-2-thiophenecarboxylic acid (242 mg, 0.78 mmol, 100% yield) as a white foam: LCMS (ES) m/e 265 (M+H)⁺.

d) N-((1S)-2-(1,3-dioxo-1,3-dihydro-2H-isoindol-2-yl)-1-{[2-(trifluoromethyl)phenyl]methyl}ethyl)-5-methyl-4-(1-methyl-4-propyl-1H-pyrazol-5-yl)-2-thiophenecarboxamide

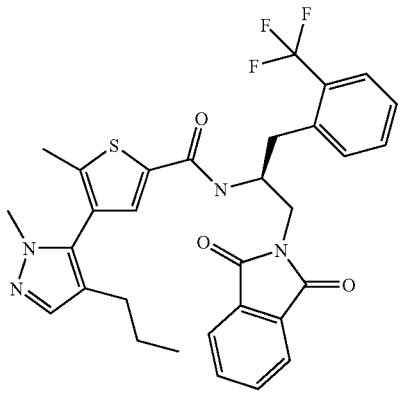 [SMILES: CCCc1cnn(C)c1-c1cc(C(=O)N[C@@H](Cc2ccccc2C(F)(F)F)CN2C(=O)c3ccccc3C2=O)sc1C]

To a solution of 5-methyl-4-(1-methyl-4-propyl-1H-pyrazol-5-yl)-2-thiophenecarboxylic acid (206 mg, 0.78 mmol), 2-{(2S)-2-amino-3-[2-(trifluoromethyl)phenyl]propyl}-1H-isoindole-1,3(2H)-dione (300 mg, 0.78 mmol)[prepared according to Preparation 6] and diisopropylethylamine (0.68 ml, 3.90 mmol) in DCM at 25° C. was added bromo-tris-pyrrolidino-phosphonium hexafluorophosphate (400 mg, 0.86 mmol) in one portion. The solution stirred at 25° C. for 12 h and was then dry loaded onto silica and purified via column chromatography (silica, 30-70% EtOAc in hexanes) yielding N-((1S)-2-(1,3-dioxo-1,3-dihydro-2H-isoindol-2-yl)-1-{[2-(trifluoromethyl)phenyl]methyl}ethyl)-5-methyl-4-(1-methyl-4-propyl-1H-pyrazol-5-yl)-2-thiophenecarboxamide (283 mg, 0.46 mmol, 60% yield) as a yellow oil: LCMS (ES) m/e 595 (M+H)⁺.

e) N-((1S)-2-amino-1-{[2-(trifluoromethyl)phenyl]methyl}ethyl)-5-methyl-4-(1-methyl-4-propyl-1H-pyrazol-5-yl)-2-thiophenecarboxamide

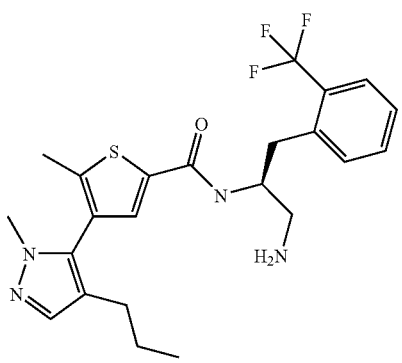 [SMILES: CCCc1cnn(C)c1-c1cc(C(=O)N[C@H](CN)Cc2ccccc2C(F)(F)F)sc1C]

To a solution of N-((1S)-2-(1,3-dioxo-1,3-dihydro-2H-isoindol-2-yl)-1-{[2-(trifluoromethyl)phenyl]methyl}ethyl)-5-methyl-4-(1-methyl-4-propyl-1H-pyrazol-5-yl)-2-thiophenecarboxamide (283 mg, 0.48 mmol) in tetrahydrofuran (2.4 ml) and methanol (2.4 ml) at 25° C. was added hydrazine (0.15 ml, 4.76 mmol) dropwise. After 12 h, the solution was concentrated, dry loaded onto silica and purified by column chromatography (5% MeOH in DCM (1% NH₄OH)). The free base was converted to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-5-methyl-4-(1-methyl-4-propyl-1H-pyrazol-5-yl)-2-thiophenecarboxamide (186 mg, 0.35 mmol, 73% yield) as a yellow solid: LCMS (ES) m/z=465 (M+H)⁺, ¹H NMR (400 MHz, DMSO-d₆) δ ppm 8.81 (br. s., 1H) 8.13 (br. s., 3H) 7.79 (s, 1H) 7.68 (d, J=7.58 Hz, 1H) 7.59 (d, J=7.07 Hz, 1H) 7.42-7.51 (m, 1H) 7.38-7.45 (m, 2H) 4.47 (br. s., 1H) 3.61 (d, J=2.78 Hz, 3H) 2.99-3.08 (m, 4H) 2.25 (s, 3H) 2.11-2.21 (m, 2H) 1.41-1.48 (m, 2H) 0.83 (br. s., 3H).

Example 116

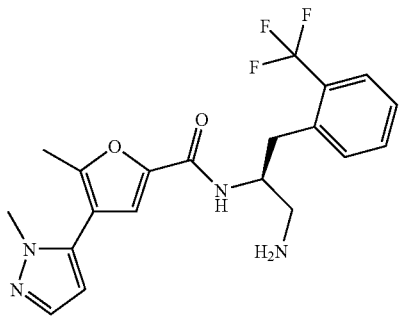 [SMILES: Cc1oc(C(=O)N[C@H](CN)Cc2ccccc2C(F)(F)F)cc1-c1ccnn1C]

Preparation of N-((1S)-2-amino-1-{[2-(trifluoromethyl)phenyl]methyl}ethyl)-5-methyl-4-(1-methyl-1H-pyrazol-5-yl)-2-furancarboxamide a) methyl 4-bromo-5-methyl-2-furancarboxylate

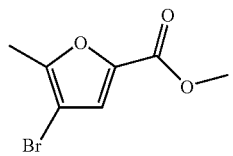

To a solution of methyl 5-methyl-2-furancarboxylate (1.5 g, 10.70 mmol) and aluminum trichloride (2.14 g, 16.06 mmol) in chloroform (21 ml) at 0° C. was added bromine (0.77 ml, 14.99 mmol). The resulting solution stirred at 0° C. and warmed to RT over 12 h. This reaction was run in batches (1.5 g and 1 g) and the batches were combined, added to ice and partitioned between H₂O-DCM. The aqueous phase was washed several times with DCM and the combined organic fractions were dried over Na₂SO₄, concentrated and purified by column chromatography (0.5-10% EtOAc in hexanes) affording the title compound (2.1 g, 54%) as a white solid; LCMS (ES) m/z=219, 221 (M, M+2)⁺.

b) methyl 5-methyl-4-(1-methyl-1H-pyrazol-5-yl)-2-furancarboxylate

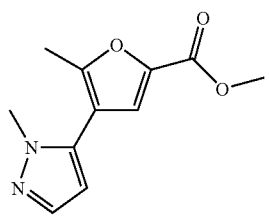

A solution of methyl 4-bromo-5-methyl-2-furancarboxylate (2.1 g, 9.59 mmol), potassium carbonate (6.63 g, 47.9 mmol), 1-methyl-5-(4,4,5,5-tetramethyl-1,3,2-dioxaborolan-2-yl)-1H-pyrazole (2.19 g, 10.55 mmol)[prepared according to Preparation 7] and bis(tri-t-butylphosphine)palladium(0) (0.24 g, 0.48 mmol) in 1,4-dioxane (40 ml) and water (8 ml) was stirred at 80° C. in a sealed tube for 1 h. 1-methyl-5-(4,4,5,5-tetramethyl-1,3,2-dioxaborolan-2-yl)-1H-pyrazole (2.19 g, 10.55 mmol) and bis(tri-t-butylphosphine)palladium(0) (0.245 g, 0.48 mmol) were added and the reaction stirred an additional 1 h and was partitioned between H$_2$O-DCM. The aqueous phase was washed several times with DCM and the combined organic fractions were dried over Na$_2$SO$_4$, concentrated and purified via column chromatography (10-40% EtOAc in hexanes) affording methyl 5-methyl-4-(1-methyl-1H-pyrazol-5-yl)-2-furancarboxylate (1.7 g, 7.72 mmol, 81% yield) as a yellow oil: LCMS (ES) m/e 221 (M+H)$^+$.

c) 5-methyl-4-(1-methyl-1H-pyrazol-5-yl)-2-furancarboxylic Acid

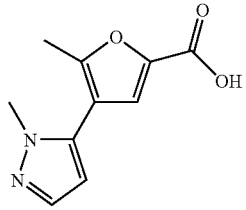

A solution of methyl 5-methyl-4-(1-methyl-1H-pyrazol-5-yl)-2-furancarboxylate (200 mg, 0.91 mmol) in 6N sodium hydroxide (2.3 ml, 13.62 mmol) and tetrahydrofuran (4.5 ml) was stirred at 70° C. in a sealed tube for 1 h. The resulting solution was cooled and then partitioned between H$_2$O-DCM. The aqueous phase was adjusted to pH ~4 and then washed several times with DCM. The combined organic fractions were dried over Na$_2$SO$_4$ and concentrated affording 5-methyl-4-(1-methyl-1H-pyrazol-5-yl)-2-furancarboxylic acid (130 mg, 0.57 mmol, 63% yield) as a yellow oil: LCMS (ES) m/e 207 (M+H)$^+$.

d) N-((1S)-2-(1,3-dioxo-1,3-dihydro-2H-isoindol-2-yl)-1-{[2-(trifluoromethyl)phenyl]methyl}ethyl)-5-methyl-4-(1-methyl-1H-pyrazol-5-yl)-2-furancarboxamide

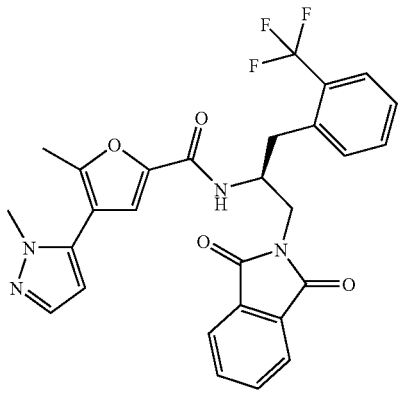 [SMILES: Cc1oc(C(=O)N[C@@H](Cc2ccccc2C(F)(F)F)CN2C(=O)c3ccccc3C2=O)cc1-c1ccnn1C]

To a solution of 5-methyl-4-(1-methyl-1H-pyrazol-5-yl)-2-furancarboxylic acid (130 mg, 0.63 mmol), 2-{(2S)-2-amino-3-[2-(trifluoromethyl)phenyl]propyl}-1H-isoindole-1,3(2H)-dione (243 mg, 0.63 mmol)[prepared in Preparation 6] and diisopropylethylamine (0.55 ml, 3.15 mmol) in DCM at 25° C. was added bromo-tris-pyrrolidino-phosphonium hexafluorophosphate (324 mg, 0.69 mmol) in one portion. The solution stirred at 25° C. for 12 h and was then dry loaded onto silica and purified via column chromatography (silica, 30-70% EtOAc in hexanes) yielding N-((1S)-2-(1,3-dioxo-1,3-dihydro-2H-isoindol-2-yl)-1-{[2-(trifluoromethyl)phenyl]methyl}ethyl)-5-methyl-4-(1-methyl-1H-pyrazol-5-yl)-2-furancarboxamide (190 mg, 0.23 mmol, 37% yield) as a clear oil: LCMS (ES) m/e 537 (M+H)$^+$.

e) N-((1S)-2-amino-1-{[2-(trifluoromethyl)phenyl]methyl}ethyl)-5-methyl-4-(1-methyl-1H-pyrazol-5-yl)-2-furancarboxamide

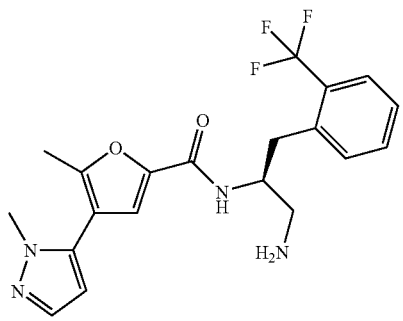 [SMILES: Cc1oc(C(=O)N[C@H](CN)Cc2ccccc2C(F)(F)F)cc1-c1ccnn1C]

To a solution of N-((1S)-2-(1,3-dioxo-1,3-dihydro-2H-isoindol-2-yl)-1-{[2-(trifluoromethyl)phenyl]methyl}ethyl)-5-methyl-4-(1-methyl-1H-pyrazol-5-yl)-2-furancarboxamide (190 mg, 0.35 mmol) in tetrahydrofuran (1.5 ml) and methanol (1.5 ml) at 25° C. was added hydrazine (0.11 ml, 3.54 mmol) dropwise. After 12 h the solution was concentrated, dry loaded onto silica and purified by column chromatography (5% MeOH in DCM (1% NH$_4$OH)). The free base was converted to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-5-methyl-4-(1-methyl-1H-pyrazol-5-yl)-2-furancarboxamide (71 mg, 0.15 mmol, 42% yield) as a yellow solid: LCMS (ES) m/z 407 (M+H)$^+$, $^1$H NMR (400 MHz, DMSO-d$_6$) δ ppm 8.60 (d, J=9.60 Hz, 1H) 8.04 (br. s., 3H) 7.70 (d, J=7.83 Hz, 1H) 7.53-7.59 (m, 2H) 7.49 (d, J=1.77 Hz, 1H) 7.38-7.45 (m, 2H) 6.33 (br. s., 1H) 4.52 (br. s., 1H) 3.80 (s, 3H) 2.98-3.09 (m, 4H) 2.38 (s, 3H).

Example 117

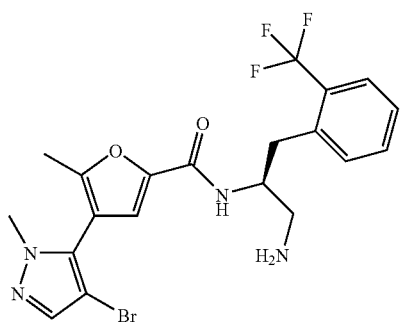 [SMILES: Cc1oc(C(=O)N[C@H](CN)Cc2ccccc2C(F)(F)F)cc1-c1c(Br)cnn1C]

Preparation of N-((1S)-2-amino-1-{[2-(trifluoromethyl)phenyl]methyl}ethyl)-4-(4-bromo-1-methyl-1H-pyrazol-5-yl)-5-methyl-2-furancarboxamide a) 4-(4-bromo-1-methyl-1H-pyrazol-5-yl)-5-methyl-2-furancarboxylic Acid

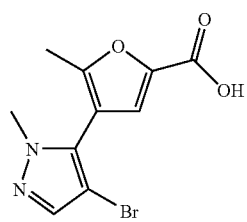 [SMILES: Cc1oc(C(=O)O)cc1-c1c(Br)cnn1C]

A solution of methyl 5-methyl-4-(1-methyl-1H-pyrazol-5-yl)-2-furancarboxylate (600 mg, 2.72 mmol)[prepared in Example 116] and n-bromosuccinimide (485 mg, 2.72 mmol) in tetrahydrofuran (13.6 ml) was stirred in a sealed tube for 1 h at 70° C. The reaction mixture was divided and half of the solution was treated with 6N sodium hydroxide (4.54 ml, 27.2 mmol) which stirred at 70° C. in a sealed tube for 4 h. The solution was partitioned between $H_2O$-DCM and the pH of the aqueous phase was adjusted to ~4 and washed several times with DCM. The combined organic fractions were dried over $Na_2SO_4$, concentrated and used directly affording 4-(4-bromo-1-methyl-1H-pyrazol-5-yl)-5-methyl-2-furancarboxylic acid (369 mg, 1.29 mmol, 48% yield) as an orange oil: LCMS (ES) m/e 285, 287 (M, M+2)$^+$.

b) 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide

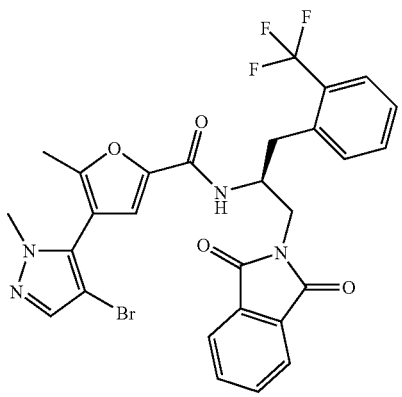

To a solution of 4-(4-bromo-1-methyl-1H-pyrazol-5-yl)-5-methyl-2-furancarboxylic acid (200 mg, 0.70 mmol), 2-{(2S)-2-amino-3-[2-(trifluoromethyl)phenyl]propyl}-1H-isoindole-1,3(2H)-dione (270 mg, 0.70 mmol)[prepared according to Preparation 6] and diisopropylethylamine (0.61 ml, 3.51 mmol) in DCM at 25° C. was added bromo-tris-pyrrolidino-phosphonium hexafluorophosphate (361 mg, 0.77 mmol) in one portion. The solution stirred at 25° C. for 1 h and was then dry loaded onto silica and purified via column chromatography (silica, 30-70% EtOAc in hexanes) yielding 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide (232 mg, 0.32 mmol, 46% yield) as a clear oil: LCMS (ES) m/e 615, 617 (M+H)$^+$.

c) N-((1S)-2-amino-1-{[2-(trifluoromethyl)phenyl]methyl}ethyl)-4-(4-bromo-1-methyl-1H-pyrazol-5-yl)-5-methyl-2-furancarboxamide

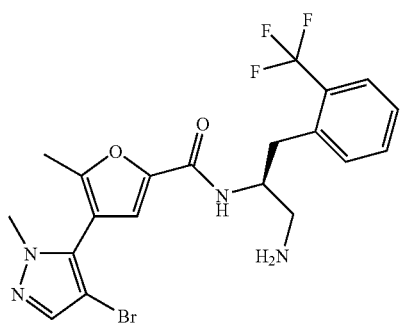 [SMILES: Cc1oc(C(=O)N[C@H](CN)Cc2ccccc2C(F)(F)F)cc1-c1c(Br)cnn1C]

To a solution of 4-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide (232 mg, 0.38 mmol) in tetrahydrofuran (2 ml) and methanol (2 ml) at 25° C. was added hydrazine (0.12 ml, 3.77 mmol) dropwise. After 12 h the solution was concentrated, dry loaded onto silica and purified by column chromatography (5% MeOH in DCM (1% $NH_4OH$)). The free base was converted to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(4-bromo-1-methyl-1H-pyrazol-5-yl)-5-methyl-2-furancarboxamide (106 mg, 0.19 mmol, 50% yield) as a yellow solid: LCMS (ES) m/z=485, 487 (M, M+2)$^+$, $^1$H NMR (400 MHz, DMSO-$d_6$) δ ppm 8.60 (d, J=9.60 Hz, 1H) 7.99 (br. s., 3H) 7.68 (s, 2H) 7.71 (d, J=8.08 Hz, 1H) 7.59 (d, J=7.33 Hz, 1H) 7.44-7.56 (m, 1H) 7.25-7.33 (m, 1H) 4.50-4.57 (m, 1H) 3.74 (s, 3H) 2.99-3.07 (m, 4H) 2.32 (s, 3H).

Example 118

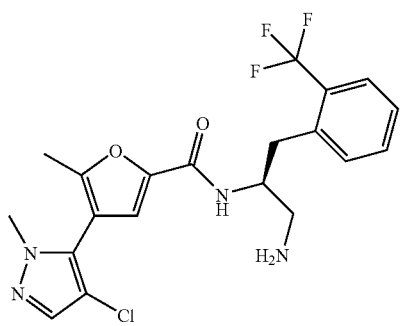 [SMILES: Cc1oc(C(=O)N[C@H](CN)Cc2ccccc2C(F)(F)F)cc1-c1c(Cl)cnn1C]

Preparation of N-((1S)-2-amino-1-{[2-(trifluoromethyl)phenyl]methyl}ethyl)-4-(4-chloro-1-methyl-1H-pyrazol-5-yl)-5-methyl-2-furancarboxamide a) 4-(4-chloro-1-methyl-1H-pyrazol-5-yl)-5-methyl-2-furancarboxylic Acid

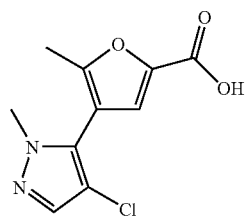 [SMILES: Cc1oc(C(=O)O)cc1-c1c(Cl)cnn1C]

A solution of methyl 5-methyl-4-(1-methyl-1H-pyrazol-5-yl)-2-furancarboxylate (300 mg, 1.36 mmol) and N-chlorosuccinimide (182 mg, 1.36 mmol) in tetrahydrofuran (6.7 ml) was stirred in a sealed tube for 1 h at 70° C. 6N sodium hydroxide (3.4 ml, 20.4 mmol) was added in one portion and the solution stirred an additional 12 h. The reaction mixture was then partitioned between $H_2O$-DCM and the pH of the aqueous phase was adjusted to ~4 and washed several times with DCM. The combined organic fractions were dried over $Na_2SO_4$, concentrated and used directly without further purification yielding 4-(4-chloro-1-methyl-1H-pyrazol-5-yl)-5-methyl-2-furancarboxylic acid (275 mg, 1.14 mmol, 84% yield) as a orange oil: LCMS (ES) m/e 241, 243 (M, M+2)$^+$.

b) 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide

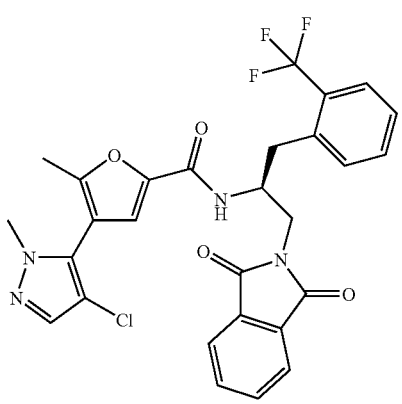

To a solution of 4-(4-chloro-1-methyl-1H-pyrazol-5-yl)-5-methyl-2-furancarboxylic acid (200 mg, 0.83 mmol), 2-{(2S)-2-amino-3-[2-(trifluoromethyl)phenyl]propyl}-1H-isoindole-1,3(2H)-dione (320 mg, 0.83 mmol)[prepared according to Preparation 6] and diisopropylethylamine (0.72 ml, 4.16 mmol) in DCM at 25° C. was added bromo-tris-pyrrolidino-phosphonium hexafluorophosphate (427 mg, 0.91 mmol) in one portion. The solution stirred at 25° C. for 12 h and was then dry loaded onto silica and purified via column chromatography (silica, 30-70% EtOAc in hexanes) yielding 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide (246 mg, 0.40 mmol, 49% yield) as a clear oil: LCMS (ES) m/e 571, 573 (M, M+2)$^+$.

c) N-((1S)-2-amino-1-{[2-(trifluoromethyl)phenyl]methyl}ethyl)-4-(4-chloro-1-methyl-1H-pyrazol-5-yl)-5-methyl-2-furancarboxamide

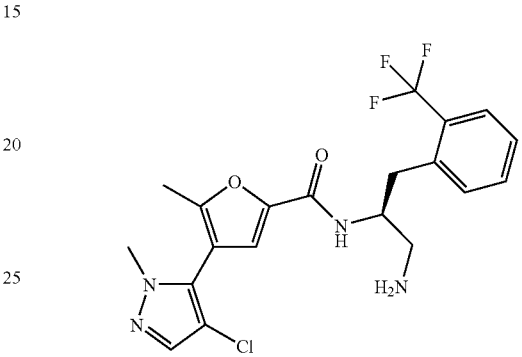

To a solution of 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide (246 mg, 0.43 mmol) in tetrahydrofuran (2.1 ml) and methanol (2.1 ml) at 25° C. was added hydrazine (135 μl, 4.31 mmol) dropwise. After 12 h the solution was concentrated, dry loaded onto silica and purified by column chromatography (5% MeOH in DCM (1% $NH_4OH$)). The free base was converted to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(4-chloro-1-methyl-1H-pyrazol-5-yl)-5-methyl-2-furancarboxamide (125 mg, 0.24 mmol, 56% yield) as a yellow solid: LCMS (ES) m/z=441, 443 (M, M+2)$^+$, $^1$H NMR (400 MHz, DMSO-d$_6$) δ ppm 8.63 (d, J=9.09 Hz, 1H) 8.04 (br. s., 3H) 7.65-7.72 (m, 2H) 7.59 (d, J=7.33 Hz, 1H) 7.57 (br. s., 1H) 7.39-7.47 (m, 1H) 7.29-7.37 (m, 1H) 4.54 (br. s., 1H) 3.73 (s, 3H) 2.98-3.09 (m, 4H) 2.33 (s, 3H).

Example 119

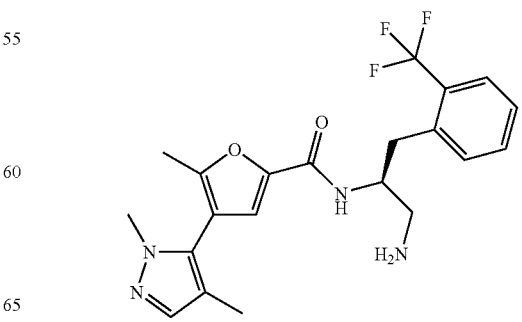

Preparation of N-((1S)-2-amino-1-{[2-(trifluoromethyl)phenyl]methyl}ethyl)-4-(1,4-dimethyl-1H-pyrazol-5-yl)-5-methyl-2-furancarboxamide a) methyl 4-(4-bromo-1-methyl-1H-pyrazol-5-yl)-5-methyl-2-furancarboxylate

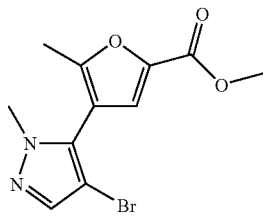

A solution of methyl 5-methyl-4-(1-methyl-1H-pyrazol-5-yl)-2-furancarboxylate (600 mg, 2.72 mmol)[prepared in Example 116] and N-bromosuccinimide (485 mg, 2.72 mmol) in tetrahydrofuran (13 ml) was stirred in a sealed tube for 1 h at 70° C. The reaction mixture was divided and half of the solution was partitioned between H₂O-DCM and the aqueous phase was washed several times with DCM. The combined organic fractions were dried over Na₂SO₄, concentrated and purified by column chromatography (5-15% EtOAc in hexanes yielding methyl 4-(4-bromo-1-methyl-1H-pyrazol-5-yl)-5-methyl-2-furancarboxylate (130 mg, 0.41 mmol, 15% yield) as an orange oil: LCMS (ES) m/e 299, 301 (M, M+2)⁺.

b) methyl 4-(1,4-dimethyl-1H-pyrazol-5-yl)-5-methyl-2-furancarboxylate

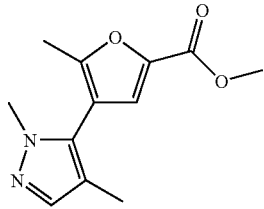

A solution of methyl 4-(4-bromo-1-methyl-1H-pyrazol-5-yl)-5-methyl-2-furancarboxylate (130 mg, 0.43 mmol), potassium carbonate (300 mg, 2.17 mmol), PdCl₂(dppf) (15.9 mg, 0.02 mmol) and trimethylboroxine (0.12 ml, 0.87 mmol) in N,N-Dimethylformamide (3.5 ml) was stirred at 110° C. in a sealed tube for 2 h. The reaction mixture was partitioned between H₂O-DCM and the aqueous phase was washed several times with DCM. The combined organic fractions were dried over Na₂SO₄, concentrated and purified via column chromatography (10-50% EtOAc in hexanes) affording methyl 4-(1,4-dimethyl-1H-pyrazol-5-yl)-5-methyl-2-furancarboxylate (60 mg, 0.26 mmol, 59% yield) as a yellow oil: LCMS (ES) m/z=235 (M+H)⁺.

c) 4-(1,4-dimethyl-1H-pyrazol-5-yl)-5-methyl-2-furancarboxylic Acid

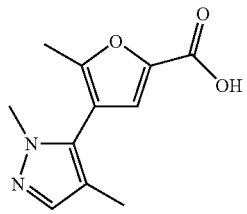 [SMILES: Cc1cnn(C)c1-c1cc(C(=O)O)oc1C]

A solution of methyl 4-(1,4-dimethyl-1H-pyrazol-5-yl)-5-methyl-2-furancarboxylate (60 mg, 0.26 mmol) in 6N sodium hydroxide (0.8 ml, 5.1 mmol) and tetrahydrofuran (2.5 ml) was stirred at 70° C. in a sealed tube for 1 h. The resulting solution was cooled and then partitioned between H₂O-DCM. The aqueous phase was adjusted to pH ~4 and then washed several times with DCM. The combined organic fractions were dried over Na₂SO₄ and concentrated affording 4-(1,4-dimethyl-1H-pyrazol-5-yl)-5-methyl-2-furancarboxylic acid (53 mg, 0.24 mmol, 94% yield) as a white foam: LCMS (ES) m/e 221 (M+H)⁺.

d) 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide

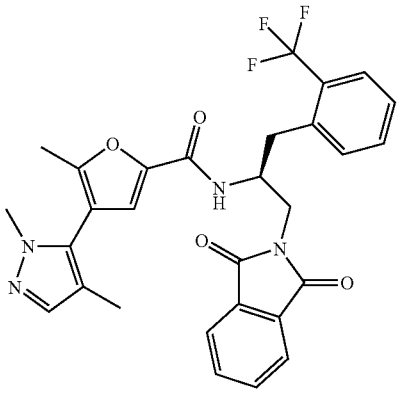 [SMILES: Cc1cnn(C)c1-c1cc(C(=O)N[C@@H](Cc2ccccc2C(F)(F)F)CN2C(=O)c3ccccc3C2=O)oc1C]

To a solution of 4-(1,4-dimethyl-1H-pyrazol-5-yl)-5-methyl-2-furancarboxylic acid (53 mg, 0.24 mmol), 2-{(2S)-2-amino-3-[2-(trifluoromethyl)phenyl]propyl}-1H-isoindole-1,3(2H)-dione (93 mg, 0.24 mmol)[prepared according to Preparation 6] and N,N-diisopropylethylamine (0.21 ml, 1.20 mmol) in dichloromethane (2.4 ml) at 25° C. was added bromo-tris-pyrrolidino-phosphonium hexafluorophosphate (124 mg, 0.26 mmol) in one portion. The solution stirred at 25° C. for 1 h and was then dry loaded onto silica and purified via column chromatography (silica, 30-70% EtOAc in hexanes) yielding 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide (113 mg, 0.21 mmol, 85% yield) as a white foam: LCMS (ES) m/e 551 (M+H)⁺.

e) N-((1S)-2-amino-1-{[2-(trifluoromethyl)phenyl]methyl}ethyl)-4-(1,4-dimethyl-1H-pyrazol-5-yl)-5-methyl-2-furancarboxamide

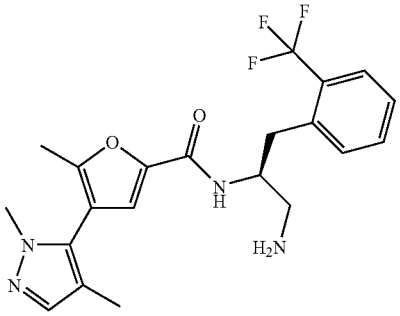 [SMILES: Cc1cnn(C)c1-c1cc(C(=O)N[C@H](CN)Cc2ccccc2C(F)(F)F)oc1C]

To a solution of 4-(1,4-dimethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-methyl-2-furancarboxamide (113 mg, 0.21 mmol) in tetrahydrofuran (1 mL) and methanol (1 mL) at 25° C. was added hydrazine (64 μl, 2.05 mmol) dropwise. After 12 h the solution was concentrated, dry loaded onto silica and purified by column chromatography (5% MeOH in DCM (1% NH$_4$OH)). The free base was converted to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-4-(1,4-dimethyl-1H-pyrazol-5-yl)-5-methyl-2-furancarboxamide (32 mg, 0.06 mmol, 32% yield) as a yellow solid: LCMS (ES) m/z=421 (M+H)$^+$, $^1$H NMR (400 MHz, DMSO-d$_6$) δ ppm 8.60 (d, J=9.09 Hz, 1H) 8.05 (br. s., 3H) 7.70 (d, J=7.58 Hz, 1H) 7.54-7.61 (m, 2H) 7.40-7.47 (m, 1H) 7.35 (s, 1H) 7.27 (s, 1H) 4.54 (br. s., 1H) 3.65 (s, 3H) 2.98-3.07 (m, 4H) 2.26 (s, 3H) 1.90 (s, 3H).

Example 120

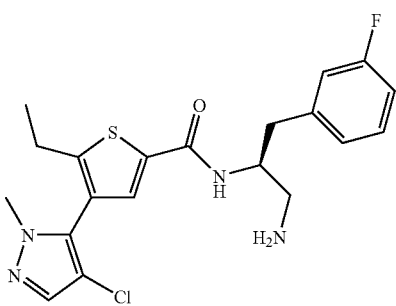

Preparation of N-{(1S)-2-amino-1-[(3-fluorophenyl)methyl]ethyl}-4-(4-chloro-1-methyl-1H-pyrazol-5-yl)-5-ethyl-2-thiophenecarboxamide The title compound was prepared as a yellow solid according to the procedure of Example 100, except substituting 2-[(2S)-2-amino-3-(3-fluorophenyl)propyl]-1H-isoindole-1,3(2H)-dione (155 mg, 0.46 mmol) [prepared according to the procedure of Preparation 6] for 2-{(2S)-2-amino-3-[2-(trifluoromethyl)phenyl]propyl}-1H-isoindole-1,3(2H)-dione: LCMS (ES) m/z=421, 423 (M, M+2)$^+$, $^1$H NMR (400 MHz, DMSO-d$_6$) δ ppm 8.76 (br. s., 1H) 8.06 (br. s., 3H) 7.85 (s, 1H) 7.69 (s, 1H) 7.28-7.36 (m, 1H) 7.12 (d, J=7.07 Hz, 2H) 7.03 (dd, J=17.05, 2.15 Hz, 1H) 4.36 (br. s., 1H) 3.69 (s, 3H) 2.93-3.02 (m, 4H) 2.67 (q, J=7.33 Hz, 2H) 1.16 (t, J=7.45 Hz, 3H).

Example 121

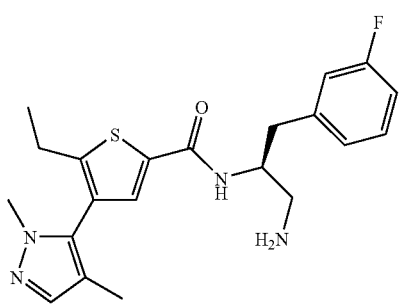 [SMILES: CCc1sc(C(=O)N[C@H](CN)Cc2cccc(F)c2)cc1-c1c(C)cnn1C]

N-{(1S)-2-amino-1-[(3-fluorophenyl)methyl]ethyl}-4-(1,4-dimethyl-1H-pyrazol-5-yl)-5-ethyl-2-thiophenecarboxamide The title compound was prepared as a yellow solid according to Example 110, except substituting 2-[(2S)-2-amino-3-(3-fluorophenyl)propyl]-1H-isoindole-1,3(2H)-dione (241 mg, 0.72 mmol) [prepared according to the procedure of Preparation 6] for 2-{(2S)-2-amino-3-[2-(trifluoromethyl)phenyl]propyl}-1H-isoindole-1,3(2H)-dione: LCMS (ES) m/z=401 (M+H)$^+$, $^1$H NMR (400 MHz, DMSO-d$_6$) δ ppm 8.76 (br. S., 1H) 8.11 (br. S., 3H) 7.79 (s, 1H) 7.37 (s, 1H) 7.28-7.36 (m, 1H) 7.12 (d, J=6.82 Hz, 2H) 7.03 (td, J=8.65, 1.64 Hz, 1H) 4.41-4.43 (m, 1H, obscured) 3.60 (br. S., 3H) 2.99-3.02 (m, 4H) 2.60 (q, J=7.33 Hz, 2H) 1.86 (s, 3H) 1.13 (t, J=7.45 Hz, 3H).

Example 122

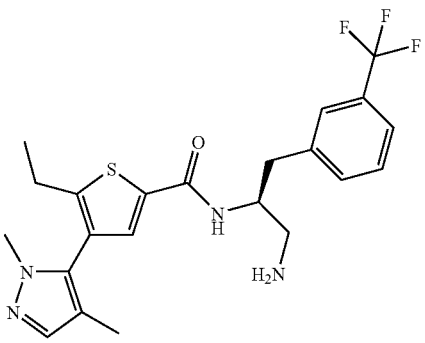 [SMILES: CCc1sc(C(=O)N[C@H](CN)Cc2cccc(C(F)(F)F)c2)cc1-c1c(C)cnn1C]

Preparation of N-((1S)-2-amino-1-{[3-(trifluoromethyl)phenyl]methyl}ethyl)-4-(1,4-dimethyl-1H-pyrazol-5-yl)-5-ethyl-2-thiophenecarboxamide The title compound was prepared as a yellow solid according to Example 110, except substituting 2-{(2S)-2-amino-3-[3-(trifluoromethyl)phenyl]propyl}-1H-isoindole-1,3(2H)-dione (277 mg, 0.72 mmol) [prepared according to the procedure of Preparation 6] for 2-{(2S)-2-amino-3-[2-(trifluoromethyl)phenyl]propyl}-1H-isoindole-1,3(2H)-dione: LCMS (ES) m/z=451 (M+H)$^+$, $^1$H NMR (400 MHz, DMSO-d$_6$) δ ppm 8.70 (br. s., 1H) 8.06 (br. s., 3H) 7.68-7.75 (m, 1H) 7.52 (s, 1H) 7.50-7.56 (m, 3H) 7.37 (s, 1H) 4.36 (d, J=8.84 Hz, 1H) 3.58 (br. s., 3H) 2.98-3.02 (m, 4H) 2.55-2.61 (m, 2H) 1.86 (s, 3H) 1.12 (t, J=7.58 Hz, 3H).

Example 123

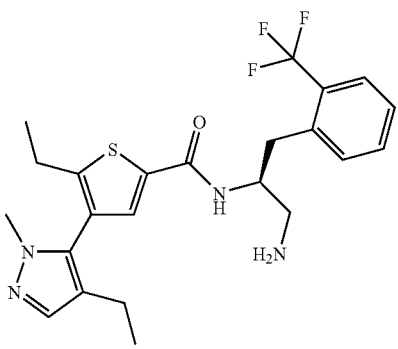 [SMILES: CCc1cnn(C)c1-c1cc(C(=O)N[C@H](CN)Cc2ccccc2C(F)(F)F)sc1CC]

Preparation of N-((1S)-2-amino-1-{[2-(trifluoromethyl)phenyl]methyl}ethyl)-5-ethyl-4-(4-ethyl-1-methyl-1H-pyrazol-5-yl)-2-thiophenecarboxamide a) methyl 4-(4-bromo-1-methyl-1H-pyrazol-5-yl)-5-ethyl-2-thiophenecarboxylate

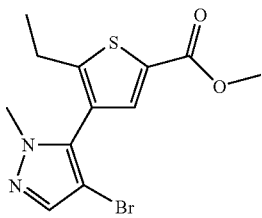

A solution of methyl 5-ethyl-4-(1-methyl-1H-pyrazol-5-yl)-2-thiophenecarboxylate (1 g, 3.99 mmol)[prepared in Example 98] and N-bromosuccinimide (0.711 g, 3.99 mmol) in tetrahydrofuran (8 ml) was stirred in a sealed tube for 1 h at 70° C. The reaction mixture was partitioned between H$_2$O-DCM and the aqueous phase was washed several times with DCM. The combined organic fractions were dried over Na$_2$SO$_4$, concentrated and purified by column chromatography (10-50% EtOAc in hexanes yielding methyl 4-(4-bromo-1-methyl-1H-pyrazol-5-yl)-5-ethyl-2-thiophenecarboxylate (1.2 g, 3.54 mmol, 89% yield) as an orange oil: LCMS (ES) m/e 329, 331 (M, M+2)$^+$.

b) methyl 4-(4-ethenyl-1-methyl-1H-pyrazol-5-yl)-5-ethyl-2-thiophenecarboxylate

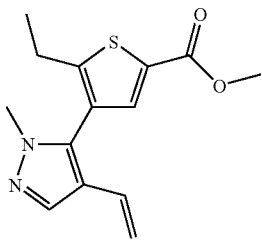

A solution of methyl 4-(4-bromo-1-methyl-1H-pyrazol-5-yl)-5-ethyl-2-thiophenecarboxylate (300 mg, 0.911 mmol), potassium carbonate (630 mg, 4.56 mmol), bis(tri-t-butylphosphine)palladium(0) (23.29 mg, 0.05 mmol) and 2,4,6-trivinylcycloboroxane-pyridine complex (110 mg, 0.45 mmol) in 1,4-dioxane (5 ml) and Water (1 ml) was stirred at 80° C. in a sealed tube for 2 h. The reaction contents were partitioned between H$_2$O-DCM and the aqueous phase was washed several times with DCM. The combined organic fractions were dried over Na$_2$SO$_4$, concentrated and purified via column chromatography (10-50% EtOAc in hexanes) affording methyl 4-(4-ethenyl-1-methyl-1H-pyrazol-5-yl)-5-ethyl-2-thiophenecarboxylate (187 mg, 0.66 mmol, 73% yield) as a clear oil: LCMS (ES) m/z=277 (M+H)$^+$.

c) methyl 5-ethyl-4-(4-ethyl-1-methyl-1H-pyrazol-5-yl)-2-thiophenecarboxylate

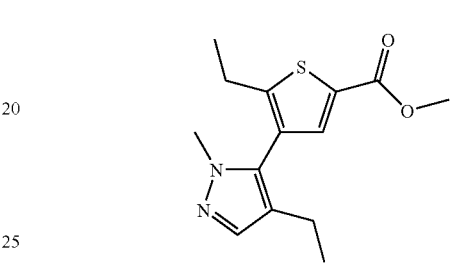

To a solution of methyl 4-(4-ethenyl-1-methyl-1H-pyrazol-5-yl)-5-ethyl-2-thiophenecarboxylate (187 mg, 0.68 mmol) in methanol (2.5 ml) was added Pd—C (7.20 mg, 0.07 mmol). The reaction mixture was hydrogenated at 1 atm (balloon) for 1 h. The solution was then purged with N$_2$, filtered through Celite and concentrated affording methyl 5-ethyl-4-(4-ethyl-1-methyl-1H-pyrazol-5-yl)-2-thiophenecarboxylate (187 mg, 0.64 mmol, 95% yield) as a clear oil which was used without further purification: LCMS (ES) m/e 279 (M+H)$^+$.

d) 5-ethyl-4-(4-ethyl-1-methyl-1H-pyrazol-5-yl)-2-thiophenecarboxylic Acid

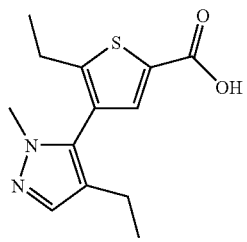 [SMILES: CCc1cnn(C)c1-c1cc(C(=O)O)sc1CC]

A solution of methyl 5-ethyl-4-(4-ethyl-1-methyl-1H-pyrazol-5-yl)-2-thiophenecarboxylate (181 mg, 0.65 mmol) in 6N sodium hydroxide (2.16 ml, 13.0 mmol) and tetrahydrofuran (5.4 ml) was stirred at 70° C. in a sealed tube for 1 h. The resulting solution was cooled and then partitioned between H$_2$O-DCM. The aqueous phase was adjusted to pH ~4 and then washed several times with DCM. The combined organic fractions were dried over Na$_2$SO$_4$ and concentrated affording 5-ethyl-4-(4-ethyl-1-methyl-1H-pyrazol-5-yl)-2-thiophenecarboxylic acid (175 mg, 0.65 mmol, 100% yield) as a white foam: LCMS (ES) m/e 265 (M+H)$^+$.

e) N-((1S)-2-(1,3-dioxo-1,3-dihydro-2H-isoindol-2-yl)-1-{[2-(trifluoromethyl)phenyl]methyl}ethyl)-5-ethyl-4-(4-ethyl-1-methyl-1H-pyrazol-5-yl)-2-thiophenecarboxamide

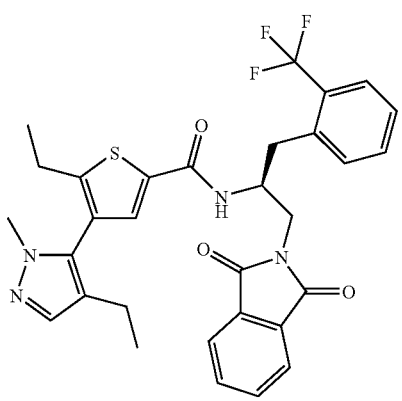 [SMILES: CCc1cnn(C)c1-c1cc(C(=O)N[C@@H](Cc2ccccc2C(F)(F)F)CN2C(=O)c3ccccc3C2=O)sc1CC]

To a solution of 5-ethyl-4-(4-ethyl-1-methyl-1H-pyrazol-5-yl)-2-thiophenecarboxylic acid (175 mg, 0.66 mmol), 2-{(2S)-2-amino-3-[2-(trifluoromethyl)phenyl]propyl}-1H-isoindole-1,3(2H)-dione (255 mg, 0.66 mmol)[prepared according to Procedure 6] and N,N-diisopropylethylamine (0.58 ml, 3.31 mmol) in Dichloromethane (4.6 ml) at 25° C. was added bromo-tris-pyrrolidino-phosphonium hexafluorophosphate (340 mg, 0.73 mmol) in one portion. The solution stirred at 25° C. for 1 h and was then dry loaded onto silica and purified via column chromatography (silica, 30-70% EtOAc in hexanes) yielding N-((1S)-2-(1,3-dioxo-1,3-dihydro-2H-isoindol-2-yl)-1-{[2-(trifluoromethyl)phenyl]methyl}ethyl)-5-ethyl-4-(4-ethyl-1-methyl-1H-pyrazol-5-yl)-2-thiophenecarboxamide (232 mg, 0.38 mmol, 57% yield) as a clear oil: LCMS (ES) m/e 595 (M+H)$^+$.

f) N-((1S)-2-amino-1-{[2-(trifluoromethyl)phenyl]methyl}ethyl)-5-ethyl-4-(4-ethyl-1-methyl-1H-pyrazol-5-yl)-2-thiophenecarboxamide

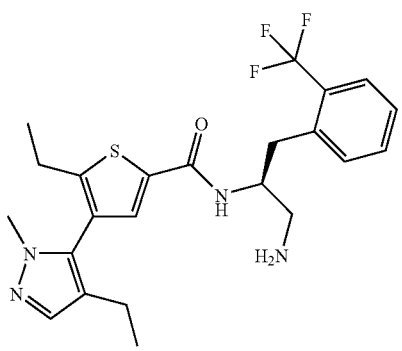 [SMILES: CCc1cnn(C)c1-c1cc(C(=O)N[C@H](CN)Cc2ccccc2C(F)(F)F)sc1CC]

To a solution of N-((1S)-2-(1,3-dioxo-1,3-dihydro-2H-isoindol-2-yl)-1-{[2-(trifluoromethyl)phenyl]methyl}ethyl)-5-ethyl-4-(4-ethyl-1-methyl-1H-pyrazol-5-yl)-2-thiophenecarboxamide (232 mg, 0.39 mmol) in tetrahydrofuran (2 mL) and methanol (2 mL) at 25° C. was added hydrazine (122 μl, 3.90 mmol) dropwise. After 12 h the solution was concentrated, dry loaded onto silica and purified by column chromatography (5% MeOH in DCM (1% NH$_4$OH)). The free base was transferred to the HCl salt by addition of excess 4M HCl in dioxane (1 ml) to the residue in MeOH (2 ml) affording the HCl salt of N-((1S)-2-amino-1-{[2-(trifluoromethyl)phenyl]methyl}ethyl)-5-ethyl-4-(4-ethyl-1-methyl-1H-pyrazol-5-yl)-2-thiophenecarboxamide (176 mg, 0.38 mmol, 97% yield) as a yellow solid: LCMS (ES) m/z=529, 531 (M, M+2)$^+$, $^1$H NMR (400 MHz, DMSO-d$_6$) δ ppm 8.64 (br. s., 1H) 7.97 (br. s., 3H) 7.65-7.73 (m, 3H) 7.57 (d, J=5.05 Hz, 2H) 7.59 (br. s., 1H) 7.44 (br. s., 1H) 4.48 (br. s., 1H) 3.69 (s, 3H) 2.98-3.12 (m, 4H) 1.24 (dd, J=6.82, 2.27 Hz, 3H) 1.16 (dd, J=6.82, 2.53 Hz, 3H).

Example 124

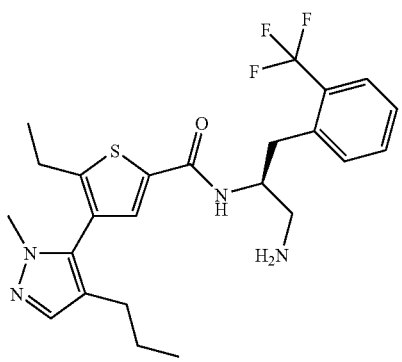 [SMILES: CCCc1cnn(C)c1-c1cc(C(=O)N[C@H](CN)Cc2ccccc2C(F)(F)F)sc1CC]

Preparation of N-((1S)-2-amino-1-{[2-(trifluoromethyl)phenyl]methyl}ethyl)-5-ethyl-4-(1-methyl-4-propyl-1H-pyrazol-5-yl)-2-thiophenecarboxamide The title compound was prepared as a yellow solid according to Example 123, except substituting (1Z)-1-propen-1-ylboronic acid (78 mg, 0.91 mmol) for 2,4,6-trivinylcycloboroxane-pyridine complex: LCMS (ES) m/z=479 (M+H)$^+$, $^1$H NMR (400 MHz, DMSO-d$_6$) δ ppm 8.63 (s, 1H) 8.01 (br. s., 3H) 7.67 (s, 2H) 7.56 (d, J=5.05 Hz, 2H) 7.38-7.46 (m, 2H) 4.42-4.47 (m, 1H) 3.59 (s, 3H) 2.98-3.02 (m, 4H) 2.66-2.71 (m, 2H) 1.40-1.47 (m, 2H) 1.13 (t, J=7.52 Hz, 3H) 0.83 (t, J=7.26 Hz, 3H).

Example 125

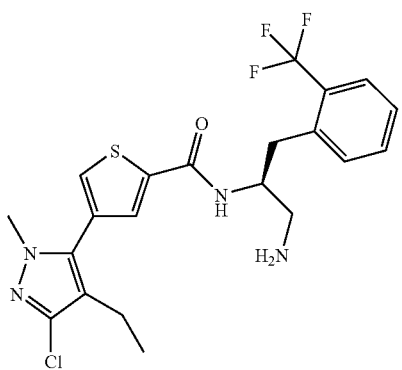

Preparation of N-((1S)-2-amino-1-{[2-(trifluoromethyl)phenyl]methyl}ethyl)-4-(3-chloro-4-ethyl-1-methyl-1H-pyrazol-5-yl)-2-thiophenecarboxamide a) methyl 4-bromo-2-thiophenecarboxylate

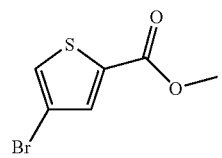

To a solution of 4-bromo-2-thiophenecarboxylic acid (25 g, 121 mmol) in methanol (241 ml) was added sulfuric acid (32 ml, 604 mmol). The resulting solution stirred at 50° C. over 4 d. The solution was partitioned between H$_2$O-DCM and the aqueous phase was washed several times with DCM. The combined organic fractions were dried over Na$_2$SO$_4$, concentrated and used directly without further purification providing methyl 4-bromo-2-thiophenecarboxylate (26 g, 118 mmol, 97% yield), LCMS (ES) m/e 222 (M+H)$^+$.

b) methyl 4-(1-methyl-1H-pyrazol-5-yl)-2-thiophenecarboxylate

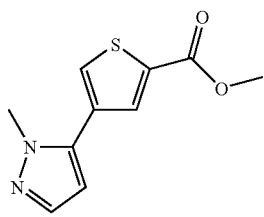

A solution of methyl 4-bromo-2-thiophenecarboxylate (2.5 g, 11.31 mmol), potassium carbonate (7.81 g, 56.5 mmol), 1-methyl-5-(4,4,5,5-tetramethyl-1,3,2-dioxaborolan-2-yl)-1H-pyrazole (2.59 g, 12.44 mmol)[prepared according to Preparation 7] and bis(tri-t-butylphosphine)palladium(0) (0.289 g, 0.56 mmol) in 1,4-dioxane (47 ml) and water (9 ml) was stirred at 80° C. in a sealed tube for 1 h. 1-methyl-5-(4,4,5,5-tetramethyl-1,3,2-dioxaborolan-2-yl)-1H-pyrazole (2.59 g, 12.44 mmol) and bis(tri-t-butylphosphine)palladium(0) (0.289 g, 0.56 mmol) were added and the reaction stirred an additional 1 h. The mixture was partitioned between H$_2$O-DCM. The aqueous phase was washed several times with DCM and the combined organic fractions were dried over Na$_2$SO$_4$, concentrated and purified via column chromatography (10-40% EtOAc in hexanes) affording methyl 4-(1-methyl-1H-pyrazol-5-yl)-2-thiophenecarboxylate (2.5 g, 11.25 mmol, 99% yield) as a yellow solid: LCMS (ES) m/e 223 (M+H)$^+$.

c) methyl 4-(4-bromo-1-methyl-1H-pyrazol-5-yl)-2-thiophenecarboxylate

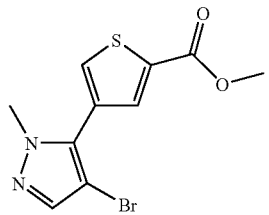

A solution of methyl 4-(1-methyl-1H-pyrazol-5-yl)-2-thiophenecarboxylate (2.5 g, 11.25 mmol) and n-bromosuccinimide (2.002 g, 11.25 mmol) in tetrahydrofuran (56.2 ml) was stirred in a sealed tube for 1 h at 70° C. The reaction mixture was partitioned between H$_2$O-DCM and the aqueous phase was washed several times with DCM. The combined organic fractions were dried over Na$_2$SO$_4$, concentrated and purified by column chromatography (10-50% EtOAc in hexanes yielding methyl 4-(4-bromo-1-methyl-1H-pyrazol-5-yl)-2-thiophenecarboxylate (2.7 g, 8.97 mmol, 80% yield) as a yellow solid: LCMS (ES) m/e 301, 303 (M, M+2)$^+$.

d) methyl 4-(4-ethenyl-1-methyl-1H-pyrazol-5-yl)-2-thiophenecarboxylate

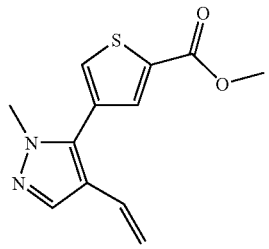

A solution of methyl 4-(4-bromo-1-methyl-1H-pyrazol-5-yl)-5-ethyl-2-thiophenecarboxylate (300 mg, 0.91 mmol), potassium carbonate (630 mg, 4.56 mmol), bis(tri-t-butylphosphine)palladium(0) (23 mg, 0.05 mmol) and 2,4,6-trivinylcycloboroxane-pyridine complex (110 mg, 0.46 mmol) in 1,4-dioxane (5 ml) and water (1 ml) was stirred at 80° C. in a sealed tube for 2 h. The reaction contents were partitioned between H$_2$O-DCM and the aqueous phase was washed several times with DCM. The combined organic fractions were dried over Na$_2$SO$_4$, concentrated and purified via column chromatography (10-50% EtOAc in hexanes) affording methyl 4-(4-ethenyl-1-methyl-1H-pyrazol-5-yl)-5-ethyl-2-thiophenecarboxylate (187 mg, 0.66 mmol, 73% yield) as a clear oil: LCMS (ES) m/z=277 (M+H)$^+$.

e) methyl 4-(4-ethyl-1-methyl-1H-pyrazol-5-yl)-2-thiophenecarboxylate

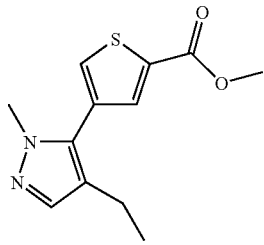

To a solution of methyl 4-(4-ethenyl-1-methyl-1H-pyrazol-5-yl)-5-ethyl-2-thiophenecarboxylate (187 mg, 0.68 mmol) in methanol (2.5 ml) was added Pd—C (7.20 mg, 0.07 mmol). The reaction mixture was hydrogenated at 1 atm (balloon) for 1 h. The solution was then purged with N$_2$, filtered through Celite and concentrated affording methyl 5-ethyl-4-(4-ethyl-1-methyl-1H-pyrazol-5-yl)-2-thiophenecarboxylate (187 mg, 0.64 mmol, 95% yield) as a clear oil which was used without further purification: LCMS (ES) m/e 279 (M+H)$^+$.

f) methyl 4-(3-chloro-4-ethyl-1-methyl-1H-pyrazol-5-yl)-2-thiophenecarboxylate

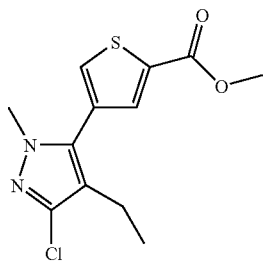

A solution of methyl 4-(4-ethyl-1-methyl-1H-pyrazol-5-yl)-2-thiophenecarboxylate (202 mg, 0.81 mmol) and NCS (108 mg, 0.81 mmol) in N,N-dimethylformamide (4 ml) was stirred in a sealed tube for 1 h at 100° C. Additional NCS (108 mg, 0.81 mmol) was added and the solution stirred 1 h. The reaction mixture was partitioned between H$_2$O-DCM and the aqueous phase was washed several times with DCM. The combined organic fractions were dried over Na$_2$SO$_4$, concentrated and purified via column chromatography (2-30% EtOAc in hexanes) affording methyl 4-(3-chloro-4-ethyl-1-methyl-1H-pyrazol-5-yl)-2-thiophenecarboxylate (135 mg, 0.45 mmol, 56% yield) as a yellow oil: LCMS (ES) m/e 285 (M+H)$^+$.

g) 4-(3-chloro-4-ethyl-1-methyl-1H-pyrazol-5-yl)-2-thiophenecarboxylic Acid

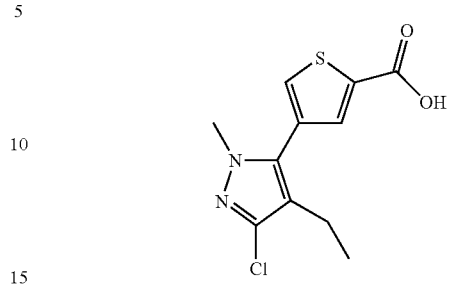

A solution of methyl 4-(3-chloro-4-ethyl-1-methyl-1H-pyrazol-5-yl)-2-thiophenecarboxylate (135 mg, 0.47 mmol) in 6N sodium hydroxide (1.6 ml, 9.48 mmol) and tetrahydrofuran (5.4 ml) was stirred at 70° C. in a sealed tube for 12 h. The resulting solution was cooled and then partitioned between H$_2$O-DCM. The aqueous phase was adjusted to pH ~4 and then washed several times with DCM. The combined organic fractions were dried over Na$_2$SO$_4$ and concentrated affording 4-(3-chloro-4-ethyl-1-methyl-1H-pyrazol-5-yl)-2-thiophenecarboxylic acid (120 mg, 0.41 mmol, 87% yield) as a white foam: LCMS (ES) m/e 270, 272 (M, M+2)$^+$.

h) 4-(3-chloro-4-ethyl-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

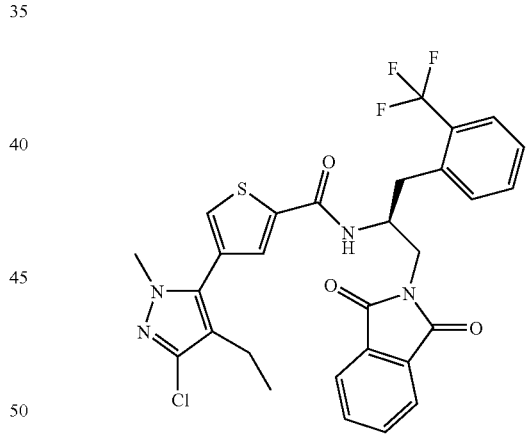

To a solution of 4-(3-chloro-4-ethyl-1-methyl-1H-pyrazol-5-yl)-2-thiophenecarboxylic acid (120 mg, 0.44 mmol), 2-{(2S)-2-amino-3-[2-(trifluoromethyl)phenyl]propyl}-1H-isoindole-1,3(2H)-dione (171 mg, 0.44 mmol)[prepared according to Preparation 6] and n,n-diisopropylethylamine (0.39 ml, 2.22 mmol) in Dichloromethane (4.6 ml) at 25° C. was added bromo-tris-pyrrolidino-phosphonium hexafluorophosphate (228 mg, 0.49 mmol) in one portion. The solution stirred at 25° C. for 1 h and was then dry loaded onto silica and purified via column chromatography (silica, 30-70% EtOAc in hexanes) yielding 4-(3-chloro-4-ethyl-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (190 mg, 0.30 mmol, 68% yield) as a white solid: LCMS (ES) m/e 601, 603 (M, M+2)$^+$.

i) N-((1S)-2-amino-1-{[2-(trifluoromethyl)phenyl]methyl}ethyl)-4-(3-chloro-4-ethyl-1-methyl-1H-pyrazol-5-yl)-2-thiophenecarboxamide

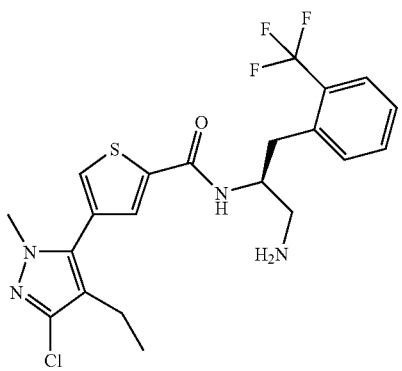

To a solution of 4-(3-chloro-4-ethyl-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (190 mg, 0.32 mmol) in tetrahydrofuran (1.58 ml) and methanol (1.58 ml) at 25° C. was added hydrazine (0.08 ml, 2.53 mmol) dropwise. After 12 h the solution was concentrated, dry loaded onto silica and purified by column chromatography (5% MeOH in DCM (1% NH$_4$OH)). The free base was transferred to the HCl salt by addition of excess 4M HCl in Ether (2 ml) to the residue in DCM (2 ml) affording the HCl salt of N-((1S)-2-amino-1-{[2-(trifluoromethyl)phenyl]methyl}ethyl)-4-(3-chloro-4-ethyl-1-methyl-1H-pyrazol-5-yl)-2-thiophenecarboxamide (145 mg, 0.26 mmol, 83% yield) as a yellow solid: LCMS (ES) m/z=471, 473 (M, M+2)$^+$, $^1$H NMR (400 MHz, DMSO-d$_6$) δ ppm 8.80 (br. s., 1H) 7.87-7.99 (m, 6H) 7.69 (d, J=7.71 Hz, 1H)) 7.57 (d, J=7.83 Hz, 1H) 7.40-7.44 (m, 1H) 4.43-4.48 (m, 1H) 3.74 (s, 3H) 2.99-3.06 (m, 4H) 2.40 (d, J=7.58 Hz, 2H) 1.04 (t, J=7.58 Hz, 3H).

Example 126

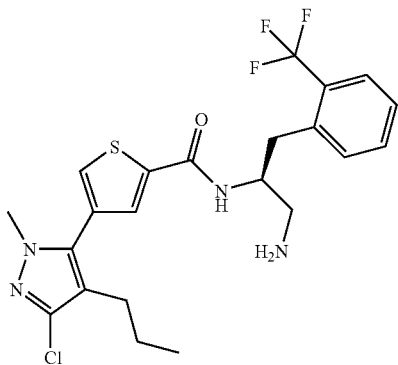 [SMILES: CCCc1c(Cl)nn(C)c1-c1csc(C(=O)N[C@H](CN)Cc2ccccc2C(F)(F)F)c1]

Preparation of N-((1S)-2-amino-1-{[2-(trifluoromethyl)phenyl]methyl}ethyl)-4-(3-chloro-1-methyl-4-propyl-1H-pyrazol-5-yl)-2-thiophenecarboxamide The title compound was prepared as a yellow solid according to Example 125, except substituting (1Z)-1-propen-1-ylboronic acid (125 mg, 1.46 mmol) for 2,4,6-trivinylcyloboroxane-pyridine complex: LCMS (ES) m/z=485, 487 (M, M+2)$^+$, $^1$H NMR (400 MHz, DMSO-d$_6$) δ ppm 8.94 (d, J=9.09 Hz, 1H) 8.05 (s, 4H) 7.98 (s, 1H) 7.69 (d, J=7.58 Hz, 1H) 7.55-7.63 (m, 1H) 7.52 (t, J=7.58 Hz, 1H) 7.42 (t, J=7.33 Hz, 1H) 4.49 (d, J=4.29 Hz, 1H) 3.74 (s, 3H) 2.98-3.09 (m, 4H) 2.37 (q, J=7.07 Hz, 2H) 1.37-1.45 (m, 2H) 0.80 (t, J=7.33 Hz, 3H).

Example 127

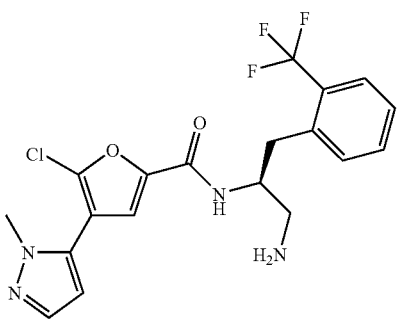

Preparation of N-((1S)-2-amino-1-{[2-(trifluoromethyl)phenyl]methyl}ethyl)-5-chloro-4-(1-methyl-1H-pyrazol-5-yl)-2-furancarboxamide a) methyl 4,5-dibromo-2-furancarboxylate

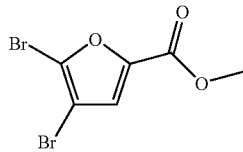

To a solution of 4,5-dibromo-2-furancarboxylic acid (25 g, 93 mmol) in methanol (185 ml) was added sulfuric acid (24.7 ml, 463 mmol). The resulting solution stirred at 50° C. over 12 h. The solution was partitioned between H$_2$O-DCM and the aqueous phase was washed several times with DCM. The combined organic fractions were dried over Na$_2$SO$_4$, concentrated and used directly without further purification providing methyl 4,5-dibromo-2-furancarboxylate (23.67 g, 83 mmol, 90% yield), LCMS (ES) m/e 283, 285, 287 (M, M+2, M+4)$^+$.

b) methyl 4-bromo-2-furancarboxylate

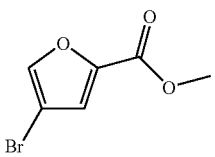

To a solution of methyl 4,5-dibromo-2-furancarboxylate (3.3 g, 11.62 mmol) in tetrahydrofuran (46 ml) at −40° C. was added isopropylmagnesium chloride (6.97 ml, 13.95 mmol). After 1 h, Water (11 ml) was added and the solution warmed to 25° C. The reaction mixture was then partitioned between H$_2$O-DCM and the aqueous phase was washed several times with DCM. The combined organic fractions were dried over Na$_2$SO$_4$, concentrated and purified by column chromatography (3% EtOAc in hexanes) affording methyl 4-bromo-2-furancarboxylate (1.4 g, 6.49 mmol, 56% yield) as a yellow solid: LCMS (ES) m/e 205, 207 (M, M+2)$^+$.

c) methyl 4-bromo-5-chloro-2-furancarboxylate

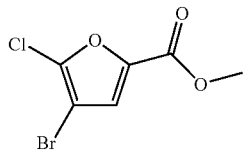

A solution of methyl 4-bromo-2-furancarboxylate (1.4 g, 6.83 mmol) and NCS (0.912 g, 6.83 mmol) in N,N-dimethylformamide (13.7 ml) was stirred in a sealed tube for 1 h at 100° C. After 1 h, the solution was partitioned between DCM-H$_2$O and the aqueous phase was washed several times with DCM. The combined organic fractions were dried over Na$_2$SO$_4$, concentrated and purified via column chromatography (2-10% EtOAc in hexanes) affording methyl 4-bromo-5-chloro-2-furancarboxylate (1.348 g, 5.12 mmol, 75% yield) as a white solid: LCMS (ES) m/e 238, 240, 242 (M, M+2, M+4)$^+$.

d) methyl 5-chloro-4-(1-methyl-1H-pyrazol-5-yl)-2-furancarboxylate

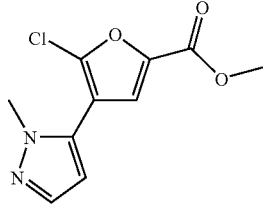

A solution of methyl 4-bromo-5-chloro-2-furancarboxylate (1.1 g, 4.59 mmol), 1-methyl-5-(4,4,5,5-tetramethyl-1,3,2-dioxaborolan-2-yl)-1H-pyrazole (1.05 g, 5.05 mmol)[prepared according to Preparation 7], potassium carbonate (3.17 g, 22.97 mmol) and bis(tri-t-butylphosphine)palladium(0) (0.117 g, 0.23 mmol) in 1,4-dioxane (19.14 ml) and water (3.83 ml) was stirred at 80° C. in a sealed tube for 1 h. The reaction mixture was partitioned between H$_2$O-DCM and the aqueous phase was washed several times with DCM. The combined organic fractions were dried over Na$_2$SO$_4$, concentrated and purified via column chromatography (silica, 4-25% EtOAc in hexanes) yielding methyl 5-chloro-4-(1-methyl-1H-pyrazol-5-yl)-2-furancarboxylate (800 mg, 2.53 mmol, 55% yield) as a yellow oil: LCMS m/e ES 240, 242 (M, M+2)$^+$.

e) 5-chloro-4-(1-methyl-1H-pyrazol-5-yl)-2-furancarboxylic Acid

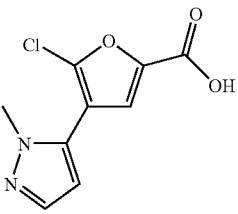

A solution of methyl 5-chloro-4-(1-methyl-1H-pyrazol-5-yl)-2-furancarboxylate (300 mg, 1.25 mmol) in 6N sodium hydroxide (4.16 ml, 24.93 mmol) and tetrahydrofuran (5.4 ml) was stirred at 70° C. in a sealed tube for 1 h. The resulting solution was cooled and then partitioned between H$_2$O-DCM. The aqueous phase was adjusted to pH ~4 and then washed several times with DCM. The combined organic fractions were dried over Na$_2$SO$_4$ and concentrated affording 5-chloro-4-(1-methyl-1H-pyrazol-5-yl)-2-furancarboxylic acid (267 mg, 0.59 mmol, 47% yield) as a white foam: LCMS (ES) m/e 265 (M+H)$^+$.

f) 5-chloro-N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)-2-furancarboxamide

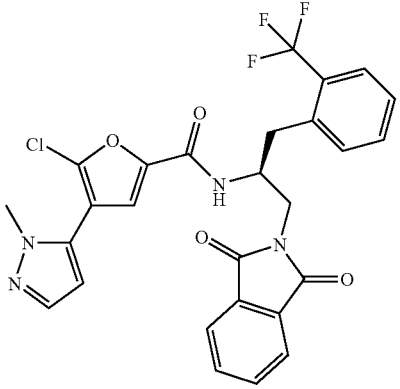 [SMILES: Cn1nccc1-c1cc(C(=O)N[C@@H](Cc2ccccc2C(F)(F)F)CN2C(=O)c3ccccc3C2=O)oc1Cl]

To a solution of 5-chloro-4-(1-methyl-1H-pyrazol-5-yl)-2-furancarboxylic acid (134 mg, 0.59 mmol), 2-{(2S)-2-amino-3-[2-(trifluoromethyl)phenyl]propyl}-1H-isoindole-1,3 (2H)-dione (228 mg, 0.59 mmol)[prepared according to Preparation 6] and N,N-diisopropylethylamine (0.52 ml, 2.96 mmol) in Dichloromethane (4.6 ml) at 25° C. was added bromo-tris-pyrrolidino-phosphonium hexafluorophosphate (304 mg, 0.65 mmol) in one portion. The solution stirred at 25° C. for 1 h and was then dry loaded onto silica and purified via column chromatography (silica, 30-70% EtOAc in hexanes) yielding 5-chloro-N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)-2-furancarboxamide (202 mg, 0.33 mmol, 55.8% yield) as a yellow oil: LCMS (ES) m/e 557, 559 (M, M+2)$^+$.

g) N-((1S)-2-amino-1-{[2-(trifluoromethyl)phenyl]methyl}ethyl)-5-chloro-4-(1-methyl-1H-pyrazol-5-yl)-2-furancarboxamide

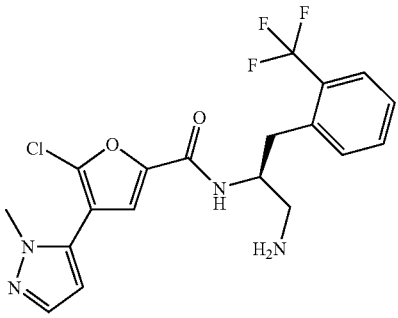 [SMILES: Cn1nccc1-c1cc(C(=O)N[C@H](CN)Cc2ccccc2C(F)(F)F)oc1Cl]

To a solution of 5-chloro-N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)-2-furancarboxamide (202 mg, 0.36 mmol) in tetrahydrofuran (1.8 ml) and methanol (1.8 ml) at 25° C. was added hydrazine (0.08 ml, 2.54 mmol) dropwise. After 12 h the solution was concentrated, dry loaded onto silica and purified by column chromatography (2% MeOH in DCM (1% NH$_4$OH)). The free base was transferred to the HCl salt by addition of excess 2M HCl in diethyl ether (2 ml) to the residue in DCM (2 ml) affording the HCl salt of N-((1S)-2-amino-1-{[2-(trifluoromethyl)phenyl]methyl}ethyl)-5-chloro-4-(1-methyl-1H-pyrazol-5-yl)-2-furancarboxamide (120 mg, 0.24 mmol, 66% yield) as a yellow solid: LCMS (ES) m/z=427, 429 (M, M+2)$^+$, $^1$H NMR (400 MHz, DMSO-d$_6$) δ ppm 8.87 (d, J=9.09 Hz, 1H) 8.11 (br. s., 3H) 7.66-7.73 (m, 2H) 7.57 (t, J=7.45 Hz, 2H) 7.53 (d, J=1.52 Hz, 1H) 7.44 (d, J=6.82 Hz, 1H) 6.50 (d, J=1.52 Hz, 1H) 4.43-4.51 (m, 1H) 3.86 (s, 3H) 2.99-3.17 (m, 4H).

Example 128

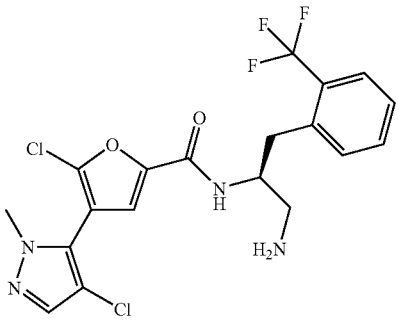 [SMILES: Cn1ncc(Cl)c1-c1cc(C(=O)N[C@H](CN)Cc2ccccc2C(F)(F)F)oc1Cl]

Preparation of N-((1S)-2-amino-1-{[2-(trifluoromethyl)phenyl]methyl}ethyl)-5-chloro-4-(4-chloro-1-methyl-1H-pyrazol-5-yl)-2-furancarboxamide a) 5-chloro-4-(4-chloro-1-methyl-1H-pyrazol-5-yl)-2-furancarboxylic Acid

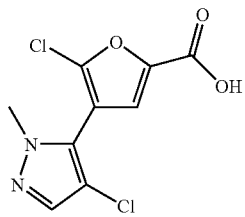 [SMILES: Cn1ncc(Cl)c1-c1cc(C(=O)O)oc1Cl]

A solution of methyl 5-chloro-4-(1-methyl-1H-pyrazol-5-yl)-2-furancarboxylate (300 mg, 1.25 mmol)[prepared according to Example 127] and n-chlorosuccinimide (166 mg, 1.25 mmol) in tetrahydrofuran (6 ml) was stirred in a sealed tube for 1 h at 70° C. 6N sodium hydroxide (4.1 ml, 24.94 mmol) was added in one portion and the solution stirred an additional 12 h. The reaction mixture was then partitioned between H$_2$O-DCM and the pH of the aqueous phase was adjusted to ~4 and washed several times with DCM. The combined organic fractions were dried over Na$_2$SO$_4$, concentrated and used directly without further purification yielding 5-chloro-4-(4-chloro-1-methyl-1H-pyrazol-5-yl)-2-furancarboxylic acid (232 mg, 0.44 mmol, 36% yield) as a yellow oil: LCMS (ES) m/e 261, 263 (M, M+2)$^+$.

b) 5-chloro-4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-furancarboxamide

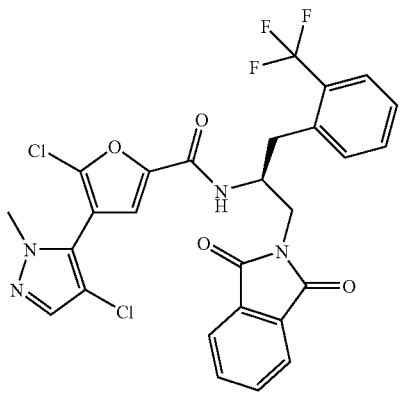 [SMILES: Cn1ncc(Cl)c1-c1cc(C(=O)N[C@@H](Cc2ccccc2C(F)(F)F)CN2C(=O)c3ccccc3C2=O)oc1Cl]

To a solution of 5-chloro-4-(4-chloro-1-methyl-1H-pyrazol-5-yl)-2-furancarboxylic acid (116 mg, 0.44 mmol), 2-{(2S)-2-amino-3-[2-(trifluoromethyl)phenyl]propyl}-1H-isoindole-1,3(2H)-dione (171 mg, 0.44 mmol)[prepared according to Preparation 6] and n,n-diisopropylethylamine (0.39 ml, 2.22 mmol) in dichloromethane (4.6 ml) at 25° C. was added bromo-tris-pyrrolidino-phosphonium hexafluorophosphate (228 mg, 0.49 mmol) in one portion. The solution stirred at 25° C. for 1 h and was then dry loaded onto silica and purified via column chromatography (silica, 30-70% EtOAc in hexanes) yielding 5-chloro-4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-furancarboxamide (116 mg, 0.19 mmol, 42% yield) as a yellow oil: LCMS (ES) m/e 591, 593 (M, M+2)$^+$.

c) N-((1S)-2-amino-1-{[2-(trifluoromethyl)phenyl]methyl}ethyl)-5-chloro-4-(4-chloro-1-methyl-1H-pyrazol-5-yl)-2-furancarboxamide

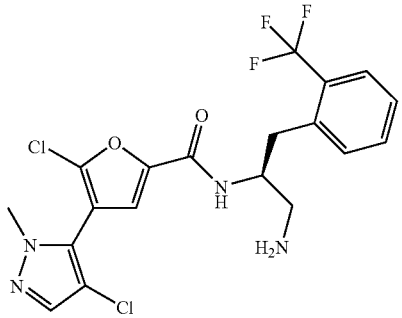 [SMILES: Cn1ncc(Cl)c1-c1cc(C(=O)N[C@H](CN)Cc2ccccc2C(F)(F)F)oc1Cl]

To a solution of 5-chloro-4-(4-chloro-1-methyl-1H-pyrazol-5-yl)-N-((1S)-2-(1,3-dioxo-1,3-dihydro-2H-isoindol-2- yl)-1-{[2-(trifluoromethyl)phenyl]methyl}ethyl)-2-furan-carboxamide (116 mg, 0.20 mmol) in tetrahydrofuran (1 ml) and methanol (1 ml) at 25° C. was added hydrazine (0.04 ml, 1.37 mmol) dropwise. After 12 h the solution was concentrated, dry loaded onto silica and purified by column chromatography (2% MeOH in DCM (1% NH$_4$OH)). The free base was transferred to the HCl salt by addition of excess 2M HCl in Ether (2 ml) to the residue in DCM (2 ml) affording the HCl salt of N-((1S)-2-amino-1-{[2-(trifluoromethyl)phenyl]methyl}ethyl)-5-chloro-4-(4-chloro-1-methyl-1H-pyrazol-5-yl)-2-furancarboxamide (68 mg, 0.13 mmol, 65% yield) as a yellow solid: LCMS (ES) m/z=461, 463 (M, M+2)$^+$, $^1$H NMR (400 MHz, DMSO-d$_6$) δ ppm 8.80 (d, J=9.09 Hz, 1H) 8.03 (br. s., 3H) 7.66-7.73 (m, 2H) 7.58-7.61 (m, 1H) 7.52-7.59 (m, 2H) 7.40-7.48 (m, 1H) 4.5-4.57 (m, 1H) 3.77 (s, 3H) 2.98-3.09 (m, 4H).

Example 129

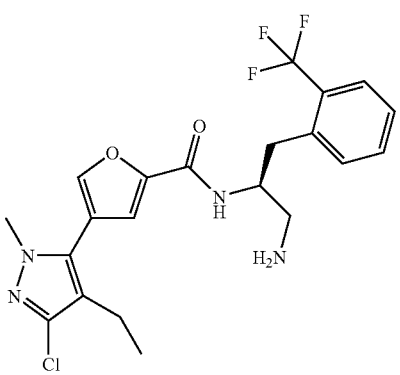 [SMILES: CCc1c(Cl)nn(C)c1-c1coc(C(=O)N[C@H](CN)Cc2ccccc2C(F)(F)F)c1]

Preparation of N-((1S)-2-amino-1-{[2-(trifluoromethyl)phenyl]methyl}ethyl)-4-(3-chloro-4-ethyl-1-methyl-1H-pyrazol-5-yl)-2-furancarboxamide The title compound was prepared as a yellow solid according to Example 125, except substituting methyl 4-bromo-2-furancarboxylate (5 g, 24.39 mmol) for methyl 4-bromo-2-thiophenecarboxylate: LCMS (ES) m/z=455, 457 (M, M+2)$^+$, $^1$H NMR (400 MHz, DMSO-d$_6$) δ ppm 8.75 (d, J=9.09 Hz, 1H) 8.23 (s, 1H) 8.05 (br. s., 3H) 7.70 (d, J=7.83 Hz, 1H) 7.53-7.60 (m, 2H) 7.42=0-7.43 (m, 2H) 4.50-4.55 (m, 1H) 3.74 (s, 3H) 2.99-3.08 (m, 4H) 2.39 (q, J=7.33 Hz, 2H) 1.03 (t, J=7.45 Hz, 3H).

Example 130

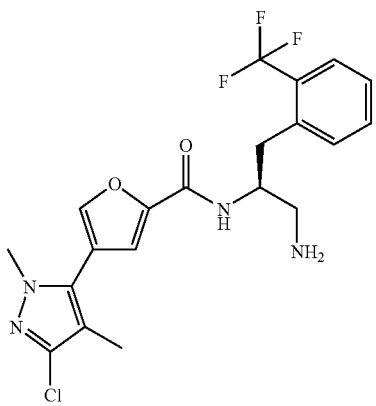 [SMILES: Cc1c(Cl)nn(C)c1-c1coc(C(=O)N[C@H](CN)Cc2ccccc2C(F)(F)F)c1]

Preparation of N-((1S)-2-amino-1-{[2-(trifluoromethyl)phenyl]methyl}ethyl)-4-(3-chloro-1,4-dimethyl-1H-pyrazol-5-yl)-2-furancarboxamide The title compound was prepared as a yellow solid according to Example 125, except substituting trimethylboroxine (0.78 ml, 5.61 mmol) for 2,4,6-trivinylcycloboroxane-pyridine complex and methyl 4-bromo-2-furancarboxylate (5 g, 24.39 mmol) for methyl 4-bromo-2-thiophenecarboxylate: LCMS (ES) m/z=441, 443 (M, M+2)$^+$, $^1$H NMR (400 MHz, DMSO-d$_6$) δ ppm 8.71 (d, J=9.35 Hz, 1H) 8.27 (s, 1H) 8.01 (br. s., 3H) 7.70 (d, J=7.58 Hz, 1H) 7.55 (t, J=6.06 Hz, 2H) 7.40-7.47 (m, 2H) 4.50-4.57 (m, 1H) 3.78 (s, 3H) 2.99-3.08 (m, 4H) 1.98 (s, 3H).

Example 131

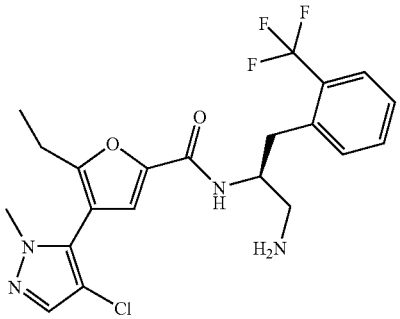 [SMILES: CCc1oc(C(=O)N[C@H](CN)Cc2ccccc2C(F)(F)F)cc1-c1c(Cl)cnn1C]

Preparation of N-((1S)-2-amino-1-{[2-(trifluoromethyl)phenyl]methyl}ethyl)-4-(4-chloro-1-methyl-1H-pyrazol-5-yl)-5-ethyl-2-furancarboxamide a) methyl 5-ethenyl-2-furancarboxylate

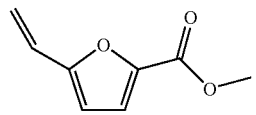

A solution of methyl 5-bromo-2-furancarboxylate (2.5 g, 12.19 mmol), potassium carbonate (8.43 g, 61.0 mmol), bis(tri-t-butylphosphine)palladium(0) (0.312 g, 0.61 mmol) and 2,4,6-trivinylcycloboroxane-pyridine complex (1.47 g, 6.10 mmol) in 1,4-dioxane (50 ml) and water (10 ml) was stirred at 80° C. in a sealed tube for 2 h. The reaction contents were partitioned between H$_2$O-DCM and the aqueous phase was washed several times with DCM. The combined organic fractions were dried over Na$_2$SO$_4$, concentrated and purified via column chromatography (10-50% EtOAc in hexanes) affording methyl 5-ethenyl-2-furancarboxylate (1.3 g, 7.09 mmol, 58% yield) as a yellow oil: LCMS (ES) m/z=153 (M+H)$^+$.

b) methyl 5-ethyl-2-furancarboxylate

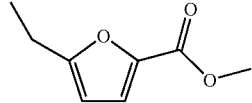

To a solution of methyl 5-ethenyl-2-furancarboxylate (1.3 g, 8.54 mmol) in methanol (15 ml) was added PdOH$_2$ (0.240 g, 1.71 mmol). The reaction mixture was hydrogenated at 1 atm (balloon) for 1 h. The solution was then purged with N$_2$, filtered through Celite and concentrated affording methyl 5-ethyl-2-furancarboxylate (1.2 g, 7.16 mmol, 84% yield) as a clear oil which was used without further purification: LCMS (ES) m/e 155 (M+H)$^+$.

c) methyl 4-bromo-5-ethyl-2-furancarboxylate

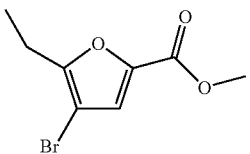

To a solution of methyl 5-ethyl-2-furancarboxylate (1.2 g, 7.78 mmol) and aluminum trichloride (1.56 g, 11.68 mmol) in chloroform (15 ml) at 25° C. was added bromine (0.56 ml, 10.90 mmol). The resulting solution stirred at 70° C. in a sealed tube for 2 h and the solution was cooled, concentrated and purified via column chromatography (silica, 5% EtOAc in hexanes) affording methyl 4-bromo-5-ethyl-2-furancarboxylate (1.1 g, 3.26 mmol, 41.8% yield) as a white solid; LCMS (ES) m/z=233, 235 (M, M+2)$^+$.

d) methyl 5-ethyl-4-(1-methyl-1H-pyrazol-5-yl)-2-furancarboxylate

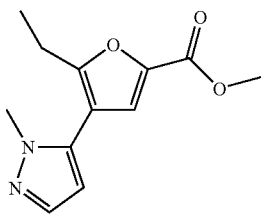

A solution of methyl 4-bromo-5-ethyl-2-furancarboxylate (1.1 g, 4.72 mmol), potassium carbonate (3.26 g, 23.60 mmol), 1-methyl-5-(4,4,5,5-tetramethyl-1,3,2-dioxaborolan-2-yl)-1H-pyrazole (1.178 g, 5.66 mmol)[prepared according to Preparation 7] and bis(tri-t-butylphosphine)palladium(0) (0.121 g, 0.24 mmol) were combined in a sealed tube and stirred at 80° C. for 1 h. LCMS showed 4:1 pdt/sm. Additional 1-methyl-5-(4,4,5,5-tetramethyl-1,3,2-dioxaborolan-2-yl)-1H-pyrazole (1.178 g, 5.66 mmol) and bis(tri-t-butylphosphine)palladium(0) (0.121 g, 0.24 mmol) were added and the solution stirred an additional 2 h where crude LCMS showed nearly complete conversion to product. The reaction contents were then partitioned between H$_2$O-DCM and the aqueous phase was washed several times with DCM. The combined organic fractions were dried over Na$_2$SO$_4$, concentrated and purified via column chromatography (10-50% EtOAc in hexanes) affording methyl 5-ethyl-4-(1-methyl-1H-pyrazol-5-yl)-2-furancarboxylate (950 mg, 3.37 mmol, 71.3% yield) as a yellow oil: LCMS (ES) m/e 235 (M+H)$^+$.

e) 4-(4-chloro-1-methyl-1H-pyrazol-5-yl)-5-ethyl-2-furancarboxylic Acid

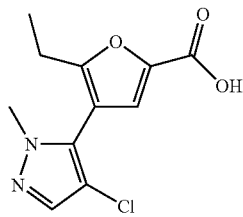 [SMILES: CCc1oc(C(=O)O)cc1-c1c(Cl)cnn1C]

A solution of methyl 5-ethyl-4-(1-methyl-1H-pyrazol-5-yl)-2-furancarboxylate (950 mg, 4.06 mmol) and N-chlorosuccinimide (542 mg, 4.06 mmol) in tetrahydrofuran (20 ml) was stirred in a sealed tube for 1 h at 70° C. 6N sodium hydroxide (13.5 ml, 81 mmol) was added in one portion and the solution stirred an additional 1 h. The reaction mixture was then partitioned between H$_2$O-DCM and the pH of the aqueous phase was adjusted to ~4 and washed several times with DCM. The combined organic fractions were dried over Na$_2$SO$_4$, concentrated and used directly without further purification yielding 4-(4-chloro-1-methyl-1H-pyrazol-5-yl)-5-ethyl-2-furancarboxylic acid (683 mg, 2.55 mmol, 62.8% yield) as a yellow oil: LCMS (ES) m/e 254, 256 (M, M+2)$^+$.

f) 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-furancarboxamide

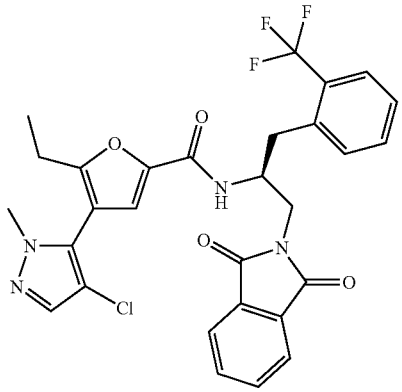 [SMILES: CCc1oc(C(=O)N[C@@H](Cc2ccccc2C(F)(F)F)CN2C(=O)c3ccccc3C2=O)cc1-c1c(Cl)cnn1C]

To a solution of 4-(4-chloro-1-methyl-1H-pyrazol-5-yl)-5-ethyl-2-furancarboxylic acid (145 mg, 0.57 mmol), 2-{(2S)-2-amino-3-[2-(trifluoromethyl)phenyl]propyl}-1H-isoindole-1,3(2H)-dione (219 mg, 0.57 mmol)[prepared according to Preparation 6] and N,N-diisopropylethylamine (0.50 ml, 2.85 mmol) in dichloromethane (4.6 ml) at 25° C. was added bromo-tris-pyrrolidino-phosphonium hexafluorophosphate (292 mg, 0.63 mmol) in one portion. The solution stirred at 25° C. for 1 h and was then dry loaded onto silica and purified via column chromatography (silica, 30-70% EtOAc in hexanes) yielding 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-furancarboxamide (250 mg, 0.41 mmol, 71% yield) as a white solid: LCMS (ES) m/e 585, 587 (M, M+2)$^+$.

g) N-((1S)-2-amino-1-{[2-(trifluoromethyl)phenyl]methyl}ethyl)-4-(4-chloro-1-methyl-1H-pyrazol-5-yl)-5-ethyl-2-furancarboxamide

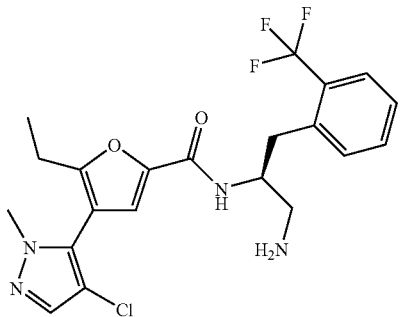 [SMILES: CCc1oc(C(=O)N[C@H](CN)Cc2ccccc2C(F)(F)F)cc1-c1c(Cl)cnn1C]

To a solution of 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-ethyl-2-furancarboxamide (250 mg, 0.43 mmol) in tetrahydrofuran (1.8 ml) and methanol (1.8 ml) at 25° C. was added hydrazine (0.13 ml, 4.27 mmol) dropwise. After 12 h the solution was concentrated, dry loaded onto silica and purified by column chromatography (2% MeOH in DCM (1% NH$_4$OH)). The free base was transferred to the HCl salt by addition of excess 2M HCl in Ether (2 ml) to the residue in DCM (2 ml) affording the HCl salt of N-((1S)-2-amino-1-{[2-(trifluoromethyl)phenyl]methyl}ethyl)-4-(4-chloro-1-methyl-1H-pyrazol-5-yl)-5-ethyl-2-furancarboxamide (166 mg, 0.30 mmol, 70% yield) as a yellow solid: LCMS (ES) m/z=455, 457 (M, M+2)$^+$, $^1$H NMR (400 MHz, DMSO-d$_6$) δ ppm 8.59 (br. s., 1H) 8.06 (br. s., 3H) 7.67 (s, 1H) 7.70 (d, J=7.83 Hz, 1H) 7.59 (d, J=4.29 Hz, 2H) 7.44 (d, J=4.04 Hz, 1H) 7.31 (d, J=5.81 Hz, 1H) 4.50-4.57 (m, 1H) 3.72 (s, 3H) 2.99-3.12 (m, 4H) 2.63 (q, J=7.33 Hz, 2H) 1.21 (t, J=7.45 Hz, 3H).

Example 132

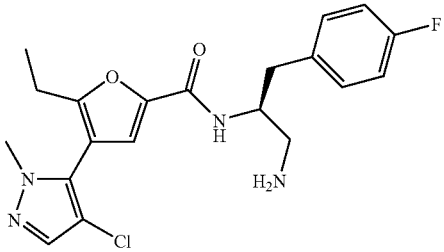 [SMILES: CCc1oc(C(=O)N[C@H](CN)Cc2ccc(F)cc2)cc1-c1c(Cl)cnn1C]

Preparation of N-{(1S)-2-amino-1-[(4-fluorophenyl)methyl]ethyl}-4-(4-chloro-1-methyl-1H-pyrazol-5-yl)-5-ethyl-2-furancarboxamide The title compound was prepared as a yellow solid according to Example 131, except substituting 2-[(2S)-2-amino-3-(4-fluorophenyl)propyl]-1H-isoindole-1,3(2H)-dione (170 mg, 0.57 mmol)[prepared according to the procedure of Preparation 6] for 2-{(2S)-2-amino-3-[2-(trifluoromethyl)phenyl]propyl}-1H-isoindole-1,3(2H)-dione: LCMS (ES) m/z=405, 407 (M, M+2)$^+$, $^1$H NMR (400 MHz, DMSO-d6) δ ppm 8.56 (d, J=8.59 Hz, 1H) 8.09 (br. s., 3H) 7.67 (s, 1H) 7.33 (s, 1H) 7.31 (dd, J=8.34, 5.81 Hz, 2H) 7.12 (t, J=8.72 Hz, 2H) 4.36-4.39 (m, 1H) 3.71 (s, 3H) 2.91-3.03 (m, 4H) 2.62 (q, J=7.58 Hz, 2H) 1.20 (t, J=7.45 Hz, 3H).

Example 133

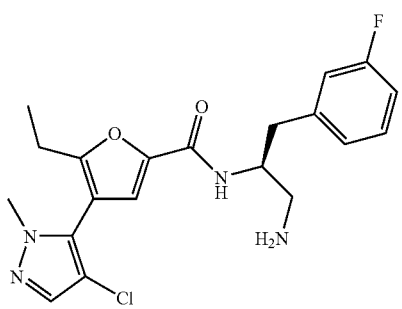 [SMILES: CCc1oc(C(=O)N[C@H](CN)Cc2cccc(F)c2)cc1-c1c(Cl)cnn1C]

Preparation of N-{(1S)-2-amino-1-[(3-fluorophenyl)methyl]ethyl}-4-(4-chloro-1-methyl-1H-pyrazol-5-yl)-5-ethyl-2-furancarboxamide The title compound was prepared as a yellow solid according to Example 131, except substituting 2-[(2S)-2-amino-3-(3-fluorophenyl)propyl]-1H-isoindole-1,3(2H)-dione (170 mg, 0.57 mmol)[prepared according to the procedure of Preparation 6] for 2-{(2S)-2-amino-3-[2-(trifluoromethyl)phenyl]propyl}-1H-isoindole-1,3(2H)-dione: LCMS (ES) m/z=405, 407 (M, M+2)$^+$, $^1$H NMR (400 MHz, DMSO-d$_6$) δ ppm 8.62 (d, J=8.59 Hz, 1H) 8.13 (br. s., 3H) 7.67 (s, 1H) 7.30-7.37 (m, 2H) 7.12 (d, J=6.32 Hz, 2H) 7.04 (t, J=8.59 Hz, 1H) 4.40-4.47 (m, 1H) 3.71 (s, 3H) 2.95-3.09 (m, 4H) 2.62 (q, J=7.07 Hz, 2H) 1.20 (t, J=7.33 Hz, 3H).

Example 134

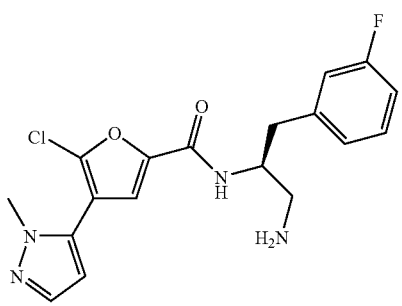 [SMILES: Cn1nccc1-c1cc(C(=O)N[C@H](CN)Cc2cccc(F)c2)oc1Cl]

Preparation of N-{(1S)-2-amino-1-[(3-fluorophenyl)methyl]ethyl}-5-chloro-4-(1-methyl-1H-pyrazol-5-yl)-2-furancarboxamide The title compound was prepared as a white foam according to the procedure of Example 127, except substituting 2-[(2S)-2-amino-3-(3-fluorophenyl)propyl]-1H-isoindole-1,3(2H)-dione (295 mg, 0.88 mmol)[prepared according the procedure of Preparation 6] for 2-{(2S)-2-amino-3-[2-(trifluoromethyl)phenyl]propyl}-1H-isoindole-1,3(2H)-dione: LCMS (ES) m/z=377, 379 (M, M+2)$^+$, $^1$H NMR (400 MHz, DMSO-d$_6$) δ ppm 8.87 (d, J=8.84 Hz, 1H) 8.16 (br. s., 3H) 7.70-7.77 (m, 1H) 7.53 (d, J=1.77 Hz, 1H) 7.32 (t, J=7.20 Hz, 1H) 7.09-7.14 (m, 1H) 7.11 (d, J=6.57 Hz, 2H) 7.04 (t, J=8.59 Hz, 1H) 6.49 (d, J=1.77 Hz, 1H) 4.41-4.44 (m, 1H) 3.86 (s, 3H) 2.95-3.00 (m, 4H).

Example 135

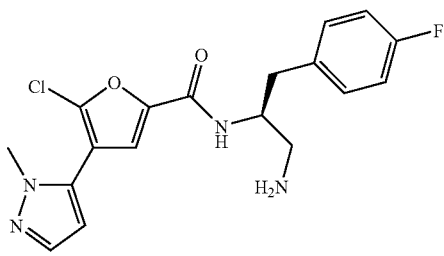 [SMILES: Cn1nccc1-c1cc(C(=O)N[C@H](CN)Cc2ccc(F)cc2)oc1Cl]

Preparation of N-{(1S)-2-amino-1-[(4-fluorophenyl)methyl]ethyl}-5-chloro-4-(1-methyl-1H-pyrazol-5-yl)-2-furancarboxamide The title compound was prepared as a white foam according to the procedure of Example 127, except substituting 2-[(2S)-2-amino-3-(4-fluorophenyl)propyl]-1H-isoindole-1,3(2H)-dione (295 mg, 0.88 mmol)[prepared according the procedure of Preparation 6] for 2-{(2S)-2-amino-3-[2-(trifluoromethyl)phenyl]propyl}-1H-isoindole-1,3(2H)-dione: LCMS (ES) m/z=377, 379 (M, M+2)$^+$, $^1$H NMR (400 MHz, DMSO-d$_6$) δ ppm 8.80 (d, J=8.84 Hz, 1H) 8.11 (br. s., 3H) 7.71 (s, 1H) 7.53 (d, J=1.77 Hz, 1H) 7.29 (dd, J=8.59, 5.56 Hz, 2H) 7.12 (t, J=8.84 Hz, 2H) 6.49 (d, J=1.77 Hz, 1H) 4.32-4.38 (m, 1H) 3.86 (s, 3H) 2.99-3.01 (m, 4H).

Example 136

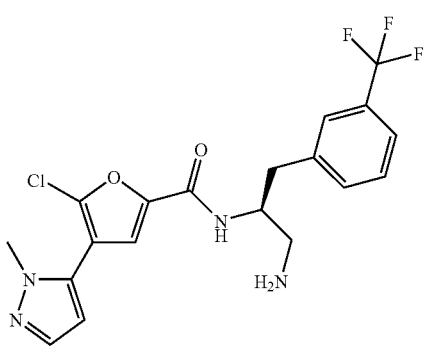 [SMILES: Cn1nccc1-c1cc(C(=O)N[C@H](CN)Cc2cccc(C(F)(F)F)c2)oc1Cl]

Preparation of N-((1S)-2-amino-1-{[3-(trifluoromethyl)phenyl]methyl}ethyl)-5-chloro-4-(1-methyl-1H-pyrazol-5-yl)-2-furancarboxamide The title compound was prepared as a white foam according to the procedure of Example 127, except substituting 2-{(2S)-2-amino-3-[3-(trifluoromethyl)phenyl]propyl}-1H-isoindole-1,3(2H)-dione (340 mg, 0.88 mmol) [prepared according the procedure of Preparation 6] for 2-{(2S)-2-amino-3-[2-(trifluoromethyl)phenyl]propyl}-1H-isoindole-1,3(2H)-dione: LCMS (ES) m/z=427, 429 (M, M+2)$^+$, $^1$H NMR (400 MHz, DMSO-d$_6$) δ ppm 8.83 (d, J=8.84 Hz, 1H)

8.11 (br. s., 3H) 7.62-7.69 (m, 2H) 7.51-7.59 (m, 4H) 6.48 (d, J=1.77 Hz, 1H) 4.39-4.44 (m, 1H) 3.85 (s, 3H) 2.97-3.05 (m, 4H).

Example 137

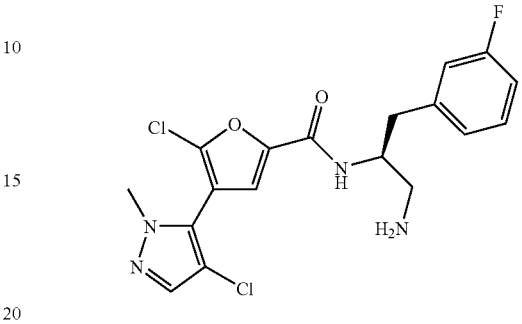

Preparation of N-{(1S)-2-amino-1-[(3-fluorophenyl)methyl]ethyl}-5-chloro-4-(4-chloro-1-methyl-1H-pyrazol-5-yl)-2-furancarboxamide The title compound was prepared as a white foam according to the procedure of Example 128, except substituting 2-[(2S)-2-amino-3-(3-fluorophenyl)propyl]-1H-isoindole-1,3(2H)-dione (321 mg, 0.96 mmol) [prepared according the procedure of Preparation 6] for 2-{(2S)-2-amino-3-[2-(trifluoromethyl)phenyl]propyl}-1H-isoindole-1,3(2H)-dione: LCMS (ES) m/z=411, 413 (M, M+2)$^+$, $^1$H NMR (400 MHz, DMSO-d$_6$) δ ppm 8.77 (d, J=8.84 Hz, 1H) 8.04 (br. s., 3H) 7.72 (s, 1H) 7.59 (s, 1H) 7.30-7.38 (m, 1H) 7.11 (d, J=7.58 Hz, 2H) 7.05 (t, J=8.59 Hz, 1H) 4.39-4.43 (m, 1H) 3.77 (s, 3H) 2.97-3.03 (m, 4H).

Example 138

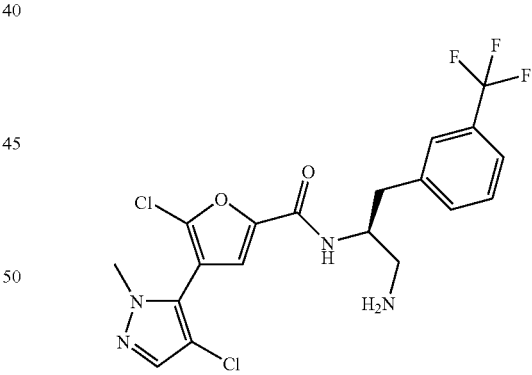

Preparation of N-((1S)-2-amino-1-{[3-(trifluoromethyl)phenyl]methyl}ethyl)-5-chloro-4-(4-chloro-1-methyl-1H-pyrazol-5-yl)-2-furancarboxamide The title compound was prepared as a white foam according to the procedure of Example 128, except substituting 2-{(2S)-2-amino-3-[3-(trifluoromethyl)phenyl]propyl}-1H-isoindole-1,3(2H)-dione (221 mg, 0.58 mmol) [prepared according the procedure of Preparation 6] for 2-{(2S)-2-amino-3-[2-(trifluoromethyl)phenyl]propyl}-1H-isoindole-1,3(2H)-dione: LCMS (ES) m/z=461, 463 (M, M+2)$^+$, $^1$H NMR (400 MHz, DMSO-d$_6$) δ ppm 8.83 (d, J=8.84 Hz, 1H)

8.10 (br. s., 3H) 7.72 (s, 1H) 7.64 (s, 1H) 7.52-7.60 (m, 4H) 4.39-4.41 (m, 1H) 3.76 (s, 3H) 2.98-3.05 (m, 4H).

Example 139

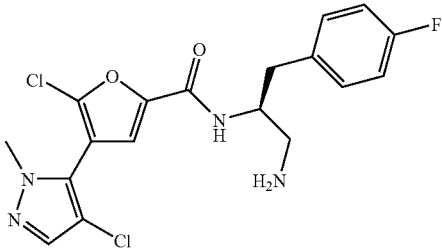 [SMILES: Cn1ncc(Cl)c1-c1cc(C(=O)N[C@H](CN)Cc2ccc(F)cc2)oc1Cl]

Preparation of N-{(1S)-2-amino-1-[(4-fluorophenyl)methyl]ethyl}-5-chloro-4-(4-chloro-1-methyl-1H-pyrazol-5-yl)-2-furancarboxamide The title compound was prepared as a white foam according to the procedure of Example 128, except substituting 2-[(2S)-2-amino-3-(4-fluorophenyl)propyl]-1H-isoindole-1,3(2H)-dione (256 mg, 0.77 mmol) [prepared according the procedure of Preparation 6] for 2-{(2S)-2-amino-3-[2-(trifluoromethyl)phenyl]propyl}-1H-isoindole-1,3(2H)-dione: LCMS (ES) m/z=411, 413 (M, M+2)$^+$, $^1$H NMR (400 MHz, DMSO-d$_6$) δ ppm 8.78 (d, J=8.59 Hz, 1H) 8.06 (br. s., 3H) 7.72 (s, 1H) 7.60 (s, 1H) 7.30 (dd, J=8.59, 5.56 Hz, 2H) 7.13 (t, J=8.84 Hz, 2H) 4.35-4.42 (m, 1H) 3.77 (s, 3H) 2.99 (br. s., 2H) 2.86-2.93 (m, 2H).

Example 140

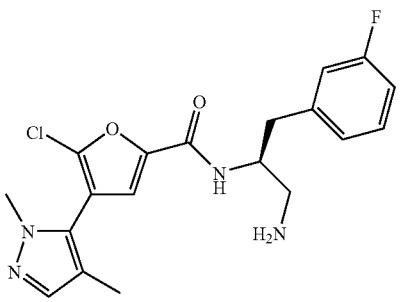 [SMILES: Cc1cnn(C)c1-c1cc(C(=O)N[C@H](CN)Cc2cccc(F)c2)oc1Cl]

Preparation of N-{(1S)-2-amino-1-[(3-fluorophenyl)methyl]ethyl}-5-chloro-4-(1,4-dimethyl-1H-pyrazol-5-yl)-2-furancarboxamide The title compound was prepared as a white solid according to the procedure of Example 127, except substituting 1,4-dimethyl-5-(4,4,5,5-tetramethyl-1,3,2-dioxaborolan-2-yl)-1H-pyrazole (1.02 g, 4.59 mmol)[prepared according to Preparation 17] for 1-methyl-5-(4,4,5,5-tetramethyl-1,3,2-dioxaborolan-2-yl)-1H-pyrazole and 2-[(2S)-2-amino-3-(3-fluorophenyl)propyl]-1H-isoindole-1,3(2H)-dione (132 mg, 0.39 mmol) [prepared according the procedure of Preparation 6] for 2-{(2S)-2-amino-3-[2-(trifluoromethyl)phenyl]propyl}-1H-isoindole-1,3(2H)-dione: LCMS (ES) m/z=391, 393 (M, M+2)$^+$, $^1$H NMR (400 MHz, DMSO-d$_6$) δ ppm 8.75 (d, J=8.84 Hz, 1H) 8.04 (br. s., 3H) 7.55 (s, 1H) 7.37 (s, 1H) 7.30-7.36 (m, 1H) 7.11-7.15 (m, 2H) 7.05-7.10 (m, 1H) 4.42 (br. s., 1H) 3.70 (s, 3H) 2.97 (br. s., 2H) 2.92-2.96 (m, 2H) 1.94 (s, 3H).

Example 141

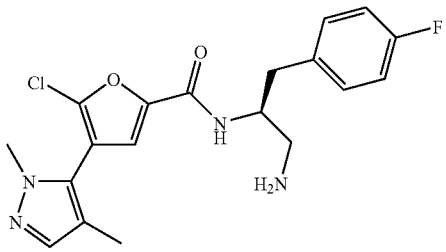 [SMILES: Cc1cnn(C)c1-c1cc(C(=O)N[C@H](CN)Cc2ccc(F)cc2)oc1Cl]

Preparation of N-{(1S)-2-amino-1-[(4-fluorophenyl)methyl]ethyl}-5-chloro-4-(1,4-dimethyl-1H-pyrazol-5-yl)-2-furancarboxamide The title compound was prepared as a yellow solid according to the procedure of Example 127, except substituting 1,4-dimethyl-5-(4,4,5,5-tetramethyl-1,3,2-dioxaborolan-2-yl)-1H-pyrazole (3.06 g, 13.78 mmol)[prepared according to Preparation 17] for 1-methyl-5-(4,4,5,5-tetramethyl-1,3,2-dioxaborolan-2-yl)-1H-pyrazole and 2-[(2S)-2-amino-3-(4-fluorophenyl)propyl]-1H-isoindole-1,3(2H)-dione (174 mg, 0.52 mmol) [prepared according the procedure of Preparation 6] for 2-{(2S)-2-amino-3-[2-(trifluoromethyl)phenyl]propyl}-1H-isoindole-1,3(2H)-dione: LCMS (ES) m/z=391, 393 (M, M+2)$^+$, $^1$H NMR (400 MHz, DMSO-d$_6$) δ ppm 8.81 (d, J=8.59 Hz, 1H) 8.14 (br. s., 3H) 7.59 (s, 1H) 7.37 (s, 1H) 7.30 (dd, J=8.59, 5.56 Hz, 2H) 7.12 (t, J=8.84 Hz, 2H) 4.32-4.38 (m, 1H) 3.70 (s, 3H) 2.98 (d, J=5.81 Hz, 2H) 2.91 (d, J=6.32 Hz, 2H) 1.94 (s, 3H).

Example 142

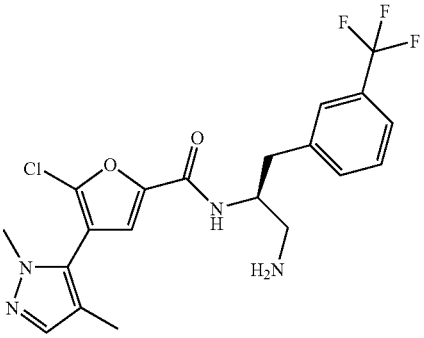 [SMILES: Cc1cnn(C)c1-c1cc(C(=O)N[C@H](CN)Cc2cccc(C(F)(F)F)c2)oc1Cl]

Preparation of N-((1S)-2-amino-1-{[3-(trifluoromethyl)phenyl]methyl}ethyl)-5-chloro-4-(1,4-dimethyl-1H-pyrazol-5-yl)-2-furancarboxamide The title compound was prepared as a yellow solid according to the procedure of Example 127, except substituting 1,4-dimethyl-5-(4,4,5,5-tetramethyl-1,3,2-dioxaborolan-2-yl)-1H-pyrazole (3.06 g, 13.78 mmol)[prepared according to Preparation 17] for 1-methyl-5-(4,4,5,5-tetramethyl-1,3,2-dioxaborolan-2-yl)-1H-pyrazole and 2-{(2S)-2-amino-3-[3-(trifluoromethyl)phenyl]propyl}-1H-isoindole-1,3(2H)-dione (200 mg, 0.52 mmol) [prepared according the procedure of Preparation 6] for 2-{(2S)-2-amino-3-[2-(trifluoromethyl)phenyl]propyl}-1H-isoindole-1,3(2H)-dione: LCMS (ES) m/z=441, 443 (M, M+2)$^+$, $^1$H NMR (400 MHz, DMSO-d$_6$) δ ppm 8.83 (br. s., 1H) 8.15 (br. s., 2H) 7.63 (br. s., 1H) 7.52-7.58 (m, 4H) 7.37 (s, 1H) 4.38-4.42 (m, 1H) 3.68 (s, 3H) 2.97-3.08 (m, 4H) 1.93 (s, 3H).

Example 143

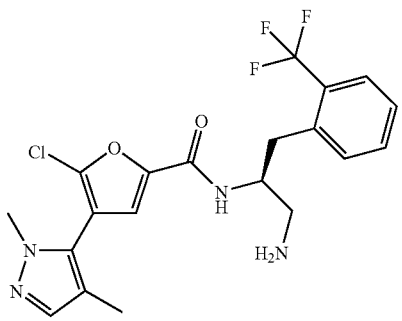 [SMILES: Cc1cnn(C)c1-c1cc(C(=O)N[C@H](CN)Cc2ccccc2C(F)(F)F)oc1Cl]

Preparation of N-((1S)-2-amino-1-{[2-(trifluoromethyl)phenyl]methyl}ethyl)-5-chloro-4-(1,4-dimethyl-1H-pyrazol-5-yl)-2-furancarboxamide The title compound was prepared as a yellow solid according to the procedure of Example 127, except substituting 1,4-dimethyl-5-(4,4,5,5-tetramethyl-1,3,2-dioxaborolan-2-yl)-1H-pyrazole (3.06 g, 13.78 mmol)[prepared according to Preparation 17] for 1-methyl-5-(4,4,5,5-tetramethyl-1,3,2-dioxaborolan-2-yl)-1H-pyrazole: LCMS (ES) m/z=441, 443 (M, M+2)$^+$, $^1$H NMR (400 MHz, DMSO-d$_6$) δ ppm 8.87 (d, J=9.35 Hz, 1H) 8.11 (br. s., 3H) 7.70 (d, J=7.83 Hz, 1H) 7.52-7.57 (m, 3H) 7.41-7.47 (m, 1H) 7.38 (s, 1H) 4.39-4.43 (m, 1H) 3.71 (s, 3H) 2.98-3.09 (m, 4H) 1.95 (s, 3H).

Example 144

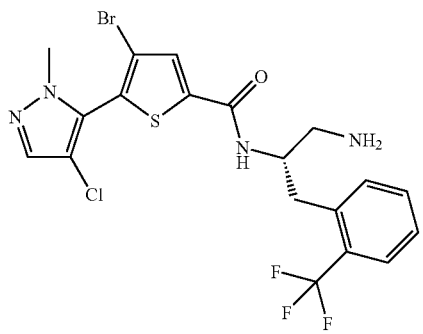 [SMILES: Cn1ncc(Cl)c1-c1sc(C(=O)N[C@H](CN)Cc2ccccc2C(F)(F)F)cc1Br]

Preparation of N-((1S)-2-amino-1-{[2-(trifluoromethyl)phenyl]methyl}ethyl)-4-bromo-5-(4-chloro-1-methyl-1H-pyrazol-5-yl)-2-thiophenecarboxamide a) 4-bromo-5-(1-methyl-1H-pyrazol-5-yl)-2-thiophenecarboxylic Acid

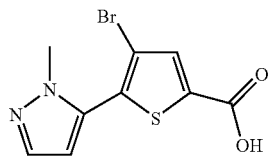

To a solution of 4,5-dibromo-2-thiophenecarboxylic acid (3.30 g, 11.54 mmol) in dioxane/H$_2$O (4:1, 100 mL) was added K$_2$CO$_3$ (5.5 g, 40.0 mmol), tetrakistriphenylphosphine Pd(0) (671 mg, 0.58 mmol) and 5-(5,5-dimethyl-1,3,2-dioxaborinane-2-yl)-1-methyl-1H-pyrazole (2.66 g, 13.71 mmol). The reaction mixture was heated to 80° C. in a sealed tube for 12 hours. The reaction mixture was partitioned between H$_2$O and CHCl$_3$. The pH of the aqueous phase was adjusted to ~3 with 6N HCl and washed several times with CHCl$_3$. The combined organic fractions were dried (Na$_2$SO$_4$), concentrated under vacuum and used directly without further purification (3.3 g, quant.): LC-MS (ES) m/z=289 (M+H)$^+$.

b) 4-bromo-5-(4-chloro-1-methyl-1H-pyrazol-5-yl)-2-thiophenecarboxylic Acid

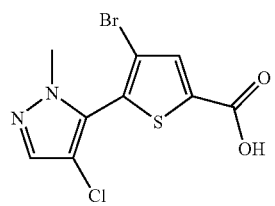

N-chlorosuccinimide (NCS) (299 mg, 2.194 mmol) was added in portions to a 30 mL sealed tube reactor containing 4-bromo-5-(1-methyl-1H-pyrazol-5-yl)-2-thiophenecarboxylic acid (503 mg, 1.23 mmol) in tetrahydrofuran (THF) (6 mL) at room temperature. The mixture was heated to 70° C. for 2 hours. Upon completion, the reaction mixture was partitioned between CHCl$_3$ and H$_2$O, the organic layer dried with Na$_2$SO$_4$, solvents removed by vacuum distillation affording the title compound (0.54 mg, quant.) which was used without further purification. LC-MS (ES) m/z=321 (M+H)$^+$ c) 4-bromo-5-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

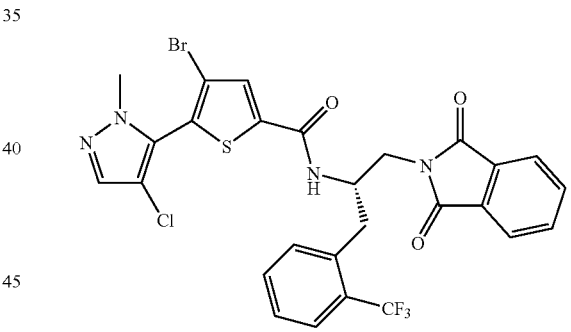

To a 50 mL round-bottomed flask was added 4-bromo-5-(4-chloro-1-methyl-1H-pyrazol-5-yl)-2-thiophenecarboxylic acid (224 mg, 0.52 mmol), 2-{(2S)-2-amino-3-[2-(trifluoromethyl)phenyl]propyl}-1H-isoindole-1,3(2H)-dione (201 mg, 0.52 mmol) [prepared according to the procedure of Preparation 6] and PyBrop (295 mg, 0.63 mmol) in chloroform (4 mL). DIEA (0.46 mL, 2.63 mmol) was added and the mixture stirred overnight at room temperature. The reaction mixture was adsorbed onto silica and purified via column chromatography (hexanes/EtOAc) affording the title compound (153 mg, 43%): LC-MS (ES) m/z=651 (M+H)$^+$.

d) N-((1S)-2-amino-1-{[2-(trifluoromethyl)phenyl]methyl}ethyl)-4-bromo-5-(4-chloro-1-methyl-1H-pyrazol-5-yl)-2-thiophenecarboxamide To a 50 mL round-bottomed flask was added 4-bromo-5-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (153 mg, 0.223 mmol) in tetrahydrofuran (THF) (2.5 mL) and Methanol (0.5 mL). Hydrazine (50 µL, 1.59 mmol) was added and the mixture stirred overnight at room temperature. Upon completion, the mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (68 mg, 0.11 mmol, 48.7% yield): LC-MS (ES) m/z=523 (M+H)$^+$, $^1$H NMR (400 MHz, DMSO-d$_6$) δ ppm 3.02-3.14 (m, 4H) 3.73 (s, 3H) 4.50 (s, 1H) 7.40-7.48 (m, 1H) 7.56-7.64 (m, 2H) 7.71 (d, J=7.83 Hz, 1H) 7.77 (s, 1H) 8.14 (s, 3H) 8.21 (s, 1H) 9.24 (d, J=9.09 Hz, 1H).

Example 145

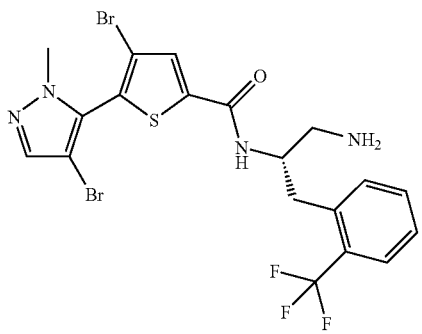 [SMILES: Cn1ncc(Br)c1-c1sc(C(=O)N[C@H](CN)Cc2ccccc2C(F)(F)F)cc1Br]

Preparation of N-((1S)-2-amino-1-{[2-(trifluoromethyl)phenyl]methyl}ethyl)-4-bromo-5-(4-bromo-1-methyl-1H-pyrazol-5-yl)-2-thiophenecarboxamide a) 4-bromo-5-(4-bromo-1-methyl-1H-pyrazol-5-yl)-2-thiophenecarboxylic Acid

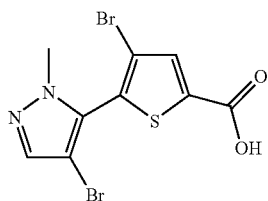 [SMILES: Cn1ncc(Br)c1-c1sc(C(=O)O)cc1Br]

The title compound was prepared according to the procedure of Example 144 except substituting N-bromosuccinimide (NBS) (287 mg, 1.596 mmol) for NCS: LC-MS (ES) m/z=364 (M+H)$^+$.

b) 4-bromo-5-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

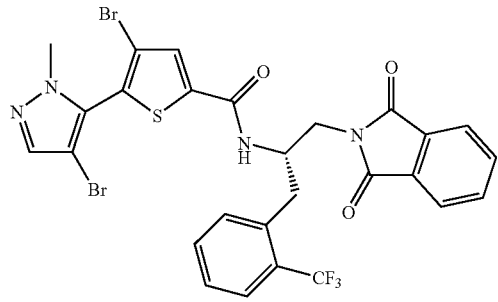 [SMILES: Cn1ncc(Br)c1-c1sc(C(=O)N[C@@H](Cc2ccccc2C(F)(F)F)CN2C(=O)c3ccccc3C2=O)cc1Br]

To a 50 mL round-bottomed flask was added 4-bromo-5-(4-bromo-1-methyl-1H-pyrazol-5-yl)-2-thiophenecarboxylic acid (238 mg, 0.52 mmol), 2-{(2S)-2-amino-3-[2-(trifluoromethyl)phenyl]propyl}-1H-isoindole-1,3(2H)-dione (209 mg, 0.54 mmol) [prepared according to the procedure of Preparation 6] and PyBrop (293 mg, 0.63 mmol) in chloroform (4 mL). DIEA (0.46 mL, 2.62 mmol) was added and the mixture stirred overnight at room temperature. The reaction mixture was adsorbed onto silica and purified via column chromatography (silica) (3:1 hex/EtOAc) affording the title compound (229 mg, 60%): LC-MS (ES) m/z=695 (M+H)$^+$.

c) N-((1S)-2-amino-1-{[2-(trifluoromethyl)phenyl]methyl}ethyl)-4-bromo-5-(4-bromo-1-methyl-1H-pyrazol-5-yl)-2-thiophenecarboxamide To a 50 mL round-bottomed flask was added 4-bromo-5-(4-bromo-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (229 mg, 0.312 mmol) in Tetrahydrofuran (THF) (2.5 mL) and methanol (0.5 mL). Hydrazine (60 µL, 1.91 mmol) was added and the mixture stirred overnight at room temperature. The reaction mixture was adsorbed onto silica gel and purified by column chromatography (90:10:1 CHCl$_3$/MeOH/NH$_4$OH; 12 g column).

The neutral compound was dissolved in MeOH (2 mL), treated with excess 2M HCl in Et$_2$O (500 mL) and concentrated affording the HCl salt of the title compound (104 mg, 0.15 mmol, 49% yield): LC-MS (ES) m/z=567 (M+H)$^+$, $^1$H NMR (400 MHz, DMSO-d$_6$) δ ppm 3.10 (s, 4H) 3.74 (s, 3H) 4.50 (s, 1H) 7.45 (ddd, J=7.96, 4.17, 4.04 Hz, 1H) 7.60 (d, J=4.04 Hz, 2H) 7.71 (d, J=7.58 Hz, 1H) 7.76 (s, 1H) 8.11 (s, 3H) 8.19 (s, 1H) 9.19 (d, J=8.84 Hz, 1H).

Example 146

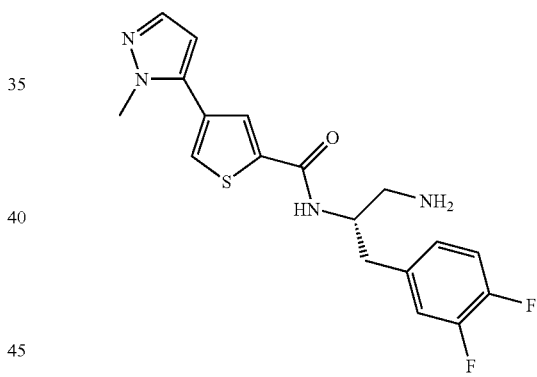

Preparation of N-{(1S)-2-amino-1-[(3,4-difluorophenyl)methyl]ethyl}-4-(1-methyl-1H-pyrazol-5-yl)-2-thiophenecarboxamide a) 4-(1-methyl-1H-pyrazol-5-yl)-2-thiophenecarboxylic Acid

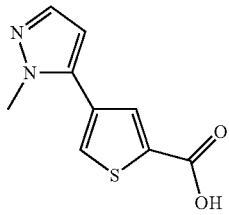

To a solution of 4-bromo-2-thiophenecarboxylic acid (3.91 g, 18.9 mmol) in dioxane/H$_2$O (4:1, 100 mL) was added Cs₂CO₃ (21.7 g, 66.6 mmol), tetrakistriphenylphosphine Pd(0) (1.1 g, 0.95 mmol) and 1-methyl-5-(4,4,5,5-tetramethyl-1,3,2-dioxaborolan-2-yl)-1H-pyrazole (3.94 g, 18.94 mmol) [prepared according to the procedure of Preparation 7]. The reaction mixture was heated to 85° C. in a sealed tube for 12 hours and partitioned between H₂O and CHCl₃. The pH of the aqueous phase was adjusted to ~3 with 6N HCl and washed several times with CHCl₃. The combined organic fractions were dried (Na₂SO₄), concentrated under vacuum and used directly without further purification (2.84 g, 13.64 mmol, 72%): LC-MS (ES) m/z=209 (M+H)⁺.

b) N-{(1S)-2-(3,4-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide

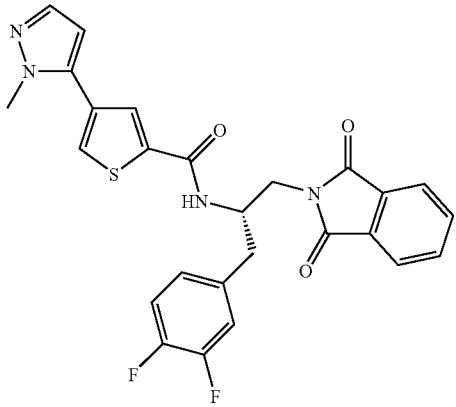 [SMILES: Cn1nccc1-c1csc(C(=O)N[C@@H](Cc2ccc(F)c(F)c2)CN2C(=O)c3ccccc3C2=O)c1]

To a 50 mL round-bottomed flask was added 4-(1-methyl-1H-pyrazol-5-yl)-2-thiophenecarboxylic acid (183 mg, 0.88 mmol), 2-[(2S)-2-amino-3-(3,4-dichlorophenyl)propyl]-1H-isoindole-1,3(2H)-dione (0.3 g, 0.85 mmol) [prepared according to the procedure of Preparation 6 except substituting N-{[(1,1-dimethylethyl)oxy]carbonyl}-3,4-difluoro-L-phenylalanine (2.03 g, 6.74 mmol) for N-{[(1,1-dimethylethyl)oxy]carbonyl}-2-(trifluoromethyl)-L-phenylalanine] and PyBrop (528 mg, 1.13 mmol) in chloroform (5 mL). DIEA (0.77 mL, 4.41 mmol) was added and the mixture stirred overnight at room temperature. The reaction mixture was adsorbed onto silica and purified via column chromatography (25-75% EtOAc/Hex) affording the title compound (149 mg, 30%): LC-MS (ES) m/z=507 (M+H)⁺ c) N-{(1S)-2-amino-1-[(3,4-difluorophenyl)methyl]ethyl}-4-(1-methyl-1H-pyrazol-5-yl)-2-thiophenecarboxamide To a 50 mL round-bottomed flask was added N-{(1S)-2-(3,4-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide (149 mg, 0.265 mmol) in Tetrahydrofuran (THF) (4 mL) and Methanol (1 mL). Hydrazine (60 µL, 1.91 mmol) was added and the mixture stirred overnight at room temperature. The mixture was adsorbed onto silica gel and purified via column chromatography (90: 10:1 CHCl₃/MeOH/NH₄OH).

The neutral compound was dissolved in MeOH (2 mL), treated with excess 2M HCl in Et₂O and concentrated affording the HCl salt of the title compound (71 mg, 0.15 mmol, 57% yield): LC-MS (ES) m/z=377 (M+H)⁺, ¹H NMR (400 MHz, DMSO-d₆) δ ppm 2.96 (d, J=6.06 Hz, 2H) 3.00-3.06 (m, 2H) 3.97 (s, 3H) 4.33-4.42 (m, 1H) 6.48 (d, J=1.77 Hz, 1H) 7.14 (s, 1H) 7.30-7.42 (m, 2H) 7.47 (d, J=1.77 Hz, 1H) 7.99 (d, J=1.26 Hz, 1H) 8.22 (s, 3H) 8.35 (d, J=1.26 Hz, 1H) 9.09 (d, J=8.59 Hz, 1H).

Example 147

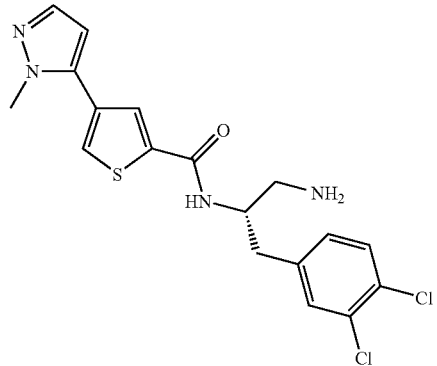 [SMILES: Cn1nccc1-c1csc(C(=O)N[C@H](CN)Cc2ccc(Cl)c(Cl)c2)c1]

Preparation of N-{(1S)-2-amino-1-[(3,4-dichlorophenyl)methyl]ethyl}-4-(1-methyl-1H-pyrazol-5-yl)-2-thiophenecarboxamide a) N-{(1S)-2-(3,4-dichlorophenyl)-1-[(1,3-dioxo-1,3-dihydro-2H-isoindol-2-yl)methyl]ethyl}-4-(1-methyl-1H-pyrazol-5-yl)-2-thiophenecarboxamide

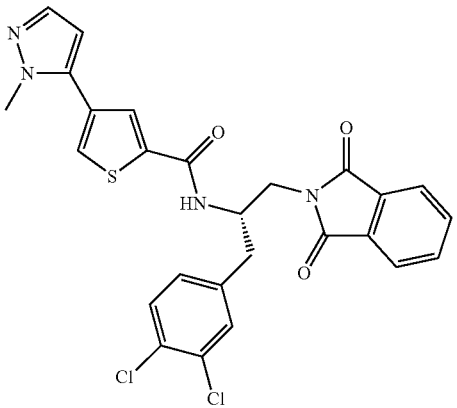 [SMILES: Cn1nccc1-c1csc(C(=O)N[C@@H](Cc2ccc(Cl)c(Cl)c2)CN2C(=O)c3ccccc3C2=O)c1]

To a 50 mL round-bottomed flask was added 4-(1-methyl-1H-pyrazol-5-yl)-2-thiophenecarboxylic acid (160 mg, 0.62 mmol) [prepared according to the procedure of Example 146], 2-[(2S)-2-amino-3-(3,4-dichlorophenyl)propyl]-1H-isoindole-1,3(2H)-dione (0.26 g, 0.67 mmol) [prepared according to the procedure of Preparation 6 except substituting 3,4-dichloro-N-{[(1,1-dimethylethyl)oxy]carbonyl}-L-phenylalanine (2.03 g, 6.07 mmol) for N-{[(1,1-dimethylethyl)oxy]carbonyl}-2-(trifluoromethyl)-L-phenylalanine] and PyBrop (376 mg, 0.80 mmol) in chloroform (4 mL). DIEA (0.55 mL, 3.15 mmol) was added and the mixture stirred overnight at room temperature. The reaction mixture was adsorbed onto silica and purified via column chromatography (25-75% EtOAc/Hex) affording the title compound (149 mg, 30%): LC-MS (ES) m/z=539 (M+H)⁺ b) N-{(1S)-2-amino-1-[(3,4-dichlorophenyl)methyl]ethyl}-4-(1-methyl-1H-pyrazol-5-yl)-2-thiophenecarboxamide To a 50 mL round-bottomed flask was added N-{(1S)-2-(3,4-dichlorophenyl)-1-[(1,3-dioxo-1,3-dihydro-2H-isoindol-2-yl)methyl]ethyl}-4-(1-methyl-1H-pyrazol-5-yl)-2-thiophenecarboxamide (211 mg, 0.34 mmol) in Tetrahydrofuran (THF) (4.5 mL) and Methanol (0.45 mL). Hydrazine (75 µL, 2.390 mmol) was added and the mixture stirred overnight at room temperature. Upon completion the mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (83 mg, 0.16 mmol, 48% yield): LC-MS (ES) m/z=411 (M+H)⁺, ¹H NMR (400 MHz, DMSO-d₆) δ ppm 2.95-3.07 (m, 4H) 3.97 (s, 3H) 4.32-4.43 (m, 1H) 6.48 (d, J=1.77 Hz, 1H) 7.29 (dd, J=8.21, 1.89 Hz, 1H) 7.47 (d, J=2.02 Hz, 1H) 7.54 (d, J=8.08 Hz, 1H) 7.60 (d, J=1.77 Hz, 1H) 8.00 (d, J=1.26 Hz, 1H) 8.22 (s, 3H) 8.35 (d, J=1.01 Hz, 1H) 9.11 (d, J=8.59 Hz, 1H).

Example 148

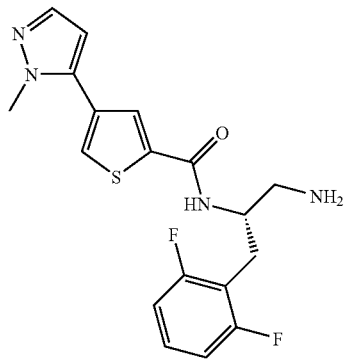 [SMILES: Cn1nccc1-c1csc(C(=O)N[C@H](CN)Cc2c(F)cccc2F)c1]

Preparation of N-{(1S)-2-amino-1-[(2,6-difluorophenyl)methyl]ethyl}-4-(1-methyl-1H-pyrazol-5-yl)-2-thiophenecarboxamide a) N-{(1S)-2-(2,6-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide

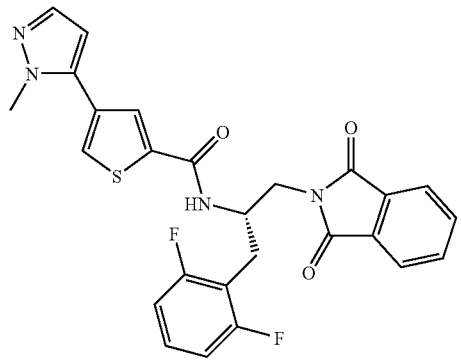 [SMILES: Cn1nccc1-c1csc(C(=O)N[C@@H](Cc2c(F)cccc2F)CN2C(=O)c3ccccc3C2=O)c1]

To a 50 mL round-bottomed flask was added 4-(1-methyl-1H-pyrazol-5-yl)-2-thiophenecarboxylic acid (160 mg, 0.62 mmol) [prepared according to the procedure of Example 146], 2-[(2S)-2-amino-3-(2,6-difluorophenyl)propyl]-1H-isoindole-1,3(2H)-dione (231 mg, 0.69 mmol) [prepared according to the procedure of Preparation 18] and PyBrop (353 mg, 0.75 mmol) in chloroform (8 mL). DIEA (0.64 mL, 3.66 mmol) was added and the mixture stirred overnight at room temperature. The reaction mixture was adsorbed onto silica and purified via column chromatography (25-75% EtOAc/Hex) affording the title compound (149 mg, 0.21 mmol, 30%): LC-MS (ES) m/z=507 (M+H)⁺ b) N-{(1S)-2-amino-1-[(2,6-difluorophenyl)methyl]ethyl}-4-(1-methyl-1H-pyrazol-5-yl)-2-thiophenecarboxamide To a 50 mL round-bottomed flask was added N-{(1S)-2-(2,6-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide (168 mg, 0.32 mmol) in Tetrahydrofuran (THF) (3.6 mL) and Methanol (0.4 mL). Hydrazine (70 µL, 2.23 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (101 mg, 0.214 mmol, 68%): LC-MS (ES) m/z=377 (M+H)⁺, ¹H NMR (400 MHz, DMSO-d₆) δ ppm 2.92-3.03 (m, 3H) 3.17 (m, 1H) 3.97 (s, 3H) 4.46 (m, 1H) 6.47 (d, J=1.77 Hz, 1H) 7.05 (t, J=7.83 Hz, 2H) 7.27-7.38 (m, 1H) 7.47 (d, J=1.77 Hz, 1H) 7.99 (d, J=1.26 Hz, 1H) 8.23 (d, J=1.26 Hz, 4H) 8.92 (d, J=8.59 Hz, 1H).

Example 149

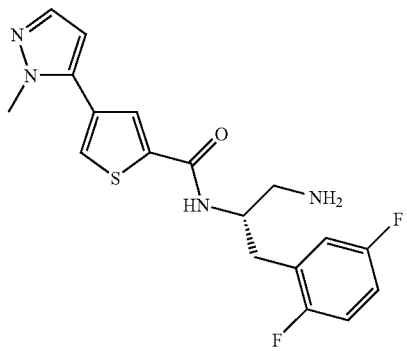 [SMILES: Cn1nccc1-c1csc(C(=O)N[C@H](CN)Cc2cc(F)ccc2F)c1]

Preparation of N-{(1S)-2-amino-1-[(2,5-difluorophenyl)methyl]ethyl}-4-(1-methyl-1H-pyrazol-5-yl)-2-thiophenecarboxamide a) N-{(1S)-2-(2,5-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide

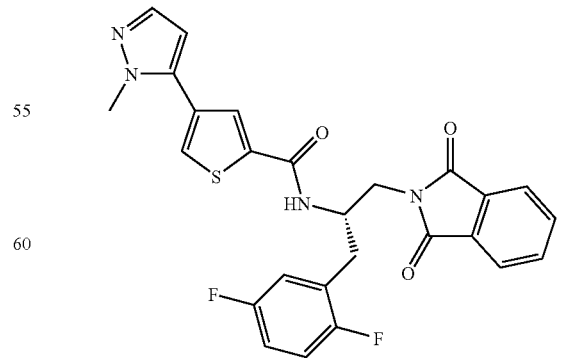

To a 50 mL round-bottomed flask was added 4-(1-methyl-1H-pyrazol-5-yl)-2-thiophenecarboxylic acid (257 mg, 0.93 mmol) [prepared according to the procedure of Example 146], 2-[(2S)-2-amino-3-(2,5-difluorophenyl)propyl]-1H-isoindole-1,3(2H)-dione (476 mg, 0.81 mmol) [prepared according to the procedure of Preparation 18 except substituting 2,5-difluoro-L-phenylalanine (3.02 g, 15.0 mmol) for 2,6-difluoro-L-phenylalanine] and PyBrop (535 mg, 1.14 mmol) in Chloroform (15 mL). DIEA (0.808 mL, 4.63 mmol) was added and the reaction stirred overnight at room temperature. The mixture was adsorbed onto silica and purified via column chromatography (25-75% EtOAc/Hex) affording the title compound (225 mg, 34%): LC-MS (ES) m/z=507 (M+H)$^+$ b) N-{(1S)-2-amino-1-[(2,5-difluorophenyl)methyl]ethyl}-4-(1-methyl-1H-pyrazol-5-yl)-2-thiophenecarboxamide To a 50 mL round-bottomed flask was added N-{(1S)-2-(2,5-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide (225 mg, 0.31 mmol) in Tetrahydrofuran (THF) (3 mL) and Methanol (0.8 mL). Hydrazine (60 µL, 1.91 mmol) was added and the reaction stirred overnight at room temperature. The mixture was adsorbed onto silica gel and purified via column chromatography (90:10:1 CHCl$_3$/MeOH/NH$_4$OH). The compound was further purified on reverse-phase HPLC (C18 column: H$_2$O/CH$_3$CN, 95-5%) affording the TFA salt which was neutralized on silica (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (90.5 mg, 0.19 mmol, 63%): LC-MS (ES) m/z=377 (M+H)$^+$, $^1$H NMR (400 MHz, DMSO-d$_6$) δ ppm 2.95-3.01 (m, 2H) 3.03-3.10 (m, 2H) 3.92-3.98 (m, 3H) 4.41-4.51 (m, 1H) 6.47 (d, J=1.77 Hz, 1H) 7.05-7.13 (m, 1H) 7.20 (td, J=9.09, 4.55 Hz, 1H) 7.27 (ddd, J=9.09, 5.81, 3.28 Hz, 1H) 7.47 (d, J=1.77 Hz, 1H) 7.99 (d, J=1.52 Hz, 1H) 8.18 (s, 3H) 8.29 (d, J=1.26 Hz, 1H) 9.03 (d, J=8.84 Hz, 1H).

Example 150

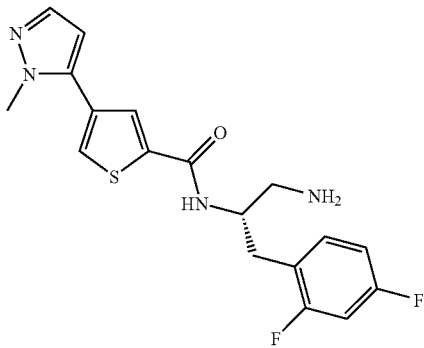 [SMILES: Cn1nccc1-c1csc(C(=O)N[C@H](CN)Cc2ccc(F)cc2F)c1]

Preparation of N-{(1S)-2-amino-1-[(2,4-difluorophenyl)methyl]ethyl}-4-(1-methyl-1H-pyrazol-5-yl)-2-thiophenecarboxamide a) N-{(1S)-2-(2,4-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide

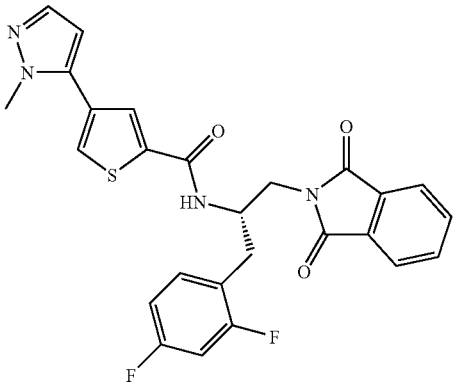 [SMILES: Cn1nccc1-c1csc(C(=O)N[C@@H](Cc2ccc(F)cc2F)CN2C(=O)c3ccccc3C2=O)c1]

To a 50 mL round-bottomed flask was added 4-(1-methyl-1H-pyrazol-5-yl)-2-thiophenecarboxylic acid (222 mg, 0.80 mmol) [prepared according to the procedure of Example 146], 2-[(2S)-2-amino-3-(2,4-difluorophenyl)propyl]-1H-isoindole-1,3(2H)-dione (331 mg, 0.78 mmol) [prepared according to the procedure of Preparation 18 except substituting 2,5-difluoro-L-phenylalanine (1.0 g, 4.97 mmol) for 2,6-difluoro-L-phenylalanine] and PyBrop (448 mg, 0.96 mmol) in chloroform (10 mL). DIEA (700 µL, 4.01 mmol) was added and the reaction stirred overnight at room temperature. The reaction mixture was adsorbed onto silica and purified via column chromatography (25-75% EtOAc/Hex) affording the title compound (249 mg, 0.36 mmol, 46%): LC-MS (ES) m/z=507 (M+H)$^+$.

b) N-{(1S)-2-amino-1-[(2,4-difluorophenyl)methyl]ethyl}-4-(1-methyl-1H-pyrazol-5-yl)-2-thiophenecarboxamide To a 50 mL round-bottomed flask was added N-{(1S)-2-(2,4-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide (249 mg, 0.36 mmol) in Tetrahydrofuran (THF) (5 mL) and Methanol (1 mL). Hydrazine (80 µL, 2.55 mmol) was added and the reaction stirred overnight at room temperature. The mixture was adsorbed onto silica gel and purified via column chromatography (90:10:1 CHCl$_3$/MeOH/NH$_4$OH). The compound was further purified on reverse-phase HPLC (C18 column: H$_2$O/CH$_3$CN, 95-5%) affording the TFA salt which was neutralized on silica (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (81 mg, 0.18 mmol, 50%): LC-MS (ES) m/z=377 (M+H)$^+$, $^1$H NMR (400 MHz, DMSO-d$_6$) δ ppm 2.88-2.98 (m, 2H) 2.98-3.09 (m, 2H) 3.93-3.98 (m, 3H) 4.38-4.47 (m, 1H) 6.47 (d, J=1.77 Hz, 1H) 7.00 (td, J=8.46, 2.27 Hz, 1H) 7.19 (td, J=9.85, 2.53 Hz, 1H) 7.38-7.45 (m, 1H) 7.47 (d, J=1.77 Hz, 1H) 7.99 (d, J=1.26 Hz, 1H) 8.18 (br. s, 3H) 8.27 (d, J=1.26 Hz, 1H) 8.99 (d, J=8.59 Hz, 1H).

Example 151

Preparation of N-((1S)-2-amino-1-{[3-(trifluoromethyl)phenyl]methyl}ethyl)-5-methyl-4-(1-methyl-1H-pyrazol-5-yl)-2-thiophenecarboxamide

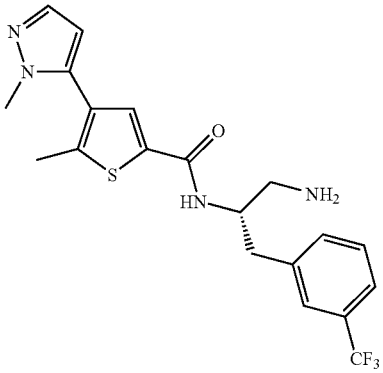 [SMILES: Cc1sc(C(=O)N[C@H](CN)Cc2cccc(C(F)(F)F)c2)cc1-c1ccnn1C]

a) methyl 5-methyl-4-(1-methyl-1H-pyrazol-5-yl)-2-thiophenecarboxylate

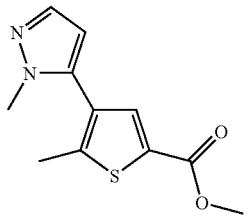

To a 125 mL sealed flask was added methyl 4-bromo-5-methyl-2-thiophenecarboxylate (1.56 g, 6.64 mmol) [Prepared according to the procedure of Preparation 10], 1-methyl-5-(4,4,5,5-tetramethyl-1,3,2-dioxaborolan-2-yl)-1H-pyrazole (1.67 g, 8.03 mmol) [prepared according to the procedure of Preparation 7], $K_2CO_3$ (2.76 g, 19.97 mmol) and $Pd(PtBu_3)_2$ (170 mg, 0.33 mmol) in 1,4-Dioxane (27 ml) and water (7 ml). The reaction mixture was heated to 85° C. in a sealed tube for 3 hours, cooled to room temperature and partitioned between $H_2O$ and $CHCl_3$. The organic fraction was dried ($Na_2SO_4$), adsorbed onto silica and purified via column chromatography (0-15% EtOAc/Hexane). (385 mg, 1.4 mmol, 30%): LC-MS (ES) m/z=237 (M+H)$^+$.

b) 5-methyl-4-(1-methyl-1H-pyrazol-5-yl)-2-thiophenecarboxylic Acid

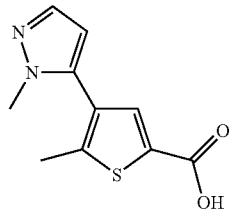

To a 100 mL round-bottomed flask was added methyl 5-methyl-4-(1-methyl-1H-pyrazol-5-yl)-2-thiophenecarboxylate (1.34 g, 5.67 mmol) in Tetrahydrofuran (THF) (31 ml). 6N NaOH (31 ml, 186 mmol) was added and the reaction mixture stirred at 70° C. overnight. The reaction mixture was neutralized by slow addition of 6N HCl and partitioned between $CHCl_3$ and $H_2O$. The layers were separated, the organic layer dried with $Na_2SO_4$ and solvent removed. The resulting solid was used without further purification (0.71 g, 2.81 mmol, 96%): LC-MS (ES) m/z=223 (M+H)$^+$.

c) N-((1S)-2-(1,3-dioxo-1,3-dihydro-2H-isoindol-2-yl)-1-{[3-(trifluoromethyl)phenyl]methyl}ethyl)-5-methyl-4-(1-methyl-1H-pyrazol-5-yl)-2-thiophenecarboxamide

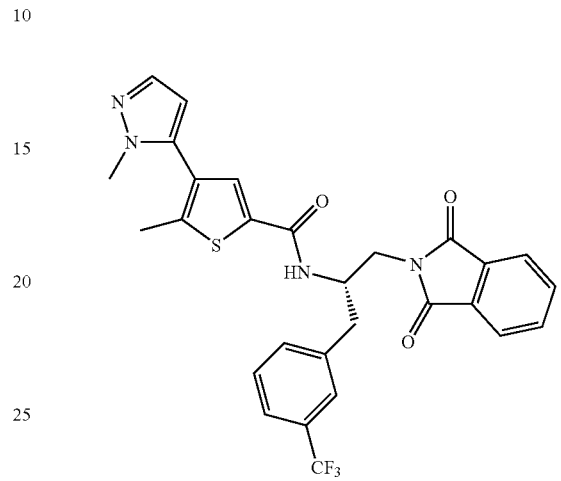

To a 50 mL round-bottomed flask was added 5-methyl-4-(1-methyl-1H-pyrazol-5-yl)-2-thiophenecarboxylic acid (201 mg, 0.91 mmol), 2-{(2S)-2-amino-3-[3-(trifluoromethyl)phenyl]propyl}-1H-isoindole-1,3(2H)-dione (301 mg, 0.87 mmol) [Prepared according to Preparation 6 except substituting N-{[(1,1-dimethylethyl)oxy]carbonyl}-3-(trifluoromethyl)-L-phenylalanine (4.98 g, 14.95 mmol) for N-{[(1,1-dimethylethyl)oxy]carbonyl}-2-(trifluoromethyl)-L-phenylalanine] and PyBrop (519 mg, 1.11 mmol) in chloroform (9 mL). DIEA (790 µL, 4.52 mmol) was added and the mixture stirred overnight at room temperature. The reaction mixture was adsorbed onto silica and purified via column chromatography (25-70% EtOAc/Hex) affording the title compound (247 mg, 45%): LC-MS (ES) m/z=553 (M+H)$^+$.

d) N-((1S)-2-amino-1-{[3-(trifluoromethyl)phenyl]methyl}ethyl)-5-methyl-4-(1-methyl-1H-pyrazol-5-yl)-2-thiophenecarboxamide To a 50 mL round-bottomed flask was added N-((1S)-2-(1,3-dioxo-1,3-dihydro-2H-isoindol-2-yl)-1-{[3-(trifluoromethyl)phenyl]methyl}ethyl)-5-methyl-4-(1-methyl-1H-pyrazol-5-yl)-2-thiophenecarboxamide (374 mg, 0.64 mmol) in Tetrahydrofuran (THF) (6 mL) and Methanol (600 µL). Hydrazine (125 µL, 3.98 mmol) was added and the reaction stirred overnight at room temperature. The mixture was adsorbed onto silica gel and purified by column chromatography (95:5:0.5 $CHCl_3$/MeOH/$NH_4OH$).

The neutral compound was dissolved in MeOH (2 mL), treated with excess 2M HCl in $Et_2O$ and concentrated affording the HCl salt of the title compound (135 mg, 0.27 mmol, 42% yield): LC-MS (ES) m/z=423 (M+H)$^+$, $^1$H NMR (400 MHz, DMSO-$d_6$) δ ppm 2.37 (s, 3H) 2.95-3.11 (m, 4H) 3.78 (s, 3H) 4.32-4.42 (m, 1H) 6.34 (d, J=1.77 Hz, 1H) 7.48-7.56 (m, 3H) 7.58-7.61 (m, 1H) 7.67 (s, 1H) 8.04 (s, 1H) 8.21 (s, 3H) 8.98 (d, J=8.59 Hz, 1H).

Example 152

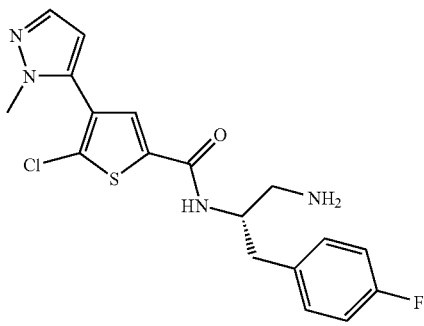 [SMILES: Cn1nccc1-c1cc(C(=O)N[C@H](CN)Cc2ccc(F)cc2)sc1Cl]

Preparation of N-{(1S)-2-amino-1-[(4-fluorophenyl)methyl]ethyl}-5-chloro-4-(1-methyl-1H-pyrazol-5-yl)-2-thiophenecarboxamide a) 5-chloro-N-{(1S)-2-(1,3-dioxo-1,3-dihydro-2H-isoindol-2-yl)-1-[(4-fluorophenyl)methyl]ethyl}-4-(1-methyl-1H-pyrazol-5-yl)-2-thiophenecarboxamide

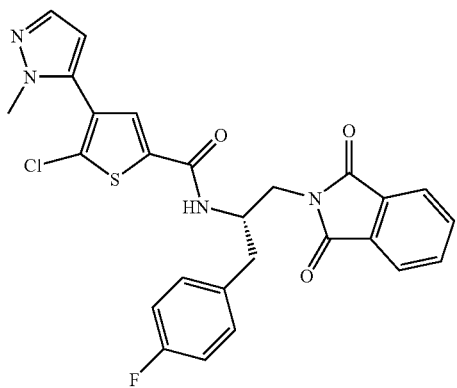 [SMILES: Cn1nccc1-c1cc(C(=O)N[C@@H](Cc2ccc(F)cc2)CN2C(=O)c3ccccc3C2=O)sc1Cl]

To a 50 mL round-bottomed flask was added 5-methyl-4-(1-methyl-1H-pyrazol-5-yl)-2-thiophenecarboxylic acid (201 mg, 0.91 mmol) [prepared according to the procedure of Example 95], 2-{(2S)-2-amino-3-[3-(trifluoromethyl)phenyl]propyl}-1H-isoindole-1,3(2H)-dione (301 mg, 0.87 mmol) [prepared according to the procedure of Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (519 mg, 1.11 mmol) in Chloroform (9 mL). DIEA (790 µL, 4.52 mmol) was added and the reaction stirred overnight at room temperature. The mixture was adsorbed onto silica and purified via column chromatography (25-70% EtOAc/Hex) affording the title compound (186 mg, 32%): LC-MS (ES) m/z=553 (M+H)+.

b) N-{(1S)-2-amino-1-[(4-fluorophenyl)methyl]ethyl}-5-chloro-4-(1-methyl-1H-pyrazol-5-yl)-2-thiophenecarboxamide To a 50 mL round-bottomed flask was added 5-chloro-N-{(1S)-2-(1,3-dioxo-1,3-dihydro-2H-isoindol-2-yl)-1-[(4-fluorophenyl)methyl]ethyl}-4-(1-methyl-1H-pyrazol-5-yl)-2-thiophenecarboxamide (185 mg, 0.34 mmol) in Tetrahydrofuran (THF) (10 mL) and Methanol (1 mL). Hydrazine (63 µL, 2.0 mmol) was added and the reaction stirred overnight at room temperature. The mixture was adsorbed onto silica gel and purified via column chromatography (90:10:1 CHCl3/MeOH/NH4OH).

The neutral compound was dissolved in MeOH (2 mL), treated with excess 2M HCl in Et2O and concentrated affording the HCl salt of the title compound (101 mg, 0.24 mmol, 72%): LC-MS (ES) m/z=393 (M+H)+, 1H NMR (400 MHz, DMSO-d6) δ ppm 2.90-3.1 (m, 4H) 3.85 (s, 3H) 4.33 (s, 1H) 6.48 (d, J=1.77 Hz, 1H) 7.10 (t, J=8.84 Hz, 2H) 7.32 (dd, J=8.46, 5.68 Hz, 2H) 7.55 (d, J=2.02 Hz, 1H) 8.19 (s, 3H) 8.23-8.28 (m, 1H) 9.25 (d, J=8.59 Hz, 1H).

Example 153

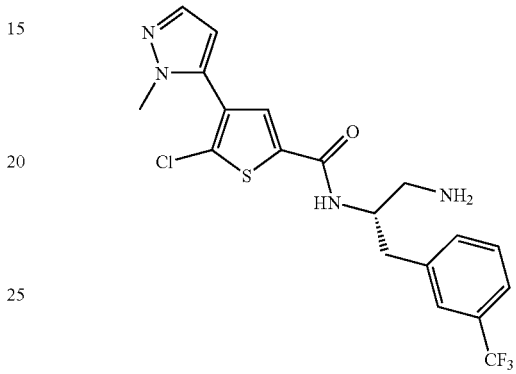

Preparation of N-((1S)-2-amino-1-{[3-(trifluoromethyl)phenyl]methyl}ethyl)-5-chloro-4-(1-methyl-1H-pyrazol-5-yl)-2-thiophenecarboxamide a) 5-chloro-N-((1S)-2-(1,3-dioxo-1,3-dihydro-2H-isoindol-2-yl)-1-{[3-(trifluoromethyl)phenyl]methyl}ethyl)-4-(1-methyl-1H-pyrazol-5-yl)-2-thiophenecarboxamide

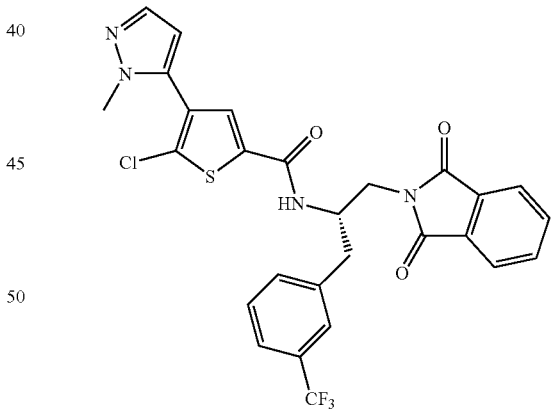

To a 50 mL round-bottomed flask was added 5-chloro-4-(1-methyl-1H-pyrazol-5-yl)-2-thiophenecarboxylic acid (226 mg, 0.93 mmol) [prepared according to the procedure of Example 95], 2-{(2S)-2-amino-3-[3-(trifluoromethyl)phenyl]propyl}-1H-isoindole-1,3(2H)-dione (519 mg, 1.349 mmol) [prepared according to Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (515 mg, 1.1 mmol) in chloroform (10 mL). DIEA (820 µL, 4.70 mmol) was added and the reaction stirred overnight at room temperature. The mixture was adsorbed onto silica and purified via column chromatography (25-70%

EtOAc/Hex) affording the title compound (379 mg, 69%): LC-MS (ES) m/z=573 (M+H)⁺.

b) N-((1S)-2-amino-1-{[3-(trifluoromethyl)phenyl]methyl}ethyl)-5-chloro-4-(1-methyl-1H-pyrazol-5-yl)-2-thiophenecarboxamide To a 50 mL round-bottomed flask was added 5-chloro-N-((1S)-2-(1,3-dioxo-1,3-dihydro-2H-isoindol-2-yl)-1-{[3-(trifluoromethyl)phenyl]methyl}ethyl)-4-(1-methyl-1H-pyrazol-5-yl)-2-thiophenecarboxamide (378 mg, 0.64 mmol) in Tetrahydrofuran (THF) (10 mL) and Methanol (1 mL). Hydrazine (122 μL, 3.89 mmol) was added and the reaction stirred overnight at room temperature. The mixture was adsorbed onto silica gel and purified by column chromatography (95:5:0.5 CHCl₃/MeOH/NH₄OH).

The neutral compound was dissolved in MeOH (2 mL), treated with excess 2M HCl in Et₂O and concentrated affording the HCl salt of the title compound (222 mg, 0.41 mmol, 64%): LC-MS (ES) m/z=443 (M+H)⁺, ¹H NMR (400 MHz, DMSO-d₆) δ ppm 3.05 (d, J=6.82 Hz, 4H) 3.84 (s, 3H) 4.37 (d, J=5.05 Hz, 1H) 6.46 (d, J=1.77 Hz, 1H) 7.49-7.57 (m, 3H) 7.58-7.61 (m, 1H) 7.67 (s, 1H) 8.20 (s, 3H) 8.24 (s, 1H) 9.31 (d, J=8.84 Hz, 1H).

Example 154

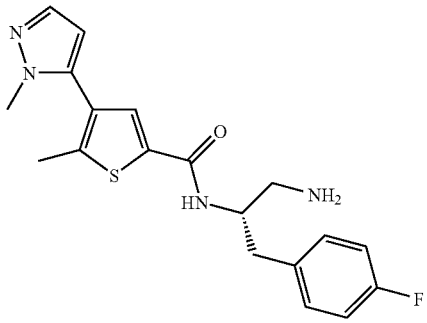 [SMILES: Cc1sc(C(=O)N[C@H](CN)Cc2ccc(F)cc2)cc1-c1ccnn1C]

Preparation of N-{(1S)-2-amino-1-[(4-fluorophenyl)methyl]ethyl}-5-methyl-4-(1-methyl-1H-pyrazol-5-yl)-2-thiophenecarboxamide a) N-{(1S)-2-(1,3-dioxo-1,3-dihydro-2H-isoindol-2-yl)-1-[(4-fluorophenyl)methyl]ethyl}-5-methyl-4-(1-methyl-1H-pyrazol-5-yl)-2-thiophenecarboxamide

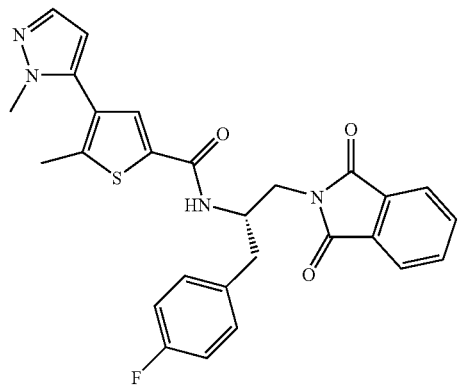

To a 50 mL round-bottomed flask was added 5-methyl-4-(1-methyl-1H-pyrazol-5-yl)-2-thiophenecarboxylic acid (200 mg, 0.90 mmol) [Prepared according to the procedure of Example 151], 2-[(2S)-2-amino-3-(4-fluorophenyl)propyl]-1H-isoindole-1,3(2H)-dione (288 mg, 0.86 mmol) [Prepared according to Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (512 mg, 1.09 mmol) in Chloroform (9 mL). DIEA (790 μL, 4.52 mmol) was added and the reaction stirred overnight at room temperature. The mixture was adsorbed onto silica and purified via column chromatography (25-70% EtOAc/Hex) affording the title compound (162 mg, 32%): LC-MS (ES) m/z=503 (M+H)⁺.

b) N-{(1S)-2-amino-1-[(4-fluorophenyl)methyl]ethyl}-5-methyl-4-(1-methyl-1H-pyrazol-5-yl)-2-thiophenecarboxamide To a 50 mL round-bottomed flask was added N-{(1S)-2-(1,3-dioxo-1,3-dihydro-2H-isoindol-2-yl)-1-[(4-fluorophenyl)methyl]ethyl}-5-methyl-4-(1-methyl-1H-pyrazol-5-yl)-2-thiophenecarboxamide (162 mg, 0.29 mmol) in Tetrahydrofuran (THF) (3 mL) and Methanol (300 μL). Hydrazine (58 μL, 1.85 mmol) was added and the reaction stirred overnight at room temperature. The mixture was adsorbed onto silica gel and purified via column chromatography (90:10:1 CHCl₃/MeOH/NH₄OH). The compound was further purified on reverse-phase HPLC (C18 column: H₂O/CH₃CN, 95-5%) affording the TFA salt which was neutralized on silica (90:10:1 CHCl₃/MeOH/NH₄OH).

The neutral compound was dissolved in MeOH (2 mL), treated with excess 2M HCl in Et₂O and concentrated affording the HCl salt of the title compound (222 mg, 0.41 mmol, 64%): LC-MS (ES) m/z=373 (M+H)⁺, ¹H NMR (400 MHz, DMSO-d₆) δ ppm 2.38 (s, 3H) 2.89-3.02 (m, 4H) 3.79 (s, 3H) 4.26-4.48 (m, 1H) 6.36 (d, J=1.77 Hz, 1H) 7.10 (t, J=8.72 Hz, 2H) 7.26-7.35 (m, 2H) 7.52 (d, J=1.77 Hz, 1H) 8.02 (s, 1H) 8.17 (s, 3H) 8.88 (d, J=8.59 Hz, 1H).

Example 155

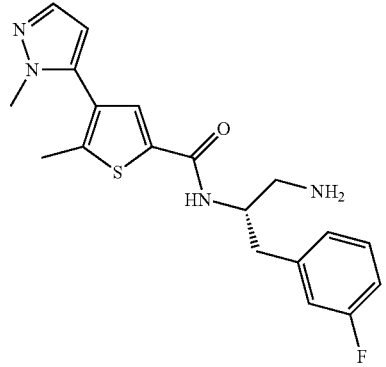 [SMILES: Cc1sc(C(=O)N[C@H](CN)Cc2cccc(F)c2)cc1-c1ccnn1C]

Preparation of N-{(1S)-2-amino-1-[(3-fluorophenyl)methyl]ethyl}-5-methyl-4-(1-methyl-1H-pyrazol-5-yl)-2-thiophenecarboxamide a) N-{(1S)-2-(1,3-dioxo-1,3-dihydro-2H-isoindol-2-yl)-1-[(3-fluorophenyl)methyl]ethyl}-5-methyl-4-(1-methyl-1H-pyrazol-5-yl)-2-thiophenecarboxamide

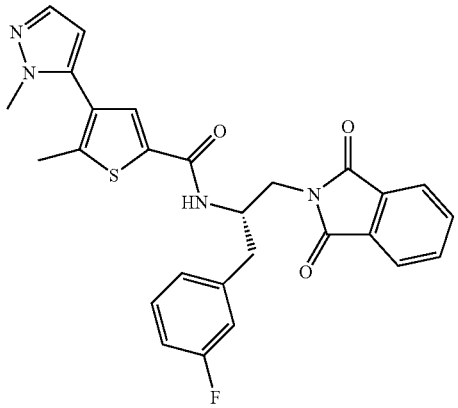 [SMILES: Cc1sc(C(=O)N[C@@H](Cc2cccc(F)c2)CN2C(=O)c3ccccc3C2=O)cc1-c1ccnn1C]

To a 50 mL round-bottomed flask was added 5-methyl-4-(1-methyl-1H-pyrazol-5-yl)-2-thiophenecarboxylic acid (200 mg, 0.90 mmol) [Prepared according to the procedure of Example 151], 2-[(2S)-2-amino-3-(3-fluorophenyl)propyl]-1H-isoindole-1,3(2H)-dione (291 mg, 0.87 mmol) [Prepared according to the procedure of preparation 6 except substituting N-{[(1,1-dimethylethyl)oxy]carbonyl}-3-fluoro-L-phenylalanine (5.03 g, 17.8 mmol) for N-{[(1,1-dimethylethyl)oxy]carbonyl}-2-(trifluoromethyl)-L-phenylalanine] and PyBrop (512 mg, 1.09 mmol) in Chloroform (9 mL). DIEA (790 μL, 4.52 mmol) was added and the mixture stirred overnight at room temperature. The mixture was adsorbed onto silica and purified via column chromatography (25-70% EtOAc/Hex) affording the title compound (250 mg, 50%): LC-MS (ES) m/z=503 (M+H)$^+$.

b) N-{(1S)-2-amino-1-[(3-fluorophenyl)methyl]ethyl}-5-methyl-4-(1-methyl-1H-pyrazol-5-yl)-2-thiophenecarboxamide To a 50 mL round-bottomed flask was added N-{(1S)-2-(1,3-dioxo-1,3-dihydro-2H-isoindol-2-yl)-1-[(3-fluorophenyl)methyl]ethyl}-5-methyl-4-(1-methyl-1H-pyrazol-5-yl)-2-thiophenecarboxamide (250 mg, 0.45 mmol) in Tetrahydrofuran (THF) (4 mL) and Methanol (400 μL). Hydrazine (66 μL, 2.10 mmol) was added and the reaction stirred overnight at room temperature. The mixture was adsorbed onto silica gel and purified via column chromatography (90:10:1 CHCl$_3$/MeOH/NH$_4$OH). The compound was further purified on reverse-phase HPLC (C18 column: H$_2$O/CH$_3$CN, 95-5%) affording the TFA salt which was neutralized on silica (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (142 mg, 0.31 mmol, 70%): LC-MS (ES) m/z=373 (M+H)$^+$, $^1$H NMR (400 MHz, DMSO-d$_6$) δ ppm 2.38 (s, 3H) 2.92-3.04 (m, 4H) 3.79 (s, 3H) 4.30-4.43 (m, 1H) 6.36 (d, J=1.77 Hz, 1H) 7.02 (td, J=8.53, 2.15 Hz, 1H) 7.13 (t, J=7.83 Hz, 2H) 7.26-7.35 (m, 1H) 7.52 (d, J=2.02 Hz, 1H) 8.04 (s, 1H) 8.19 (s, 3H) 8.93 (d, J=8.34 Hz, 1H).

Example 156

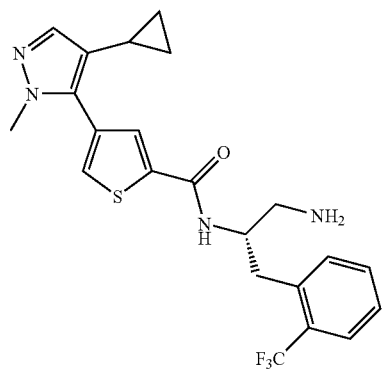 [SMILES: Cn1ncc(C2CC2)c1-c1csc(C(=O)N[C@H](CN)Cc2ccccc2C(F)(F)F)c1]

Preparation of N-((1S)-2-amino-1-{[2-(trifluoromethyl)phenyl]methyl}ethyl)-4-(4-cyclopropyl-1-methyl-1H-pyrazol-5-yl)-2-thiophenecarboxamide a) methyl 4-(4-bromo-1-methyl-1H-pyrazol-5-yl)-2-thiophenecarboxylate

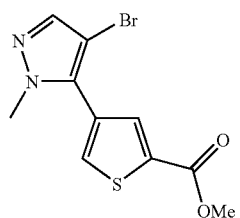 [SMILES: COC(=O)c1cc(-c2c(Br)cnn2C)cs1]

NBS (747 mg, 4.20 mmol) was added in portions to a 50 mL sealed tube reactor containing methyl 4-(1-methyl-1H-pyrazol-5-yl)-2-thiophenecarboxylate (860 mg, 3.48 mmol) [prepared according to the procedure of Example 37] in Tetrahydrofuran (THF) (17 mL) at room temperature. The mixture was heated to 70° C. for 1.5 hours, cooled to room temperature and partitioned between CHCl$_3$ and H$_2$O. The organic layer was dried with Na$_2$SO$_4$, adsorbed onto silica and purified via column chromatography (20-40% EtOAc/hexanes) affording the title compound (867 mg, 83%): LC-MS (ES) m/z=303 (M+H)$^+$.

b) methyl 4-(4-cyclopropyl-1-methyl-1H-pyrazol-5-yl)-2-thiophenecarboxylate

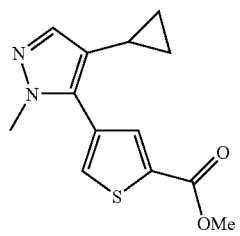 [SMILES: COC(=O)c1cc(-c2c(C3CC3)cnn2C)cs1]

To a 20 mL sealed tube reactor was added methyl 4-(4-bromo-1-methyl-1H-pyrazol-5-yl)-2-thiophenecarboxylate (505 mg, 1.68 mmol), cyclopropylboronic acid (447 mg, 5.20 mmol), Cesium Carbonate (1.90 g, 5.84 mmol) and PdCl$_2$ (dppf)-CH₂Cl₂Adduct (43.6 mg, 0.05 mmol) in Tetrahydrofuran (THF) (8.5 mL). The reaction was heated to 70° C. for 1.5 hours, cooled and partitioned between CHCl₃ and H₂O. The organic layer was dried with Na₂SO₄, adsorbed onto silica and purified via column chromatography (20-40% EtOAc/Hexane) affording the title compound (0.42 g, 1.60 mmol, 95%): LC-MS (ES) m/z=251 (M+H)⁺.

c) 4-(4-cyclopropyl-1-methyl-1H-pyrazol-5-yl)-2-thiophenecarboxylic Acid

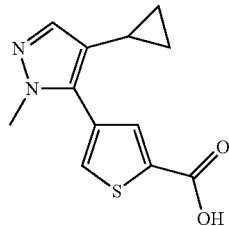 [SMILES: Cn1ncc(C2CC2)c1-c1csc(C(=O)O)c1]

To a 100 mL round-bottomed flask was added methyl 4-(4-cyclopropyl-1-methyl-1H-pyrazol-5-yl)-2-thiophenecarboxylate (0.42 g, 1.60 mmol) in Tetrahydrofuran (THF) (8 ml). 6N NaOH (8 ml, 48.0 mmol) was added slowly and the reaction stirred at 70° C. overnight. The reaction was cooled and partitioned between CHCl₃ and H₂O. The pH of the aqueous layer was adjusted to ~3 by the addition of 6N HCl. The layers were separated, the organic layer dried with Na₂SO₄ and solvent removed affording the title compound (0.42 g, 1.60 mmol, 95%) which was used without further purification: LC-MS (ES) m/z=249 (M+H)⁺.

d) 4-(4-cyclopropyl-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

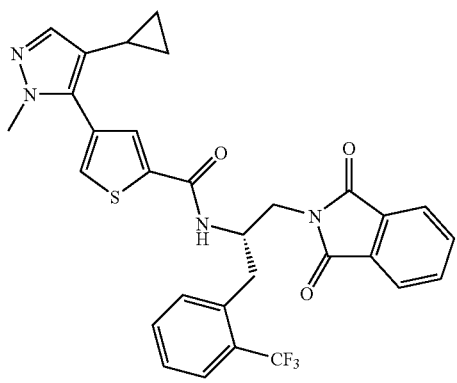 [SMILES: Cn1ncc(C2CC2)c1-c1csc(C(=O)N[C@@H](Cc2ccccc2C(F)(F)F)CN2C(=O)c3ccccc3C2=O)c1]

To a 50 mL round-bottomed flask was added 4-(4-cyclopropyl-1-methyl-1H-pyrazol-5-yl)-2-thiophenecarboxylic acid (105 mg, 0.42 mmol), 2-{(2S)-2-amino-3-[2-(trifluoromethyl)phenyl]propyl}-1H-isoindole-1,3(2H)-dione (152 mg, 0.39 mmol) [prepared according to Preparation 6] and PyBrop (246 mg, 0.52 mmol) in Chloroform (6 mL). DIEA (370 µL, 2.19 mmol) was added and the mixture stirred overnight at room temperature. The mixture was adsorbed onto silica and purified via column chromatography (25-70% EtOAc/Hex) affording the title compound (171 mg, 66%): LC-MS (ES) m/z=579 (M+H)⁺.

e) N-((1S)-2-amino-1-{[2-(trifluoromethyl)phenyl]methyl}ethyl)-4-(4-cyclopropyl-1-methyl-1H-pyrazol-5-yl)-2-thiophenecarboxamide To a 50 mL round-bottomed flask was added 4-(4-cyclopropyl-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (102 mg, 0.18 mmol) in Tetrahydrofuran (THF) (5 mL) and Methanol (2 mL). Hydrazine (40 µL, 1.27 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (65 mg, 0.12 mmol, 66% yield): LC-MS (ES) m/z=449 (M+H)⁺, ¹H NMR (400 MHz, DMSO-d₆) δ ppm 0.45-0.54 (m, 2H) 0.76-0.83 (m, 2H) 1.62-1.71 (m, 1H) 3.03-3.21 (m, 4H) 3.82 (s, 3H) 4.46-4.56 (m, 1H) 7.21 (s, 1H) 7.42 (t, J=7.45 Hz, 1H) 7.53 (t, J=7.45 Hz, 1H) 7.66 (dd, J=19.96, 7.58 Hz, 2H) 7.95 (d, J=1.26 Hz, 1H) 8.18 (s, 3H) 8.24 (d, J=1.26 Hz, 1H) 9.11 (d, J=9.09 Hz, 1H).

Example 157

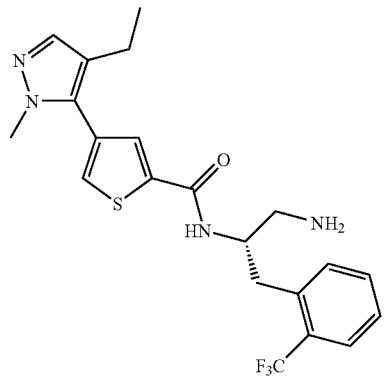 [SMILES: CCc1cnn(C)c1-c1csc(C(=O)N[C@H](CN)Cc2ccccc2C(F)(F)F)c1]

Preparation of N-((1S)-2-amino-1-{[2-(trifluoromethyl)phenyl]methyl}ethyl)-4-(4-ethyl-1-methyl-1H-pyrazol-5-yl)-2-thiophenecarboxamide a) methyl 4-(4-ethenyl-1-methyl-1H-pyrazol-5-yl)-2-thiophenecarboxylate

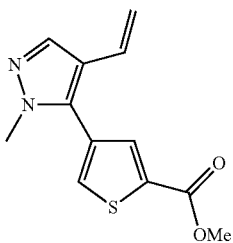 [SMILES: C=Cc1cnn(C)c1-c1csc(C(=O)OC)c1]

To a 5 mL sealed tube reactor was added methyl 4-(4-bromo-1-methyl-1H-pyrazol-5-yl)-2-thiophenecarboxylate (473 mg, 1.57 mmol) [prepared according to the procedure of Example 156], pyridine-triethenylboroxine (1:1) (666 mg, 2.77 mmol), Pd(PtBu₃)₂ (16.8 mg, 0.03 mmol) and Cs₂CO₃

(1.72 g, 5.28 mmol) in 1,4-Dioxane (6.3 mL) and water (1.6 mL). The reaction was heated at 70° C. for 2 hours and partitioned between CHCl₃ (75 mL)/H₂O (75 mL). The organic layer was dried with Na₂SO₄, adsorbed onto silica and purified via column chromatography (25-70% EtOAc/Hexane) affording the desired product: LC-MS (ES) m/z=249 (M+H)⁺.

b) methyl 4-(4-ethyl-1-methyl-1H-pyrazol-5-yl)-2-thiophenecarboxylate

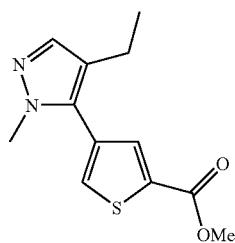 [SMILES: CCc1cnn(C)c1-c1csc(C(=O)OC)c1]

To a 100 mL round-bottomed flask was added methyl 4-(4-ethenyl-1-methyl-1H-pyrazol-5-yl)-2-thiophenecarboxylate and 10% Pd/C in ethyl acetate (15 mL). The mixture was evacuated slightly, refilled with H₂ from a balloon and stirred vigorously under an atmosphere of H₂ for 1 hour. The reaction was filtered through a 0.2 μm PTFE membrane filter and used without further purification (153 mg, 0.60 mmol, 87%): LC-MS (ES) m/z=251 (M+H)⁺.

c) 4-(4-ethyl-1-methyl-1H-pyrazol-5-yl)-2-thiophenecarboxylic Acid

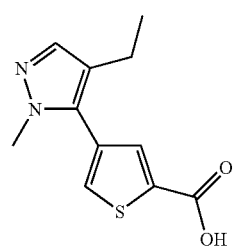 [SMILES: CCc1cnn(C)c1-c1csc(C(=O)O)c1]

To a 100 mL round-bottomed flask was added methyl 4-(4-ethyl-1-methyl-1H-pyrazol-5-yl)-2-thiophenecarboxylate (192 mg, 0.77 mmol) in Tetrahydrofuran (THF) (4 mL). 6N NaOH (4 mL, 24.0 mmol) was added slowly, the reaction stirred at 70° C. overnight. The reaction was cooled to room temperature, partitioned between CHCl₃ and H₂O and the pH of the aqueous layer adjusted to pH 3 by the addition of 6N HCl. The layers were separated, the organic layer dried with Na₂SO₄ and solvent removed affording the title compound (181 mg, quant.) used without further purification: LC-MS (ES) m/z=237 (M+H)⁺.

d) N-((1S)-2-(1,3-dioxo-1,3-dihydro-2H-isoindol-2-yl)-1-{[2-(trifluoromethyl)phenyl]methyl}ethyl)-4-(4-ethyl-1-methyl-1H-pyrazol-5-yl)-2-thiophenecarboxamide

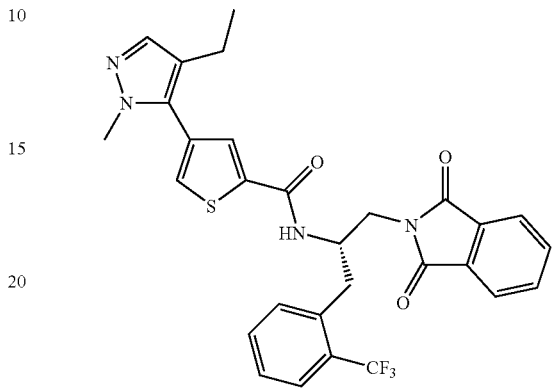

To a 50 mL round-bottomed flask was added 4-(4-ethyl-1-methyl-1H-pyrazol-5-yl)-2-thiophenecarboxylic acid (106 mg, 0.45 mmol), 2-{(2S)-2-amino-3-[2-(trifluoromethyl)phenyl]propyl}-1H-isoindole-1,3(2H)-dione (164 mg, 0.43 mmol) [prepared according to Preparation 6] and PyBrop (254 mg, 0.54 mmol) in Chloroform (6 mL). DIEA (400 μL, 2.29 mmol) was added and the reaction stirred overnight at room temperature. The mixture was adsorbed onto silica and purified via column chromatography (25-70% EtOAc/Hex) affording the title compound (182 mg, 0.32 mmol, 71%): LC-MS (ES) m/z=567 (M+H)⁺.

e) N-((1S)-2-amino-1-{[2-(trifluoromethyl)phenyl]methyl}ethyl)-4-(4-ethyl-1-methyl-1H-pyrazol-5-yl)-2-thiophenecarboxamide To a 50 mL round-bottomed flask was added N-((1S)-2-(1,3-dioxo-1,3-dihydro-2H-isoindol-2-yl)-1-{[2-(trifluoromethyl)phenyl]methyl}ethyl)-4-(4-ethyl-1-methyl-1H-pyrazol-5-yl)-2-thiophenecarboxamide (101 mg, 0.18 mmol) in Tetrahydrofuran (THF) (5 mL) and Methanol (2 mL). Hydrazine (40 μL, 1.27 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (65 mg, 0.12 mmol, 68%): LC-MS (ES) m/z=437 (M+H)⁺, ¹H NMR (400 MHz, DMSO-d₆) δ ppm 1.10 (t, J=7.45 Hz, 3H) 2.44 (q, J=7.41 Hz, 2H) 2.94-3.17 (m, 4H) 3.80 (s, 3H) 4.41-4.57 (m, 1H) 7.37-7.45 (m, 2H) 7.53 (t, J=7.45 Hz, 1H) 7.66 (dd, J=19.96, 7.58 Hz, 2H) 7.88 (d, J=1.01 Hz, 1H) 8.16 (s, 4H) 9.10 (d, J=8.84 Hz, 1H).

Example 158

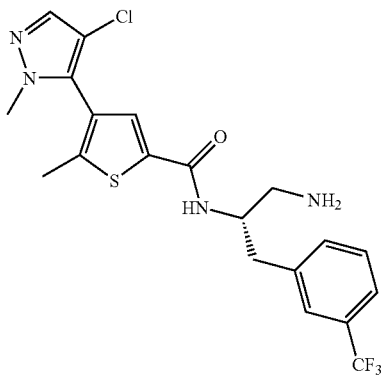 [SMILES: Cc1sc(C(=O)N[C@H](CN)Cc2cccc(C(F)(F)F)c2)cc1-c1c(Cl)cnn1C]

Preparation of N-((1S)-2-amino-1-{[3-(trifluoromethyl)phenyl]methyl}ethyl)-4-(4-chloro-1-methyl-1H-pyrazol-5-yl)-5-methyl-2-thiophenecarboxamide a) 4-(4-chloro-1-methyl-1H-pyrazol-5-yl)-5-methyl-2-thiophenecarboxylic Acid

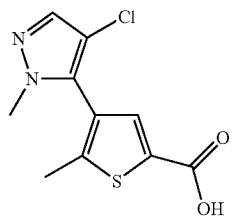 [SMILES: Cc1sc(C(=O)O)cc1-c1c(Cl)cnn1C]

NCS (1.355 g, 10.15 mmol) was added in portions to a 150 mL sealed tube reactor containing methyl 5-methyl-4-(1-methyl-1H-pyrazol-5-yl)-2-thiophenecarboxylate (2.0 g, 8.46 mmol) [prepared according to the procedure of Preparation 10] in Tetrahydrofuran (THF) (40 ml) at room temperature. The mixture was heated to 70° C. for 2 h. 6N NaOH (28 ml, 168 mmol) was added and the mixture stirred at 70° C. for an additional 2 h. The mixture was cooled to room temperature and partitioned between CHCl$_3$ and H$_2$O. The pH of the aqueous layer was adjusted to ~3 by the addition of 6N HCl. The aqueous phase was washed several times with DCM and the combined organic fractions were dried with Na$_2$SO$_4$ and concentrated affording the title compound (2.36 g, 9.19 mmol, quant.): LC-MS (ES) m/z=257 (M+H)$^+$.

b) 4-(4-chloro-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-methyl-2-thiophenecarboxamide

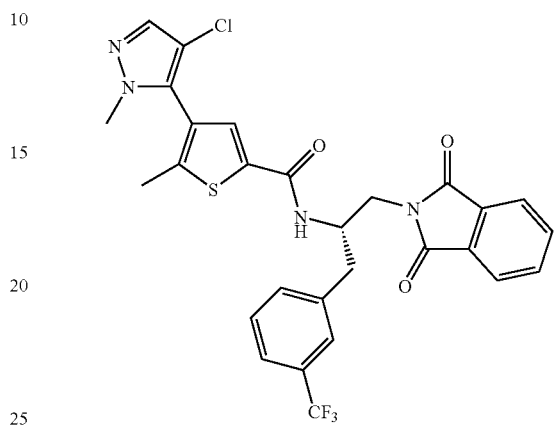

To a 50 mL round-bottomed flask was added 4-(4-chloro-1-methyl-1H-pyrazol-5-yl)-5-methyl-2-thiophenecarboxylic acid (181 mg, 0.70 mmol), 2-{(2S)-2-amino-3-[3-(trifluoromethyl)phenyl]propyl}-1H-isoindole-1,3(2H)-dione (250 mg, 0.65 mmol) [Prepared according to the procedure of Preparation 6 except substituting N-{[(1,1-dimethylethyl)oxy]carbonyl}-3-(trifluoromethyl)-L-phenylalanine (4.98 g, 15.0 mmol) for N-{[(1,1-dimethylethyl)oxy]carbonyl}-2-(trifluoromethyl)-L-phenylalanine] and PyBrop (399 mg, 0.85 mmol) in chloroform (8 mL). DIEA (620 μL, 3.55 mmol) was added and the reaction stirred overnight at room temperature. The mixture was adsorbed onto silica and purified via column chromatography (25-70% EtOAc/Hex) affording the title compound (319 mg, 0.50 mmol, 71%): LC-MS (ES) m/z=587 (M+H)$^+$.

c) N-((1S)-2-amino-1-{[3-(trifluoromethyl)phenyl]methyl}ethyl)-4-(4-chloro-1-methyl-1H-pyrazol-5-yl)-5-methyl-2-thiophenecarboxamide To a 50 mL round-bottomed flask was added 4-(4-chloro-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-methyl-2-thiophenecarboxamide (319 mg, 0.50 mmol) in Tetrahydrofuran (THF) (4.9 mL) and Methanol (0.5 mL). Hydrazine (119 μL, 3.79 mmol) was added and the reaction stirred overnight at room temperature. The mixture was adsorbed onto silica gel and purified by column chromatography (95:5:0.5 CHCl$_3$/MeOH/NH$_4$OH).

The neutral compound was dissolved in MeOH (2 mL), treated with excess 2M HCl in Et$_2$O and concentrated affording the HCl salt of the title compound (204 mg, 0.39 mmol, 79%): LC-MS (ES) m/z=457 (M+H)$^+$, $^1$H NMR (400 MHz, DMSO-d$_6$) δ ppm 2.33 (s, 3H) 2.95-3.10 (m, 4H) 3.71 (s, 3H) 4.31-4.41 (m, 1H) 7.49-7.61 (m, 3H) 7.66 (s, 1H) 7.69 (s, 1H) 7.94 (s, 1H) 8.16 (s, 3H) 8.90 (s, 1H).

Example 159

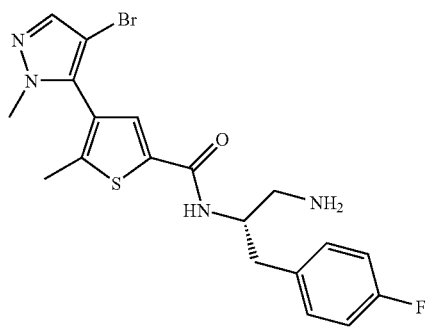

Preparation of N-{(1S)-2-amino-1-[(4-fluorophenyl)methyl]ethyl}-4-(4-bromo-1-methyl-1H-pyrazol-5-yl)-5-methyl-2-thiophenecarboxamide a) 4-(4-bromo-1-methyl-1H-pyrazol-5-yl)-5-methyl-2-thiophenecarboxylic Acid

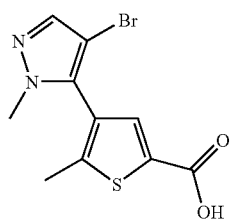 [SMILES: Cc1sc(C(=O)O)cc1-c1c(Br)cnn1C]

NBS (1.84 g, 10.33 mmol) was added in portions to a 150 mL sealed tube reactor containing methyl 5-methyl-4-(1-methyl-1H-pyrazol-5-yl)-2-thiophenecarboxylate (2 g, 8.46 mmol) [prepared according to the procedure of Preparation 10] in Tetrahydrofuran (THF) (40 ml) at room temperature. The mixture was heated to 70° C. for 1 h. 6N NaOH (28 ml, 168 mmol) was then added and the mixture stirred at 70° C. for 2 h. The mixture was partitioned between CHCl$_3$ and H$_2$O and the aqueous layer was made acidic with 6N HCl. The aqueous phase was washed several times with CHCl$_3$ and the organic fractions were combined, dried over Na$_2$SO$_4$ and concentrated affording the title compound (2.68 g, 8.9 mmol, quant.): LC-MS (ES) m/z=302 (M+H)$^+$.

b) 4-(4-bromo-1-methyl-1H-pyrazol-5-yl)-N-{(1S)-2-(1,3-dioxo-1,3-dihydro-2H-isoindol-2-yl)-1-[(4-fluorophenyl)methyl]ethyl}-5-methyl-2-thiophenecarboxamide

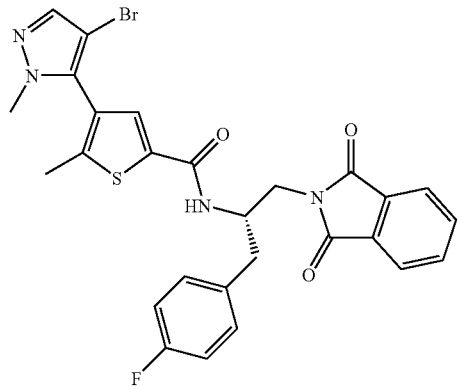

To a 50 mL round-bottomed flask was added 4-(4-bromo-1-methyl-1H-pyrazol-5-yl)-5-methyl-2-thiophenecarboxylic acid (256 mg, 0.85 mmol), 2-[(2S)-2-amino-3-(4-fluorophenyl)propyl]-1H-isoindole-1,3(2H)-dione (1272 mg, 3.80 mmol) [prepared according to the procedure of Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (485 mg, 1.03 mmol) in Chloroform (8.5 mL). DIEA (750 µL, 4.29 mmol) was added and the reaction stirred overnight at room temperature. The mixture was adsorbed onto silica and purified via column chromatography (25-70% EtOAc/Hex) affording the title compound (319 mg, 0.50 mmol, 71%): LC-MS (ES) m/z=583 (M+H)$^+$.

c) N-{(1S)-2-amino-1-[(4-fluorophenyl)methyl]ethyl}-4-(4-bromo-1-methyl-1H-pyrazol-5-yl)-5-methyl-2-thiophenecarboxamide To a 50 mL round-bottomed flask was added 4-(4-bromo-1-methyl-1H-pyrazol-5-yl)-N-{(1S)-2-(1,3-dioxo-1,3-dihydro-2H-isoindol-2-yl)-1-[(4-fluorophenyl)methyl]ethyl}-5-methyl-2-thiophenecarboxamide (133 mg, 0.21 mmol) in Tetrahydrofuran (THF) (3 mL) and Methanol (1 mL). Hydrazine (50 µL, 1.59 mmol) was added and the reaction stirred overnight at room temperature. The mixture was adsorbed onto silica gel and purified via column chromatography (95:5:0.5 CHCl$_3$/MeOH/NH$_4$OH).

The neutral compound was dissolved in MeOH (2 mL), treated with excess 2M HCl in Et$_2$O and concentrated affording the HCl salt of the title compound (90 mg, 0.17 mmole, 83%): LC-MS (ES) m/z=453 (M+H)$^+$, $^1$H NMR (400 MHz, DMSO-d$_6$) δ ppm 2.33 (s, 3H) 2.82-3.08 (m, 4H) 3.72 (s, 3H) 4.24-4.39 (m, 1H) 7.11 (t, J=8.84 Hz, 2H) 7.26-7.35 (m, 2H) 7.69 (s, 1H) 7.89 (s, 1H) 8.03-8.25 (m, 3H) 8.73-8.90 (m, 1H).

Example 160

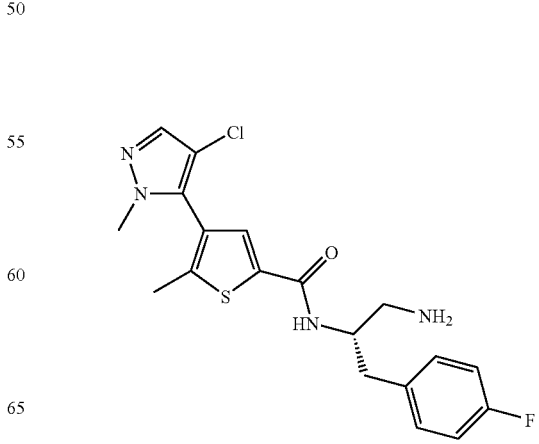

251

Preparation of N-{(1S)-2-amino-1-[(4-fluorophenyl)methyl]ethyl}-4-(4-chloro-1-methyl-1H-pyrazol-5-yl)-5-methyl-2-thiophenecarboxamide a) 4-(4-chloro-1-methyl-1H-pyrazol-5-yl)-N-{(1S)-2-(1,3-dioxo-1,3-dihydro-2H-isoindol-2-yl)-1-[(4-fluorophenyl)methyl]ethyl}-5-methyl-2-thiophenecarboxamide

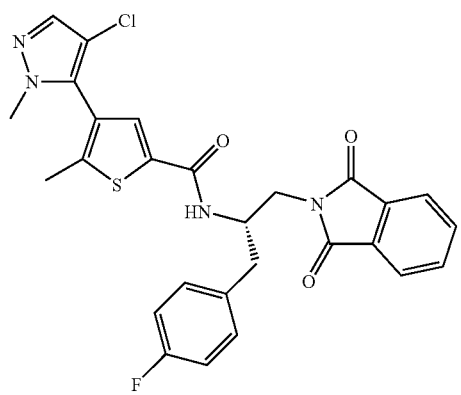 [SMILES: Cc1sc(C(=O)N[C@@H](Cc2ccc(F)cc2)CN2C(=O)c3ccccc3C2=O)cc1-c1c(Br)cnn1C]

To a 50 mL round-bottomed flask was added 4-(4-chloro-1-methyl-1H-pyrazol-5-yl)-5-methyl-2-thiophenecarboxylic acid (276 mg, 1.08 mmol) [Prepared according to the procedure of Example 158], 2-[(2S)-2-amino-3-(4-fluorophenyl)propyl]-1H-isoindole-1,3(2H)-dione (317 mg, 0.95 mmol) [prepared according to the procedure of Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (612 mg, 1.31 mmol) in Chloroform (14 mL). DIEA (940 µL, 5.38 mmol) was added and the reaction stirred overnight at room temperature. The mixture was adsorbed onto silica and purified via column chromatography (25-70% EtOAc/Hex) affording the title compound (319 mg, 0.50 mmol, 71%): LC-MS (ES) m/z=537 (M+H)+.

c) N-{(1S)-2-amino-1-[(4-fluorophenyl)methyl]ethyl}-4-(4-chloro-1-methyl-1H-pyrazol-5-yl)-5-methyl-2-thiophenecarboxamide To a 50 mL round-bottomed flask was added 4-(4-chloro-1-methyl-1H-pyrazol-5-yl)-N-{(1S)-2-(1,3-dioxo-1,3-dihydro-2H-isoindol-2-yl)-1-[(4-fluorophenyl)methyl]ethyl}-5-methyl-2-thiophenecarboxamide (145 mg, 0.25 mmol) in Tetrahydrofuran (THF) (4 mL) and Methanol (1 mL). Hydrazine (60 µL, 1.91 mmol) was added and the reaction stirred overnight at room temperature. The mixture was adsorbed onto silica gel and purified by column chromatography (95:5:0.5 CHCl$_3$/MeOH/NH$_4$OH).

The neutral compound was dissolved in MeOH (2 mL), treated with excess 2M HCl in Et$_2$O and concentrated affording the HCl salt of the title compound (88 mg, 0.19 mmol, 77%): LC-MS (ES) m/z=407 (M+H)+, $^1$H NMR (400 MHz, DMSO-d$_6$) δ ppm 2.34 (s, 3H) 2.81-3.10 (m, 4H) 3.72 (s, 3H) 4.25-4.40 (m, 1H) 7.10 (t, J=8.84 Hz, 2H) 7.31 (dd, J=8.21, 5.68 Hz, 2H) 7.69 (s, 1H) 7.94 (s, 1H) 8.15 (s, 3H) 8.85 (s, 1H).

252

Example 161

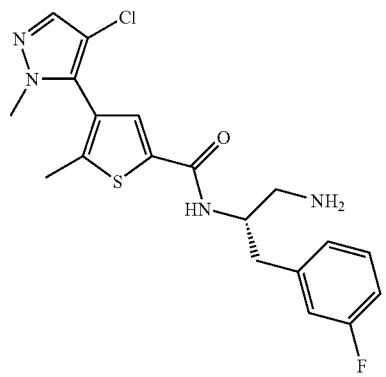

Preparation of N-{(1S)-2-amino-1-[(3-fluorophenyl)methyl]ethyl}-4-(4-chloro-1-methyl-1H-pyrazol-5-yl)-5-methyl-2-thiophenecarboxamide a) 4-(4-chloro-1-methyl-1H-pyrazol-5-yl)-N-{(1S)-2-(1,3-dioxo-1,3-dihydro-2H-isoindol-2-yl)-1-[(3-fluorophenyl)methyl]ethyl}-5-methyl-2-thiophenecarboxamide

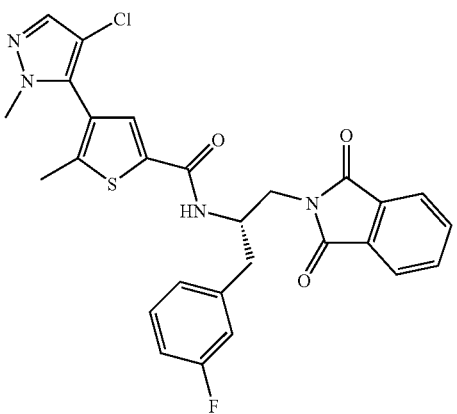 [SMILES: Cc1sc(C(=O)N[C@@H](Cc2cccc(F)c2)CN2C(=O)c3ccccc3C2=O)cc1-c1c(Cl)cnn1C]

To a 50 mL round-bottomed flask was added 4-(4-chloro-1-methyl-1H-pyrazol-5-yl)-5-methyl-2-thiophenecarboxylic acid (187 mg, 0.73 mmol) [prepared according to the procedure of Example 158], 2-[(2S)-2-amino-3-(3-fluorophenyl)propyl]-1H-isoindole-1,3(2H)-dione (233 mg, 0.70 mmol) [prepared according to the procedure of Preparation 6 except substituting N-{[(1,1-dimethylethyl)oxy]carbonyl}-3-fluoro-L-phenylalanine (5.03 g, 17.8 mmol) for N-{[(1,1-dimethylethyl)oxy]carbonyl}-2-(trifluoromethyl)-L-phenylalanine] and PyBrop (412 mg, 0.88 mmol) in Chloroform (9 mL). DIEA (640 µL, 3.66 mmol) was added and the reaction stirred overnight at room temperature. The mixture was adsorbed onto silica and purified via column chromatography (25-70% EtOAc/Hex) affording the title compound (180 mg, 0.30 mmol, 42%): LC-MS (ES) m/z=537 (M+H)+.

b) N-{(1S)-2-amino-1-[(3-fluorophenyl)methyl]ethyl}-4-(4-chloro-1-methyl-1H-pyrazol-5-yl)-5-methyl-2-thiophenecarboxamide To a 50 mL round-bottomed flask was added 4-(4-chloro-1-methyl-1H-pyrazol-5-yl)-N-{(1S)-2-(1,3-dioxo-1,3-dihydro-2H-isoindol-2-yl)-1-[(3-fluorophenyl)methyl]ethyl}-5-methyl-2-thiophenecarboxamide (186 mg, 0.31 mmol) in Tetrahydrofuran (THF) (4 mL) and Methanol (1 mL). Hydrazine (76 µL, 2.42 mmol) was added and the reaction stirred overnight at room temperature. The mixture was adsorbed onto silica gel and purified via column chromatography (95:5:0.5 CHCl₃/MeOH/NH₄OH).

The neutral compound was dissolved in MeOH (2 mL), treated with excess 2M HCl in Et₂O and concentrated affording the HCl salt of the title compound (108 mg, 0.231, 74%): LC-MS (ES) m/z=407 (M+H)⁺, ¹H NMR (400 MHz, DMSO-d₆) δ ppm 2.34 (s, 3H) 2.91-3.03 (m, 4H) 3.71 (s, 3H) 4.31-4.41 (m, 1H) 7.02 (td, J=8.59, 2.02 Hz, 1H) 7.13 (t, J=7.07 Hz, 2H) 7.26-7.36 (m, 1H) 7.69 (s, 1H) 7.95 (s, 1H) 8.15 (s, 3H) 8.88 (d, J=6.32 Hz, 1H).

Example 162

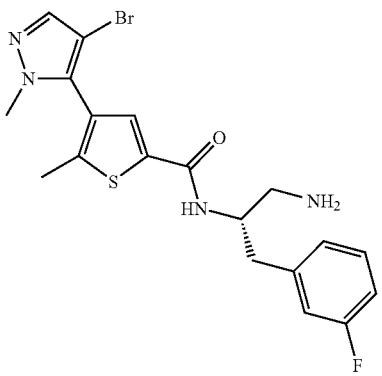 [SMILES: Cc1sc(C(=O)N[C@H](CN)Cc2cccc(F)c2)cc1-c1c(Br)cnn1C]

Preparation of N-{(1S)-2-amino-1-[(3-fluorophenyl)methyl]ethyl}-4-(4-bromo-1-methyl-1H-pyrazol-5-yl)-5-methyl-2-thiophenecarboxamide a) 4-(4-bromo-1-methyl-1H-pyrazol-5-yl)-N-{(1S)-2-(1,3-dioxo-1,3-dihydro-2H-isoindol-2-yl)-1-[(3-fluorophenyl)methyl]ethyl}-5-methyl-2-thiophenecarboxamide

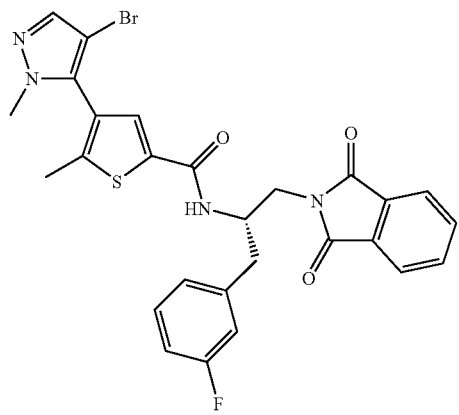 [SMILES: Cc1sc(C(=O)N[C@@H](Cc2cccc(F)c2)CN2C(=O)c3ccccc3C2=O)cc1-c1c(Br)cnn1C]

To a 50 mL round-bottomed flask was added 4-(4-bromo-1-methyl-1H-pyrazol-5-yl)-5-methyl-2-thiophenecarboxylic acid (191 mg, 0.63 mmol) [prepared according to the procedure of Example 159], 2-[(2S)-2-amino-3-(3-fluorophenyl)propyl]-1H-isoindole-1,3(2H)-dione (209 mg, 0.62 mmol) [prepared according to the procedure of Preparation 6 except substituting N-{[(1,1-dimethylethyl)oxy]carbonyl}-3-fluoro-L-phenylalanine (5.03 g, 17.8 mmol) for N-{[(1,1-dimethylethyl)oxy]carbonyl}-2-(trifluoromethyl)-L-phenylalanine] and PyBrop (359 mg, 0.77 mmol) in chloroform (7 mL). DIEA (560 µL, 3.21 mmol) was added and the reaction stirred overnight at room temperature. The mixture was adsorbed onto silica and purified via column chromatography (25-70% EtOAc/Hex) affording the title compound (171 mg, 0.29 mmol, 46%): LC-MS (ES) m/z=583 (M+H)⁺.

b) N-{(1S)-2-amino-1-[(3-fluorophenyl)methyl]ethyl}-4-(4-bromo-1-methyl-1H-pyrazol-5-yl)-5-methyl-2-thiophenecarboxamide To a 50 mL round-bottomed flask was added 4-(4-bromo-1-methyl-1H-pyrazol-5-yl)-N-{(1S)-2-(1,3-dioxo-1,3-dihydro-2H-isoindol-2-yl)-1-[(3-fluorophenyl)methyl]ethyl}-5-methyl-2-thiophenecarboxamide (171 mg, 0.29 mmol) in Tetrahydrofuran (THF) (3 mL) and Methanol (1 mL). Hydrazine (66 µL, 2.10 mmol) was added and the reaction stirred overnight at room temperature. The mixture was adsorbed onto silica gel and purified by column chromatography (95:5:0.5 CHCl₃/MeOH/NH₄OH).

The neutral compound was dissolved in MeOH (2 mL), treated with excess 2M HCl in Et₂O and concentrated affording the HCl salt of the title compound (123 mg, 0.26 mmol, 88%): LC-MS (ES) m/z=453 (M+H)⁺, ¹H NMR (400 MHz, DMSO-d₆) δ ppm 2.33 (s, 3H) 2.91-3.03 (m, 4H) 3.72 (s, 3H) 4.31-4.41 (m, 1H) 7.02 (td, J=8.46, 2.02 Hz, 1H) 7.12 (d, J=7.33 Hz, 2H) 7.27-7.35 (m, 1H) 7.64-7.71 (m, 1H) 7.92 (s, 1H) 8.14 (s, 3H) 8.79-8.93 (m, 1H).

Example 163

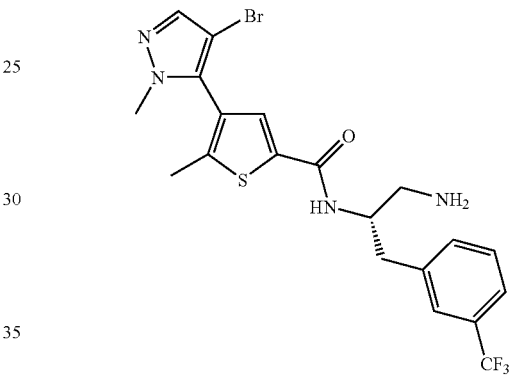

Preparation of N-((1S)-2-amino-1-{[3-(trifluoromethyl)phenyl]methyl}ethyl)-4-(4-bromo-1-methyl-1H-pyrazol-5-yl)-5-methyl-2-thiophenecarboxamide a) 4-(4-bromo-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-methyl-2-thiophenecarboxamide

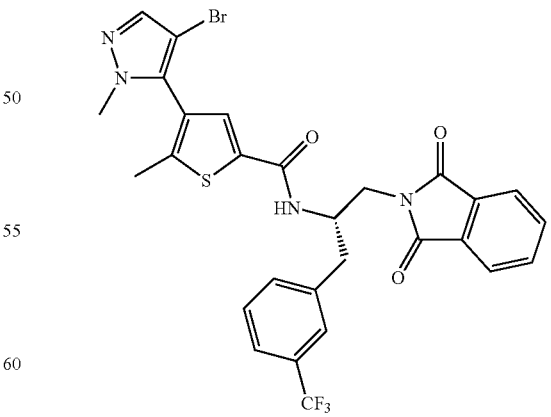

To a 50 mL round-bottomed flask was added 4-(4-bromo-1-methyl-1H-pyrazol-5-yl)-5-methyl-2-thiophenecarboxylic acid (180 mg, 0.60 mmol) [prepared according to the procedure of Example 159], 2-{(2S)-2-amino-3-[3-(trifluoromethyl)phenyl]propyl}-1H-isoindole-1,3(2H)-dione (203 mg, 0.58 mmol) [prepared according to the procedure of Preparation 6 except substituting N-{[(1,1-dimethylethyl)oxy]carbonyl}-3-(trifluoromethyl)-L-phenylalanine (4.98 g, 15.0 mmol) for N-{[(1,1-dimethylethyl)oxy]carbonyl}-2-(trifluoromethyl)-L-phenylalanine] and PyBrop (340 mg, 0.72 mmol) in Chloroform (6 mL). DIEA (530 µL, 3.03 mmol) was added and the reaction stirred overnight at room temperature. The mixture was adsorbed onto silica and purified via column chromatography (25-70% EtOAc/Hex) affording the title compound (259 mg, 0.41 mmol, 69%): LC-MS (ES) m/z=633 (M+H)$^+$.

b) N-((1S)-2-amino-1-{[3-(trifluoromethyl)phenyl]methyl}ethyl)-4-(4-bromo-1-methyl-1H-pyrazol-5-yl)-5-methyl-2-thiophenecarboxamide To a 50 mL round-bottomed flask was added 4-(4-bromo-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-methyl-2-thiophenecarboxamide (259 mg, 0.41 mmol) in Tetrahydrofuran (THF) (3 mL) and Methanol (1 mL). Hydrazine (90 µL, 2.87 mmol) was added and the reaction stirred overnight at room temperature. The mixture was adsorbed onto silica gel and purified via column chromatography (95:5:0.5 CHCl$_3$/MeOH/NH$_4$OH).

The neutral compound was dissolved in MeOH (2 mL), treated with excess 2M HCl in Et$_2$O and concentrated affording the HCl salt of the title compound (172 mg, 0.33 mmol, 80%): LC-MS (ES) m/z=503 (M+H)$^+$, $^1$H NMR (400 MHz, DMSO-d$_6$) δ ppm 2.32 (s, 3H) 3.03 (d, J=6.06 Hz, 4H) 3.71 (d, J=5.81 Hz, 3H) 4.31-4.41 (m, 1H) 7.49-7.56 (m, 2H) 7.60 (d, J=6.82 Hz, 1H) 7.64-7.71 (m, 2H) 7.93 (d, J=12.88 Hz, 1H) 8.18 (s, 3H) 8.88-8.99 (m, 1H).

Example 164

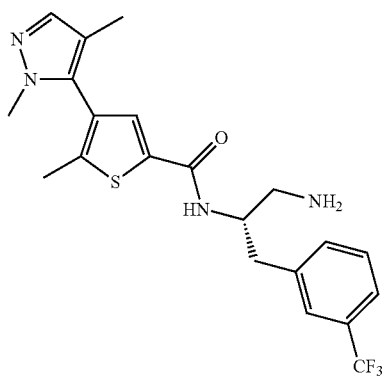 [SMILES: Cc1cnn(C)c1-c1cc(C(=O)N[C@H](CN)Cc2cccc(C(F)(F)F)c2)sc1C]

Preparation of N-((1S)-2-amino-1-{[3-(trifluoromethyl)phenyl]methyl}ethyl)-4-(1,4-dimethyl-1H-pyrazol-5-yl)-5-methyl-2-thiophenecarboxamide a) methyl 4-(4-bromo-1-methyl-1H-pyrazol-5-yl)-5-methyl-2-thiophenecarboxylate

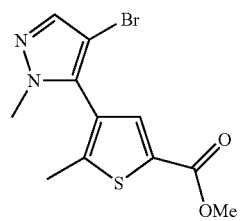 [SMILES: COC(=O)c1cc(-c2c(Br)cnn2C)c(C)s1]

NBS (2.03 g, 11.41 mmol) was added in portions to a 75 mL sealed tube reactor containing methyl 5-methyl-4-(1-methyl-1H-pyrazol-5-yl)-2-thiophenecarboxylate (2.1 g, 8.89 mmol) [prepared according to the procedure of Preparation 10] in Tetrahydrofuran (THF) (40 ml) at room temperature. The mixture was heated to 70° C. for 1 hour. The reaction mixture was partitioned between CHCl$_3$ and H$_2$O, the organic layer dried with Na$_2$SO$_4$, the reaction mixture adsorbed onto silica and purified via column chromatography (15-40% EtOAc/Hex) affording the title compound (2.57 g, 8.15 mmol, 92%): LC-MS (ES) m/z=316 (M+H)$^+$.

b) methyl 4-(1,4-dimethyl-1H-pyrazol-5-yl)-5-methyl-2-thiophenecarboxylate

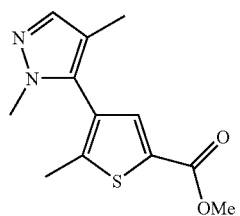 [SMILES: COC(=O)c1cc(-c2c(C)cnn2C)c(C)s1]

To a 350 mL sealed flask reactor was added methyl 4-(4-bromo-1-methyl-1H-pyrazol-5-yl)-5-methyl-2-thiophenecarboxylate (2.57 g, 8.15 mmol), trimethylboroxine (2.27 ml, 16.31 mmol), K$_2$CO$_3$ (3.47 g, 25.1 mmol) and Pd(dppf)Cl$_2$ (426 mg, 0.83 mmol) in N,N-Dimethylformamide (DMF) (41 ml). The reaction was heated at 110° C. for 1 hour. The mixture was partitioned between CHCl$_3$/H$_2$O, organic layer separated and dried with Na$_2$SO$_4$. The resulting material was adsorbed onto silica and purified via column chromatography (0-15% EtOAc/Hexane) affording the title compound (1.3 g, 4.76 mmol, 58%): LC-MS (ES) m/z=251 (M+H)$^+$.

c) 4-(1,4-dimethyl-1H-pyrazol-5-yl)-5-methyl-2-thiophenecarboxylic Acid

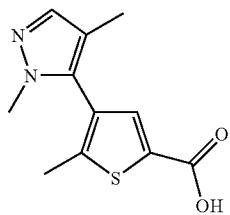 [SMILES: Cc1cnn(C)c1-c1cc(C(=O)O)sc1C]

To a 100 mL round-bottomed flask was added methyl 4-(1,4-dimethyl-1H-pyrazol-5-yl)-5-methyl-2-thiophenecarboxylate (1.31 g, 5.23 mmol) in Tetrahydrofuran (THF) (25 mL). 6N NaOH (30 mL, 180 mmol) was added slowly and the reaction stirred at 70° C. overnight. The reaction was cooled to room temperature, partitioned between CHCl$_3$ and H$_2$O and the pH of the aqueous layer adjusted to pH 3 by the addition of 6N HCl. The layers were separated, the organic layer was dried with Na$_2$SO$_4$ and the solvent was removed affording the title compound (1.3 g, 5.5 mmol, quant.) which was used without further purification: LC-MS (ES) m/z=237 (M+H)$^+$.

d) 4-(1,4-dimethyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-methyl-2-thiophenecarboxamide

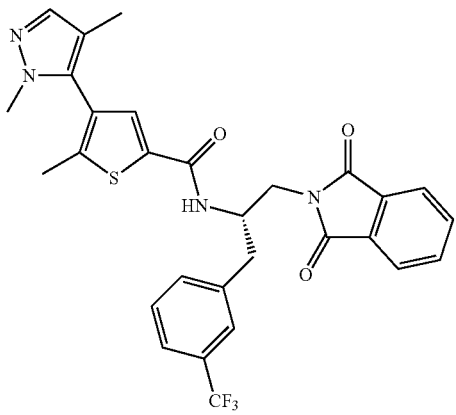

To a 50 mL round-bottomed flask was added 4-(1,4-dimethyl-1H-pyrazol-5-yl)-5-methyl-2-thiophenecarboxylic acid (170 mg, 0.68 mmol), 2-{(2S)-2-amino-3-[3-(trifluoromethyl)phenyl]propyl}-1H-isoindole-1,3(2H)-dione (256 mg, 0.67 mmol) [prepared according to the procedure of Preparation 6 except substituting N-{[(1,1-dimethylethyl)oxy]carbonyl}-3-(trifluoromethyl)-L-phenylalanine (4.98 g, 15.0 mmol) for N-{[(1,1-dimethylethyl)oxy]carbonyl}-2-(trifluoromethyl)-L-phenylalanine] and PyBrop (387 mg, 0.83 mmol) in chloroform (7 mL). DIEA (600 µL, 3.44 mmol) was added and the reaction stirred overnight at room temperature. The mixture was adsorbed onto silica and purified via column chromatography (25-70% EtOAc/Hex) affording the title compound (311 mg, 0.55 mmol, 80%): LC-MS (ES) m/z=567 (M+H)⁺.

e) N-((1S)-2-amino-1-{[3-(trifluoromethyl)phenyl]methyl}ethyl)-4-(1,4-dimethyl-1H-pyrazol-5-yl)-5-methyl-2-thiophenecarboxamide To a 50 mL round-bottomed flask was added 4-(1,4-dimethyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-methyl-2-thiophenecarboxamide (311 mg, 0.55 mmol) in Tetrahydrofuran (THF) (4 mL) and Methanol (1.4 mL). Hydrazine (122 µL, 3.89 mmol) was added and the reaction stirred overnight at room temperature. The mixture was adsorbed onto silica gel and purified via column chromatography (95:5:0.5 CHCl₃/MeOH/NH₄OH).

The neutral compound was dissolved in MeOH (2 mL), treated with excess 2M HCl in Et₂O and concentrated affording the HCl salt of the title compound (234 mg, 0.44 mmol, 79%): LC-MS (ES) m/z=437 (M+H)⁺, ¹H NMR (400 MHz, DMSO-d₆) δ ppm 1.87 (s, 3H) 2.26 (s, 3H) 3.03 (d, J=6.82 Hz, 4H) 3.62 (s, 3H) 4.31-4.41 (m, 1H) 7.38 (s, 1H) 7.49-7.56 (m, 2H) 7.58-7.61 (m, 1H) 7.65 (s, 1H) 7.87 (s, 1H) 8.20 (s, 3H) 8.89 (d, J=8.59 Hz, 1H).

Example 165

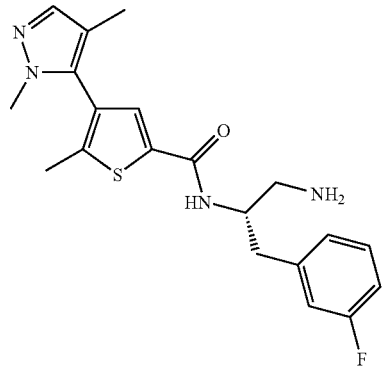 [SMILES: Cc1cnn(C)c1-c1cc(C(=O)N[C@H](CN)Cc2cccc(F)c2)sc1C]

Preparation of N-{(1S)-2-amino-1-[(3-fluorophenyl)methyl]ethyl}-4-(1,4-dimethyl-1H-pyrazol-5-yl)-5-methyl-2-thiophenecarboxamide a) 4-(1,4-dimethyl-1H-pyrazol-5-yl)-N-{(1S)-2-(1,3-dioxo-1,3-dihydro-2H-isoindol-2-yl)-1-[(3-fluorophenyl)methyl]ethyl}-5-methyl-2-thiophenecarboxamide

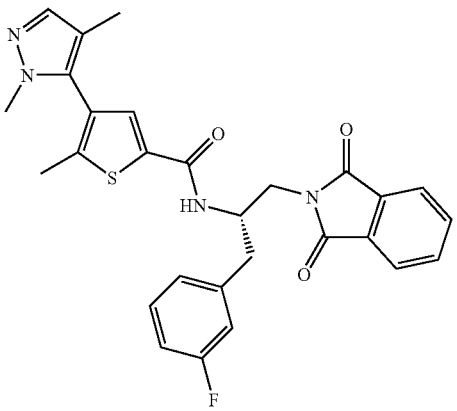 [SMILES: Cc1cnn(C)c1-c1cc(C(=O)N[C@@H](Cc2cccc(F)c2)CN2C(=O)c3ccccc3C2=O)sc1C]

To a 50 mL round-bottomed flask was added 4-(1,4-dimethyl-1H-pyrazol-5-yl)-5-methyl-2-thiophenecarboxylic acid (207 mg, 0.83 mmol) [prepared according to the procedure of Example 164], 2-[(2S)-2-amino-3-(3-fluorophenyl)propyl]-1H-isoindole-1,3(2H)-dione (279 mg, 0.83 mmol) [Prepared according to the procedure of Preparation 6 except substituting N-{[(1,1-dimethylethyl)oxy]carbonyl}-3-fluoro-L-phenylalanine (5.03 g, 17.8 mmol) for N-{[(1,1-dimethylethyl)oxy]carbonyl}-2-(trifluoromethyl)-L-phenylalanine] and PyBrop (469 mg, 1.00 mmol) in chloroform (8 mL). DIEA (730 µL, 4.18 mmol) was added and the reaction stirred overnight at room temperature. The mixture was adsorbed onto silica and purified via column chromatography (25-70% EtOAc/Hex) affording the title compound (209 mg, 0.36 mmol, 43%): LC-MS (ES) m/z=517 (M+H)⁺.

b) N-{(1S)-2-amino-1-[(3-fluorophenyl)methyl]ethyl}-4-(1,4-dimethyl-1H-pyrazol-5-yl)-5-methyl-2-thiophenecarboxamide To a 50 mL round-bottomed flask was added 4-(1,4-dimethyl-1H-pyrazol-5-yl)-N-{(1S)-2-(1,3-dioxo-1,3-dihydro- 2H-isoindol-2-yl)-1-[(3-fluorophenyl)methyl]ethyl}-5-methyl-2-thiophenecarboxamide (201 mg, 0.39 mmol) in Tetrahydrofuran (THF) (4 mL) and Methanol (1 mL). Hydrazine (86 µL, 2.74 mmol) was added and the reaction stirred overnight at room temperature. The mixture was adsorbed onto silica gel and purified via column chromatography (95:5:0.5 CHCl$_3$/MeOH/NH$_4$OH).

The neutral compound was dissolved in MeOH (2 mL), treated with excess 2M HCl in Et$_2$O and concentrated affording the HCl salt of the title compound (163 mg, 0.34 mmol, 87%): LC-MS (ES) m/z=387 (M+H)$^+$, $^1$H NMR (400 MHz, DMSO-d$_6$) δ ppm 1.88 (s, 3H) 2.27 (s, 3H) 2.87-3.09 (m, 4H) 3.17 3.63 (s, 3H) 4.28-4.45 (m, 1H) 6.97-7.06 (m, 1H) 7.13 (t, J=7.20 Hz, 2H) 7.27-7.35 (m, 1H) 7.38 (s, 1H) 7.89 (s, 1H) 8.20 (s, 3H) 8.88 (d, J=7.58 Hz, 1H).

Example 166

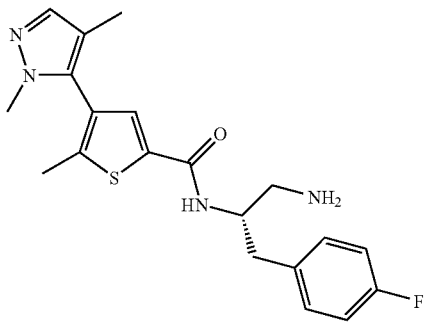 [SMILES: Cc1cnn(C)c1-c1cc(C(=O)N[C@H](CN)Cc2ccc(F)cc2)sc1C]

Preparation of N-{(1S)-2-amino-1-[(4-fluorophenyl)methyl]ethyl}-4-(1,4-dimethyl-1H-pyrazol-5-yl)-5-methyl-2-thiophenecarboxamide a) 4-(1,4-dimethyl-1H-pyrazol-5-yl)-N-{(1S)-2-(1,3-dioxo-1,3-dihydro-2H-isoindol-2-yl)-1-[(4-fluorophenyl)methyl]ethyl}-5-methyl-2-thiophenecarboxamide

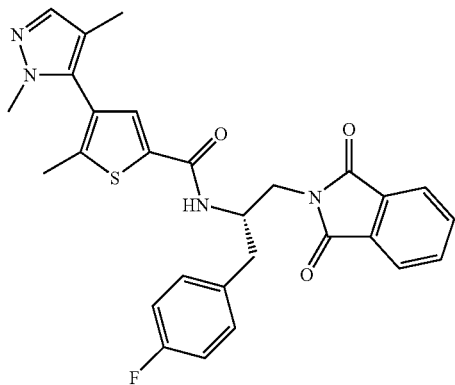 [SMILES: Cc1cnn(C)c1-c1cc(C(=O)N[C@@H](Cc2ccc(F)cc2)CN2C(=O)c3ccccc3C2=O)sc1C]

To a 50 mL round-bottomed flask was added 4-(1,4-dimethyl-1H-pyrazol-5-yl)-5-methyl-2-thiophenecarboxylic acid (253 mg, 1.02 mmol) [prepared according to the procedure of Example 164], 2-[(2S)-2-amino-3-(4-fluorophenyl)propyl]-1H-isoindole-1,3(2H)-dione (335 mg, 1.00 mmol) [prepared according to the procedure of Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (574 mg, 1.23 mmol) in chloroform (10 mL). DIEA (930 µL, 5.32 mmol) was added and the reaction stirred overnight at room temperature. The mixture was adsorbed onto silica and purified via column chromatography (25-70% EtOAc/Hex) affording the title compound (132 mg, 0.25 mmol, 24%): LC-MS (ES) m/z=517 (M+H)$^+$.

b) N-{(1S)-2-amino-1-[(4-fluorophenyl)methyl]ethyl}-4-(1,4-dimethyl-1H-pyrazol-5-yl)-5-methyl-2-thiophenecarboxamide To a 50 mL round-bottomed flask was added 4-(1,4-dimethyl-1H-pyrazol-5-yl)-N-{(1S)-2-(1,3-dioxo-1,3-dihydro-2H-isoindol-2-yl)-1-[(4-fluorophenyl)methyl]ethyl}-5-methyl-2-thiophenecarboxamide (132 mg, 0.26 mmol) in Tetrahydrofuran (THF) (2 mL) and Methanol (1 mL). Hydrazine (57 µL, 1.82 mmol) was added and the reaction stirred overnight at room temperature. The mixture was adsorbed onto silica gel and purified via column chromatography (95:5:0.5 CHCl$_3$/MeOH/NH$_4$OH).

The neutral compound was dissolved in MeOH (2 mL), treated with excess 2M HCl in Et$_2$O and concentrated affording the HCl salt of the title compound (104 mg, 0.22 mmol, 84%): LC-MS (ES) m/z=387 (M+H)$^+$, $^1$H NMR (400 MHz, DMSO-d$_6$) δ ppm 1.88 (s, 3H) 2.27 (s, 3H) 2.84-3.11 (m, 4H) 3.63 (s, 3H) 4.24-4.39 (m, 1H) 7.10 (t, J=8.72 Hz, 2H) 7.31 (dd, J=8.21, 5.68 Hz, 2H) 7.38 (s, 1H) 7.87 (s, 1H) 8.18 (s, 3H) 8.83 (s, 1H).

Example 167

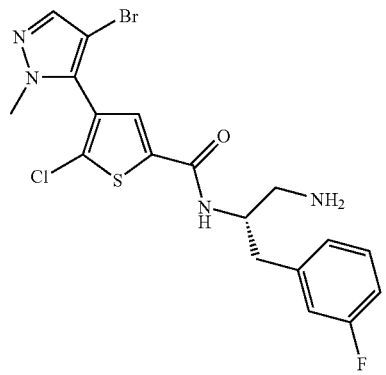 [SMILES: Cn1ncc(Br)c1-c1cc(C(=O)N[C@H](CN)Cc2cccc(F)c2)sc1Cl]

Preparation of N-{(1S)-2-amino-1-[(3-fluorophenyl)methyl]ethyl}-4-(4-bromo-1-methyl-1H-pyrazol-5-yl)-5-chloro-2-thiophenecarboxamide a) 4-(4-bromo-1-methyl-1H-pyrazol-5-yl)-5-chloro-2-thiophenecarboxylic Acid

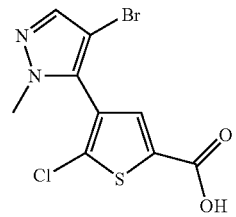 [SMILES: Cn1ncc(Br)c1-c1cc(C(=O)O)sc1Cl]

NBS (1.243 g, 6.98 mmol) was added in portions to a 150 mL sealed tube reactor containing methyl 5-chloro-4-(1-methyl-1H-pyrazol-5-yl)-2-thiophenecarboxylate (1.47 g, 5.73 mmol) [Prepared according to the procedure of Example 151]

in Tetrahydrofuran (THF) (40 ml) at room temperature. The mixture was heated to 70° C. for 1 h. 6N NaOH (20 ml, 120 mmol) was then added and the mixture stirred at 70° C. for an additional 2 h. The mixture was partitioned between CHCl₃ and H₂O, the organic layer dried with Na₂SO₄ and concentrated affording the title compound which was used without further purification (385 mg, 1.4 mmol, 30%): LC-MS (ES) m/z=302 (M+H)⁺.

b) 4-(4-bromo-1-methyl-1H-pyrazol-5-yl)-5-chloro-N-{(1S)-2-(1,3-dioxo-1,3-dihydro-2H-isoindol-2-yl)-1-[(3-fluorophenyl)methyl]ethyl}-2-thiophenecarboxamide

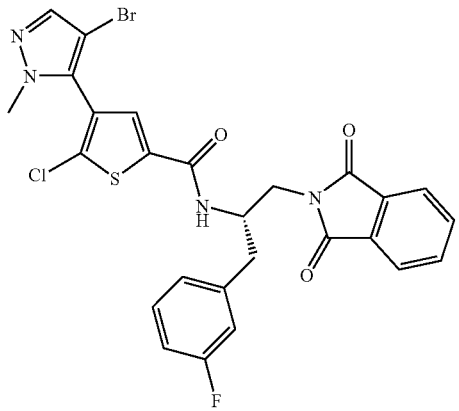 [SMILES: Cn1ncc(Br)c1-c1cc(C(=O)N[C@@H](Cc2cccc(F)c2)CN2C(=O)c3ccccc3C2=O)sc1Cl]

To a 50 mL round-bottomed flask was added 4-(4-bromo-1-methyl-1H-pyrazol-5-yl)-5-chloro-2-thiophenecarboxylic acid (204 mg, 0.60 mmol), 2-[(2S)-2-amino-3-(3-fluorophenyl)propyl]-1H-isoindole-1,3(2H)-dione (215 mg, 0.64 mmol) [prepared according to the procedure of Preparation 6 except substituting N-{[(1,1-dimethylethyl)oxy]carbonyl}-3-fluoro-L-phenylalanine (5.03 g, 17.7 mmol) for N-{[(1,1-dimethylethyl)oxy]carbonyl}-2-(trifluoromethyl)-L-phenylalanine] and PyBrop (380 mg, 0.81 mmol) in chloroform (6 mL). DIEA (570 µL, 3.26 mmol) was added and the reaction stirred overnight at room temperature. The mixture was adsorbed onto silica and purified via column chromatography (25-70% EtOAc/Hex) affording the title compound (247 mg, 45%): LC-MS (ES) m/z=603 (M+H)⁺.

c) N-{(1S)-2-amino-1-[(3-fluorophenyl)methyl]ethyl}-4-(4-bromo-1-methyl-1H-pyrazol-5-yl)-5-chloro-2-thiophenecarboxamide To a 50 mL round-bottomed flask was added 4-(4-bromo-1-methyl-1H-pyrazol-5-yl)-5-chloro-N-{(1S)-2-(1,3-dioxo-1,3-dihydro-2H-isoindol-2-yl)-1-[(3-fluorophenyl)methyl]ethyl}-2-thiophenecarboxamide (133 mg, 0.22 mmol) in Tetrahydrofuran (THF) (3 mL) and Methanol (1.2 mL). Hydrazine (50 µL, 1.59 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (145 mg, 0.30 mmol, 66% yield): LC-MS (ES) m/z=473 (M+H)⁺, ¹H NMR (400 MHz, DMSO-d₆) δ ppm 2.91-3.03 (m, 4H) 3.77 (s, 3H) 4.30-4.41 (m, 1H) 7.04 (td, J=8.53, 2.15 Hz, 1H) 7.12 (d, J=7.07 Hz, 2H) 7.28-7.36 (m, 1H) 7.74 (s, 1H) 8.02-8.14 (m, 4H) 9.06 (s, 1H).

Example 168

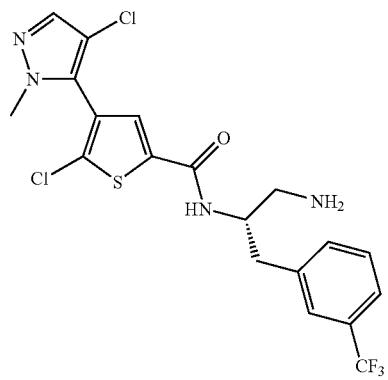 [SMILES: Cn1ncc(Cl)c1-c1cc(C(=O)N[C@H](CN)Cc2cccc(C(F)(F)F)c2)sc1Cl]

Preparation of N-((1S)-2-amino-1-{[3-(trifluoromethyl)phenyl]methyl}ethyl)-5-chloro-4-(4-chloro-1-methyl-1H-pyrazol-5-yl)-2-thiophenecarboxamide a) 5-chloro-4-(4-chloro-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-2-thiophenecarboxamide

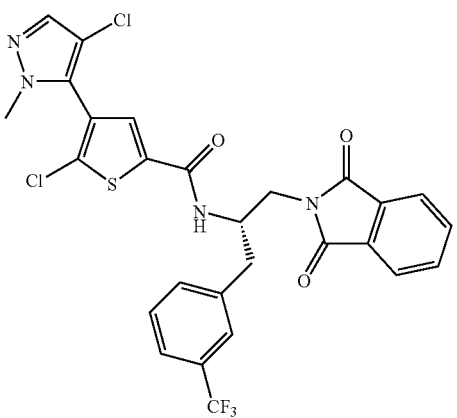 [SMILES: Cn1ncc(Cl)c1-c1cc(C(=O)N[C@@H](Cc2cccc(C(F)(F)F)c2)CN2C(=O)c3ccccc3C2=O)sc1Cl]

To a 50 mL round-bottomed flask was added 5-chloro-4-(4-chloro-1-methyl-1H-pyrazol-5-yl)-2-thiophenecarboxylic acid (264 mg, 0.95 mmol) [prepared according to the procedure of Example 96], 2-{(2S)-2-amino-3-[3-(trifluoromethyl)phenyl]propyl}-1H-isoindole-1,3(2H)-dione (306 mg, 0.80 mmol) [prepared according to the procedure of Preparation 6 except substituting N-{[(1,1-dimethylethyl)oxy]carbonyl}-3-(trifluoromethyl)-L-phenylalanine (4.98 g, 15.0 mmol) for N-{[(1,1-dimethylethyl)oxy]carbonyl}-2-(trifluoromethyl)-L-phenylalanine] and PyBrop (450 mg, 0.96 mmol) in chloroform (7 mL). DIEA (660 µl, 3.78 mmol) was added and the reaction stirred overnight at room temperature. The mixture was adsorbed onto silica and purified via column chromatography (25-70% EtOAc/Hex) affording the title compound (303 mg, 0.44 mmol, 56%): LC-MS (ES) m/z=607 (M+H)⁺.

b) N-((1S)-2-amino-1-{[3-(trifluoromethyl)phenyl]methyl}ethyl)-5-chloro-4-(4-chloro-1-methyl-1H-pyrazol-5-yl)-2-thiophenecarboxamide To a 50 mL round-bottomed flask was added 5-chloro-4-(4-chloro-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-2-thiophenecarboxamide (303 mg, 0.50 mmol) in Tetrahydrofuran (THF) (4 mL) and Methanol (1.5 mL). Hydrazine (120 µL, 3.82 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (177 mg, 0.31 mmol, 61% yield): LC-MS (ES) m/z=479 (M+H)$^+$, $^1$H NMR (400 MHz, DMSO-d₆) δ ppm 2.97-3.08 (m, 4H) 3.76 (s, 3H) 4.28-4.44 (m, 1H) 7.50-7.61 (m, 3H) 7.66 (s, 1H) 7.71-7.75 (m, 1H) 8.10 (s, 4H) 9.16 (d, J=8.59 Hz, 1H).

Example 169

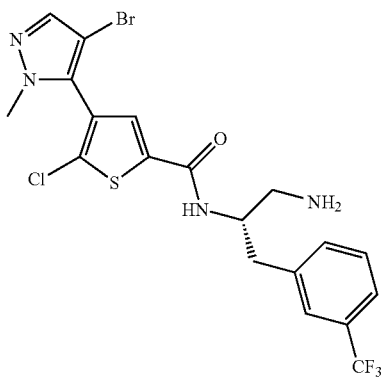

Preparation of N-((1S)-2-amino-1-{[3-(trifluoromethyl)phenyl]methyl}ethyl)-4-(4-bromo-1-methyl-1H-pyrazol-5-yl)-5-chloro-2-thiophenecarboxamide a) 4-(4-bromo-1-methyl-1H-pyrazol-5-yl)-5-chloro-N-((1S)-2-(1,3-dioxo-1,3-dihydro-2H-isoindol-2-yl)-1-{[3-(trifluoromethyl)phenyl]methyl}ethyl)-2-thiophenecarboxamide

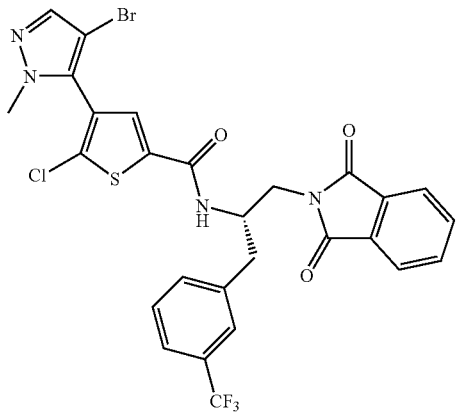

To a 50 mL round-bottomed flask was added 4-(4-bromo-1-methyl-1H-pyrazol-5-yl)-5-chloro-2-thiophenecarboxylic acid (183 mg, 0.54 mmol) [prepared according to the procedure of Example 167], 2-{(2S)-2-amino-3-[3-(trifluoromethyl)phenyl]propyl}-1H-isoindole-1,3(2H)-dione (201 mg, 0.52 mmol) [prepared according to the procedure of Preparation 6 except substituting N-{[(1,1-dimethylethyl)oxy]carbonyl}-3-(trifluoromethyl)-L-phenylalanine (4.98 g, 15.0 mmol) for N-{[(1,1-dimethylethyl)oxy]carbonyl}-2-(trifluoromethyl)-L-phenylalanine] and PyBrop (298 mg, 0.64 mmol) in chloroform (5 mL). DIEA (470 µL, 2.69 mmol) was added and the reaction stirred overnight at room temperature. The mixture was adsorbed onto silica and purified via column chromatography (25-70% EtOAc/Hex) affording the title compound (246 mg, 0.36 mmol, 69%): LC-MS (ES) m/z=653 (M+H)$^+$.

d) N-((1S)-2-amino-1-{[3-(trifluoromethyl)phenyl]methyl}ethyl)-4-(4-bromo-1-methyl-1H-pyrazol-5-yl)-5-chloro-2-thiophenecarboxamide To a 50 mL round-bottomed flask was added 4-(4-bromo-1-methyl-1H-pyrazol-5-yl)-5-chloro-N-((1S)-2-(1,3-dioxo-1,3-dihydro-2H-isoindol-2-yl)-1-{[3-(trifluoromethyl)phenyl]methyl}ethyl)-2-thiophenecarboxamide (246 mg, 0.38 mmol) in Tetrahydrofuran (THF) (4 mL) and Methanol (1 mL). Hydrazine (0.083 mL, 2.64 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (134 mg, 0.22 mmol, 57% yield): LC-MS (ES) m/z=523 (M+H)$^+$, $^1$H NMR (400 MHz, DMSO-d₆) δ ppm 3.04 (d, J=4.55 Hz, 4H) 3.76 (s, 3H) 4.29-443 (m, 1H) 7.50-7.61 (m, 3H) 7.66 (s, 1H) 7.70-7.75 (m, 1H) 8.06-8.18 (m, 4H) 9.17 (s, 1H).

Example 170

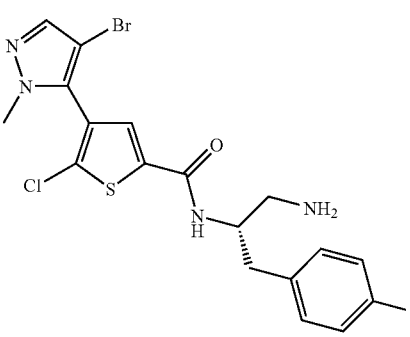

Preparation of N-{(1S)-2-amino-1-[(4-fluorophenyl)methyl]ethyl}-4-(4-bromo-1-methyl-1H-pyrazol-5-yl)-5-chloro-2-thiophenecarboxamide a) 4-(4-bromo-1-methyl-1H-pyrazol-5-yl)-5-chloro-N-{(1S)-2-(1,3-dioxo-1,3-dihydro-2H-isoindol-2-yl)-1-[(4-fluorophenyl)methyl]ethyl}-2-thiophenecarboxamide

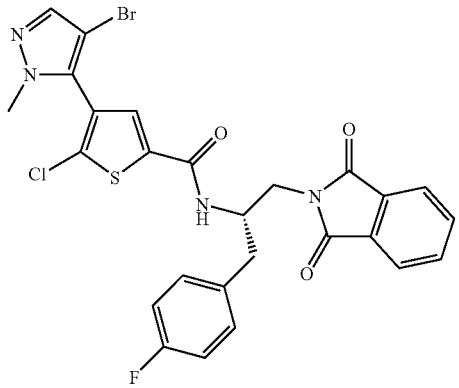

To a 50 mL round-bottomed flask was added 4-(4-bromo-1-methyl-1H-pyrazol-5-yl)-5-chloro-2-thiophenecarboxylic acid (340 mg, 1.00 mmol) [prepared according to the procedure of Example 167], 2-[(2S)-2-amino-3-(4-fluorophenyl)propyl]-1H-isoindole-1,3(2H)-dione (374 mg, 1.12 mmol) [prepared according to the procedure of Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (626 mg, 1.34 mmol) in chloroform (10 mL). DIEA (980 µL, 5.61 mmol) was added and the reaction stirred overnight at room temperature. The mixture was adsorbed onto silica and purified via column chromatography (25-70% EtOAc/Hex) affording the title compound (229 mg, 0.35 mmol, 31%): LC-MS (ES) m/z=603 (M+H)$^+$.

b) N-{(1S)-2-amino-1-[(4-fluorophenyl)methyl]ethyl}-4-(4-bromo-1-methyl-1H-pyrazol-5-yl)-5-chloro-2-thiophenecarboxamide To a 50 mL round-bottomed flask was added 4-(4-bromo-1-methyl-1H-pyrazol-5-yl)-5-chloro-N-{(1S)-2-(1,3-dioxo-1,3-dihydro-2H-isoindol-2-yl)-1-[(4-fluorophenyl)methyl]ethyl}-2-thiophenecarboxamide (229 mg, 0.38 mmol) in Tetrahydrofuran (THF) (4 mL) and Methanol (1.2 mL). Hydrazine (90 µL, 2.87 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (99 mg, 0.17 mmol, 45% yield): LC-MS (ES) m/z=473 (M+H)$^+$, $^1$H NMR (400 MHz, DMSO-d$_6$) δ ppm 2.90 (d, J=6.82 Hz, 2H) 2.95-3.06 (m, 2H) 3.77 (s, 3H) 4.27-4.39 (m, 1H) 7.11 (t, J=8.72 Hz, 2H) 7.26-7.35 (m, 2H) 7.74 (s, 1H) 8.01-8.21 (m, 4H) 9.06 (s, 1H).

Example 171

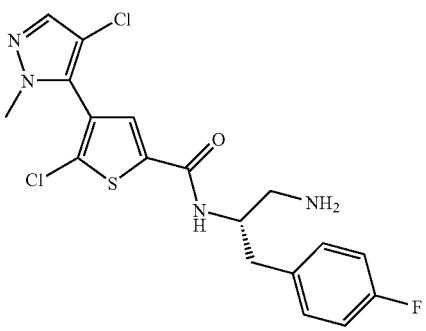 [SMILES: Cn1ncc(Br)c1-c1cc(C(=O)N[C@H](CN)Cc2ccc(F)cc2)sc1Cl]

Preparation of N-{(1S)-2-amino-1-[(4-fluorophenyl)methyl]ethyl}-5-chloro-4-(4-chloro-1-methyl-1H-pyrazol-5-yl)-2-thiophenecarboxamide a) 5-chloro-4-(4-chloro-1-methyl-1H-pyrazol-5-yl)-N-{(1S)-2-(1,3-dioxo-1,3-dihydro-2H-isoindol-2-yl)-1-[(4-fluorophenyl)methyl]ethyl}-2-thiophenecarboxamide

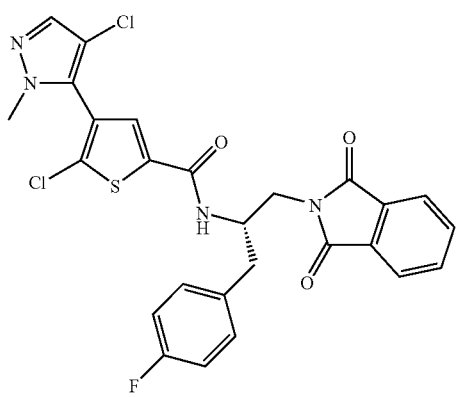 [SMILES: Cn1ncc(Cl)c1-c1cc(C(=O)N[C@@H](Cc2ccc(F)cc2)CN2C(=O)c3ccccc3C2=O)sc1Cl]

To a 50 mL round-bottomed flask was added 5-chloro-4-(4-chloro-1-methyl-1H-pyrazol-5-yl)-2-thiophenecarboxylic acid (320 mg, 1.16 mmol) [prepared according to the procedure of Example 168], 2-[(2S)-2-amino-3-(4-fluorophenyl)propyl]-1H-isoindole-1,3(2H)-dione (318 mg, 0.95 mmol) [prepared according to the procedure of Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (535 mg, 1.14 mmol) in Chloroform (9.5 mL). DIEA (840 µl, 4.81 mmol) was added and the reaction stirred overnight at room temperature. The mixture was adsorbed onto silica and purified via column chromatography (25-70% EtOAc/Hex) affording the title compound (106 mg, 0.16 mmol, 17%): LC-MS (ES) m/z=557 (M+H)$^+$.

b) N-{(1S)-2-amino-1-[(4-fluorophenyl)methyl]ethyl}-5-chloro-4-(4-chloro-1-methyl-1H-pyrazol-5-yl)-2-thiophenecarboxamide To a 50 mL round-bottomed flask was added 5-chloro-4-(4-chloro-1-methyl-1H-pyrazol-5-yl)-N-{(1S)-2-(1,3-dioxo-1,3-dihydro-2H-isoindol-2-yl)-1-[(4-fluorophenyl)methyl]ethyl}-2-thiophenecarboxamide (106 mg, 0.19 mmol) in Tetrahydrofuran (THF) (3 mL) and Methanol (1.5 mL). Hydrazine (45 µL, 1.43 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (65 mg, 0.12 mmol, 65% yield): LC-MS (ES) m/z=429 (M+H)$^+$, $^1$H NMR (400 MHz, DMSO-d$_6$) δ ppm 2.82-3.10 (m, 4H) 3.77 (s, 3H) 4.27-4.38 (m, 1H) 7.11 (t, J=8.72 Hz, 2H) 7.26-7.35 (m, 2H) 7.68-7.76 (m, 1H) 8.10 (s, 4H) 9.11 (d, J=7.33 Hz, 1H).

Example 172

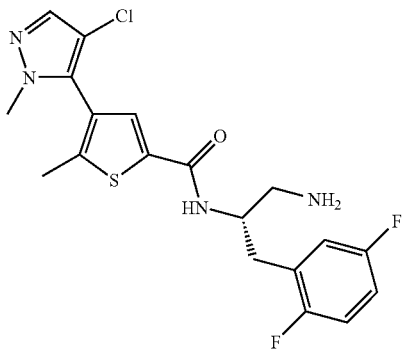 [SMILES: Cc1sc(C(=O)N[C@H](CN)Cc2cc(F)ccc2F)cc1-c1c(Cl)cnn1C]

Preparation of N-{(1S)-2-amino-1-[(2,5-difluorophenyl)methyl]ethyl}-4-(4-chloro-1-methyl-1H-pyrazol-5-yl)-5-methyl-2-thiophenecarboxamide a) 4-(4-chloro-1-methyl-1H-pyrazol-5-yl)-N-{(1S)-2-(2,5-difluorophenyl)-1-[(1,3-dioxo-1,3-dihydro-2H-isoindol-2-yl)methyl]ethyl}-5-methyl-2-thiophenecarboxamide

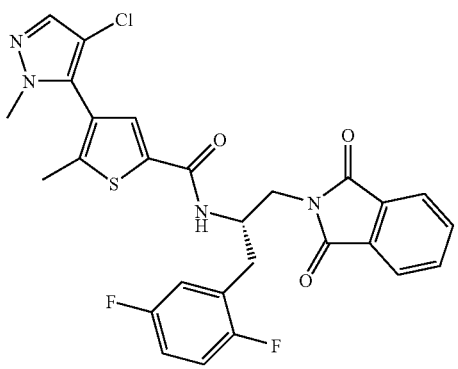 [SMILES: Cc1sc(C(=O)N[C@@H](Cc2cc(F)ccc2F)CN2C(=O)c3ccccc3C2=O)cc1-c1c(Cl)cnn1C]

To a 50 mL round-bottomed flask was added 4-(4-chloro-1-methyl-1H-pyrazol-5-yl)-5-methyl-2-thiophenecarboxylic acid (219 mg, 0.85 mmol) [prepared according to the procedure of Example 158], 2-[(2S)-2-amino-3-(2,5-difluorophenyl)propyl]-1H-isoindole-1,3(2H)-dione (290 mg, 0.82 mmol) [prepared according to the procedure of Preparation 18 except substituting 2,5-difluoro-L-phenylalanine (3.02 g, 15.0 mmol) for 2,6-difluoro-L-phenylalanine] and PyBrop (481 mg, 1.03 mmol) in chloroform (8.5 mL). DIEA (750 µL, 4.29 mmol) was added and the reaction stirred overnight at room temperature. The mixture was adsorbed onto silica and purified via column chromatography (25-70% EtOAc/Hex) affording the title compound (246 mg, 0.44 mmol, 52%): LC-MS (ES) m/z=555 (M+H)$^+$.

b) N-{(1S)-2-amino-1-[(2,5-difluorophenyl)methyl]ethyl}-4-(4-chloro-1-methyl-1H-pyrazol-5-yl)-5-methyl-2-thiophenecarboxamide To a 50 mL round-bottomed flask was added 4-(4-chloro-1-methyl-1H-pyrazol-5-yl)-N-{(1S)-2-(2,5-difluorophenyl)-1-[(1,3-dioxo-1,3-dihydro-2H-isoindol-2-yl)methyl]ethyl}-5-methyl-2-thiophenecarboxamide (246 mg, 0.44 mmol) in Tetrahydrofuran (THF) (4 mL) and Methanol (1 mL). Hydrazine (100 µL, 3.19 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (147 mg, 0.28 mmol, 64% yield): LC-MS (ES) m/z=425 (M+H)$^+$, $^1$H NMR (400 MHz, DMSO-d$_6$) δ ppm 2.34 (s, 3H) 2.93-3.07 (m, 4H) 3.71 (s, 3H) 4.34-4.50 (m, 1H) 7.04-7.14 (m, 1H) 7.19 (td, J=9.03, 4.67 Hz, 2H) 7.69 (s, 1H) 7.93 (s, 1H) 8.14 (s, 3H) 8.87 (d, J=8.59 Hz, 1H).

Example 173

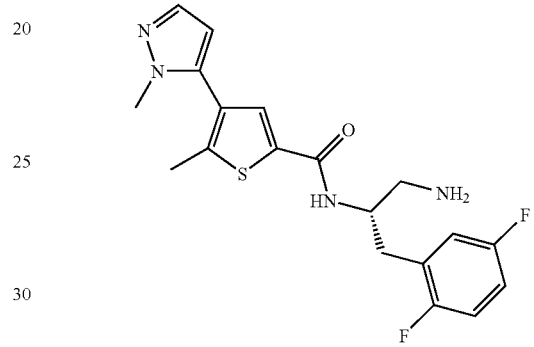

Preparation of N-{(1S)-2-amino-1-[(2,5-difluorophenyl)methyl]ethyl}-5-methyl-4-(1-methyl-1H-pyrazol-5-yl)-2-thiophenecarboxamide a) N-{(1S)-2-(2,5-difluorophenyl)-1-[(1,3-dioxo-1,3-dihydro-2H-isoindol-2-yl)methyl]ethyl}-5-methyl-4-(1-methyl-1H-pyrazol-5-yl)-2-thiophenecarboxamide

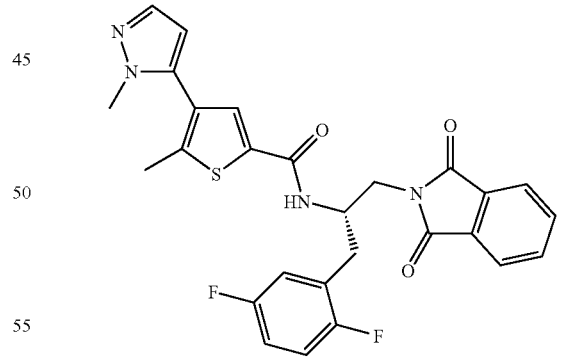

To a 50 mL round-bottomed flask was added 5-methyl-4-(1-methyl-1H-pyrazol-5-yl)-2-thiophenecarboxylic acid (171 mg, 0.77 mmol) [prepared according to the procedure of Example 151], 2-[(2S)-2-amino-3-(2,5-difluorophenyl)propyl]-1H-isoindole-1,3(2H)-dione (270 mg, 0.77 mmol) [prepared according to the procedure of Preparation 18 except substituting 2,5-difluoro-L-phenylalanine (3.02 g, 15.0 mmol) for 2,6-difluoro-L-phenylalanine] and PyBrop (436 mg, 0.93 mmol) in chloroform (7.5 mL). DIEA (680 µL, 3.89 mmol) was added and the reaction stirred overnight at room temperature. The mixture was adsorbed onto silica and purified via column chromatography (25-70% EtOAc/Hex) affording the title compound (246 mg, 0.44 mmol, 52%): LC-MS (ES) m/z=521 (M+H)⁺.

b) N-{(1S)-2-amino-1-[(2,5-difluorophenyl)methyl]ethyl}-5-methyl-4-(1-methyl-1H-pyrazol-5-yl)-2-thiophenecarboxamide To a 50 mL round-bottomed flask was added N-{(1S)-2-(2,5-difluorophenyl)-1-[(1,3-dioxo-1,3-dihydro-2H-isoindol-2-yl)methyl]ethyl}-5-methyl-4-(1-methyl-1H-pyrazol-5-yl)-2-thiophenecarboxamide (243 mg, 0.47 mmol) in Tetrahydrofuran (THF) (4 mL) and Methanol (1 mL). Hydrazine (0.103 mL, 3.27 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (132 mg, 0.27 mmol, 58% yield): LC-MS (ES) m/z=391 (M+H)⁺, ¹H NMR (400 MHz, DMSO-d₆) δ ppm 2.38 (s, 3H) 2.87-3.10 (m, 4H) 3.78 (s, 3H) 4.36-4.47 (m, 1H) 6.35 (d, J=1.77 Hz, 1H) 7.05-7.13 (m, 1H) 7.16-7.28 (m, 2H) 7.52 (d, J=1.52 Hz, 1H) 8.00 (s, 1H) 8.16 (s, 3H) 8.88 (d, J=8.59 Hz, 1H).

Example 174

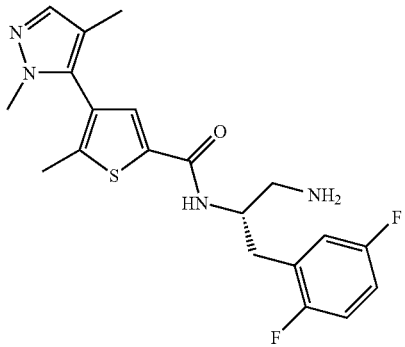 [SMILES: Cc1cnn(C)c1-c1cc(C(=O)N[C@H](CN)Cc2cc(F)ccc2F)sc1C]

Preparation of N-{(1S)-2-amino-1-[(2,5-difluorophenyl)methyl]ethyl}-4-(1,4-dimethyl-1H-pyrazol-5-yl)-5-methyl-2-thiophenecarboxamide a) N-{(1S)-2-(2,5-difluorophenyl)-1-[(1,3-dioxo-1,3-dihydro-2H-isoindol-2-yl)methyl]ethyl}-4-(1,4-dimethyl-1H-pyrazol-5-yl)-5-methyl-2-thiophenecarboxamide

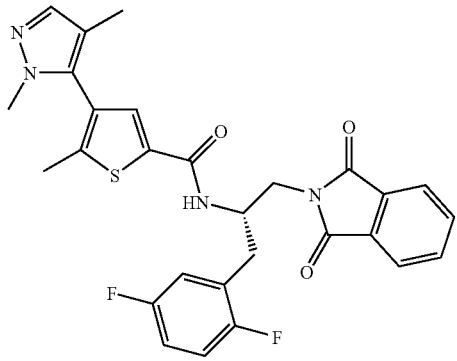 [SMILES: Cc1cnn(C)c1-c1cc(C(=O)N[C@@H](Cc2cc(F)ccc2F)CN2C(=O)c3ccccc3C2=O)sc1C]

To a 50 mL round-bottomed flask was added 4-(1,4-dimethyl-1H-pyrazol-5-yl)-5-methyl-2-thiophenecarboxylic acid (208 mg, 0.88 mmol) [prepared according to the procedure of Example 164], 2-[(2S)-2-amino-3-(2,5-difluorophenyl)propyl]-1H-isoindole-1,3(2H)-dione (288 mg, 0.82 mmol) [prepared according to the procedure of Preparation 18 except substituting 2,5-difluoro-L-phenylalanine (3.02 g, 15.0 mmol) for 2,6-difluoro-L-phenylalanine] and PyBrop (503 mg, 1.07 mmol) in Chloroform (8.5 mL). DIEA (770 μL, 4.41 mmol) was added and the reaction stirred overnight at room temperature. The mixture was adsorbed onto silica and purified via column chromatography (25-70% EtOAc/Hex) affording the title compound (292 mg, 0.55 mmol, 62%): LC-MS (ES) m/z=535 (M+H)⁺.

b) N-{(1S)-2-amino-1-[(2,5-difluorophenyl)methyl]ethyl}-4-(1,4-dimethyl-1H-pyrazol-5-yl)-5-methyl-2-thiophenecarboxamide To a 50 mL round-bottomed flask was added N-{(1S)-2-(2,5-difluorophenyl)-1-[(1,3-dioxo-1,3-dihydro-2H-isoindol-2-yl)methyl]ethyl}-4-(1,4-dimethyl-1H-pyrazol-5-yl)-5-methyl-2-thiophenecarboxamide (292 mg, 0.55 mmol) in Tetrahydrofuran (THF) (5 mL) and Methanol (1 mL) Hydrazine (120 μL, 3.82 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (163 mg, 0.32 mmol, 59% yield): LC-MS (ES) m/z=405 (M+H)⁺, ¹H NMR (400 MHz, DMSO-d₆) δ ppm 1.88 (s, 3H) 2.27 (s, 3H) 2.94-3.06 (m, 4H) 3.63 (s, 3H) 4.35-4.49 (m, 1H) 7.05-7.12 (m, 1H) 7.16-7.27 (m, 2H) 7.38 (s, 1H) 7.86 (s, 1H) 8.16 (s, 3H) 8.83 (d, J=8.84 Hz, 1H).

Example 175

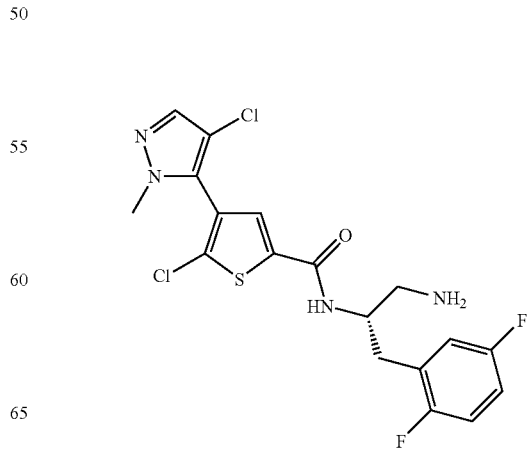

Preparation of N-{(1S)-2-amino-1-[(2,5-difluorophenyl)methyl]ethyl}-5-chloro-4-(4-chloro-1-methyl-1H-pyrazol-5-yl)-2-thiophenecarboxamide a) 5-chloro-4-(4-chloro-1-methyl-1H-pyrazol-5-yl)-N-{(1S)-2-(2,5-difluorophenyl)-1-[(1,3-dioxo-1,3-dihydro-2H-isoindol-2-yl)methyl]ethyl}-2-thiophenecarboxamide

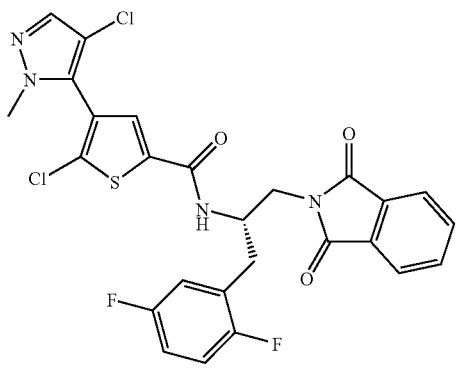 [SMILES: Cn1ncc(Cl)c1-c1cc(C(=O)N[C@@H](Cc2cc(F)ccc2F)CN2C(=O)c3ccccc3C2=O)sc1Cl]

To a 50 mL round-bottomed flask was added 5-chloro-4-(4-chloro-1-methyl-1H-pyrazol-5-yl)-2-thiophenecarboxylic acid (235 mg, 0.85 mmol) [prepared according to the procedure of Example 96], 2-[(2S)-2-amino-3-(2,5-difluorophenyl)propyl]-1H-isoindole-1,3(2H)-dione (290 mg, 0.82 mmol) [prepared according to the procedure of Preparation 18 except substituting 2,5-difluoro-L-phenylalanine (3.02 g, 15.0 mmol) for 2,6-difluoro-L-phenylalanine] and PyBrop (479 mg, 1.02 mmol) in chloroform (8.5 mL). DIEA (742 µL, 4.25 mmol) was added and the reaction stirred overnight at room temperature. The mixture was adsorbed onto silica and purified via column chromatography (25-70% EtOAc/Hex) affording the title compound (174 mg, 0.30 mmol, 36%): LC-MS (ES) m/z=575 (M+H)$^+$.

b) N-{(1S)-2-amino-1-[(2,5-difluorophenyl)methyl]ethyl}-5-chloro-4-(4-chloro-1-methyl-1H-pyrazol-5-yl)-2-thiophenecarboxamide To a 50 mL round-bottomed flask was added 5-chloro-4-(4-chloro-1-methyl-1H-pyrazol-5-yl)-N-{(1S)-2-(2,5-difluorophenyl)-1-[(1,3-dioxo-1,3-dihydro-2H-isoindol-2-yl)methyl]ethyl}-2-thiophenecarboxamide (174 mg, 0.30 mmol) in Tetrahydrofuran (THF) (3.6 mL) and Methanol (1 mL). Hydrazine (70 µL, 2.23 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (115 mg, 0.21 mmol, 70% yield): LC-MS (ES) m/z=445 (M+H)$^+$, $^1$H NMR (400 MHz, DMSO-d$_6$) δ ppm 2.88-3.09 (m, 4H) 3.76 (s, 3H) 4.33-4.48 (m, 1H) 7.06-7.15 (m, 1H) 7.20 (td, J=9.09, 4.55 Hz, 2H) 7.74 (s, 1H) 8.10 (s, 1H) 8.13 (s, 3H) 9.14 (d, J=8.84 Hz, 1H).

Example 176

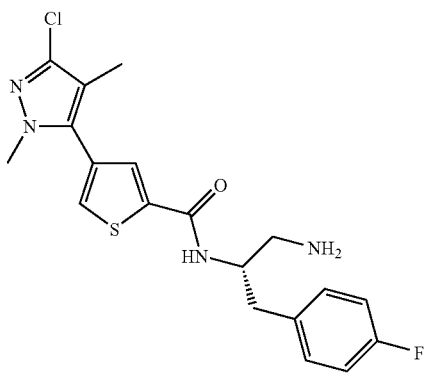 [SMILES: Cc1c(Cl)nn(C)c1-c1csc(C(=O)N[C@H](CN)Cc2ccc(F)cc2)c1]

Preparation of N-{(1S)-2-amino-1-[(4-fluorophenyl)methyl]ethyl}-4-(3-chloro-1,4-dimethyl-1H-pyrazol-5-yl)-2-thiophenecarboxamide a) methyl 4-(1,4-dimethyl-1H-pyrazol-5-yl)-2-thiophenecarboxylate

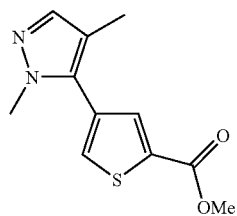 [SMILES: COC(=O)c1cc(-c2c(C)cnn2C)cs1]

To a 350 mL sealed flask reactor was added methyl 4-(4-bromo-1-methyl-1H-pyrazol-5-yl)-2-thiophenecarboxylate (3.45 g, 11.46 mmol) [prepared according to the procedure of Example 156], trimethylboroxine (2.7 ml, 19.40 mmol), K$_2$CO$_3$ (4.75 g, 34.4 mmol) and Pd(dppf)Cl$_2$ (599 mg, 1.17 mmol) in N,N-Dimethylformamide (DMF) (57 mL). The reaction was heated at 110° C. for 1 hour, cooled to room temperature and partitioned between CHCl$_3$/H$_2$O. The organic layer was separated, dried with Na$_2$SO$_4$, adsorbed onto silica and purified via column chromatography (0-30% EtOAc/Hexane) affording the title compound (2.07 g, 8.76 mmol, 76%): LC-MS (ES) m/z=251 (M+H)$^+$.

b) methyl 4-(3-chloro-1,4-dimethyl-1H-pyrazol-5-yl)-2-thiophenecarboxylate

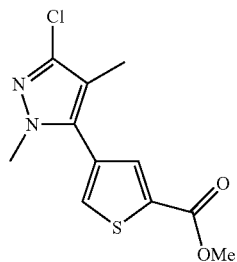 [SMILES: COC(=O)c1cc(-c2c(C)c(Cl)nn2C)cs1]

NCS (1.78 g, 13.09 mmol) was added in portions to a 125 mL sealed tube reactor containing methyl 4-(1,4-dimethyl-1H-pyrazol-5-yl)-2-thiophenecarboxylate (2.07 g, 8.76 mmol) in Tetrahydrofuran (THF) (40 ml) at room temperature. The mixture was heated to 100° C. for 1 hour. Upon completion the product was partitioned between CHCl$_3$ and H$_2$O, the organic layer dried with Na$_2$SO$_4$, solvents removed by vacuum distillation affording the title compound (2.18 g, 7.97 mmol, 91%) which was used without further purification: LC-MS (ES) m/z=271 (M+H)$^+$.

c) 4-(3-chloro-1,4-dimethyl-1H-pyrazol-5-yl)-2-thiophenecarboxylic Acid

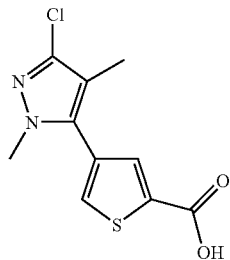 [SMILES: Cc1c(Cl)nn(C)c1-c1csc(C(=O)O)c1]

To a 100 mL round-bottomed flask was added methyl 4-(3-chloro-1,4-dimethyl-1H-pyrazol-5-yl)-2-thiophenecarboxylate (2.15 g, 7.94 mmol) in Tetrahydrofuran (THF) (30 ml). 6N NaOH (30 mL, 180 mmol) was added slowly and the reaction stirred at 70° C. overnight. The reaction was cooled to room temperature, partitioned between CHCl$_3$ and H$_2$O and the pH of the aqueous layer adjusted to ~3 by the addition of 6N HCl. The layers were separated, the organic layer dried with Na$_2$SO$_4$ and solvent removed affording the title compound (1.35 g, 5.26 mmol, 66%) which was used in the next step without further purification LC-MS (ES) m/z=257 (M+H)$^+$.

d) 4-(3-chloro-1,4-dimethyl-1H-pyrazol-5-yl)-N-{(1S)-2-(1,3-dioxo-1,3-dihydro-2H-isoindol-2-yl)-1-[(4-fluorophenyl)methyl]ethyl}-2-thiophenecarboxamide

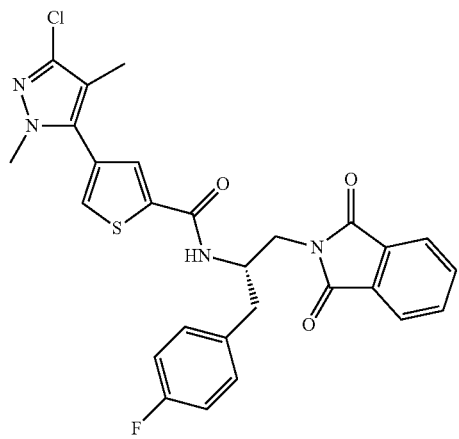 [SMILES: Cc1c(Cl)nn(C)c1-c1csc(C(=O)N[C@@H](Cc2ccc(F)cc2)CN2C(=O)c3ccccc3C2=O)c1]

To a 50 mL round-bottomed flask was added 4-(3-chloro-1,4-dimethyl-1H-pyrazol-5-yl)-2-thiophenecarboxylic acid (294 mg, 1.14 mmol), 2-[(2S)-2-amino-3-(4-fluorophenyl)propyl]-1H-isoindole-1,3(2H)-dione (409 mg, 1.22 mmol) [prepared according to the procedure of Preparation 6 except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (645 mg, 1.38 mmol) in chloroform (10 mL). DIEA (1 mL, 5.73 mmol) was added and the reaction stirred overnight at room temperature. The mixture was adsorbed onto silica and purified via column chromatography (25-70% EtOAc/Hex) affording the title compound (534 mg, 0.92 mmol, 81%): LC-MS (ES) m/z=537 (M+H)$^+$.

c) N-{(1S)-2-amino-1-[(4-fluorophenyl)methyl]ethyl}-4-(3-chloro-1,4-dimethyl-1H-pyrazol-5-yl)-2-thiophenecarboxamide To a 50 mL round-bottomed flask was added 4-(3-chloro-1,4-dimethyl-1H-pyrazol-5-yl)-N-{(1S)-2-(1,3-dioxo-1,3-dihydro-2H-isoindol-2-yl)-1-[(4-fluorophenyl)methyl]ethyl}-2-thiophenecarboxamide (534 mg, 0.994 mmol) in Tetrahydrofuran (THF) (9 mL) and Methanol (1 mL). Hydrazine (220 μL, 7.01 mmol) was added and the reaction stirred overnight at room temperature. The reaction mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (354 mg, 0.70 mmol, 70% yield): LC-MS (ES) m/z=407 (M+H)$^+$, $^1$H NMR (400 MHz, DMSO-d$_6$) δ ppm 1.99 (s, 3H) 2.91-3.02 (m, 4H) 3.79 (s, 3H) 4.30-4.41 (m, 1H) 7.10 (t, J=8.84 Hz, 2H) 7.27-7.36 (m, 2H) 8.01 (d, J=1.26 Hz, 1H) 8.15 (s, 3H) 8.21 (d, J=1.26 Hz, 1H) 9.04 (d, J=8.34 Hz, 1H).

Example 177

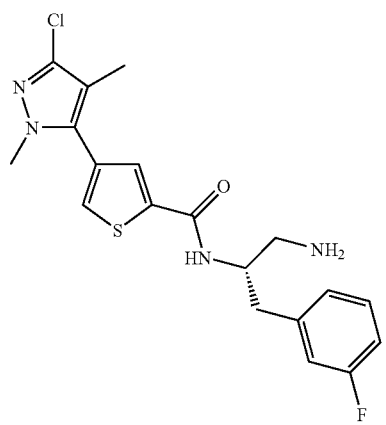 [SMILES: Cc1c(Cl)nn(C)c1-c1csc(C(=O)N[C@H](CN)Cc2cccc(F)c2)c1]

Preparation of N-{(1S)-2-amino-1-[(3-fluorophenyl)methyl]ethyl}-4-(3-chloro-1,4-dimethyl-1H-pyrazol-5-yl)-2-thiophenecarboxamide a) 4-(3-chloro-1,4-dimethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide

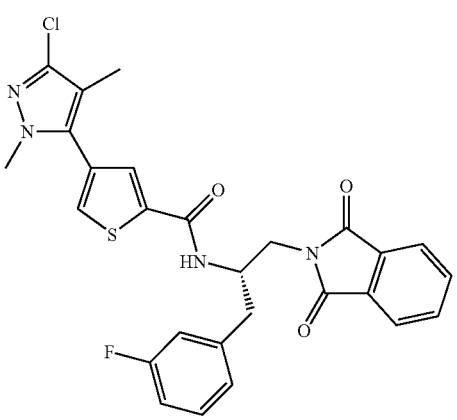

To a 50 mL round-bottomed flask was added 4-(3-chloro-1,4-dimethyl-1H-pyrazol-5-yl)-2-thiophenecarboxylic acid (291 mg, 1.13 mmol) [prepared according to the procedure of Example 176], 2-[(2S)-2-amino-3-(3-fluorophenyl)propyl]-1H-isoindole-1,3(2H)-dione (409 mg, 1.22 mmol) [prepared according to the procedure of Preparation 6 except substituting N-{[(1,1-dimethylethyl)oxy]carbonyl}-3-fluoro-L-phenylalanine (5.03 g, 17.8 mmol) for N-{[(1,1-dimethylethyl)oxy]carbonyl}-2-(trifluoromethyl)-L-phenylalanine] and PyBrop (654 mg, 1.39 mmol) in chloroform (10 mL). DIEA (1 mL, 5.73 mmol) was added and the reaction stirred overnight at room temperature. The mixture was adsorbed onto silica and purified via column chromatography (25-70% EtOAc/Hex) affording the title compound (427 mg, 0.76 mmol, 67%): LC-MS (ES) m/z=537 (M+H)+.

b) N-{(1S)-2-amino-1-[(3-fluorophenyl)methyl]ethyl}-4-(3-chloro-1,4-dimethyl-1H-pyrazol-5-yl)-2-thiophenecarboxamide To a 50 mL round-bottomed flask was added 4-(3-chloro-1,4-dimethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide (427 mg, 0.79 mmol) in Tetrahydrofuran (THF) (7.5 mL) and Methanol (1 mL). Hydrazine (175 µL, 5.58 mmol) was added and the solution stirred at 25° C. overnight. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (296 mg, 0.59 mmol, 74% yield): LC-MS (ES) m/z=407 (M+H)+, $^1$H NMR (400 MHz, DMSO-d$_6$) δ ppm 1.99 (s, 3H) 2.95-3.06 (m, 4H) 3.79 (s, 3H) 4.33-4.45 (m, 1H) 7.02 (td, J=8.59, 2.02 Hz, 1H) 7.09-7.18 (m, 2H) 7.26-7.36 (m, 1H) 8.01 (d, J=1.01 Hz, 1H) 8.16 (s, 3H) 8.22 (s, 1H) 9.07 (d, J=8.34 Hz, 1H).

Example 178

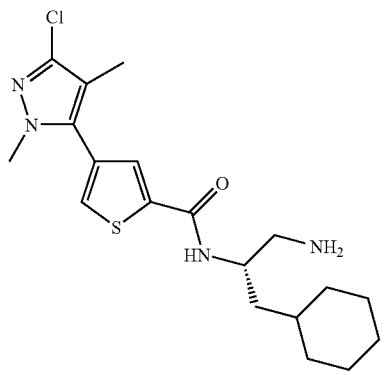 [SMILES: Cc1c(Cl)nn(C)c1-c1csc(C(=O)N[C@H](CN)CC2CCCCC2)c1]

Preparation of N-[(1S)-2-amino-1-(cyclohexylmethyl)ethyl]-4-(3-chloro-1,4-dimethyl-1H-pyrazol-5-yl)-2-thiophenecarboxamide a) 4-(3-chloro-1,4-dimethyl-1H-pyrazol-5-yl)-N-{(1S)-2-cyclohexyl-1-[(1,3-dioxo-1,3-dihydro-2H-isoindol-2-yl)methyl]ethyl}-2-thiophenecarboxamide

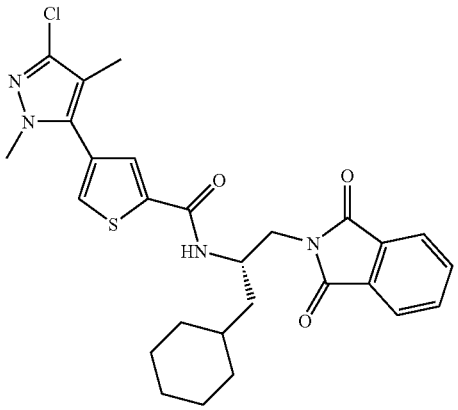 [SMILES: Cc1c(Cl)nn(C)c1-c1csc(C(=O)N[C@@H](CC2CCCCC2)CN2C(=O)c3ccccc3C2=O)c1]

To a 50 mL round-bottomed flask was added 4-(3-chloro-1,4-dimethyl-1H-pyrazol-5-yl)-2-thiophenecarboxylic acid (150 mg, 0.58 mmol) [prepared according to the procedure of Example 176], 2-[(2S)-2-amino-3-cyclohexylpropyl]-1H-isoindole-1,3(2H)-dione (176 mg, 0.54 mmol) [prepared according to the procedure of Preparation 6, except substituting 3-cyclohexyl-N-{[(1,1-dimethylethyl)oxy]carbonyl}-L-alanine (5 g, 18.4 mmol) for N-{[(1,1-dimethylethyl)oxy]carbonyl}-2-(trifluoromethyl)-L-phenylalanine] and PyBrop (336 mg, 0.72 mmol) in chloroform (6 mL). DIEA (520 µL, 2.98 mmol) was added and the reaction stirred overnight at room temperature. The mixture was adsorbed onto silica and purified via column chromatography (25-70% EtOAc/Hex) affording the title compound (336 mg, 0.61 mmol, quant.): LC-MS (ES) m/z=526 (M+H)+.

b) N-[(1S)-2-amino-1-(cyclohexylmethyl)ethyl]-4-(3-chloro-1,4-dimethyl-1H-pyrazol-5-yl)-2-thiophenecarboxamide To a 50 mL round-bottomed flask was added 4-(3-chloro-1,4-dimethyl-1H-pyrazol-5-yl)-N-{(1S)-2-cyclohexyl-1-[(1,3-dioxo-1,3-dihydro-2H-isoindol-2-yl)methyl]ethyl}-2-thiophenecarboxamide (366 mg, 0.697 mmol) in Tetrahydrofuran (THF) (6.5 mL) and Methanol (1 mL). Hydrazine (155 µL, 4.94 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (173 mg, 0.35 mmol, 50% yield): LC-MS (ES) m/z=395 (M+H)+, $^1$H NMR (400 MHz, DMSO-d$_6$) δ ppm 0.80-0.92 (m, 1H) 0.92-1.01 (m, 1H) 1.13 (d, J=6.57 Hz, 2H) 1.22 (d, J=12.88 Hz, 1H) 1.29 (s, 1H) 1.32-1.43 (m, 1H) 1.48-1.56 (m, 1H) 1.58 (d, J=5.05 Hz, 1H) 1.63 (s, 3H) 1.73-1.84 (m, 1H) 1.99 (s, 3H) 2.94 (d, J=5.31 Hz, 2H) 3.78 (s, 3H) 4.22-4.36 (m, 1H) 8.03 (s, 1H) 8.05 (s, 3H) 8.19 (s, 1H) 8.80 (d, J=8.59 Hz, 1H).

Example 179

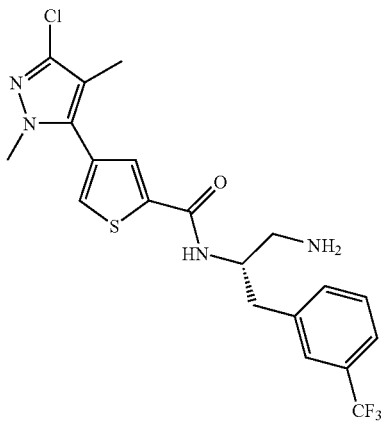 [SMILES: Cc1c(Cl)nn(C)c1-c1csc(C(=O)N[C@H](CN)Cc2cccc(C(F)(F)F)c2)c1]

Preparation of N-((1S)-2-amino-1-{[3-(trifluoromethyl)phenyl]methyl}ethyl)-4-(3-chloro-1,4-dimethyl-1H-pyrazol-5-yl)-2-thiophenecarboxamide a) 4-(3-chloro-1,4-dimethyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-2-thiophenecarboxamide

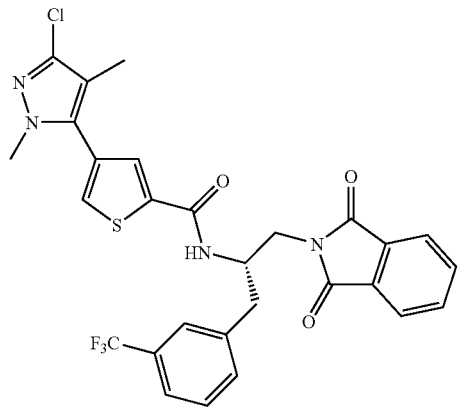 [SMILES: Cc1c(Cl)nn(C)c1-c1csc(C(=O)N[C@@H](Cc2cccc(C(F)(F)F)c2)CN2C(=O)c3ccccc3C2=O)c1]

To a 50 mL round-bottomed flask was added 4-(3-chloro-1,4-dimethyl-1H-pyrazol-5-yl)-2-thiophenecarboxylic acid (238 mg, 0.93 mmol) [prepared according to the procedure of Example 176], 2-{(2S)-2-amino-3-[3-(trifluoromethyl)phenyl]propyl}-1H-isoindole-1,3(2H)-dione (355 mg, 0.92 mmol) [prepared according to the procedure of Preparation 6, except substituting N-{[(1,1-dimethylethyl)oxy]carbonyl}-3-(trifluoromethyl)-L-phenylalanine (5.0 g, 15.0 mmol) for N-{[(1,1-dimethylethyl)oxy]carbonyl}-2-(trifluoromethyl)-L-phenylalanine] and PyBrop (532 mg, 1.13 mmol) in chloroform (9.5 mL). DIEA (820 µL, 4.70 mmol) was added and the reaction stirred overnight at room temperature. The mixture was adsorbed onto silica and purified via column chromatography (25-70% EtOAc/Hex) affording the title compound (448 mg, 0.72 mmol, 78%): LC-MS (ES) m/z=587 (M+H)$^+$.

b) N-((1S)-2-amino-1-{[3-(trifluoromethyl)phenyl]methyl}ethyl)-4-(3-chloro-1,4-dimethyl-1H-pyrazol-5-yl)-2-thiophenecarboxamide To a 50 mL round-bottomed flask was added 4-(3-chloro-1,4-dimethyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-2-thiophenecarboxamide (468 mg, 0.80 mmol) in Tetrahydrofuran (THF) (7.5 mL) and Methanol (1 mL). Hydrazine (175 µL, 5.58 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (321 mg, 0.58 mmol, 72% yield): LC-MS (ES) m/z=457 (M+H)$^+$, $^1$H NMR (400 MHz, DMSO-d$_6$) δ ppm 1.98 (s, 3H) 3.05 (d, J=7.07 Hz, 4H) 3.77 (s, 3H) 4.33-4.44 (m, 1H) 7.49-7.57 (m, 2H) 7.58-7.62 (m, 1H) 7.66 (s, 1H) 8.01 (d, J=1.26 Hz, 1H) 8.11 (s, 3H) 8.17 (d, J=1.26 Hz, 1H) 9.02 (d, J=8.59 Hz, 1H).

Example 180

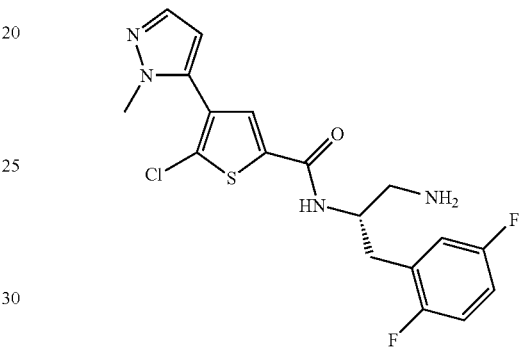

Preparation of N-{(1S)-2-amino-1-[(2,5-difluorophenyl)methyl]ethyl}-5-chloro-4-(1-methyl-1H-pyrazol-5-yl)-2-thiophenecarboxamide a) 5-chloro-N-{(1S)-2-(2,5-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide

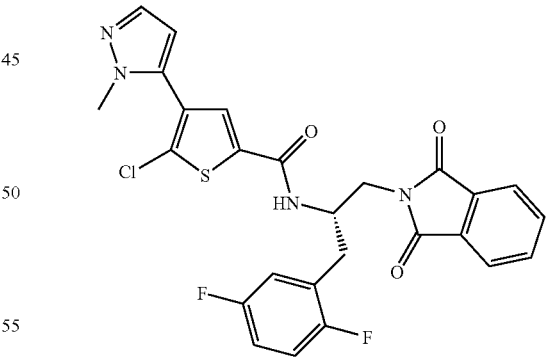

To a 50 mL round-bottomed flask was added 5-chloro-4-(1-methyl-1H-pyrazol-5-yl)-2-thiophenecarboxylic acid (147 mg, 0.61 mmol), 2-[(2S)-2-amino-3-(2,5-difluorophenyl)propyl]-1H-isoindole-1,3(2H)-dione (216 mg, 0.61 mmol) [prepared according to the procedure of Preparation 18 except substituting 2,5-difluoro-L-phenylalanine (3.02 g, 15.0 mmol) for 2,6-difluoro-L-phenylalanine] and PyBrop (341.4 mg, 0.73 mmol) in chloroform (6 mL). DIEA (530 µL, 3.03 mmol) was added and the reaction stirred overnight at room temperature. The mixture was adsorbed onto silica and purified via column chromatography (25-70% EtOAc/Hex)

b) N-{(1S)-2-amino-1-[(2,5-difluorophenyl)methyl]ethyl}-5-chloro-4-(1-methyl-1H-pyrazol-5-yl)-2-thiophenecarboxamide To a 50 mL round-bottomed flask was added 5-chloro-N-{(1S)-2-(2,5-difluorophenyl)-1-[(1,3-dioxo-1,3-dihydro-2H-isoindol-2-yl)methyl]ethyl}-4-(1-methyl-1H-pyrazol-5-yl)-2-thiophenecarboxamide (233 mg, 0.43 mmol) in Tetrahydrofuran (THF) (5 mL) and Methanol (1 mL). Hydrazine (95 µL, 3.03 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (165 mg, 0.32 mmol, 75% yield): LC-MS (ES) m/z=411 (M+H)$^+$, $^1$H NMR (400 MHz, DMSO-d$_6$) δ ppm 2.88-3.14 (m, 4H) 3.85 (s, 3H) 4.37-4.50 (m, 1H) 6.48 (d, J=1.77 Hz, 1H) 7.09 (t, J=8.34 Hz, 1H) 7.19 (dt, J=9.09, 4.55 Hz, 1H) 7.29 (ddd, J=8.84, 5.68, 3.16 Hz, 1H) 7.55 (d, J=1.52 Hz, 1H) 8.22 (s, 3H) 8.27 (s, 1H) 9.32 (d, J=8.84 Hz, 1H).

Example 181

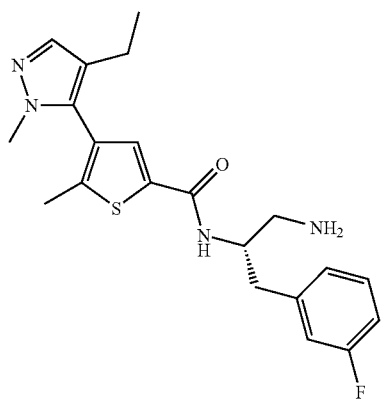 [SMILES: CCc1cnn(C)c1-c1cc(C(=O)N[C@H](CN)Cc2cccc(F)c2)sc1C]

Preparation of N-{(1S)-2-amino-1-[(3-fluorophenyl)methyl]ethyl}-4-(4-ethyl-1-methyl-1H-pyrazol-5-yl)-5-methyl-2-thiophenecarboxamide The title compound was prepared according to the procedure of Example 109, except substituting 2-[(2S)-2-amino-3-(3-fluorophenyl)propyl]-1H-isoindole-1,3(2H)-dione (184 mg, 0.55 mmol) for 2-{(2S)-2-amino-3-[2-(trifluoromethyl)phenyl]propyl}-1H-isoindole-1,3(2H)-dione [prepared according to Preparation 6]: LC-MS (ES) m/z=401 (M+H)$^+$, $^1$H NMR (400 MHz, DMSO-d$_6$) δ ppm 1.04 (t, J=7.33 Hz, 3H) 2.13-2.33 (m, 5H) 2.86-3.08 (m, 4H) 3.60 (s, 3H) 4.27-4.43 (m, 1H) 6.96-7.07 (m, 1H) 7.11 (d, J=6.32 Hz, 2H) 7.30 (s, 1H) 7.43 (s, 1H) 7.85 (s, 1H) 8.19 (s, 3H) 8.85 (s, 1H).

Example 182

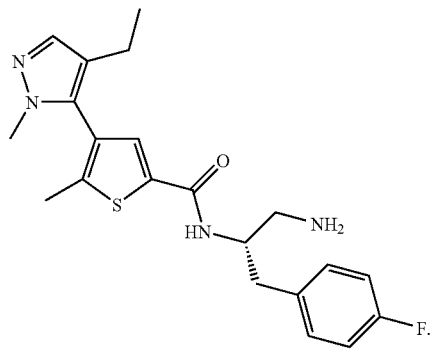 [SMILES: CCc1cnn(C)c1-c1cc(C(=O)N[C@H](CN)Cc2ccc(F)cc2)sc1C]

Preparation of N-{(1S)-2-amino-1-[(4-fluorophenyl)methyl]ethyl}-4-(4-ethyl-1-methyl-1H-pyrazol-5-yl)-5-methyl-2-thiophenecarboxamide The title compound was prepared according to the procedure of Example 109, except substituting 2[(2S)-2-amino-3-(4-fluorophenyl)propyl]-1H-isoindole-1,3(2H)-dione (207 mg, 0.62 mmol) for 2-{(2S)-2-amino-3-[2-(trifluoromethyl)phenyl]propyl}-1H-isoindole-1,3(2H)-dione [prepared according to Preparation 6]: LC-MS (ES) m/z=401 (M+H)$^+$, $^1$H NMR (400 MHz, DMSO-d$_6$) δ ppm 1.04 (t, J=7.20 Hz, 3H) 2.25 (s, 5H) 2.88-3.00 (m, 4H) 3.61 (s, 3H) 4.25-4.40 (m, 1H) 7.01-7.17 (m, 2H) 7.26-7.35 (m, 2H) 7.42 (s, 1H) 7.82 (s, 1H) 8.17 (s, 3H) 8.81 (s, 1H).

Example 183

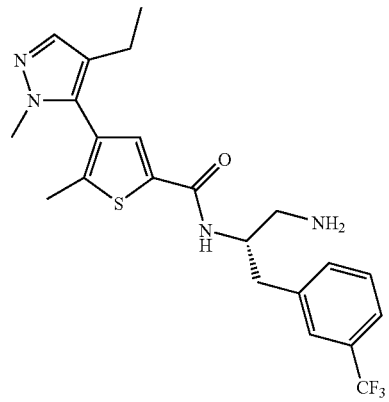 [SMILES: CCc1cnn(C)c1-c1cc(C(=O)N[C@H](CN)Cc2cccc(C(F)(F)F)c2)sc1C]

Preparation of N-((1S)-2-amino-1-{[3-(trifluoromethyl)phenyl]methyl}ethyl)-4-(4-ethyl-1-methyl-1H-pyrazol-5-yl)-5-methyl-2-thiophenecarboxamide The title compound was prepared according to the procedure of Example 109, except substituting 2-{(2S)-2-amino-3-[3-(trifluoromethyl)phenyl]propyl}-1H-isoindole-1,3(2H)-dione (158 mg, 0.41 mmol) for 2-{(2S)-2-amino-3-[2-(trifluoromethyl)phenyl]propyl}-1H-isoindole-1,3(2H)-dione [prepared according to Preparation 6]: LC-MS (ES) m/z=451 (M+H)$^+$, $^1$H NMR (400 MHz, DMSO-d$_6$) δ ppm 1.04 (t, J=7.33 Hz, 3H) 2.24 (s, 5H) 3.03 (d, J=6.32 Hz, 4H) 3.59 (s, 3H) 4.35 (s, 1H) 7.42 (s, 1H) 7.46-7.57 (m, 2H) 7.59

(d, J=6.57 Hz, 1H) 7.64 (s, 1H) 7.84 (s, 1H) 8.20 (s, 3H) 8.88 (s, 1H).

Example 184

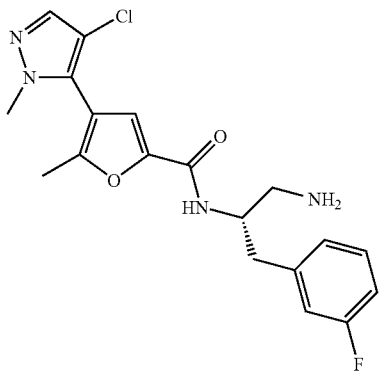

Preparation of N-{(1S)-2-amino-1-[(3-fluorophenyl)methyl]ethyl}-4-(4-chloro-1-methyl-1H-pyrazol-5-yl)-5-methyl-2-furancarboxamide a) methyl 5-methyl-2-furancarboxylate

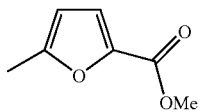

To a 200 mL round-bottomed flask with condenser was added 5-methyl-2-furancarboxylic acid (2.5 g, 19.82 mmol) in Methanol (100 mL). $H_2SO_4$ (10.5 mL, 197 mmol) was added slowly at room temperature. The reaction mixture was heated to 50° C. overnight. The reaction mixture was cooled to 0° C. and a saturated solution of $NaHCO_3$ was added to neutral pH followed by 5N NaOH to pH 10. $CHCl_3$ was added and the organic phase was separated, dried with $Na_2SO_4$ and concentrated affording the title compound (2.3 g, 16.3 mmol, 82%): LC-MS (ES) m/z=141 $(M+H)^+$.

b) methyl 4-bromo-5-methyl-2-furancarboxylate

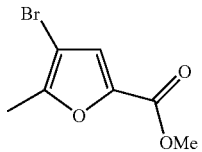

To a solution of methyl 5-methyl-2-furancarboxylate (2.33 g, 16.29 mmol) and aluminum chloride (3.3 g, 24.75 mmol) in chloroform (50 ml) at room temperature was added $Br_2$ (1.1 ml, 21.35 mmol). The resulting solution was stirred at room temperature in a 150 mL sealed tube reactor for 2 hours. Upon completion, the solution was cooled in an ice bath, $H_2O$ added and reaction partitioned between $CHCl_3/H_2O$. The organic layer was washed with $NaHCO_3$ and then $Na_2S_2O_3$. The organic layer was dried with $Na_2SO_4$, concentrated, adsorbed onto silica and purified via column chromatography (0-20% EtOAc/Hexanes) affording the title compound (2.13 g, 9.72 mmol, 60%): LC-MS (ES) m/z=221 $(M+H)^+$.

c) methyl 5-methyl-4-(1-methyl-1H-pyrazol-5-yl)-2-furancarboxylate

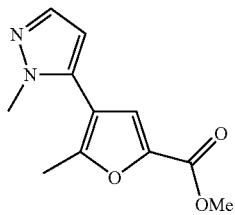 [SMILES: COC(=O)c1cc(-c2ccnn2C)c(C)o1]

To a 5 mL sealed flask reactor was added methyl 4-bromo-5-methyl-2-furancarboxylate (1.13 g, 5.16 mmol), 1-methyl-5-(4,4,5,5-tetramethyl-1,3,2-dioxaborolan-2-yl)-1H-pyrazole (1.31 g, 6.30 mmol) [prepared according to the procedure of Preparation 7], $K_3PO_4$ (3.87 g, 18.23 mmol) and $Pd_2(dba)_3$ (153 mg, 0.17 mmol) and $P(OMe)_3$ (32 µL, 0.27 mmol) in 1,4-Dioxane (23 mL). The reaction was heated at 95° C. for 4 hours, cooled to room temperature and partitioned between $CHCl_3/H_2O$. The organic layer was separated, dried with $Na_2SO_4$, adsorbed onto silica and purified via column chromatography (0-15% EtOAc/Hexanes) affording the title compound (967 mg, 4.39 mmol, 85%): LC-MS (ES) m/z=271 $(M+H)^+$.

d) 4-(4-chloro-1-methyl-1H-pyrazol-5-yl)-5-methyl-2-furancarboxylic Acid

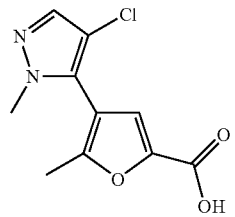 [SMILES: Cc1oc(C(=O)O)cc1-c1c(Cl)cnn1C]

NCS (709 mg, 5.31 mmol) was added in portions to a 150 mL sealed tube reactor containing methyl 5-methyl-4-(1-methyl-1H-pyrazol-5-yl)-2-furancarboxylate (967 mg, 4.39 mmol) in Tetrahydrofuran (THF) (20 mL) at room temperature. The mixture was heated to 70° C. for 1 hour. 6N NaOH (20 mL, 120 mmol) was then added and the mixture stirred at 70° C. for an additional 2 h. The mixture was partitioned between $CHCl_3$ and $H_2O$ and the pH of the aqueous phase was adjusted to ~3 with 6N HCl. The organic layer was separated, dried with $Na_2SO_4$ and concentrated affording the title compound (1.13 g, 4.41 mmol, quant.) which was used without further purification: LC-MS (ES) m/z=241 $(M+H)^+$.

e) 4-(4-chloro-1-methyl-1H-pyrazol-5-yl)-N-{(1S)-2-(1,3-dioxo-1,3-dihydro-2H-isoindol-2-yl)-1-[(3-fluorophenyl)methyl]ethyl}-5-methyl-2-furancarboxamide

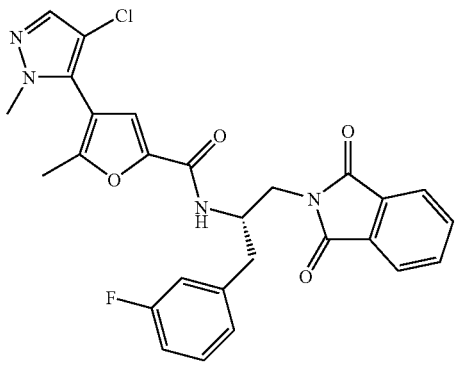 [SMILES: Cc1oc(C(=O)N[C@@H](Cc2cccc(F)c2)CN2C(=O)c3ccccc3C2=O)cc1-c1c(Cl)cnn1C]

To a 50 mL round-bottomed flask was added 4-(4-chloro-1-methyl-1H-pyrazol-5-yl)-5-methyl-2-furancarboxylic acid (244 mg, 0.95 mmol), 2-[(2S)-2-amino-3-(3-fluorophenyl)propyl]-1H-isoindole-1,3(2H)-dione (320 mg, 0.95 mmol) [prepared according to the procedure of Preparation 6, except substituting N-{[(1,1-dimethylethyl)oxy]carbonyl}-3-fluoro-L-phenylalanine (5.0 g, 17.8 mmol) for N-{[(1,1-dimethylethyl)oxy]carbonyl}-2-(trifluoromethyl)-L-phenylalanine] and PyBrop (533 mg, 1.14 mmol) in chloroform (9 mL). DIEA (830 µL, 4.75 mmol) was added and the reaction stirred overnight at room temperature. The mixture was adsorbed onto silica and purified via column chromatography (25-70% EtOAc/Hex) affording the title compound (242 mg, 0.465 mmol, 49%): LC-MS (ES) m/z=521 (M+H)+.

f) N-{(1S)-2-amino-1-[(3-fluorophenyl)methyl]ethyl}-4-(4-chloro-1-methyl-1H-pyrazol-5-yl)-5-methyl-2-furancarboxamide To a 50 mL round-bottomed flask was added 4-(4-chloro-1-methyl-1H-pyrazol-5-yl)-N-{(1S)-2-(1,3-dioxo-1,3-dihydro-2H-isoindol-2-yl)-1-[(3-fluorophenyl)methyl]ethyl}-5-methyl-2-furancarboxamide (238 mg, 0.46 mmol) in Tetrahydrofuran (THF) (3.6 mL) and Methanol (1 mL). Hydrazine (100 µL, 3.19 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (157 mg, 0.32 mmol, 71% yield): LC-MS (ES) m/z=391 (M+H)+, $^1$H NMR (400 MHz, DMSO-d$_6$) δ ppm 2.31 (s, 3H) 2.91-3.03 (m, 4H) 3.73 (s, 3H) 4.36-4.49 (m, 1H) 7.03 (t, J=7.71 Hz, 1H) 7.07-7.14 (m, 2H) 7.29-7.37 (m, 1H) 7.39 (s, 1H) 7.67 (s, 1H) 8.14 (s, 3H) 8.65 (d, J=8.59 Hz, 1H).

Example 185

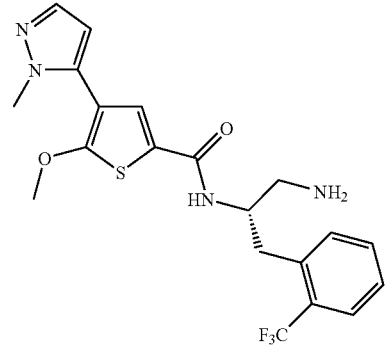 [SMILES: COc1sc(C(=O)N[C@H](CN)Cc2ccccc2C(F)(F)F)cc1-c1ccnn1C]

Preparation of N-((1S)-2-amino-1-{[2-(trifluoromethyl)phenyl]methyl}ethyl)-5-(methyloxy)-4-(1-methyl-1H-pyrazol-5-Vl)-2-thiophenecarboxamide a) 5-(methyloxy)-2-thiophenecarboxylic Acid

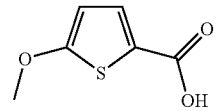

2-(methyloxy)thiophene (1.01 g, 8.85 mmol) was added slowly over 15 min to a 100 mL round-bottomed flask containing 2.5M nBuLi in hexanes (3.8 mL, 9.50 mmol) in Tetrahydrofuran (THF) (40 mL) at −78° C. After warming to room temperature and stirring for 2 h, the mixture was cooled to −35° C. and crushed solid CO$_2$ was added. The mixture warmed to room temperature over 3 hours and was cooled in an ice bath and quenched with NH$_4$Cl(sat.). The cold reaction mixture was partitioned between CHCl$_3$/H$_2$O, the aqueous layer was made acidic with 6N HCl. The separated organic layer was dried with Na$_2$SO$_4$ and concentrated affording the title compound (1.3 g, 8.05 mmol, 91%) which was used without further purification: LC-MS (ES) m/z=159 (M+H)+.

b) methyl 5-(methyloxy)-2-thiophenecarboxylate

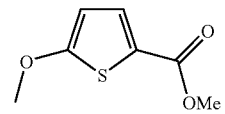

To a 200 mL round-bottomed flask fitted with a condenser was added 5-(methyloxy)-2-thiophenecarboxylic acid (1.3 g, 8.22 mmol) in Methanol (40 mL). H$_2$SO$_4$ (5 mL, 94 mmol) was added slowly at room temperature and the reaction stirred at 50° C. overnight. The mixture was cooled to 0° C. and sat. NaHCO$_3$ was added to neutral pH followed by 5N NaOH to pH 10. The mixture was partitioned between H$_2$O/CHCl$_3$ and the organic phase was separated and dried over Na$_2$SO$_4$. The solution was adsorbed onto silica and purified via column chromatography (5-50% EtOAc/Hexanes) affording the title compound (827 mg, 4.56 mmol, 56%): LC-MS (ES) m/z=173 (M+H)+.

c) methyl 4-bromo-5-(methyloxy)-2-thiophenecarboxylate

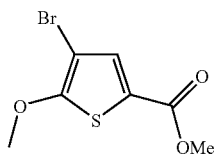

NBS (903 mg, 5.07 mmol) was added in portions to a 5 mL sealed tube reactor containing methyl 5-(methyloxy)-2-thiophenecarboxylate (0.73 g, 4.23 mmol) in N,N-Dimethylformamide (DMF) (20 mL) at room temperature and the reaction stirred for 1 hour. Additional NBS (249 mg) was added and after 1 h at room temperature the product was partitioned between CHCl$_3$ and H$_2$O. The organic layer was dried with Na$_2$SO$_4$, adsorbed onto silica and purified via column chromatography (0-25% EtOAc/Hexanes) affording the title compound (825 mg, 3.19 mmol, 75%): LC-MS (ES) m/z=252 (M+H)$^+$.

d) methyl 5-(methyloxy)-4-(1-methyl-1H-pyrazol-5-yl)-2-thiophenecarboxylate

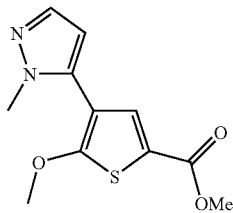 [SMILES: COC(=O)c1cc(-c2ccnn2C)c(OC)s1]

To a 350 mL sealed flask reactor was added methyl 4-bromo-5-(methyloxy)-2-thiophenecarboxylate (772 mg, 3.07 mmol), 1-methyl-5-(4,4,5,5-tetramethyl-1,3,2-dioxaborolan-2-yl)-1H-pyrazole (773 mg, 3.72 mmol) [prepared according to the procedure of Preparation 7], K$_2$CO$_3$ (1.419 g, 10.27 mmol) and Pd(P t—Bu$_3$)$_2$ (103 mg, 0.20 mmol) in 1,4-Dioxane (12 mL) and Water (3 mL). The reaction was heated at 85° C. for 2 hours. The mixture was partitioned between CHCl$_3$/H$_2$O and the aqueous layer made acidic with 6N HCl. The separated organic layer was dried over Na$_2$SO$_4$ and evaporated. The resulting material was adsorbed onto silica and purified via column chromatography (0-50% EtOAc/Hexane) affording the title compound (967 mg, 4.39 mmol, 85%): LC-MS (ES) m/z=253 (M+H)$^+$.

e) 5-(methyloxy)-4-(1-methyl-1H-pyrazol-5-yl)-2-thiophenecarboxylic Acid

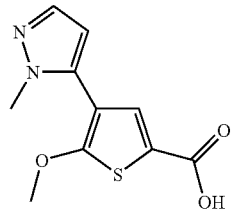 [SMILES: COc1sc(C(=O)O)cc1-c1ccnn1C]

To a 100 mL round-bottomed flask was added methyl 5-(methyloxy)-4-(1-methyl-1H-pyrazol-5-yl)-2-thiophenecarboxylate (203 mg, 0.805 mmol) in Tetrahydrofuran (THF) (4 mL). 6N NaOH (4 mL, 24.0 mmol) was added slowly, the reaction mixture stirred overnight at 70° C. The mixture was neutralized by addition of 6N HCl and partitioned between CHCl$_3$ and H$_2$O. The layers were separated, the organic layer dried over Na$_2$SO$_4$ and concentrated affording the title compound (152 mg, 0.64 mmol, 79%), which was used in the next step without further purification: LC-MS (ES) m/z=239 (M+H)$^+$.

f) N-((1S)-2-(1,3-dioxo-1,3-dihydro-2H-isoindol-2-yl)-1-{[2-(trifluoromethyl)phenyl]methyl}ethyl)-5-(methyloxy)-4-(1-methyl-1H-pyrazol-5-yl)-2-thiophenecarboxamide

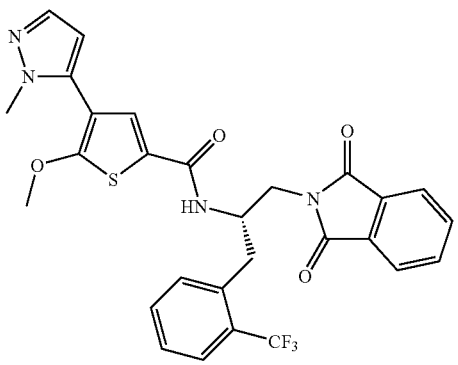 [SMILES: COc1sc(C(=O)N[C@@H](Cc2ccccc2C(F)(F)F)CN2C(=O)c3ccccc3C2=O)cc1-c1ccnn1C]

To a 50 mL round-bottomed flask was added 5-(methyloxy)-4-(1-methyl-1H-pyrazol-5-yl)-2-thiophenecarboxylic acid (148 mg, 0.62 mmol), 2-{(2S)-2-amino-3-[2-(trifluoromethyl)phenyl]propyl}-1H-isoindole-1,3(2H)-dione (242 mg, 0.63 mmol) [prepared according to the procedure of Preparation 6] and PyBrop (356 mg, 0.76 mmol) in Chloroform (6 mL). DIEA (550 µL, 3.15 mmol) was added and the reaction stirred overnight at room temperature. The mixture was adsorbed onto silica and purified via column chromatography (25-70% EtOAc/Hex) affording the title compound (303 mg, 0.51 mmol, 82%): LC-MS (ES) m/z=569 (M+H)$^+$.

g) N-((1S)-2-amino-1-{[2-(trifluoromethyl)phenyl]methyl}ethyl)-5-(methyloxy)-4-(1-methyl-1H-pyrazol-5-yl)-2-thiophenecarboxamide To a 50 mL round-bottomed flask was added N-((1S)-2-(1,3-dioxo-1,3-dihydro-2H-isoindol-2-yl)-1-{[2-(trifluoromethyl)phenyl]methyl}ethyl)-5-(methyloxy)-4-(1-methyl-1H-pyrazol-5-yl)-2-thiophenecarboxamide (303 mg, 0.51 mmol) in Tetrahydrofuran (THF) (4 mL) and Methanol (1 mL). Hydrazine (110 µL, 3.50 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (122 mg, 0.23 mmol, 45% yield): LC-MS (ES) m/z=439 (M+H)$^+$, $^1$H NMR (400 MHz, DMSO-d$_6$) δ ppm 2.93-3.02 (m, 1H) 3.03-3.14 (m, 3H) 3.82 (s, 3H) 3.98 (s, 3H) 4.41-4.53 (m, 1H) 6.32 (s, 1H) 7.38-7.49 (m, 2H) 7.52-7.63 (m, 2H) 7.68 (d, J=7.58 Hz, 1H) 8.01 (s, 1H) 8.17 (s, 3H) 8.93 (d, J=8.84 Hz, 1H).

Example 186

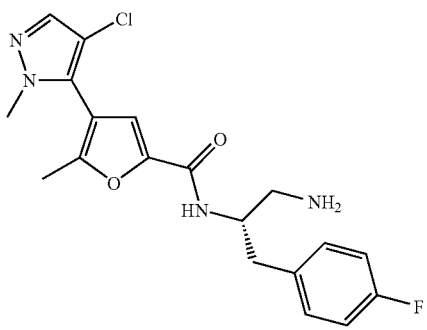 [SMILES: Cc1oc(C(=O)N[C@H](CN)Cc2ccc(F)cc2)cc1-c1c(Cl)cnn1C]

Preparation of N-{(1S)-2-amino-1-[(4-fluorophenyl)methyl]ethyl}-4-(4-chloro-1-methyl-1H-pyrazol-5-yl)-5-methyl-2-furancarboxamide a) 4-(4-chloro-1-methyl-1H-pyrazol-5-yl)-N-{(1S)-2-(1,3-dioxo-1,3-dihydro-2H-isoindol-2-yl)-1-[(4-fluorophenyl)methyl]ethyl}-5-methyl-2-furancarboxamide

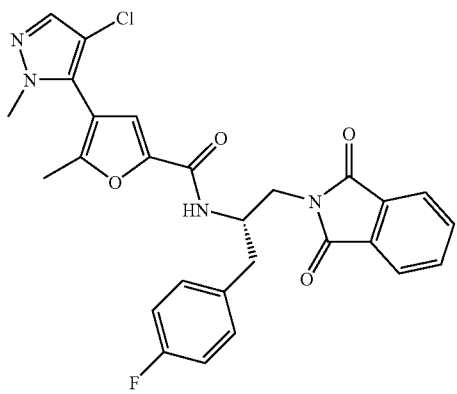

To a 50 mL round-bottomed flask was added 4-(4-chloro-1-methyl-1H-pyrazol-5-yl)-5-methyl-2-furancarboxylic acid (248 mg, 0.97 mmol) [prepared according to the procedure of Example 184], 2-[(2S)-2-amino-3-(4-fluorophenyl)propyl]-1H-isoindole-1,3(2H)-dione (321 mg, 0.96 mmol) [prepared according to the procedure of Preparation 6, except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (557 mg, 1.19 mmol) in chloroform (9.5 mL). DIEA (840 µL, 4.81 mmol) was added and the reaction stirred overnight at room temperature. The mixture was adsorbed onto silica and purified via column chromatography (25-70% EtOAc/Hex) affording the title compound (167 mg, 0.26 mmol, 67%): LC-MS (ES) m/z=521 (M+H)$^+$.

b) N-{(1S)-2-amino-1-[(4-fluorophenyl)methyl]ethyl}-4-(4-chloro-1-methyl-1H-pyrazol-5-yl)-5-methyl-2-furancarboxamide To a 50 mL round-bottomed flask was added 4-(4-chloro-1-methyl-1H-pyrazol-5-yl)-N-{(1S)-2-(1,3-dioxo-1,3-dihydro-2H-isoindol-2-yl)-1-[(4-fluorophenyl)methyl]ethyl}-5-methyl-2-furancarboxamide (144 mg, 0.27 mmol) in Tetrahydrofuran (THF) (2.5 mL) and Methanol (1 mL). Hydrazine (60 µL, 1.91 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (100 mg, 0.21 mmol, 74% yield): LC-MS (ES) m/z=391 (M+H)$^+$, $^1$H NMR (400 MHz, DMSO-d$_6$) δ ppm 2.31 (s, 3H) 2.83-2.93 (m, 2H) 2.94-3.04 (m, 2H) 3.73 (s, 3H) 4.32-4.44 (m, 1H) 7.12 (t, J=8.59 Hz, 2H) 7.25-7.33 (m, 2H) 7.35 (s, 1H) 7.67 (s, 1H) 8.07 (s, 3H) 8.57 (d, J=8.59 Hz, 1H).

Example 187

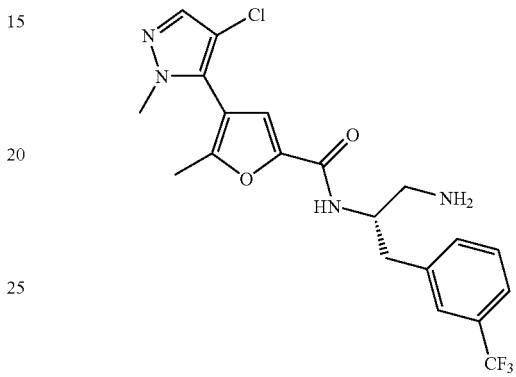

Preparation of N-((1S)-2-amino-1-{[3-(trifluoromethyl)phenyl]methyl}ethyl)-4-(4-chloro-1-methyl-1H-pyrazol-5-yl)-5-methyl-2-furancarboxamide a) 4-(4-chloro-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-methyl-2-furancarboxamide

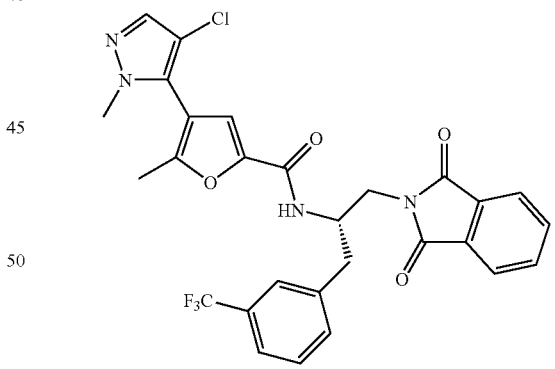

To a 50 mL round-bottomed flask was added 4-(4-chloro-1-methyl-1H-pyrazol-5-yl)-5-methyl-2-furancarboxylic acid (230 mg, 0.90 mmol) [prepared according to the procedure of Example 184], 2-{(2S)-2-amino-3-[3-(trifluoromethyl)phenyl]propyl}-1H-isoindole-1,3(2H)-dione (348 mg, 0.90 mmol) [prepared according to the procedure of Preparation 6, except substituting N-{[(1,1-dimethylethyl)oxy]carbonyl}-3-(trifluoromethyl)-L-phenylalanine (4.98 g, 15.0 mmol) for N-{[(1,1-dimethylethyl)oxy]carbonyl}-2-(trifluoromethyl)-L-phenylalanine] and PyBrop (502 mg, 1.07 mmol) in chloroform (8.5 mL). DIEA (790 µL, 4.52 mmol) was added and the reaction stirred overnight at room temperature. The mixture was adsorbed onto silica and purified via column chromatography (25-70% EtOAc/Hex) affording the title compound (247 mg, 0.43 mmol, 48%): LC-MS (ES) m/z=571 (M+H)⁺.

b) N-((1S)-2-amino-1-{[3-(trifluoromethyl)phenyl]methyl}ethyl)-4-(4-chloro-1-methyl-1H-pyrazol-5-yl)-5-methyl-2-furancarboxamide To a 50 mL round-bottomed flask was added 4-(4-chloro-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-methyl-2-furancarboxamide (247 mg, 0.433 mmol) in Tetrahydrofuran (THF) (4 mL) and Methanol (1 mL). Hydrazine (95 µL, 3.03 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (206 mg, 0.38 mmol, 88% yield): LC-MS (ES) m/z=441 (M+H)⁺, ¹H NMR (400 MHz, DMSO-d₆) δ ppm 2.30 (s, 3H) 2.97-3.08 (m, 4H) 3.71 (s, 3H) 4.35-4.49 (m, 1H) 7.36 (s, 1H) 7.54 (dt, J=19.20, 7.20 Hz, 3H) 7.62-7.68 (m, 2H) 8.14 (s, 3H) 8.65 (d, J=8.84 Hz, 1H).

Example 188

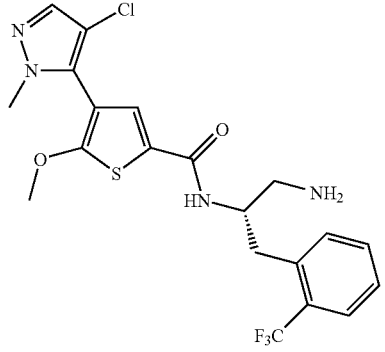 [SMILES: COc1sc(C(=O)N[C@H](CN)Cc2ccccc2C(F)(F)F)cc1-c1c(Cl)cnn1C]

Preparation of N-((1S)-2-amino-1-{[2-(trifluoromethyl)phenyl]methyl}ethyl)-4-(4-chloro-1-methyl-1H-pyrazol-5-yl)-5-(methyloxy)-2-thiophenecarboxamide a) 4-(4-chloro-1-methyl-1H-pyrazol-5-yl)-5-(methyloxy)-2-thiophenecarboxylic Acid

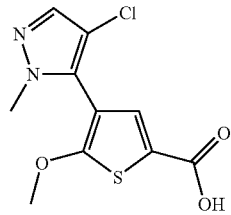 [SMILES: COc1sc(C(=O)O)cc1-c1c(Cl)cnn1C]

NCS (382 mg, 2.80 mmol) was added in portions to a 50 mL sealed tube reactor containing methyl 5-(methyloxy)-4-(1-methyl-1H-pyrazol-5-yl)-2-thiophenecarboxylate (642 mg, 2.54 mmol) [prepared according to the procedure of Example 185] in Tetrahydrofuran (THF) (12 mL) at room temperature. The mixture was heated to 70° C. for 1 hour. The reaction was cooled to room temperature, 6N NaOH (10 mL, 60.0 mmol) was added and the mixture stirred an additional 3 h at 70° C. The mixture was partitioned between CHCl₃ and H₂O and the aqueous layer was made acidic with 6N HCl. The organic layer was dried over Na₂SO₄ and concentrated affording the title compound (759 mg, 2.51 mmol, 98%) which was used without further purification: LC-MS (ES) m/z=273 (M+H)⁺.

b) 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-(methyloxy)-2-thiophenecarboxamide

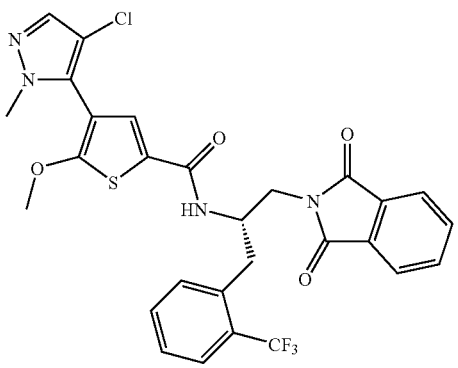 [SMILES: COc1sc(C(=O)N[C@@H](Cc2ccccc2C(F)(F)F)CN2C(=O)c3ccccc3C2=O)cc1-c1c(Cl)cnn1C]

To a 50 mL round-bottomed flask was added 4-(4-chloro-1-methyl-1H-pyrazol-5-yl)-5-(methyloxy)-2-thiophenecarboxylic acid (85 mg, 0.31 mmol), 2-{(2S)-2-amino-3-[2-(trifluoromethyl)phenyl]propyl}-1H-isoindole-1,3(2H)-dione (119 mg, 0.31 mmol) [prepared according to the procedure of Preparation 6] and PyBrop (180 mg, 0.384 mmol) in chloroform (3.5 mL). DIEA (270 µL, 1.54 mmol) was added and the reaction stirred overnight at room temperature. The mixture was adsorbed onto silica and purified via column chromatography (25-70% EtOAc/Hex) affording the title compound (94 mg, 0.14 mmol, 45%): LC-MS (ES) m/z=603 (M+H)⁺.

c) N-((1S)-2-amino-1-{[2-(trifluoromethyl)phenyl]methyl}ethyl)-4-(4-chloro-1-methyl-1H-pyrazol-5-yl)-5-(methyloxy)-2-thiophenecarboxamide To a 50 mL round-bottomed flask was added 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-5-(methyloxy)-2-thiophenecarboxamide (94 mg, 0.16 mmol) in Tetrahydrofuran (THF) (2 mL) and Methanol (1 mL). Hydrazine (35 µL, 1.12 mmol) was added and the reaction stirred overnight at room temperature. The mixture was adsorbed onto silica gel and purified via column chromatography (90:10:1 CHCl₃/MeOH/NH₄OH).

The neutral compound was dissolved in MeOH (2 mL), treated with excess 2M HCl in Et₂O and concentrated affording the HCl salt of the title compound (27 mg, 0.05 mmol, 31% yield): LC-MS (ES) m/z=473 (M+H)⁺, ¹H NMR (400 MHz, DMSO-d₆) δ ppm 2.93-3.14 (m, 4H) 3.73 (s, 3H) 4.00 (s, 3H) 4.41-4.54 (m, 1H) 7.43 (t, J=7.45 Hz, 1H) 7.57 (ddd, J=14.59, 7.58, 7.39 Hz, 2H) 7.62-7.65 (m, 1H) 7.69 (d, J=7.83 Hz, 1H) 7.82-7.89 (m, 1H) 8.12 (s, 3H) 8.80 (d, J=9.09 Hz, 1H).

Example 189

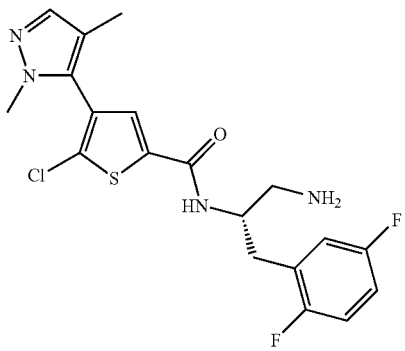 [SMILES: Cc1cnn(C)c1-c1cc(C(=O)N[C@H](CN)Cc2cc(F)ccc2F)sc1Cl]

Preparation of N-{(1S)-2-amino-1-[(2,5-difluorophenyl)methyl]ethyl}-5-chloro-4-(1,4-dimethyl-1H-pyrazol-5-yl)-2-thiophenecarboxamide a) methyl 5-chloro-4-(1,4-dimethyl-1H-pyrazol-5-yl)-2-thiophenecarboxylate

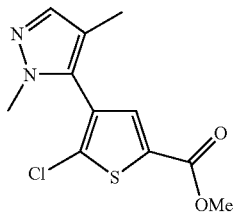 [SMILES: COC(=O)c1cc(-c2c(C)cnn2C)c(Cl)s1]

To a 350 mL sealed flask reactor was added methyl 4-bromo-5-chloro-2-thiophenecarboxylate (409 mg, 1.60 mmol) [prepared according to the procedure of Example 95], 1,4-dimethyl-5-(4,4,5,5-tetramethyl-1,3,2-dioxaborolan-2-yl)-1H-pyrazole (388 mg, 1.75 mmol) [prepared according to the procedure of Preparation 17], K$_2$CO$_3$ (676 mg, 4.89 mmol) and Pd(PtBu$_3$)$_2$ (32 mg, 0.06 mmol) in 1,4-Dioxane (6 mL) and water (1.5 mL). The reaction was heated at 85° C. for 3 hours. The reaction was partitioned between CHCl$_3$/H$_2$O and the pH of the aqueous layer was adjusted to ~3 with 6N HCl. The separated organic layer was dried with Na$_2$SO$_4$, adsorbed onto silica and purified via column chromatography (10-65% EtOAc/Hexanes) affording the title compound (106 mg, 0.39 mmol, %); LC-MS (ES) m/z=271 (M+H)$^+$.

b) 5-chloro-4-(1,4-dimethyl-1H-pyrazol-5-yl)-2-thiophenecarboxylic Acid

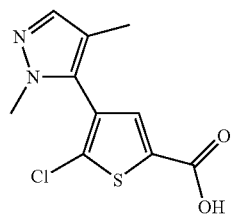 [SMILES: Cc1cnn(C)c1-c1cc(C(=O)O)sc1Cl]

To a 100 mL round-bottomed flask was added methyl 5-chloro-4-(1,4-dimethyl-1H-pyrazol-5-yl)-2-thiophenecarboxylate (106 mg, 0.39 mmol) in Tetrahydrofuran (THF) (2 mL). 6N NaOH (2 mL, 12.00 mmol) was added slowly and the reaction mixture stirred overnight at 70° C. The reaction was cooled to room temperature, partitioned between CHCl$_3$ and H$_2$O and the pH of the aqueous layer was adjusted to ~3 by the addition of 6N HCl. The layers were separated, the organic layer dried over Na$_2$SO$_4$ and concentrated affording the desired compound (96 mg, 0.37 mmol, 95%): LC-MS (ES) m/z=257 (M+H)$^+$.

c) 5-chloro-N-{(1S)-2-(2,5-difluorophenyl)-1-[(1,3-dioxo-1,3-dihydro-2H-isoindol-2-yl)methyl]ethyl}-4-(1,4-dimethyl-1H-pyrazol-5-yl)-2-thiophenecarboxamide

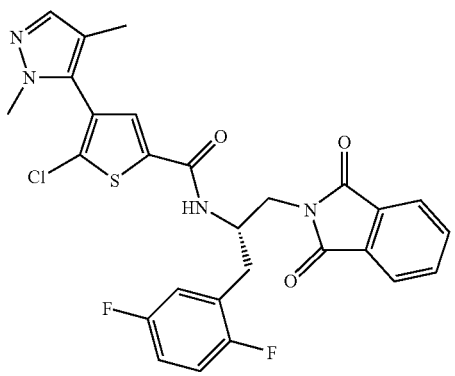 [SMILES: Cc1cnn(C)c1-c1cc(C(=O)N[C@@H](Cc2cc(F)ccc2F)CN2C(=O)c3ccccc3C2=O)sc1Cl]

To a 50 mL round-bottomed flask was added 5-chloro-4-(1,4-dimethyl-1H-pyrazol-5-yl)-2-thiophenecarboxylic acid (96 mg, 0.37 mmol), 2-[(2S)-2-amino-3-(2,5-difluorophenyl)propyl]-1H-isoindole-1,3(2H)-dione (125 mg, 0.40 mmol) [prepared according to the procedure of Preparation 18 except substituting 2,5-difluoro-L-phenylalanine (3.02 g, 15.0 mmol) for 2,6-difluoro-L-phenylalanine] and PyBrop (225 mg, 0.48 mmol) in chloroform (4 mL). DIEA (330 µL, 1.89 mmol) was added and the reaction stirred overnight at room temperature. The mixture was adsorbed onto silica and purified via column chromatography (25-70% EtOAc/Hex) affording the title compound (98 mg, 0.13 mmol, 34%): LC-MS (ES) m/z=535 (M+H)$^+$.

d) N-{(1S)-2-amino-1-[(2,5-difluorophenyl)methyl]ethyl}-5-chloro-4-(1,4-dimethyl-1H-pyrazol-5-yl)-2-thiophenecarboxamide To a 50 mL round-bottomed flask was added 5-chloro-N-{(1S)-2-(2,5-difluorophenyl)-1-[(1,3-dioxo-1,3-dihydro-2H-isoindol-2-yl)methyl]ethyl}-4-(1,4-dimethyl-1H-pyrazol-5-yl)-2-thiophenecarboxamide (98 mg, 0.18 mmol) in Tetrahydrofuran (THF) (3 mL) and Methanol (1 mL). Hydrazine (40 µL, 1.27 mmol) was added and the reaction stirred overnight at room temperature. The mixture was adsorbed onto silica gel and purified via column chromatography (90:10:1 CHCl3/MeOH/NH4OH).

The neutral compound was dissolved in MeOH (2 mL), treated with excess 2M HCl in Et$_2$O and concentrated affording the HCl salt of the title compound (52 mg, 0.10 mmol, 56% yield): LC-MS (ES) m/z=425 (M+H)$^+$, $^1$H NMR (400 MHz, DMSO-d6) δ ppm 1.94 (s, 3H) 2.87-3.09 (m, 4H) 3.69 (s, 3H) 4.42 (d, J=6.32 Hz, 1H) 7.10 (ddd, J=12.00, 8.34, 3.41 Hz, 1H) 7.20 (td, J=9.16, 4.67 Hz, 1H) 7.27 (ddd, J=8.97, 5.56, 3.16 Hz, 1H) 7.39 (s, 1H) 8.06 (s, 1H) 8.13 (s, 3H) 9.13 (d, J=8.84 Hz, 1H).

Example 190

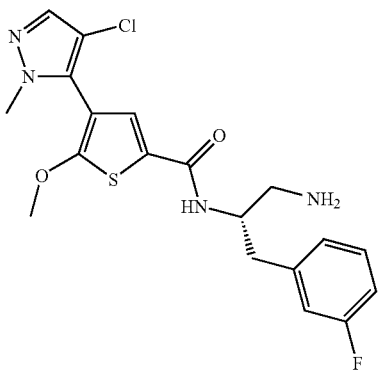 [SMILES: COc1sc(C(=O)N[C@H](CN)Cc2cccc(F)c2)cc1-c1c(Cl)cnn1C]

Preparation of N-{(1S)-2-amino-1-[(3-fluorophenyl)methyl]ethyl}-4-(4-chloro-1-methyl-1H-pyrazol-5-yl)-5-(methyloxy)-2-thiophenecarboxamide a) 4-(4-chloro-1-methyl-1H-pyrazol-5-yl)-N-{(1S)-2-(1,3-dioxo-1,3-dihydro-2H-isoindol-2-yl)-1-[(3-fluorophenyl)methyl]ethyl}-5-(methyloxy)-2-thiophenecarboxamide

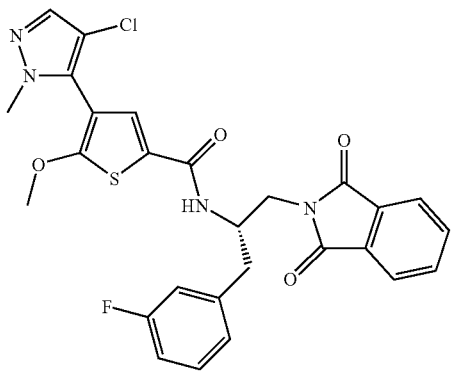 [SMILES: COc1sc(C(=O)N[C@@H](Cc2cccc(F)c2)CN2C(=O)c3ccccc3C2=O)cc1-c1c(Cl)cnn1C]

To a 50 mL round-bottomed flask was added 4-(4-chloro-1-methyl-1H-pyrazol-5-yl)-5-(methyloxy)-2-thiophenecarboxylic acid (220 mg, 0.81 mmol) [prepared according to the procedure of Example 188], 2-[(2S)-2-amino-3-(3-fluorophenyl)propyl]-1H-isoindole-1,3(2H)-dione (281 mg, 0.84 mmol) [prepared according to the procedure of Preparation 6, except substituting N-{[(1,1-dimethylethyl)oxy]carbonyl}-3-fluoro-L-phenylalanine (5.03 g, 17.8 mmol) for N-{[(1,1-dimethylethyl)oxy]carbonyl}-2-(trifluoromethyl)-L-phenylalanine] and PyBrop (472 mg, 1.0 mmol) in Chloroform (8 mL). DIEA (710 μL, 4.07 mmol) was added and the reaction stirred overnight at room temperature. The mixture was adsorbed onto silica and purified via column chromatography (25-70% EtOAc/Hex) affording the title compound (281 mg, 0.51 mmol, 63%): LC-MS (ES) m/z=553 (M+H)$^+$.

b) N-{(1S)-2-amino-1-[(3-fluorophenyl)methyl]ethyl}-4-(4-chloro-1-methyl-1H-pyrazol-5-yl)-5-(methyloxy)-2-thiophenecarboxamide To a 50 mL round-bottomed flask was added 4-(4-chloro-1-methyl-1H-pyrazol-5-yl)-N-{(1S)-2-(1,3-dioxo-1,3-dihydro-2H-isoindol-2-yl)-1-[(3-fluorophenyl)methyl]ethyl}-5-(methyloxy)-2-thiophenecarboxamide (281 mg, 0.51 mmol) in Tetrahydrofuran (THF) (4.5 mL) and Methanol (1 mL). Hydrazine (120 μL, 3.82 mmol) was added and the reaction stirred overnight at room temperature. The mixture was adsorbed onto silica gel and purified via column chromatography (90:10:1 CHCl$_3$/MeOH/NH$_4$OH).

The neutral compound was dissolved in MeOH (2 mL), treated with excess 2M HCl in Et$_2$O and concentrated affording the HCl salt of the title compound (145 mg, 0.28 mmol, 55% yield): LC-MS (ES) m/z=423 (M+H)$^+$, $^1$H NMR (400 MHz, DMSO-d$_6$) δ ppm 2.86-3.04 (m, 4H) 3.71 (s, 3H) 4.02 (s, 3H) 4.31-4.41 (m, 1H) 7.00-7.07 (m, 1H) 7.11 (d, J=7.58 Hz, 2H) 7.28-7.36 (m, 1H) 7.64 (s, 1H) 7.73-7.78 (m, 1H) 7.98 (s, 3H) 8.54 (s, 1H).

Example 191

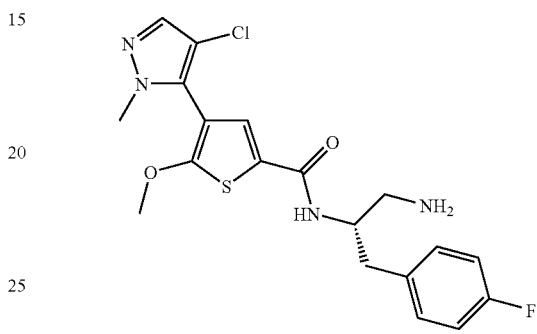

Preparation of N-{(1S)-2-amino-1-[(4-fluorophenyl)methyl]ethyl}-4-(4-chloro-1-methyl-1H-pyrazol-5-yl)-5-(methyloxy)-2-thiophenecarboxamide a) 4-(4-chloro-1-methyl-1H-pyrazol-5-yl)-N-{(1S)-2-(1,3-dioxo-1,3-dihydro-2H-isoindol-2-yl)-1-[(4-fluorophenyl)methyl]ethyl}-5-(methyloxy)-2-thiophenecarboxamide

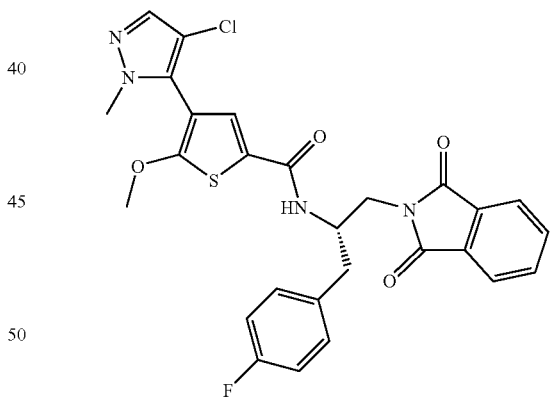

To a 50 mL round-bottomed flask was added 4-(4-chloro-1-methyl-1H-pyrazol-5-yl)-5-(methyloxy)-2-thiophenecarboxylic acid (208 mg, 0.76 mmol) [prepared according to the procedure of Example 188], 2-[(2S)-2-amino-3-(4-fluorophenyl)propyl]-1H-isoindole-1,3(2H)-dione (257 mg, 0.77 mmol) [prepared according to the procedure of Preparation 6, except substituting N-{[(1,1-dimethylethyl)oxy]carbonyl}-4-fluoro-L-phenylalanine (4.95 g, 17.5 mmol) for N-{[(1,1-dimethylethyl)oxy]carbonyl}-2-(trifluoromethyl)-L-phenylalanine] and PyBrop (435 mg, 0.93 mmol) in chloroform (7.6 mL). DIEA (670 μL, 3.84 mmol) was added and the reaction stirred overnight at room temperature. The mixture was adsorbed onto silica and purified via column chromatography (25-70% EtOAc/Hex) affording the title compound (238 mg, 0.43 mmol, 56%): LC-MS (ES) m/z=553 (M+H)$^+$.

b) N-{(1S)-2-amino-1-[(4-fluorophenyl)methyl]ethyl}-4-(4-chloro-1-methyl-1H-pyrazol-5-yl)-5-(methyloxy)-2-thiophenecarboxamide To a 50 mL round-bottomed flask was added 4-(4-chloro-1-methyl-1H-pyrazol-5-yl)-N-{(1S)-2-(1,3-dioxo-1,3-dihydro-2H-isoindol-2-yl)-1-[(4-fluorophenyl)methyl]ethyl}-5-(methyloxy)-2-thiophenecarboxamide (238 mg, 0.43 mmol) in Tetrahydrofuran (THF) (4 mL) and Methanol (1 mL). Hydrazine (95 µL, 3.03 mmol) was added and the reaction stirred overnight at room temperature. The mixture was adsorbed onto silica gel and purified via column chromatography (90:10:1 $CHCl_3$/MeOH/$NH_4OH$).

The neutral compound was dissolved in MeOH (2 mL), treated with excess 2M HCl in $Et_2O$ and concentrated affording the HCl salt of the title compound (113 mg, 0.22 mmol, 50% yield): LC-MS (ES) m/z=423 (M+H)$^+$, $^1$H NMR (400 MHz, DMSO-$d_6$) δ ppm 2.82-2.92 (m, 2H) 2.93-3.03 (m, 2H) 3.71 (s, 3H) 4.02 (s, 3H) 4.26-4.37 (m, 1H) 7.11 (t, J=8.46 Hz, 2H) 7.26-7.32 (m, 2H) 7.64 (s, 1H) 7.69-7.84 (m, 1H) 7.95 (s, 3H) 8.45-8.52 (m, 1H).

Example 192

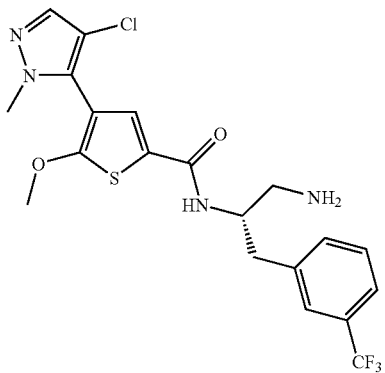 [SMILES: COc1sc(C(=O)N[C@H](CN)Cc2cccc(C(F)(F)F)c2)cc1-c1c(Cl)cnn1C]

Preparation of N-((1S)-2-amino-1-{[3-(trifluoromethyl)phenyl]methyl}ethyl)-4-(4-chloro-1-methyl-1H-pyrazol-5-yl)-5-(methyloxy)-2-thiophenecarboxamide a) 4-(4-chloro-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-(methyloxy)-2-thiophenecarboxamide

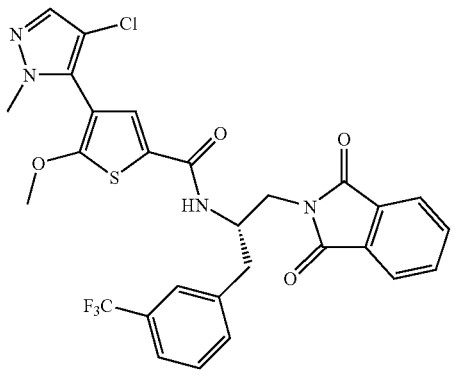 [SMILES: COc1sc(C(=O)N[C@@H](Cc2cccc(C(F)(F)F)c2)CN2C(=O)c3ccccc3C2=O)cc1-c1c(Cl)cnn1C]

To a 50 mL round-bottomed flask was added 4-(4-chloro-1-methyl-1H-pyrazol-5-yl)-5-(methyloxy)-2-thiophenecarboxylic acid (210 mg, 0.77 mmol) [prepared according to the procedure of Example 188], 2-{(2S)-2-amino-3-[3-(trifluoromethyl)phenyl]propyl}-1H-isoindole-1,3(2H)-dione (294 mg, 0.764 mmol) [prepared according to the procedure of Preparation 6, except substituting N-{[(1,1-dimethylethyl)oxy]carbonyl}-3-(trifluoromethyl)-L-phenylalanine (4.98 g, 15.0 mmol) for N-{[(1,1-dimethylethyl)oxy]carbonyl}-2-(trifluoromethyl)-L-phenylalanine] and PyBrop (442 mg, 0.94 mmol) in chloroform (7.6 mL). DIEA (670 µL, 3.84 mmol) was added and the reaction stirred overnight at room temperature. The mixture was adsorbed onto silica and purified via column chromatography (25-70% EtOAc/Hex) affording the title compound (238 mg, 0.43 mmol, 56%): LC-MS (ES) m/z=603 (M+H)$^+$.

b) N-((1S)-2-amino-1-{[3-(trifluoromethyl)phenyl]methyl}ethyl)-4-(4-chloro-1-methyl-1H-pyrazol-5-yl)-5-(methyloxy)-2-thiophenecarboxamide To a 50 mL round-bottomed flask was added 4-(4-chloro-1-methyl-1H-pyrazol-5-yl)-N-((1S)-2-(1,3-dioxo-1,3-dihydro-2H-isoindol-2-yl)-1-{[3-(trifluoromethyl)phenyl]methyl}ethyl)-5-(methyloxy)-2-thiophenecarboxamide (203 mg, 0.34 mmol) in Tetrahydrofuran (THF) (3 mL) and Methanol (1 mL). Hydrazine (80 µL, 2.55 mmol) was added and the reaction stirred overnight at room temperature. The mixture was adsorbed onto silica gel and purified via column chromatography (90:10:1 $CHCl_3$/MeOH/$NH_4OH$).

The neutral compound was dissolved in MeOH (2 mL), treated with excess 2M HCl in $Et_2O$ and concentrated affording the HCl salt of the title compound (86 mg, 0.15 mmol, 44% yield): LC-MS (ES) m/z=473 (M+H)$^+$, $^1$H NMR (400 MHz, DMSO-$d_6$) δ ppm 2.92-3.08 (m, 4H) 3.70 (s, 3H) 4.01 (s, 3H) 4.30-4.42 (m, 1H) 7.50-7.60 (m, 3H) 7.61-7.66 (m, 2H) 7.73-7.81 (m, 1H) 8.00 (s, 3H) 8.52-8.68 (m, 1H).

Example 193

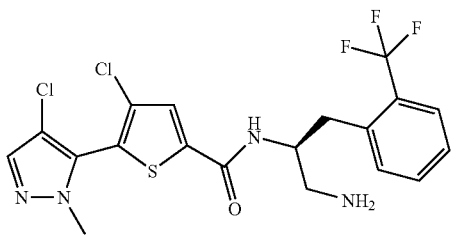 [SMILES: Cn1ncc(Cl)c1-c1sc(C(=O)N[C@H](CN)Cc2ccccc2C(F)(F)F)cc1Cl]

Preparation of N-((1S)-2-amino-1-{[2-(trifluoromethyl)phenyl]methyl}ethyl)-4-chloro-5-(4-chloro-1-methyl-1H-pyrazol-5-yl)-2-thiophenecarboxamide a) 4-chloro-5-(1-methyl-1H-pyrazol-5-yl)-2-thiophenecarboxylic Acid

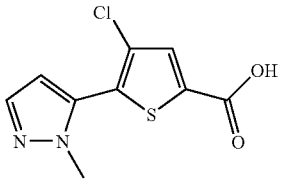

To a solution of 5-bromo-4-chloro-2-thiophenecarboxylic acid (482 mg, 2 mmol) in dioxane/$H_2O$ (4:1, 10 mL) was added 1,1'-bis(diphenylphosphino)ferrocenedichloro Palladium (II) dichloromethane complex (16.3 mg, 0.02 mmol), potassium carbonate (828 mg, 6 mmol) and 5-(5,5-dimethyl-1,3,2-dooxaborinan-2-yl)-1-methyl-1H-pyrazole (832 mg, 4 mmol)[prepared according to Preparation 7]. The reaction mixture was heated to 80° C. in a sealed tube for 20 hrs. The reaction mixture was poured into H₂O (100 mL) and extracted with DCM. The organic layer was dried over Na₂SO₄, concentrated and purified using silica (EtOAc/hexane (0-45% gradient)) affording the title compound as a white solid (401.7 mg, 83%): LC-MS (ES) m/z=243 (M+H)⁺.

b) 4-chloro-5-(4-chloro-1-methyl-1H-pyrazol-5-yl)-2-thiophenecarboxylic Acid

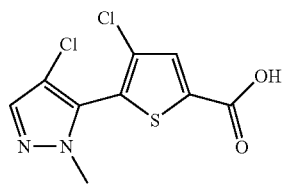 [SMILES: Cn1ncc(Cl)c1-c1sc(C(=O)O)cc1Cl]

A solution of 4-chloro-5-(1-methyl-1H-pyrazol-5-yl)-2-thiophenecarboxylic acid (121 mg, 0.5 mmol) and N-chlorosuccinimide (67 mg, 0.5 mmol) in THF (5 mL) was stirred in a sealed tube at 70° C. After 4 hrs, the solution was concentrated and partitioned between DCM and H₂O. The aqueous layer was extracted several times with DCM. The organic fractions were combined, concentrated and azeotropically dried with toluene to give the title compound as a brown oil (136 mg, 98%): LC-MS (ES) m/z=278 (M+H)⁺.

c). 4-chloro-5-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

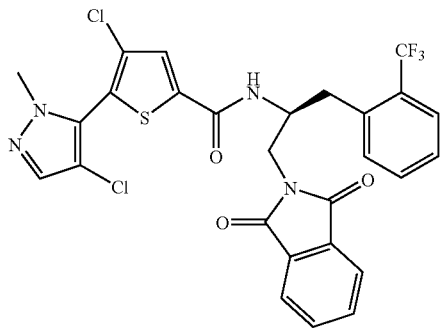 [SMILES: Cn1ncc(Cl)c1-c1sc(C(=O)N[C@@H](Cc2ccccc2C(F)(F)F)CN2C(=O)c3ccccc3C2=O)cc1Cl]

To a solution of 4-chloro-5-(4-chloro-1-methyl-1H-pyrazol-5-yl)-2-thiophenecarboxylic acid (136.1 mg, 0.49 mmol), 2-{(2S)-2-amino-3-[2-(trifluoromethyl)phenyl]propyl}-1H-isoindole-1,3(2H)-dione (179 mg, 0.51 mmol)[prepared according to Preparation 6], diisopropylethyl amine (260 uL, 1.5 mmol) in DCM (5 mL) was added PyBrop (341 mg, 0.75 mmol) in one portion. After 1 h, the reaction contents were partitioned between H₂O/DCM. The aqueous phase was washed several times with DCM and the combined organic fractions were dried over Na₂SO₄, concentrated and purified via column chromatography (silica, gradient 0-50% ethyl acetate/hexane) affording the title compound (242 mg, 82%) as a white solid: LCMS (ES) m/z=607 (M+H)⁺.

d) N-((1S)-2-amino-1-{[2-(trifluoromethyl)phenyl]methyl}ethyl)-4-chloro-5-(4-chloro-1-methyl-1H-pyrazol-5-yl)-2-thiophenecarboxamide To a solution of 4-chloro-5-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (242 mg, 0.4 mmol) in THF-MeOH (1:1, 4 mL) was added hydrazine (75 uL, 2.42 mmol). After 12 h, the solution was concentrated. The resulting residue was partitioned between DCM and H₂O. The organics were washed three times with water and acidified to pH ~1 with 6N aqueous HCl solution. The resulting mixture was extracted with water. The aqueous fractions were combined and concentrated to afford the di-HCl salt of the desired product as a light yellow solid (77 mg, 40%): LCMS (ES) m/z 477 (M+H)⁺, ¹H NMR (400 MHz, DMSO-d₆) δ ppm 3.08-3.11 (m, 4H) 3.75 (s, 3H) 4.50 (br. s., 1H) 7.45 (t, J=6.95 Hz, 1H) 7.55-7.63 (m, 2H) 7.71 (d, J=7.83 Hz, 1H) 7.78 (s, 1H) 8.02-8.10 (m, 3H) 8.12 (s, 1H) 9.12 (d, J=9.09 Hz, 1H)

Example 194

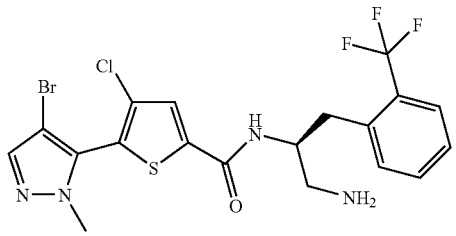 [SMILES: Cn1ncc(Br)c1-c1sc(C(=O)N[C@H](CN)Cc2ccccc2C(F)(F)F)cc1Cl]

Preparation of N-((1S)-2-amino-1-{[2-(trifluoromethyl)phenyl]methyl}ethyl)-4-chloro-5-(4-bromo-1-methyl-1H-pyrazol-5-yl)-2-thiophenecarboxamide The title compound was prepared as a light yellow solid according to the procedure of Example 193, except substituting N-bromosuccinimide (89 mg, 0.5 mmol) for and N-chlorosuccinimide: LCMS (ES) m/z 522 (M+H)⁺, ¹H NMR (400 MHz, DMSO-d₆) δ ppm 3.0-3.13 (m, 4H) 3.76 (s, 3H) 4.50 (br. s., 1H) 7.46 (d, J=7.58 Hz, 1H) 7.55-7.66 (m, 2H) 7.71 (d, J=7.83 Hz, 1H) 7.78 (s, 1H) 8.04 (br. s., 4H).

Example 195

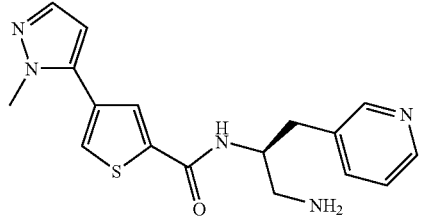 [SMILES: Cn1nccc1-c1csc(C(=O)N[C@H](CN)Cc2cccnc2)c1]

Preparation of N-[(1S)-2-amino-1-(3-pyridinylmethyl)ethyl]-4-(1-methyl-1H-pyrazol-5-yl)-2-thiophenecarboxamide The title compound was prepared as a light yellow solid according to the procedure of Example 6, except substituting 4-bromo-2-thiophenecarboxylic acid (62 mg, 0.3 mmol) for 5-bromo-2-thiophenecarboxylic acid and substituting 2-[(2S)-2-amino-3-(3-pyridinyl)propyl]-1H-isoindole-1,3(2H)-dione-HCl (84 mg, 0.3 mmol)[prepared according to Preparation 19] for 2-{(2S)-2-amino-3-[2-(trifluoromethyl)phenyl]propyl}-1H-isoindole-1,3(2H)-dione-HCl: LC-MS (ES) m/z=342 (M+H)⁺, ¹H NMR (CD₃OD, 400 MHz) δ ppm 3.17 (dd, J=13.89, 10.86 Hz, 1H) 3.33-3.36 (m, 2H) 3.36-3.44 (m, 1H) 3.96 (s, 3H) 4.70 (dd, J=14.02, 6.19 Hz, 1H) 6.47 (s, 1H) 7.51 (s, 1H) 7.88 (d, J=1.26 Hz, 1H) 7.94 (s, 1H) 8.02 (t, J=6.32 Hz, 1H) 8.61 (d, J=7.83 Hz, 1H) 8.76 (br. s., 1H) 8.89 (br. s., 1H).

Example 196

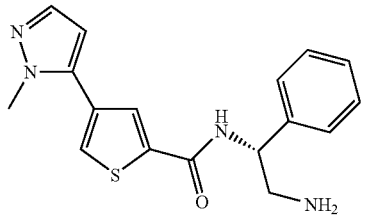 [SMILES: Cn1nccc1-c1csc(C(=O)N[C@@H](CN)c2ccccc2)c1]

Preparation of N-[(1R)-2-amino-1-phenylethyl]-4-(1-methyl-1H-pyrazol-5-yl)-2-thiophenecarboxamide The title compound was prepared as a white solid according to the procedure of Example 20, except substituting 4-bromo-2-thiophenecarboxylic acid (83 mg, 0.4 mmol) for 4,5-dibromo-2-thiophenecarboxylic acid and substituting 1,1-dimethylethyl[(2R)-2-amino-2-phenylethyl]carbamate (94 mg, 0.4 mmol) [prepared according to the procedure of Preparation 1] for 1,1-dimethylethyl (3-amino-4-phenylbutyl)carbamate: LC-MS (ES) m/z=327 (M+H)+, $^1$H NMR (CD$_3$OD, 400 MHz) δ ppm 3.44 (d, J=4.29 Hz, 1H) 3.63 (br. s., 1H) 4.18 (s, 3H) 5.47 (dd, J=10.36, 4.55 Hz, 1H) 6.88 (d, J=2.78 Hz, 1H) 7.38 (d, J=7.07 Hz, 1H) 7.44 (t, J=7.33 Hz, 2H) 7.55 (d, J=7.83 Hz, 2H) 8.08 (d, J=2.53 Hz, 1H) 8.18 (d, J=1.26 Hz, 1H) 8.42 (d, J=1.26 Hz, 1H).

Example 197

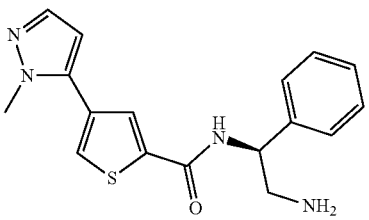 [SMILES: Cn1nccc1-c1csc(C(=O)N[C@H](CN)c2ccccc2)c1]

Preparation of N-[(1S)-2-amino-1-phenylethyl]-4-(1-methyl-1H-pyrazol-5-yl)-2-thiophenecarboxamide The title compound was prepared as a white solid according to the procedure of Example 20, except substituting 4-bromo-2-thiophenecarboxylic acid (83 mg, 0.4 mmol) for 4,5-dibromo-2-thiophenecarboxylic acid and substituting 1,1-dimethylethyl[(2S)-2-amino-2-phenylethyl]carbamate (94 mg, 0.4 mmol) [prepared according to the procedure of Preparation 1] for 1,1-dimethylethyl (3-amino-4-phenylbutyl)carbamate: LC-MS (ES) m/z 327 (M+H)+, $^1$H NMR (400 MHz, MeOD) δ ppm 3.44 (d, J=2.78 Hz, 1H) 3.60 (br. s., 1H) 4.06 (br. s., 3H) 5.47 (dd, J=10.36, 4.29 Hz, 1H) 6.70 (br. s., 1H) 7.38 (d, J=6.82 Hz, 1H) 7.44 (t, J=7.20 Hz, 2H) 7.53 (d, J=7.58 Hz, 2H) 7.79 (br. s., 1H) 8.04 (br. s., 1H) 8.32 (br. s., 1H).

Example 198

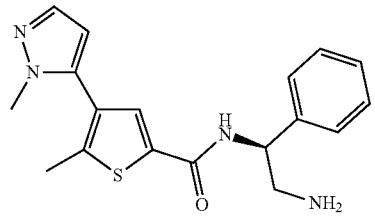

Preparation of N-[(1S)-2-amino-1-phenylethyl]-5-methyl-4-(1-methyl-1H-pyrazol-5-yl)-2-thiophenecarboxamide a) methyl 5-methyl-4-(1-methyl-1H-pyrazol-5-yl)-2-thiophenecarboxylate

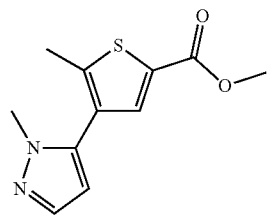

A solution of methyl 4-bromo-5-methyl-2-thiophenecarboxylate (2 g, 8.51 mmol)[prepared in Preparation 10], potassium carbonate (5.88 g, 42.5 mmol), 1-methyl-5-(4,4,5,5-tetramethyl-1,3,2-dioxaborolan-2-yl)-1H-pyrazole (2.12 g, 10.21 mmol)[prepared according to Preparation 7] and bis (tri-t-butylphosphine)palladium(0) (0.22 g, 0.43 mmol) in 1,4-Dioxane (35 ml) and H$_2$O (7 ml) was stirred at 80° C. in a sealed tube for 1 h. The reaction mixture was then partitioned between H$_2$O-DCM and the aqueous phase was washed several times with DCM. The combined organic fractions were dried over Na$_2$SO$_4$, concentrated and purified via column chromatography (silica, 25% EtOAc in hexanes) affording methyl 5-methyl-4-(1-methyl-1H-pyrazol-5-yl)-2-thiophenecarboxylate. This reaction was run in several batches (1 g, 3×2 g) which were combined for workup and purification affording the title compound (5.5 g, 78% combined yield) as a viscous yellow oil: LC-MS (ES) m/e 236 (M+H)+.

b) 5-methyl-4-(1-methyl-1H-pyrazol-5-yl)-2-thiophenecarboxylic Acid

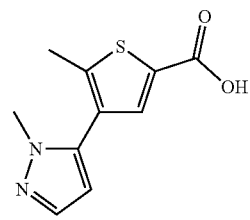

A solution of methyl 5-methyl-4-(1-methyl-1H-pyrazol-5-yl)-2-thiophenecarboxylate (94 mg, 0.4 mmol) in 6N sodium hydroxide (0.67 ml, 4 mmol) and tetrahydrofuran (4 ml) was stirred at 70° C. in a sealed tube for 1 h. The resulting solution was cooled and then partitioned between H$_2$O-DCM. The aqueous phase was adjusted to pH ~3 and then washed several times with DCM. The combined organic fractions were dried over Na$_2$SO$_4$ and concentrated affording the desired product (67 mg, 0.3 mmol, 75% yield) as a yellow oil: LC-MS (ES) m/e 223 (M+H)$^+$.

c) 1,1-dimethylethyl[(2S)-2-({[5-methyl-4-(1-methyl-1H-pyrazol-5-yl)-2-thienyl]carbonyl}amino)-2-phenylethyl]carbamate

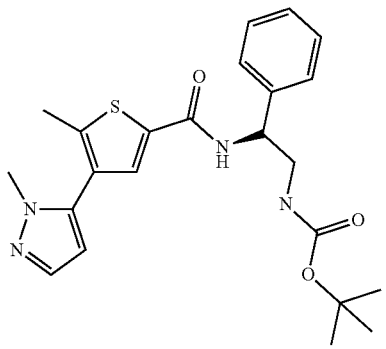

To a solution of 5-methyl-4-(1-methyl-1H-pyrazol-5-yl)-2-thiophenecarboxylic acid (67 mg, 0.3 mmol), 1,1-dimethylethyl[(2S)-2-amino-2-phenylethyl]carbamate (71 mg, 0.3 mmol) [prepared according to the procedure of Preparation 1] and diisopropylethylamine (0.16 ml, 0.9 mmol) in DCM at 25° C. was added bromo-tris-pyrrolidino-phosphonium hexafluorophosphate (210 mg, 0.45 mmol) in one portion. The solution stirred at 25° C. for 12 h and was then partitioned between H$_2$O-DCM. The aqueous phase was washed several times with DCM and the combined organic fractions were dried over Na$_2$SO$_4$, concentrated and purified via column chromatography (silica, 30-70% EtOAc in hexanes) yielding the title compound (87 mg, 0.2 mmol, 65% yield) as a yellow foam: LC-MS (ES) m/e 441 (M+H)$^+$.

d). N-[(1S)-2-amino-1-phenylethyl]-5-methyl-4-(1-methyl-1H-pyrazol-5-yl)-2-thiophenecarboxamide To a solution of 1,1-dimethylethyl[(2S)-2-({[4-(1,4-dimethyl-1H-pyrazol-5-yl)-2-thienyl]carbonyl}amino)-2-phenylethyl]carbamate (87 mg, 0.2 mmol) in DCM (2 mL) was added 4N HCl solution in dioxane (0.5 mL, 2 mmol) which stirred at ambient temperature for 15 h. The solution was extracted with water three times. The aqueous fractions were combined and concentrated to afford the di-HCl salt of the title compound as a white solid (26 mg, 0.06 mmol, 32%): LC-MS (ES) m/z 341 (M+H)$^+$, $^1$H NMR (400 MHz, MeOD) δ ppm 2.49 (br. s., 3H) 3.43 (d, J=4.80 Hz, 1H) 3.55 (d, J=10.36 Hz, 1H) 3.95 (s, 3H) 5.41-5.43 (m, 1H) 6.66 (d, J=2.27 Hz, 1H) 7.38 (d, J=7.07 Hz, 1H) 7.44 (t, J=7.33 Hz, 2H) 7.48-7.53 (m, 2H) 7.94-8.02 (m, 2H).

Example 199

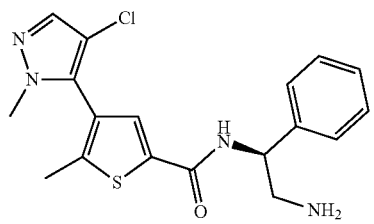 [SMILES: Cc1sc(C(=O)N[C@H](CN)c2ccccc2)cc1-c1c(Cl)cnn1C]

Preparation of N-[(1S)-2-amino-1-phenylethyl]-4-(4-chloro-1-methyl-1H-pyrazol-5-yl)-5-methyl-2-thiophenecarboxamide The title compound was prepared as a white solid according to the procedure of Example 24, except substituting 5-methyl-4-(1-methyl-1H-pyrazol-5-yl)-2-thiophenecarboxylic acid (89 mg, 0.4 mmol) [prepared according to Example 198] for 4-(1-methyl-1H-pyrazol-5-yl)-2-thiophenecarboxylic acid and substituting 1,1-dimethylethyl (2-amino-3-phenylpropyl)carbamate (94 mg, 0.4 mmol) [prepared according to the procedure of Preparation 1] for 1,1-dimethylethyl (3-amino-4-phenylbutyl)carbamate: LC-MS (ES) m/z 375 (M+H)$^+$, $^1$H NMR (400 MHz, MeOD) δ ppm 2.38-2.41 (m, 1H), 3.38 (d, J=1.52 Hz, 1H) 3.49 (d, J=10.86 Hz, 1H) 3.73 (br. s., 3H) 5.41 (d, J=3.54 Hz, 1H) 7.30-7.50 (m, 5H) 7.54-7.62 (m, 1H) 7.81 (br. s., 1H).

Example 200

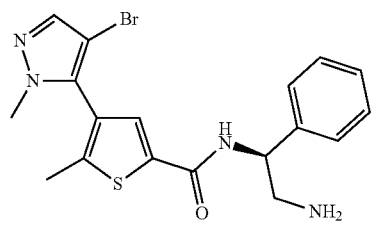 [SMILES: Cc1sc(C(=O)N[C@H](CN)c2ccccc2)cc1-c1c(Br)cnn1C]

Preparation of N-[(1S)-2-amino-1-phenylethyl]-4-(4-bromo-1-methyl-1H-pyrazol-5-yl)-5-methyl-2-thiophenecarboxamide The title compound was prepared as a white solid according to the procedure of Example 24, except substituting 5-methyl-4-(1-methyl-1H-pyrazol-5-yl)-2-thiophenecarboxylic acid (168 mg, 0.5 mmol) [prepared according to Example 198] for 4-(1-methyl-1H-pyrazol-5-yl)-2-thiophenecarboxylic acid, N-bromosuccinimide (88.5 mg, 0.5 mmol) for N-chlorosuccinimide and 1,1-dimethylethyl (2-amino-3-phenylpropyl)carbamate (71 mg, 0.3 mmol) [prepared according to the procedure of Preparation 1] for 1,1-dimethylethyl (3-amino-4-phenylbutyl)carbamate: LC-MS (ES) m/z 341 (M+H)$^+$, $^1$H NMR (400 MHz, MeOD) δ ppm 2.39 (d, J=4.04 Hz, 3H) 3.42 (br. s., 1H) 3.55 (br. s., 1H) 3.75-3.78 (m, 3H) 5.45 (m, 1H) 7.37 (d, J=7.07 Hz, 1H) 7.40-7.46 (m, 2H) 7.49 (br. s., 2H) 7.59-7.68 (m, 1H) 7.80-7.88 (m, 1H).

Example 201

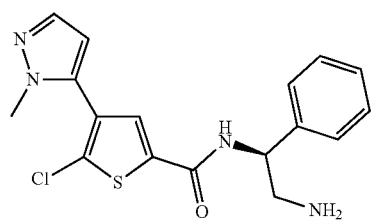

303

Preparation of N-[(1S)-2-amino-1-phenylethyl]-5-chloro-4-(1-methyl-1H-pyrazol-5-yl)-2-thiophenecarboxamide a) methyl 5-chloro-4-(1-methyl-1H-pyrazol-5-yl)-2-thiophenecarboxylate

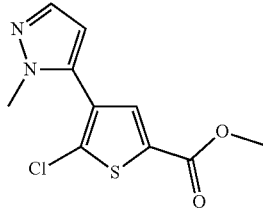

A solution of methyl 4-bromo-5-chloro-2-thiophenecarboxylate (2.56 g, 10.00 mmol)[prepared according to Example 95], 5-(5,5-dimethyl)-1,3,2-dioxaborinane-2-yl)-1-methyl-1H-pyrazole (3.88 g, 20.0 mmol)[prepared according to Preparation 7], potassium carbonate (4.15 g, 30.0 mmol) and 1,1'-bis(diphenylphosphino)ferrocenedichloro palladium (II) dichloromethane complex (0.073 g, 0.1 mmol) in 1,4-Dioxane (12 mL) and water (3.00 mL) were heated at 80° C. in a sealed tube. After 3 hrs, another batch of 5-(5,5-dimethyl)-1,3,2-dioxaborinane-2-yl)-1-methyl-1H-pyrazole (1.94 g, 10.0 mmol) and 1,1'-bis(diphenylphosphino)ferrocenedichloro palladium (II) dichloromethane complex (0.073 g, 0.1 mmol) were added. After 2 hr, the mixture was concentrated and purified by silica gel eluting with 0-35% ethyl acetate/hexane affording the title compound as a yellow solid (1.74 g, 3.35 mmol, 34%): LC-MS (ES) m/z 257 (M+H)$^+$.

b) 5-chloro-4-(1-methyl-1H-pyrazol-5-yl)-2-thiophenecarboxylic Acid

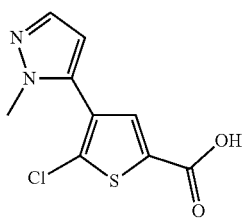

A solution of methyl 5-chloro-4-(1-methyl-1H-pyrazol-5-yl)-2-thiophenecarboxylate (304 mg, 1.18 mmol) in 6N sodium hydroxide (2 ml, 12 mmol) and Tetrahydrofuran (10 ml) was stirred at 70° C. in a sealed tube for 1 h. The resulting solution was cooled and then partitioned between H$_2$O-DCM. The aqueous phase was adjusted to pH ~3 and then washed several times with DCM. The combined organic fractions were dried over Na$_2$SO$_4$ and concentrated affording the desired product (276 mg, 1.14 mmol, 96% yield) as a yellow oil: LC-MS (ES) m/e 244 (M+H)$^+$.

304 c) 1,1-dimethylethyl[(2S)-2-({[5-chloro-4-(1-methyl-1H-pyrazol-5-yl)-2-thienyl]carbonyl}amino)-2-phenylethyl]carbamate

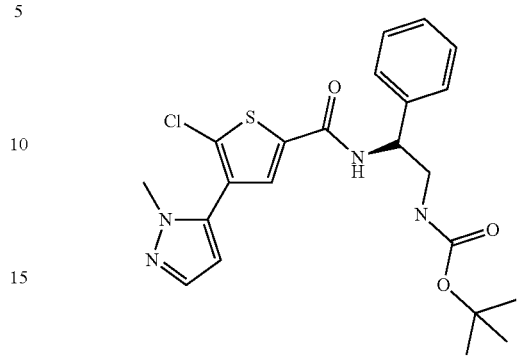

To a solution of 5-chloro-4-(1-methyl-1H-pyrazol-5-yl)-2-thiophenecarboxylic acid (60 mg, 0.25 mmol), 1,1-dimethylethyl[(2S)-2-amino-2-phenylethyl]carbamate (58 mg, 0.25 mmol) [prepared according to the procedure of Preparation 1] and diisopropylethylamine (0.12 ml, 0.75 mmol) in DCM at 25° C. was added bromo-tris-pyrrolidino-phosphonium hexafluorophosphate (190 mg, 0.41 mmol) in one portion. The solution stirred at 25° C. for 12 h and was then partitioned between H$_2$O-DCM. The aqueous phase was washed several times with DCM and the combined organic fractions were dried over Na$_2$SO$_4$, concentrated and purified via column chromatography (silica, 30-70% EtOAc in hexanes) yielding the title compound (90 mg, 0.20 mmol, 79% yield) as a colorless oil: LC-MS (ES) m/e 461 (M+H)$^+$.

d). N-[(1S)-2-amino-1-phenylethyl]-5-chloro-4-(1-methyl-1H-pyrazol-5-yl)-2-thiophenecarboxamide To a solution of 1,1-dimethylethyl[(2S)-2-({[5-chloro-4-(1-methyl-1H-pyrazol-5-yl)-2-thienyl]carbonyl}amino)-2-phenylethyl]carbamate (90 mg, 0.20 mmol) in DCM (2 mL) was added 4N HCl solution in dioxane (0.5 mL, 2 mmol). After 15 h, the solution was extracted with water three times. The aqueous fractions were combined and concentrated to afford the di-HCl salt of the title compound as a white solid (63 mg, 0.14 mmol, 74%): LC-MS (ES) m/z 361 (M+H)$^+$, $^1$H NMR (400 MHz, MeOD) δ ppm 3.41 (dd, J=13.01, 4.17 Hz, 1H) 3.63 (d, J=10.86 Hz, 1H) 4.08 (s, 3H) 5.45 (dd, J=10.48, 4.17 Hz, 1H) 6.87 (d, J=2.27 Hz, 1H) 7.36 (d, J=7.33 Hz, 1H) 7.42 (t, J=7.33 Hz, 2H) 7.54 (d, J=7.07 Hz, 2H) 8.14 (d, J=2.27 Hz, 1H) 8.27 (s, 1H).

Example 202

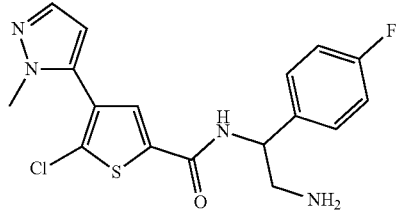 [SMILES: Cn1nccc1-c1cc(C(=O)NC(CN)c2ccc(F)cc2)sc1Cl]

Preparation of N-[2-amino-1-(4-fluorophenyl)ethyl]-5-chloro-4-(1-methyl-1H-pyrazol-5-yl)-2-thiophenecarboxamide The title compound was prepared as a white solid according to the procedure of Example 201, except substituting 1,1-dimethylethyl[2-amino-2-(4-fluorophenyl)ethyl]carbamate (63 mg, 0.25 mmol) [prepared according to the procedure of Preparation 16] for 1,1-dimethylethyl[(2S)-2-amino-2-phenylethyl]carbamate: LC-MS (ES) m/z=379 (M+H)+, 1H NMR (CD3OD, 400 MHz) δ ppm 3.40 (dd, J=13.01, 4.42 Hz, 1H) 3.66 (d, J=2.02 Hz, 1H) 4.03-4.15 (m, 3H) 5.46 (dd, J=10.36, 4.29 Hz, 1H) 6.84 (d, J=2.53 Hz, 1H) 7.15 (t, J=8.72 Hz, 2H) 7.60 (dd, J=8.59, 5.05 Hz, 2H) 8.10 (d, J=2.53 Hz, 1H) 8.29 (s, 1H).

Example 203

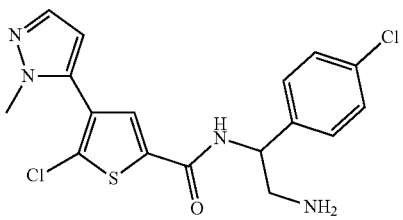 [SMILES: Cn1nccc1-c1cc(C(=O)NC(CN)c2ccc(Cl)cc2)sc1Cl]

Preparation of N-[2-amino-1-(4-chlorophenyl)ethyl]-5-chloro-4-(1-methyl-1H-pyrazol-5-yl)-2-thiophenecarboxamide The title compound was prepared as a white solid according to the procedure of Example 201, except substituting 1,1-dimethylethyl[2-amino-2-(4-chlorophenyl)ethyl]carbamate (45 mg, 0.17 mmol) [prepared according to the procedure of Preparation 16] for 1,1-dimethylethyl[(2S)-2-amino-2-phenylethyl]carbamate: LC-MS (ES) m/z=396 (M+H)+, 1H NMR (CD3OD, 400 MHz) δ ppm 3.40 (d, J=4.55 Hz, 1H) 3.58 (d, J=10.36 Hz, 1H) 3.98 (s, 3H) 5.41 (d, J=4.55 Hz, 1H) 6.71 (s, 1H) 7.43 (dt, J=4.74, 2.31 Hz, 2H) 7.47-7.56 (m, 2H) 7.92 (br. s., 1H) 8.13 (s, 1H).

Example 204

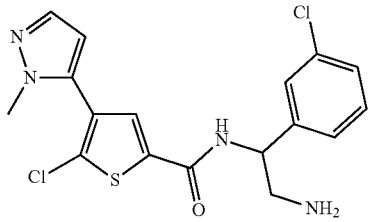 [SMILES: Cn1nccc1-c1cc(C(=O)NC(CN)c2cccc(Cl)c2)sc1Cl]

Preparation of N-[2-amino-1-(3-chlorophenyl)ethyl]-5-chloro-4-(1-methyl-1H-pyrazol-5-yl)-2-thiophenecarboxamide The title compound was prepared as a white solid according to the procedure of Example 201, except substituting 1,1-dimethylethyl[2-amino-2-(3-chlorophenyl)ethyl]carbamate (67 mg, 0.25 mmol) [prepared according to the procedure of Preparation 16] for 1,1-dimethylethyl[(2S)-2-amino-2-phenylethyl]carbamate: LC-MS (ES) m/z=396 (M+H)+, 1H NMR (CD3OD, 400 MHz) δ ppm 3.41 (dd, J=12.76, 4.93 Hz, 5H) 3.36-3.47 (m, 3H) 3.63 (s, 2H) 3.59 (d, J=10.61 Hz, 6H) 3.95 (s, 9H) 4.02 (d, J=3.03 Hz, 15H) 5.41 (dd, J=9.09, 3.79 Hz, 8H) 6.67 (d, J=2.27 Hz, 3H) 6.78 (br. s., 4H) 7.33-7.49 (m, 23H) 7.56 (br. s., 7H) 8.06 (br. s., 8H) 8.16 (d, J=16.93 Hz, 6H).

Example 205

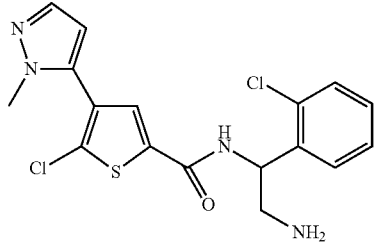

Preparation of N-[2-amino-1-(2-chlorophenyl)ethyl]-5-chloro-4-(1-methyl-1H-pyrazol-5-yl)-2-thiophenecarboxamide The title compound was prepared as a white solid according to the procedure of Example 201, except substituting 1,1-dimethylethyl[2-amino-2-(2-chlorophenyl)ethyl]carbamate (67 mg, 0.25 mmol) [prepared according to the procedure of Preparation 16] for 1,1-dimethylethyl[(2S)-2-amino-2-phenylethyl]carbamate: LC-MS (ES) m/z=396 (M+H)+, 1H NMR (CD3OD, 400 MHz) δ ppm 3.39 (br. s., 1H) 3.56 (d, J=10.86 Hz, 1H) 4.05 (d, J=3.03 Hz, 3H) 5.87 (dd, J=10.74, 3.41 Hz, 1H) 6.81 (br. s., 1H) 7.39 (br. s., 2H) 7.50 (d, J=6.57 Hz, 1H) 7.70 (d, J=7.07 Hz, 1H) 8.04 (br. s., 1H) 8.26 (br. s., 1H).

Example 206

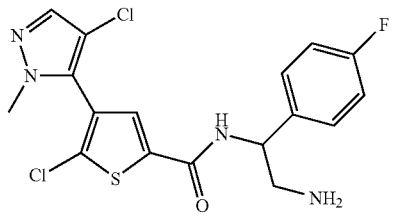 [SMILES: Cn1ncc(Cl)c1-c1cc(C(=O)NC(CN)c2ccc(F)cc2)sc1Cl]

Preparation of N-[2-amino-1-(4-fluorophenyl)ethyl]-5-chloro-4-(4-chloro-1-methyl-1H-pyrazol-5-yl)-2-thiophenecarboxamide a) 1,1-dimethylethyl[2-({[4-chloro-5-(4-chloro-1-methyl-1H-pyrazol-5-yl)-2-thienyl]carbonyl}amino)-2-(4-fluorophenyl)ethyl]carbamate

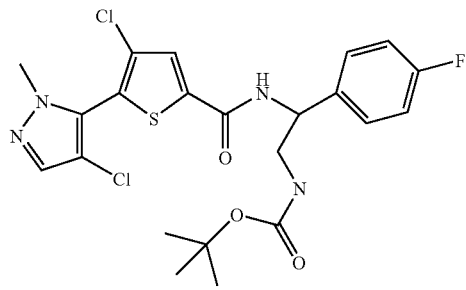 [SMILES: Cn1ncc(Cl)c1-c1sc(C(=O)NC(CNC(=O)OC(C)(C)C)c2ccc(F)cc2)cc1Cl]

To a solution of 4-chloro-5-(4-chloro-1-methyl-1H-pyrazol-5-yl)-2-thiophenecarboxylic acid (67 mg, 0.24 mmol)

[prepared according to Example 193], 1,1-dimethylethyl[2-amino-2-(4-fluorophenyl)ethyl]carbamate (61 mg, 0.24 mmol) [prepared according to the procedure of Preparation 16], diisopropylethyl amine (126 uL, 0.72 mmol) in DCM (5 mL) was added PyBrop (168 mg, 0.36 mmol) in one portion. After 1 h, the reaction contents were partitioned between H$_2$O/DCM. The aqueous phase was washed several times with DCM and the combined organic fractions were dried over Na$_2$SO$_4$, concentrated and purified via column chromatography (silica, gradient 0-50% ethyl acetate/hexane) affording the title compound (93 mg, 0.18 mmol, 76%) as a white solid: LCMS (ES) m/z=514 (M+H)$^+$.

b). N-[2-amino-1-(4-fluorophenyl)ethyl]-5-chloro-4-(4-chloro-1-methyl-1H-pyrazol-5-yl)-2-thiophenecarboxamide To a solution of 1,1-dimethylethyl[2-({[4-chloro-5-(4-chloro-1-methyl-1H-pyrazol-5-yl)-2-thienyl]carbonyl}amino)-2-(4-fluorophenyl)ethyl]carbamate (90 mg, 0.17 mmol) in DCM (2 mL) was added 4N HCl solution in dioxane (0.43 mL, 1.75 mmol). After 15 h, the solution was extracted with water three times. The aqueous fractions were combined and concentrated to afford the di-HCl salt of the title compound as a white solid (39.6 mg, 0.09 mmol, 52%): LC-MS (ES) m/z 414 (M+H)$^+$, $^1$HNMR (400 MHz, MeOD) δ ppm 3.42 (d, J=2.78 Hz, 1H) 3.56 (br. s., 1H) 3.79 (s, 3H) 5.43 (dd, J=10.23, 4.67 Hz, 1H) 7.11-7.22 (m, 2H) 7.49-7.57 (m, 2H) 7.60 (s, 1H) 7.93 (br. s., 1H).

Example 207

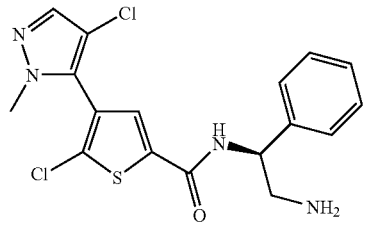 [SMILES: Cn1ncc(Cl)c1-c1cc(C(=O)N[C@H](CN)c2ccccc2)sc1Cl]

Preparation of N-[(1S)-2-amino-1-phenylethyl]-5-chloro-4-(4-chloro-1-methyl-1H-pyrazol-5-yl)-2-thiophenecarboxamide The title compound was prepared as a white solid according to the procedure of Example 206, except substituting 1,1-dimethylethyl[(2S)-2-amino-2-phenylethyl]carbamate (57 mg, 0.24 mmol) [prepared according to the procedure of Preparation 1] for 1,1-dimethylethyl[2-amino-2-(4-fluorophenyl)ethyl]carbamate: LC-MS (ES) m/z 396 (M+H)$^+$, $^1$H NMR (400 MHz, MeOD) δ ppm 3.42 (br. s., 1H) 3.57 (d, J=11.12 Hz, 1H) 3.80 (s, 3H) 5.44 (dd, J=10.36, 4.29 Hz, 1H) 7.37 (d, J=2.53 Hz, 1H) 7.40-7.47 (m, 2H) 7.48-7.55 (m, 2H) 7.60 (s, 1H) 7.95 (br. s., 1H).

Example 208

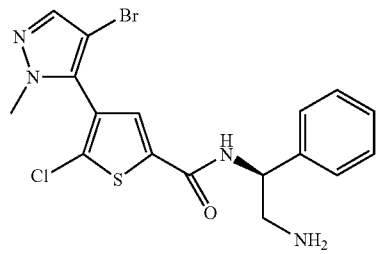 [SMILES: Cn1ncc(Br)c1-c1cc(C(=O)N[C@H](CN)c2ccccc2)sc1Cl]

Preparation N-[(1S)-2-amino-1-phenylethyl]-4-(4-bromo-1-methyl-1H-pyrazol-5-yl)-5-chloro-2-thiophenecarboxamide a) 4-(4-bromo-1-methyl-1H-pyrazol-5-yl)-5-chloro-2-thiophenecarboxylic Acid

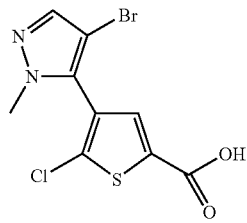 [SMILES: Cn1ncc(Br)c1-c1cc(C(=O)O)sc1Cl]

To a solution of methyl 5-chloro-4-(1-methyl-1H-pyrazol-5-yl)-2-thiophenecarboxylate (300 mg, 1.169 mmol)[prepared according to the procedure of Example 193] in THF (10 ml) was added N-bromosuccinimide (212 mg, 1.19 mmol). The mixture was sealed and heated at 70° C. After 2 h, a solution of 6N NaOH (2.0 ml, 6.0 M, 11.84 mmol) was added in one portion. The resulting mixture stirred for an additional 2 h and was partitioned between DCM-H$_2$O. The pH of the aqueous phase was adjusted to ~3 and extracted several times with DCM. The combined organic fractions were dried over Na$_2$SO$_4$, concentrated affording the title compound as a colorless oil (105 mg, 28%): LC-MS (ES) m/z=322 (M+H)$^+$.

b) 1,1-dimethylethyl[(2S)-2-({[4-(4-bromo-1-methyl-1H-pyrazol-5-yl)-5-chloro-2-thienyl]carbonyl}amino)-2-phenylethyl]carbamate

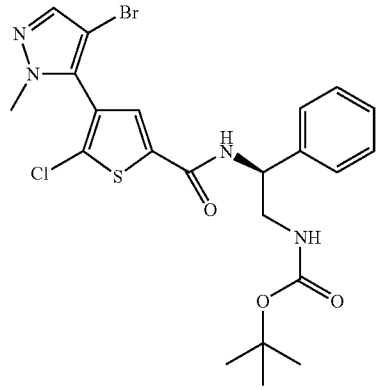 [SMILES: Cn1ncc(Br)c1-c1cc(C(=O)N[C@H](CNC(=O)OC(C)(C)C)c2ccccc2)sc1Cl]

To a solution of 4-(4-bromo-1-methyl-1H-pyrazol-5-yl)-5-chloro-2-thiophenecarboxylic acid (80 mg, 0.25 mmol), 1,1-dimethylethyl[(2S)-2-amino-2-phenylethyl]carbamate (59 mg, 0.25 mmol) [prepared according to the procedure of Preparation 1], diisopropylethyl amine (128 uL, 0.75 mmol)

in DCM (5 mL) was added PyBrop (168 mg, 0.36 mmol) in one portion. After 3 h, the reaction contents were partitioned between H₂O/DCM. The aqueous phase was washed several times with DCM and the combined organic fractions were dried over Na₂SO₄, concentrated and purified via column chromatography (silica, gradient 0-50% ethyl acetate/hexane) affording the title compound (110 mg, 0.18 mmol, 73%) as a white solid: LCMS (ES) m/z=540 (M+H)⁺.

c). N-[(1S)-2-amino-1-phenylethyl]-4-(4-bromo-1-methyl-1H-pyrazol-5-yl)-5-chloro-2-thiophenecarboxamide To a solution of 1,1-dimethylethyl[(2S)-2-({[4-(4-bromo-1-methyl-1H-pyrazol-5-yl)-5-chloro-2-thienyl]carbonyl}amino)-2-phenylethyl]carbamate (81 mg, 0.15 mmol) in DCM (2 mL) was added 4N HCl solution in dioxane (0.38 mL, 1.5 mmol) After 15 h, the solution was extracted with water three times. The aqueous fractions were combined and concentrated to afford the di-HCl salt of the title compound as a white solid (18.3 mg, 0.04 mmol, 26%): LC-MS (ES) m/z 440 (M+H)⁺, ¹H NMR (400 MHz, MeOD) δ ppm 3.40 (d, J=13.89 Hz, 1H) 3.60 (br. s., 1H) 3.80 (br. s., 3H) 5.38-5.50 (m, 1H) 7.37 (d, J=7.33 Hz, 1H) 7.43 (t, J=7.45 Hz, 2H) 7.52 (d, J=7.58 Hz, 2H) 7.61 (s, 1H) 8.02 (br. s., 1H)

Example 209

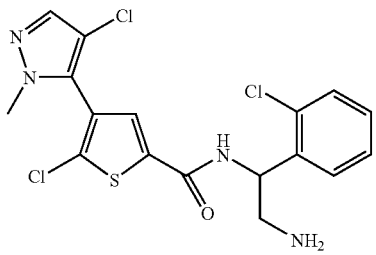 [SMILES: Cn1ncc(Cl)c1-c1cc(C(=O)NC(CN)c2ccccc2Cl)sc1Cl]

Preparation N-[2-amino-1-(2-chlorophenyl)ethyl]-5-chloro-4-(4-chloro-1-methyl-1H-pyrazol-5-yl)-2-thiophenecarboxamide The title compound was prepared as a white solid according to the procedure of Example 206, except substituting 1,1-dimethylethyl[2-amino-2-(3-chlorophenyl)ethyl]carbamate (67 mg, 0.25 mmol) [prepared according to the procedure of Preparation 16] for 1,1-dimethylethyl[2-amino-2-(4-fluorophenyl)ethyl]carbamate: LC-MS (ES) m/z 430 (M+H)⁺, ¹H NMR (400 MHz, MeOD) δ ppm 3.45 (d, J=5.56 Hz, 2H) 3.72-3.81 (m, 3H) 5.86 (dd, J=9.22, 4.42 Hz, 1H) 7.41 (d, J=2.02 Hz, 2H) 7.48-7.55 (m, 1H) 7.58 (br. s., 2H) 7.83 (s, 1H)

Example 210

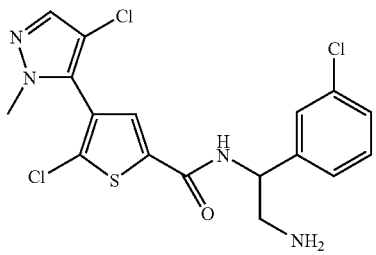 [SMILES: Cn1ncc(Cl)c1-c1cc(C(=O)NC(CN)c2cccc(Cl)c2)sc1Cl]

Preparation N-[2-amino-1-(3-chlorophenyl)ethyl]-5-chloro-4-(4-chloro-1-methyl-1H-pyrazol-5-yl)-2-thiophenecarboxamide The title compound was prepared as a white solid according to the procedure of Example 206, except substituting 1,1-dimethylethyl[2-amino-2-(3-chlorophenyl)ethyl]carbamate (67 mg, 0.25 mmol) [prepared according to the procedure of Preparation 16] for 1,1-dimethylethyl[2-amino-2-(4-fluorophenyl)ethyl]carbamate: LC-MS (ES) m/z 430 (M+H)⁺, 1 HNMR (400 MHz, MeOD) δ ppm 3.44 (d, J=3.54 Hz, 1H) 3.55 (d, J=10.61 Hz, 1H) 3.80 (s, 3H) 5.42 (dd, J=10.36, 4.29 Hz, 1H) 7.35-7.49 (m, 3H) 7.55 (s, 1H) 7.59 (s, 1H) 7.95 (d, J=14.40 Hz, 1H)

Example 211

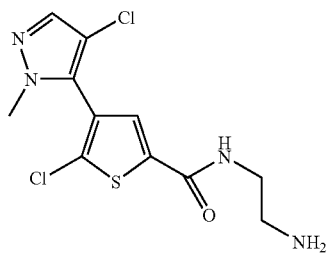 [SMILES: Cn1ncc(Cl)c1-c1cc(C(=O)NCCN)sc1Cl]

Preparation N-(2-aminoethyl)-5-chloro-4-(4-chloro-1-methyl-1H-pyrazol-5-yl)-2-thiophenecarboxamide The title compound was prepared as a white solid according to the procedure of Example 206, except substituting 1,1-dimethylethyl (2-aminoethyl)carbamate (58 mg, 0.36 mmol) for 1,1-dimethylethyl[2-amino-2-(4-fluorophenyl)ethyl]carbamate: LC-MS (ES) m/z 320 (M+H)⁺, ¹H NMR (400 MHz, MeOD) δ ppm 3.17 (d, J=5.81 Hz, 2H) 3.66 (br. s., 2H) 3.78 (s, 3H) 7.60 (s, 1H) 7.66 (s, 1H)

Example 212

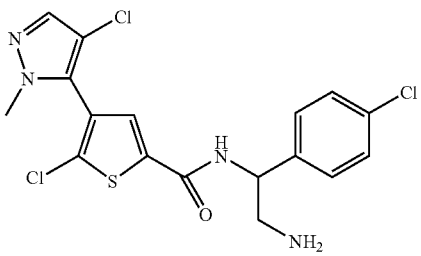 [SMILES: Cn1ncc(Cl)c1-c1cc(C(=O)NC(CN)c2ccc(Cl)cc2)sc1Cl]

Preparation N-[2-amino-1-(4-chlorophenyl)ethyl]-5-chloro-4-(4-chloro-1-methyl-1H-pyrazol-5-yl)-2-thiophenecarboxamide The title compound was prepared as a white solid according to the procedure of Example 206, except substituting 1,1-dimethylethyl[2-amino-2-(4-chlorophenyl)ethyl]carbamate (65 mg, 0.24 mmol) [prepared according to the procedure of Preparation 16] for 1,1-dimethylethyl[2-amino-2-(4-fluorophenyl)ethyl]carbamate: LC-MS (ES) m/z 431 (M+H)⁺, 1 HNMR (400 MHz, MeOD) δ ppm 3.43 (d, J=4.55

Hz, 1H) 3.53 (d, J=10.11 Hz, 1H) 3.79 (s, 3H) 5.43 (dd, J=10.36, 4.55 Hz, 1H) 7.43-7.47 (m, 2H) 7.48-7.53 (m, 2H) 7.60 (s, 1H) 7.94 (s, 1H)

Example 213

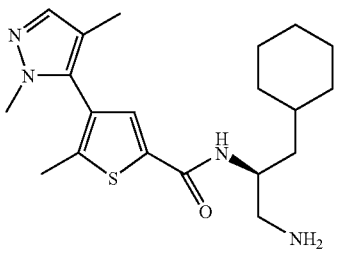 [SMILES: Cc1cnn(C)c1-c1cc(C(=O)N[C@H](CN)CC2CCCCC2)sc1C]

Preparation N-[(1S)-2-amino-1-(cyclohexylmethyl)ethyl]-4-(1,4-dimethyl-1H-pyrazol-5-yl)-5-methyl-2-thiophenecarboxamide The title compound was prepared as an off-white solid according to the procedure of Example 99, except substituting 2-[(2S)-2-amino-3-cyclohexylpropyl]-1H-isoindole-1,3(2H)-dione (73 mg, 0.25 mmol) [prepared according to the procedure of Preparation 6] for 2-{(2S)-2-amino-3-[2-(trifluoromethyl)phenyl]propyl}-1H-isoindole-1,3(2H)-dione: LC-MS (ES) m/z 375 (M+H)$^+$, $^1$H NMR (400 MHz, MeOD) δ ppm 0.91-0.99 (m, 1H), 1.01-1.10 (m., 1H) 1.39-1.47 (m., 3H) 1.37-1.48 (m, 2H) 1.65-1.77 (m, 5H) 1.89 (br. s., 1H) 2.10 (s, 3H) 2.45 (s, 3H) 3.07-3.16 (m, 2H) 3.91-3.98 (m, 3H) 4.42 (br. s., 1H) 7.91 (br. s., 1H) 8.24 (s, 1H)

Example 214

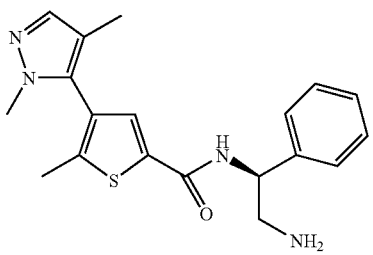 [SMILES: Cc1cnn(C)c1-c1cc(C(=O)N[C@H](CN)c2ccccc2)sc1C]

Preparation N-[(1S)-2-amino-1-phenylethyl]-4-(1,4-dimethyl-1H-pyrazol-5-yl)-5-methyl-2-thiophenecarboxamide a) 1,1-dimethylethyl[(2S)-2-({[4-(1,4-dimethyl-1H-pyrazol-5-yl)-5-methyl-2-thienyl]carbonyl}amino)-2-phenylethyl]carbamate

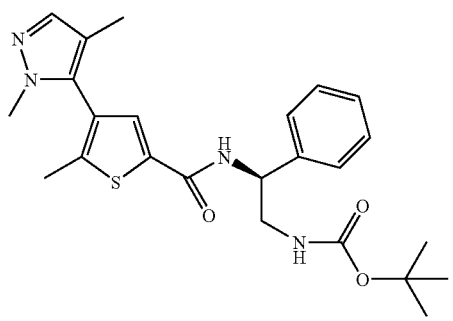 [SMILES: Cc1cnn(C)c1-c1cc(C(=O)N[C@H](CNC(=O)OC(C)(C)C)c2ccccc2)sc1C]

To a solution of 5-chloro-4-(4-chloro-1-methyl-1H-pyrazol-5-yl)-2-thiophenecarboxylic acid (110 mg, 0.4 mmol) [prepared in Experiment 99], 2-[(2S)-2-amino-4-methylpentyl]-1H-isoindole-1,3(2H)-dione (99 mg, 0.4 mmol) [prepared according to the procedure of Preparation 1] and diisopropylethylamine (0.2 ml, 1.2 mmol) in DCM at 25° C. was added bromo-tris-pyrrolidino-phosphonium hexafluorophosphate (280 mg, 0.6 mmol) in one portion. The solution stirred at 25° C. for 12 h and was then partitioned between H$_2$O-DCM. The aqueous phase was washed several times with DCM and the combined organic fractions were dried over Na$_2$SO$_4$, concentrated and purified via column chromatography (silica, 30-70% EtOAc in hexanes) yielding the title compound (113 mg, 0.22 mmol, 56% yield) as a colorless oil: LC-MS (ES) m/e 506 (M+H)+.

d). N-[(1S)-2-amino-1-phenylethyl]-5-chloro-4-(1-methyl-1H-pyrazol-5-yl)-2-thiophenecarboxamide To a solution of 1,1-dimethylethyl[(2S)-2-({[4-(1,4-dimethyl-1H-pyrazol-5-yl)-5-methyl-2-thienyl]carbonyl}amino)-2-phenylethyl]carbamate (99 mg, 0.22 mmol) in DCM (2 mL) was added 4N HCl solution in dioxane (0.5 mL, 2 mmol). After 15 h, the solution was extracted with water three times. The aqueous fractions were combined and concentrated to afford the di-HCl salt of the title compound as an off-white solid (40 mg, 0.11 mmol, 52%): LC-MS (ES) m/z 355 (M+H)$^+$, $^1$H NMR (400 MHz, MeOD) δ ppm 1.99-2.14 (m, 3H) 2.43 (s, 3H) 3.39 (d, J=9.85 Hz, 1H)) 3.60 (d, J=9.85 Hz, 1H) 3.92 (br. s., 3H) 5.44 (d, J=8.84 Hz, 1H) 7.36 (d, J=2.53 Hz, 1H) 7.43 (t, J=5.94 Hz, 2H) 7.49-7.57 (m, 2H) 8.03 (br. s., 1H) 8.14 (br. s., 1H).

Example 215

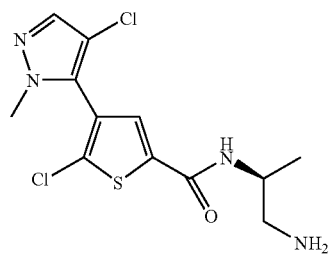 [SMILES: C[C@@H](CN)NC(=O)c1cc(-c2c(Cl)cnn2C)c(Cl)s1]

Preparation N-[(1S)-2-amino-1-methylethyl]-5-chloro-4-(4-chloro-1-methyl-1H-pyrazol-5-yl)-2-thiophenecarboxamide The title compound was prepared as an off-white solid according to the procedure of Example 106, except substituting 2-[(2S)-2-aminopropyl]-1H-isoindole-1,3(2H)-dione (74 mg, 0.36 mmol) for 2-[(2S)-2-amino-3-cyclohexylpropyl]-1H-isoindole-1,3(2H)-dione: LC-MS (ES) m/z 333 (M+H)$^+$, $^1$H NMR (400 MHz, MeOD) δ ppm 1.37 (d, J=6.82 Hz, 3H) 3.11-3.14 (m, 2H) 3.79 (s, 3H) 4.38-4.40 (m, 1H) 7.60 (br. s., 1H) 7.83 (d, J=2.27 Hz, 1H).

Example 216

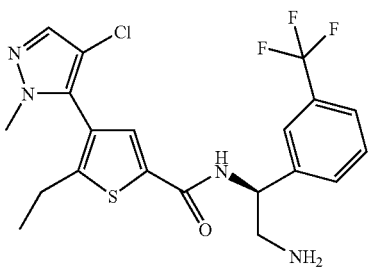 [SMILES: CCc1sc(C(=O)N[C@H](CN)c2cccc(C(F)(F)F)c2)cc1-c1c(Cl)cnn1C]

Preparation N-{(1S)-2-amino-1-[3-(trifluoromethyl)phenyl]ethyl}-4-(4-chloro-1-methyl-1H-pyrazol-5-yl)-5-ethyl-2-thiophenecarboxamide The title compound was prepared as an off-white solid according to the procedure of Example 100, except substituting 2-{(2S)-2-amino-3-[3-(trifluoromethyl)phenyl]propyl}-1H-isoindole-1,3(2H)-dione (348 mg, 1.0 mmol) [prepared according to the procedure of Preparation 6] for 2-{(2S)-2-amino-3-[2-(trifluoromethyl)phenyl]propyl}-1H-isoindole-1,3(2H)-dione: LC-MS (ES) m/z 471 (M+H)$^+$, $^1$H NMR (400 MHz, MeOD) δ ppm 1.24 (t, J=7.33 Hz, 3H) 2.54 (d, J=8.84 Hz, 2H) 2.74 (q, J=7.24 Hz, 2H) 3.05-3.16 (m, 1H) 3.26 (d, J=4.80 Hz, 1H) 3.66-3.79 (m, 3H) 4.54 (br. s., 1H) 7.47-7.56 (m, 2H) 7.57-7.76 (m, 4H).

Example 217

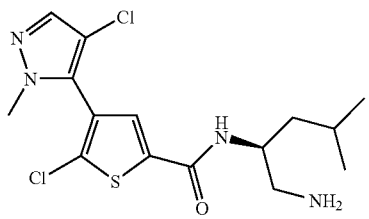 [SMILES: CC(C)C[C@@H](CN)NC(=O)c1cc(-c2c(Cl)cnn2C)c(Cl)s1]

Preparation N-[(1S)-1-(aminomethyl)-3-methylbutyl]-5-chloro-4-(4-chloro-1-methyl-1H-pyrazol-5-yl)-2-thiophenecarboxamide The title compound was prepared as an off-white solid according to the procedure of Example 106, except substituting 2-[(2S)-2-amino-4-methylpentyl]-1H-isoindole-1,3(2H)-dione (99 mg, 0.4 mmol) for 2-[(2S)-2-amino-3-cyclohexylpropyl]-1H-isoindole-1,3(2H)-dione: LC-MS (ES) m/z 376 (M+H)$^+$, $^1$H NMR (400 MHz, MeOD) δ ppm 0.99 (t, J=6.44 Hz, 6H) 1.42 (s, 1H) 1.63-1.80 (m, 2H) 3.04 (br. s., 1H) 3.14 (d, J=3.54 Hz, 1H) 3.80 (s, 3H) 4.42 (br. s., 1H) 7.59 (s, 1H) 7.84 (d, J=6.06 Hz, 1H).

Experiment 218

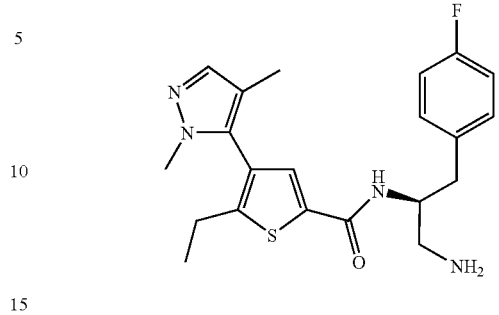

Preparation N-{(1S)-2-amino-1-[(4-fluorophenyl)methyl]ethyl}-4-(1,4-dimethyl-1H-pyrazol-5-yl)-5-ethyl-2-thiophenecarboxamide a) methyl 4-(4-bromo-1-methyl-1H-pyrazol-5-yl)-5-ethyl-2-thiophenecarboxylate

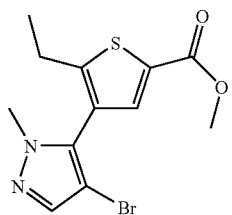 [SMILES: CCc1sc(C(=O)OC)cc1-c1c(Br)cnn1C]

To a solution of methyl 5-ethyl-4-(1-methyl-1H-pyrazol-5-yl)-2-thiophenecarboxylate (600 mg, 2.40 mmol) [prepared according to Example 98] in Tetrahydrofuran (THF) (10 ml) was added N-bromosuccinimide (512 mg, 2.88 mmol). The mixture stirred in a sealed tube at 70° C. for 2 h. The reaction mixture was then concentrated and purified with silica gel using a 0-5% gradient (ethyl acetate/hexane) to afford the title compound as an off-white solid: LC-MS (ES) m/z 330 (M+H)$^+$.

b) methyl 4-(1,4-dimethyl-1H-pyrazol-5-yl)-5-ethyl-2-thiophenecarboxylate

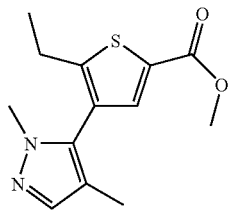 [SMILES: CCc1sc(C(=O)OC)cc1-c1c(C)cnn1C]

A solution of methyl 4-(4-bromo-1-methyl-1H-pyrazol-5-yl)-5-ethyl-2-thiophenecarboxylate (635 mg, 1.93 mmol), potassium carbonate (1.33 g, 9.64 mmol), PdCl$_2$(dppf) (141 mg, 0.19 mmol) and trimethylboroxine (0.54 ml, 3.86 mmol) in N,N-dimethylformamide (3 ml) was stirred at 110° C. in a sealed tube for 2 h. This reaction mixture was concentrated and partitioned between H$_2$O-DCM. The aqueous phase was washed several times with DCM and the combined organic fractions were dried over Na$_2$SO$_4$, concentrated and purified via column chromatography (10-50% EtOAc in hexanes)

c) 4-(1,4-dimethyl-1H-pyrazol-5-yl)-5-ethyl-2-thiophenecarboxylic Acid

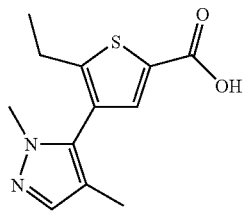 [SMILES: CCc1sc(C(=O)O)cc1-c1c(C)cnn1C]

A solution of methyl 4-(1,4-dimethyl-1H-pyrazol-5-yl)-5-ethyl-2-thiophenecarboxylate (488 mg, 1.85 mmol) in 6N sodium hydroxide (3.08 ml, 18.5 mmol) and Tetrahydrofuran (10 ml) was stirred at 70° C. in a sealed tube for 1 h. The resulting solution was cooled and then partitioned between H₂O-DCM. The aqueous phase was adjusted to pH ~4 and then washed several times with DCM. The combined organic fractions were dried over Na₂SO₄ and concentrated affording the title compound as a yellow foam (448 mg, 1.79 mmol, 96% yield) as a yellow oil: LCMS (ES) m/e 251 (M+H)+.

d) 4-(1,4-dimethyl-1H-pyrazol-5-yl)-N-{(1S)-2-(1,3-dioxo-1,3-dihydro-2H-isoindol-2-yl)-1-[(4-fluorophenyl)methyl]ethyl}-5-ethyl-2-thiophenecarboxamide

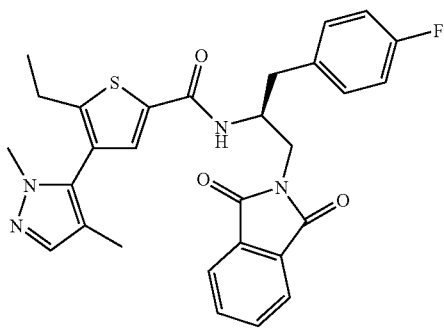 [SMILES: CCc1sc(C(=O)N[C@@H](Cc2ccc(F)cc2)CN2C(=O)c3ccccc3C2=O)cc1-c1c(C)cnn1C]

To a solution of 4-(1,4-dimethyl-1H-pyrazol-5-yl)-5-ethyl-2-thiophenecarboxylic acid (250 mg, 1.0 mmol), 2-{(2S)-2-amino-3-[4-(fluoromethyl)phenyl]propyl}-1H-isoindole-1,3(2H)-dione (313 mg, 1.05 mmol)[prepared according to the procedure of Preparation 6] and diisopropylethylamine (0.52 ml, 3 mmol) in DCM at 25° C. was added bromo-tris-pyrrolidino-phosphonium hexafluorophosphate (746 mg, 1.6 mmol) in one portion. The solution stirred at 25° C. for 12 h and was then partitioned between H₂O-DCM. The aqueous phase was washed several times with DCM and the combined organic fractions were dried over Na₂SO₄, concentrated and purified via column chromatography (silica, 30-70% EtOAc in hexanes) yielding the title compound as a yellow solid (490 mg, 0.92 mmol, 92% yield) as a yellow foam: LCMS (ES) m/e 531 (M+H)+.

e) N-{(1S)-2-amino-1-[(4-fluorophenyl)methyl]ethyl}-4-(1,4-dimethyl-1H-pyrazol-5-yl)-5-ethyl-2-thiophenecarboxamide To a solution of 4-(1,4-dimethyl-1H-pyrazol-5-yl)-N-{(1S)-2-(1,3-dioxo-1,3-dihydro-2H-isoindol-2-yl)-1-[(4-fluorophenyl)methyl]ethyl}-5-ethyl-2-thiophenecarboxamide (400 mg, 0.75 mmol) in methanol (8 ml) at 25° C. was added hydrazine (0.12 ml, 3.77 mmol) dropwise. After 12 h, the solution was concentrated, dry loaded onto silica and purified by column chromatography (5% MeOH in DCM (1% NH₄OH)). The free base was transferred to the HCl salt by addition of excess 4M HCl in dioxane (1 ml) to the residue in MeOH (2 ml) affording the HCl salt of the title compound as a yellow solid: LC-MS (ES) m/z 401 (M+H)+, ¹H NMR (400 MHz, MeOD) δ ppm 1.28 (t, J=7.58 Hz, 3H) 2.07 (s, 3H) 2.75 (m, 2H) 3.02 (d, J=6.32 Hz, 2H) 3.22 (br. s., 2H) 3.92 (d, J=2.27 Hz, 3H) 4.53 (br. s., 1H) 7.02 (t, J=8.59 Hz, 2H) 7.34 (m, 2H), 7.80 (s, 1H) 8.13-8.25 (m, 1H).

Example 219

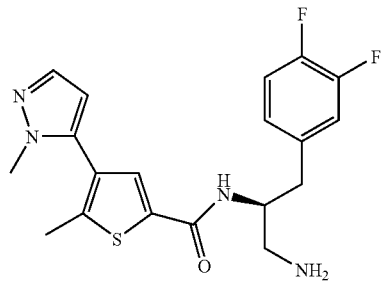 [SMILES: Cc1sc(C(=O)N[C@H](CN)Cc2ccc(F)c(F)c2)cc1-c1ccnn1C]

Preparation N-{(1S)-2-amino-1-[(3,4-difluorophenyl)methyl]ethyl}-5-methyl-4-(1-methyl-1H-pyrazol-5-yl)-2-thiophenecarboxamide The title compound was prepared as a yellow solid according to the procedure of Example 103, except substituting 2-[(2S)-2-amino-3-(2,4-difluorophenyl)propyl]-1H-isoindole-1,3(2H)-dione (332 mg, 1.05 mmol) [Prepared according to the procedure of Preparation 6] for 2-[(2S)-2-amino-3-cyclohexylpropyl]-1H-isoindole-1,3(2H)-dione: LC-MS (ES) m/z 391 (M+H)+, ¹H NMR (400 MHz, MeOD) δ ppm 2.44 (s, 3H) 2.91-3.02 (m, 2H) 3.16 (d, J=10.11 Hz, 1H) 3.24 (dd, J=13.14, 3.54 Hz, 1H) 3.82 (s, 3H) 4.50 (d, J=3.54 Hz, 1H) 6.44 (d, J=2.02 Hz, 1H) 7.05-7.13 (m, 1H) 7.15-7.25 (m, 2H), 7.67-7.70 (m, 2H).

Example 220

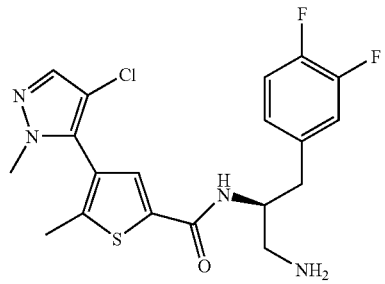

Preparation N-{(1S)-2-amino-1-[(3,4-difluorophenyl)methyl]ethyl}-4-(4-chloro-1-methyl-1H-pyrazol-5-yl)-5-methyl-2-thiophenecarboxamide The title compound was prepared as a yellow solid according to the procedure of Example 102, except substituting 2-[(2S)-2-amino-3-(2,4-difluorophenyl)propyl]-1H-isoindole-1,3(2H)-dione (332 mg, 1.05 mmol) [Prepared according to the procedure of Preparation 6] for 2-[(2S)-2-amino-3-cyclohexylpropyl]-1H-isoindole-1,3(2H)-dione: LC-MS (ES) m/z 425 (M+H)+, ¹H NMR (400 MHz, MeOD) δ ppm 2.40 (s, 3H) 2.95-3.03 (m, 2H) 3.23-3.26 (m, 2H) 3.76 (br, s, 3H) 4.96-4.52 (m, 1H), 7.07-7.15 (m, 2H) 7.22-7.28 (m, 1H) 7.55-7.77 (m, 2H).

Example 221

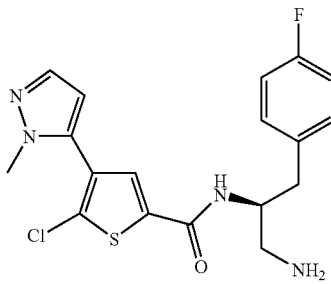

Preparation N-{(1S)-2-amino-1-[(3,4-difluorophenyl)methyl]ethyl}-5-chloro-4-(1-methyl-1H-pyrazol-5-yl)-2-thiophenecarboxamide The title compound was prepared as a yellow solid according to the procedure of Example 104, except substituting 2-[(2S)-2-amino-3-(2,4-difluorophenyl)propyl]-1H-isoindole-1,3(2H)-dione (332 mg, 1.05 mmol) [Prepared according to the procedure of Preparation 6] for 2-[(2S)-2-amino-3-cyclohexylpropyl]-1H-isoindole-1,3(2H)-dione: LC-MS (ES) m/z 411 (M+H)+, 1H NMR (400 MHz, MeOD) δ ppm 3.02 (d, J=7.33 Hz, 2H) 3.24 (d, J=6.82 Hz, 2H) 4.01 (d, J=7.58 Hz, 3H) 4.52 (d, J=7.07 Hz, 1H) 6.78 (d, J=11.87 Hz, 1H) 7.08-7.21 (m, 1H) 7.26-7.28 (m, 1H) 7.94-8.08 (m, 2H).

Example 222

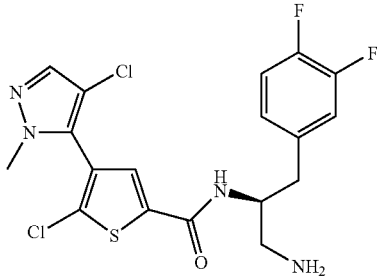

Preparation N-{(1S)-2-amino-1-[(3,4-difluorophenyl)methyl]ethyl}-5-chloro-4-(4-chloro-1-methyl-1H-pyrazol-5-yl)-2-thiophenecarboxamide The title compound was prepared as an off-white solid according to the procedure of Example 106, except substituting 2-[(2S)-2-amino-3-(2,4-difluorophenyl)propyl]-1H-isoindole-1,3(2H)-dione (332 mg, 1.05 mmol) [Prepared according to the procedure of Preparation 6] for 2-[(2S)-2-amino-3-cyclohexylpropyl]-1H-isoindole-1,3(2H)-dione: LC-MS (ES) m/z 446 (M+H)+, 1H NMR (400 MHz, MeOD) δ ppm 2.95-3.05 (m, 2H) 3.22-3.23 (m, 2H) 3.79 (s, 3H) 4.52 (br. s., 1H) 7.08-7.21 (m, 2H) 7.27-7.26 (m, 2H) 7.60 (s, 1H) 7.83 (br. s., 1H)

Example 223

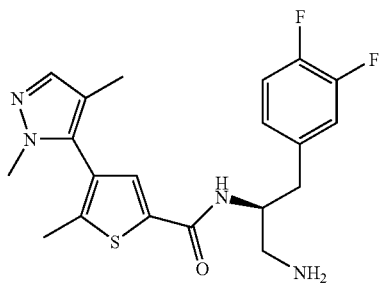

Preparation N-{(1S)-2-amino-1-[(3,4-difluorophenyl)methyl]ethyl}-4-(1,4-dimethyl-1H-pyrazol-5-yl)-5-methyl-2-thiophenecarboxamide The title compound was prepared as a yellow solid according to the procedure of Example 99, except substituting 2-[(2S)-2-amino-3-(2,4-difluorophenyl)propyl]-1H-isoindole-1,3(2H)-dione (332 mg, 1.05 mmol) [prepared according to Preparation 6] for 2-{(2S)-2-amino-3-[2-(trifluoromethyl)phenyl]propyl}-1H-isoindole-1,3(2H)-dione: LC-MS (ES) m/z 405 (M+H)+, 1H NMR (400 MHz, MeOD) δ ppm 2.09 (s, 15H) 2.42 (s, 3H) 3.04 (d, J=7.07 Hz, 2H) 3.27 (d, J=4.80 Hz, 2H) 3.88-4.01 (m, 3H) 4.54 (br. s., 1H) 7.08-7.21 (m, 2H) 7.29 (d, J=7.58 Hz, 1H) 7.92 (br. s., 1H) 8.15-8.26 (m, 1H).

Example 224

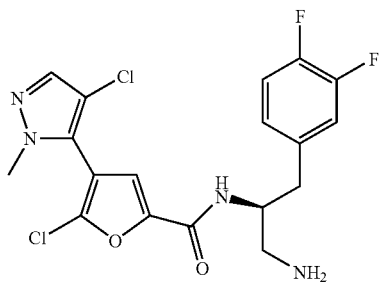 [SMILES: Cn1ncc(Cl)c1-c1cc(C(=O)N[C@H](CN)Cc2ccc(F)c(F)c2)oc1Cl]

Preparation N-{(1S)-2-amino-1-[(3,4-difluorophenyl)methyl]ethyl}-5-chloro-4-(4-chloro-1-methyl-1H-pyrazol-5-yl)-2-furancarboxamide a) methyl 4-(1-methyl-1H-pyrazol-5-yl)-2-furancarboxylate

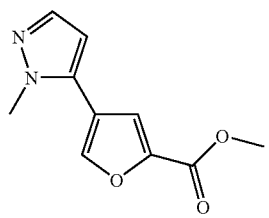

A solution of methyl 4-bromo-2-furancarboxylate (470 mg, 2.29 mmol), potassium carbonate (1584 mg, 11.46 mmol), 1-methyl-5-(4,4,5,5-tetramethyl-1,3,2-dioxaborolan-2-yl)-1H-pyrazole (525 mg, 2.52 mmol)[prepared according to Preparation 7] and bis-(tri-t-butylphosphine) Palladium (0) (58.6 mg, 0.12 mmol) in 1,4-dioxane (9.55 ml) and water (1.9 ml) was stirred at 80° C. After 1 hr, the solution was partitioned between H$_2$O-DCM and the aqueous phase was washed several times with DCM. The combined organic fractions were dried over Na$_2$SO$_4$, concentrated and purified via column chromatography (30% EtOAc in hexanes) affording the title compound (124 mg, 0.60 mmol, 26% yield) as a white powder: LCMS (ES) m/e 206 (M+H)$^+$.

b) methyl 5-chloro-4-(4-chloro-1-methyl-1H-pyrazol-5-yl)-2-furancarboxylate

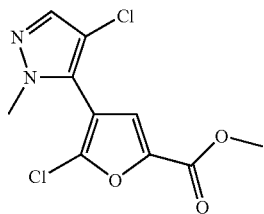

A solution of methyl 4-(1-methyl-1H-pyrazol-5-yl)-2-furancarboxylate (412 mg, 2.0 mmol) and N-chlorosuccinimide (267 mg, 2.0 mmol) in DMF (10 mL) was heated at 75° C. for 30 minutes. Another batch of N-chlorosuccinimide (267 mg, 2.0 mmol) was added. After 1 hr, the mixture was concentrated and purified using silica gel and eluting with 0-55% ethyl acetate/hexane to afford the title compound as a white solid (225 mg, 0.82 mmol, 71% yield): LCMS (ES) m/e 276 (M+H)$^+$.

c) 5-chloro-4-(4-chloro-1-methyl-1H-pyrazol-5-yl)-2-furancarboxylic Acid

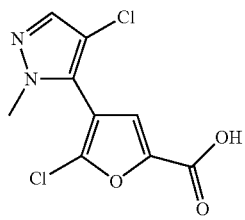 [SMILES: Cn1ncc(Cl)c1-c1cc(C(=O)O)oc1Cl]

A solution of methyl 5-chloro-4-(4-chloro-1-methyl-1H-pyrazol-5-yl)-2-furancarboxylate (224 mg, 0.82 mmol) in 6N sodium hydroxide (1.36 ml, 8.2 mmol) and tetrahydrofuran (5 ml) was stirred at 70° C. in a sealed tube for 1 h. The resulting solution was cooled and then partitioned between H$_2$O-DCM. The aqueous phase was adjusted to pH ~4 and then washed several times with DCM. The combined organic fractions were dried over Na$_2$SO$_4$ and concentrated affording the title compound (201 mg, 0.77 mmol, 94% yield) as a yellow oil: LCMS (ES) m/e 262 (M+H)$^+$.

d) 5-chloro-4-(4-chloro-1-methyl-1H-pyrazol-5-yl)-N-{(1S)-2-(3,4-difluorophenyl)-1-[(1,3-dioxo-1,3-dihydro-2H-isoindol-2-yl)methyl]ethyl}-2-furancarboxamide

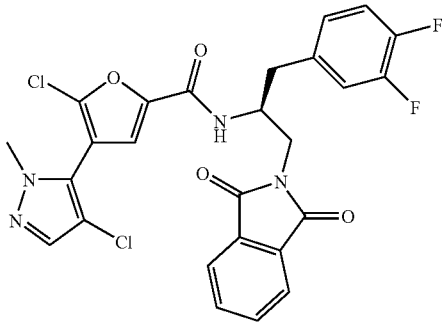 [SMILES: Cn1ncc(Cl)c1-c1cc(C(=O)N[C@@H](Cc2ccc(F)c(F)c2)CN2C(=O)c3ccccc3C2=O)oc1Cl]

To a solution of 5-chloro-4-(4-chloro-1-methyl-1H-pyrazol-5-yl)-2-furancarboxylic acid (200 mg, 0.77 mmol)[prepared according to the procedure of Preparation 6], 2-[(2S)-2-amino-3-(2,4-difluorophenyl)propyl]-1H-isoindole-1,3(2H)-dione (254 mg, 0.80 mmol) and N,N-diisopropylethylamine (0.40 ml, 2.30 mmol) in DCM (10 ml) was added bromo-tris-pyrrolidino-phosphonium hexafluorophosphate (536 mg, 1.15 mmol). After stirring at ambient temperature for 20 hrs, the mixture was concentrated and purified with silica gel column eluting with gradient (0-50% ethyl acetate/hexanes) to afford the title compounds as an off-white foamy solid (304 mg, 0.54 mmol, 71% yield): LCMS (ES) m/e 560(M+H)+.

e) N-{(1S)-2-amino-1-[(3,4-difluorophenyl)methyl]ethyl}-5-chloro-4-(4-chloro-1-methyl-1H-pyrazol-5-yl)-2-furancarboxamide To a solution of 5-chloro-4-(4-chloro-1-methyl-1H-pyrazol-5-yl)-N-{(1S)-2-(3,4-difluorophenyl)-1-[(1,3-dioxo-1,3-dihydro-2H-isoindol-2-yl)methyl]ethyl}-2-furancarboxamide (304 mg, 0.54 mmol) in methanol (5 ml) at 25° C. was added hydrazine (0.08 ml, 2.7 mmol) dropwise. After 12 h, the solution was concentrated, dry loaded onto silica and purified by column chromatography (5% MeOH in DCM (1% NH$_4$OH)). The free base was converted to the HCl salt by addition of excess 4M HCl in dioxane (1 ml) to the residue in MeOH (2 ml) affording the HCl salt of the title compound as a yellow solid: LC-MS (ES) m/z 430(M+H)$^+$, $^1$H NMR (400 MHz, MeOD) δ ppm 2.91-3.05 (m, 2H) 3.17-3.28 (m, 2H) 3.81 (s, 3H) 4.57 (d, J=9.60 Hz, 1H) 7.12 (br. s., 1H) 7.18-7.28 (m., 2H) 7.36-7.39 (m, 1H) 7.58 (s, 1H).

Example 225

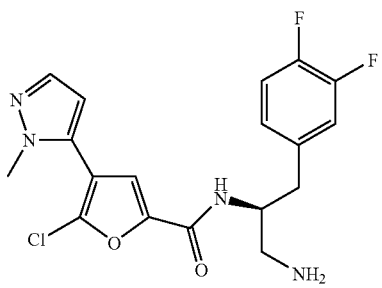

Preparation N-{(1S)-2-amino-1-[(3,4-difluorophenyl)methyl]ethyl}-5-chloro-4-(1-methyl-1H-pyrazol-5-yl)-2-furancarboxamide The title compound was prepared as an off-white solid according to the procedure of Example 127, except substituting 2-[(2S)-2-amino-3-(2,4-difluorophenyl)propyl]-1H-isoindole-1,3(2H)-dione (147 mg, 0.46 mmol) [prepared according to the procedure of Preparation 6] for 2-{(2S)-2-amino-3-[2-(trifluoromethyl)phenyl]propyl}-1H-isoindole-1,3(2H)-dione: LC-MS (ES) m/z 395 (M+H)$^+$, $^1$H NMR (400 MHz, MeOD) δ ppm 2.90-3.06 (m, 2H) 3.18-3.24 (m, 2H) 3.98 (d, J=17.68 Hz, 3H) 4.52-4.64 (m, 1H) 6.67 (d, J=1.77 Hz, 1H) 7.19 (dd, J=10.11, 8.59 Hz, 2H) 7.26 (td, J=9.73, 2.27 Hz, 1H) 7.51 (d, J=19.96 Hz, 1H) 7.93 (br. s., 1H).

Example 226

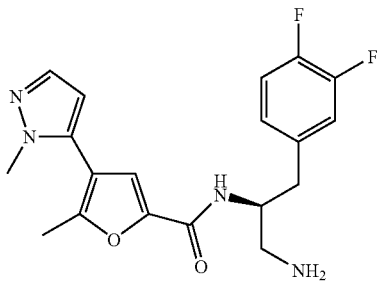

Preparation N-{(1S)-2-amino-1-[(3,4-difluorophenyl)methyl]ethyl}-5-methyl-4-(1-methyl-1H-pyrazol-5-yl)-2-furancarboxamide a) methyl 4-bromo-5-methyl-2-furancarboxylate

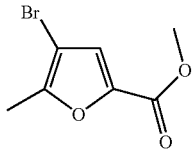

Methyl 4,5-dibromo-2-furancarboxylate (3.7 g, 13.03 mmol) [prepared according to Example 127] and trans-dichlorobis(triphenylphosphine)Palladium (II) (0.46 g, 0.65 mmol) were combined in THF (50 ml) to give a yellow suspension. A THF solution of methylzinc chloride (11.40 ml, 22.81 mmol) was added dropwise at room temperature. After stirring at ambient temperature for 20 h, the solution was concentrated and purified using silica gel and eluting with 0-30% ethyl acetate/hexane to generate the title compound as a white solid (1.45 g, 6.61 mmol, 51% yield): LC-MS (ES) m/z 220 (M+H)$^+$.

b) 5-methyl-4-(1-methyl-1H-pyrazol-5-yl)-2-furancarboxylic Acid

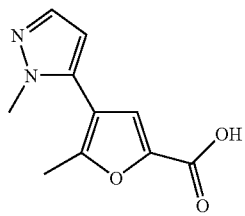

To a solution of methyl 4-bromo-5-methyl-2-furancarboxylate (500 mg, 2.28 mmol), 1-methyl-5-(4,4,5,5-tetramethyl-1,3,2-dioxaborolan-2-yl)-1H-pyrazole (950 mg, 4.57 mmol)[prepared according to Preparation 7] and potassium carbonate (315 mg, 2.28 mmol) in 1,4-dioxane (8 mL) and water (2.0 mL) was added bis(tri-t-butylphosphine)Palladium (0) (117 mg, 0.23 mmol). The mixture was heated to 80° C. and after 15 h the reaction mixture was concentrated. The residue was partitioned between DCM and water. The organic layer was concentrated and dissolved in tetrahydrofuran (THF) (8.0 mL). The solution was treated with 6N aqueous solution of sodium hydroxide (3.80 mL, 22.83 mmol) and heated to 75° C. After 15 h, the reaction mixture was concentrated and partitioned between DCM and water. The aqueous layer was acidified to pH ~3 with 2N HCl aqueous solution and extracted several times with DCM. The organic fractions were combined and concentrated to afford the title compound as a yellow solid (401 mg, 1.95 mmol, 85% yield): LC-MS (ES) m/z 207 (M+H)$^+$.

c) N-{(1S)-2-(3,4-difluorophenyl)-1-[(1,3-dioxo-1,3-dihydro-2H-isoindol-2-yl)methyl]ethyl}-5-methyl-4-(1-methyl-1H-pyrazol-5-yl)-2-furancarboxamide

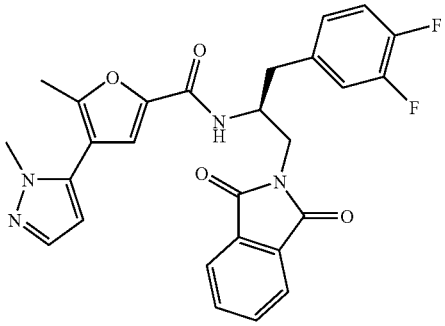 [SMILES: Cc1oc(C(=O)N[C@@H](Cc2ccc(F)c(F)c2)CN2C(=O)c3ccccc3C2=O)cc1-c1ccnn1C]

To a solution of 5-methyl-4-(1-methyl-1H-pyrazol-5-yl)-2-furancarboxylic acid (200 mg, 0.97 mmol), 2-[(2S)-2-amino-3-(2,4-difluorophenyl)propyl]-1H-isoindole-1,3(2H)-dione (322 mg, 1.02 mmol)[prepared according to the procedure of Preparation 6] and N,N-diisopropylethylamine (0.51 ml, 2.91 mmol) in DCM (10 ml) was added bromo-tris-pyrrolidino-phosphonium hexafluorophosphate (678 mg, 1.46 mmol). After stirring at ambient temperature for 20 h, the mixture was concentrated and purified using silica gel and eluting with a 0-50% ethyl acetate/hexane gradient to afford the title compound as an off-white foamy solid (181 mg, 0.36 mmol, 37% yield): LCMS (ES) m/e 505 (M+H)+.

e) N-{(1S)-2-amino-1-[(3,4-difluorophenyl)methyl]ethyl}-5-methyl-4-(1-methyl-1H-pyrazol-5-yl)-2-furancarboxamide To a solution of N-{(1S)-2-(3,4-difluorophenyl)-1-[(1,3-dioxo-1,3-dihydro-2H-isoindol-2-yl)methyl]ethyl}-5-methyl-4-(1-methyl-1H-pyrazol-5-yl)-2-furancarboxamide (176 mg, 0.35 mmol) in methanol (5 ml) at 25° C. was added hydrazine (0.22 ml, 0.7 mmol) dropwise. After 12 h, the solution was concentrated, dry loaded onto silica and purified by column chromatography (5% MeOH in DCM (1% NH$_4$OH)). The free base was converted to the HCl salt by addition of excess 4M HCl in dioxane (1 ml) to the residue in MeOH (2 ml) affording the HCl salt of the title compound as an off-white solid:
LC-MS (ES) m/z 430(M+H)$^+$, $^1$H NMR (400 MHz, MeOD) δ ppm 2.91-3.05 (m, 2H) 3.17-3.28 (m, 2H) 3.81 (s, 3H) 4.57 (d, J=9.60 Hz, 1H) 7.12 (br. s., 1H) 7.18-7.28 (m., 2H) 7.36-7.39 (m, 1H) 7.58 (s, 1H)

Example 227

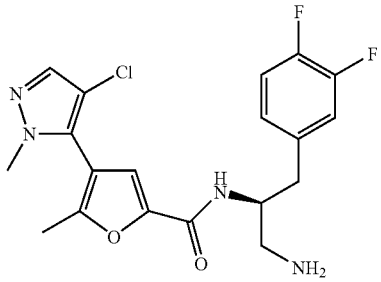 [SMILES: Cc1oc(C(=O)N[C@H](CN)Cc2ccc(F)c(F)c2)cc1-c1c(Cl)cnn1C]

Preparation N-{(1S)-2-amino-1-[(3,4-difluorophenyl)methyl]ethyl}-4-(4-chloro-1-methyl-1H-pyrazol-5-yl)-5-methyl-2-furancarboxamide a) 4-(4-chloro-1-methyl-1H-pyrazol-5-yl)-5-methyl-2-furancarboxylic Acid

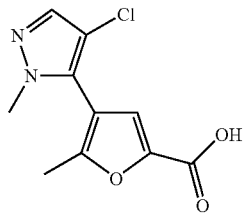 [SMILES: Cc1oc(C(=O)O)cc1-c1c(Cl)cnn1C]

To a solution of 5-methyl-4-(1-methyl-1H-pyrazol-5-yl)-2-furancarboxylic acid (150 mg, 0.73 mmol)[prepared in Example 126] in THF (10 ml) was added N-chlorosuccinimide (97 mg, 0.73 mmol). After stirring at 70° C. for 20 h in a sealed tube, the mixture was partitioned between H$_2$O-DCM and the pH of the aqueous phase was adjusted to ~4. The aqueous phase was washed several times with DCM and the combined organic fractions were dried over Na$_2$SO$_4$ and concentrated affording the title compound as an off-white foamy solid (152 mg, 0.63 mmol, 87% yield): LC-MS (ES) m/z 241 (M+H)$^+$.

b) 4-(4-chloro-1-methyl-1H-pyrazol-5-yl)-N-{(1S)-2-(3,4-difluorophenyl)-1-[(1,3-dioxo-1,3-dihydro-2H-isoindol-2-yl)methyl]ethyl}-5-methyl-2-furancarboxamide

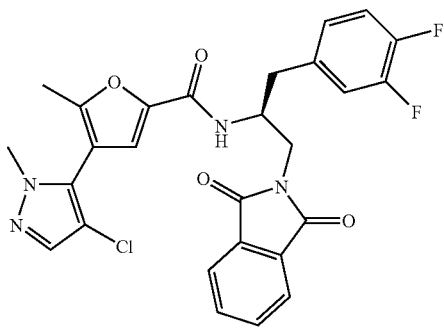 [SMILES: Cc1oc(C(=O)N[C@@H](Cc2ccc(F)c(F)c2)CN2C(=O)c3ccccc3C2=O)cc1-c1c(Cl)cnn1C]

To a solution of 4-(4-chloro-1-methyl-1H-pyrazol-5-yl)-5-methyl-2-furancarboxylic acid (150 mg, 0.62 mmol), 2-[(2S)-2-amino-3-(3,4-difluorophenyl)propyl]-1H-isoindole-1,3(2H)-dione (207 mg, 0.65 mmol)[prepared according to the procedure of Preparation 6] and N,N-diisopropylethyl amine (0.33 ml, 1.87 mmol) in DCM (10 ml) was added bromo-tris-pyrrolidino-phosphonium hexafluorophosphate (436 mg, 0.94 mmol). After stirring at ambient temperature for 20 h, the mixture was concentrated and purified using silica gel and eluting with a gradient of 0-50% ethyl acetate/hexane to afford the title compound as an off-white foam (200 mg, 0.35 mmol, 57% yield): LC-MS (ES) m/z 539 (M+H)$^+$.

c) N-{(1S)-2-amino-1-[(3,4-difluorophenyl)methyl]ethyl}-4-(4-chloro-1-methyl-1H-pyrazol-5-yl)-5-methyl-2-furancarboxamide To a solution of 4-(4-chloro-1-methyl-1H-pyrazol-5-yl)-N-{(1S)-2-(3,4-difluorophenyl)-1-[(1,3-dioxo-1,3-dihydro-2H-isoindol-2-yl)methyl]ethyl}-5-methyl-2-furancarboxamide (210 mg, 0.39 mmol) in methanol (5 ml) at 25° C. was added hydrazine (0.02 ml, 0.78 mmol) dropwise. After 12 h, the solution was concentrated, dry loaded onto silica and purified by column chromatography (5% MeOH in DCM (1% NH$_4$OH)). The free base was converted to the HCl salt by addition of excess 4M HCl in dioxane (1 ml) to the residue in MeOH (2 ml) affording the HCl salt of the title compound as an off-white solid: LC-MS (ES) m/z 409(M+H)$^+$, $^1$H NMR (400 MHz, MeOD) δ ppm 2.38 (s, 3H) 2.98 (d, J=9.35 Hz, 1H) 3.01 (d, J=5.56 Hz, 1H) 3.23 (dd, J=13.01, 8.97 Hz, 2H) 3.73-3.83 (m, 3H) 4.56 (d, J=9.35 Hz, 1H) 7.17 (s, 1H) 7.18-7.32 (m, 3H) 7.57 (s, 1H).

Example 228

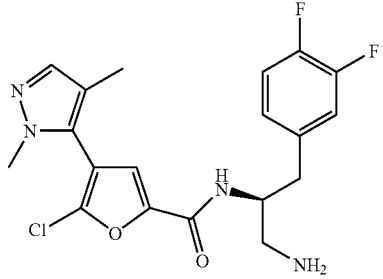 [SMILES: Cc1cnn(C)c1-c1cc(C(=O)N[C@H](CN)Cc2ccc(F)c(F)c2)oc1Cl]

Preparation of N-{(1S)-2-amino-1-[(3,4-difluorophenyl)methyl]ethyl}-5-chloro-4-(1,4-dimethyl-1H-pyrazol-5-yl)-2-furancarboxamide The title compound was prepared as an off-white solid according to the procedure of Example 118, except substituting 2-[(2S)-2-amino-3-(3,4-difluorophenyl)propyl]-1H-isoindole-1,3(2H)-dione (253 mg, 0.8 mmol)[prepared according to the procedure of Preparation 6] for 2-{(2S)-2-amino-3-[2-(trifluoromethyl)phenyl]propyl}-1H-isoindole-1,3(2H)-dione: LC-MS (ES) m/z 409 (M+H)$^+$, $^1$H NMR (400 MHz, MeOD) δ ppm 2.05-2.15 (m, 3H) 2.91-3.07 (m, 2H) 3.16-3.26 m., 2H) 3.91 (br. s., 3H) 4.57-4.59 (m., 1H) 7.09-7.31 (m, 3H) 7.51 (br. s., 1H) 8.07 (br. s., 1H)

Example 229

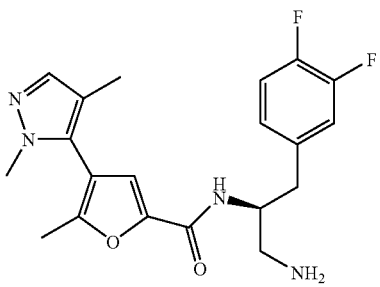 [SMILES: Cc1cnn(C)c1-c1cc(C(=O)N[C@H](CN)Cc2ccc(F)c(F)c2)oc1C]

Preparation of N-{(1S)-2-amino-1-[(3,4-difluorophenyl)methyl]ethyl}-4-(1,4-dimethyl-1H-pyrazol-5-yl)-5-methyl-2-furancarboxamide The title compound was prepared as a yellow solid according to the procedure of Example 119, except substituting 2-[(2S)-2-amino-3-(3,4-difluorophenyl)propyl]-1H-isoindole-1,3(2H)-dione (302 mg, 0.95 mmol) [prepared according to the procedure of Preparation 6] for 2-{(2S)-2-amino-3-[2-(trifluoromethyl)phenyl]propyl}-1H-isoindole-1,3(2H)-dione: LC-MS (ES) m/z 389 (M+H)$^+$, $^1$H NMR (400 MHz, MeOD) δ ppm 2.04-2.15 (m, 3H) 2.35-2.47 (m, 3H) 2.99-3.02 (m, 2H) 3.18-3.24 (m, 2H) 3.86-3.96 (m, 3H) 4.56-4.62 (m, 1H) 7.16-7.26 (m, 4H) 8.07 (s, 1H).

Example 230

N-{(1S)-2-amino-1-[(3-fluorophenyl)methyl]ethyl}-4-(4-chloro-1-ethyl-1H-pyrazol-5-yl)-2-thiophenecarboxamide

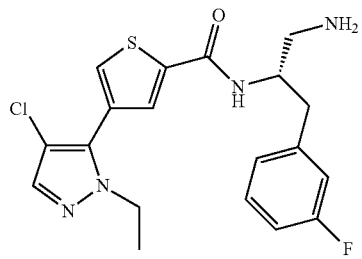 [SMILES: CCn1ncc(Cl)c1-c1csc(C(=O)N[C@H](CN)Cc2cccc(F)c2)c1]

a) 4-(4-chloro-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide

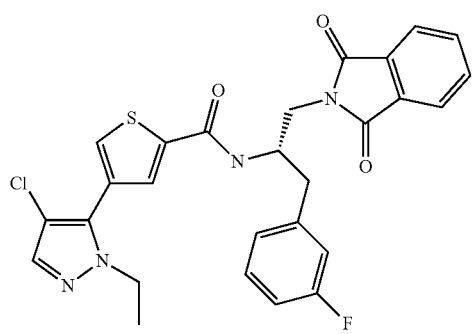 [SMILES: CCn1ncc(Cl)c1-c1csc(C(=O)N[C@@H](Cc2cccc(F)c2)CN2C(=O)c3ccccc3C2=O)c1]

To a solution of 4-(4-chloro-1-ethyl-1H-pyrazol-5-yl)-2-thiophenecarboxylic acid (220 mg, 0.857 mmol) [from Example 92] in DCM (5 mL) at 25° C. was added PyBrOP (440 mg, 0.857 mmol) in one portion, followed by addition of DIPEA (1.5 mL, 8.59 mmol). After 10 min, diamine 2-[(2S)-2-amino-3-(3-fluorophenyl)propyl]-1H-isoindole-1,3(2H)-dione (256 mg, 0.857 mmol) was added to above solution. After 2 h, the solution was concentrated and purified via column chromatography (silica, 20-50% EtOAc/Hexane) affording the title compound (0.39 g, 81%) as a white solid: LC-MS (ES) m/z=537 (M+H)$^+$.

b) N-{(1S)-2-amino-1-[(3-fluorophenyl)methyl]ethyl}-4-(4-chloro-1-ethyl-1H-pyrazol-5-yl)-2-thiophenecarboxamide

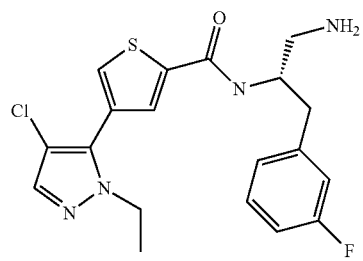 [SMILES: CCn1ncc(Cl)c1-c1csc(C(=O)N[C@H](CN)Cc2cccc(F)c2)c1]

At RT, NH$_2$NH$_2$ (0.11 mL, 3.54 mmol) was added to 4-(4-chloro-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide (380 mg, 0.708 mmol) in MeOH (4 mL). After 10 h, the solvent was removed under vacuum to give a residue, which was dissolved in DCM (15 mL), and washed with H$_2$O (10 mL×3).

To the above DCM solution was added aqueous HCl (12 N, 2.95 mL, 35.4 mmol). After 1 h, the aqueous phase was separated, and washed with DCM (10 ml×3). Water was removed under high vacuum to give the title compound (160 mg, 47%) as a white solid: LC-MS (ES) m/z=407 (M+H)$^+$, $^1$H NMR (d$_6$-DMSO, 400 MHz) δ ppm 9.18-8.8 (m, 1H), 8.28-8.08 (m, 4H), 8.04 (s, 1H), 7.27-7.43 (m, 1), 7.08-7.24 (m, 2H), 6.91-7.08 (m, 1H), 4.4-4.34 (m, 1H), 4.14 (q, J=7.3 Hz, 2H), 3.15-2.80 (m, 4H), and 1.29 (t, J=7.3 Hz, 3H).

Example 231

N-((1S)-2-amino-1-{[3-(trifluoromethyl)phenyl]methyl}ethyl)-4-(4-chloro-1-ethyl-1H-pyrazol-5-yl)-2-thiophenecarboxamide

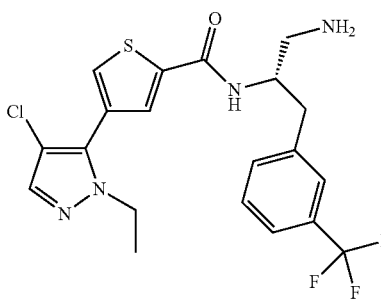

The title compound was prepared as an off-white solid according to the procedure of Example 230, except substituting 2-{(2S)-2-amino-3-[3-(trifluoromethyl)phenyl]propyl}-1H-isoindole-1,3(2H)-dione (339 mg, 0.97 mmol) for 2-[(2S)-2-amino-3-(3-fluorophenyl)propyl]-1H-isoindole-1,3(2H)-dione: LC-MS (ES) m/z=457 (M+H)$^+$, $^1$H NMR (d$_4$-MeOD, 400 MHz) δ ppm 7.92 (br s, 1H), 7.89-7.80 (m, 1H), 7.63-7.59 (m, 3H), 7.56-7.48 (m, 2H), 4.61-4.53 (m, 1H), 4.21-4.15 (m, 2H), 3.46-3.21 (m, 2H), 3.18-3.02 (m, 2H), and 1.35 (t, J=7.3 Hz, 3H).

Example 232

N-{(1S)-2-amino-1-[(4-fluorophenyl)methyl]ethyl}-4-(4-chloro-1-ethyl-1H-pyrazol-5-yl)-2-thiophenecarboxamide

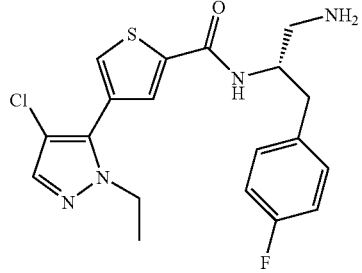 [SMILES: CCn1ncc(Cl)c1-c1csc(C(=O)N[C@H](CN)Cc2ccc(F)cc2)c1]

The title compound was prepared as an off-white solid according to the procedure of Example 230, except substituting 2-[(2S)-2-amino-3-(4-fluorophenyl)propyl]-1H-isoindole-1,3(2H)-dione (584 mg, 1.95 mmol) for 2-[(2S)-2-amino-3-(3-fluorophenyl)propyl]-1H-isoindole-1,3(2H)-dione: LC-MS (ES) m/z=407 (M+H)$^+$, $^1$H NMR (d$_4$-MeOD, 400 MHz) δ ppm 7.93 (d, J=1.3 Hz, 1H), 7.85 (d, J=1.3 Hz, 1H), 7.59 (s, 1H), 7.34-7.31 (m, 2H), 7.05-7.01 (m, 2H), 4.52 (m, 1H), 4.19 (q, J=7.3 Hz, 2H), 3.26-3.12 (m, 2H), 3.05-2.94 (m, 2H), and 1.36 (t, J=7.3 Hz, 3H).

Example 233

N-{(1S)-2-amino-1-[(3,4-difluorophenyl)methyl]ethyl}-4-(4-chloro-1-ethyl-1H-pyrazol-5-yl)-2-thiophenecarboxamide

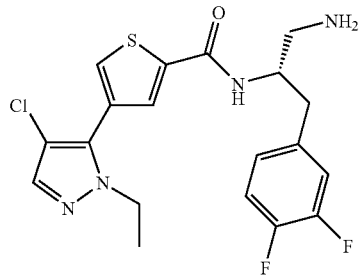 [SMILES: CCn1ncc(Cl)c1-c1csc(C(=O)N[C@H](CN)Cc2ccc(F)c(F)c2)c1]

The title compound was prepared as an off-white solid according to the procedure of Example 230, except substituting 2-[(2S)-2-amino-3-(3,4-difluorophenyl)propyl]-1H-isoindole-1,3(2H)-dione (200 mg, 0.63 mmol) for 2-[(2S)-2-amino-3-(3-fluorophenyl)propyl]-1H-isoindole-1,3(2H)-dione: LC-MS (ES) m/z=425(M+H)$^+$, $^1$H NMR (d$_6$-DMSO, 400 MHz) δ ppm 8.88 (d, J=8.3 Hz, 1H), 8.16-8.06 (m, 4H), 7.71 (s, 1H), 7.39-7.30 (m, 2H), 7.12 (m, 1H), 4.35 (m, 1H), 4.14 (q, J=7.1 Hz, 2H), 3.08-2.87 (m, 4H), and 1.29 (t, J=7.1 Hz, 3H).

Example 234

N-{(1S)-2-amino-1-[(3-fluorophenyl)methyl]ethyl}-4-(4-bromo-1-ethyl-1H-pyrazol-5-yl)-2-thiophenecarboxamide

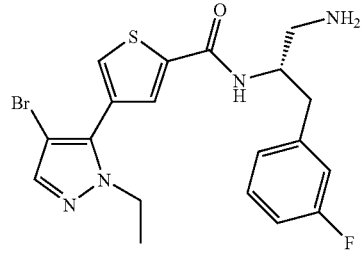

a) 4-(4-bromo-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide

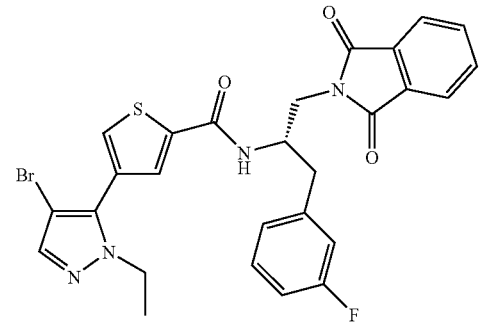

The title compound was prepared as an off-white solid according to the procedure of Example 93, except substituting 2-[(2S)-2-amino-3-(3-fluorophenyl)propyl]-1H-isoindole-1,3(2H)-dione (149 mg, 0.50 mmol) for 2-{(2S)-2-amino-3-[2-(trifluoromethyl)phenyl]propyl}-1H-isoindole-1,3(2H)-dione: LC-MS (ES) m/z=582 (M+H)$^+$.

b) N-{(1S)-2-amino-1-[(3-fluorophenyl)methyl]ethyl}-4-(4-bromo-1-ethyl-1H-pyrazol-5-yl)-2-thiophenecarboxamide

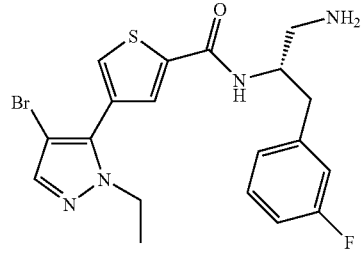

The title compound was prepared as an off-white solid according to the procedure of Example 230(b), except substituting N-{(1S)-2-amino-1-[(3-fluorophenyl)methyl]ethyl}-4-(4-bromo-1-ethyl-1H-pyrazol-5-yl)-2-thiophenecarboxamide (240 mg, 0.41 mmol) for 4-(4-chloro-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide: LC-MS (ES) m/z=452(M+H)$^+$, $^1$H NMR (d$_6$-DMSO, 400 MHz) δ ppm 9.24-8.85 (m, 1H), 8.26-8.13 (m, 4H), 8.03 (s, 1H), 7.03 (s, 1H), 7.34-7.29 (m, 1H), 7.16-7.13 (m, 2H), 7.05-7.00 (m, 1H), 4.39 (m, 1H), 4.14 (q, J=7.3 Hz, 2H), 3.06-2.96 (m, 4H), and 1.28 (t, J=7.3 Hz, 3H).

Example 235

N-((1S)-2-amino-1-{[2-(trifluoromethyl)phenyl]methyl}ethyl)-5-chloro-4-(4-chloro-1-ethyl-1H-pyrazol-5-yl)-2-thiophenecarboxamide

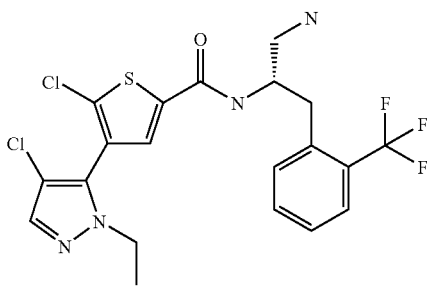 [SMILES: CCn1ncc(Cl)c1-c1cc(C(=O)N[C@H](CN)Cc2ccccc2C(F)(F)F)sc1Cl]

a) Methyl 5-chloro-4-(1-ethyl-1H-pyrazol-5-yl)-2-thiophenecarboxylate

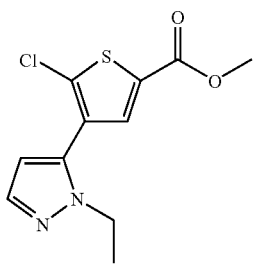 [SMILES: CCn1nccc1-c1cc(C(=O)OC)sc1Cl]

To a solution of methyl 4-bromo-5-chloro-2-thiophenecarboxylate (300 mg, 1.17 mmol) in THF (2 mL) was added Na$_2$CO$_3$ (2M, 1.76 mL, 3.52 mmol), Pd(dppf)Cl$_2$ (86, 0.117 mmol) and 1-ethyl-5-(4,4,5,5-tetramethyl-1,3,2-dioxaborolan-2-yl)-1H-pyrazole (313 mg, 1.41 mmol). The reaction mixture was heated to 80° C. in a sealed tube under N$_2$. After 2 h, the reaction mixture was concentrated under vacuum and purified on silica (EtOAc/Hex, 20-50%) to afford the title compound (0.272 g, 82%) as a light yellow syrup: LC-MS (ES) m/z=271 (M+H)$^+$.

b) Methyl 5-chloro-4-(4-chloro-1-ethyl-1H-pyrazol-5-yl)-2-thiophenecarboxylate

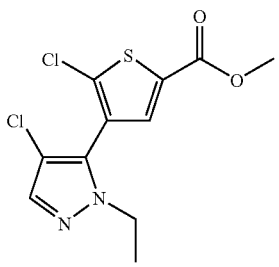 [SMILES: CCn1ncc(Cl)c1-c1cc(C(=O)OC)sc1Cl]

Methyl 5-chloro-4-[(1Z)-1-(1-ethyl-2-methylidenehydrazino)-1-propen-1-yl]-2-thiophenecarboxylate (260 mg, 0.96 mmol) and 1-chloro-2,5-pyrrolidinedione (154 mg, 1.15 mmol) in THF (4 mL) were heated at 70° C. under N$_2$ for 2 h, concentrated and purified on silica (EtOAc/Hex, 10-30%) to afford the title compound (0.281 g, 83%) as a syrup: LC-MS (ES) m/z=305 (M+H)$^+$.

c) 5-chloro-4-(4-chloro-1-ethyl-1H-pyrazol-5-yl)-2-thiophenecarboxylic Acid

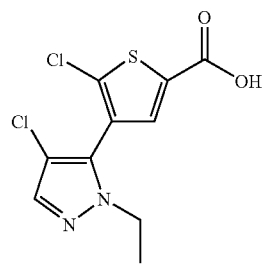 [SMILES: CCn1ncc(Cl)c1-c1cc(C(=O)O)sc1Cl]

To a solution of methyl 5-chloro-4-(4-chloro-1-ethyl-1H-pyrazol-5-yl)-2-thiophenecarboxylate (260 mg, 0.85 mmol) in THF/H$_2$O (4 mL/1 mL) was added KOH (478 mg, 8.52 mmol). The reaction mixture was heated to 50° C. for 4 h. After the mixture was concentrated and diluted with H$_2$O, the pH was adjusted to 3. The mixture was extracted with DCM (5 mL×3). The collected organic layers were concentrated under vacuum to give a crude acid, which was used directly without further purification.

d) 5-chloro-4-(4-chloro-1-ethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

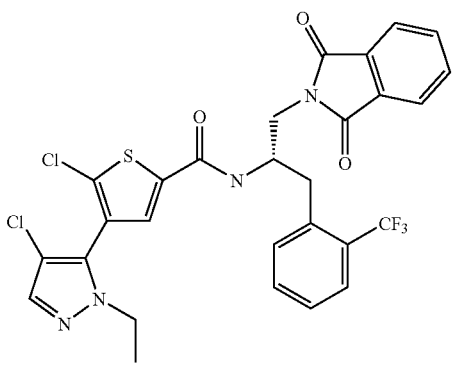 [SMILES: CCn1ncc(Cl)c1-c1cc(C(=O)N[C@@H](Cc2ccccc2C(F)(F)F)CN2C(=O)c3ccccc3C2=O)sc1Cl]

To a solution of 5-chloro-4-(4-chloro-1-ethyl-1H-pyrazol-5-yl)-2-thiophenecarboxylic acid (~0.85 mmol) in DCM (5 mL) at 25° C. was added bromo-tris-pyrrolidino phosphoniumhexafluorophosphate (PyBrOP) (477 mg, 1.02 mmol) in one portion, followed by the addition of DIPEA (0.744 mL, 4.26 mmol). After stirring for 10 min, diamine 2-{(2S)-2-amino-3-[2-(trifluoromethyl)phenyl]propyl}-1H-isoindole-1,3(2H)-dione (356 mg, 1.02 mmol) was added to the above solution. After 2 h, the solution was concentrated and purified via column chromatography (silica, 20-50% EtOAc/Hexane)

331 affording the title compound (0.416 g, 79%) as a white solid: LC-MS (ES) m/z=621 (M+H)⁺.

e) N-((1S)-2-amino-1-{[2-(trifluoromethyl)phenyl]methyl}ethyl)-5-chloro-4-(4-chloro-1-ethyl-1H-pyrazol-5-yl)-2-thiophenecarboxamide

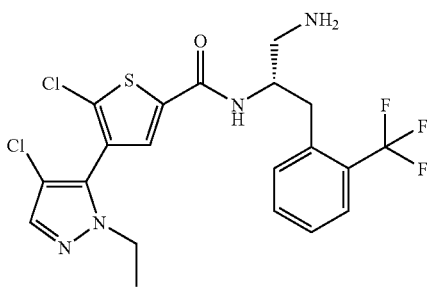 [SMILES: CCn1ncc(Cl)c1-c1cc(C(=O)N[C@H](CN)Cc2ccccc2C(F)(F)F)sc1Cl]

5-Chloro-4-(4-chloro-1-ethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (410 mg, 0.66 mmol) was dissolved in MeOH (2 mL) and was treated with NH$_2$NH$_2$ (1.04 mL, 33 mmol). The reaction was stirred over 5 h at RT, concentrated and purified by reverse-phase HPLC (C18 column: H$_2$O/CH$_3$CN, 95-5%) to afford the bis-TFA salt of the title compound. The bis-TFA salt was dissolved in water and neutralized by ammonium hydroxide. The mixture was extracted with DCM (5 mL×3), dried over Na$_2$SO$_4$ and concentrated to give a free base of the title compound, which was dissolved in MeOH (2 mL), and treated with HCl (4 M in dioxane, 1.6 mL). After stirring overnight, the reaction solution was concentrated to give the title compound (160 mg, 42%) as a di-HCl salt: LC-MS: m/z=491 (M+H)⁺, ¹H NMR (d$_6$-DMSO, 400 MHz) δ ppm 9.34 (J=8.8 Hz, 1H), 8.38-8.03 (m, 3H), 7.77 (s, 1H), 7.69-7.59 (m, 2H), 7.53 (dd, J=7.3, 7.3 Hz, 1H), 7.42 (dd, J=7.6, 7.6 Hz, 1H), 4.48 (m, 1H), 4.13-4.00 (m, 2H), 3.17-2.90 (m, 4H), and 1.29 (m, 3H).

Example 236

N-{(1S)-2-amino-1-[(3-fluorophenyl)methyl]ethyl}-5-chloro-4-(4-chloro-1-ethyl-1H-pyrazol-5-yl)-2-thiophenecarboxamide

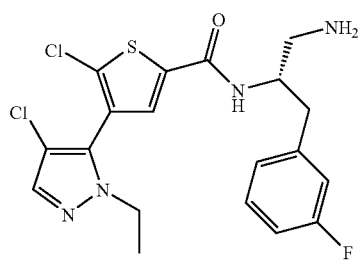

332 a) 5-chloro-4-(4-chloro-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide

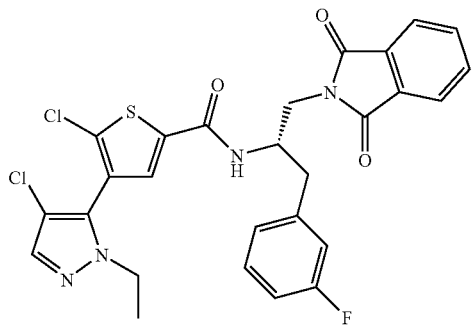 [SMILES: CCn1ncc(Cl)c1-c1cc(C(=O)N[C@@H](Cc2cccc(F)c2)CN2C(=O)c3ccccc3C2=O)sc1Cl]

To a solution of 5-chloro-4-(4-chloro-1-ethyl-1H-pyrazol-5-yl)-2-thiophenecarboxylic acid (180 mg, 0.618 mmol) [from Example 235(c)] in DCM (5 mL) at 25° C. was added PyBrOP in one portion, followed by addition of DIPEA (0.54 mL, 3.09 mmol). After stirring for 10 min, 2-[(2S)-2-amino-3-(3-fluorophenyl)propyl]-1H-isoindole-1,3(2H)-dione (203 mg, 0.68 mmol) was added to above solution in one portion. After stirring for 2 h, the solution was concentrated and purified via column chromatography (silica, 20-50% EtOAc/Hexane) affording the title compound (285 mg, 77%) as a white solid: LC-MS (ES) m/z=571 (M+H)⁺.

b) N-{(1S)-2-amino-1-[(3-fluorophenyl)methyl]ethyl}-5-chloro-4-(4-chloro-1-ethyl-1H-pyrazol-5-yl)-2-thiophenecarboxamide

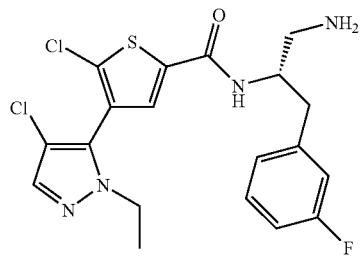 [SMILES: CCn1ncc(Cl)c1-c1cc(C(=O)N[C@H](CN)Cc2cccc(F)c2)sc1Cl]

At RT, NH$_2$NH$_2$ (0.15 ml, 4.78 mmol) was added to 5-chloro-4-(4-chloro-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide (280 mg, 0.49 mmol) in MeOH (5 mL). After 10 h the solvent was removed under vacuum. The resulting residue was dissolved in DCM (15 mL), and washed with H$_2$O (10 mL×3). To the DCM solution was added HCl (12 N, 1.0 mL). After 1 h, the aqueous phase was separated and washed with DCM (10 ml×3). Water was removed under high vacuum to give the tilte compound (179 mg, 67.5%) as an off-white solid: LC-MS (ES) m/z=441 (M+H)⁺, ¹H NMR (d$_4$-MeOD, 400 MHz) δ ppm 7.72-7.67 (m, 1H), 7.62 (s, 1H), 7.35-7.29 (m, 1H), 7.14-7.17 (m, 2H), 7.00-6.96 (m, 1H), 4.53 (m, 1H), 4.14-3.97 (m, 2H), 3.37-3.15 (m, 2H), 3.07-2.97 (m, 2H), and 1.33 (t, J=7.1 Hz, 3H).

Example 237

N-{(1S)-2-amino-1-[(4-fluorophenyl)methyl]ethyl}-5-chloro-4-(4-chloro-1-ethyl-1H-pyrazol-5-yl)-2-thiophenecarboxamide

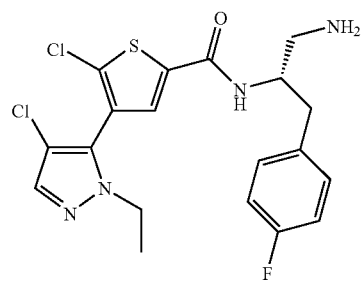 [SMILES: CCn1ncc(Cl)c1-c1cc(C(=O)N[C@H](CN)Cc2ccc(F)cc2)sc1Cl]

The title compound (190 mg, 70%) was prepared as an off-white solid according to the procedure of Example 236, except substituting 2-[(2S)-2-amino-3-(4-fluorophenyl)propyl]-1H-isoindole-1,3(2H)-dione (231 mg, 0.77 mmol) for 2-[(2S)-2-amino-3-(3-fluorophenyl)propyl]-1H-isoindole-1,3(2H)-dione: LC-MS (ES) m/z 441 (M+H)$^+$, $^1$H NMR (d$_4$-MeOD, 400 MHz, no calibration of chemical shift of MeOD solvent peak) δ ppm 6.09 (s, 1H), 6.08 (s, 1H), 5.78-5.75 (m, 2H), 5.53-5.48 (m, 2H), 2.96 (m, 1H), 2.51 (m, 2H), 1.71-1.67 (m, 1H), 1.62-1.54 (m, 1H), 1.49-1.38 (m, 2H), and −0.21 (t, J=7.3 Hz, 3H).

Example 238

N-((1S)-2-amino-1-{[3-(trifluoromethyl)phenyl]methyl}ethyl)-5-chloro-4-(4-chloro-1-ethyl-1H-pyrazol-5-yl)-2-thiophenecarboxamide

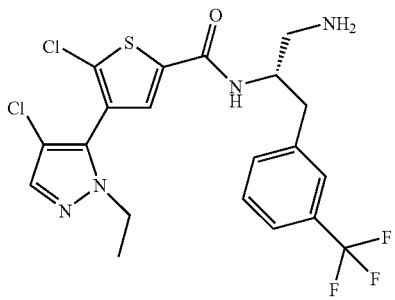 [SMILES: CCn1ncc(Cl)c1-c1cc(C(=O)N[C@H](CN)Cc2cccc(C(F)(F)F)c2)sc1Cl]

The title compound (228 mg, 58.2%) was prepared as an off-white solid according to the procedure of Example 236, except substituting 2-{(2S)-2-amino-3-[3-(trifluoromethyl)phenyl]propyl}-1H-isoindole-1,3(2H)-dione (156 mg, 0.45 mmol) for 2-[(2S)-2-amino-3-(3-fluorophenyl)propyl]-1H-isoindole-1,3(2H)-dione: LC-MS (ES) m/z 491(M+H)$^+$, $^1$H NMR (d$_4$-MeOD, 400 MHz) δ ppm 7.66-7.49 (m, 6H), 4.60-4.47 (m, 1H), 4.09-4.01 (m, 2H), 3.36-3.18 (m, 2H), 3.16-3.01 (m, 2H), and 1.33 (t, J=7.1 Hz, 3H).

Example 239

N-((1S)-2-amino-1-{[2-(trifluoromethyl)phenyl]methyl}ethyl)-4-(1-methyl-1H-pyrazol-5-yl)-5-(trifluoromethyl)-2-thiophenecarboxamide

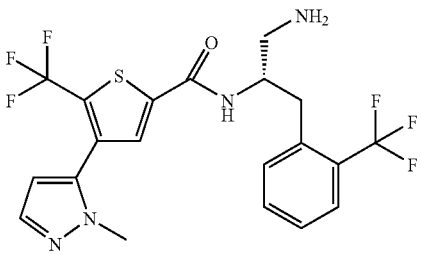 [SMILES: Cn1nccc1-c1cc(C(=O)N[C@H](CN)Cc2ccccc2C(F)(F)F)sc1C(F)(F)F]

a) methyl 4-bromo-5-iodo-2-thiophenecarboxylate

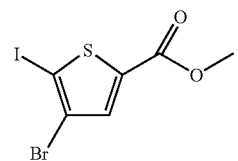

At −78° C., nBuLi (2.05 mL, 5.13 mmol) was added to a solution of methyl 4,5-dibromo-2-thiophenecarboxylate (1.4 g, 4.67 mmol) in THF (10 mL). After the mixture was stirred for 30 min, I$_2$ (1.185 g, 4.67 mmol) was added in 3 mL THF. After the resulting solution was stirred at −78° C. for 1 h, it was quenched with Na$_2$S$_2$O$_3$ at −78° C., and warmed to RT. The reaction mixture was extracted with DCM, dried over Na$_2$SO$_4$, and concentrated. The crude product was purified on silica (EtOAc/Hex, 0-10%) to give the title compound (1.3 g, 56%) as a yellow solid: LC-MS (ES) m/z 348(M+H)$^+$.

b) methyl 4-bromo-5-(trifluoromethyl)-2-thiophenecarboxylate

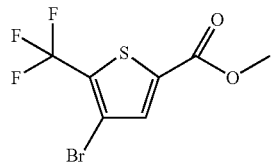

To a solution of methyl 4-bromo-5-iodo-2-thiophenecarboxylate (500 mg, 1.44 mmol), copper (I) iodide (137 mg, 0.72 mmol) and potassium fluoride (251 mg, 4.32 mmol) in DMF/HMPA (5 ml/5 mL) was added methyl difluoro(fluorosulfonyl)acetate (1.1 g, 5.76 mmol). The mixture was heated at 70° C. under N$_2$ in a sealed tube. After 1 h, the reaction was quenched with NH$_4$Cl (sat'd) (2 mL), extracted with ether (5 mL×5) and washed with distilled water (5 mL×5). The combined organic phase was dried over Mg$_2$SO$_4$ and purified on silica (EtOAc/Hex, 20-50%) to afford the title compound (0.82 g) containing a 60% inseparable impurity: LC-MS m/z (ES) 290 (M+H)+.

c) methyl 4-(1-methyl-1H-pyrazol-5-yl)-5-(trifluoromethyl)-2-thiophenecarboxylate

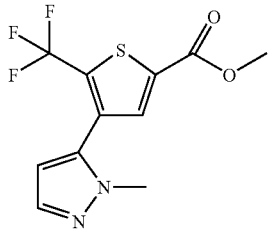 [SMILES: COC(=O)c1cc(-c2ccnn2C)c(C(F)(F)F)s1]

A mixture of methyl 4-bromo-5-(trifluoromethyl)-2-thiophenecarboxylate (0.8 g, 40% purity, 1.11 mmol), 1-methyl-5-(4,4,5,5-tetramethyl-1,3,2-dioxaborolan-2-yl)-1H-pyrazole (0.299 g, 1.434 mmol), tetrakis (0.128 g, 0.11 mmol) and K$_2$CO$_3$ (0.459 g, 3.32 mmol) in dioxane/H$_2$O (5 mL/1 mL) was heated to 70° C. in a sealed tube. After 12 h, the reaction mixture was concentrated under vacuum and purified on silica (EtOAc/Hex, 40-60%) to afford the title compound (0.25 g, 70%) as a light yellow solid: LC-MS (ES) m/z 291 (M+H)+.

d) 4-(1-methyl-1H-pyrazol-5-yl)-5-(trifluoromethyl)-2-thiophenecarboxylic Acid

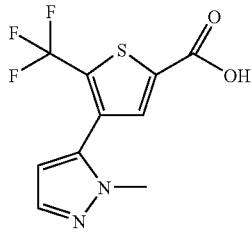 [SMILES: Cn1nccc1-c1cc(C(=O)O)sc1C(F)(F)F]

To a solution of methyl 4-(1-methyl-1H-pyrazol-5-yl)-5-(trifluoromethyl)-2-thiophenecarboxylate (250 mg, 0.77 mmol), in THF/H$_2$O (3 mL/0.3 mL), was added KOH (217 mg, 3.88 mmol). The reaction mixture was heated to 50° C. for 4 h. After the mixture was concentrated and diluted with H$_2$O, the pH was adjusted to 3. The mixture was extracted with DCM (5 mL×3). The collected organic layers were concentrated under vacuum to give crude acid (235 mg, 80% pure) which was used directly in the next step without further purification: LC-MS (ES) 277 (M+H)+.

e) N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)-5-(trifluoromethyl)-2-thiophenecarboxamide

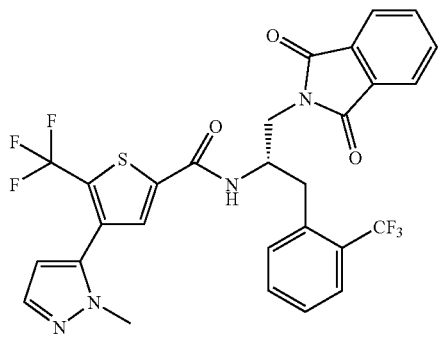 [SMILES: Cn1nccc1-c1cc(C(=O)N[C@@H](Cc2ccccc2C(F)(F)F)CN2C(=O)c3ccccc3C2=O)sc1C(F)(F)F]

At room temperature, a mixture of 4-(1-methyl-1H-pyrazol-5-yl)-5-(trifluoromethyl)-2-thiophenecarboxylic acid (235 mg, 80% purity, 0.68 mmol), phosphoniumhexafluorophosphate (PyBrOP) (381 mg, 0.19 mmol), DIPEA (0.59 mL, 3.4 mmol) and 2-{(2S)-2-amino-3-[2-(trifluoromethyl)phenyl]propyl}-1H-isoindole-1,3(2H)-dione (261 mg, 0.75 mmol) in DCM (5 mL) was stirred for 2 h. The reaction solution was concentrated and purified via column chromatography (silica, 20-50% EtOAc/Hexane) affording the title compound (386 mg, 86%) as a white solid: LC-MS (ES) 607 (M+H)+ f) N-((1S)-2-amino-1-{[2-(trifluoromethyl)phenyl]methyl}ethyl)-4-(1-methyl-1H-pyrazol-5-yl)-5-(trifluoromethyl)-2-thiophenecarboxamide

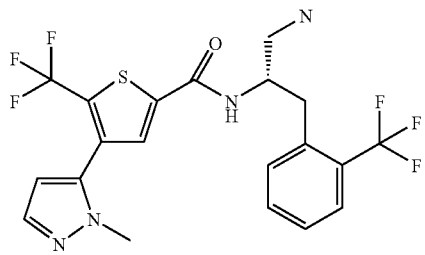 [SMILES: Cn1nccc1-c1cc(C(=O)N[C@H](CN)Cc2ccccc2C(F)(F)F)sc1C(F)(F)F]

N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)-5-(trifluoromethyl)-2-thiophenecarboxamide (150 mg, 0.25 mmol) was dissolved in MeOH (5 mL) and was treated with NH$_2$NH$_2$ (0.76 mL, 24.2 mmol). The reaction was stirred over 5 h, concentrated and purified by reverse-phase HPLC (C18 column: H$_2$O/CH$_3$CN, 95-5%) to afford the bis-TFA salt of the title compound. The bis-TFA salt was dissolved in water, and ammonium hydroxide (0.32 mL, 30% wt %, 2.46 mmol) was added. The mixture was extracted with DCM (5 mL×3), dried over Na$_2$SO$_4$ and concentrated to give a free base of the title compound. The free base compound was dissolved in MeOH (2 mL), and treated with HCl (4 M in dioxane, 0.62 mL, 2.48 mmol). After stirring overnight, the reaction solution was concentrated to give the title compound (90 mg, 66%) as a white solid LC-MS (ES) m/z 477 (M+H)+, $^1$H NMR (d$_6$-DMSO, 400 MHz) δ ppm 8.00 (d, J=1.1 Hz, 1H), 7.77 (d, J=1.8 Hz, 1H), 7.72 (d, J=7.8 Hz, 1H), 7.59-7.52 (m, 2H), 7.44 (d, J=7.4 Hz, 1H), 6.57 (d, J=2.0 Hz, 1H), 4.67 (m, 1H), 3.87 (s, 3H), and 3.37-3.14 (m, 4H).

Example 240

N-((1S)-2-amino-1-{[2-(trifluoromethyl)phenyl]methyl}ethyl)-4-(1-ethyl-4-methyl-1H-pyrazol-5-yl)-2-thiophenecarboxamide

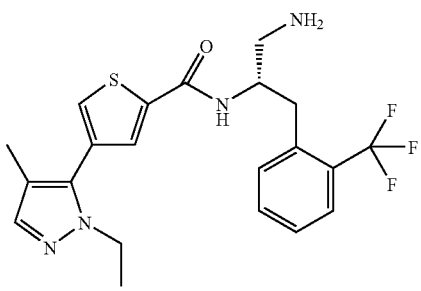 [SMILES: CCn1ncc(C)c1-c1csc(C(=O)N[C@H](CN)Cc2ccccc2C(F)(F)F)c1]

a) 1-ethyl-4-methyl-5-(4,4,5,5-tetramethyl-1,3,2-dioxaborolan-2-yl)-1H-pyrazole

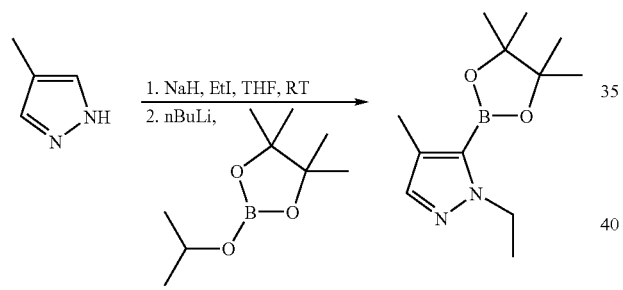

To a suspension of NaH (4.3 g, 60%, 108 mmol) in THF (200 mL) at RT was added 4-methyl-1H-pyrazole (6.8 g, 83 mmol) dropwise. After 30 min, EtI (8.03 mL, 99 mmol) was added dropwise. After the reaction was complete (2 h), the reaction solution was diluted with saturated aqueous NH₄Cl and extracted with ether. The ether fractions, were washed with water (3×100 mL), and dried over MgSO₄.

At 0° C., to the above ether solution of 4-methylpyrazole was added n-BuLi (36.4 mL, 2.5 M in Hexane, 91 mmol) dropwise. The reaction solution was stirred for 1 hour at RT and then cooled to −78° C. [*J. Heterocyclic Chem.* 41, 931 (2004)]. To the reaction solution was added 2-isopropoxy-4,4,5,5-tetramethyl-1,3,2-dioxaborolane (18.49 g, 99 mmol). After 15 min at −78° C., the reaction was allowed to warm to 0° C. over 1 hour. The reaction was diluted with saturated NH₄Cl solution and extracted with DCM. The organics were dried over Na₂SO₄ and concentrated under vacuum to afford 1-ethyl-4-methyl-5-(4,4,5,5-tetramethyl-1,3,2-dioxaborolan-2-yl)-1H-pyrazole (16 g, 80% purity) as a syrup which was used without further purification: LC-MS (ES) m/z 155 (M+H)⁺ for [RB(OH)2].

b) methyl 4-(1-ethyl-4-methyl-1H-pyrazol-5-yl)-2-thiophenecarboxylate

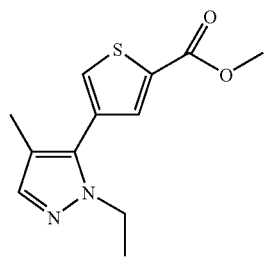

A mixture of methyl 4-bromo-2-thiophenecarboxylate (300 mg, 1.36 mmol), 1-ethyl-4-methyl-5-(4,4,5,5-tetramethyl-1,3,2-dioxaborolan-2-yl)-1H-pyrazole (449 mg, 1.9 mmol), Pd(Ph₃P)₄ (157 mg, 0.136 mmol), and K₂CO₃ (536 mg, 4.07 mmol) was heated at 70° C. for 2 h, concentrated and purified on silica (EtOAc/Hex, 10-30%) to afford the title compound (0.27 g, 79%) as a syrup: LC-MS m/z=251 (M+H)⁺.

c) 4-(1-ethyl-4-methyl-1H-pyrazol-5-yl)-2-thiophenecarboxylic Acid

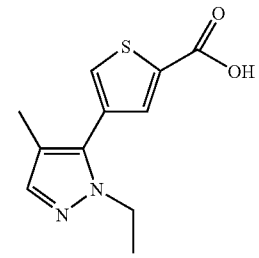 [SMILES: CCn1ncc(C)c1-c1csc(C(=O)O)c1]

To a solution of methyl 4-(1-ethyl-4-methyl-1H-pyrazol-5-yl)-2-thiophenecarboxylate (270 mg, 1.08 mmol) in THF/H₂O (2 mL/0.4 mL) was added KOH (303 mg, 1.79 mmol). The reaction mixture was heated to 50° C. for 4 h. After the mixture was concentrated and diluted with H₂O, the pH was adjusted to 3. The mixture was extracted with DCM (5 mL×3). The collected organic layers were concentrated under vacuum to give the crude acid (240 mg), which was used directly in the next step without further purification: LC-MS m/z=237 (M+H)⁺.

d) N-((1S)-2-(1,3-dioxo-1,3-dihydro-2H-isoindol-2-yl)-1-{[2-(trifluoromethyl)phenyl]methyl}ethyl)-4-(1-ethyl-4-methyl-1H-pyrazol-5-yl)-2-thiophenecarboxamide

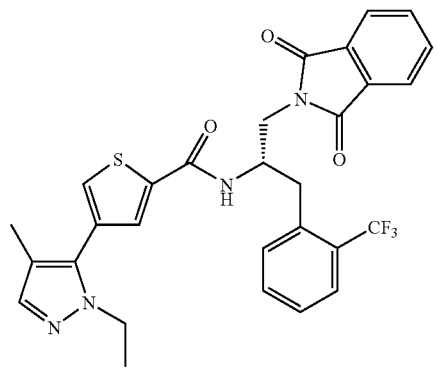 [SMILES: CCn1ncc(C)c1-c1csc(C(=O)N[C@@H](Cc2ccccc2C(F)(F)F)CN2C(=O)c3ccccc3C2=O)c1]

339

To a mixture of 4-(1-ethyl-4-methyl-1H-pyrazol-5-yl)-2-thiophenecarboxylic acid (240 mg, 1.02 mmol) and bromo-tris-pyrrolidino phosphoniumhexafluorophosphate (Pybrop) (568 mg, 1.22 mmol) was added DIPEA (1.77 ml, 10.16 mmol). After 10 min, 2-{(2S,4Z)-2-amino-4-[(1E)-1-(trifluoromethyl)-1-propen-1-yl]-4,6-heptadiene-1-yl}-1H-isoindole-1,3(2H)-dione (425 mg, 1.22 mmol) was added. After 2 h, the solution was concentrated and purified via column chromatography (silica, 20-50% EtOAc/Hexane) affording the title compound (365 mg, 63%) as a white solid: LC-MS (ES) m/z 567 (M+H)$^+$.

e) N-((1S)-2-amino-1-{[2-(trifluoromethyl)phenyl]methyl}ethyl)-4-(1-ethyl-4-methyl-1H-pyrazol-5-yl)-2-thiophenecarboxamide

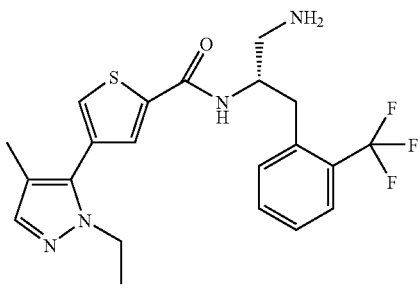 [SMILES: CCn1ncc(C)c1-c1csc(C(=O)N[C@H](CN)Cc2ccccc2C(F)(F)F)c1]

N-((1S)-2-(1,3-dioxo-1,3-dihydro-2H-isoindol-2-yl)-1-{[2-(trifluoromethyl)phenyl]methyl}ethyl)-4-(1-ethyl-4-methyl-1H-pyrazol-5-yl)-2-thiophenecarboxamide (365 mg, 0.64 mmol) was dissolved in MeOH (8 mL) and was treated with NH$_2$NH$_2$ (0.1 mL, 3.22 mmol). The reaction was stirred over 5 h, concentrated and purified by reverse-phase HPLC (C18 column: H$_2$O/CH$_3$CN, 95-5%) to afford the bis-TFA salt of the title compound. The bis-TFA salt was dissolved in water, and ammonium hydroxide (4.18 mL, 30% wt %, 32.2 mmol) was added. The mixture was extracted with DCM (5 mL×3), dried over Na$_2$SO$_4$ and concentrated to give a free base of the title compound. The free base compound was dissolved in MeOH (2 mL) and treated with HCl (4 M in dioxane, 3.22 mL, 12.88 mml). After stirring overnight, the reaction solution was concentrated to give the title compound (190 mg, 56.7%) as a white solid: LC-MS (ES) m/z 437 (M+H)$^+$, NMR (d$_6$-DMSO, 400 MHz) δ ppm 8.96 (m, 1H), 8.17-8.04 (m, 4H), 7.87 (s, 1H), 7.69 (d, J=7.6 Hz, 1H), 7.62 (m, 1H), 7.53 (dd, J=7.3, 7.3 Hz, 1H), 7.42 (d, J=7.6 Hz, 1H), 7.38 (s, 1H), 4.50 (m, 1H), 4.09 (q, J=7.3 Hz, 2H), 3.18-2.98 (m, 4H), 2.00 (s, 3H), and 1.27 (t, J=7.3 Hz, 3H).

Example 241

(N-{(1S)-2-amino-1-[(3-fluorophenyl)methyl]ethyl}-4-(1-ethyl-4-methyl-1H-pyrazol-5-yl)-2-thiophenecarboxamide

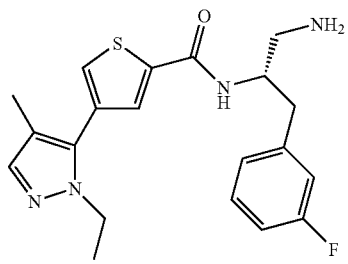 [SMILES: CCn1ncc(C)c1-c1csc(C(=O)N[C@H](CN)Cc2cccc(F)c2)c1]

340 a) N-{(1S)-2-(1,3-dioxo-1,3-dihydro-2H-isoindol-2-yl)-1-[(3-fluorophenyl)methyl]ethyl}-4-(1-ethyl-4-methyl-1H-pyrazol-5-yl)-2-thiophenecarboxamide

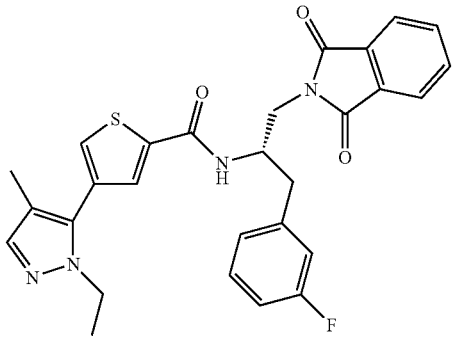 [SMILES: CCn1ncc(C)c1-c1csc(C(=O)N[C@@H](Cc2cccc(F)c2)CN2C(=O)c3ccccc3C2=O)c1]

To a solution of 4-(1-ethyl-4-methyl-1H-pyrazol-5-yl)-2-thiophenecarboxylic acid (125 mg, 0.53 mmol) [from Example 240(c)] in DCM (5 mL) at 25° C. was added bromo-tris-pyrrolidino phosphoniumhexafluorophosphate(PyBrOP) in one portion (350 mg, 0.75 mmol), followed by addition of DIPEA (0.7 ml, 4.0 mmol). After 10 min, 2-{(2S)-2-amino-3-[3-(trifluoromethyl)phenyl]propyl}-1H-isoindole-1,3(2H)-dione (180 mg, 0.60 mmol) was added to above solution. After 2 h, the reaction mixture was concentrated and purified via column chromatography (silica, 20-50% EtOAc/Hexane) affording the title compound (258 mg, 94%) as a white solid: LC-MS (ES) m/z 517 (M+H)$^+$.

b) N-{(1S)-2-amino-1-[(3-fluorophenyl)methyl]ethyl}-4-(1-ethyl-4-methyl-1H-pyrazol-5-yl)-2-thiophenecarboxamide

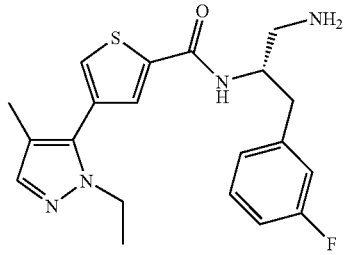 [SMILES: CCn1ncc(C)c1-c1csc(C(=O)N[C@H](CN)Cc2cccc(F)c2)c1]

At RT, NH$_2$NH$_2$ (0.1 mL, 3.19 mmol) was added to N-{(1S)-2-(1,3-dioxo-1,3-dihydro-2H-isoindol-2-yl)-1-[(3-fluorophenyl)methyl]ethyl}-4-(1-ethyl-4-methyl-1H-pyrazol-5-yl)-2-thiophenecarboxamide (252 mg, 0.49 mmol) in MeOH (5 ml). After 10 h, the solvent was removed under vacuum. The resulting residue was dissolved in DCM (10 mL) and washed with H$_2$O (10 mL×3).

To the above DCM solution was added HCl (36%, 2 mL). After 1 h, the aqueous phase was separated and washed with DCM (10 ml×3). Water was removed under high vacuum to give the title compound (170 mg, 72%) as an off-white solid: LC-MS (ES) m/z 387 (M+H)$^+$, NMR (d$_6$-DMSO, 400 MHz) δ ppm 8.87 (d, J=8.9 Hz, 1H), 8.08 (br s, 2H), 8.01 (s, 1H), 7.08 (s, 1H), 7.37 (s, 1H), 7.35-7.29 (m, 1H), 7.16-7.10 (m, 2H), 7.05-7.00 (m, 1H), 4.38 (m, 1H), 4.07 (q, J=7.3 Hz, 2H), 3.04-2.94 (m, 4H), 2.00 (s, 3H), and 1.26 (t, J=7.3 Hz, 3H).

Example 242

N-((1S)-2-amino-1-{[3-(trifluoromethyl)phenyl]methyl}ethyl)-4-(1-ethyl-4-methyl-1H-pyrazol-5-yl)-2-thiophenecarboxamide

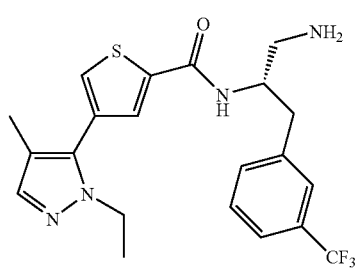 [SMILES: CCn1ncc(C)c1-c1csc(C(=O)N[C@H](CN)Cc2cccc(C(F)(F)F)c2)c1]

The title compound (180 mg, 67%) was prepared as an off-white solid according to the procedure of Example 241, except substituting 2-{(2S)-2-amino-3-[3-(trifluoromethyl)phenyl]propyl}-1H-isoindole-1,3(2H)-dione (220 mg, 0.63 mmol) for 2-[(2S)-2-amino-3-(3-fluorophenyl)propyl]-1H-isoindole-1,3(2H)-dione: LC-MS (ES) m/z 437 (M+H)$^+$, NMR (d$_6$-DMSO, 400 MHz) δ ppm 8.96 (d, J=8.84 Hz, 1H), 8.15 (m, 2H), 8.04 (d, J=1.3 Hz, 1H), 7.86 (d, J=1.3 Hz, 1H), 7.69-7.49 (m, 4H), 7.36 (s, 1H), 4.39 (m, 1H), 4.09 (q, J=7.1 Hz, 2H), 3.11-3.00 (m, 4H), 1.99 (s, 3H), and 1.25 (t, J=7.1 Hz, 3H).

Example 243

N-{(1S)-2-amino-1-[(4-fluorophenyl)methyl]ethyl}-4-(1-ethyl-4-methyl-1H-pyrazol-5-yl)-2-thiophenecarboxamide

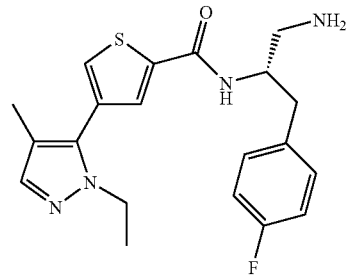 [SMILES: CCn1ncc(C)c1-c1csc(C(=O)N[C@H](CN)Cc2ccc(F)cc2)c1]

The title compound was prepared as an off-white solid according to the procedure of Example 241, except substituting 2-[(2S)-2-amino-3-(4-fluorophenyl)propyl]-1H-isoindole-1,3(2H)-dione (160 mg, 0.536 mmol) for 2-[(2S)-2-amino-3-(3-fluorophenyl)propyl]-1H-isoindole-1,3(2H)-dione: LC-MS (ES) m/z 387 (M+H)$^+$, NMR (d$_6$-DMSO, 400 MHz) δ ppm 8.90 (d, J=8.6 Hz, 1H), 8.13 (m, 2H), 8.03 (d, J=1.3 Hz, 1H), 7.87 (d, J=1.3 Hz, 1H), 7.38-7.30 (m, 3H), 7.12-7.08 (m, 2H), 4.36 (m, 1H), 4.07 (q, J=7.1 Hz, 2H), 3.07-2.97 (m, 2H), 2.96-2.88 (m, 2H), 2.00 (s, 3H), and 1.25 (t, J=7.1 Hz, 3H).

Example 244

N-{(1S)-2-amino-1-[(3,4-difluorophenyl)methyl]ethyl}-4-(1-ethyl-4-methyl-1H-pyrazol-5-yl)-2-thiophenecarboxamide

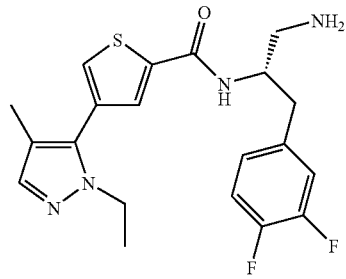 [SMILES: CCn1ncc(C)c1-c1csc(C(=O)N[C@H](CN)Cc2ccc(F)c(F)c2)c1]

The title compound (210 mg, 72%) was prepared as an off-white solid according to the procedure of Example 241, except substituting 2-[(2S)-2-amino-3-(3,4-difluorophenyl)propyl]-1H-isoindole-1,3(2H)-dione (240 mg, 0.76 mmol) for 2-[(2S)-2-amino-3-(3-fluorophenyl)propyl]-1H-isoindole-1,3(2H)-dione: LC-MS (ES) m/z 405 (M+H)$^+$, NMR (d$_6$-DMSO, 400 MHz) δ ppm 8.99 (d, J=8.34 Hz, 1H), 8.16 (m, 2H), 8.09 (d, J=1.0 Hz, 1H), 7.87 (d, J=1.0 Hz, 1H), 7.40-7.30 (m, 3H), 7.13 (br s, 1H), 4.36 (m, 1H), 4.08 (q, J=7.3 Hz, 2H), 3.06-2.99 (m, 2H), 2.96-2.33 (m, 2H), 2.00 (s, 3H), and 1.26 (t, J=7.3 Hz, 3H).

Example 245

N-((1S)-2-amino-1-{[2-(trifluoromethyl)phenyl]methyl}ethyl)-5-chloro-4-(1-ethyl-4-methyl-1H-pyrazol-5-yl)-2-thiophenecarboxamide

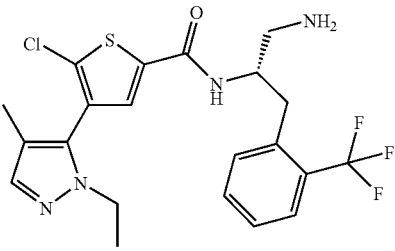 [SMILES: CCn1ncc(C)c1-c1cc(C(=O)N[C@H](CN)Cc2ccccc2C(F)(F)F)sc1Cl]

a) Methyl 5-chloro-4-(1-ethyl-4-methyl-1H-pyrazol-5-yl)-2-thiophenecarboxylate

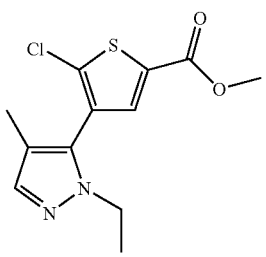

A mixture of methyl 4-bromo-5-chloro-2-thiophenecarboxylate (230 mg, 0.9 mmol), 1-ethyl-4-methyl-5-(4,4,5,5-tetramethyl-1,3,2-dioxaborolan-2-yl)-1H-pyrazole (425 mg, 1.8 mmol), PdCl$_2$(dppf) (65.9 mg, 0.09 mmol), and sodium carbonate (2N aq, 1.35 mL, 2.7 mmol) in THF (5 mL) was heated to 70° C. in a sealed tube. Afte 5 h, the reaction mixture was concentrated under vacuum and purified on silica (EtOAc/Hex, 40-60%) to afford the title compound (241 mg, 92%) as a light yellow solid: LC-MS (ES) m/z=285 (M+H)$^+$.

b) 5-chloro-4-(1-ethyl-4-methyl-1H-pyrazol-5-yl)-2-thiophenecarboxylic Acid

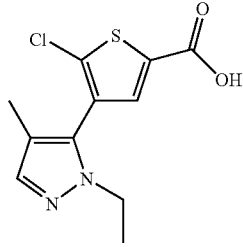 [SMILES: CCn1ncc(C)c1-c1cc(C(=O)O)sc1Cl]

To a solution of methyl 5-chloro-4-(1-ethyl-4-methyl-1H-pyrazol-5-yl)-2-thiophenecarboxylate (260 mg, 0.90 mmol) in THF/H$_2$O (2 mL/2 mL) was added KOH (201 mg, 3.6 mmol). The reaction mixture was heated to 50° C. for 4 h. After the mixture was concentrated and diluted with H$_2$O, the pH was adjusted to 3. The mixture was extracted with DCM (5 mL×3). The collected organic layers were concentrated under vacuum to give crude 5-chloro-4-(1-ethyl-4-methyl-1H-pyrazol-5-yl)-2-thiophenecarboxylic acid, which was used directly without further purification: LC-MS (ES) m/z 271 (M+H)$^+$.

c) 5-chloro-N-((1S)-2-(1,3-dioxo-1,3-dihydro-2H-isoindol-2-yl)-1-{[2-(trifluoromethyl)phenyl]methyl}ethyl)-4-(1-ethyl-4-methyl-1H-pyrazol-5-yl)-2-thiophenecarboxamide

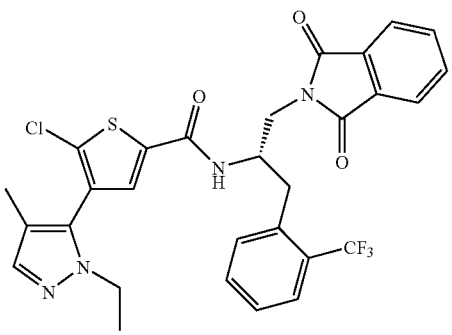 [SMILES: CCn1ncc(C)c1-c1cc(C(=O)N[C@@H](Cc2ccccc2C(F)(F)F)CN2C(=O)c3ccccc3C2=O)sc1Cl]

To the above acid in DCM (5 mL) at 25° C. was added bromo-tris-pyrrolidino phosphoniumhexafluorophosphate (PyBrOP) (542 mg, 1.16 mmol) in one portion, followed by addition of DIPEA (0.16 mL, 0.90 mmol). After 10 min, 2-{(2S)-2-amino-3-[2-(trifluoromethyl)phenyl]propyl}-1H-isoindole-1,3(2H)-dione (312 mg, 0.90 mmol) was added in one portion. After 2 h, the reaction solution was concentrated and purified via column chromatography (silica, 20-50% EtOAc/Hexane) affording the title compound (278 mg, 49% for two steps) as a white solid: LC-MS (ES) m/z 601 (M+H)$^+$.

d) N-((1S)-2-amino-1-{[2-(trifluoromethyl)phenyl]methyl}ethyl)-5-chloro-4-(1-ethyl-4-methyl-1H-pyrazol-5-yl)-2-thiophenecarboxamide

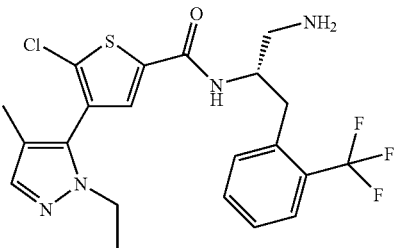 [SMILES: CCn1ncc(C)c1-c1cc(C(=O)N[C@H](CN)Cc2ccccc2C(F)(F)F)sc1Cl]

5-Chloro-N-((1S)-2-(1,3-dioxo-1,3-dihydro-2H-isoindol-2-yl)-1-{[2-(trifluoromethyl)phenyl]methyl}ethyl)-4-(1-ethyl-4-methyl-1H-pyrazol-5-yl)-2-thiophenecarboxamide (255 mg, 0.42 mmol) was dissolved in MeOH (2 mL) and was treated with NH$_2$NH$_2$ (0.13 mL, 4.2 mmol). The reaction was stirred over 5 h, concentrated and purified by reverse-phase HPLC (C18 column: H$_2$O/CH$_3$CN, 95-5%) to afford the bis-TFA salt of the title compound. The bis-TFA salt was dissolved in water and ammonium hydroxide was added. The mixture was extracted with DCM (5 mL×3), dried over Na$_2$SO$_4$ and concentrated to give a free base of the title compound. The free base compound was dissolved in MeOH (1 mL) and treated with HCl (4 M in dioxane, 2.1 mL). After stirring overnight, the mixture was concentrated to give 120 mg of the title compound (120 mg, 49%) as an off-white solid: LC-MS (ES) m/z 471 (M+H)$^+$, $^1$H NMR (d$_4$-MeOD, 400 MHz) δ ppm 7.91 (br s, 2 h), 7.71 (m, 1H), 7.59 (m, 1H), 7.53 (m, 1H), 7.44 (m, 1H), 4.65 (m, 1H), 4.21 (m, 2H), 3.37-3.14 (m, 4H), 2.07 (s, 3H), and 1.40 (m, 3H).

Example 246

N-{(1S)-2-amino-1-[(3-fluorophenyl)methyl]ethyl}-5-chloro-4-(1-ethyl-4-methyl-1H-pyrazol-5-yl)-2-thiophenecarboxamide

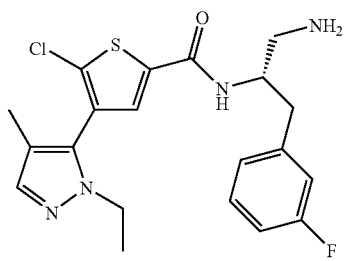 [SMILES: CCn1ncc(C)c1-c1cc(C(=O)N[C@H](CN)Cc2cccc(F)c2)sc1Cl]

345 a) 5-chloro-N-{(1S)-2-(1,3-dioxo-1,3-dihydro-2H-isoindol-2-yl)-1-[(3-fluorophenyl)methyl]ethyl}-4-(1-ethyl-4-methyl-1H-pyrazol-5-yl)-2-thiophenecarboxamide

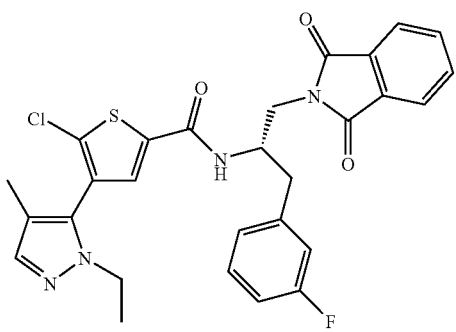 [SMILES: CCn1ncc(C)c1-c1cc(C(=O)N[C@@H](Cc2cccc(F)c2)CN2C(=O)c3ccccc3C2=O)sc1Cl]

To a solution of 5-chloro-4-(1-ethyl-4-methyl-1H-pyrazol-5-yl)-2-thiophenecarboxylic acid (130 mg, 0.48 mmol) [from Example 245(b)] in DCM (5 mL) at 25° C. was added PyBrOP (250 mg, 0.54 mmol) in one portion, followed by addition of DIPEA (0.7 mL, 4.01 mmol). After 10 min, 2-[(2S)-2-amino-3-(3-fluorophenyl)propyl]-1H-isoindole-1,3(2H)-dione (150 mg, 0.50 mmol) was added to above solution. After 2 h, the reaction mixture was concentrated and purified via column chromatography (silica, 20-50% EtOAc/Hexane) affording the title compound (210 mg, 79%) as a white solid: LC-MS m/z (ES) 551 (M+H)$^+$.

b) N-{(1S)-2-amino-1-[(3-fluorophenyl)methyl]ethyl}-5-chloro-4-(1-ethyl-4-methyl-1H-pyrazol-5-yl)-2-thiophenecarboxamide

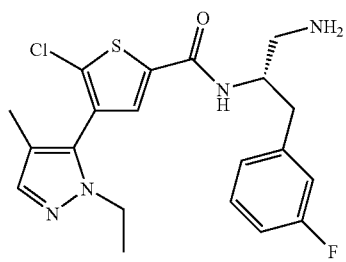 [SMILES: CCn1ncc(C)c1-c1cc(C(=O)N[C@H](CN)Cc2cccc(F)c2)sc1Cl]

At RT, NH$_2$NH$_2$ (0.1 mL, 3.19 mmol) was added to 5-chloro-N-{(1S)-2-(1,3-dioxo-1,3-dihydro-2H-isoindol-2-yl)-1-[(3-fluorophenyl)methyl]ethyl}-4-(1-ethyl-4-methyl-1H-pyrazol-5-yl)-2-thiophenecarboxamide (201 mg, 0.36 mmol) in MeOH (3 mL). After 10 h, the solvent was removed under vacuum. The resulting residue was taken into DCM (10 mL) and washed with H$_2$O (10 mL×3). To the DCM solution was added HCl (36%, 2 mL). After 1 h, the aqueous phase was separated and washed with DCM (10 ml×3). Water was removed under high vacuum to give the title compound (101 mg, 53%) as an off-white solid: LC-MS (ES) m/z 421 (M+H)$^+$, $^1$H NMR (d$_6$-DMSO, 400 MHz) δ ppm 9.02 (d, J=8.3 Hz, 1H), 8.08 (s, 2H), 7.97 (s, 1H), 7.42 (s, 1H), 7.32 (m, 1H), 7.15-7.09 (m, 1H), 7.06-7.01 (m, 1H), 4.35 (m, 1H), 3.95 (m, 2H), 3.05-2.98 (m, 2H), 2.96-2.88 (m, 2H), and 1.92 (s, 3H), and 1.24 (t, J=6.6 Hz, 3H).

Example 247

N-{(1S)-2-amino-1-[(3,4-difluorophenyl)methyl]ethyl}-5-chloro-4-(1-ethyl-4-methyl-1H-pyrazol-5-yl)-2-thiophenecarboxamide

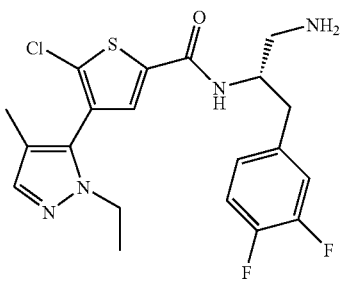 [SMILES: CCn1ncc(C)c1-c1cc(C(=O)N[C@H](CN)Cc2ccc(F)c(F)c2)sc1Cl]

The title compound (95 mg, 50.2%) was prepared according to the procedure of Example 246, except substituting 2-[(2S)-2-amino-3-(3,4-difluorophenyl)propyl]-1H-isoindole-1,3(2H)-dione (152 mg, 0.48 mmol) for 2-[(2S)-2-amino-3-(3-fluorophenyl)propyl]-1H-isoindole-1,3(2H)-dione: LC-MS (ES) m/z 439 (M+H)$^+$, $^1$H NMR (d$_6$-DMSO, 400 MHz) δ ppm 9.10 (d, J=8.6 Hz, 1H), 8.13 (s, 2H), 8.03 (s, 1H), 7.42 (s, 1H), 7.39-7.30 (m, 2H), 7.15-7.10 (m, 1H), 4.33 (m, 1H), 3.95 (m, 2H), 3.05-2.99 (m, 2H), 2.96-2.88 (m, 2H), 1.92, and 1.24 (t, J=6.3 Hz, 3H).

Example 248

N-((1S)-2-amino-1-{[2-(trifluoromethyl)phenyl]methyl}ethyl)-4-(1,4-diethyl-1H-pyrazol-5-yl)-2-thiophenecarboxamide

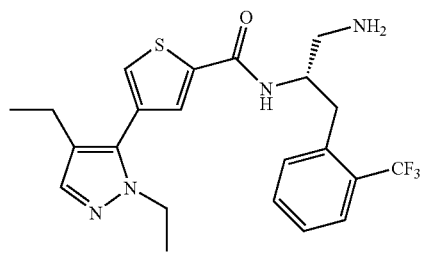 [SMILES: CCc1cnn(CC)c1-c1csc(C(=O)N[C@H](CN)Cc2ccccc2C(F)(F)F)c1]

a) Methyl 4-(4-ethenyl-1-ethyl-1H-pyrazol-5-yl)-2-thiophenecarboxylate

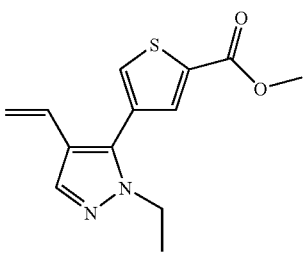 [SMILES: C=Cc1cnn(CC)c1-c1csc(C(=O)OC)c1]

A mixture of methyl 4-(4-bromo-1-ethyl-1H-pyrazol-5-yl)-2-thiophenecarboxylate (200 mg, 0.64 mmol), Pd(Ph$_3$P)$_4$ (73.3 mg, 0.06 mmol), and tributyl(ethenyl)stannane (302 mg, 0.95 mmol) was heated at 90° C. for 1 h under N$_2$ in a sealed tube. The mixture was purified on Silica (10%-20%

EtOAc in Hex) to give the title compound (151 mg, 76%): LC-MS (ES) m/z 263 (M+H)⁺.

b) Methyl 4-(1,4-diethyl-1H-pyrazol-5-yl)-2-thiophenecarboxylate

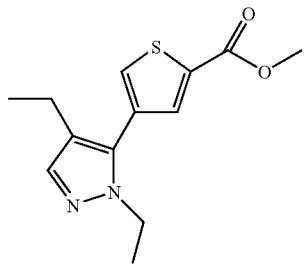 [SMILES: CCc1cnn(CC)c1-c1csc(C(=O)OC)c1]

Pd/C (12 mg, 10%) was added to a solution of ethyl 4-(4-ethenyl-1-ethyl-1H-pyrazol-5-yl)-2-thiophenecarboxylate (150 mg, 0.57 mmol) in EtOH. The air in the system was removed by vacuum. The reaction mixture was stirred for 10 h under a balloon of hydrogen gas. The reaction was diluted with MeOH (2 mL) and filtered through Celite. Concentration of the reaction solution gave the title compound (149 mg, 94%) as a yellow oil: LC-MS (ES) m/z 265 (M+H)⁺.

c) 4-(1,4-diethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

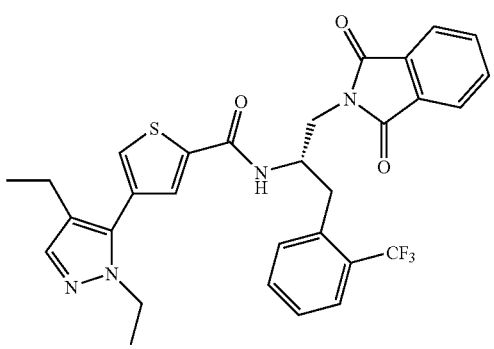 [SMILES: CCc1cnn(CC)c1-c1csc(C(=O)N[C@@H](Cc2ccccc2C(F)(F)F)CN2C(=O)c3ccccc3C2=O)c1]

To a solution of methyl 4-(1,4-diethyl-1H-pyrazol-5-yl)-2-thiophenecarboxylate (149 mg, 0.56 mmol) in THF/H₂O (5 mL/5 mL) was added KOH (158 mg, 2.82 mmol). The reaction mixture was heated to 50° C. for 4 h. After the mixture was concentrated and diluted with H₂O, the pH was adjusted to 3. The mixture was extracted with DCM (5 mL×3). The collected organic layers were concentrated under vacuum to give a crude acid, which was used directly without of further purification: LC-MS (ES) m/z 251 (M+H)⁺.

To the above acid in DCM (5 mL) at 25° C. was added bromo-tris-pyrrolidino phosphoniumhexafluorophosphate (PyBrOP) (315 mg, 0.68 mmol) in one portion, followed by the addition of DIPEA (0.98 mL, 5.64 mmol) and 2-{(2S)-2-amino-3-[2-(trifluoromethyl)phenyl]propyl}-1H-isoindole-1,3(2H)-dione (196 mg, 0.56 mmol). After 2 h, the solution was concentrated and purified via column chromatography (silica, 20-50% EtOAc/Hexane) affording the title compound (0.315 g, 94%) as a white solid: LC-MS (ES) m/z 581 (M+H)⁺.

d) N-((1S)-2-amino-1-{[2-(trifluoromethyl)phenyl]methyl}ethyl)-4-(1,4-diethyl-1H-pyrazol-5-yl)-2-thiophenecarboxamide

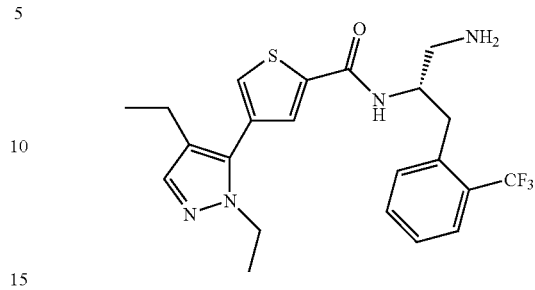

4-(1,4-diethyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (310 mg, 0.53 mmol) was dissolved in MeOH (1 mL) and was treated with NH₂NH₂ (0.34 mL, 10.68 mmol). The reaction was stirred over 5 h, concentrated and purified by reverse-phase HPLC (C18 column: H₂O/CH₃CN, 95-5%) to afford the bis-TFA salt of the title compound. The bis-TFA salt was dissolved in water (2 mL) and ammonium hydroxide (3.47 mL, 30%, 26.7 mmol) was added. The mixture was extracted with DCM (5 mL×3), dried over Na₂SO₄ and concentrated to give a free base of the title compound. The free base was dissolved in MeOH (1 mL) and treated with HCl (4 M in dioxane, 2.1 mL). After stirring overnight, the reaction solution was concentrated to give the title compound (140 mg, 48%) as an off-white solid: LC-MS (ES) m/z 451 (M+H)⁺, ¹H NMR (d₆-DMSO, 400 MHz) δ ppm 8.25-8.23 (m, 1H), 8.16-8.14 (m, 1H), 8.10-8.08 (m, 1H), 7.71-7.67 (m, 1H), 7.65-7.61 (m, 1H), 7.52-7.47 (m, 1H), 7.44-7.39 (m, 1H), 4.69 (m, 1H), 4.45-4.37 (m, 2H), 3.39-3.18 (m, 4H), 2.63-2.55 (m, 2H), 1.49-1.44 (m, 3H), and 1.24-1.19 (m, 3H).

Example 249

N-{(1S)-2-amino-1-[(3-fluorophenyl)methyl]ethyl}-5-chloro-4-(1,4-dimethyl-1H-pyrazol-5-yl)-2-thiophenecarboxamide

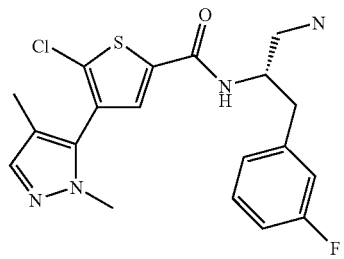 [SMILES: Cc1cnn(C)c1-c1cc(C(=O)N[C@H](CN)Cc2cccc(F)c2)sc1Cl]

a) methyl 5-chloro-4-(1,4-dimethyl-1H-pyrazol-5-yl)-2-thiophenecarboxylate

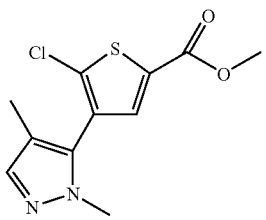 [SMILES: COC(=O)c1cc(-c2c(C)cnn2C)c(Cl)s1]

Method A:

To a solution of methyl 4-bromo-5-chloro-2-thiophenecarboxylate (500 mg, 1.96 mmol) in THF (10 mL) was added aqueous Na$_2$CO$_3$ (2N, 3 mL, 6.0 mmol), PdCl$_2$(dppf) (143 mg, 0.196 mmol) and 1,4-dimethyl-5-(4,4,5,5-tetramethyl-1,3,2-dioxaborolan-2-yl)-1H-pyrazole (522 mg, 2.35 mmol). The reaction mixture was heated to 70° C. in a sealed tube. After 2 h, the reaction mixture was concentrated under vacuum and purified on silica (EtOAc/Hex, 10-20%) to afford the title compound (410 mg, 77%) as a tan solid: LC-MS (ES) m/z 271 (M+H)$^+$.

Method B:

To a 250 mL sealed flask was added 1,4-dimethyl-5-(4,4,5,5-tetramethyl-1,3,2-dioxaborolan-2-yl)-1H-pyrazole (10.43 g, 47.0 mmol), potassium carbonate (16.23 g, 117 mmol), methyl 4-bromo-5-chloro-2-thiophenecarboxylate (10 g, 39.1 mmol) and bis(tri-t-butylphosphine)palladium(0) (1.6 g, 3.13 mmol) in 1,4-dioxane (120 mL) and H$_2$O (20 ml). After stirring for 90 min at 70° C., the reaction solution was diluted with DCM (100 mL) and washed with H$_2$O. The organic layer was dried Na$_2$SO$_4$, filtered and concentrated. The residue was purified on silica gel (hexanes/EtOAC, 10-30%) to give the title compound (7.6 g, 72%) as a tan solid: LC-MS (ES) m/z 271 (M+H)$^+$.

b) 5-chloro-4-(1,4-dimethyl-1H-pyrazol-5-yl)-2-thiophenecarboxylic Acid

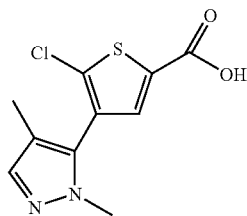 [SMILES: Cc1cnn(C)c1-c1cc(C(=O)O)sc1Cl]

To a solution of methyl 5-chloro-4-(1,4-dimethyl-1H-pyrazol-5-yl)-2-thiophenecarboxylate (7.6 g, 28.1 mmol) in THF/H$_2$O (30 mL/5 mL) was added KOH (4.72 g, 84 mmol). The reaction mixture was heated to 50° C. for 1 h. After the mixture was concentrated and diluted with H$_2$O, the pH was adjusted to 3. The mixture was extracted with DCM (50 mL×3). The collected organic layers were concentrated under vacuum to give the crude acid (6.8 g, 94%), which was used directly in the next step without further purification: LCMS (ES) m/z 257 (M+H)$^+$.

c) 5-chloro-4-(1,4-dimethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide

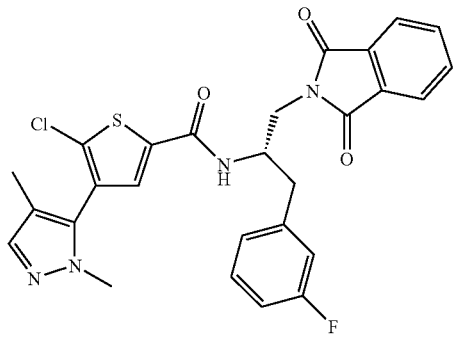 [SMILES: Cc1cnn(C)c1-c1cc(C(=O)N[C@@H](Cc2cccc(F)c2)CN2C(=O)c3ccccc3C2=O)sc1Cl]

To a 500 mL round-bottomed flask was added 5-chloro-4-(1,4-dimethyl-1H-pyrazol-5-yl)-2-thiophenecarboxylic acid (6.8 g, 26.5 mmol), 2-[(2S)-2-amino-3-(3-fluorophenyl)propyl]-1H-isoindole-1,3(2H)-dione (8.69 g, 29.1 mmol), N,N-diisopropylethylamine (14 mL, 80 mmol) and Pybrop (18.52 g, 39.7 mmol) in dichloromethane (DCM) (100 mL). After stirring at RT for 1 h, the reaction solution was washed with H$_2$O (2×100 mL) and the organic layer was dried Na$_2$SO$_4$, filtered and concentrated. The crude product was added to a silica gel column and was eluted with (EtOAc/hexanes, 1:1) to give the title compound (6.1 g, 42.9%) as a white solid: LCMS (ES) m/z 537 (M+H)$^+$.

d) N-{(1S)-2-amino-1-[(3-fluorophenyl)methyl]ethyl}-5-chloro-4-(1,4-dimethyl-1H-pyrazol-5-yl)-2-thiophenecarboxamide

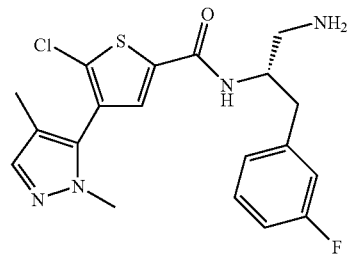 [SMILES: Cc1cnn(C)c1-c1cc(C(=O)N[C@H](CN)Cc2cccc(F)c2)sc1Cl]

At RT, NH$_2$NH$_2$ (4 mL, 127 mmol) was added to 5-chloro-4-(1,4-dimethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide (5.2 g, 9.68 mmol) in MeOH (30 ml). After 10 h, the solvent was removed under vacuum. The resulting residue was taken into DCM (200 mL) and washed with H$_2$O (50 mL×5).

To the above DCM solution was added HCl (36%, 50 mL, 600 mmol). After 1 h, the aqueous phase was separated and washed with DCM (50 ml×5). Water was removed under high vacuum to give the title compound (3.8 g, 79%) as a white solid: LC-MS (ES) m/z 407 (M+H)$^+$, NMR (d$_4$-MeOD, 400 MHz) δ ppm 8.75 (d, J=8.8 Hz, 1H), 7.88 (s, 1H), 7.85 (m, 1H), 7.34-7.29 (m, 1H), 7.15-7.09 (m, 2H), 7.00-6.95 (m, 1H), 4.54 (m, 1H), 3.88 (s, 3H), 3.26-3.18 (m, 2H), 3.09-2.98 (m, 2H), and 2.08 (s, 3H).

Example 250

N-((1S)-2-amino-1-{[3-(trifluoromethyl)phenyl]methyl}ethyl)-5-chloro-4-(1,4-dimethyl-1H-pyrazol-5-yl)-2-thiophenecarboxamide

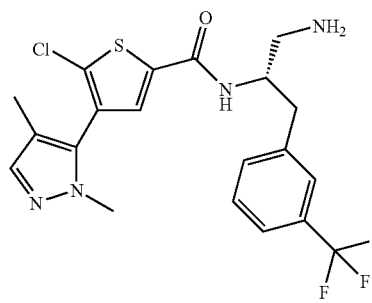

The title compound was prepared as a white solid (180 mg, 68%) according to the procedure of Example 249, except substituting 2-{(2S)-2-amino-3-[3-(trifluoromethyl)phenyl]propyl}-1H-isoindole-1,3(2H)-dione (209 mg, 0.6 mmol) for 2-[(2S)-2-amino-3-(3-fluorophenyl)propyl]-1H-isoindole-1, 3(2H)-dione: LC-MS (ES) m/z 457 (M+H)+, NMR (d4-MeOD, 400 MHz) δ ppm 7.94 (s, 1H), 7.90 (s, 1H), 7.65-7.60 (m, 2H), 7.55-7.48 (m, 2H), 4.55 (m, 1), 3.89 (s, 3H), 3.37-3.27 (m, 2H), 3.16-3.06 (m, 2H), and 2.08 (s, 3H).

Example 251

N-{(1S)-2-amino-1-[(4-fluorophenyl)methyl]ethyl}-5-chloro-4-(1,4-dimethyl-1H-pyrazol-5-yl)-2-thiophenecarboxamide

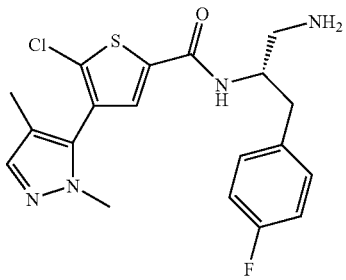 [SMILES: Cc1cnn(C)c1-c1cc(C(=O)N[C@H](CN)Cc2ccc(F)cc2)sc1Cl]

The title compound was prepared as white solid (95 mg, 39%) according to the procedure of Example 249, except substituting 2-[(2S)-2-amino-3-(4-fluorophenyl)propyl]-1H-isoindole-1,3(2H)-dione (584 mg, 1.96 mmol) for 2-[(2S)-2-amino-3-(3-fluorophenyl)propyl]-1H-isoindole-1,3(2H)-dione: LC-MS (ES) m/z 407 (M+H)+, NMR (d4-MeOD, 400 MHz) δ ppm 7.81 (s, 2H), 7.35-7.31 (m, 2H), 7.06-7.01 (m, 2H), 4.51 (m, 1H), 3.89 (s, 3H), 3.25-3.16 (m, 2H), 3.05-2.94 (m, 2H), and 2.07 (s, 3H).

Example 252

N-{(1S)-2-amino-1-[(3-fluorophenyl)methyl]ethyl}-4-(1-ethyl-4-methyl-1H-pyrazol-5-yl)-2-furancarboxamide

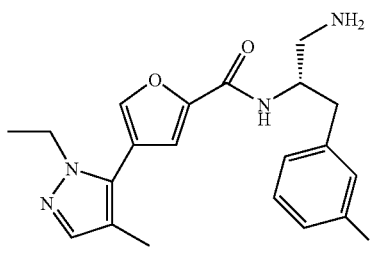

a) methyl 4-(1-ethyl-4-methyl-1H-pyrazol-5-yl)-2-furancarboxylate

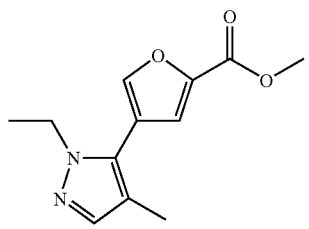 [SMILES: CCn1ncc(C)c1-c1coc(C(=O)OC)c1]

To a solution of methyl 4-bromo-2-furancarboxylate (500 mg, 2.439 mmol) in THF (5 mL) was added aqueous Na2CO3 (2N, 3.6 mL, 7.2 mmol), PdCl2(dppf) (160 mg, 0.22 mmol), and 1-ethyl-4-methyl-5-(4,4,5,5-tetramethyl-1,3,2-dioxaborolan-2-yl)-1H-pyrazole (700 mg, 2.96 mmol). The reaction mixture was heated to 70° C. in a sealed tube. After 2 h, the reaction mixture was concentrated under vacuum and purified on silica (EtOAc/Hex, 20-40%) to afford the title compound (460 mg, 76%) as a light yellow solid: LC-MS (ES) m/z 235 (M+H)+.

b) N-{(1S)-2-(1,3-dioxo-1,3-dihydro-2H-isoindol-2-yl)-1-[(3-fluorophenyl)methyl]ethyl}-4-(1-ethyl-4-methyl-1H-pyrazol-5-yl)-2-furancarboxamide

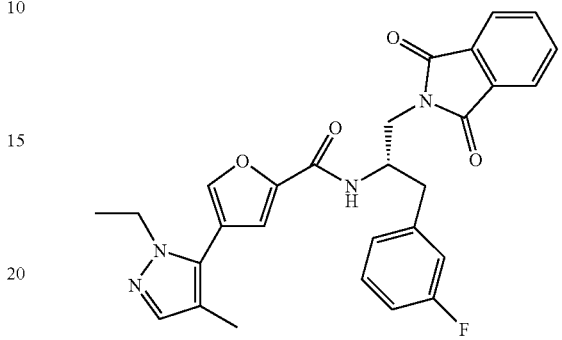

To a solution of methyl 4-(1-ethyl-4-methyl-1H-pyrazol-5-yl)-2-furancarboxylate (210 mg, 0.90 mmol) in THF/H2O (5 mL/0.5 mL) was added KOH (200 mg, 3.56 mmol). The reaction mixture was heated to 50° C. for 4 h. After the mixture was concentrated and diluted with H2O (2 mL), the pH was adjusted to 3. The mixture was extracted with DCM (5 mL×3). The collected organic layers were concentrated under vacuum to give a crude acid, which was used directly in the next step without further purification: LC-MS (ES) m/z 221 (M+H)+.

To the crude 4-(1-ethyl-4-methyl-1H-pyrazol-5-yl)-2-furancarboxylic acid in DCM (5 mL) at 25° C. was added PyBrOP (370 mg, 0.79 mmol) in one portion, followed by the addition of DIPEA (0.8 mL, 4.58 mmol). After 10 min, 2-[(2S)-2-amino-3-(3-fluorophenyl)propyl]-1H-isoindole-1,3(2H)-dione (220 mg, 0.74 mmol) was added to the reaction solution. After 2 h, the reaction mixture was concentrated and purified via column chromatography (silica, 20-50% EtOAc/Hexane) affording the title compound (164 mg, 54%) as a white solid: LC-MS (ES) m/z 501 (M+H)+.

c) N-{(1S)-2-amino-1-[(3-fluorophenyl)methyl]ethyl}-4-(1-ethyl-4-methyl-1H-pyrazol-5-yl)-2-furancarboxamide

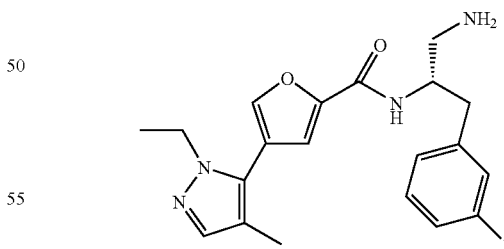

At RT, NH2NH2 (0.1 mL, 3.19 mmol) was added to a solution of N-{(1S)-2-(1,3-dioxo-1,3-dihydro-2H-isoindol-2-yl)-1-[(3-fluorophenyl)methyl]ethyl}-4-(1-ethyl-4-methyl-1H-pyrazol-5-yl)-2-furancarboxamide (150 mg, 0.3 mmol) in MeOH (5 mL). After 10 h, the solvent was removed under vacuum. The resulting residue was taken into DCM (10 mL) and washed with H2O (10 mL×3).

To the DCM solution was added HCl (36%, 1 mL, 12 mmol). After 1 h, the aqueous phase was separated, and washed with DCM (10 ml×3). Water was removed under high vacuum to give the title compound (80 mg, 57%) as an off-white solid: LC-MS (ES) m/z 371 (M+H)+, NMR (d4-MeOD, 400 MHz) δ ppm 8.19 (s, 1H), 8.05 (s, 1H), 7.44 (s, 1H), 7.32 (m, 1H), 7.16-7.08 (m, 2H), 6.97 (m, 1H), 4.62 (m, 1H), 4.37 (q, J=7.1 Hz, 2H), 3.38-3.18 (m, 2H), 3.10-2.99 (m, 2H), 2.15 (s, 3H), and 1.46 (t, J=7.1 Hz, 3H).

Example 253

N-{(1S)-2-amino-1-[(3-fluorophenyl)methyl]ethyl}-4-(4-chloro-1-ethyl-1H-pyrazol-5-yl)-2-furancarboxamide

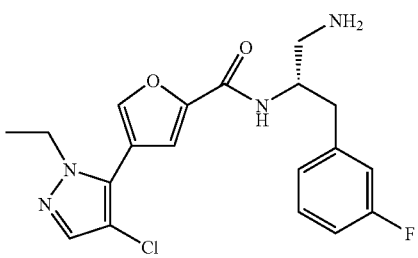 [SMILES: CCn1ncc(Cl)c1-c1coc(C(=O)N[C@H](CN)Cc2cccc(F)c2)c1]

a) methyl 4-(1-ethyl-1H-pyrazol-5-yl)-2-furancarboxylate

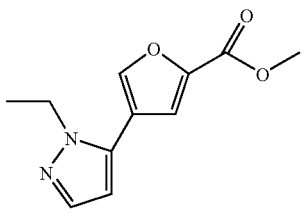 [SMILES: CCn1nccc1-c1coc(C(=O)OC)c1]

To a solution of methyl 4-bromo-2-furancarboxylate (1.0 g, 4.88 mmol) in THF (20 mL) was added aqueous Na2CO3 (2N, 8 mL, 16 mmol.), PdCl2(dppf) (0.35 g, 0.49 mmol) and 1-ethyl-5-(4,4,5,5-tetramethyl-1,3,2-dioxaborolan-2-yl)-1H-pyrazole (1.3 g, 5.85 mmol). The reaction mixture was heated to 70° C. in a sealed tube. After 2 h, the reaction mixture was concentrated under vacuum and purified on silica (EtOAc/Hex, 20-40%) to afford the title compound (0.8 g, 74.5%) as a light yellow solid: LC-MS (ES) m/z=221 (M+H)+.

b) methyl 4-(4-chloro-1-ethyl-1H-pyrazol-5-yl)-2-furancarboxylate

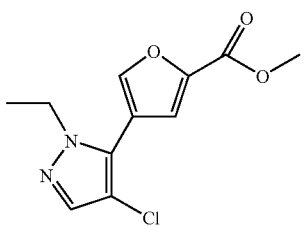 [SMILES: CCn1ncc(Cl)c1-c1coc(C(=O)OC)c1]

A mixture of methyl 4-(1-ethyl-1H-pyrazol-5-yl)-2-furancarboxylate (300 mg, 1.36 mmol) and NCS (218 mg, 1.63 mmol) in THF (5 mL) was heated to 70° C. in a sealed tube. After 5 h, the reaction mixture was concentrated and purified via column chromatography (silica, 10-20% EtOAc/Hexane) affording the title compound (260 mg, 75%) as a white solid: LC-MS (ES) m/z 255 (M+H)+.

c) 4-(4-chloro-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-furancarboxamide

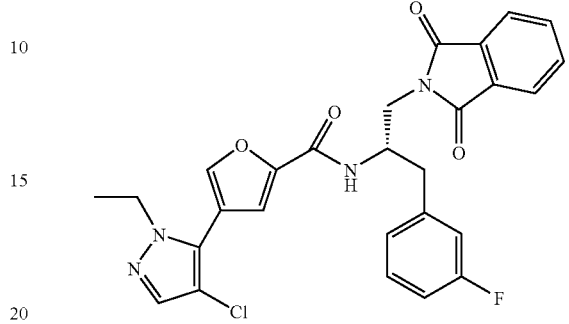

To a solution of methyl 4-(4-chloro-1-ethyl-1H-pyrazol-5-yl)-2-furancarboxylate (250 mg, 0.98 mmol) in THF/H2O (5 mL/0.5 mL) was added KOH (200 mg, 3.56 mmol). The reaction mixture was heated to 50° C. for 4 h. After the mixture was concentrated and diluted with H2O (2 mL), the pH was adjusted to 3. The mixture was extracted with DCM (5 mL×3). The collected organic layers were concentrated under vacuum to give a crude acid, which was used directly without further purification: LC-MS (ES) m/z 241 (M+H)+.

To the above crude acid in DCM (5 mL) at 25° C. was added PyBrOP (550 mg, 1.18 mmol) in one portion, followed by the addition of DIPEA (0.7 mL, 4.01 mmol). After 10 min, 2-[(2S)-2-amino-3-(3-fluorophenyl)propyl]-1H-isoindole-1,3(2H)-dione (322 mg, 1.08 mmol) was added to the reaction solution. After 2 h, the reaction mixture was concentrated and purified via column chromatography (silica, 20-50% EtOAc/Hexane) affording the title compound (360 mg, 70%) as a white solid: LC-MS (ES) m/z 521 (M+H)+.

d) N-{(1S)-2-amino-1-[(3-fluorophenyl)methyl]ethyl}-4-(4-chloro-1-ethyl-1H-pyrazol-5-yl)-2-furancarboxamide

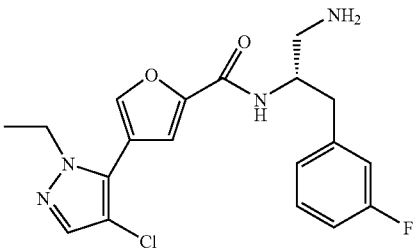 [SMILES: CCn1ncc(Cl)c1-c1coc(C(=O)N[C@H](CN)Cc2cccc(F)c2)c1]

At RT, NH2NH2 (0.15 mL, 4.78 mmol) was added to a solution of 4-(4-chloro-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-furancarboxamide (350 mg, 0.67 mmol) in MeOH (5 mL). After 10 h, the solvent was removed under vacuum. The resulting residue was taken into DCM (15 mL) and washed with H2O (10 mL×3).

To the above DCM solution was added HCl (36%, 2 mL, 23.7 mmol)). After 1 h, the aqueous phase was separated and washed with DCM (10 ml×3). Water was removed under high vacuum to give the title compound (260 mg, 78%) as an off-white solid: LC-MS (ES) m/z 391 (M+H)+. NMR (d6-DMSO, 400 MHz) δ ppm 8.70 (m, 1H), 8.29 (s, 1H), 8.02 (m, 2H), 7.70 (s, 1H), 7.50-7.45 (m, 1H), 7.36-7.30 (m, 1H), 7.14-7.08 (m, 2H), 7.06-7.01 (m, 1H), 4.43 (m, 1H), 4.16 (q, J=7.3 Hz, 2H), 3.04-2.88 (m, 4H), and 1.30 (t, J=7.3 Hz, 3H).

Example 254

N-[2-amino-1-(phenylmethyl)ethyl]-3-methyl-4-(1-methyl-1H-pyrazol-5-yl)-2-thiophenecarboxamide

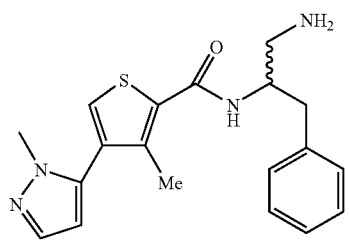 [SMILES: Cc1c(-c2ccnn2C)csc1C(=O)NC(CN)Cc1ccccc1]

a) methyl 4-bromo-3-{[(trifluoromethyl)sulfonyl]oxy}-2-thiophenecarboxylate

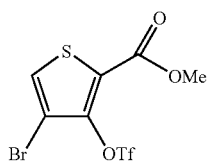 [SMILES: COC(=O)c1scc(Br)c1OS(=O)(=O)C(F)(F)F]

To a solution of methyl 4-bromo-3-{[(trifluoromethyl)sulfonyl]oxy}-2-thiophenecarboxylate (0.948 g, 4.0 mmol) in CH$_2$Cl$_2$ (5 mL) and pyridine (1 mL) at 0° C. was added Tf$_2$O (1.0 mL, 6.0 mmol). The mixture was stirred for 1 h, poured onto ice water (10 mL) and extracted with CH$_2$Cl$_2$ (5 mL×3). The collected organic layers were dried (Na$_2$SO$_4$) and concentrated to give a red syrup which was used directly in the next step without further purification: LC-MS (ES) m/z 370 (M+H)$^+$.

b) methyl 4-bromo-3-methyl-2-thiophenecarboxylate

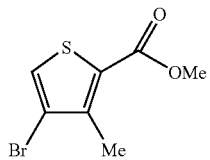 [SMILES: COC(=O)c1scc(Br)c1C]

To a solution of methyl 4-bromo-3-{[(trifluoromethyl)sulfonyl]oxy}-2-thiophenecarboxylate (825 mg, 2.25 mmol) in dioxane/H$_2$O (5 mL/1 mL) was added K$_2$CO$_3$ (930 mg, 6.75 mmol), tetrakistriphenylphosphine Pd(0) (260 mg, 0.22 mmol), and methylboronic acid (175 mg, 2.91 mmol). The reaction mixture was heated to 70° C. in a sealed tube for 12 h. The reaction solution was concentrated under vacuum and purified on silica gel (hexanes/EtOAc, 9:1) to give the title compound (441 mg, 84%) as a brown solid: LC-MS (ES) m/z 236 (M+H)$^+$.

c) methyl 4-[1-(dimethylamino)ethenyl]-3-methyl-2-thiophenecarboxylate

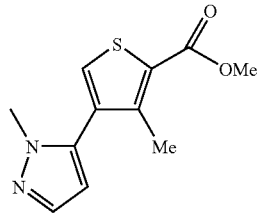 [SMILES: COC(=O)c1scc(-c2ccnn2C)c1C]

To a solution of methyl 4-bromo-3-methyl-2-thiophenecarboxylate (300 mg, 1.27 mmol) in dioxane/H$_2$O (5 mL/1 mL) was added K$_2$CO$_3$ (525 mg, 3.80 mmol), tetrakistriphenylphosphine Pd(0) (15 mg, 0.01 mmol), and 1-methyl-5-(4,4,5,5-tetramethyl-1,3,2-dioxaborolan-2-yl)-1H-pyrazole (345 mg, 1.7 mmol). The reaction mixture was heated to 70° C. in a sealed tube for 2 h. The reaction solution was concentrated under vacuum and purified on silica gel (hexanes/EtOAc, 9:1 to 4:1) to give the title compound (270 mg, 90%): LC-MS (ES) m/z 237 (M+H)$^+$.

d) 1,1-dimethylethyl[2-({[3-methyl-4-(1-methyl-1H-pyrazol-5-yl)-2-thienyl]carbonyl}amino)-3-phenylpropyl]carbamate

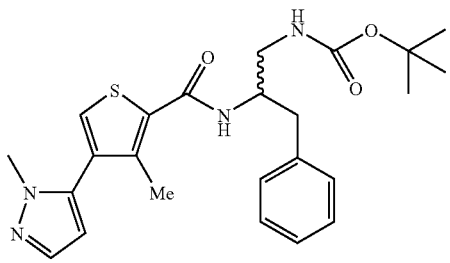 [SMILES: Cc1c(-c2ccnn2C)csc1C(=O)NC(CNC(=O)OC(C)(C)C)Cc1ccccc1]

To a solution of methyl 4-[1-(dimethylamino)ethenyl]-3-methyl-2-thiophenecarboxylate (50 mg, 0.21 mmol) in THF/H$_2$O (2 mL/0.5 mL) was added KOH (122 mg, 2.1 mmol). The resulting mixture was heated to 50° C. for 2 h. The THF was removed under vacuum and the aqueous layer was acidified with 6 N HCl to pH 3 and extracted with CH$_2$Cl$_2$ (5 mL×3). The organic fractions was dried over Na$_2$SO$_4$ and concentrated to give the crude 3-methyl-4-(1-methyl-1H-pyrazol-5-yl)-2-thiophenecarboxylic acid, which was used directly in the next step.

To a solution of the crude 3-methyl-4-(1-methyl-1H-pyrazol-5-yl)-2-thiophenecarboxylic acid in DCM (2 mL) was added PyBrop (0.14 g, 0.3 mmol) and DIPEA (0.1 mL, 0.57 mmol). After 15 min, 1,1-dimethylethyl (2-amino-3-phenylpropyl)carbamate was added to the reaction in one portion and stirred for 2 h at RT. The reaction solution was concentrated under vacuum and purified on silica gel (EtOAc/Hexane, 20-50%) to give the title compound (51 mg, 49% for two steps) as a solid: LC-MS (ES) m/z 455 (M+H)$^+$.

e) N-[2-amino-1-(phenylmethyl)ethyl]-3-methyl-4-(1-methyl-1H-pyrazol-5-yl)-2-thiophenecarboxamide

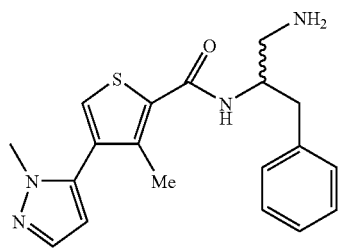 [SMILES: Cc1c(-c2ccnn2C)csc1C(=O)NC(CN)Cc1ccccc1]

To a solution of 1,1-dimethylethyl[2-({[3-methyl-4-(1-methyl-1H-pyrazol-5-yl)-2-thienyl]carbonyl}amino)-3-phenylpropyl]carbamate (51 mg, 0.11 mmol) in DCM (1 mL) was added TFA (1 mL). The reaction was stirred over 5 h, concentrated and purified by reverse-phase HPLC (C18 column: $H_2O/CH_3CN$, 40-10%) to afford the bis-TFA salt of the title compound. (16 mg, 41%): LC-MS (ES) m/z 355 (M+H)$^+$. NMR (d$_4$-MeOD, 400 MHz) δ ppm 7.64 (s, 1H), 7.56 (d, J=1.8 Hz, 1H), 7.36-7.30 (m, 4H), 7.28-7.21 (m, 1H), 6.30 (d, J=2.0 Hz, 1H), 4.58 (m, 1H), 3.69 (s, 3H), 3.27-3.13 (m, 2H), 3.07-2.93 (m, 2H), and 2.13 (s, 3H).

Example 255

N-((1S)-2-amino-1-{[2-(trifluoromethyl)phenyl]methyl}ethyl)-4-[1-methyl-4-(trifluoromethyl)-1H-pyrazol-5-yl]-2-thiophenecarboxamide

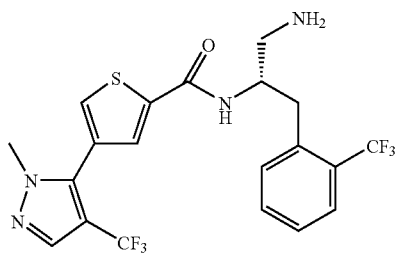 [SMILES: Cn1ncc(C(F)(F)F)c1-c1csc(C(=O)N[C@H](CN)Cc2ccccc2C(F)(F)F)c1]

a) methyl 4-(1-methyl-1H-pyrazol-5-yl)-2-thiophenecarboxylate

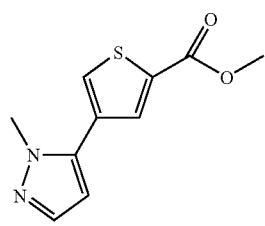

To a solution of methyl 4-bromo-2-thiophenecarboxylate (1.0 g, 4.5 mmol) in dioxane/$H_2O$ (5:1, 12 mL) was added $K_2CO_3$ (1.86 mg, 13.5 mmol), tetrakistriphenylphosphine Pd(0) (300 mg, 0.25 mmol), and 1-methyl-5-(4,4,5,5-tetramethyl-1,3,2-dioxaborolan-2-yl)-1H-pyrazole (1.23 g, 5.9 mmol). The reaction mixture was heated to 75° C. in a sealed tube for 2 h. The reaction mixture was concentrated and purified on silica gel (EtOAc/Hex 10-40%) to give the title compound (701 mg, 70%) as a white solid: LC-MS (ES) m/z 223 (M+H)$^+$.

b) methyl 4-(4-iodo-1-methyl-1H-pyrazol-5-yl)-2-thiophenecarboxylate

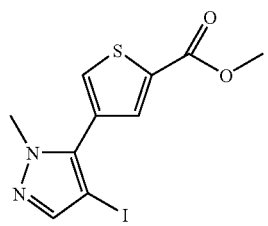

To a solution of methyl 4-(1-methyl-1H-pyrazol-5-yl)-2-thiophenecarboxylate (700 mg, 3.15 mmol) in THF (5 mL) was added NIS (922 mg, 4.09 mmol) in one portion. The reaction mixture was stirred at 75° C. for 10 h, and then cooled to room temperature. The reaction mixture was concentrated and purified on silica gel (EtOAc/Hex 10-20%) to give the title compound (470 mg, 43%) as an off white solid: LC-MS (ES) m/z 350 (M+H)$^+$.

c) methyl 4-[1-methyl-4-(trifluoromethyl)-1H-pyrazol-5-yl]-2-thiophenecarboxylate

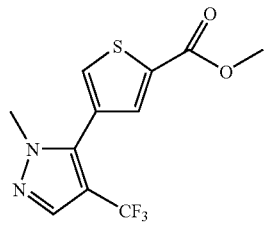

To a solution of methyl 4-(4-iodo-1-methyl-1H-pyrazol-5-yl)-2-thiophenecarboxylate (470 mg, 1.35 mmol), copper (I) iodide (256 mg, 1.35 mmol) and potassium fluoride (78 mg, 1.35 mmol) in anhydrous DMF/HMPA (2 ml/2 mL) was added triethyl(trifluoromethyl)silane (745 mg, 4.04 mmol). The mixture was heated to 70° C. under $N_2$ in a sealed tube. After 10 h, the reaction was quenched with $NH_4Cl$ (sat'd) (2 mL), extracted with ether (5 mL×5) and washed with distilled water (5 mL×5). The combined organic phase was dried over $Mg_2SO_4$ and purified on silica (EtOAc/Hex, 10-30%) to afford the title compound (0.29 g, 74%) as a yellow syrup: LC-MS (ES) m/z 291 (M+H)$^+$.

d) N-((1S)-2-(1,3-dioxo-1,3-dihydro-2H-isoindol-2-yl)-1-{[2-(trifluoromethyl)phenyl]methyl}ethyl)-4-[1-methyl-4-(trifluoromethyl)-1H-pyrazol-5-yl]-2-thiophenecarboxamide

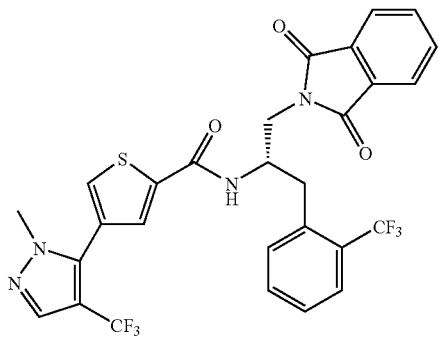 [SMILES: Cn1ncc(C(F)(F)F)c1-c1csc(C(=O)N[C@@H](Cc2ccccc2C(F)(F)F)CN2C(=O)c3ccccc3C2=O)c1]

To a solution of methyl 4-[1-methyl-4-(trifluoromethyl)-1H-pyrazol-5-yl]-2-thiophenecarboxylate (150 mg, 0.52 mmol) in THF/H$_2$O (2 mL/0.5 mL) was added KOH (116 mg, 2.0 mmol). The reaction mixture was heated to 50° C. for 2 h. After the mixture was concentrated and diluted with H$_2$O, the pH was adjusted to 3. The mixture was extracted with DCM (5 mL×3). The collected organic layers were concentrated under vacuum to give the crude acid, which was used directly in the next step without further purification: LC-MS (ES) m/z 277 (M+H)$^+$.

To the above acid in DCM (5 mL) at 25° C. was added bromo-tris-pyrrolidino phosphoniumhexafluorophosphate (PyBrOP) (279 mg, 0.59 mmol) in one portion, followed by the addition of DIPEA (0.5 mL, 2.87 mmol) and 2-{(2S)-2-amino-3-[2-(trifluoromethyl)phenyl]propyl}-1H-isoindole-1,3(2H)-dione (174 mg, 0.5 mmol). After 2 h, the solution was concentrated and purified via column chromatography (silica, 1-10% MeOH/CHCl$_3$) affording the title compound (0.21 g, 67% for 2 steps): LC-MS (ES) m/z 607 (M+H)$^+$.

e) N-((1S)-2-amino-1-{[2-(trifluoromethyl)phenyl]methyl}ethyl)-4-[1-methyl-4-(trifluoromethyl)-1H-pyrazol-5-yl]-2-thiophenecarboxamide

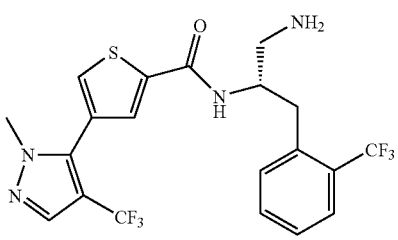 [SMILES: Cn1ncc(C(F)(F)F)c1-c1csc(C(=O)N[C@H](CN)Cc2ccccc2C(F)(F)F)c1]

N-((1S)-2-(1,3-dioxo-1,3-dihydro-2H-isoindol-2-yl)-1-{[2-(trifluoromethyl)phenyl]methyl}ethyl)-4-[1-methyl-4-(trifluoromethyl)-1H-pyrazol-5-yl]-2-thiophenecarboxamide (210 mg, 0.35 mmol) was dissolved in MeOH (2 mL) and was treated with NH$_2$NH$_2$ (0.5 mL, 15.9 mmol). The reaction was stirred over 10 h, concentrated and purified by reverse-phase HPLC (C18 column: H$_2$O/CH$_3$CN, 40-10%) to afford the bis-TFA salt of the title compound. The bis-TFA salt was dissovled in water, and neutralized with ammonium hydroxide. The mixture was extracted with DCM, dried over Na$_2$SO$_4$, and concentrated to give a free base of the title compound. The free base compound was dissolved in MeOH and treated with HCl (aq). After stirring overnight, the reaction was concentrated to give the title compound (95 mg, 57%) as a white solid. LC-MS: LC-MS (ES) m/z 477 (M+H)$^+$. NMR (d$_6$-DMSO, 400 MHz): 6 ppm 8.92 (d, J=9.1 Hz, 1H), 8.06 (m, 4H), 7.99 (s, 1H), 7.69 (d, J=7.6 Hz, 1H), 7.59 (d, J=7.6 Hz, 1H), 7.53 (m, 1H), 7.43 (m, 1H), 4.49 (m, 1H), 3.83 (s, 3H), and 3.14-2.99 (m, 4H).

Example 256

N-((1S)-2-amino-1-{[2-(trifluoromethyl)phenyl]methyl}ethyl)-4-(1-propyl-1H-pyrazol-5-yl)-2-thiophenecarboxamide

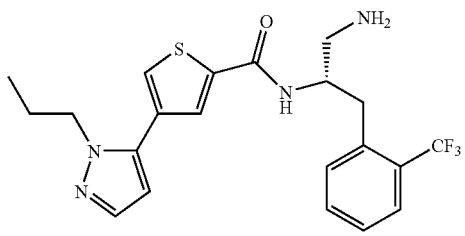 [SMILES: CCCn1nccc1-c1csc(C(=O)N[C@H](CN)Cc2ccccc2C(F)(F)F)c1]

a) 1-propyl-5-(4,4,5,5-tetramethyl-1,3,2-dioxaborolan-2-yl)-1H-pyrazole

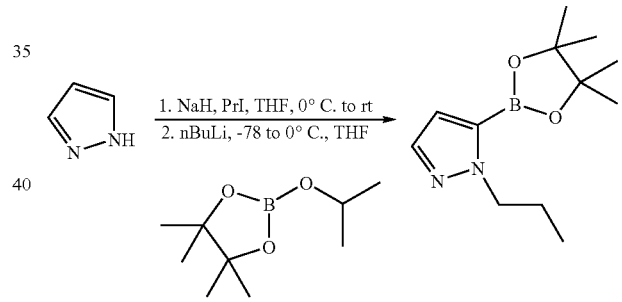

To a suspension of NaH (60% in mineral oil, 4.0 g, 100 mmol) in THF (200 mL) was added 1H-pyrazole (6.8 g, 100 mmol) at 0° C. portionwise. After stirring at RT for 1 h, PrI (17.85 g, 105 mmol) was added dropwise at 0° C. The reaction mixture was stirred for 10 h and monitored by LC-MS: m/e=111 (M+H)$^+$. After the reaction was complete, NaI was removed by filtration. The resulting 1-propyl-1H-pyrazole containing THF solution was used directly in the next step.

To the above THF solution of 1-propyl-1H-pyrazole was added n-BuLi (2.5M in Hexane, 40 mL, 100 mmol) at −78° C. The reaction solution was stirred for 2 hours at RT and then re-cooled to −78° C. [J. Heterocyclic Chem. 41, 931 (2004)]. To the reaction solution was added 2-isopropoxy-4,4,5,5-tetramethyl-1,3,2-dioxaborolane (18.6 g, 100 mmol). After 30 min at −78° C., the reaction was quenched with saturated NH$_4$Cl solution and extracted with DCM. The organics were dried over Na$_2$SO$_4$ and concentrated under vacuum to afford the title compound as a brown solid which was used directly without further purification: LC-MS (ES) m/z 154 (M+H)$^+$ for [RB(OH)2].

b) methyl 4-(1-propyl-1H-pyrazol-5-yl)-2-thiophenecarboxylate

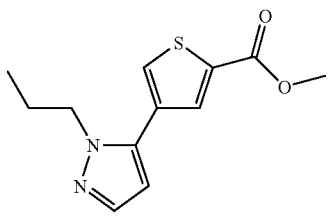 [SMILES: CCCn1nccc1-c1csc(C(=O)OC)c1]

To a solution of methyl 4-bromo-2-thiophenecarboxylate (221 mg, 1.0 mmol) in dioxane/H$_2$O (5:1, 6 mL) was added K$_2$CO$_3$ (414 mg, 3.0 mmol), tetrakistriphenylphosphine Pd(0) (60 mg, 0.05 mmol), and 1-propyl-5-(4,4,5,5-tetramethyl-1,3,2-dioxaborolan-2-yl)-1H-pyrazole (404 mg, 1.5 mmol). The reaction mixture was heated to 70° C. in a sealed tube for 2 h. The reaction mixture was concentrated and purified on silica gel (EtOAc/Hex 10-40%) to give the title compound (176 mg, 70%) as a white solid: LC-MS (ES) m/z 251 (M+H)$^+$.

c) N-((1S)-2-(1,3-dioxo-1,3-dihydro-2H-isoindol-2-yl)-1-{[2-(trifluoromethyl)phenyl]methyl}ethyl)-4-(1-propyl-1H-pyrazol-5-yl)-2-thiophenecarboxamide

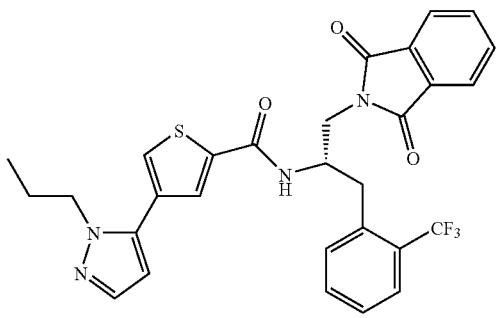 [SMILES: CCCn1nccc1-c1csc(C(=O)N[C@@H](Cc2ccccc2C(F)(F)F)CN2C(=O)c3ccccc3C2=O)c1]

To a solution of methyl 4-(1-propyl-1H-pyrazol-5-yl)-2-thiophenecarboxylate (160 mg, 0.64 mmol) in THF/H$_2$O (2 mL/1 mL) was added KOH (151 mg, 2.56 mmol). The reaction mixture was heated to 50° C. for 2 h. After the mixture was concentrated and diluted with H$_2$O, the pH was adjusted to 3. The mixture was extracted with DCM (5 mL×3). The collected organic layers were concentrated under vacuum to give the crude acid, which was used directly in the next step without further purification. LCMS (ES) m/z=237 (M+H)$^+$.

To the above acid in DCM (2 mL) at 25° C. was added bromo-tris-pyrrolidino phosphoniumhexafluorophosphate (PyBrOP) (298 mg, 0.64 mmol) in one portion, followed by the addition of DIPEA (0.2 mL, 1.15 mmol) and 2-{(2S)-2-amino-3-[2-(trifluoromethyl)phenyl]propyl}-1H-isoindole-1,3(2H)-dione (208 mg, 0.6 mmol). After 1 h, the solution was concentrated and purified via column chromatography (silica, 1-10% MeOH/CHCl$_3$) affording the title compound (0.22 g, 61% for 2 steps): LC-MS (ES) m/z 567 (M+H)$^+$.

d) N-((1S)-2-amino-1-{[2-(trifluoromethyl)phenyl]methyl}ethyl)-4-(1-propyl-1H-pyrazol-5-yl)-2-thiophenecarboxamide

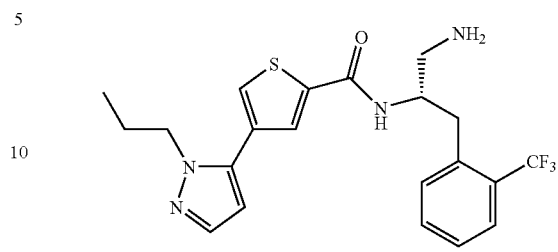

N-((1S)-2-(1,3-dioxo-1,3-dihydro-2H-isoindol-2-yl)-1-{[2-(trifluoromethyl)phenyl]methyl}ethyl)-4-(1-propyl-1H-pyrazol-5-yl)-2-thiophenecarboxamide (220 mg, 0.36 mmol) was dissolved in MeOH (2 mL) and was treated with NH$_2$NH$_2$ (0.3 mL, 9.56 mmol). The reaction was stirred over 10 h, concentrated and purified by reverse-phase HPLC (C18 column: H$_2$O/CH$_3$CN, 95-5%) to afford the bis-TFA salt of the title compound. The bis-TFA salt was dissolved in water and neutralized with ammonium hydroxide. The mixture was extracted with DCM, dried over Na$_2$SO$_4$, and concentrated to give a free base of the title compound. The free base compound was dissolved in MeOH (2 mL) and treated with HCl (4M in dioxane). After stirring overnight, the reaction solution was concentrated to give the title compound (112 mg, 57%) as an off white solid: LC-MS (ES) m/z 437 (M+H)$^+$, NMR (d$_6$-DMSO, 400 MHz): 6 ppm 9.06-8.99 (m, 1H), 8.23-8.02 (m, 4H), 7.92 (br s, 1H), 7.69 (d, J=7.8 Hz, 1H), 7.62-7.49 (m, 3H), 7.42 (m, 1H), 4.50 (m, 1H), 4.20 (m, 2H), 3.15-2.99 (m, 4H), 1.74 (m, 2H), and 0.80 (t, J=7.3 Hz, 3H).

Example 257

N-((1S)-2-amino-1-{[2-(trifluoromethyl)phenyl]methyl}ethyl)-4-(4-chloro-1-propyl-1H-pyrazol-5-yl)-2-thiophenecarboxamide

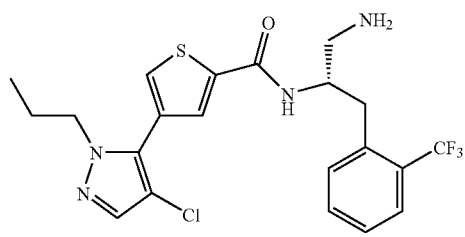 [SMILES: CCCn1ncc(Cl)c1-c1csc(C(=O)N[C@H](CN)Cc2ccccc2C(F)(F)F)c1]

a) methyl 4-(4-chloro-1-propyl-1H-pyrazol-5-yl)-2-thiophenecarboxylate

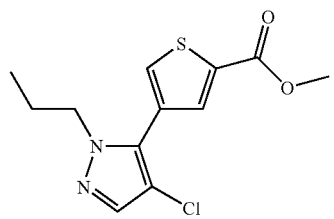 [SMILES: CCCn1ncc(Cl)c1-c1csc(C(=O)OC)c1]

A mixture of methyl 4-(1-propyl-1H-pyrazol-5-yl)-2-thiophenecarboxylate (250 mg, 1.0 mmol) and NCS (200 mg, 1.5 mmol) in THF (5 mL) was heated to 70° C. in a sealed tube. After 2 h, the reaction mixture was concentrated and purified via column chromatography (silica, 10% EtOAc/

Hexane) affording the title compound (199 mg, 70%) as a white solid: LC-MS (ES) m/z 285 (M+H)⁺.

b) 4-(4-chloro-1-propyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide

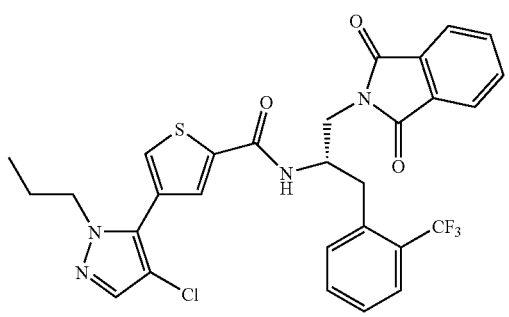 [SMILES: CCCn1ncc(Cl)c1-c1csc(C(=O)N[C@@H](Cc2ccccc2C(F)(F)F)CN2C(=O)c3ccccc3C2=O)c1]

To a solution of methyl 4-(4-chloro-1-propyl-1H-pyrazol-5-yl)-2-thiophenecarboxylate (199 mg, 0.7 mmol) in THF/H₂O (2 mL/0.5 mL) was added KOH (100 mg, 1.7 mmol). The reaction mixture was heated to 50° C. for 2 h. After the mixture was concentrated and diluted with H₂O, the pH was adjusted to 3. The mixture was extracted with DCM (5 mL×3). The collected organic layers were concentrated under vacuum to give the crude acid, which was used directly in the next step without further purification: LC-MS (ES) m/z 271 (M+H)⁺.

To the above acid in DCM (5 mL) at 25° C. was added bromo-tris-pyrrolidino phosphoniumhexafluorophosphate (PyBrOP) (326 mg, 0.7 mmol) in one portion, followed by the addition of DIPEA (0.3 mL, 1.15 mmol) and 2-{(2S)-2-amino-3-[2-(trifluoromethyl)phenyl]propyl}-1H-isoindole-1,3(2H)-dione (232 mg, 0.7 mmol). After 10 min, the solution was concentrated and purified via column chromatography (silica, 1-10% MeOH/CHCl₃) affording the title compound (312 mg, 74% for 2 steps): LC-MS (ES) m/z 601 (M+H)⁺.

c) N-((1S)-2-amino-1-{[2-(trifluoromethyl)phenyl]methyl}ethyl)-4-(4-chloro-1-propyl-1H-pyrazol-5-yl)-2-thiophenecarboxamide

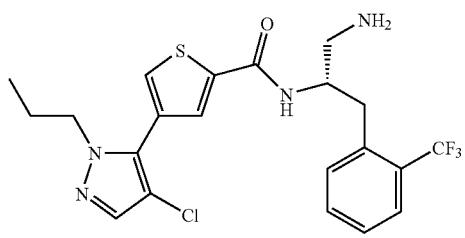 [SMILES: CCCn1ncc(Cl)c1-c1csc(C(=O)N[C@H](CN)Cc2ccccc2C(F)(F)F)c1]

4-(4-Chloro-1-propyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-2-thiophenecarboxamide (312 mg, 0.52 mmol) was dissolved in MeOH (2 mL) and was treated with NH₂NH₂ (0.5 mL, 15.9 mmol). The reaction was stirred over 10 h, concentrated and purified by reverse-phase HPLC (C18 column: H₂O/CH₃CN, 95-5%) to afford the bis-TFA salt of the title compound. The bis-TFA salt was dissovled in water and neutralized with ammonium hydroxide. The mixture was extracted with DCM, dried over Na₂SO₄, and concentrated to give a free base of the title compound. The free base compound was dissolved in MeOH (2 mL) and treated with HCl (aq). After stirring overnight, the reaction was concentrated to give the title compound (185 mg, 66%) as an off white solid: LC-MS (ES) m/z 471 (M+H)⁺, NMR (d₄-MeOD, 400 MHz) δ ppm 7.92 (m, 2H), 7.74-7.68 (m, 1H), 7.60 (s, 1H), 7.58-7.51 (m, 2H), 7.45-7.41 (m, 1H), 4.67 (m, 1H), 4.15 (t, J=7.1 Hz, 2H), 3.37-3.09 (m, 4H), 1.77 (m, 2H), and 0.82 (t, J=7.6 Hz, 3H).

Example 258

N-{(1S)-2-amino-1-[(3,4-difluorophenyl)methyl]ethyl}-5-chloro-4-(4-chloro-1-ethyl-1H-pyrazol-5-yl)-2-thiophenecarboxamide

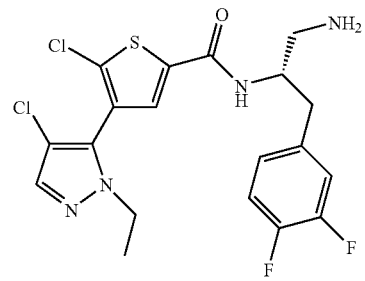 [SMILES: CCn1ncc(Cl)c1-c1cc(C(=O)N[C@H](CN)Cc2ccc(F)c(F)c2)sc1Cl]

a) methyl 5-chloro-4-(1-ethyl-1H-pyrazol-5-yl)-2-thiophenecarboxylate

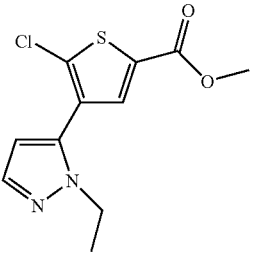 [SMILES: CCn1nccc1-c1cc(C(=O)OC)sc1Cl]

To a 100 mL sealed flask was added 1-ethyl-5-(4,4,5,5-tetramethyl-1,3,2-dioxaborolan-2-yl)-1H-pyrazole (2.61 g, 11.74 mmol), potassium carbonate (3.25 g, 23.48 mmol), methyl 4-bromo-5-chloro-2-thiophenecarboxylate (2 g, 7.83 mmol) and bis(tri-t-butylphosphine)palladium(0) (0.4 g, 0.78 mmol) in 1,2-dimethoxyethane (DME) (50 mL) and H₂O (10 ml). After stirring for 3 h at 70° C., the reaction solution was diluted with DCM (100 mL) and washed with H₂O. The organic layer was dried Na₂SO₄, filtered and concentrated. The residue was purified on silica gel [EtOAc/hexanes, 10-30%] to give the product [1.8 g, 85%] as an off white solid: LC-MS (ES) m/z 271 (M+H)⁺.

b) methyl 5-chloro-4-(4-chloro-1-ethyl-1H-pyrazol-5-yl)-2-thiophenecarboxylate

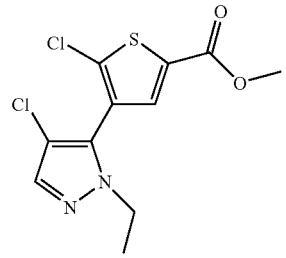 [SMILES: CCn1ncc(Cl)c1-c1cc(C(=O)OC)sc1Cl]

Methyl 5-chloro-4-(1-ethyl-1H-pyrazol-5-yl)-2-thiophenecarboxylate (1.8 g, 6.65 mmol) and NCS (1.3 g, 9.74 mmol)

in THF (10 mL) were heated to 70° C. under N₂ for 2 h. The reaction solution was concentrated and purified on silica (EtOAc/Hex, 10-30%) to afford the title compound (1.5 g, 74%) as a syrup: LC-MS (ES) m/z 305 (M+H)⁺.

b) N-{(1S)-2-amino-1-[(3,4-difluorophenyl)methyl]ethyl}-5-chloro-4-(4-chloro-1-ethyl-1H-pyrazol-5-yl)-2-thiophenecarboxamide

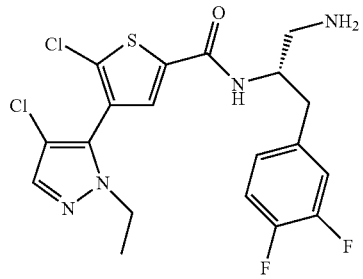 [SMILES: CCn1ncc(Cl)c1-c1cc(C(=O)N[C@H](CN)Cc2ccc(F)c(F)c2)sc1Cl]

The title compound (290 mg, 58.4%) was prepared as an off-white solid according to the procedure of Example 236, except substituting 5-chloro-4-(4-chloro-1-ethyl-1H-pyrazol-5-yl)-N-{(1S)-2-(3,4-difluorophenyl)-1-[(1,3-dioxo-1,3-dihydro-2H-isoindol-2-yl)methyl]ethyl}-2-thiophenecarboxamide (526 mg, 1.662 mmol) for 5-chloro-4-(4-chloro-1-ethyl-1H-pyrazol-5-yl)-N-{(1S)-2-(1,3-dioxo-1,3-dihydro-2H-isoindol-2-yl)-1-[(3-fluorophenyl)methyl]ethyl}-2-thiophenecarboxamide: LC-MS (ES) m/z 459 (M+H)⁺, NMR (d₄-MeOD, 400 MHz) δ ppm 7.76 (m, 1H), 7.62 (s, 1H), 7.28-7.22 (m, 1H), 7.20-7.10 (m, 2H), 4.52 (m, 1H), 4.07 (m, 2H), 3.27-3.16 (m 2H), 3.05-2.94 (m, 2H), and 1.34 (m, 3H).

Example 259

N-{(1S)-2-amino-1-[(3,4-difluorophenyl)methyl]ethyl}-5-chloro-4-(4-chloro-1-ethyl-1H-pyrazol-5-yl)-2-furancarboxamide

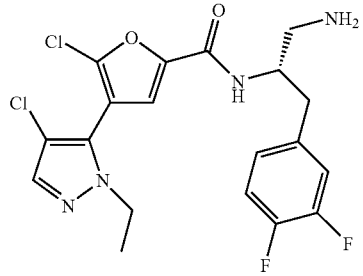 [SMILES: CCn1ncc(Cl)c1-c1cc(C(=O)N[C@H](CN)Cc2ccc(F)c(F)c2)oc1Cl]

a) methyl 5-chloro-4-(1-ethyl-1H-pyrazol-5-yl)-2-furancarboxylate

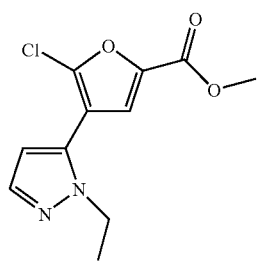 [SMILES: CCn1nccc1-c1cc(C(=O)OC)oc1Cl]

To a 100 mL sealed flask was added 1-ethyl-5-(4,4,5,5-tetramethyl-1,3,2-dioxaborolan-2-yl)-1H-pyrazole (2.61 g, 11.74 mmol), potassium carbonate (3.25 g, 23.48 mmol), methyl 4-bromo-5-chloro-2-furancarboxylate (1.85 g, 8.33 mmol) and bis(tri-t-butylphosphine)palladium(0) (0.16 g, 0.31 mmol) in 1,2-Dimethoxyethane (DME) (30 mL) and H₂O (5 mL). After stirring for 2 h at 75° C., the reaction solution was diluted with DCM (100 mL) and washed with H₂O. The organic layer was dried Na₂SO₄, filtered and concentrated. The residue was purified on silica gel [EtOAc/hexanes, 10-30%] to give the product (0.8 g, 50.1%) as an off-white solid: LC-MS (ES) m/z 255 (M+H)⁺.

b) methyl 5-chloro-4-(4-chloro-1-ethyl-1H-pyrazol-5-yl)-2-furancarboxylate

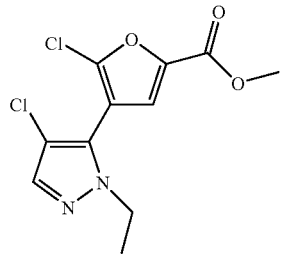

A mixture of methyl 5-chloro-4-(1-ethyl-1H-pyrazol-5-yl)-2-furancarboxylate (800 mg, 3.14 mmol) and NCS (600 mg, 4.49 mmol) in THF (5 mL) was heated to 70° C. in a sealed tube. After 2 h, the reaction mixture was concentrated and purified via column chromatography (silica, 10-20% EtOAc/Hexane) affording the title compound (710 mg, 78%) as a white solid: LC-MS (ES) m/z 289 (M+H)⁺.

c) 5-chloro-4-(4-chloro-1-ethyl-1H-pyrazol-5-yl)-N-{(1S)-2-(3,4-difluorophenyl)-1-[(1,3-dioxo-1,3-dihydro-2H-isoindol-2-yl)methyl]ethyl}-2-furancarboxamide

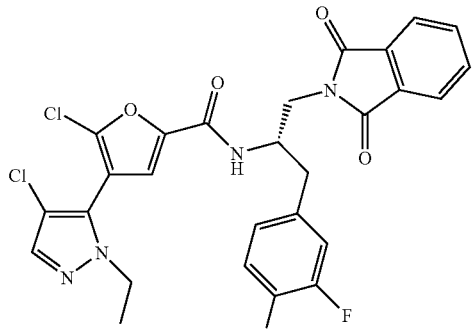

To a solution of methyl 5-chloro-4-(4-chloro-1-ethyl-1H-pyrazol-5-yl)-2-furancarboxylate (480 mg, 1.66 mmol) in THF/H₂O (5 mL/1 mL) was added KOH (460 mg, 8.20 mmol). The reaction mixture was heated to 50° C. for 4 h. After the mixture was concentrated and diluted with H₂O (2 mL), the pH was adjusted to 3. The mixture was extracted with DCM (10 mL×3). The collected organic layers were concentrated under vacuum to give a crude acid (420 mg, 92%), which was used directly without further purification: LC-MS (ES) m/z 275 (M+H)+.

To the above acid (400 mg) in DCM (5 mL) at 25° C. was added PyBrOP (881 mg, 1.89 mmol) in one portion, followed by the addition of DIPEA (1.5 mL, 8.59 mmol). After 10 min, 2-[(2S)-2-amino-3-(3,4-difluorophenyl)propyl]-1H-isoindole-1,3(2H)-dione (506 mg, 1.60 mmol) was added. After 2 h, the reaction mixture was concentrated and purified via column chromatography (silica, 30-50% EtOAc/Hexane) affording the title compound (655 mg, 79%) as a white solid: LC-MS (ES) m/z 573 (M+H)+.

c) N-{(1S)-2-amino-1-[(3,4-difluorophenyl)methyl]ethyl}-5-chloro-4-(4-chloro-1-ethyl-1H-pyrazol-5-yl)-2-furancarboxamide

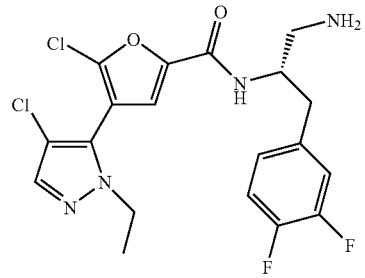 [SMILES: CCn1ncc(Cl)c1-c1cc(C(=O)N[C@H](CN)Cc2ccc(F)c(F)c2)oc1Cl]

At RT, NH$_2$NH$_2$ (0.5 mL, 15.93 mmol) was added to a solution of 5-chloro-4-(4-chloro-1-ethyl-1H-pyrazol-5-yl)-N-{(1S)-2-(3,4-difluorophenyl)-1-[(1,3-dioxo-1,3-dihydro-2H-isoindol-2-yl)methyl]ethyl}-2-furancarboxamide (610 mg, 1.06 mmol) in MeOH (5 mL). After 10 h, the solvent was removed under vacuum. The resulting residue was taken into DCM (20 mL) and washed with H$_2$O (20 mL×3).

To the DCM solution was added HCl (36%, 10 mL, 120 mmol). After 1 h, the aqueous phase was separated and washed with DCM (30 ml×3). Water was removed under high vacuum to give the title compound (410 mg, 87%) as an off-white solid: LC-MS (ES) m/z 443 (M+H)+, NMR (d$_4$-MeOD, 400 MHz) δ ppm 7.61 (s, 1H), 7.36 (s, 1H), 7.29-7.10 (m, 3H), 4.57 (m, 1H), 4.09 (q, J=7.3 Hz, 2H), 3.27-3.23 (m, 1H), 3.20-3.14 (m, 1H), 3.06-3.01 (m, 1H), 2.97-2.92 (m, 1H), and 1.36 (t, J=7.3 Hz, 3H).

Example 260

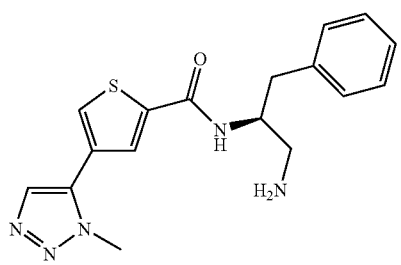 [SMILES: Cn1nncc1-c1csc(C(=O)N[C@H](CN)Cc2ccccc2)c1]

Preparation of N-[(1S)-2-amino-1-(phenylmethyl)ethyl]-4-(1-methyl-1H-1,2,3-triazol-5-yl)-2-thiophenecarboxamide a) 1,1-dimethylethyl[(2S)-2-({[4-(1-methyl-1H-1,2,3-triazol-5-yl)-2-thienyl]carbonyl}amino)-3-phenylpropyl]carbamate

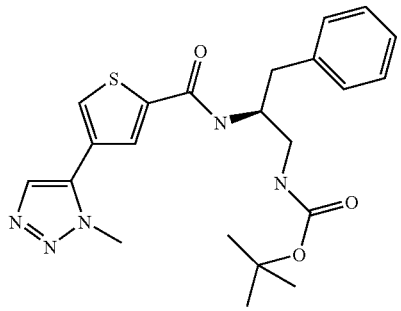 [SMILES: Cn1nncc1-c1csc(C(=O)N[C@H](CNC(=O)OC(C)(C)C)Cc2ccccc2)c1]

A mixture of 1,1-dimethylethyl ((2S)-2-{[(4-bromo-2-thienyl)carbonyl]amino}-3-phenylpropyl)carbamate (prepared according to Preparation 22 except substituting 2-[(2S)-2-amino-3-phenylpropyl]-1H-isoindole-1,3(2H)-dione for 2-[(2S)-2-amino-3-(2,4-dichlorophenyl)propyl]-1H-isoindole-1,3(2H)-dione) (236 mg, 0.537 mmol), 1-methyl-5-(tributylstannanyl)-1H-1,2,3-triazole (200 mg, 0.537 mmol) (prepared according to patent IPN WO97/01553), Pd(PPh$_3$)$_2$Cl$_2$ (37.7 mg, 0.054 mmol), TRIETHYLAMINE (74.9 µl, 0.537 mmol) and toluene (3 ml) was degassed by N$_2$ and sealed. The reaction mixture was heated at 110° C. for 4 hr. LC/MS showed the reaction was completed. The reaction mixture was concentrated and purified via column chromatography (silica, 70% EtOAc in hexane) to give the title product (120 mg, 51%) LCMS (ES) m/z=442.2 (M+H)

b) N-[(1S)-2-amino-1-(phenylmethyl)ethyl]-4-(1-methyl-1H-1,2,3-triazol-5-yl)-2-thiophenecarboxamide A solution of 1,1-dimethylethyl[(2S)-2-({[4-(1-methyl-1H-1,2,3-triazol-5-yl)-2-thienyl]carbonyl}amino)-3-phenylpropyl]carbamate (60 mg, 0.14 mmol) in TFA-DCM (4 ml, 1:3) was stirred at rt for 1 h. LCMS showed the reaction was completed. The reaction mixture was concentrated and the residue was purified by reverse phase HPLC (5%-65% acetonitrile in water with 0.1% TFA) to give 42.2 mg (67%) of the TFA salt as a white solid. LCMS (ES) m/z 342.2 (M+H)+, $^1$H NMR (400 MHz, METHANOL-d4) δ ppm 8.06 (d, J=1.52 Hz, 1H), 7.87-7.91 (m, 2H), 7.34-7.21 (m, 5H), 4.55 (m, 1H), 4.19 (s, 3H), 3.30-3.21 (m, 1H), 3.09-3.18 (m, 1H), 3.01 (d, J=7.6 Hz, 2H)

Example 261

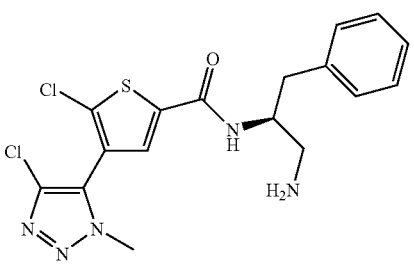

Preparation of N-[(1S)-2-amino-1-(phenylmethyl)ethyl]-5-chloro-4-(4-chloro-1-methyl-1H-1,2,3-triazol-5-yl)-2-thiophenecarboxamide a) 1,1-Dimethylethyl[(2S)-2-({[5-chloro-4-(4-chloro-1-methyl-1H-1,2,3-triazol-5-yl)-2-thienyl]carbonyl}amino)-3-phenylpropyl]carbamate

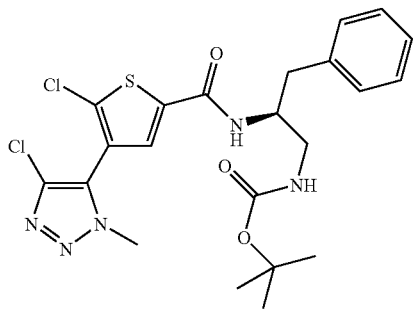 [SMILES: Cn1nnc(Cl)c1-c1cc(C(=O)N[C@H](CNC(=O)OC(C)(C)C)Cc2ccccc2)sc1Cl]

To a solution of 1,1-dimethylethyl[(2S)-2-({[4-(1-methyl-1H-1,2,3-triazol-5-yl)-2-thienyl]carbonyl}amino)-3-phenylpropyl]carbamate (70 mg, 0.16 mmol) in 2 ml of DMF was added NCS (42.3 mg, 0.32 mmol). The reaction mixture was heated at 50° C. for 2 hr and then diluted with 50 ml of EtOAc. The organic layer was washed with $H_2O$ and concentrated to give the title product as a crude mixture, which was used in next step without purification. LCMS (ES) m/z=510.2 (M+H)

b) N-[(1S)-2-amino-1-(phenylmethyl)ethyl]-5-chloro-4-(4-chloro-1-methyl-1H-1,2,3-triazol-5-yl)-2-thiophenecarboxamide A solution of 1,1-dimethylethyl[(2S)-2-({[5-chloro-4-(4-chloro-1-methyl-1H-1,2,3-triazol-5-yl)-2-thienyl]carbonyl}amino)-3-phenylpropyl]carbamate (crude from a) in TFA-DCM (4 ml, 1:3) was stirred at rt for 1 h. The reaction mixture was concentrated and the residue was purified by reverse phase HPLC (5%-65% acetonitrile in water with 0.1% TFA) to give 10 mg (12% two steps) of white solid as TFA salt. LCMS (ES) m/z 410.0/412.0 (M+H)+, 1H NMR (400 MHz, METHANOL-d4) δ ppm 7.62 (s, 1H), 7.32-7.25 (m, 5H), 4.55 (m, 1H), 4.02 (s, 3H), 3.21 (m, 1H), 3.10 (m, 1H), 2.98 (d, 2H).

Example 262

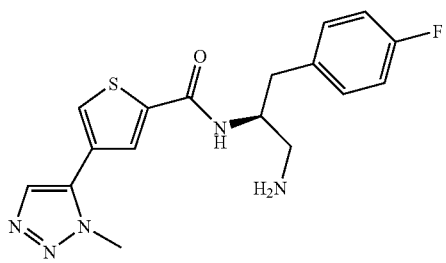 [SMILES: Cn1nncc1-c1csc(C(=O)N[C@H](CN)Cc2ccc(F)cc2)c1]

Preparation of N-{(1S)-2-amino-1-[(4-fluorophenyl)methyl]ethyl}-4-(1-methyl-1H-1,2,3-triazol-5-yl)-2-thiophenecarboxamide The title compound was prepared as a white solid according to the procedure of Example 260, except substituting 1,1-dimethylethyl[(2S)-2-{[(4-bromo-2-thienyl)carbonyl]amino}-3-(4-fluorophenyl)propyl]carbamate (123 mg, 0.27 mmol) for 1,1-dimethylethyl ((2S)-2-{[(4-bromo-2-thienyl)carbonyl]amino}-3-phenylpropyl)carbamate. LCMS (ES) m/z 360.2 (M+H)+, 1H NMR (400 MHz, METHANOL-d4) δ ppm 8.05 (d, J=1.6 Hz, 1H), 7.89-7.91 (m, 2H), 7.33-7.30 (m, 2H), 7.06-7.02 (m, 2H), 4.55 (m, 1H), 4.20 (s, 3H), 3.23 (m, 1H), 3.17 (m, 1H), 2.99 (m, 2H).

Example 263

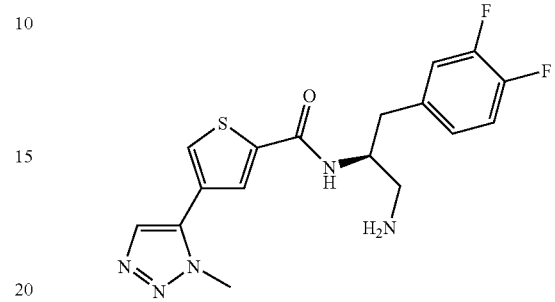

Preparation of N-{(1S)-2-amino-1-[(3,4-difluorophenyl)methyl]ethyl}-4-(1-methyl-1H-1,2,3-triazol-5-yl)-2-thiophenecarboxamide a) 1,1-Dimethylethyl[(2S)-3-(3,4-difluorophenyl)-2-({[4-(1-methyl-1H-1,2,3-triazol-5-yl)-2-thienyl]carbonyl}amino)propyl]carbamate

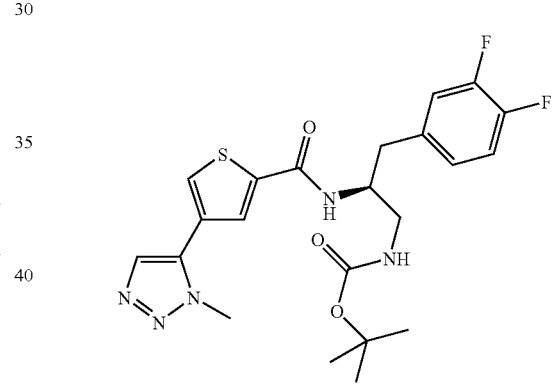

A solution of 1,1-dimethylethyl[(2S)-2-{[(4-bromo-2-thienyl)carbonyl]amino}-3-(3,4-di-fluorophenyl)propyl]carbamate (50 mg, 0.11 mmol), 1-methyl-5-(4,4,5,5-tetramethyl-1,3,2-dioxaborolan-2-yl)-1H-1,2,3-triazole (44 mg, 0.21 mmol), $Na_2CO_3$ (2N, 0.1 ml) and $PddppfCl_2$ (8.6 mg, 0.01 mmol) in 3 ml of 1,4-dioxane was irradiated in MW reactor at 150° C. for 20 min. The crude reaction mixture was purified by column chromatography (silica, 70% EtOAc in hexane) to give the title product (29 mg, 46%): LCMS (ES) m/z=478.2 (M+H).

b) N-{(1S)-2-amino-1-[(4-fluorophenyl)methyl]ethyl}-4-(1-methyl-1H-1,2,3-triazol-5-yl)-2-thiophenecarboxamide The title compound was prepared according to Example 260b) except substituting 1,1-dimethylethyl[(2S)-3-(3,4-difluorophenyl)-2-({[4-(1-methyl-1H-1,2,3-triazol-5-yl)-2-thienyl]carbonyl}amino)propyl]carbamate (29 mg, 0.06 mmol) for 1,1-dimethylethyl[(2S)-2-({[4-(1-methyl-1H-1,2,3-triazol-5-yl)-2-thienyl]carbonyl}amino)-3-phenylpropyl]carbamate. LCMS (ES) m/z 378.2 (M+H)+, 1H NMR (400 MHz, METHANOL-d4) δ ppm 8.07 (d, J=1.6 Hz, 1H), 7.88-7.91 (m, 2H), 7.23-7.09 (m, 3H), 4.55 (m, 1H), 4.20 (s, 3H), 3.24 (m, 1H), 3.15 (m, 1H), 2.98 (m, 2H).

Example 264

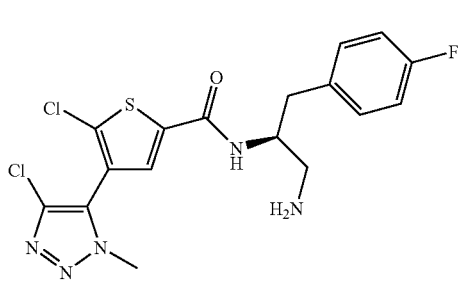 [SMILES: Cn1nnc(Cl)c1-c1cc(C(=O)N[C@H](CN)Cc2ccc(F)cc2)sc1Cl]

Preparation of N-{(1S)-2-amino-1-[(4-fluorophenyl)methyl]ethyl}-5-chloro-4-(4-chloro-1-methyl-1H-1,2,3-triazol-5-yl)-2-thiophenecarboxamide The title compound was prepared as a white solid according to the procedure of Example 261, except substituting 1,1-dimethylethyl[(2S)-2-({[4-(1-methyl-1H-1,2,3-triazol-5-yl)-2-thienyl]carbonyl}amino)-3-(4-fluorophenyl)propyl]carbamate (68 mg, 0.15 mmol) for 1,1-dimethylethyl[(2S)-2-({[4-(1-methyl-1H-1,2,3-triazol-5-yl)-2-thienyl]carbonyl}amino)-3-phenylpropyl]carbamate. LCMS (ES) m/z 428.0/430.0 (M+H)+, $^1$H NMR (400 MHz, METHANOL-d4) δ ppm 7.66 (s, 1H), 7.30 (m, 2H), 7.04 (m, 2H), 4.55 (m, 1H), 4.02 (s, 3H, 3.21-3.10 (m, 2H), 2.98 (m, 2H).

Example 265

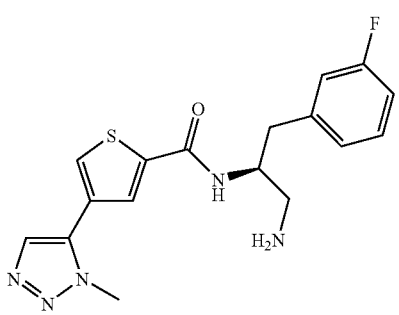

Preparation N-{(1S)-2-amino-1-[(3-fluorophenyl)methyl]ethyl}-4-(1-methyl-1H-1,2,3-triazol-5-yl)-2-thiophenecarboxamide The title compound was prepared as a white solid according to the procedure of Example 263, except substituting 1,1-dimethylethyl[(2S)-2-{[(4-bromo-2-thienyl)carbonyl]amino}-3-(3-fluorophenyl)propyl]carbamate (300 mg, 0.66 mmol) for 1,1-dimethylethyl[(2S)-2-{[(4-bromo-2-thienyl)carbonyl]amino}-3-(3,4-difluorophenyl)propyl]carbamate. LCMS (ES) m/z 360.2 (M+H)+, $^1$H NMR (400 MHz, METHANOL-d4) δ ppm 8.06 (d, J=1.6 Hz, 1H), 7.90 (m, 2H), 7.33-7.30 (m, 1H), 7.13-7.09 (m, 2H), 6.98-6.95 (m, 1H), 4.55 (m, 1H), 4.19 (s, 3H), 3.24 (m, 1H), 3.17 (m, 1H), 3.04-2.99 (m, 2H).

Example 266

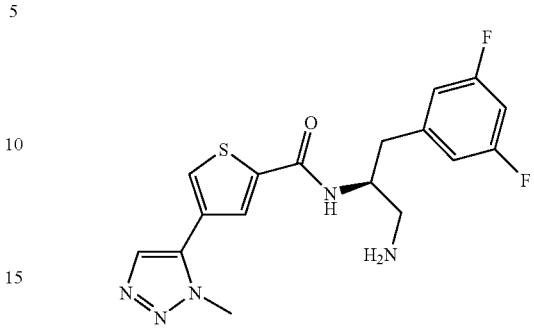

Preparation N-{(1S)-2-amino-1-[(3,5-difluorophenyl)methyl]ethyl}-4-(1-methyl-1H-1,2,3-triazol-5-yl)-2-thiophenecarboxamide The title compound was prepared as a white solid according to the procedure of Example 263, except substituting 1,1-dimethylethyl[(2S)-2-{[(4-bromo-2-thienyl)carbonyl]amino}-3-(3,5-difluorophenyl)propyl]carbamate (300 mg, 0.66 mmol) for 1,1-dimethylethyl[(2S)-2-{[(4-bromo-2-thienyl)carbonyl]amino}-3-(3,4-difluorophenyl)propyl]carbamate. LCMS (ES) m/z 378.2 (M+H)+, $^1$H NMR (400 MHz, METHANOL-d4) δ ppm 8.06 (d, J=1.6 Hz, 1H), 7.91 (m, 2H), 6.96-6.93 (m, 2H), 6.84-6.83 (m, 1H), 4.55 (m, 1H), 4.19 (s, 3H), 3.24 (m, 1H), 3.19 (m, 1H), 3.05-2.98 (m, 2H).

Example 267

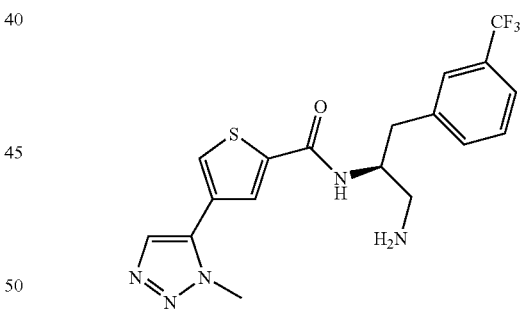

Preparation N-{(1S)-2-amino-1-[(3-trifluoromethylphenyl)methyl]ethyl}-4-(1-methyl-1H-1,2,3-triazol-5-yl)-2-thiophenecarboxamide The title compound was prepared as a white solid according to the procedure of Example 263, except substituting 1,1-dimethylethyl[(2S)-2-{[(4-bromo-2-thienyl)carbonyl]amino}-3-(3-(trifluoromethyl)phenyl)propyl]carbamate (500 mg, 0.99 mmol) for 1,1-dimethylethyl[(2S)-2-{[(4-bromo-2-thienyl)carbonyl]amino}-3-(3,4-difluorophenyl)propyl]carbamate. LCMS (ES) m/z 410.2 (M+H)+, $^1$H NMR (400 MHz, METHANOL-d4) δ ppm 8.06 (d, J=1.2 Hz, 1H), 7.97 (s, 1H), 7.91 (s, 1H), 7.72 (d, J=1.2 Hz, 1H) 7.54 (m, 2H), 7.44 (m, 1H), 4.55 (m, 1H), 4.21 (s, 3H), 3.30-3.10 (m, 4H).

Example 268

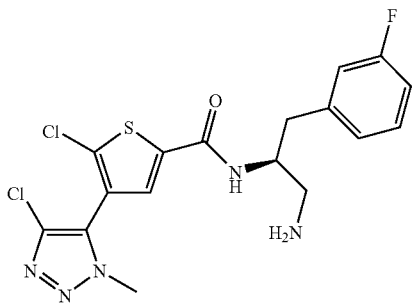 [SMILES: Cn1nnc(Cl)c1-c1cc(C(=O)N[C@H](CN)Cc2cccc(F)c2)sc1Cl]

Preparation of N-{(1S)-2-amino-1-[(3-fluorophenyl)methyl]ethyl}-5-chloro-4-(4-chloro-1-methyl-1H-1,2,3-triazol-5-yl)-2-thiophenecarboxamide The title compound was prepared as a white solid according to the procedure of Example 261, except substituting 1,1-dimethylethyl[(2S)-2-({[4-(1-methyl-1H-1,2,3-triazol-5-yl)-2-thienyl]carbonyl}amino)-3-(3-fluorophenyl)propyl]carbamate (50 mg, 0.11 mmol) for 1,1-dimethylethyl[(2S)-2-({[4-(1-methyl-1H-1,2,3-triazol-5-yl)-2-thienyl]carbonyl}amino)-3-phenylpropyl]carbamate. LCMS (ES) m/z 428.0/430.0 (M+H)+, 1H NMR (400 MHz, METHANOL-d4) δ ppm 7.63 (s, 1H), 7.33 (m, 1H), 7.12-7.07 (m, 3H), 4.55 (m, 1H), 4.02 (s, 3H), 3.23-2.98 (m, 4H).

Example 269

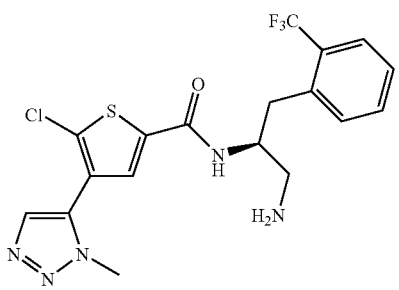 [SMILES: Cn1nncc1-c1cc(C(=O)N[C@H](CN)Cc2ccccc2C(F)(F)F)sc1Cl]

Preparation of N-{(1S)-2-amino-1-[(2-(trifluoromethyl)phenyl)methyl]ethyl}-5-chloro-4-(1-methyl-1H-1,2,3-triazol-5-yl)-2-thiophenecarboxamide a) methyl 5-chloro-4-(1-methyl-1H-1,2,3-triazol-5-yl)-2-thiophenecarboxylate

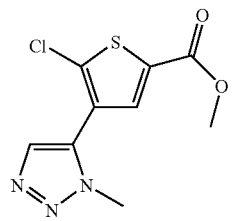 [SMILES: COC(=O)c1cc(-c2cnnn2C)c(Cl)s1]

A mixture of 1-methyl-5-(tributylstannanyl)-1H-1,2,3-triazole (2.0 g, 5.37 mmol), methyl 4-bromo-5-chloro-2-thiophenecarboxylate (1.25 g, 4.9 mmol), Pd(PPh3)2Cl2 (171 mg, 0.244 mmol), TRIETHYLAMINE (0.68 ml, 4.89 mmol) and toluene (3 ml) was heated at 110° C. for 4 hr under N2. The reaction mixture was purified via column chromatography (silica, 50%-70% EtOAc in hexane) to give the title compound as a white solid (400 mg, 32%): LCMS (ES) m/z 258.2 (M+H)+.

b) 5-Chloro-4-(1-methyl-1H-1,2,3-triazol-5-yl)-2-thiophenecarboxylic Acid

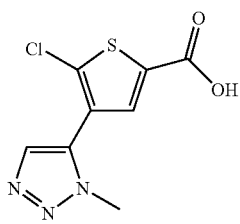

A solution of methyl 5-chloro-4-(1-methyl-1H-1,2,3-triazol-5-yl)-2-thiophenecarboxylate (400 mg, 1.55 mmol) and 1N LiOH (2.0 ml, 2.0 mmol) in THF (6 ml) was stirred at rt overnight. After removal of THF, the residue was diluted with 10 ml of H2O and washed with DCM (10 ml×2). The aqueous layer was acidified to pH 3 with 1N HCl and then extracted with EtOAc (30 ml×4). The organic layers were combined and concentrated to give 370 mg of the title compound as a white solid. LCMS (ES) m/z 244.0 (M+H)+ c) 5-Chloro-N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)-2-thiophenecarboxamide

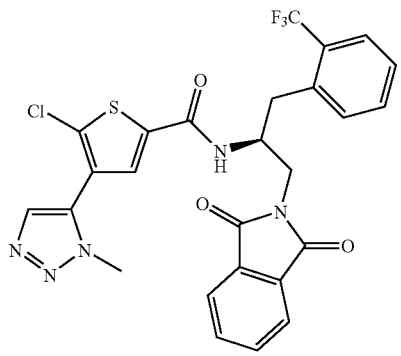 [SMILES: Cn1nncc1-c1cc(C(=O)N[C@@H](Cc2ccccc2C(F)(F)F)CN2C(=O)c3ccccc3C2=O)sc1Cl]

A solution of 5-chloro-4-(1-methyl-1H-1,2,3-triazol-5-yl)-2-thiophenecarboxylic acid (370 mg, 1.52 mmol), 2-{(2S)-2-amino-3-[3-(trifluoromethyl)phenyl]propyl}-1H-isoindole-1,3(2H)-dione (from Preparation 6, 529 mg, 1.52 mmol), PyBrop (708 mg, 1.52 mmol) and DIPEA (2.65 ml, 15.2 mmol) in 20 ml of DCM was stirred at rt for 2 hr. The reaction mixture was diluted with 50 ml of DCM and washed with H2O, 0.1N HCl and brine. The organic layer was concentrated and the residue was purified via column chromatography (silica, 50%-70% EtOAc in hexane) to give the title compound as a white solid (700 mg, 80%): LCMS (ES) m/z 574.0 (M+H)+.

d) N-{(1S)-2-amino-1-[(2-(trifluoromethyl)phenyl)methyl]ethyl}-5-chloro-4-(1-methyl-1H-1,2,3-triazol-5-yl)-2-thiophenecarboxamide A solution of 5-chloro-N-((1S)-2-(1,3-dioxo-1,3-dihydro-2H-isoindol-2-yl)-1-{[2-(trifluoromethyl)phenyl]

methyl}ethyl)-4-(1-methyl-1H-1,2,3-triazol-5-yl)-2-thiophenecarboxamide (700 mg, 1.22 mmol) and hydrazine (0.19 mL, 6.1 mmol) in 5 mL of MeOH was stirred at rt overnight, diluted with 200 ml of H$_2$O and extracted with DCM (100 ml×2). The combined organic layers were concentrated and the resulting solid was dissolved in 6N HCl (50 ml). The aqueous layer was washed with DCM (50 ml×2). The organic layers were discarded and the remaining aqueous solution was concentrated to give the product as an HCl salt (490 mg, 75%): LCMS (ES) m/z 444.0 (M+H)$^+$, $^1$H NMR (400 MHz, METHANOL-d4) δ ppm 8.10 (m, 1H), 7.92 (m, 1H), 7.73 (m, 1H), 7.57 (m, 1H), 7.44 (m, 1H), 4.65 (m, 1H), 4.17 (s, 3H), 3.25-3.11 (m, 4H).

Example 270

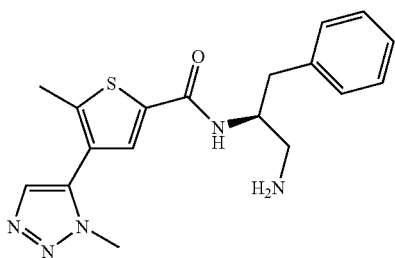 [SMILES: Cc1sc(C(=O)N[C@H](CN)Cc2ccccc2)cc1-c1cnnn1C]

Preparation of N-[(1S)-2-amino-1-(phenylmethyl)ethyl]-5-methyl-4-(1-methyl-1H-1,2,3-triazol-5-yl)-2-thiophenecarboxamide The title compound was prepared as an off-white solid according to the procedure of Example 269, except substituting methyl 4-bromo-5-methyl-2-thiophenecarboxylate (from Preparation 10) for methyl 4-bromo-5-chloro-2-thiophenecarboxylate and 2-{(2S)-2-amino-3-phenylpropyl}-1H-isoindole-1,3(2H)-dione (preparation 5) for 2-{(2S)-2-amino-3-[3-(trifluoromethyl)phenyl]propyl}-1H-isoindole-1,3(2H)-dione. LCMS (ES) m/z 356.2 (M+H)$^+$, $^1$H NMR (400 MHz, METHANOL-d4) δ ppm 8.60 (s, 1H), 8.01 (s, 1H), 7.34-7.21 (m, 5H), 4.55 (m, 1H), 4.26 (s, 3H), 3.25 (m, 2H), 3.03 (m, 2H), 2.21 (s, 3H).

Example 271

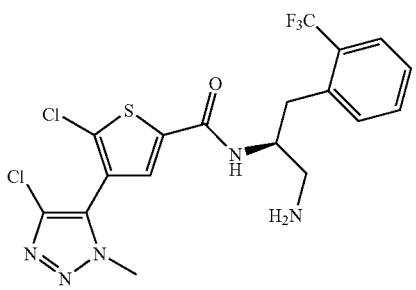

Preparation of N-{(1S)-2-amino-1-[(2-(trifluoromethyl)phenyl)methyl]ethyl}-5-chloro-4-(4-chloro-1-methyl-1H-1,2,3-triazol-5-yl)-2-thiophenecarboxamide The title compound was prepared as a white solid according to the procedure of Example 261, except substituting N-{(1S)-2-amino-1-[(2-(trifluoromethyl)phenyl)methyl]ethyl}-5-chloro-4-(1-methyl-1H-1,2,3-triazol-5-yl)-2-thiophenecarboxamide (120 mg, 0.27 mmol) for 1,1-dimethylethyl[(2S)-2-({[4-(1-methyl-1H-1,2,3-triazol-5-yl)-2-thienyl]carbonyl}amino)-3-phenylpropyl]carbamate. LCMS (ES) m/z 478.0/480.0 (M+H)$^+$, $^1$H NMR (400 MHz, METHANOL-d4) δ ppm 7.79 (s, 1H), 7.73 (d, J=7.6 Hz, 1H), 7.56 (m, 2H), 7.45 (m, 1H), 4.65 (m, 1H), 4.05 (s, 3H), 3.29-3.10 (m, 4H).

Example 272

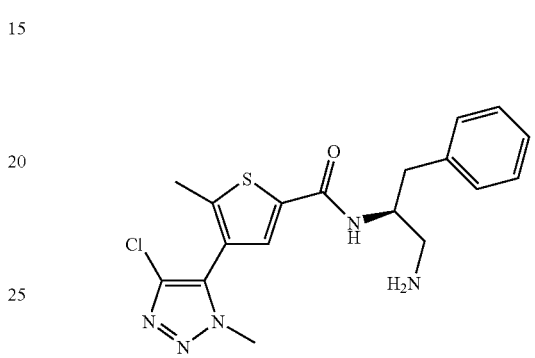

Preparation of N-[(1S)-2-amino-1-(phenylmethyl)ethyl]-4-(4-chloro-1-methyl-1H-1,2,3-triazol-5-yl)-5-methyl-2-thiophenecarboxamide The title compound was prepared as a white solid according to the procedure of Example 261, except substituting 1,1-dimethylethyl[(2S)-2-({[5-methyl-4-(1-methyl-1H-1,2,3-triazol-5-yl)-2-thienyl]carbonyl}amino)-3-phenylpropyl]carbamate (prepared in Example 270) for 1,1-dimethylethyl[(2S)-2-({[4-(1-methyl-1H-1,2,3-triazol-5-yl)-2-thienyl]carbonyl}amino)-3-phenylpropyl]carbamate. LCMS (ES) m/z 390.2 (M+H)$^+$, $^1$H NMR (400 MHz, METHANOL-d4) δ ppm 7.72 (s, 1H), 7.31-7.22 (m, 5H), 4.55 (m, 1H), 3.99 (s, 3H), 3.19 (m, 2H), 3.02 (m, 2H), 2.41 (s, 3H).

Example 273

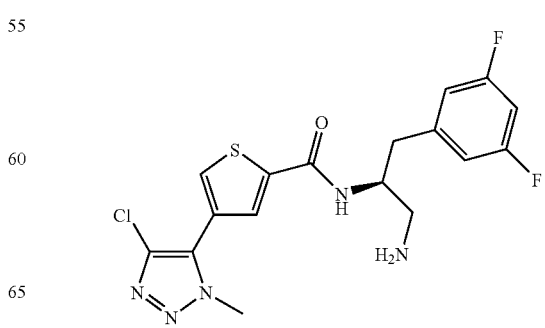

Preparation of N-{(1S)-2-amino-1-[(3,5-difluorophenyl)methyl]ethyl}-4-(4-chloro-1-methyl-1H-1,2,3-triazol-5-yl)-2-thiophenecarboxamide a) Methyl 4-(1-methyl-1H-1,2,3-triazol-5-yl)-2-thiophenecarboxylate

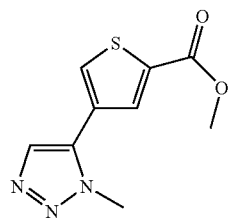

The title compound was prepared according to the procedure of Example 269 a), except substituting methyl 4-bromo-2-thiophenecarboxylate for methyl 4-bromo-5-chloro-2-thiophenecarboxylate. LCMS (ES) m/z 224.0 (M+H)+.

b) methyl 4-(4-chloro-1-methyl-1H-1,2,3-triazol-5-yl)-2-thiophenecarboxylate

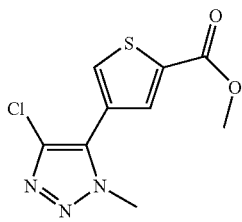 [SMILES: COC(=O)c1cc(-c2c(Cl)nnn2C)cs1]

A solution of methyl 4-(1-methyl-1H-1,2,3-triazol-5-yl)-2-thiophenecarboxylate (500 mg, 2.24 mmol) and NCS (1196 mg, 8.96 mmol) in N,N-Dimethylformamide (DMF) (10 ml) was heated at 50° C. for 2 hr. The reaction mixture was diluted with 50 ml of EtOAc. The organic layer was washed with H₂O (50 ml×2) and brine (50 ml), and then concentrated to give 460 mg of a crude mixture, which was used in next step without further separation. LCMS (ES) m/z 258.0 (M+H)+.

c) 4-(4-chloro-1-methyl-1H-1,2,3-triazol-5-yl)-2-thiophenecarboxylic Acid

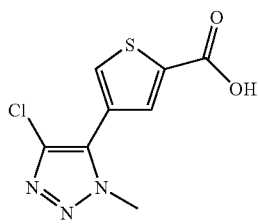

The title compound was prepared following the procedure of Example 269 b), except substituting methyl 4-(4-chloro-1-methyl-1H-1,2,3-triazol-5-yl)-2-thiophenecarboxylate for methyl 4-(1-methyl-1H-1,2,3-triazol-5-yl)-5-chloro-2-thiophenecarboxylate. LCMS (ES) m/z 244.0 (M+H)+.

d) N-{(1S)-2-amino-1-[(3,5-difluorophenyl)methyl]ethyl}-4-(4-chloro-1-methyl-1H-1,2,3-triazol-5-yl)-2-thiophenecarboxamide The title compound was prepared following the procedure of Example 269c-d), except substituting 4-(4-chloro-1-methyl-1H-1,2,3-triazol-5-yl)-2-thiophenecarboxylic acid for 4-(1-methyl-1H-1,2,3-triazol-5-yl)-5-chloro-2-thiophenecarboxylic acid and substituting 2-[(2S)-2-amino-3-(3,5-difluorophenyl)propyl]-1H-isoindole-1,3(2H)-dione for 2-{(2S)-2-amino-3-[3-(trifluoromethyl)phenyl]propyl}-1H-isoindole-1,3(2H)-dione. LCMS (ES) m/z 412.0/414.0 (M+H)+, ¹H NMR (400 MHz, METHANOL-d4) δ ppm 8.13 (m, 1H), 8.06 (m, 1H), 6.97 (m, 2H), 6.82 (m, 1H), 4.55 (m, 1H), 4.16 (s, 3H), 3.26 (m 2H), 3.04 (m, 2H).

Example 274

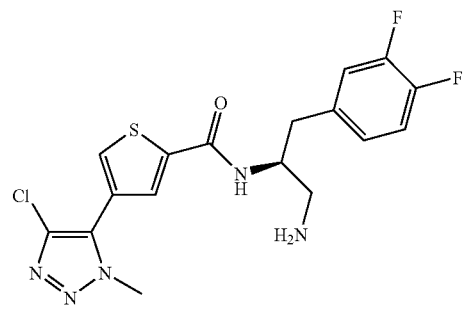 [SMILES: Cn1nnc(Cl)c1-c1csc(C(=O)N[C@H](CN)Cc2ccc(F)c(F)c2)c1]

Preparation of N-{(1S)-2-amino-1-[(3,4-difluorophenyl)methyl]ethyl}-4-(4-chloro-1-methyl-1H-1,2,3-triazol-5-yl)-2-thiophenecarboxamide The title compound was prepared following the procedure of Example 273, except substituting 2-[(2S)-2-amino-3-(3,4-difluorophenyl)propyl]-1H-isoindole-1,3(2H)-dione (82 mg, 0.15 mmol) for 2-[(2S)-2-amino-3-(3,5-difluorophenyl)propyl]-1H-isoindole-1,3(2H)-dione. LCMS (ES) m/z 412.0/414.0 (M+H)+, ¹H NMR (400 MHz, METHANOL-d4) δ ppm 8.12 (d, J=1 Hz, 1H), 8.05 (d, J=1 Hz, 1H) 7.30-7.10 (m, 3H), 4.55 (m, 1H), 4.16 (s, 3H), 3.26 (m 2H), 2.99 (m, 2H).

Example 275

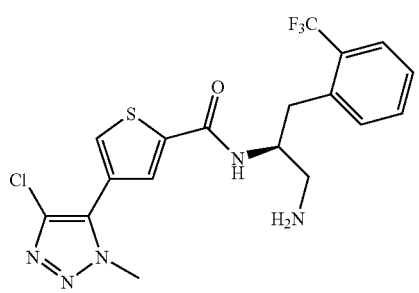 [SMILES: Cn1nnc(Cl)c1-c1csc(C(=O)N[C@H](CN)Cc2ccccc2C(F)(F)F)c1]

Preparation of N-{(1S)-2-amino-1-[(2-(trifluoromethyl)phenyl)methyl]ethyl}-4-(4-chloro-1-methyl-1H-1,2,3-triazol-5-yl)-2-thiophenecarboxamide The title compound was prepared following the procedure of Example 274, except substituting 2-[(2S)-2-amino-3-(2-

(trifluoromethyl)phenyl)propyl]-1H-isoindole-1,3(2H)-dione (130 mg, 0.23 mmol) for 2-[(2S)-2-amino-3-(3,5-difluorophenyl)propyl]-1H-isoindole-1,3(2H)-dione. LCMS (ES) m/z 444.0/446.0 (M+H)$^+$, $^1$H NMR (400 MHz, METHANOL-d4) δ ppm 8.13 (d, J=1 Hz, 1H), 8.09 (d, J=1 Hz, 1H), 7.72 (m, 1H), 7.56 (m, 2H), 7.43 (m, 1H), 4.60 (m, 1H), 4.17 (s, 3H), 3.26-3.15 (m, 4H).

Example 276

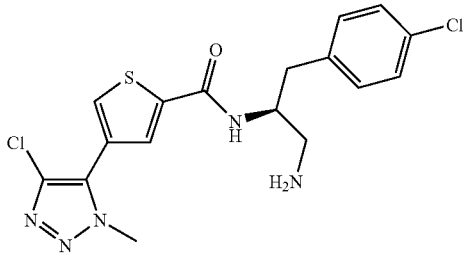 [SMILES: Cn1nnc(Cl)c1-c1csc(C(=O)N[C@H](CN)Cc2ccc(Cl)cc2)c1]

Preparation of N-{(1S)-2-amino-1-[(4-chlorophenyl)methyl]ethyl}-4-(4-chloro-1-methyl-1H-1,2,3-triazol-5-yl)-2-thiophenecarboxamide The title compound was prepared following the procedure of Example 273, except substituting 2-[(2S)-2-amino-3-(4-chlorophenyl)propyl]-1H-isoindole-1,3(2H)-dione (73 mg, 0.14 mmol) for 2-[(2S)-2-amino-3-(3,5-difluorophenyl)propyl]-1H-isoindole-1,3(2H)-dione. LCMS (ES) m/z 410.0/412.0 (M+H)$^+$, $^1$H NMR (400 MHz, METHANOL-d4) δ ppm 8.12 (d, J=1 Hz, 1H), 8.03 (d, J=1 Hz, 1H), 7.31 (m, 4H), 4.55 (m, 1H), 4.15 (s, 3H), 3.26 (m 2H), 3.05 (m, 2H).

Example 277

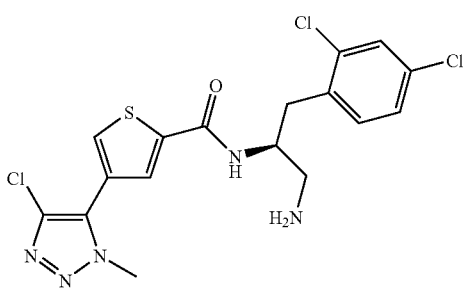 [SMILES: Cn1nnc(Cl)c1-c1csc(C(=O)N[C@H](CN)Cc2ccc(Cl)cc2Cl)c1]

Preparation of N-{(1S)-2-amino-1-[(2,4-dichlorophenyl)methyl]ethyl}-4-(4-chloro-1-methyl-1H-1,2,3-triazol-5-yl)-2-thiophenecarboxamide The title compound was prepared following the procedure of Example 273, except substituting 2-[(2S)-2-amino-3-(2,4-dichlorophenyl)propyl]-1H-isoindole-1,3(2H)-dione (67 mg, 0.12 mmol) for 2-[(2S)-2-amino-3-(3,5-difluorophenyl)propyl]-1H-isoindole-1,3(2H)-dione. LCMS (ES) m/z 444.0/448.0 (M+H)$^+$, $^1$H NMR (400 MHz, METHANOL-d4) δ ppm 8.12 (d, J=1 Hz, 1H), 8.03 (d, J=1 Hz, 1H), 7.49 (d, 1H), 7.38 (d, 1H), 7.25 (m, 1H), 4.60 (m, 1H), 4.16 (s, 3H), 3.30-3.09 (m, 4H).

Example 278

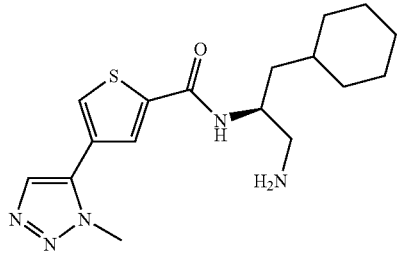 [SMILES: Cn1nncc1-c1csc(C(=O)N[C@H](CN)CC2CCCCC2)c1]

Preparation N-[(1S)-2-amino-1-(cyclohexylmethyl)ethyl]-4-(1-methyl-1H-1,2,3-triazol-5-yl)-2-thiophenecarboxamide The title compound was prepared as a white solid according to the procedure of Example 263, except substituting 1,1-dimethylethyl[(2S)-2-{[(4-bromo-2-thienyl)carbonyl]amino}-3-(cyclohexyl)propyl]carbamate (300 mg, 0.67 mmol) for 1,1-dimethylethyl[(2S)-2-{[(4-bromo-2-thienyl)carbonyl]amino}-3-(3,4-difluorophenyl)propyl]carbamate. LCMS (ES) m/z 348.2 (M+H)$^+$, $^1$H NMR (400 MHz, METHANOL-d4) δ ppm 8.09 (d, J=1 Hz, 1H), 8.03 (d, J=1 Hz, 1H), 7.91 (s, 1H), 4.48 (m, 1H), 4.22 (s, 3H), 3.20 (m 1H), 3.05 (m, 1H), 2.00-0.95 (m, 13H).

Example 279

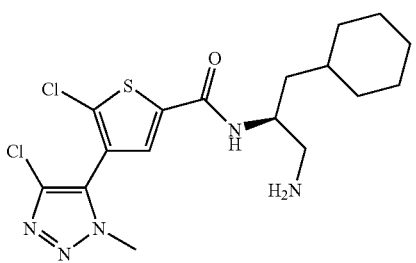 [SMILES: Cn1nnc(Cl)c1-c1cc(C(=O)N[C@H](CN)CC2CCCCC2)sc1Cl]

Preparation of N-[(1S)-2-amino-1-(cyclohexylmethyl)ethyl]-5-chloro-4-(4-chloro-1-methyl-1H-1,2,3-triazol-5-yl)-2-thiophenecarboxamide The title compound was prepared as a white solid according to the procedure of Example 261, except substituting 1,1-dimethylethyl[(2S)-2-({[4-(1-methyl-1H-1,2,3-triazol-5-yl)-2-thienyl]carbonyl}amino)-3-cyclolhexylpropyl]carbamate (50 mg, 0.11 mmol) for 1,1-dimethylethyl[(2S)-2-({[4-(1-methyl-1H-1,2,3-triazol-5-yl)-2-thienyl]carbonyl}amino)-3-phenylpropyl]carbamate. LCMS (ES) m/z 416.0/418.0 (M+H)$^+$, $^1$H NMR (400 MHz, METHANOL-d4) δ ppm 7.74 (s, 1H), 4.48 (m, 1H), 4.04 (s, 3H), 3.40-2.95 (m 2H), 1.90-0.95 (m, 13H).

Example 280

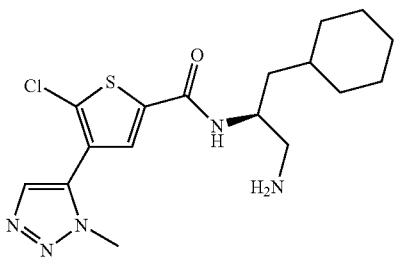 [SMILES: Cn1nncc1-c1cc(C(=O)N[C@H](CN)CC2CCCCC2)sc1Cl]

Preparation of N-[(1S)-2-amino-1-(cyclohexylmethyl)ethyl]-5-chloro-4-(1-methyl-1H-1,2,3-triazol-5-yl)-2-thiophenecarboxamide The title compound was prepared as a white solid according to the procedure of Example 269, except substituting 2-[(2S)-2-amino-3-cyclohexylpropyl]-1H-isoindole-1,3(2H)-dione for 2-{(2S)-2-amino-3-[3-(trifluoromethyl)phenyl]propyl}-1H-isoindole-1,3(2H)-dione. LCMS (ES) m/z 382.2 (M+H)⁺, ¹H NMR (400 MHz, METHANOL-d4) δ ppm 7.93 (s, 1H), 7.81 (m, 1H), 4.43 (m, 1H), 4.10 (s, 3H), 3.17 (m 1H), 3.05 (m, 1H), 2.00-0.90 (m, 13H).

Example 281

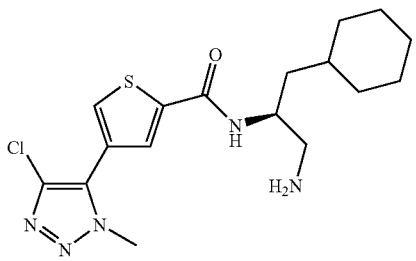 [SMILES: Cn1nnc(Cl)c1-c1csc(C(=O)N[C@H](CN)CC2CCCCC2)c1]

Preparation of N-[(1S)-2-amino-1-(cyclohexylmethyl)ethyl]-4-(4-chloro-1-methyl-1H-1,2,3-triazol-5-yl)-2-thiophenecarboxamide The title compound was prepared as an off white solid according to the procedure of 261, except substituting 1,1-dimethylethyl[(2S)-2-({[4-(1-methyl-1H-1,2,3-triazol-5-yl)-2-thienyl]carbonyl}amino)-3-cyclolhexylpropyl]carbamate (100 mg, 0.22 mmol) for 1,1-dimethylethyl[(2S)-2-({[4-(1-methyl-1H-1,2,3-triazol-5-yl)-2-thienyl]carbonyl}amino)-3-phenylpropyl]carbamate, and the amount of NCS was reduced to 1 eq. LCMS (ES) m/z 382.2 (M+H)⁺, ¹H NMR (400 MHz, METHANOL-d4) δ ppm 8.15 (d, J=1 Hz, 1H), 8.08 (d, J=1 Hz, 1H), 4.45 (m, 1H), 4.16 (s, 3H), 3.14 (m 1H), 3.05 (m, 1H), 2.00-0.90 (m, 13H).

Example 282

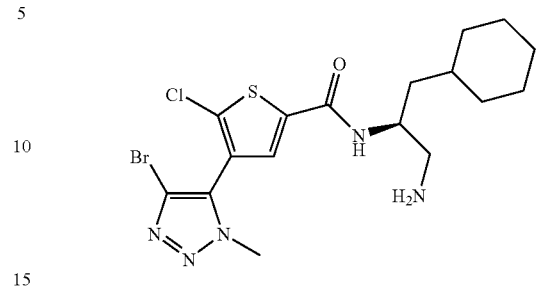

Preparation of N-[(1S)-2-amino-1-(cyclohexylmethyl)ethyl]-5-chloro-4-(4-bromo-1-methyl-1H-1,2,3-triazol-5-yl)-2-thiophenecarboxamide A solution of 1,1-dimethylethyl[(2S)-2-({[5-chloro-4-(1-methyl-1H-1,2,3-triazol-5-yl)-2-thienyl]carbonyl}amino)-3-cyclohexylpropyl]carbamate (140 mg, 0.29 mmol, prepared in Example 280) and NBS (103 mg, 0.58 mmol) in 2 mL of DMF was heated at 100° C. for 2 hours. The reaction mixture was purified by reverse phase HPLC (5-65% acetonitrile in H₂O with 1% TFA) to give the title compound 14.1 mg (8%) as a white solid. LCMS (ES) m/z 462.0 (M+H)⁺, ¹H NMR (400 MHz, METHANOL-d4) δ ppm 7.75 (s, 1H), 4.43 (m, 1H), 4.05 (s, 3H), 3.17 (m 1H), 3.05 (m, 1H), 2.00-0.90 (m, 13H).

Example 283

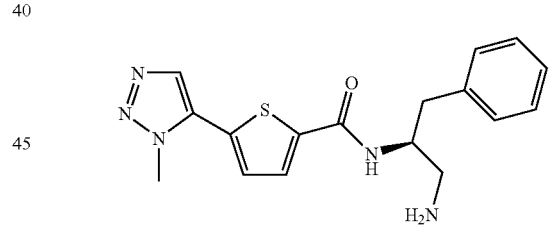

Preparation of N-[(1S)-2-amino-1-(phenylmethyl)ethyl]-5-(1-methyl-1H-1,2,3-triazol-5-yl)-2-thiophenecarboxamide The title compound was prepared as a white solid according to the procedure of Example 260, except substituting 1,1-dimethylethyl[(2S)-2-{[(5-bromo-2-thienyl)carbonyl]amino}-3-phenylpropyl]carbamate (270 mg, 0.62 mmol) for 1,1-dimethylethyl ((2S)-2-{[(4-bromo-2-thienyl)carbonyl]amino}-3-phenylpropyl)carbamate. LCMS (ES) m/z 342.2 (M+H)⁺, ¹H NMR (400 MHz, METHANOL-d4) δ ppm 7.96 (s, 1H), 7.75 (d, J=3.6 Hz, 1H), 7.47 (d, J=3.6 Hz, 1H), 7.31-7.22 (m, 5H), 4.55 (m, 1H), 4.21 (s, 3H), 3.20 (m, 2H) 2.99 (m, 2H).

Example 284

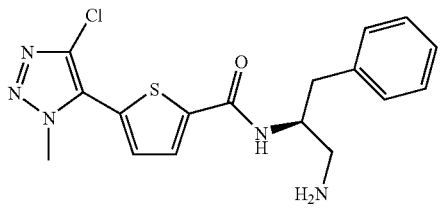 [SMILES: Cn1nnc(Cl)c1-c1ccc(C(=O)N[C@H](CN)Cc2ccccc2)s1]

Preparation of N-[(1S)-2-amino-1-(phenylmethyl)ethyl]-5-(4-chloro-1-methyl-1H-1,2,3-triazol-5-yl)-2-thiophenecarboxamide The title compound was prepared as a white solid according to the procedure of Example 261, except substituting 1,1-dimethylethyl[(2S)-2-({[5-(1-methyl-1H-1,2,3-triazol-5-yl)-2-thienyl]carbonyl}amino)-3-phenylpropyl]carbamate (68 mg, 0.15 mmol) for 1,1-dimethylethyl[(2S)-2-({[4-(1-methyl-1H-1,2,3-triazol-5-yl)-2-thienyl]carbonyl}amino)-3-phenylpropyl]carbamate. LCMS (ES) m/z 376.2 (M+H)$^+$, $^1$H NMR (400 MHz, METHANOL-d4) $\delta$ ppm 7.82 (m, 1H), 7.55 (d, J=3.6 Hz, 1H), 7.47 (d, J=3.6 Hz, 1H), 7.32-7.23 (m, 5H), 4.55 (m, 1H), 4.19 (s, 3H), 3.20 (m, 2H), 3.02 (m, 2H).

Example 285

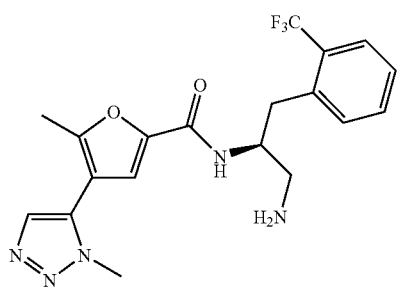 [SMILES: Cc1oc(C(=O)N[C@H](CN)Cc2ccccc2C(F)(F)F)cc1-c1cnnn1C]

Preparation of N-((1S)-2-amino-1-{[2-(trifluoromethyl)phenyl]methyl}ethyl)-5-methyl-4-(1-methyl-1H-1,2,3-triazol-5-yl)-2-furancarboxamide The title compound was prepared as an off-white solid according to the procedure of Example 269, except substituting methyl 4-bromo-5-methyl-2-furancarboxylate (ref. Bach, T.; Kruger, L. *Synlett* 1998, 1185-1186) for methyl 4-bromo-5-chloro-2-thiophenecarboxylate. LCMS (ES) m/z 408.2 (M+H)$^+$, $^1$H NMR (400 MHz, METHANOL-d4) $\delta$ ppm 8.09 (s, 1H), 7.71 (m, 1H), 7.55 (m, 2H), 7.43 (m, 2H), 4.68 (m, 1H), 4.13 (s, 3H), 3.25-3.15 (m, 4H), 2.48 (s, 3H).

Example 286

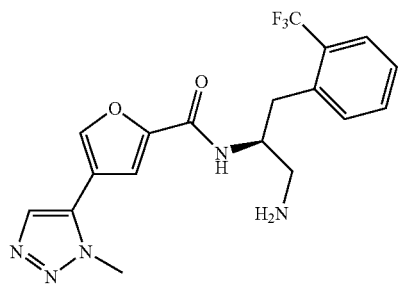 [SMILES: Cn1nncc1-c1coc(C(=O)N[C@H](CN)Cc2ccccc2C(F)(F)F)c1]

Preparation of N-((1S)-2-amino-1-{[2-(trifluoromethyl)phenyl]methyl}ethyl)-4-(1-methyl-1H-1,2,3-triazol-5-yl)-2-furancarboxamide The title compound was prepared as a white solid according to the procedure of Example 260, except substituting 1,1-dimethylethyl[(2S)-2-{[(4-bromo-2-furanyl)carbonyl]amino}-3-(2-(trifluoromethyl)phenyl)propyl]carbamate (200 mg, 0.4 mmol) for 1,1-dimethylethyl ((2S)-2-{[(4-bromo-2-thienyl)carbonyl]amino}-3-phenylpropyl)carbamate. LCMS (ES) m/z 394.2 (M+H)$^+$, $^1$H NMR (400 MHz, METHANOL-d4) $\delta$ ppm 8.23 (s, 1H), 7.93 (s, 1H), 7.71 (d, 1H), 7.54 (m, 2H), 7.43 (m, 2H), 4.75 (m, 1H), 4.18 (s, 3H), 3.30-3.10 (m, 4H).

Example 287

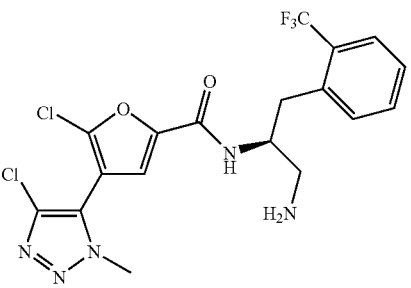 [SMILES: Cn1nnc(Cl)c1-c1cc(C(=O)N[C@H](CN)Cc2ccccc2C(F)(F)F)oc1Cl]

Preparation of N-((1S)-2-amino-1-{[2-(trifluoromethyl)phenyl]methyl}ethyl)-5-chloro-4-(4-chloro-1-methyl-1H-1,2,3-triazol-5-yl)-2-furancarboxamide The title compound was prepared as a white solid according to the procedure of Example 261, except substituting 1,1-dimethylethyl[(2S)-2-({[4-(1-methyl-1H-1,2,3-triazol-5-yl)-2-furanyl]carbonyl}amino)-3-(2-(trifluoromethyl)phenyl)propyl]carbamate (90 mg, 0.18 mmol) for 1,1-dimethylethyl [(2S)-2-({[4-(1-methyl-1H-1,2,3-triazol-5-yl)-2-thienyl]carbonyl}amino)-3-phenylpropyl]carbamate. LCMS (ES) m/z 462.0/464.0 (M+H)$^+$, $^1$H NMR (400 MHz, METHANOL-d4) $\delta$ ppm 7.73 (m, 1H), 7.56 (m, 2H), 7.45 (m, 1H), 7.40 (s, 1H), 4.75 (m, 1H), 4.05 (s, 3H), 3.30-3.10 (m, 4H).

Example 288

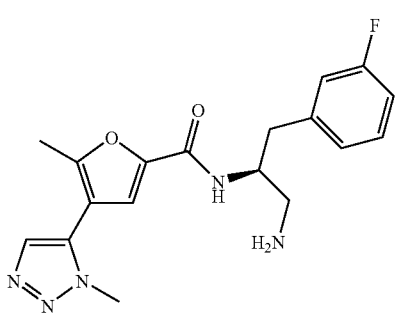 [SMILES: Cc1oc(C(=O)N[C@H](CN)Cc2cccc(F)c2)cc1-c1cnnn1C]

Preparation of N-((1S)-2-amino-1-{[3-fluorophenyl]methyl}ethyl)-5-methyl-4-(1-methyl-1H-1,2,3-triazol-5-yl)-2-furancarboxamide The title compound was prepared as an off-white solid according to the procedure of Example 269, except substituting methyl 4-bromo-5-methyl-2-furancarboxylate for methyl 4-bromo-5-chloro-2-thiophenecarboxylate and 2-{(2S)-2-amino-3-[3-fluorophenyl]propyl}-1H-isoindole-1,3(2H)-dione for 2-{(2S)-2-amino-3-[2-(trifluoromethyl)phenyl]propyl}-1H-isoindole-1,3(2H)-dione. LCMS (ES) m/z 358.2 (M+H)$^+$, $^1$H NMR (400 MHz, METHANOL-d4) δ ppm 8.47 (s, 1H), 7.44 (s, 1H), 7.35 (m, 1H), 7.15 (m, 2H), 6.96 (m, 1H), 4.65 (m, 1H), 4.22 (s, 3H), 3.25 (m, 2H), 3.04 (m, 2H), 2.49 (s, 3H).

Example 289

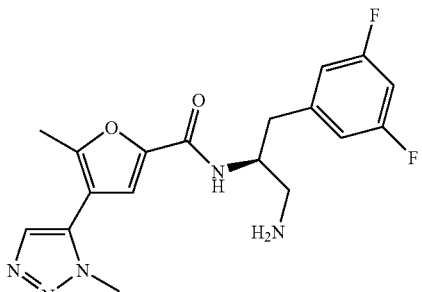

Preparation of N-((1S)-2-amino-1-{[3,5-difluorophenyl]methyl}ethyl)-5-methyl-4-(1-methyl-1H-1,2,3-triazol-5-yl)-2-furancarboxamide The title compound was prepared as an off-white solid according to the procedure of Example 269, except substituting methyl 4-bromo-5-methyl-2-furanocarboxylate for methyl 4-bromo-5-chloro-2-thiophenecarboxylate and 2-{(2S)-2-amino-3-[3,5-difluorophenyl]propyl}-1H-isoindole-1,3(2H)-dione for 2-{(2S)-2-amino-3-[2-(trifluoromethyl)phenyl]propyl}-1H-isoindole-1,3(2H)-dione. LCMS (ES) m/z 376.2 (M+H)$^+$, $^1$H NMR (400 MHz, METHANOL-d4) δ ppm 8.30 (s, 1H), 7.43 (s, 1H), 6.95 (m, 2H), 6.82 (m, 1H), 4.53 (m, 1H), 4.18 (s, 3H), 3.25 (m, 2H), 3.07 (m, 2H), 2.48 (s, 3H).

Example 290

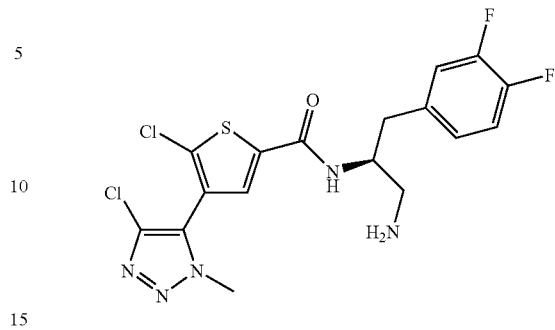

Preparation of N-{(1S)-2-amino-1-[(3,4-difluorophenyl)methyl]ethyl}-5-chloro-4-(4-chloro-1-methyl-1H-1,2,3-triazol-5-yl)-2-thiophenecarboxamide The title compound was prepared as a white solid according to the procedure of Example 261, except substituting N-{(1S)-2-(3,4-difluorophenyl)-1-[(1,3-dioxo-1,3-dihydro-2H-isoindol-2-yl)methyl]ethyl}-4-(1-methyl-1H-1,2,3-triazol-5-yl)-2-thiophenecarboxamide (prepared according to Example 263) for 1,1-dimethylethyl[(2S)-2-({[4-(1-methyl-1H-1,2,3-triazol-5-yl)-2-thienyl]carbonyl}amino)-3-phenylpropyl]carbamate and following Example 269 for deprotection. LCMS (ES) m/z 446.0/448.0 (M+H)$^+$, $^1$H NMR (400 MHz, METHANOL-d4) δ ppm 7.88 (s, 1H), 7.20-7.15 (m, 3H), 4.53 (m, 1H), 4.05 (s, 3H), 3.23 (m, 2H), 3.00 (m, 2H).

Example 291

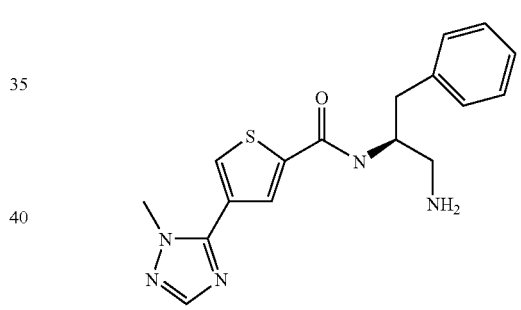

Preparation of N-[(1S)-2-amino-1-(phenylmethyl)ethyl]-4-(1-methyl-1H-1,2,4-triazol-5-yl)-2-thiophenecarboxamide a) 1,1-dimethylethyl[(2S)-2-({[4-(1-methyl-1H-1,2,4-triazol-5-yl)-2-thienyl]carbonyl}amino)-3-phenylpropyl]carbamate

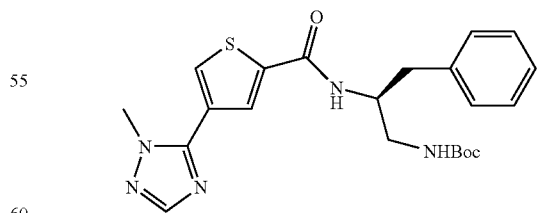

A suspension of 1,1-dimethylethyl ((2S)-2-{[(4-bromo-2-thienyl)carbonyl]amino}-3-phenylpropyl)carbamate (prepared according to preparation 22 except substituting 2-[(2S)-2-amino-3-phenylpropyl]-1H-isoindole-1,3(2H)-dione for 2-[(2S)-2-amino-3-(2,4-dichlorophenyl)propyl]-1H-isoindole-1,3(2H)-dione) (200 mg, 0.455 mmol), 5,5,5',5'-tetramethyl-2,2'-bi-1,3,2-dioxaborinane (123 mg, 0.546 mmol), potassium acetate (134 mg, 1.366 mmol), and PdCl$_2$(dppf)$_2$ (16.7 mg, 0.023 mmol) in dry THF (3 ml) was charged into a sealed tube and heated to 80° C. for one hour. 5-Iodo-1-methyl-1H-1,2,4-triazole (114 mg, 0.546 mmol), 2M sodium carbonate (0.34 ml, 0.683 mmol) and Pd(Ph$_3$P)$_4$ (26.3 mg, 0.023 mmol) were then added. The mixture was heated at 85° C. for 2 hours. The solvent was removed and the residue was purified by biotage (70% H/E) to give the title product (120 mg, 60%)

b) N-[(1S)-2-amino-1-(phenylmethyl)ethyl]-4-(1-methyl-1H-1,2,4-triazol-5-yl)-2-thiophenecarboxamide

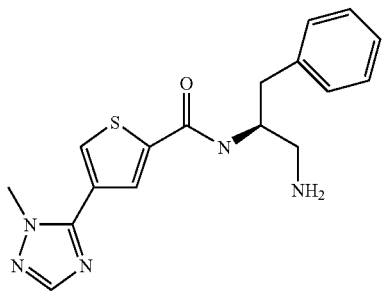 [SMILES: Cn1ncnc1-c1csc(C(=O)N[C@H](CN)Cc2ccccc2)c1]

TFA (1 ml) was added to a solution of 1,1-dimethylethyl [(2S)-2-({[4-(1-methyl-1H-1,2,4-triazol-5-yl)-2-thienyl] carbonyl}amino)-3-phenylpropyl]carbamate (100 mg, 0.226 mmol) in DCM (5 ml). The reaction was stirred at RT for 30 min. The solvent was removed and the residue was purified by reverse phase HPLC (10% org~60% org) to give the title compound as a white solid (90 mg, 87%). LC-MS (ES) m/z 342.2 (M+H)$^+$, $^1$H NMR (d$_4$-MeOH, 400 MHz) δ 8.23 (s, 1H), 8.03 (m, 2H), 7.22-7.31 (m, 5H), 4.60 (m, 1H), 4.08 (s, 3H), 3.10-3.20 (m, 2H), 3.00 (m, 2H).

Example 292

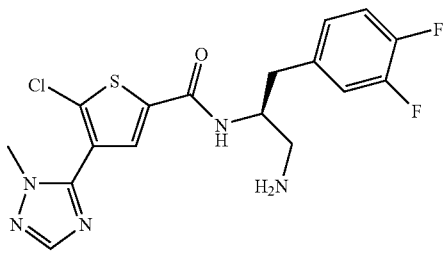 [SMILES: Cn1ncnc1-c1cc(C(=O)N[C@H](CN)Cc2ccc(F)c(F)c2)sc1Cl]

Preparation of N-{(1S)-2-amino-1-[(3,4-difluorophenyl)methyl]ethyl}-5-chloro-4-(1-methyl-1H-1,2,4-triazol-5-yl)-2-thiophenecarboxamide a) 1,1-dimethylethyl[(2S)-3-(3,4-difluorophenyl)-2-({[4-(1-methyl-1H-1,2,4-triazol-5-yl)-2-thienyl] carbonyl}amino)propyl]carbamate

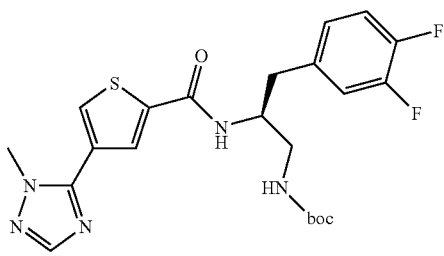

This intermediate was prepared according to the procedure of Example 291 a) except substituting 1,1-dimethylethyl [(2S)-2-{[(4-bromo-2-thienyl)carbonyl]amino}-3-(3,4-difluorophenyl)propyl]carbamate for 1,1-dimethylethyl ((2S)-2-{[(4-bromo-2-thienyl)carbonyl]amino}-3-phenylpropyl) carbamate. LC-MS (ES) m/z=478.2 (M+H)$^+$ b) N-{(1S)-2-amino-1-[(3,4-difluorophenyl)methyl] ethyl}-5-chloro-4-(1-methyl-1H-1,2,4-triazol-5-yl)-2-thiophenecarboxamide A solution of 1,1-dimethylethyl[(2S)-3-(3,4-difluorophenyl)-2-({[4-(1-methyl-1H-1,2,4-triazol-5-yl)-2-thienyl] carbonyl}amino)propyl]carbamate (279 mg, 0.497 mmol) and NCS (133 mg, 0.993 mmol) in N,N-Dimethylformamide (DMF) (3 ml) was heated at 110° C. for 1 hr. The crude reaction mixture was concentrated and the residue was purified by flash column chromatography on silica gel (DCM: MeOH:NH$_4$OH 9:1:1) to give the product as a free base, which was treated with 0.13 mL of 2N HCl aq. (2 eq.) to give 75 mg of HCl salt as an off-white solid. LC-MS (ES) m/z=412 (M+H)$^+$, $^1$H NMR (CD$_3$OD, 400 MHz) δ 8.80 (s, 1H), 8.18 (s, 1H), 7.3-7.1 (m, 3H), 4.54 (m, 1H), 4.11 (s, 3H), 3.26 (d, J=7 Hz, 2H), 3.03 (d, J=8 Hz, 2H).

Example 293

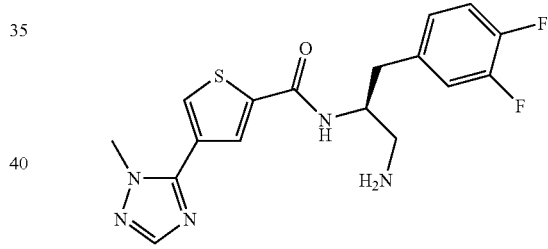

Preparation of N-{(1S)-2-amino-1-[(3,4-difluorophenyl)methyl]ethyl}-4-(1-methyl-1H-1,2,4-triazol-5-yl)-2-thiophenecarboxamide The title compound was prepared an off-white solid according to the procedure of Example 291 except substituting 1,1-dimethylethyl[(2S)-2-{[(4-bromo-2-thienyl)carbonyl]amino}-3-(3,4-difluorophenyl)propyl]carbamate for 1,1-dimethylethyl ((2S)-2-{[(4-bromo-2-thienyl)carbonyl] amino}-3-phenylpropyl)carbamate. The final product was purified by flash column chromatography on silica gel (DCM: MeOH:NH$_4$OH 9:1:1) to give a free base, which was treated with 2N HCl aq. solution to give the HCl salt. LC-MS (ES) m/z=378 (M+H)$^+$, $^1$H NMR (CD$_3$OD, 400 MHz) δ 8.78 (s, 1H), 8.50 (d, J=2 Hz, 1H), 8.36 (d, J=2 Hz, 1H), 7.3-7.1 (m, 3H), 4.57 (m, 1H), 4.23 (s, 3H), 3.27 (d, J=8 Hz, 2H), 3.04 (d, J=8 Hz, 2H).

Example 294

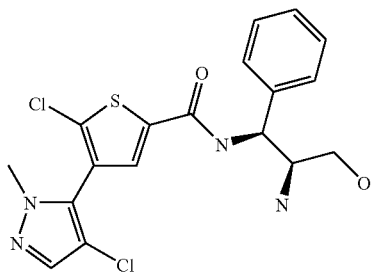 [SMILES: Cn1ncc(Cl)c1-c1cc(C(=O)N[C@@H](c2ccccc2)[C@H](N)CO)sc1Cl]

Preparation of N-[(1S,2S)-2-amino-3-hydroxy-1-phenylpropyl]-5-chloro-4-(4-chloro-1-methyl-1H-pyrazol-5-yl)-2-thiophenecarboxamide a) 1,1-dimethylethyl[(1S,2S)-2-amino-1-({[(1,1-dimethylethyl)(dimethyl)silyl]oxy}methyl)-2-phenylethyl]carbamate

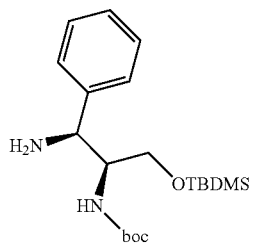

The title compound was prepared according to Preparation 1 except substituting 1,1-dimethylethyl[(1R,2R)-1-({[(1,1-dimethylethyl)(dimethyl)silyl]oxy}methyl)-2-hydroxy-2-phenylethyl]carbamate (ref. Veeresa, G.; Datta, Apurba. *Stereoselective synthesis of chloramphenicol from D-serine*. Tetrahedron Letters (1998), 39(46), 8503-8504.) for 1,1-dimethylethyl (2-hydroxy-2-phenylethyl)carbamate.

b) N-[(1S,2S)-2-amino-3-hydroxy-1-phenylpropyl]-5-chloro-4-(4-chloro-1-methyl-1H-pyrazol-5-yl)-2-thiophenecarboxamide This intermediate was prepared according to the procedures of Example 261, except substituting 1,1-dimethylethyl [(1S,2S)-2-amino-1-({[(1,1-dimethylethyl)(dimethyl)silyl]oxy}methyl)-2-phenylethyl]carbamate for 1,1-dimethylethyl (2-amino-2-phenylethyl)carbamate. LC-MS (ES) m/z=425.0/427.0 (M+H)+, 1H NMR (CD3OD, 400 MHz) δ 7.86 (s, 1H), 7.59 (s, 1H), 7.56-7.38 (m, 5H), 5.50 (m, 1H), 3.91-3.84 (m, 3H).

Example 295

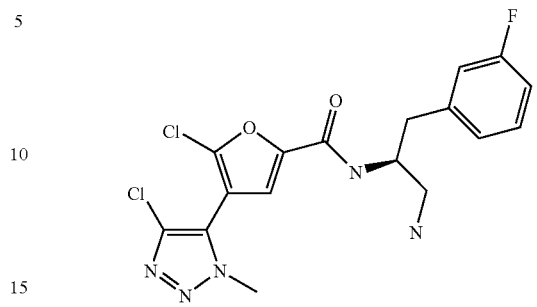

Preparation of N-{(1S)-2-amino-1-[(3-fluorophenyl)methyl]-ethyl}-5-chloro-4-(4-chloro-1-methyl-1H-1,2,3-triazol-5-yl)-2-furancarboxamide a) Methyl 4-bromo-5-chloro-2-furancarboxylate

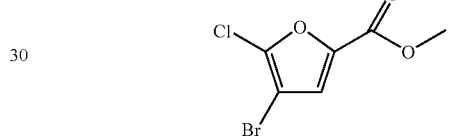

Isopropylmagnesium chloride (1.20 ml, 2.40 mmol) was added dropwise to a solution of methyl 4,5-dibromo-2-furancarboxylate (568 mg, 2.0 mmol) in Tetrahydrofuran (THF) (16 ml) at 0° C. The resulting mixture was stirred at this temperature for 30 min and then cooled to −78° C. A solution of hexylchloroethane (568 mg, 2.401 mmol) in THF (1 mL) was added dropwise, and the resulting mixture was stirred at this temperature for 1 hr. The reaction was quenched with addition of NH4Cl (sat. aq) and the resulting mixture was stirred at rt overnight. Ether and water were added and the aqueous layer was discarded. The organic layer was washed with brine, dried (Na2SO4) and concentrated to give 0.34 g of the product containing its isopropyl ester.

b) N-{(1S)-2-amino-1-[(3-fluorophenyl)methyl]ethyl}-5-chloro-4-(4-chloro-1-methyl-1H-1,2,3-triazol-5-yl)-2-furancarboxamide The title compound was prepared according to the procedure of Example 273, except substituting methyl 4-bromo-5-chloro-2-furancarboxylate for methyl 4-bromo-2-thiophenecarboxylate, and substituting 2-[(2S)-2-amino-3-(3-fluorophenyl)propyl]-1H-isoindole-1,3(2H)-dione for 2-{(2S)-2-amino-3-[2-(trifluoromethyl)phenyl]propyl}-1H-isoindole-1,3(2H)-dione. The final product was purified by RP-HPLC and converted to HCl salt with 2N HCl aqueous solution. LC-MS (ES) m/z=412.0/414.0 (M+H)+, 1H NMR (CD3OD, 400 MHz) δ 7.44 (s, 1H), 7.33 (m, 1H), 7.14-7.07 (m, 2H), 6.98 (m, 1H), 4.55 (m, 1H), 4.05 (s, 3H), 3.25-2.98 (m, 4H).

Example 296

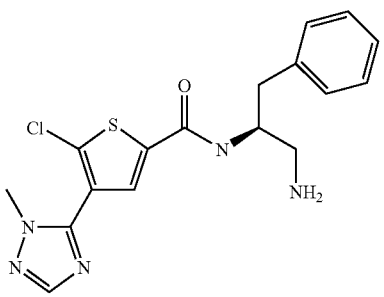 [SMILES: Cn1ncnc1-c1cc(C(=O)N[C@H](CN)Cc2ccccc2)sc1Cl]

Preparation of N-[(1S)-2-amino-1-(phenylmethyl)ethyl]-5-chloro-4-(1-methyl-1H-1,2,4-triazol-5-yl)-2-thiophenecarboxamide

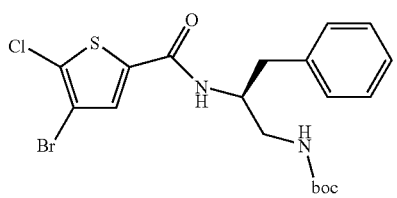

a) 1,1-dimethylethyl ((2S)-2-{[(4-bromo-5-chloro-2-thienyl)carbonyl]amino}-3-phenylpropyl)carbamate A solution of 1,1-dimethylethyl ((2S)-2-{[(4-bromo-2-thienyl)carbonyl]amino}-3-phenylpropyl)carbamate (prepared according to Preparation 22), except substituting 2-[(2S)-2-amino-3-phenylpropyl]-1H-isoindole-1,3(2H)-dione for 2-[(2S)-2-amino-3-(2,4-dichlorophenyl)propyl]-1H-isoindole-1,3(2H)-dione (200 mg, 0.455 mmol) and NCS (61 mg, 0.455 mmol) in DMF (3 ml) was heated at 50° C. in a sealed tube for 2 hours. The solvent was removed and the residue was purified by biotage (30% Hex/EtOAc) to give the title product (140 mg, 65%).

b) N-[(1S)-2-amino-1-(phenylmethyl)ethyl]-5-chloro-4-(1-methyl-1H-1,2,4-triazol-5-yl)-2-thiophenecarboxamide The title compound was prepared as a white solid according the procedure of Example 291, except substituting 1,1-dimethylethyl ((2S)-2-{[(4-bromo-5-chloro-2-thienyl)carbonyl]amino}-3-phenylpropyl)carbamate for 1,1-dimethylethyl ((2S)-2-{[(4-bromo-2-thienyl)carbonyl]amino}-3-phenylpropyl)carbamate. LC-MS (ES) m/z 376.2 (M+H)$^+$, $^1$H NMR (d$_4$-MeOH, 400 MHz) δ 8.12 (s, 1H), 7.74 (s, 1H), 7.31-7.35 (m, 5H), 4.58 (m, 1H), 3.94 (s, 3H), 3.35 (m, 2H), 3.05 (m, 2H).

Example 297

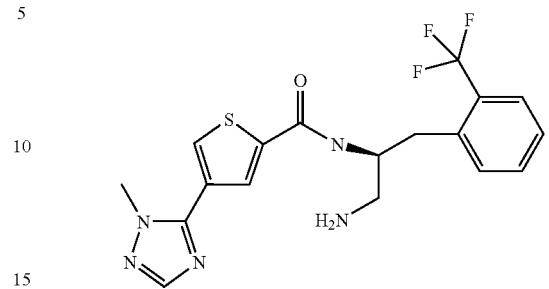

Preparation of N-((1S)-2-amino-1-{[2-(trifluoromethyl)phenyl]methyl}ethyl)-4-(1-methyl-1H-1,2,4-triazol-5-yl)-2-thiophenecarboxamide The title compound was prepared as a white solid according to the procedure of Example 291, except substituting 1,1-dimethylethyl {(2S)-2-{[(4-bromo-2-thienyl)carbonyl]amino}-3-[2-(trifluoromethyl)phenyl]propyl}-carbamate for 1,1-dimethylethyl ((2S)-2-{[(4-bromo-2-thienyl)carbonyl]amino}-3-phenylpropyl)carbamate; LC-MS (ES) m/z 410.2 (M+H)$^+$, $^1$H NMR (d$_4$-MeOH, 400 MHz) δ 8.33 (m, 2H), 7.73 (m, 1H), 7.41-7.56 (m, 4H), 4.70 (m, 1H), 4.13 (s, 3H), 3.36 (m, 2H), 3.18 (m, 2H).

Example 298

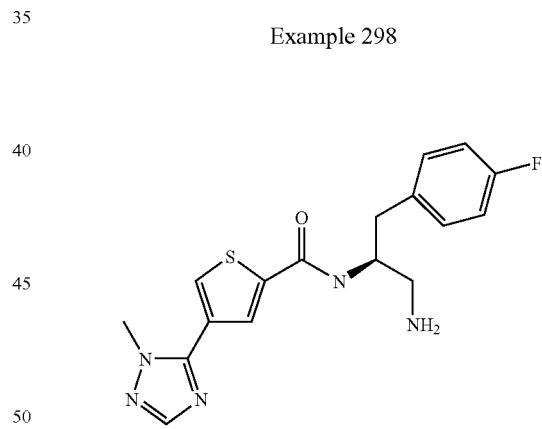

Preparation of N-{(1S)-2-amino-1-[(4-fluorophenyl)methyl]ethyl}-4-(1-methyl-1H-1,2,4-triazol-5-yl)-2-thiophenecarboxamide The title compound was prepared as a white solid according to the procedure of Example 291, except substituting 1,1-dimethylethyl[(2S)-2-{[(4-bromo-2-thienyl)carbonyl]amino}-3-(4-fluorophenyl)propyl]carbamate for 1,1-dimethylethyl ((2S)-2-{[(4-bromo-2-thienyl)carbonyl]amino}-3-phenylpropyl)carbamate. LC-MS (ES) m/z 360.2 (M+H)$^+$, $^1$H NMR (d$_4$-MeOH, 400 MHz) δ 8.24 (s, 1H), 8.06 (m, 2H), 7.29-7.34 (m, 2H), 7.01-7.05 (m, 2H), 4.66 (m, 1H), 4.08 (s, 3H), 3.23 (m, 2H), 3.15 (m, 2H).

Example 299

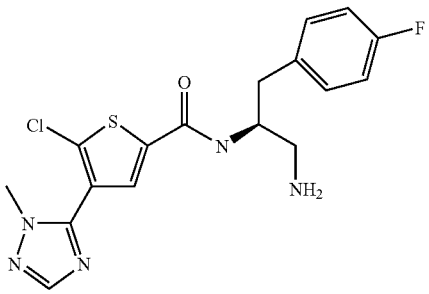 [SMILES: Cn1ncnc1-c1cc(C(=O)N[C@H](CN)Cc2ccc(F)cc2)sc1Cl]

Preparation of N-{(1S)-2-amino-1-[(4-fluorophenyl)methyl]ethyl}-5-chloro-4-(1-methyl-1H-1,2,4-triazol-5-yl)-2-thiophenecarboxamide The title compound was prepared as a white solid according to the procedure of Example 292, except substituting 1,1-dimethylethyl[(2S)-2-{[(4-bromo-2-thienyl)carbonyl]amino}-3-(4-fluorophenyl)propyl]carbamate for 1,1-dimethylethyl [(2S)-2-{[(4-bromo-2-thienyl)carbonyl]amino}-3-(3,4-difluorophenyl)propyl]carbamate. The final compound was purified by RP-HPLC to give the title compound as a white solid. LC-MS (ES) m/z 394.2 (M+H)$^+$, $^1$H NMR (d$_4$-MeOH, 400 MHz) δ 8.10 (s, 1H), 7.70 (s, 1H), 7.28-7.31 (m, 2H), 7.01-7.06 (m, 2H), 4.56 (m, 1H), 3.92 (s, 3H), 3.21 (m, 2H), 2.96 (m, 2H).

Example 300

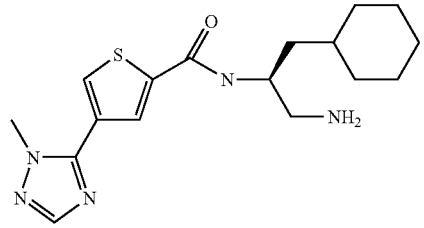 [SMILES: Cn1ncnc1-c1csc(C(=O)N[C@H](CN)CC2CCCCC2)c1]

Preparation of N-[(1S)-2-amino-1-(cyclohexylmethyl)ethyl]-4-(1-methyl-1H-1,2,4-triazol-5-yl)-2-thiophenecarboxamide The title compound was prepared as a white solid according to the procedure of Example 291, except substituting 1,1-dimethylethyl ((2S)-2-{[(4-bromo-2-thienyl)carbonyl]amino}-3-cyclohexylpropyl)carbamate for 1,1-dimethylethyl ((2S)-2-{[(4-bromo-2-thienyl)carbonyl]amino}-3-phenylpropyl)carbamate. LC-MS (ES) m/z 348.2 (M+H)$^+$, $^1$H NMR (d$_4$-MeOH, 400 MHz) δ 8.27 (m, 1H), 8.13 (s, 1H), 8.02 (s, 1H), 4.56 (m, 1H), 4.11 (s, 3H), 3.16 (m, 1H), 3.02 (m, 1H), 1.17-1.95 (m, 13H)

Example 301

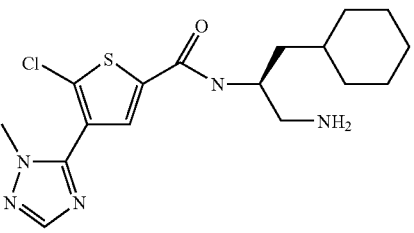 [SMILES: Cn1ncnc1-c1cc(C(=O)N[C@H](CN)CC2CCCCC2)sc1Cl]

Preparation of N-[(1S)-2-amino-1-(cyclohexylmethyl)ethyl]-5-chloro-4-(1-methyl-1H-1,2,4-triazol-5-yl)-2-thiophenecarboxamide The title compound was prepared as a white solid according to the procedure of Example 292, except substituting 1,1-dimethylethyl ((2S)-2-{[(4-bromo-2-thienyl)carbonyl]amino}-3-cyclohexylpropyl)carbamate for 1,1-dimethylethyl[(2S)-2-{[(4-bromo-2-thienyl)carbonyl]amino}-3-(3,4-difluorophenyl)propyl]carbamate. The final compound was purified by RP-HPLC to give the title compound as a white solid. LC-MS (ES) m/z 382.2 (M+H)$^+$, $^1$H NMR (d$_4$-MeOH, 400 MHz) δ 8.10 (s, 1H), 7.82 (s, br, 1H), 4.42 (m, 1H), 3.94 (s, 3H), 3.16-3.30 (m, 1H), 2.98-3.10 (m, 1H), 1.06-1.96 (m, 13H)

Example 302

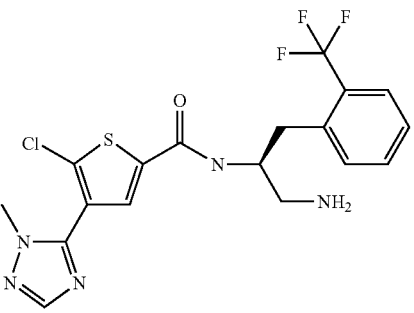 [SMILES: Cn1ncnc1-c1cc(C(=O)N[C@H](CN)Cc2ccccc2C(F)(F)F)sc1Cl]

Preparation of N-((1S)-2-amino-1-{[2-(trifluoromethyl)phenyl]methyl}ethyl)-5-chloro-4-(1-methyl-1H-1,2,4-triazol-5-yl)-2-thiophenecarboxamide The title compound was prepared as a white solid according to the procedure of Example 292, except substituting 1,1-dimethylethyl {(2S)-2-{[(4-bromo-2-thienyl)carbonyl]amino}-3-[2-(trifluoromethyl)phenyl]propyl}carbamate for 1,1-dimethylethyl[(2S)-2-{[(4-bromo-2-thienyl)carbonyl]amino}-3-(3,4-difluorophenyl)propyl]carbamate; The final compound was purified by RP-HPLC to give the title compound as a white solid. LC-MS (ES) m/z 444.0 (M+H)$^+$, $^1$H NMR (d$_4$-MeOH, 400 MHz) δ 8.20 (s, br, 1H), 7.86 (s, br, 1H), 7.71 (m, 1H), 7.42-7.56 (m, 3H), 4.63 (m, 1H), 3.96 (s, 3H), 3.09-3.27 (m, 4H).

Example 303

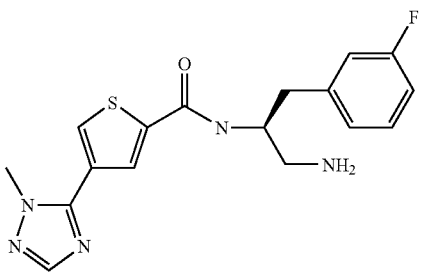 [SMILES: Cn1ncnc1-c1csc(C(=O)N[C@H](CN)Cc2cccc(F)c2)c1]

Preparation of N-{(1S)-2-amino-1-[(3-fluorophenyl)methyl]ethyl}-4-(1-methyl-1H-1,2,4-triazol-5-yl)-2-thiophenecarboxamide The title compound was prepared as a white solid according to the procedure of Example 291, except substituting 1,1-dimethylethyl[(2S)-2-{[(4-bromo-2-thienyl)carbonyl]amino}-3-(3-fluorophenyl)propyl]carbamate for 1,1-dimethylethyl ((2S)-2-{[(4-bromo-2-thienyl)carbonyl]amino}-3-phenylpropyl)carbamate; LC-MS (ES) m/z 360.2 (M+H)$^+$, $^1$H NMR (d$_4$-MeOH, 400 MHz) δ 8.24 (s, 1H), 8.02 (m, 2H), 7.30 (m, 1H) 7.06-7.13 (m, 2H), 6.96 (m, 1H), 4.63 (m, 1H), 4.08 (s, 3H), 3.09-3.27 (m, 4H).

Example 304

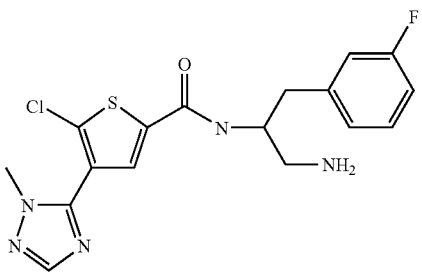 [SMILES: Cn1ncnc1-c1cc(C(=O)NC(CN)Cc2cccc(F)c2)sc1Cl]

Preparation of N-{(1S)-2-amino-1-[(3-fluorophenyl)methyl]ethyl}-5-chloro-4-(1-methyl-1H-1,2,4-triazol-5-yl)-2-thiophenecarboxamide The title compound was prepared as a white solid according to the procedure of Example 292, except substituting 1,1-dimethylethyl[(2S)-2-{[(4-bromo-2-thienyl)carbonyl]amino}-3-(3-fluorophenyl)propyl]carbamate for 1,1-dimethylethyl [(2S)-2-{[(4-bromo-2-thienyl)carbonyl]amino}-3-(3,4-difluorophenyl)propyl]carbamate; The final compound was purified by RP-HPLC to give the title compound as a white solid. LC-MS (ES) m/z 394.0 (M+H)$^+$, $^1$H NMR (d$_4$-MeOH, 400 MHz) δ 8.10 (s, 1H), 7.70 (s, 1H), 7.31 (m, 1H), 6.97-7.11 (m, 3H), 4.52 (m, 1H), 3.92 (s, 3H), 2.96-3.26 (m, 4H)

Example 305

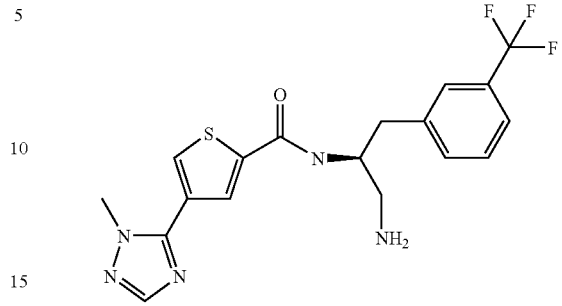

Preparation of N-((1S)-2-amino-1-{[3-(trifluoromethyl)phenyl]methyl}ethyl)-4-(1-methyl-1H-1,2,4-triazol-5-yl)-2-thiophenecarboxamide The title compound was prepared as a white solid according to Example 291, except substituting 1,1-dimethylethyl {(2S)-2-{[(4-bromo-2-thienyl)carbonyl]amino}-3-[3-(trifluoromethyl)phenyl]propyl}carbamate for 1,1-dimethylethyl ((2S)-2-{[(4-bromo-2-thienyl)carbonyl]amino}-3-phenylpropyl)carbamate; The final compound was purified by RP-HPLC, and converted to HCl salt with 2N HCl aqueous solution. LC-MS (ES) m/z 410.2 (M+H)$^+$, $^1$H NMR (d$_4$-MeOH, 400 MHz) δ 8.81 (s, 1H), 8.51 (d, J=1 Hz, 1H), 8.39 (d, J=1 Hz, 1H), 7.64 (m, 2H), 7.50 (m, 2H), 4.66 (m, 1H), 4.23 (s, 3H), 3.30 (m, 2H), 3.15 (m, 2H).

Example 306

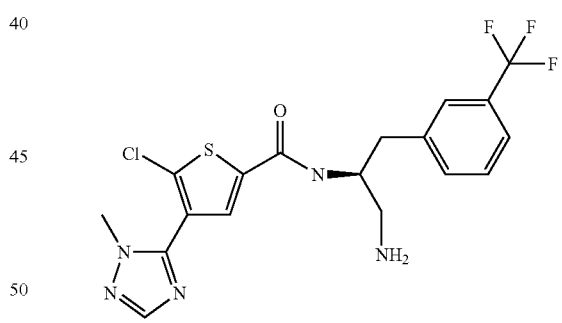

Preparation of N-((1S)-2-amino-1-{[3-(trifluoromethyl)phenyl]methyl}ethyl)-5-chloro-4-(1-methyl-1H-1,2,4-triazol-5-yl)-2-thiophenecarboxamide The title compound was prepared as a white solid according to Example 292, except substituting 1,1-dimethylethyl {(2S)-2-{[(4-bromo-2-thienyl)carbonyl]amino}-3-[3-(trifluoromethyl)phenyl]propyl}carbamate for 1,1-dimethylethyl [(2S)-2-{[(4-bromo-2-thienyl)carbonyl]amino}-3-(3,4-difluorophenyl)propyl]carbamate. The final compound was purified by RP-HPLC, and converted to HCl salt with 2N HCl aqueous solution. LC-MS (ES) m/z 440.0 (M+H)$^+$, $^1$H NMR (d$_4$-MeOH, 400 MHz) δ 8.53 (s, 1H), 8.02 (s, 1H), 7.50-7.64 (m, 4H), 4.56 (m, 1H), 4.03 (s, 3H), 3.10-3.27 (m, 4H).

Example 307

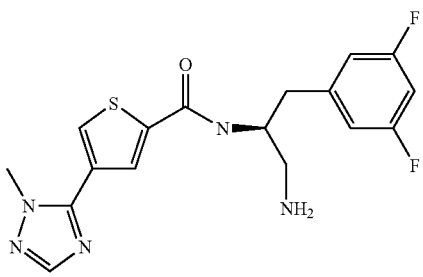 [SMILES: Cn1ncnc1-c1csc(C(=O)N[C@H](CN)Cc2cc(F)cc(F)c2)c1]

Preparation of N-{(1S)-2-amino-1-[(3,5-difluorophenyl)methyl]ethyl}-4-(1-methyl-1H-1,2,4-triazol-5-yl)-2-thiophenecarboxamide The title compound was prepared as a white solid according to Example 291, except substituting 1,1-dimethylethyl [(2S)-2-{[(4-bromo-2-thienyl)carbonyl]amino}-3-(3,5-difluorophenyl)propyl]carbamate for 1,1-dimethylethyl ((2S)-2-{[(4-bromo-2-thienyl)carbonyl]amino}-3-phenylpropyl)carbamate; The final compound was purified by RP-HPLC, and converted to HCl salt with 2N HCl aqueous solution. LC-MS (ES) m/z 378.2 (M+H)$^+$, $^1$H NMR (d$_4$-MeOH, 400 MHz) δ 8.68 (s, 1H), 8.47 (d, J=1 Hz, 1H), 8.35 (d, J=1 Hz, 1H), 6.96 (m, 2H), 6.80 (m, 1H), 4.60 (m, 1H), 4.21 (s, 3H), 3.28 (m, 2H), 3.08 (m, 2H).

Example 308

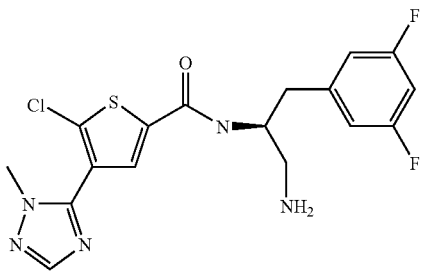 [SMILES: Cn1ncnc1-c1cc(C(=O)N[C@H](CN)Cc2cc(F)cc(F)c2)sc1Cl]

Preparation of N-{(1S)-2-amino-1-[(3,5-difluorophenyl)methyl]ethyl}-5-chloro-4-(1-methyl-1H-1,2,4-triazol-5-yl)-2-thiophenecarboxamide The title compound was prepared as a white solid according to Example 292, except substituting 1,1-dimethylethyl [(2S)-2-{[(4-bromo-2-thienyl)carbonyl]amino}-3-(3,5-difluorophenyl)propyl]carbamate for 1,1-dimethyl ethyl [(2S)-2-{[(4-bromo-2-thienyl)carbonyl]amino}-3-(3,4-difluorophenyl)propyl]carbamate; The final compound was purified by RP-HPLC, and converted to HCl salt with 2N HCl aqueous solution. LC-MS (ES) m/z 412.0 (M+H)$^+$, $^1$H NMR (d$_4$-MeOH, 400 MHz) δ 8.44 (s, 1H), 7.98 (s, 1H), 6.96 (m, 2H), 6.82 (m, 1H), 4.66 (m, 1H), 4.01 (s, 3H), 3.20-3.25 (m, 2H), 3.02-3.05 (m, 2H).

Example 309

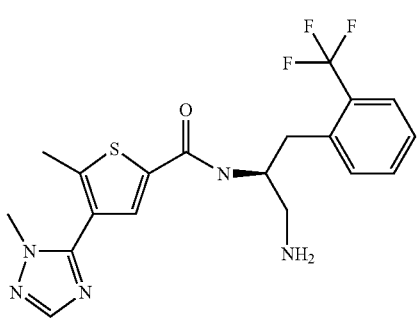 [SMILES: Cc1sc(C(=O)N[C@H](CN)Cc2ccccc2C(F)(F)F)cc1-c1ncnn1C]

Preparation of N-((1S)-2-amino-1-{[2-(trifluoromethyl)phenyl]methyl}ethyl)-5-methyl-4-(1-methyl-1H-1,2,4-triazol-5-yl)-2-thiophenecarboxamide a) 1,1-dimethylethyl {(2S)-2-{[(4-bromo-5-methyl-2-thienyl)carbonyl]amino}-3-[2-(trifluoromethyl)phenyl]propyl}carbamate

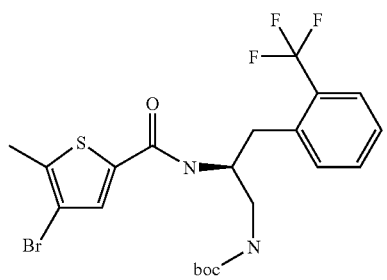

This intermediate was prepared according to Preparation 22, except substituting 4-bromo-5-methyl-2-thiophenecarboxylic acid (Bioorganic & Medicinal Chemistry Letters (2002), 12(3), 491-495) for 4-bromo-2-thiophenecarboxylic acid, and substituting 2-{(2S)-2-amino-3-[2-(trifluoromethyl)phenyl]propyl}-1H-isoindole-1,3(2H)-dione for 2-[(2S)-2-amino-3-(2,4-dichlorophenyl)propyl]-1H-isoindole-1,3(2H)-dione.

b) N-((1S)-2-amino-1-{[2-(trifluoromethyl)phenyl]methyl}ethyl)-5-methyl-4-(1-methyl-1H-1,2,4-triazol-5-yl)-2-thiophenecarboxamide The title compound was prepared as a white solid according to the procedure of Example 291, except substituting 1,1-dimethylethyl {(2S)-2-{[(4-bromo-5-methyl-2-thienyl)carbonyl]amino}-3-[2-(trifluoromethyl)phenyl]propyl}carbamate for 1,1-dimethylethyl ((2S)-2-{[(4-bromo-2-thienyl)carbonyl]amino}-3-phenylpropyl)carbamate: The final compound was purified by RP-HPLC, and converted to HCl salt with 2N HCl aqueous solution. LC-MS (ES) m/z 424.2 (M+H)$^+$, $^1$H NMR (d$_4$-MeOH, 400 MHz) δ 8.68 (s, 1H), 8.04 (s, 1H), 7.70 (m, 1H), 7.58 (m, 1H), 7.52 (m, 1H), 7.43 (m, 1H), 4.65 (m, 1H), 4.05 (s, 3H), 3.16-3.28 (m, 4H), 2.59 (s, 3H)

Example 310

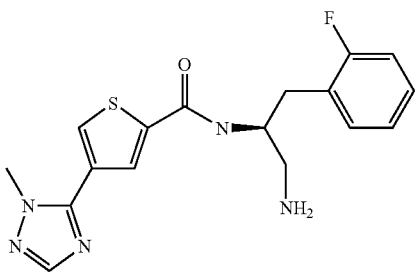 [SMILES: Cn1ncnc1-c1csc(C(=O)N[C@H](CN)Cc2ccccc2F)c1]

Preparation of N-{(1S)-2-amino-1-[(2-fluorophenyl)methyl]ethyl}-4-(1-methyl-1H-1,2,4-triazol-5-yl)-2-thiophenecarboxamide The title compound was prepared as a white solid according to the procedure of Example 291, except substituting 1,1-dimethylethyl[(2S)-2-{[(4-bromo-2-thienyl)carbonyl]amino}-3-(2-fluorophenyl)propyl]carbamate for 1,1-dimethylethyl ((2S)-2-{[(4-bromo-2-thienyl)carbonyl]amino}-3-phenylpropyl)carbamate; LC-MS (ES) m/z 360.2 (M+H)$^+$, $^1$H NMR (d$_4$-MeOH, 400 MHz) δ 8.60 (s, 1H), 8.43 (d, J=1 Hz, 1H), 8.24 (d, J=1 Hz, 1H), 7.37 (m, 1H), 7.27 (m, 1H), 7.08 (m, 2H), 4.66 (m, 1H), 4.19 (s, 3H), 3.27 (m, 2H), 3.10 (s, 2H)

Example 311

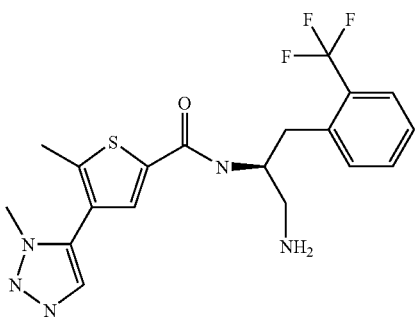 [SMILES: Cc1sc(C(=O)N[C@H](CN)Cc2ccccc2C(F)(F)F)cc1C1=CNNN1C]

Preparation of N-((1S)-2-amino-1-{[2-(trifluoromethyl)phenyl]methyl}ethyl)-5-methyl-4-(1-methyl-1H-1,2,3-triazol-5-yl)-2-thiophenecarboxamide The title compound was prepared as a white solid according to the procedure of Example 260, except substituting 1,1-dimethylethyl {(2S)-2-{[(4-bromo-5-methyl-2-thienyl)carbonyl]amino}-3-[2-(trifluoromethyl)phenyl]propyl}carbamate for 1,1-dimethylethyl ((2S)-2-{[(4-bromo-2-thienyl)carbonyl]amino}-3-phenylpropyl)carbamate. The final compound was purified by RP-HPLC, and converted to HCl salt with 2N HCl aqueous solution. LC-MS (ES) m/z 360.2 (M+H)$^+$, $^1$H NMR (d$_4$-MeOH, 400 MHz) δ 8.31 (s, 1H), 7.94 (s, 1H), 7.70 (m, 1H), 7.56 (m, 2H), 7.43 (m, 1H), 4.65 (m, 1H), 4.19 (s, 3H), 3.15-3.28 (m, 4H), 2.50 (s, 3H).

Example 312

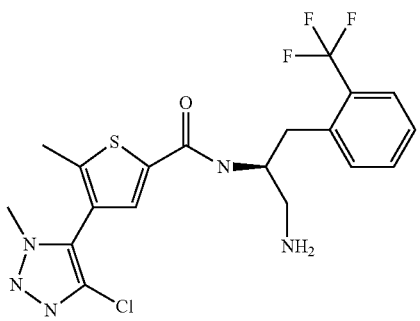 [SMILES: Cc1sc(C(=O)N[C@H](CN)Cc2ccccc2C(F)(F)F)cc1C1=C(Cl)NNN1C]

Preparation of N-((1S)-2-amino-1-{[2-(trifluoromethyl)phenyl]methyl}ethyl)-4-(4-chloro-1-methyl-1H-1,2,3-triazol-5-yl)-5-methyl-2-thiophenecarboxamide The title compound was prepared as a white solid according to Example 261, except substituting 1,1-dimethylethyl {(2S)-2-{[(4-bromo-5-methyl-2-thienyl)carbonyl]amino}-3-[2-(trifluoromethyl)phenyl]propyl}carbamate for 1,1-dimethylethyl ((2S)-2-{[(4-bromo-2-thienyl)carbonyl]amino}-3-phenylpropyl)carbamate. The final compound was purified by RP-HPLC, and converted to HCl salt with 2N HCl aqueous solution. LC-MS (ES) m/z 458.0 (M+H)$^+$, $^1$H NMR (d$_4$-MeOH, 400 MHz) δ 7.70 (m, 2H), 7.55 (m, 2H), 7.44 (m, 1H), 4.67 (m, 1H), 3.99 (s, 3H), 3.12-3.21 (m, 4H), 2.42 (s, 3H).

Example 313

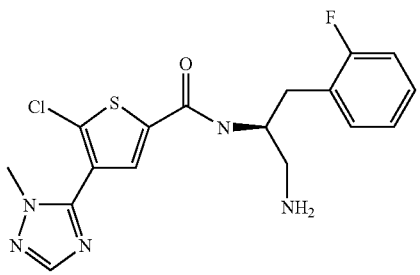 [SMILES: Cn1ncnc1-c1cc(C(=O)N[C@H](CN)Cc2ccccc2F)sc1Cl]

Preparation of N-{(1S)-2-amino-1-[(2-fluorophenyl)methyl]ethyl}-5-chloro-4-(1-methyl-1H-1,2,4-triazol-5-yl)-2-thiophenecarboxamide The title compound was prepared as a white solid according to the procedure of Example 292, except substituting 1,1-dimethylethyl[(2S)-2-{[(4-bromo-2-thienyl)carbonyl]amino}-3-(4-fluorophenyl)propyl]carbamate for 1,1-dimethylethyl [(2S)-2-{[(4-bromo-2-thienyl)carbonyl]amino}-3-(3,4-difluorophenyl)propyl]carbamate. The final compound was purified by RP-HPLC, and converted to HCl salt with 2N HCl aqueous solution. LC-MS (ES) m/z 394.2 (M+H)$^+$, $^1$H NMR (d₄-MeOH, 400 MHz) δ 8.49 (s, 1H), 7.95 (s, 1H), 7.27-7.36 (m, 2H), 7.06-7.13 (m, 2H), 4.61 (m, 1H), 4.03 (s, 3H), 3.02-3.25 (m, 4H).

Example 314

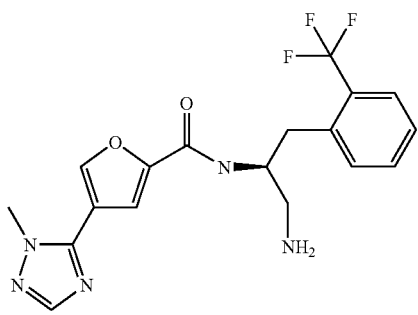 [SMILES: Cn1ncnc1-c1coc(C(=O)N[C@H](CN)Cc2ccccc2C(F)(F)F)c1]

Preparation of N-((1S)-2-amino-1-{[2-(trifluoromethyl)phenyl]methyl}ethyl)-4-(1-methyl-1H-1,2,4-triazol-5-yl)-2-furancarboxamide The title compound was prepared as a white solid according to Example 291, except substituting 1,1-dimethylethyl {(2S)-2-{[(4-bromo-2-furanyl)carbonyl]amino}-3-[2-(trifluoromethyl)phenyl]propyl}carbamate for 1,1-dimethylethyl ((2S)-2-{[(4-bromo-2-thienyl)carbonyl]amino}-3-phenylpropyl)carbamate. The final compound was purified by RP-HPLC, and converted to HCl salt with 2N HCl aqueous solution. LC-MS (ES) m/z 394.2 (M+H)⁺, ¹H NMR (d₄-MeOH, 400 MHz) δ 8.50 (s, 1H), 8.43 (s, 1H), 7.71 (m, 1H), 7.61 (s, 1H), 7.54 (m, 2H), 7.42 (m, 1H), 4.66 (m, 1H), 4.14 (s, 3H), 3.25 (m, 2H), 3.14 (m, 2H).

Example 315

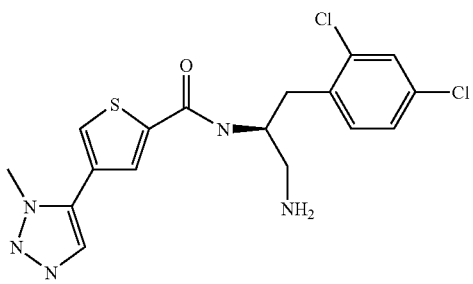 [SMILES: CN1NNC=C1c1csc(C(=O)N[C@H](CN)Cc2ccc(Cl)cc2Cl)c1]

Preparation of N-{(1S)-2-amino-1-[(2,4-dichlorophenyl)methyl]ethyl}-4-(1-methyl-1H-1,2,3-triazol-5-yl)-2-thiophenecarboxamide The title compound was prepared as a white solid according to Example 260, except substituting 1,1-dimethylethyl [(2S)-2-{[(4-bromo-2-thienyl)carbonyl]amino}-3-(2,4-dichlorophenyl)propyl]carbamate (from Preparation 22) for 1,1-dimethylethyl ((2S)-2-{[(4-bromo-2-thienyl)carbonyl]amino}-3-phenylpropyl)carbamate. The final compound was purified by RP-HPLC, and converted to HCl salt with 2N HCl aqueous solution. LC-MS (ES) m/z 410.0 (M+H)⁺, ¹H NMR (d₄-MeOH, 400 MHz) δ 8.23 (s, 1H), 8.14 (m, 2H), 7.47 (d, J=1 Hz, 1H), 7.41 (d, J=1 Hz, 1H), 7.25 (m, 1H), 4.68 (m, 1H), 4.30 (s, 3H), 3.11-3.28 (m, 4H).

Example 316

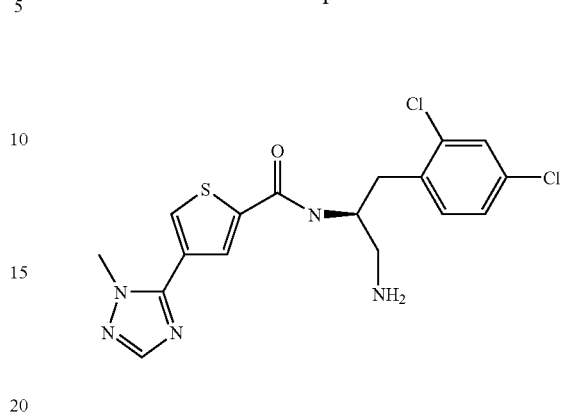

Preparation of N-{(1S)-2-amino-1-[(2,4-dichlorophenyl)methyl]ethyl}-4-(1-methyl-1H-1,2,4-triazol-5-yl)-2-thiophenecarboxamide The title compound was prepared as a white solid according to Example 291, except substituting 1,1-dimethylethyl [(2S)-2-{[(4-bromo-2-thienyl)carbonyl]amino}-3-(2,4-dichlorophenyl)propyl]carbamate (from Preparation 22) for 1,1-dimethylethyl ((2S)-2-{[(4-bromo-2-thienyl)carbonyl]amino}-3-phenylpropyl)carbamate. The final compound was purified by RP-HPLC, and converted to HCl salt with 2N HCl aqueous solution. LC-MS (ES) m/z 410.0 (M+H)⁺, ¹H NMR (d₄-MeOH, 400 MHz) δ 8.71 (s, 1H), 8.47 (d, J=1 Hz, 1H), 8.34 (d, J=1 Hz, 1H), 7.45 (m, 2H), 7.23 (m, 1H), 4.71 (m, 1H), 4.23 (s, 3H), 3.14-3.22 (m, 4H)

Example 317

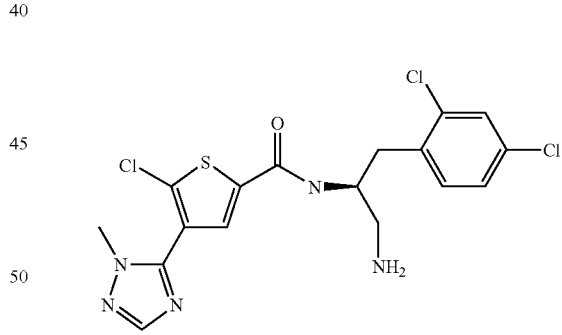

Preparation of N-{(1S)-2-amino-1-[(2,4-dichlorophenyl)methyl]ethyl}-5-chloro-4-(1-methyl-1H-1,2,4-triazol-5-yl)-2-thiophenecarboxamide The title compound was prepared as a white solid according to the procedure of Example 292, except substituting 1,1-dimethylethyl[(2S)-2-{[(4-bromo-2-thienyl)carbonyl]amino}-3-(2,4-dichlorophenyl)propyl]carbamate for 1,1-dimethyl ethyl [(2S)-2-{[(4-bromo-2-thienyl)carbonyl]amino}-3-(3,4-difluorophenyl)propyl]carbamate. The final compound was purified by RP-HPLC, and converted to HCl salt with 2N HCl aqueous solution. LC-MS (ES) m/z 446.2

(M+H)+, 1H NMR (d4-MeOH, 400 MHz) δ 8.65 (s, 1H), 8.11 (s, 1H), 7.44 (m, 2H), 7.25 (m, 1H), 4.68 (m, 1H), 4.08 (s, 3H), 3.10-3.23 (m, 4H).

Example 318

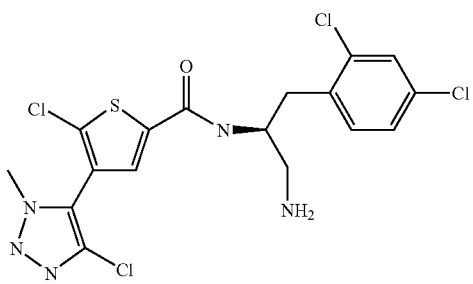 [SMILES: CN1NNC(Cl)=C1c1cc(C(=O)N[C@H](CN)Cc2ccc(Cl)cc2Cl)sc1Cl]

Preparation of N-{(1S)-2-amino-1-[(2,4-dichlorophenyl)methyl]ethyl}-5-chloro-4-(4-chloro-1-methyl-1H-1,2,3-triazol-5-yl)-2-thiophenecarboxamide The title compound was prepared as a white solid according to Example 261, except substituting 1,1-dimethylethyl [(2S)-2-{[(4-bromo-2-thienyl)carbonyl]amino}-3-(2,4-dichlorophenyl)propyl]carbamate (from Preparation 21) for 1,1-dimethylethyl ((2S)-2-{[(4-bromo-2-thienyl)carbonyl]amino}-3-phenylpropyl)carbamate. The final compound was purified by RP-HPLC, and converted to HCl salt with 2N HCl aqueous solution. LC-MS (ES) m/z 480.0 (M+H)+, 1H NMR (d4-MeOH, 400 MHz) δ 7.80 (m, 1H), 7.48 (m, 1H), 7.39 (m, 1H), 7.27 (m, 1H), 4.66 (m, 1H), 4.05 (s, 3H), 3.08-3.14 (m, 4H)

Example 319

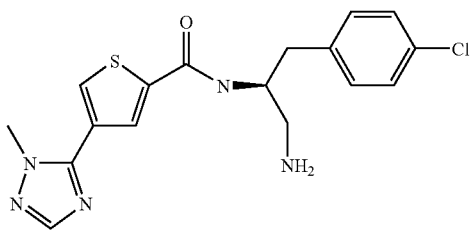 [SMILES: Cn1ncnc1-c1csc(C(=O)N[C@H](CN)Cc2ccc(Cl)cc2)c1]

Preparation of N-{(1S)-2-amino-1-[(4-chlorophenyl)methyl]ethyl}-4-(1-methyl-1H-1,2,4-triazol-5-yl)-2-thiophenecarboxamide The title compound was prepared as a white solid according to Example 291, except substituting 1,1-dimethylethyl [(2S)-2-{[(4-bromo-2-thienyl)carbonyl]amino}-3-(4-chlorophenyl)propyl]carbamate for 1,1-dimethylethyl ((2S)-2-{[(4-bromo-2-thienyl)carbonyl]amino}-3-phenylpropyl)carbamate. The final compound was purified by RP-HPLC, and converted to HCl salt with 2N HCl aqueous solution. LC-MS (ES) m/z 376.2 (M+H)+, 1H NMR (d4-MeOH, 400 MHz) δ 8.68 (s, 1H), 8.46 (d, J=1 Hz, 1H), 8.29 (d, J=1 Hz, 1H), 7.27-7.34 (m, 4H), 4.57 (m, 1H), 4.21 (s, 3H), 3.25 (m, 2H), 3.04 (m, 2H)

Example 320

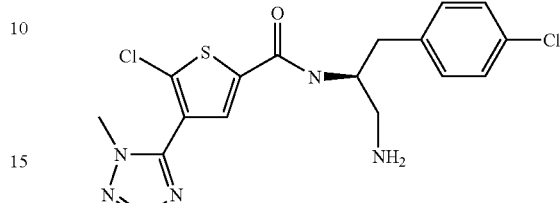

Preparation of N-{(1S)-2-amino-1-[(4-chlorophenyl)methyl]ethyl}-5-chloro-4-(1-methyl-1H-1,2,4-triazol-5-yl)-2-thiophenecarboxamide The title compound was prepared as a white solid according to Example 292, except substituting 1,1-dimethylethyl [(2S)-2-{[(4-bromo-2-thienyl)carbonyl]amino}-3-(4-chlorophenyl)propyl]carbamate for 1,1-dimethylethyl [(2S)-2-{[(4-bromo-2-thienyl)carbonyl]amino}-3-(3,4-difluorophenyl)propyl]carbamate. The final compound was purified by RP-HPLC, and converted to HCl salt with 2N HCl aqueous solution. LC-MS (ES) m/z 410.0 (M+H)+, 1H NMR (d4-MeOH, 400 MHz) δ 8.47 (s, 1H), 7.97 (s, 1H), 7.30 (m, 4H), 4.60 (m, 1H), 4.03 (s, 3H), 3.22 (m, 2H), 3.00 (m, 2H).

Example 321

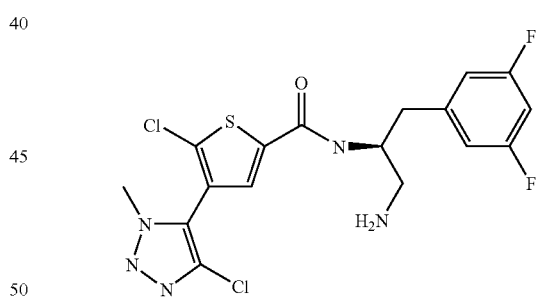

Preparation of N-{(1S)-2-amino-1-[(3,5-difluorophenyl)methyl]ethyl}-5-chloro-4-(4-chloro-1-methyl-1H-1,2,3-triazol-5-yl)-2-thiophenecarboxamide The title compound was prepared as a white solid according to Example 261, except substituting 1,1-dimethylethyl [(2S)-2-{[(4-bromo-2-thienyl)carbonyl]amino}-3-(3,5-difluorophenyl)propyl]carbamate for 1,1-dimethylethyl ((2S)-2-{[(4-bromo-2-thienyl)carbonyl]amino}-3-phenylpropyl)carbamate; The final compound was purified by RP-HPLC, and converted to HCl salt with 2N HCl aqueous solution. LC-MS (ES) m/z 446.0 (M+H)+, 1H NMR (d4-MeOH, 400 MHz) δ 7.80 (s, 1H), 6.95 (m, 2H), 6.84 (m, 1H), 4.62 (m, 1H), 4.04 (s, 3H), 3.20 (m, 2H), 3.01 (m, 2H).

Example 322

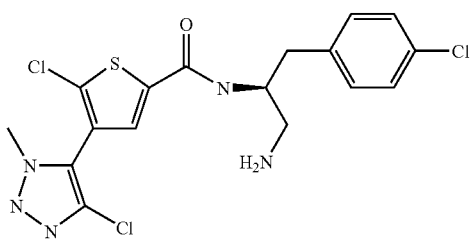 [SMILES: CN1NNC(Cl)=C1c1cc(C(=O)N[C@H](CN)Cc2ccc(Cl)cc2)sc1Cl]

Preparation of N-{(1S)-2-amino-1-[(4-chlorophenyl)methyl]ethyl}-5-chloro-4-(4-chloro-1-methyl-1H-1,2,3-triazol-5-yl)-2-thiophenecarboxamide The title compound was prepared as a white solid according to Example 261, except substituting 1,1-dimethylethyl [(2S)-2-{[(4-bromo-2-thienyl)carbonyl]amino}-3-(4-chlorophenyl)propyl]carbamate for 1,1-dimethylethyl ((2S)-2-{[(4-bromo-2-thienyl)carbonyl]amino}-3-phenylpropyl)carbamate; The final compound was purified by RP-HPLC, and converted to HCl salt with 2N HCl aqueous solution. LC-MS (ES) m/z 444.0 (M+H)$^+$, $^1$H NMR (d$_4$-MeOH, 400 MHz) δ 7.73 (s, 1H), 7.30 (m, 4H), 4.66 (m, 1H), 4.04 (s, 3H), 3.18 (m, 2H), 2.99 (m, 2H).

Example 323

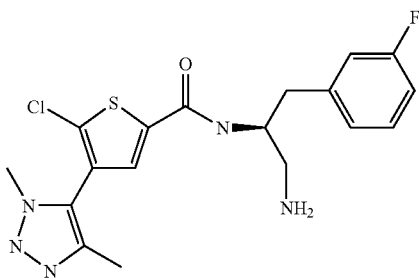 [SMILES: CC1=C(c2cc(C(=O)N[C@H](CN)Cc3cccc(F)c3)sc2Cl)N(C)NN1]

Preparation of N-{(1S)-2-amino-1-[(3-fluorophenyl)methyl]ethyl}-5-chloro-4-(1,4-dimethyl-1H-1,2,3-triazol-5-yl)-2-thiophenecarboxamide a) 4-(1,4-dimethyl-1H-1,2,3-triazol-5-yl)-2-thiophenecarboxylic Acid

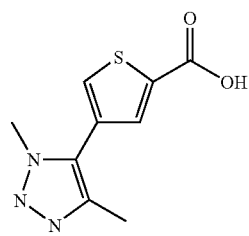

This intermediate was prepared according to the procedures of Example 269 a) and b) except substituting 1,4-dimethyl-5-(tributylstannanyl)-1H-1,2,3-triazole (from Preparation 21) for 1-methyl-5-(tributylstannanyl)-1H-1,2,3-triazole and substituting methyl 4-bromo-2-thiophenecarboxylate for methyl 4-bromo-5-chloro-2-thiophenecarboxylate. LC-MS (ES) m/z 224.2 (M+H)$^+$.

b) 4-(1,4-Dimethyl-1H-1,2,3-triazol-5-yl)-N-{(1S)-2-(1,3-dioxo-1,3-dihydro-2H-isoindol-2-yl)-1-[(3-fluorophenyl)methyl]ethyl}-2-thiophenecarboxamide

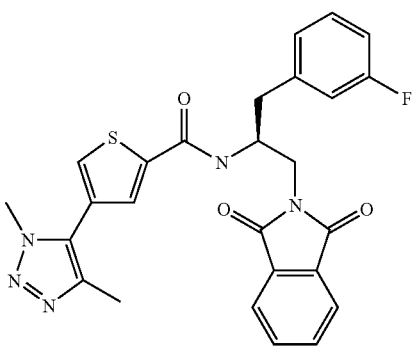 [SMILES: Cc1nnn(C)c1-c1csc(C(=O)N[C@@H](Cc2cccc(F)c2)CN2C(=O)c3ccccc3C2=O)c1]

This intermediate was prepared according to the procedure of Example 269 c) except substituting 4-(1,4-dimethyl-1H-1,2,3-triazol-5-yl)-2-thiophenecarboxylic acid for 5-chloro-4-(1-methyl-1H-1,2,3-triazol-5-yl)-2-thiophenecarboxylic acid, and substituting 2-[(2S)-2-amino-3-(3-fluorophenyl)propyl]-1H-isoindole-1,3(2H)-dione for 2-{(2S)-2-amino-3-[2-(trifluoromethyl)phenyl]propyl}-1H-isoindole-1,3(2H)-dione. LC-MS (ES) m/z 504.2 (M+H)$^+$.

c) 5-chloro-4-(1,4-dimethyl-1H-1,2,3-triazol-5-yl)-N-{(1S)-2-(1,3-dioxo-1,3-dihydro-2H-isoindol-2-yl)-1-[(3-fluorophenyl)methyl]ethyl}-2-thiophenecarboxamide

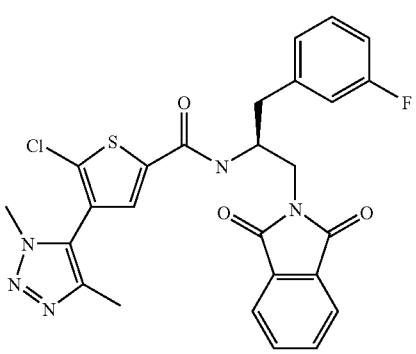 [SMILES: Cc1nnn(C)c1-c1cc(C(=O)N[C@@H](Cc2cccc(F)c2)CN2C(=O)c3ccccc3C2=O)sc1Cl]

A solution of 4-(1,4-dimethyl-1H-1,2,3-triazol-5-yl)-N-{(1S)-2-(1,3-dioxo-1,3-dihydro-2H-isoindol-2-yl)-1-[(3-fluorophenyl)methyl]ethyl}-2-thiophenecarboxamide (254 mg, 0.454 mmol), and NCS (60.6 mg, 0.454 mmol) in N,N-Dimethylformamide (DMF) (5 mL) to was heated at 40° C. overnight. The reaction mixture was taken into EtOAc, which was washed with H$_2$O 3× and brine, dried (Na$_2$SO$_4$) and concentrated. The residue was purified on a 25 g Biotage column, which was eluted with 50-100% EtOAc/hexane to give 76 mg (28%) of product as a white foamy solid and 63 mg of recovered starting material. LC-MS (ES) m/z 538.0 (M+H)$^+$.

d) N-{(1S)-2-amino-1-[(3-fluorophenyl)methyl]ethyl}-5-chloro-4-(1,4-dimethyl-1H-1,2,3-triazol-5-yl)-2-thiophenecarboxamide The title compound was prepared as a white solid according to the procedure of Example 269d), except substituting 5-chloro-4-(1,4-dimethyl-1H-1,2,3-triazol-5-yl)-N-{(1S)-2-(1,3-dioxo-1,3-dihydro-2H-isoindol-2-yl)-1-[(3-fluorophenyl)methyl]ethyl}-2-thiophenecarboxamide for 5-chloro-N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)-2-thiophenecarboxamide. The final compound was purified by RP-HPLC, and converted to HCl salt with 2N HCl aqueous solution. LC-MS (ES) m/z 408.2 (M+H)+, 1H NMR (d4-MeOH, 400 MHz) δ 7.88 (m, 1H), 7.30 (m, 1H), 7.10 (m, 2H), 6.96 (m, 1H), 4.65 (m, 1H), 4.10 (s, 3H), 3.21 (m, 2H), 3.03 (m, 2H), 2.06 (s, 3H).

Example 324

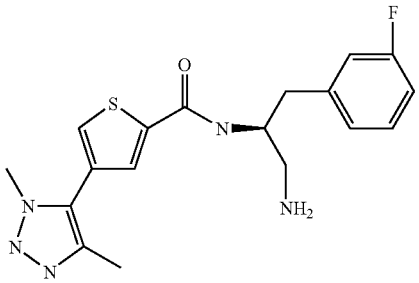 [SMILES: CC1=C(c2csc(C(=O)N[C@H](CN)Cc3cccc(F)c3)c2)N(C)NN1]

Preparation of N-{(1S)-2-amino-1-[(3-fluorophenyl)methyl]ethyl}-4-(1,4-dimethyl-1H-1,2,3-triazol-5-yl)-2-thiophenecarboxamide The title compound was prepared as a white solid according to the procedures of Example 323 a), b) and d), except substituting 4-(1,4-dimethyl-1H-1,2,3-triazol-5-yl)-N-{(1S)-2-(1,3-dioxo-1,3-dihydro-2H-isoindol-2-yl)-1-[(3-fluorophenyl)methyl]ethyl}-2-thiophenecarboxamide for 5-chloro-4-(1,4-dimethyl-1H-1,2,3-triazol-5-yl)-N-{(1S)-2-(1,3-dioxo-1,3-dihydro-2H-isoindol-2-yl)-1-[(3-fluorophenyl)methyl]ethyl}-2-thiophenecarboxamide. LC-MS (ES) m/z 374.2 (M+H)+, 1H NMR (d4-MeOH, 400 MHz) δ 8.09 (d, J=1 Hz, 1H), 8.06 (d, J=1 Hz, 1H), 7.31 (m, 1H), 7.16 (m, 1H), 6.96 (m, 1H), 4.56 (m, 1H), 4.20 (s, 3H), 3.23 (m, 2H), 3.05 (m, 2H), 2.47 (s, 3H).

Example 325

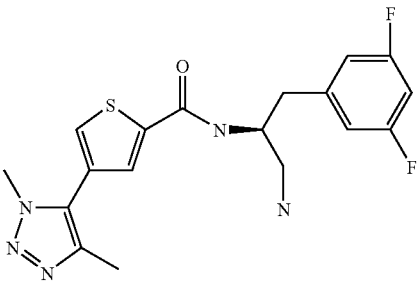 [SMILES: Cc1nnn(C)c1-c1csc(C(=O)N[C@H](CN)Cc2cc(F)cc(F)c2)c1]

Preparation of N-{(1S)-2-amino-1-[(3,5-difluorophenyl)methyl]ethyl}-4-(1,4-dimethyl-1H-1,2,3-triazol-5-yl)-2-thiophenecarboxamide The title compound was prepared as a white solid according to the procedures of Example 323 a), b) and d), except substituting 2-[(2S)-2-amino-3-(3,5-difluorophenyl)propyl]-1H-isoindole-1,3(2H)-dione for 2-[(2S)-2-amino-3-(3-fluorophenyl)propyl]-1H-isoindole-1,3(2H)-dione. LC-MS (ES) m/z 392.2 (M+H)+, 1H NMR (d4-MeOH, 400 MHz) δ 8.13 (m, 2H), 6.99 (m, 2H), 6.79 (m, 1H), 4.59 (m, 1H), 4.22 (s, 3H), 3.26 (m, 2H), 3.06 (m, 2H), 2.49 (s, 3H).

Example 326

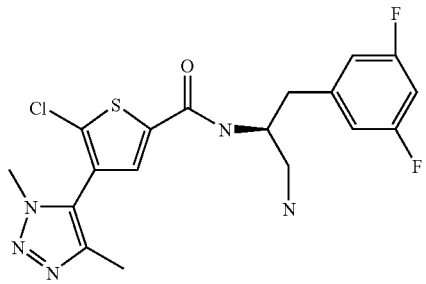 [SMILES: Cc1nnn(C)c1-c1cc(C(=O)N[C@H](CN)Cc2cc(F)cc(F)c2)sc1Cl]

Preparation of N-{(1S)-2-amino-1-[(3,5-difluorophenyl)methyl]ethyl}-5-chloro-4-(1,4-dimethyl-1H-1,2,3-triazol-5-yl)-2-thiophenecarboxamide The title compound was prepared as a white solid according to the procedure of Example 323, except substituting 2-[(2S)-2-amino-3-(3,5-difluorophenyl)propyl]-1H-isoindole-1,3(2H)-dione for 2-[(2S)-2-amino-3-(3-fluorophenyl)propyl]-1H-isoindole-1,3(2H)-dione. LC-MS (ES) m/z 426.2 (M+H)+, 1H NMR (d4-MeOH, 400 MHz) δ 7.88 (s, 1H), 6.96 (m, 2H), 6.82 (m, 1H), 4.62 (m, 1H), 4.07 (s, 3H), 3.22 (m, 2H), 3.05 (m, 2H), 2.34 (s, 3H).

Example 327

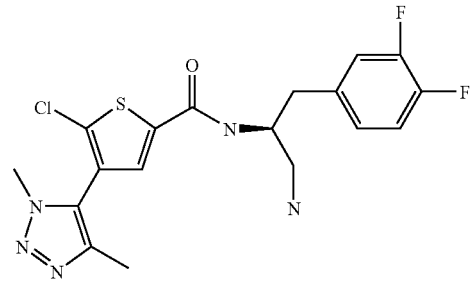 [SMILES: Cc1nnn(C)c1-c1cc(C(=O)N[C@H](CN)Cc2ccc(F)c(F)c2)sc1Cl]

Preparation of N-{(1S)-2-amino-1-[(3,4-difluorophenyl)methyl]ethyl}-5-chloro-4-(1,4-dimethyl-1H-1,2,3-triazol-5-yl)-2-thiophenecarboxamide The title compound was prepared as a white solid according to the procedure of Example 323, except substituting substituting 2-[(2S)-2-amino-3-(3,4-difluorophenyl)propyl]-1H-isoindole-1,3(2H)-dione for 2-[(2S)-2-amino-3-(3-fluorophenyl)propyl]-1H-isoindole-1,3(2H)-dione. LC-MS (ES)

m/z 426.2 (M+H)⁺, ¹H NMR (d₄-MeOH, 400 MHz) δ 7.87 (s, 1H), 7.12-7.26 (m, 3H), 4.62 (m, 1H), 4.08 (s, 3H), 3.21 (m, 2H), 3.00 (m, 2H), 2.36 (s, 3H).

Example 328

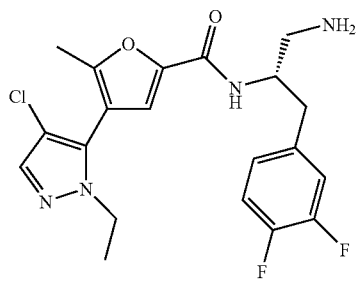 [SMILES: CCn1ncc(Cl)c1-c1cc(C(=O)N[C@H](CN)Cc2ccc(F)c(F)c2)oc1C]

N-{(1S)-2-amino-1-[(3,4-difluorophenyl)methyl]-ethyl}-4-(4-chloro-1-ethyl-1H-pyrazol-5-yl)-5-methyl-2-furancarboxamide a) methyl 4-bromo-5-methyl-2-furancarboxylate

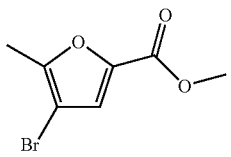

To a solution of methyl 4,5-dibromo-2-furancarboxylate (4.5 g, 15.85 mmol) and BIS(TRIPHENYLPHOSPHINE)PALLADIUM(II) CHLORIDE (0.38 g, 0.541 mmol) in THF (100 mL) at RT was added chloro(methyl)zinc (15 mL, 30 mmol) dropwise. After stirring for 10 h, the reaction was quenched with NH₄Cl (sat'd) (50 mL). The mixture was extracted with EtOAc (50 mL×3), and the collected organic layers were dried over MgSO₄. Solvent was removed under vacuum and the resulting residue was purified via column chromatography (silica, EtOAc/Hex 10-20%) to give the title compound (2.5 g, 72%) as a white solid: LC-MS (ES) m/z 220 (M+H)⁺.

b) methyl 4-(1-ethyl-1H-pyrazol-5-yl)-5-methyl-2-furancarboxylate

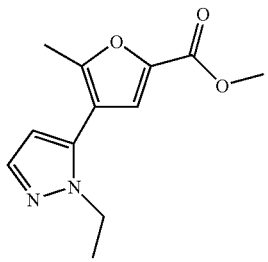 [SMILES: CCn1nccc1-c1cc(C(=O)OC)oc1C]

To a 100 mL sealed flask was added 1-ethyl-5-(4,4,5,5-tetramethyl-1,3,2-dioxaborolan-2-yl)-1H-pyrazole (2.2 g, 9.91 mmol), potassium carbonate (2.84 g, 20.54 mmol), methyl 4-bromo-5-methyl-2-furancarboxylate (1.5 g, 6.85 mmol) and BIS(TRI-T-BUTYLPHOSPHINE)PALLADIUM(0) (0.175 g, 0.34 mmol) in 1,2-dimethoxyethane (6 mL) and H₂O (1 mL). After stirring for 2 h at 72° C., the reaction solution was diluted with DCM (50 mL) and washed with H₂O. The organic layer was dried Na₂SO₄, filtered and concentrated. The residue was purified on silica gel [EtOAC/hexanes, 10-30%] to give the product [1.1 g, 68.6%] as an off white solid: LC-MS (ES) m/z 235 (M+H)⁺.

c) methyl 4-(4-chloro-1-ethyl-1H-pyrazol-5-yl)-5-methyl-2-furancarboxylate

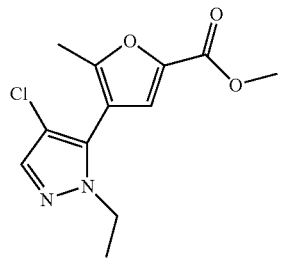 [SMILES: CCn1ncc(Cl)c1-c1cc(C(=O)OC)oc1C]

A mixture of methyl 4-(1-ethyl-1H-pyrazol-5-yl)-5-methyl-2-furancarboxylate (950 mg, 4.06 mmol) and NCS (650 mg, 4.87 mmol) in THF (10 mL) was heated at 70° C. in a sealed tube. After 2 h, the reaction mixture was concentrated and purified via column chromatography (silica, 10-20% EtOAc/Hexane) affording the title compound (970 mg, 89%) as a white solid: LC-MS (ES) m/z 269 (M+H)⁺.

d) 4-(4-chloro-1-ethyl-1H-pyrazol-5-yl)-N-{(1S)-2-(3,4-difluorophenyl)-1-[(1,3-dioxo-1,3-dihydro-2H-isoindol-2-yl)methyl]ethyl}-5-methyl-2-furancarboxamide

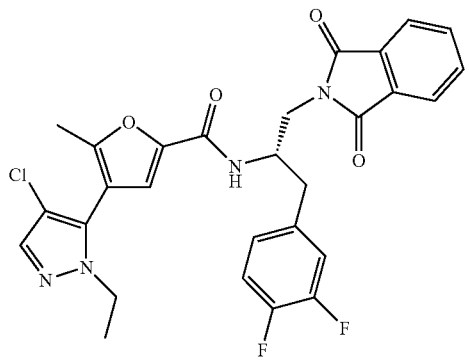 [SMILES: CCn1ncc(Cl)c1-c1cc(C(=O)N[C@@H](Cc2ccc(F)c(F)c2)CN2C(=O)c3ccccc3C2=O)oc1C]

To a solution of methyl 4-(4-chloro-1-ethyl-1H-pyrazol-5-yl)-5-methyl-2-furancarboxylate (500 mg, 1.86 mmol) in THF/H₂O (5 mL/1 mL) was added KOH (500 mg, 8.91 mmol). The reaction mixture was heated to 50° C. for 4 h. The mixture was concentrated, diluted with H₂O (2 mL) and the pH was adjusted to 3. The mixture was extracted with DCM (10 mL×3). The collected organic layers were concentrated under vacuum to give a crude acid (460 mg, 97%), which was used directly without further purification: LC-MS (ES) m/z 255 (M+H)⁺.

To the above acid (221 mg, 0.869 mmol) in DCM (5 mL) at 25° C. was added PyBrOP (480 mg, 1.03 mmol) in one portion, followed by addition of DIPEA (1.0 mL, 5.73 mmol).

After 10 min, 2-[(2S)-2-amino-3-(3,4-difluorophenyl)propyl]-1H-isoindole-1,3(2H)-dione (250 mg, 0.79 mmol) was added to the reaction solution. After 1 h, the reaction mixture was concentrated and purified via column chromatography (silica, 30-50% EtOAc/Hexane) affording the title compound (401 mg, 92%) as a white solid: LC-MS (ES) m/z 553 (M+H)$^+$.

e) N-{(1S)-2-amino-1-[(3,4-difluorophenyl)methyl]ethyl}-4-(4-chloro-1-ethyl-1H-pyrazol-5-yl)-5-methyl-2-furancarboxamide

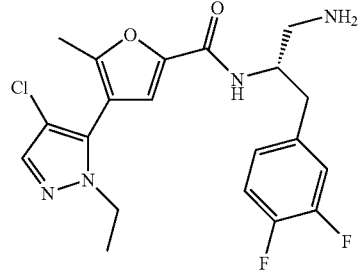 [SMILES: CCn1ncc(Cl)c1-c1cc(C(=O)N[C@H](CN)Cc2ccc(F)c(F)c2)oc1C]

At rt, NH$_2$NH$_2$ (0.5 mL, 15.93 mmol) was added to 4-(4-chloro-1-ethyl-1H-pyrazol-5-yl)-N-{(1S)-2-(3,4-difluorophenyl)-1-[(1,3-dioxo-1,3-dihydro-2H-isoindol-2-yl)methyl]ethyl}-5-methyl-2-furancarboxamide (260 mg, 0.47 mmol) in MeOH (5 mL). After 48 h, the solvent was removed under vacuum. The resulting residue was taken into DCM (20 mL), and washed with H$_2$O (20 mL×3).

To the DCM solution was added HCl (36%, 10 mL, 120 mmol). After 1 h, the aqueous phase was separated, and washed with DCM (30 ml×3). Water was removed under high vacuum to give the title compound (140 mg, 69.7%) as an off-white solid: LC-MS (ES) m/z 423 (M+H)$^+$, NMR (d$_4$-MeOD, 400 MHz) δ ppm 7.59 (s, 1H), 7.27-7.16 (m, 3H), 7.13-7.08 (m, 1H), 4.56 (m, 1H), 4.06 (q, J=7.3 Hz, 2H), 3.26-3.22 (m, 1H), 3.17-3.11 (m, 1H), 3.05-3.00 (m, 1H), 2.97-2.91 (m, 1H), 2.36 (s, 3H), and 1.33 (t, J=7.3 Hz, 3H).

Example 329

Capsule Composition

An oral dosage form for administering the present invention is produced by filing a standard two piece hard gelatin capsule with the ingredients in the proportions shown in Table I, below.

TABLE I

| INGREDIENTS | AMOUNTS |
| --- | --- |
| N-[2-amino-1-(phenylmethyl)ethyl]-4-bromo-5-(1-methyl-1H-pyrazol-5-yl)-2-furancarboxamide (Compound of Example 1) | 25 mg |
| Lactose | 55 mg |
| Talc | 16 mg |
| Magnesium Stearate | 4 mg |

Example 330

Injectable Parenteral Composition

An injectable form for administering the present invention is produced by stirring 1.5% by weight of N-(2-amino-1-phenylethyl)-5-(1-methyl-1H-pyrazol-5-yl)-2-thiophenecarboxamide (Compound of Example 2) in 10% by volume propylene glycol in water.

Example 331

Tablet Composition

The sucrose, calcium sulfate dihydrate and an Akt inhibitor as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| N-[2-amino-1-(phenylmethyl)ethyl]-5-(1-methyl-1H-pyrazol-5-yl)-2-thiophenecarboxamide (Compound of Example 3) | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound:
N-{(1S)-2-amino-1-[(3,4-difluorophenyl)methyl]ethyl]-5-chloro-4-(4-chloro-1-methyl-1H-pyrazol-5-yl)-2-furancarboxamide;
or a pharmaceutically acceptable salt thereof.

2. A compound of claim 1 which is:
N-{(1S)-2-amino-1-[(3,4-difluorophenyl)methyl]ethyl]-5-chloro-4-(4-chloro-1-methyl-1H-pyrazol-5-yl)-2-furancarboxamide.

3. A pharmaceutical composition comprising a compound according to claim 1 and a pharmaceutically acceptable carrier.

4. A pharmaceutical composition comprising a compound according to claim 2 and a pharmaceutically acceptable carrier.

5. A process for preparing a pharmaceutical composition containing a pharmaceutically acceptable carrier and a compound of claim 1 which process comprises bringing the compound of claim 43 into association with a pharmaceutically acceptable carrier.

6. a method of inhibiting Akt activity in a mammal in need thereof, which comprises administering to such mammal a therapeutically effective amount of a compound of claim 1.

7. The method of claim 6 wherein the mammal is a human.

8. A pharmaceutical composition according to claim 3, wherein the composition is in tablet form.

9. A pharmaceutical composition according to claim 4, wherein the composition is in tablet form.

10. A method of treating or lessening the severity of cancer, wherein said cancer is selected from:
brain cancer (gliomas), glioblastomas, medulloblastoma, prostate cancer, breast cancer, inflammatory breast cancer, colon cancer, head and neck cancer, kidney cancer, Wilm's tumor, renal cancer, lung cancer, endometrial cancer, gastric cancer, liver cancer and ovarian cancer,
in a human in need thereof, which comprises administering to such human a therapeutically effective amount of a compound of claim 1.

11. A method of treating or lessening the severity of cancer, wherein said cancer is selected from:
Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Megakaryoblastic leukemia, multiple myeloma, acute megakaryocytic leukemia, promyelocytic leukemia and Erythroleukemia,
in a human in need thereof, which comprises administering to such human a therapeutically effective amount of a compound of claim 1.

12. A method of treating or lessening the severity of cancer, wherein said cancer is selected from:
malignant lymphoma, hodgkins lymphoma, non-hodgkins lymphoma, lymphoblastic T cell lymphoma, Burkitt's lymphoma and follicular lymphoma, in a human in need thereof, which comprises administering to such human a therapeutically effective amount of a compound of claim 1.

13. A method of treating or lessening the severity of cancer, wherein said cancer is selected from:
pancreatic cancer, Bannayan-Zonana syndrome, Cowden disease, and Lhermitte-Duclos disease,
in a human in need thereof, which comprises administering to such human a therapeutically effective amount of a compound of claim 1.

14. A pharmaceutically acceptable salt of the compound:

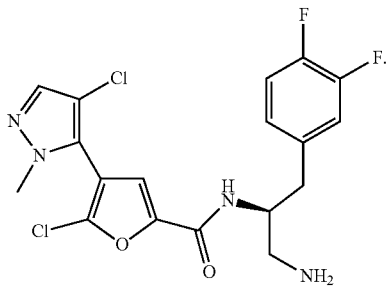 [SMILES: Cn1ncc(Cl)c1-c1cc(C(=O)N[C@H](CN)Cc2ccc(F)c(F)c2)oc1Cl]

15. A pharmaceutical composition comprising a compound according to claim 14 and a pharmaceutically acceptable carrier.

16. A pharmaceutical composition according to claim 15, wherein the composition is in tablet form.

17. A method of treating or lessening the severity of cancer, wherein said cancer is selected from:
brain cancer (gliomas), glioblastomas, medulloblastoma, prostate cancer, breast cancer, inflammatory breast cancer, colon cancer, head and neck cancer, kidney cancer, Wilm's tumor, renal cancer, lung cancer, endometrial cancer, gastric cancer, liver cancer and ovarian cancer, in a human in need thereof, which comprises administering to such human a therapeutically effective amount of a compound of claim 14.

18. A method of treating or lessening the severity of cancer, wherein said cancer is selected from:
Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Megakaryoblastic leukemia, multiple myeloma, acute megakaryocytic leukemia, promyelocytic leukemia and Erythroleukemia,
in a human in need thereof, which comprises administering to such human a therapeutically effective amount of a compound of claim 14.

19. A method of treating or lessening the severity of cancer, wherein said cancer is selected from:
malignant lymphoma, hodgkins lymphoma, non-hodgkins lymphoma, lymphoblastic T cell lymphoma, Burkitt's lymphoma and follicular lymphoma,
in a human in need thereof, which comprises administering to such human a therapeutically effective amount of a compound of claim 14.

20. A method of treating or lessening the severity of cancer, wherein said cancer is selected from:
pancreatic cancer, Bannayan-Zonana syndrome, Cowden disease, and Lhermitte-Duclos disease,
in a human in need thereof, which comprises administering to such human a therapeutically effective amount of a compound of claim 14.

21. A process for preparing a pharmaceutical composition containing a pharmaceutically acceptable carrier and a compound of claim 14 which process comprises bringing the compound of claim 14 into association with a pharmaceutically acceptable carrier.

22. A method of treating or lessening the severity of cancer, wherein said cancer is selected from:
Multiple myeloma, melanoma, mesothelioma, sarcoma, Ewing's sarcoma, Rhabdomyosarcoma, osteosarcoma, and thyroid cancer,
in a human in need thereof, which comprises administering to such human a therapeutically effective amount of a compound of claim 2.

23. A method of treating or lessening the severity of cancer, wherein said cancer is selected from:
Multiple myeloma, melanoma, mesothelioma, sarcoma, Ewing's sarcoma, Rhabdomyosarcoma, osteosarcoma, and thyroid cancer,
in a human in need thereof, which comprises administering to such human a therapeutically effective amount of a compound of claim 14.

24. A method of treating or lessening the severity of Lymphoblastic T cell leukemia, in a human in need thereof, which comprises administering to such human a therapeutically effective amount of a compound of claim 2.

25. A method of treating or lessening the severity of Chronic myelogenous leukemia, in a human in need thereof, which comprises administering to such human a therapeutically effective amount of a compound of claim 2.

26. A method of treating or lessening the severity of Chronic lymphocytic leukemia, in a human in need thereof, which comprises administering to such human a therapeutically effective amount of a compound of claim 2.

27. A method of treating or lessening the severity of Hairy-cell leukemia, in a human in need thereof, which comprises administering to such human a therapeutically effective amount of a compound of claim 2.

28. A method of treating or lessening the severity of acute lymphoblastic leukemia, in a human in need thereof, which comprises administering to such human a therapeutically effective amount of a compound of claim 2.

29. A method of treating or lessening the severity of acute myelogenous leukemia, in a human in need thereof, which comprises administering to such human a therapeutically effective amount of a compound of claim 2.

30. A method of treating or lessening the severity of Chronic neutrophilic leukemia, in a human in need thereof, which comprises administering to such human a therapeutically effective amount of a compound of claim 2.

31. A method of treating or lessening the severity of Acute lymphoblastic T cell leukemia, in a human in need thereof, which comprises administering to such human a therapeutically effective amount of a compound of claim 2.

32. A method of treating or lessening the severity of Plasmacytoma, in a human in need thereof, which comprises administering to such human a therapeutically effective amount of a compound of claim 2.

33. A method of treating or lessening the severity of Immunoblastic large cell leukemia, in a human in need thereof, which comprises administering to such human a therapeutically effective amount of a compound of claim 2.

34. A method of treating or lessening the severity of Mantle cell leukemia, in a human in need thereof, which comprises administering to such human a therapeutically effective amount of a compound of claim 2.

35. A method of treating or lessening the severity of Megakaryoblastic leukemia, in a human in need thereof, which comprises administering to such human a therapeutically effective amount of a compound of claim 2.

36. A method of treating or lessening the severity of multiple myeloma, in a human in need thereof, which comprises administering to such human a therapeutically effective amount of a compound of claim 2.

37. A method of treating or lessening the severity of acute megakaryocytic leukemia, in a human in need thereof, which comprises administering to such human a therapeutically effective amount of a compound of claim 2.

38. A method of treating or lessening the severity of promyelocytic leukemia, in a human in need thereof, which comprises administering to such human a therapeutically effective amount of a compound of claim 2.

39. A method of treating or lessening the severity of Erythroleukemia, in a human in need thereof, which comprises administering to such human a therapeutically effective amount of a compound of claim 2.

40. A method of treating or lessening the severity of Lymphoblastic T cell leukemia, in a human in need thereof, which comprises administering to such human a therapeutically effective amount of a compound of claim 14.

41. A method of treating or lessening the severity of Chronic myelogenous leukemia, in a human in need thereof, which comprises administering to such human a therapeutically effective amount of a compound of claim 14.

42. A method of treating or lessening the severity of Chronic lymphocytic leukemia, in a human in need thereof, which comprises administering to such human a therapeutically effective amount of a compound of claim 14.

43. A method of treating or lessening the severity of Hairy-cell leukemia, in a human in need thereof, which comprises administering to such human a therapeutically effective amount of a compound of claim 14.

44. A method of treating or lessening the severity of acute lymphoblastic leukemia, in a human in need thereof, which comprises administering to such human a therapeutically effective amount of a compound of claim 14.

45. A method of treating or lessening the severity of acute myelogenous leukemia, in a human in need thereof, which comprises administering to such human a therapeutically effective amount of a compound of claim 14.

46. A method of treating or lessening the severity of Chronic neutrophilic leukemia, in a human in need thereof, which comprises administering to such human a therapeutically effective amount of a compound of claim 14.

47. A method of treating or lessening the severity of Acute lymphoblastic T cell leukemia, in a human in need thereof, which comprises administering to such human a therapeutically effective amount of a compound of claim 14.

48. A method of treating or lessening the severity of Plasmacytoma, in a human in need thereof, which comprises administering to such human a therapeutically effective amount of a compound of claim 14.

49. A method of treating or lessening the severity of Immunoblastic large cell leukemia, in a human in need thereof, which comprises administering to such human a therapeutically effective amount of a compound of claim 14.

50. A method of treating or lessening the severity of Mantle cell leukemia, in a human in need thereof, which comprises administering to such human a therapeutically effective amount of a compound of claim 14.

51. A method of treating or lessening the severity of Megakaryoblastic leukemia, in a human in need thereof, which comprises administering to such human a therapeutically effective amount of a compound of claim 14.

52. A method of treating or lessening the severity of multiple myeloma, in a human in need thereof, which comprises administering to such human a therapeutically effective amount of a compound of claim 14.

53. A method of treating or lessening the severity of acute megakaryocytic leukemia, in a human in need thereof, which comprises administering to such human a therapeutically effective amount of a compound of claim 14.

54. A method of treating or lessening the severity of promyelocytic leukemia, in a human in need thereof, which comprises administering to such human a therapeutically effective amount of a compound of claim 14.

55. A method of treating or lessening the severity of Erythroleukemia, in a human in need thereof, which comprises administering to such human a therapeutically effective amount of a compound of claim 14.

56. A method of treating or lessening the severity of melanoma, in a human in need thereof, which comprises administering to such human a therapeutically effective amount of a compound of claim 14.

57. A method of treating or lessening the severity of mesothelioma, in a human in need thereof, which comprises administering to such human a therapeutically effective amount of a compound of claim 1.

58. A method of treating or lessening the severity of sarcoma, in a human in need thereof, which comprises administering to such human a therapeutically effective amount of a compound of claim 1.

59. A method of treating or lessening the severity of thyroid cancer, in a human in need thereof, which comprises administering to such human a therapeutically effective amount of a compound of claim 1.

60. A method of treating or lessening the severity of brain cancer, in a human in need thereof, which comprises administering to such human a therapeutically effective amount of a compound of claim 1.

61. A method of treating or lessening the severity of breast cancer, in a human in need thereof, which comprises administering to such human a therapeutically effective amount of a compound of claim 1.

62. A method of treating or lessening the severity of prostate cancer, in a human in need thereof, which comprises administering to such human a therapeutically effective amount of a compound of claim 1.

63. A method of treating or lessening the severity of lung cancer, in a human in need thereof, which comprises administering to such human a therapeutically effective amount of a compound of claim 1.

64. A method of treating or lessening the severity of colon cancer, in a human in need thereof, which comprises administering to such human a therapeutically effective amount of a compound of claim 1.

\* \* \* \* \*

UNITED STATES PATENT AND TRADEMARK OFFICE
CERTIFICATE OF CORRECTION

| | | |
|---|---|---|
| PATENT NO. | : 8,410,158 B2 | Page 1 of 1 |
| APPLICATION NO. | : 12/526111 | |
| DATED | : April 2, 2013 | |
| INVENTOR(S) | : Seefeld et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 627 days.

Signed and Sealed this
Second Day of December, 2014

Michelle K. Lee
*Deputy Director of the United States Patent and Trademark Office*

SEQUENCE LISTING

<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: Biotinylated Synthetic peptide

<400> SEQUENCE: 1

Ala Arg Lys Arg Glu Arg Ala Tyr Ser Phe Gly His His Ala
 1               5                  10

<210> SEQ ID NO 2

-continued

```
<211> LENGTH: 26
<212> TYPE: DNA
<213> ORGANISM: Artificial Sequence
<220> FEATURE:
<223> OTHER INFORMATION: Primer

<400> SEQUENCE: 2 tataggat ccatgagcga cgtggc                                              26

<210> SEQ ID NO 3
<211> LENGTH: 29
<212> TYPE: DNA
<213> ORGANISM: Atificial Sequence

<400> SEQUENCE: 3
aaatttctcg agtcaggccg tgctgctgg                                         29

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
acctggcggc cacgctactt cctcc                                             25

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ctcgagcatg caactagagg gcc                                               23
```